(12) United States Patent
Bjornson et al.

(10) Patent No.: US 10,335,409 B2
(45) Date of Patent: Jul. 2, 2019

(54) INHIBITORS OF HEPATITIS C VIRUS

(71) Applicant: Gilead Pharmasset LLC, Foster City, CA (US)

(72) Inventors: Kyla Bjornson, San Lorenzo, CA (US); Eda Canales, San Mateo, CA (US); Jeromy J. Cottell, Redwood City, CA (US); Kapil K. Karki, Foster City, CA (US); Ashley A. Katana, North Olmsted, OH (US); Darryl Kato, San Francisco, CA (US); Tetsuya Kobayashi, Pleasanton, CA (US); John O. Link, San Francisco, CA (US); Ruben Martinez, San Diego, CA (US); Barton W. Phillips, San Mateo, CA (US); Hyung-jung Pyun, Fremont, CA (US); Michael Sangi, San Mateo, CA (US); Adam J. Schrier, Redwood City, CA (US); Dustin Siegel, Half Moon Bay, CA (US); James G. Taylor, Burlingame, CA (US); Chinh V. Tran, San Diego, CA (US); Teresa A. Trejo Martin, Belmont, CA (US); Randall W. Vivian, San Mateo, CA (US); Zheng-Yu Yang, Palo Alto, CA (US); Jeff Zablocki, Los Altos, CA (US); Sheila Zipfel, San Mateo, CA (US)

(73) Assignee: Gilead Pharmasset LLC, Foster City, CA (US)

(*) Notice: Subject to any disclaimer, the term of this patent is extended or adjusted under 35 U.S.C. 154(b) by 0 days.

(21) Appl. No.: 16/005,111

(22) Filed: Jun. 11, 2018

(65) Prior Publication Data
US 2019/0008858 A1 Jan. 10, 2019

Related U.S. Application Data

(63) Continuation of application No. 15/488,035, filed on Apr. 14, 2017, now abandoned, which is a
(Continued)

(51) Int. Cl.
| | |
|---|---|
| A61K 38/00 | (2006.01) |
| A61K 31/498 | (2006.01) |
| C07D 498/16 | (2006.01) |
| A61K 31/4985 | (2006.01) |
| C07D 498/22 | (2006.01) |
| A61K 31/4745 | (2006.01) |
| A61K 31/506 | (2006.01) |
| A61K 31/519 | (2006.01) |
| A61K 45/06 | (2006.01) |
| C07K 5/087 | (2006.01) |
| C07K 5/08 | (2006.01) |
| C07K 5/083 | (2006.01) |

(Continued)

(52) U.S. Cl.
CPC ............ *A61K 31/498* (2013.01); *A61K 31/10* (2013.01); *A61K 31/401* (2013.01); *A61K 31/4745* (2013.01); *A61K 31/4985* (2013.01); *A61K 31/506* (2013.01); *A61K 31/519* (2013.01); *A61K 38/06* (2013.01); *A61K 38/21* (2013.01); *A61K 45/06* (2013.01); *C07D 241/36* (2013.01); *C07D 403/14* (2013.01); *C07D 498/16* (2013.01); *C07D 498/22* (2013.01); *C07K 5/08* (2013.01); *C07K 5/0808* (2013.01); *C07K 5/0812* (2013.01); *C07K 5/0827* (2013.01); *A61K 38/00* (2013.01)

(58) Field of Classification Search
None
See application file for complete search history.

(56) References Cited

U.S. PATENT DOCUMENTS

| | | |
|---|---|---|
| 6,867,185 B2 | 3/2005 | Campbell et al. |
| 6,995,174 B2 | 2/2006 | Wang et al. |
| (Continued) | | |

FOREIGN PATENT DOCUMENTS

| | | |
|---|---|---|
| EP | 1343807 A2 | 4/2009 |
| EP | 1924593 A1 | 9/2009 |
| (Continued) | | |

OTHER PUBLICATIONS

Arasappan, et al., "Discovery of Narlaprevir (SCH 900518): A Potent, Second Generation HCV NS3 Serine Protease Inhibitor," ACS Med. Chem. Lett., 1:64-69 (2010).
(Continued)

*Primary Examiner* — Thomas S Heard
(74) *Attorney, Agent, or Firm* — Sheppard Mullin Richter & Hampton LLP

(57) ABSTRACT

Compounds of Formula I are disclosed

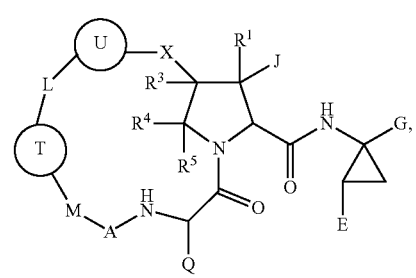

As well as pharmaceutically acceptable salts thereof. Methods of using said compounds and pharmaceutical compositions containing said compounds are also disclosed.

2 Claims, No Drawings

Related U.S. Application Data continuation of application No. 15/185,273, filed on Jun. 17, 2016, now Pat. No. 9,655,944, which is a continuation of application No. 14/996,961, filed on Jan. 15, 2016, now abandoned, which is a continuation of application No. 13/934,090, filed on Jul. 2, 2013, now Pat. No. 9,296,782.

(60) Provisional application No. 61/798,524, filed on Mar. 15, 2013, provisional application No. 61/667,806, filed on Jul. 3, 2012.

(51) Int. Cl.
*A61K 38/21* (2006.01)
*A61K 38/06* (2006.01)
*A61K 31/10* (2006.01)
*A61K 31/401* (2006.01)
*C07D 241/36* (2006.01)
*C07D 403/14* (2006.01)

(56) References Cited

U.S. PATENT DOCUMENTS

| | | | |
|---|---|---|---|
| 7,041,698 B2 | 5/2006 | Ripka et al. |
| 7,879,797 B2 | 2/2011 | Hollowav et al. |
| RE42,375 E | 5/2011 | Nakajima et al. |
| 7,973,040 B2 | 7/2011 | Harper et al. |
| 8,030,307 B2 | 10/2011 | Moore et al. |
| 8,080,654 B2 | 12/2011 | Harper et al. |
| 8,106,059 B2 | 1/2012 | Holsinger et al. |
| 8,106,187 B2 | 1/2012 | Scalone et al. |
| 8,119,592 B2 | 2/2012 | Beigelman et al. |
| 8,163,693 B2 | 4/2012 | Chen et al. |
| 8,163,921 B2 | 4/2012 | Sin et al. |
| 8,178,491 B2 | 5/2012 | Cho et al. |
| 8,178,520 B2 | 5/2012 | Di Francesco et al. |
| 8,211,891 B2 | 7/2012 | Gai et al. |
| 8,216,999 B2 | 7/2012 | Holloway et al. |
| 8,263,549 B2 | 9/2012 | Moore et al. |
| 8,349,869 B2 | 1/2013 | Simmen et al. |
| 8,362,035 B2 | 1/2013 | Berkenbusch et al. |
| 8,420,596 B2 | 4/2013 | Ku et al. |
| 8,431,733 B2 | 4/2013 | Dener |
| 8,445,430 B2 | 5/2013 | Zhanqetal |
| 8,461,107 B2 | 6/2013 | Liverton et al. |
| 8,530,497 B2 | 9/2013 | Yanq et al. |
| 8,563,505 B2 | 10/2013 | Hiebert et al. |
| 9,220,748 B2 | 12/2015 | Or et al. |
| 9,296,782 B2 | 3/2016 | Bjornson et al. |
| 2004/0077551 A1 | 4/2004 | Campbell et al. |
| 2007/0027071 A1 | 2/2007 | Holloway et al. |
| 2009/0005387 A1 | 1/2009 | Niu et al. |
| 2009/0258891 A1 | 10/2009 | Di Francesco et al. |
| 2009/0269305 A1 | 10/2009 | Seiwert et al. |
| 2009/0274652 A1 | 11/2009 | Sin et al. |
| 2009/0274657 A1 | 11/2009 | Gai et al. |
| 2010/0003214 A1 | 1/2010 | Gai et al. |
| 2010/0029666 A1 | 2/2010 | Harper et al. |
| 2010/0099695 A1 | 4/2010 | Liverton et al. |
| 2010/0124545 A1 | 5/2010 | Zhanqetal |
| 2010/0150866 A1 | 6/2010 | Wanq et al. |
| 2010/0160403 A1 | 6/2010 | Link et al. |
| 2010/0183551 A1 | 7/2010 | Harper et al. |
| 2010/0298210 A1 | 11/2010 | Liverton et al. |
| 2011/0002884 A1 | 1/2011 | McCauley et al. |
| 2011/0028494 A1 | 2/2011 | Holloway et al. |
| 2011/0123496 A1 | 5/2011 | Gai et al. |
| 2011/0224134 A1 | 9/2011 | Harper et al. |
| 2012/0034187 A1 | 2/2012 | Llinas-Brunet et al. |
| 2012/0070416 A1 | 3/2012 | Or et al. |
| 2012/0094897 A1 | 4/2012 | Buckman et al. |
| 2012/0095211 A1 | 4/2012 | Buckman et al. |
| 2012/0101031 A1 | 4/2012 | Chen et al. |
| 2012/0101032 A1 | 4/2012 | Buckman et al. |
| 2012/0101049 A1 | 4/2012 | Chen et al. |
| 2012/0121624 A1 | 5/2012 | Liverton et al. |
| 2012/0190866 A1 | 7/2012 | Cho et al. |
| 2012/0230949 A1 | 9/2012 | Perrone et al. |
| 2012/0232247 A1 | 9/2012 | Sonq et al. |
| 2013/0017991 A1 | 1/2013 | Niu et al. |
| 2013/0115190 A1 | 5/2013 | Hiebert et al. |
| 2013/0129671 A1 | 5/2013 | Sun et al. |
| 2013/0131105 A1 | 5/2013 | Petter et al. |
| 2013/0142754 A1 | 6/2013 | Raiamani et al. |
| 2013/0144036 A1 | 6/2013 | Gai et al. |
| 2013/0178413 A1 | 7/2013 | McCauley et al. |
| 2013/0274463 A1 | 10/2013 | Chen et al. |
| 2014/0274884 A1 | 9/2014 | Bjornson et al. |

FOREIGN PATENT DOCUMENTS

| | | |
|---|---|---|
| EP | 2268285 A1 | 1/2011 |
| EP | 2268619 A1 | 1/2011 |
| EP | 2271345 A1 | 1/2011 |
| EP | 2331552 A1 | 6/2011 |
| EP | 2331553 A1 | 5/2013 |
| EP | 2079480 A2 | 6/2013 |
| EP | 2382198 A1 | 7/2013 |
| EP | 2250174 A2 | 8/2013 |
| WO | WO 03/099316 | 12/2003 |
| WO | WO 2004/093798 A2 | 11/2004 |
| WO | WO 2004/094452 | 11/2004 |
| WO | WO 2005/051410 | 6/2005 |
| WO | WO 2006/020276 A2 | 2/2006 |
| WO | WO 2006/119061 A2 | 11/2006 |
| WO | WO 2007/001406 A2 | 1/2007 |
| WO | WO 2007/014926 A1 | 2/2007 |
| WO | WO 2007/015824 | 2/2007 |
| WO | WO 2007/016441 A1 | 2/2007 |
| WO | WO 2007/044893 A2 | 4/2007 |
| WO | WO 2007/044933 A1 | 4/2007 |
| WO | WO 2007/131966 A1 | 11/2007 |
| WO | WO 2007/148135 A1 | 12/2007 |
| WO | WO 2008/005511 A2 | 1/2008 |
| WO | WO 2008/051475 A2 | 5/2008 |
| WO | WO 2008/051477 A2 | 5/2008 |
| WO | WO 2008/051514 A2 | 5/2008 |
| WO | WO 2008/057208 A2 | 5/2008 |
| WO | WO 2008/057209 A1 | 5/2008 |
| WO | WO 2008/134397 A1 | 11/2008 |
| WO | WO 2008/137779 A2 | 11/2008 |
| WO | WO 2008/141227 A1 | 11/2008 |
| WO | WO 2009/010804 A1 | 1/2009 |
| WO | WO 2009/055335 A2 | 4/2009 |
| WO | WO 2009/064975 A1 | 5/2009 |
| WO | WO 2009/070692 A1 | 6/2009 |
| WO | WO 2009/073719 A1 | 6/2009 |
| WO | WO 2009/079353 A1 | 6/2009 |
| WO | WO 2009/082697 A1 | 7/2009 |
| WO | WO 2009/094443 A1 | 7/2009 |
| WO | WO 2009/108507 A1 | 9/2009 |
| WO | WO 2009/117594 A1 | 9/2009 |
| WO | WO 2009/134624 A1 | 11/2009 |
| WO | WO 2009/134987 A1 | 11/2009 |
| WO | WO 2010/011566 A1 | 1/2010 |
| WO | WO 2010/021717 A2 | 2/2010 |
| WO | WO 2010/030359 A2 | 3/2010 |
| WO | WO 2010/033466 A1 | 3/2010 |
| WO | WO 2010/036551 A1 | 4/2010 |
| WO | WO 2010/036896 A1 | 4/2010 |
| WO | WO 2010/045266 A1 | 4/2010 |
| WO | WO 2010/048468 A1 | 4/2010 |
| WO | WO 2010/065577 A1 | 6/2010 |
| WO | WO 2010/068761 A2 | 6/2010 |
| WO | WO 2010/080389 A1 | 7/2010 |
| WO | WO 2010/132163 A1 | 11/2010 |
| WO | WO 2010/135748 A1 | 11/2010 |
| WO | WO 2011/014487 A1 | 2/2011 |
| WO | WO 2011/038293 A1 | 3/2011 |
| WO | WO 2011/041551 A1 | 4/2011 |
| WO | WO 2011/049908 A2 | 4/2011 |
| WO | WO 2011/112558 A2 | 9/2011 |
| WO | WO 2011/156337 A2 | 12/2011 |

(56) References Cited

FOREIGN PATENT DOCUMENTS

| WO | WO 2012/019299 A1 | 2/2012 |
|---|---|---|
| WO | WO 2012/037259 A1 | 3/2012 |
| WO | WO 2012/040040 A1 | 3/2012 |
| WO | WO 2012/040167 A1 | 3/2012 |
| WO | WO 2012/040242 A1 | 3/2012 |
| WO | WO 2012/047764 A1 | 4/2012 |
| WO | WO 2012/054874 A1 | 4/2012 |
| WO | WO 2012/061248 A2 | 5/2012 |
| WO | WO 2012/092409 A2 | 7/2012 |
| WO | WO 2012/092411 A2 | 7/2012 |
| WO | WO 2012/151195 | 11/2012 |
| WO | WO 2012/171332 A1 | 12/2012 |
| WO | WO 2012/173983 A1 | 12/2012 |
| WO | WO 2012/176149 A1 | 12/2012 |
| WO | WO 2013/028465 A1 | 2/2013 |
| WO | WO 2013/066753 A1 | 5/2013 |
| WO | WO 2013/074386 A2 | 5/2013 |
| WO | WO 2013/106506 A1 | 7/2013 |
| WO | WO 2014/145095 A1 | 9/2014 |

OTHER PUBLICATIONS

Chen et al., "Discovery of Small-Molecule Inhibitors of HCV N53-4A Protease as Potential Therapeutic Agents against HCV Infectiob," Current Medicinal Chemistry, 12, 2317-2342(2005).
Ciesek, et al., "Second-wave Protease Inhibitors: Choosing an Heir," Clin Liver Dis, doi: 10.1016/j.cld.2011.05.014 (2011 ).
Communication dated Mar. 6, 2016 for European Application No. 13739324.5.
Cummings, et al., "Induced-Fit Binding of the Macrocyclic Noncovalent Inhibitor TMC435 to its HCV NS3/NS4A Protease Target," Angew. Chem. Int. Ed., 49: 1652-1655 (2010).
Duan, et al., "Discovery of Novel P3-oxo Inhibitor of Hepatitis C Virus NS3/4A Serine Protease," Bioorganic & Medicinal Chemistry Letters, doi: 10.1016/j.bmcl.2012.02.039 (2012).
Examination Report dated Oct. 17, 2013 for Pakistan Application No. 442/2013.
Flores, et al., "HCV-NS3 Inhibitors: Determination of their Kinetic Parameters and Mechanism," Biochimica et Biophysica Acta, 1794: 1441-1448 (2009).
Foster, et al., "Telaprevir Alone or with Peg interferon and Ribavirin Reduces HCV RNA in Patients with Chronic Genotype 2 but Not Genotype 3 Infections," Gastroenterology, 141: 881-880 (2011 ).
Fusco, et al., "New Protease Inhibitors for HCV—Help is on the way," Journal of Hepatology, 54: 1087-1089 (2011 ).
Gallo, et al., "Structural Characterization of the Hepatitis C Virus NS3 Protease from Genotype 3a: The Basis of the Genotype 1 b vs. 3a Inhibitor Potency Shift," Virology, 405: 424-438 (2010).
Gottwein, et al., "Differential Efficacy of Protease Inhibitors Against HCV Genotypes 2a, 3a, 5a, and 6a NS3/4A Protease Recombinant Viruses," Gastroenterology, 141: 1067-1079 (2011 ).
Halfon, et al., "Hepatitis C Virus Resistance to Protease Inhibitors," Journal of Hepatology, 55: 192-206 (2011 ).
Harper, et al., "Discovery of MK-5172, a Macrocyclic Hepatitis C Virus NS3/4a Protease Inhibitor," ACS Medicinal Chemistry Letters, dx.doi.org/10.1021/ml300017p (2012).
Harper, et al., "Inhibitors of the Hepatitis C Virus NS3 Protease with Basic Amine Functionality at the P3-Amino Acid N-Terminus: Discovery and Optimization of a New Series of P2-P4 Macrocycles," J. Med. Chem., 52: 4820-4837 (2009).
Hinrichsen, et al., "Short-term Antiviral Efficacy of BILN 2061, a Hepatitis C Virus Serine Protease Inhibitor, in Hepatitis C Genotype 1 Patients," Gastroenterology, 127: 134 7-1355 (2004 ).
Huang, et al., "Discovery of Hepatitis C Virus NS3-NS4A Complex Inhibitors," Hepatitis C Antiviral Drug Discovery and Development, edited by Seng-Lai Tan and Yupeng He, Caister Academic Press, Chapter 11, 215-235 (2011).
Imhof, et al., "Genotype Differences in Susceptibility and Resistance Development of Hepatitis C Virus to Protease Inhibitors Telaprevir (VX-950) and Danoprevir (ITMN-191 )," Hepatology, 53: 1090-1099 (2011 ).

International Preliminary Report on Patentability for PCT/US2013/049119 dated Jan. 6, 2015.
International Search Report and Written Opinion for PCT/US2013/049119 dated Nov. 5, 2013.
Lallos, et al., "In Vitro Resistance and Cross-Resistance Profiles of IDX320, a Potent Macrocyclic HCV Protease Inhibitor," 5th International Workshop on Hepatitis C—Resistance and New Compounds, Boston, Jun. 24-25, 2010.
Lenz, et al., "In Vitro Resistance Profile of the Hepatitis C Virus NS3/4A Protease Inhibitor TMC435," Antimicrobial Agents and Chemotherapy, 54(5): 1878-1887 (2010).
Lin, et al., "In Vitro Resistance Studies of Hepatitis C Virus Serine Protease Inhibitors, VX-950 and BILN 2061," The Journal of Biological Chemistry, 279(17): 17508-17514 (2004).
Lin, et al., "VX-950, a Novel Hepatitis C Virus (HCV) NS3-4A Protease Inhibitor, Exhibits Potent Antiviral Activities in HCV Replicon Cells," Antimicrobial Agents and Chemotherapy, 50(5): 1813-1822 (2006).
Liu-Young, et al., "Hepatitis C Protease and Polymerase Inhibitors in Development," AIDS Patient Care and STDs, 22(6): 449-457 (2008).
Liverton, et al, "Molecular Modeling Based Approach to Potent P2-P4 Macrocyclic Inhibitors of Hepatitis C NS3/4A Protease," J. Am. Chem. Soc. 130: 4607-4609 (2008).
Liverton, et al., "MK-7009, a Potent and Selective Inhibitor of Hepatitis C Virus NS3/4A Protease," Antimicrobial Agents and Chemotherapy, 54(1 ): 305-311 (2010).
Lu, et al., "Drug-target Residence Time: Critical Information for Lead Optimization," Current Opinion in Chemical Biology, 14: 467-474 (2010).
McCauley, et al., "Bismacrocyclic Inhibitors of Hepatitis C NS3/4a Protease," Angew. Chem. Int. Ed., 47: 9104-9107 (2008).
McCauley, et al., "Discovery of Vaniprevir (MK-7009), a Macrocyclic Hepatitis C Virus NS3/4a Protease Inhibitor" J. Med. Chem., doi: 10.1021/jm9015526, A-U (2009).
McCauley, et al., "Discovery of Vaniprevir (MK-7009), a Macrocyclic Hepatitis C Virus NS3/4a Protease Inhibitor" J. Med. Chem., 53: 2443-2463 (2010).
Monteagudo, et al., "The Metabolism and Disposition of a Potent Inhibitor of Hepatitis C Virus NS3/4A Protease," Xenobiotica, (2010), 40(12): 826-839.
Moreau, et al., "Discovery of Hepatitis C Virus NS3-4A Protease Inhibitors with Improved Barrier to Resistance and Favorable Liver Distribution," Journal of Medicinal Chemistry, dx.doi.orq/10.1021/im400121 t (2013).
Nature Outlook Hepatitis C, 474(7350): S1-S21, Jun. 9, 2011.
Notification of Deliciency dated Apr. 7, 2015 for Vietnam Application No. 1-2014-04304.
Official Communication of Chilean Patent Application 3634-2014 dated Apr. 24, 2017 (12 pages).
Örtqvist, et al., "Structure-activity Relationships of HCV NS3 Protease Inhibitors Evaluated on the Drug-Resistant Variants A 156T and D168V," Antiviral Therapy, 15: 841-852 (2010).
Paolucci, et al., "Naturally Occurring Mutations to HCV Protease Inhibitors in Treatment-naïve Patients," Virology Journal, 9(245): 1-8 (2012).
Paulson, et al., "Comparison of HCV NS3 Protease and NS5B Polymerase Inhibitor Activity in 1 a, 1 b and 2a Replicons and 2a Infectious Virus," Antiviral Research, 83: 135-142 (2009).
Pompei, et al., "Novel P2-P4 Macrocyclic Inhibitors of HCV NS3/4A Protease by P3 Succinamide Fragment Depeptidization Strategy," Bioorganic & Medicinal Chemistry Letters, 20: 168-174 (2010).
Raboisson, et al., "Structure-activity Relationship Study on a Novel Series of Cyclopentane-containing Macrocyclic Inhibitors of the Hepatitis C Virus NS3/4A Protease Leading to the Discovery of TMC435350," Bioorganic & Medicinal Chemistry Letters, 18, 4853-4858 (2008).
Reiser, et al., "Antiviral Efficacy of NS3-Serine Protease Inhibitor BILN-2061 in Patients with Chronic Genotype 2 and 3 Hepatitis C," Hepatology, 41 (4 ): 832-835 (2005).
Rieger, et al., "Pharmacokinetic Analysis and Liver Concentrations of a Series of Macrocyclic Peptidomimetic Inhibitors of HCV

(56) References Cited

OTHER PUBLICATIONS

NS3/4A Protease: Identification of ITMN-191, a Potent NS3/4A Protease Inhibitor with High Liver Exposure Across Multiple Species," Poster T1795, Digestive Disease Week, May 20-25, 2006, Los Anqeles, CA.

Ronn, et al., "Evaluation of a Diverse Set of Potential P1 Carboxylic Acid Bioisosteres in Hepatitis C Virus NS3 Protease Inhibitors," Bioorganic & Medicinal Chemistry, 15: 4057-4068 (2007).

Ronn, et al., "Exploration of Acyl Sulfonamides as Carboxylic Acid Replacements in Protease Inhibitors of the Hepatitis C Virus Full-length NS3," Bioorganic & Medicinal Chemistry, 14: 544-559 (2006).

Rudd, et al., "Discovery of MK-1220: A Macrocyclic Inhibitor of Hepatitis C Virus NS3/4A Protease with Improved Preclinical Plasma Exposure," ACS Med. Chem. Lett., 2: 207-212 (2011).

Sarrazin, et al., "Antiviral Strategies in Hepatitis C Virus Infection," Journal of Hepatology, S88-S100 (2012).

Search Report dated Jul. 22, 2015 for Panama Application No. 90482-01.

Seiwert, et al., "Preclinical Characteristics of ITMN-191, an Orally Active Inhibitor of the HCV NS3/4A Protease Nominated for Preclinical Development," Poster #T1793, Digestive Disease Week, May 20-25, 2006, Los Anqeles, CA.

Soriano, et al., "Directly Acting Antivirals Against Hepatitis C Virus," J. Antimicrob. Chemother., 66: 1673-1686 (2011).

Summa, et al., "MK-5172, a Selective Inhibitor of Hepatitis C Virus NS3/4a Protease with Broad Activity across Genotypes and Resistant Variants," Antimicrobial Agents and Chemotherapy, 56(8): 4161-4167 (2012).

Tong, et al., "Impact of Naturally Occurring Variants of HCV Protease on the Binding of Different Classes of Protease Inhibitors," American Chemical Society, 45(5): 1353-1361 (2006).

Tong, et al., "Preclinical Characterization of the Antiviral Activity of SCH 900518 (Narlaprevir), a Novel Mechanism-Based Inhibitor of Hepatitis C Virus NS3 Protease," Antimicrobial Agents and Chemotherapy, 54(6) 2365-2370 (2010).

Venkatraman, et al., "Macrocyclic Inhibitors of HCV NS3 Protease," Expert Opin. Ther. Patents, 19(9), 1277-1303 (2009).

Ward, JW Heptatis C virus prevention, care, and treatment: from policy to practice, Clin Infect Dis. Jul. 2012; 55 Suppl 1:S58-63.

Xue, et al., "Molecular Modeling Study on the Resistance Mechanism of HCV NS3/4A Serine Protease Mutants R155K, A156V and D168A to TMC435," Antiviral Research, 93: 126-137 (2012).

Zeng, et al., "Epimerization Reaction of a Substituted Vinylcyclopropane Catalyzed by Ruthenium Carbenes: Mechanistic Analysis," J. Org. Chem., 71: 8864-8875 (2006).

INHIBITORS OF HEPATITIS C VIRUS

CROSS-REFERENCE TO RELATED APPLICATIONS

This application is a continuation of U.S. application Ser. No. 15/488,035, filed on Apr. 14, 2017, which is a continuation of U.S. application Ser. No. 15/185,273, filed Jun. 17, 2016, now U.S. Pat. No. 9,655,944, which is a continuation of U.S. application Ser. No. 14/996,961, filed on Jan. 15, 2016 (abandoned), which is a continuation of U.S. application Ser. No. 13/934,090, filed Jul. 2, 2013, now U.S. Pat. No. 9,296,782, which claims the benefit of U.S. Provisional Application No. 61/798,524, filed on Mar. 15, 2013, and U.S. Application No. 61/667,806, filed Jul. 3, 2012; which are herein incorporated by reference in their entirety.

FIELD

Novel small molecule inhibitors of viral replication are disclosed, compositions containing such compounds, and therapeutic methods comprising the administration of such compounds are also disclosed.

BACKGROUND

The hepatitis C virus (HCV), a member of the hepacivirus genera within the Flaviviridae family, is the leading cause of chronic liver disease worldwide (Boyer, N. et al. *J Hepatol.* 2000, 32, 98-112). Consequently, a significant focus of current antiviral research is directed toward the development of improved methods for the treatment of chronic HCV infections in humans (Ciesek, S., von Hahn T., and Manns, M P., *Clin. Liver Dis.*, 2011, 15, 597-609, Soriano, V. et al, *J. Antimicrob. Chemother.*, 2011, 66, 1573-1686; Brody, H., Nature Outlook, 2011, 474, S1-S7; Gordon. C. P., et al., *J. Med. Chem.* 2005, 48. 1-20; Maradpour, D., et al., *Nat. Rev. Micro.* 2007, 5, 453-463).

Virologic cures of patients with chronic HCV infection are difficult to achieve because of the prodigious amount of daily virus production in chronically infected patients and the high spontaneous mutability of HCV (Neumann, et al., *Science* 1998, 282, 103-7; Fukimoto, et al., *Hepatology*, 1996, 24, 1351-4; Domingo, et al., *Gene* 1985, 40, 1-8; Martell. et al., *J. Virol.* 1992, 66, 3225-9). HCV treatment is further complicated by the fact that HCV is genetically diverse and expressed as several different genotypes and numerous subtypes. For example, HCV is currently classified into six major genotypes (designated 1-6), many subtypes (designated a, b, c, and so on), and about 100 different strains (numbered 1, 2, 3, and so on).

HCV is distributed worldwide with genotypes 1, 2, and 3 predominate within the United States, Europe, Australia, and East Asia (Japan, Taiwan, Thailand, and China). Genotype 4 is largely found in the Middle East, Egypt and central Africa while genotype 5 and 6 are found predominantly in South Africa and South East Asia respectively (Simmonds, P. et al. *J Virol.* 84: 4597-4610, 2010).

The combination of ribavirin, a nucleoside analog, and interferon-alpha (α) (IFN), is utilized for the treatment of multiple genotypes of chronic HCV infections in humans. However, the variable clinical response observed within patients and the toxicity of this regimen have limited its usefulness. Addition of a HCV protease inhibitor (telaprevir or boceprevir) to the ribavirin and IFN regimen improves 12-week post-treatment virological response (SVR12) rates substantially. However, the regimen is currently only approved for genotype 1 patients and toxicity and other side effects remain.

The use of directing acting antivirals to treat multiple genotypes of HCV infection has proven challenging due to the variable activity of antivirals against the different genotypes. HCV protease inhibitors frequently have compromised in vitro activity against HCV genotypes 2 and 3 compared to genotype 1 (See, e.g., Table 1 of Summa, V. et al., *Antimicrobial Agents and Chemotherapy*, 2012, 56, 4161-4167; Gottwein, J, et al, *Gastroenterology*, 2011, 141, 1067-1079). Correspondingly, clinical efficacy has also proven highly variable across HCV genotypes. For example, therapies that are highly effective against HCV genotype 1 and 2 may have limited or no clinical efficacy against genotype 3. (Moreno, C. et al, Poster 895, 61$^{st}$ AASLD Meeting, Boston, Mass., USA, Oct. 29-Nov. 2, 2010; Graham, F., et al, Gastroenterology, 2011, 141, 881-889; Foster, G. R et a. EASL 45$^{th}$ Annual Meeting, Apr. 14-18, 2010, Vienna, Austria.) In some cases, antiviral agents have good clinical efficacy against genotype 1, but lower and more variable against genotypes 2 and 3 (Reiser, M. et al., *Hepatology*, 2005, 41, 832-835.) To overcome the reduced efficacy in genotype 3 patients, substantially higher doses of antiviral agents may be required to achieve substantial viral load reductions (Fraser, I P et al., Abstract #48, HEP DART 2011, Koloa, Hi., December 2011.)

Antiviral agents that are less susceptible to viral resistance are also needed. For example, resistance mutations at positions 155 and 168 in the HCV protease frequently cause a substantial decrease in antiviral efficacy of HCV protease inhibitors (Mani, N. *Ann Forum Collab HIV Res.*, 2012, 14, 1-8; Romano, K P et al, *PNAS*, 2010, 107, 20986-20991; Lenz O, *Antimicrobial agents and chemotherapy*, 2010, 54, 1878-1887.)

In view of the limitations of current HCV therapy, there is a need to develop more effective anti-HCV therapies. It would also be useful to provide therapies that are effective against multiple HCV genotypes and subtypes.

SUMMARY

Novel compounds that inhibit the hepatitis C virus (HCV) NS3 protease are disclosed. In certain embodiments, the compounds disclosed inhibit multiple genotypes of the hepatitis C virus. These compounds are useful for the treatment of HCV infection and the related symptoms.

In one embodiment, a compound of Formula (IV):

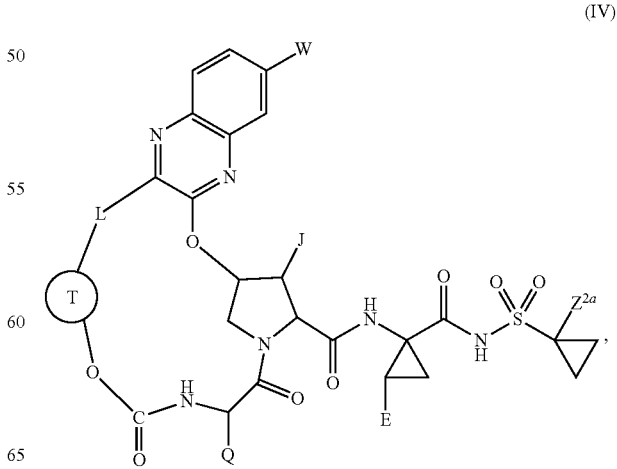

or a stereoisomer, or a mixture of stereoisomers, or a pharmaceutically acceptable salt thereof, is provided, wherein:

- J is $C_1$-$C_4$ alkyl or $C_3$-$C_6$ carbocyclyl, wherein $C_1$-$C_4$ alkyl or $C_3$-$C_6$ carbocyclyl is optionally substituted with halogen —OH, aryl or cyano;
- ⊙ is $C_3$-$C_5$ carbocyclylene that is attached to L and to the remainder of the compound through two adjacent carbons, wherein said $C_3$-$C_5$ carbocyclylene is optionally substituted with $C_1$-$C_4$ alkyl, $C_1$-$C_3$ haloalkyl, halogen, —OH, or cyano, or ⊙ is $C_5$-$C_8$ bicyclic carbocyclylene that is attached to L and to the remainder of the compound through two adjacent carbons;
- L is $C_3$-$C_6$ alkylene, $C_3$-$C_6$ alkenylene or —$(CH_2)_3$- cyclopropyl-, optionally substituted with 1-4 halogen, —OH, or cyano;
- Q is $C_2$-$C_4$ alkyl or $C_3$-$C_6$ carbocyclyl optionally substituted with $C_1$-$C_3$ alkyl, halogen, —OH, or cyano;
- E is $C_1$-$C_3$ alkyl or $C_2$-$C_3$ alkenyl, optionally substituted with $C_1$-$C_3$ alkyl, halogen. —OH, or cyano;
- W is H, —OH, —O($C_1$-$C_3$)alkyl, —O($C_1$-$C_3$)haloalkyl, halogen or cyano; and
- $Z^{2a}$ is H or $C_1$-$C_3$ alkyl, halogen, —OH, or cyano.

In a further embodiment of Formula (IV), ⊙ is $C_3$-$C_6$ carbocyclylene that is attached to L and to the remainder of the compound of Formula IV through two adjacent carbons, wherein said $C_3$-$C_6$ carbocyclene is optionally substituted with $C_1$-$C_4$ alkyl or $C_1$-$C_3$ haloalkyl.

In a further embodiment of Formula (IV), ⊙ is $C_3$-$C_6$ carbocyclylene that is attached to L and to the remainder of the compound of Formula IV through two adjacent carbons, wherein the $C_3$-$C_6$ carbocyclene is optionally substituted with methyl, ethyl or trifluoromethyl.

In a further embodiment of Formula (IV), ⊙ is cyclopropylene.

In a further embodiment of Formula (IV), ⊙ is $C_6$-$C_8$ bridged bicyclic carbocyclylene or $C_6$-$C_8$ fused bicyclic carbocyclylene that is attached to L and to the remainder of the compound of Formula IV through two adjacent carbons.

In a further embodiment of Formula (IV), L is $C_3$-$C_6$ alkylene, substituted with 1-4 halogens. In another embodiment of Formula (IV), L is $C_5$ alkylene, substituted with two halogens. In some embodiments, the halogens are each fluoro.

In a further embodiment of Formula (IV), L is $C_3$-$C_6$ alkylene.

In a further embodiment of Formula (IV), L is $C_5$ alkylene.

In a further embodiment of Formula (IV), Q is t-butyl or $C_5$-$C_6$ carbocyclyl.

In a further embodiment of Formula (IV), Q is t-butyl.

In a further embodiment of Formula (IV), E is $C_1$-$C_3$ alkyl optionally substituted with 1-3 halogen atoms.

In a further embodiment of Formula (IV), E is difluoromethyl.

In a further embodiment of Formula (IV), W is hydrogen, —O($C_1$-$C_3$)alkyl, halogen or cyano.

In a further embodiment of Formula (IV), W is methoxy.

In a further embodiment of Formula (IV), $Z^{2a}$ is hydrogen or methyl.

In a further embodiment of Formula (IV), $Z^{2a}$ is methyl.

In one embodiment, a compound of Formula (I):

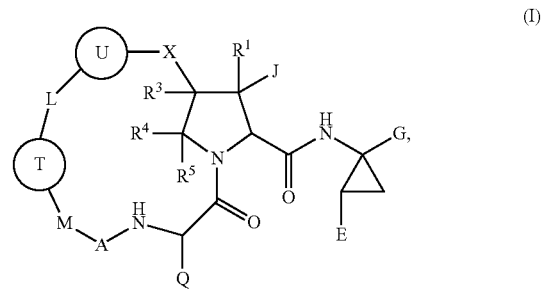

(I)

or a stereoisomer, or a mixture of stereoisomers, or a pharmaceutically acceptable salt thereof, is provided, wherein:

- J is $J^1$, $J^2$, $J^3$, $J^4$, $J^5$, $J^6$, $J^7$, $J^8$ or $J^9$;
- ⊙ is $T^1$, $T^2$, $T^3$, $T^4$, $T^5$, $T^6$, $T^7$, $T^8$, $T^9$, $T^{10}$, $T^{11}$, $T^{12}$, $T^{13}$ or $T^{14}$;
- L is $L^1$, $L^2$, $L^3$, $L^4$, $L^5$, $L^6$, $L^7$, $L^8$, $L^9$, or $L^{10}$;
- X is —O—, —$CH_2$—, —OC(O)—, —C(O)O—, —C(O)—, —$SO_2$—, —S(O)—, —N($R^{16}$)—, —S—, =N—O— or a bond;
- A is —C(O)—, —S(O)$_2$—, a 6-10 membered arylene, 5-10 membered heteroarylene, or 4-10 membered heterocyclene, wherein any of said arylene, heterocyclene, or heteroarylene is optionally substituted with 1-4 $Z^1$ groups;
- M is a bond, $C_1$-$C_6$ alkylene, —O—, or —N($R^{16}$)—;
- $R^1$ is H or F;
- $R^3$, $R^4$, and $R^5$ are each independently selected from H or $Z^1$;
- Q is $Q^1$, $Q^2$, $Q^3$, $Q^4$, $Q^5$, $Q^6$ or $Q^7$ or;
- E is $E^1$, $E^2$, $E^3$, $E^4$, $E^5$, or $E^6$;
- G is —$CO_2$H, —$CONHSO_2Z^2$, tetrazolyl, —CONHP(O)($R^{16}$)$_2$, —P(O)(OH)($R^{16}$), and —P(O)($R^{16}$)$_2$;
- ⊙ is $U^1$, $U^2$, $U^3$, $U^4$, $U^5$, $U^6$ or $U^7$;
- $J^1$ is halogen;
- $J^2$ is —OH and $R^1$ is H;
- $J^3$ is —$NR^{17}R^{18}$ and $R^1$ is H;
- $J^4$ is $C_1$-$C_8$ alkyl;
- $J^5$ is $C_1$-$C_8$ alkyl substituted with 1-4 $Z^3$ groups;
- $J^6$ is $C_3$-$C_8$ carbocyclyl optionally substituted with 1-4 $Z^3$ groups;
- $J^7$ is $C_6$-$C_{10}$ aryl, 5-10 membered heteroaryl, or 4-10 membered heterocyclyl optionally substituted with 1-4 $Z^3$ groups;
- $J^8$ is $C_1$-$C_8$ alkoxy optionally substituted with 1-4 $Z^3$ groups and $R^1$ is H;
- $J^9$ is $C_3$-$C_8$ carbocyclyloxy optionally substituted with 1-4 $Z^3$ groups and $R^1$ is H;
- $T^1$ is $C_3$-$C_8$ carbocyclylene that is attached to L and M through two adjacent carbons;
- $T^2$ is $C_3$-$C_8$ carbocyclylene that is attached to L and M through two adjacent carbons, wherein said carbocyclylene is substituted with 1-4 $C_1$-$C_8$ alkyl groups;
- $T^3$ is $C_3$-$C_8$ carbocyclylene that is attached to L and M through two adjacent carbons, wherein said carbocyclylene is substituted with 1-4 halogen atoms and said carbocyclylene is optionally substituted with 1-4 $C_1$-$C_6$ alkyl groups;
- $T^4$ is $C_3$-$C_8$ carbocyclylene that is attached to L and M through two adjacent carbons, wherein said carbocyclylene is optionally substituted with a $C_1$-$C_8$ alkyl group, wherein said alkyl group is optionally substituted with 1-4 $Z^3$ groups;

$T^5$ is 4-10 membered heterocyclene that is attached to L and M through two adjacent carbons;

$T^6$ is 4-10 membered heterocyclene that is attached to L through a carbon atom and attached to M through an N atom, wherein said heterocyclene is optionally substituted with 1-4 $Z^1$ groups;

$T^7$ is 4-10 membered heterocyclene that is attached to M through a carbon atom and attached to L through an N atom, wherein said heterocyclene is optionally substituted with 1-4 $Z^1$ groups;

$T^8$ is 4-10 membered heterocyclene that is attached to L and M through two adjacent carbons, wherein said heterocyclene is optionally substituted with 1-4 $Z^1$ groups;

$T^9$ is $C_5$-$C_{12}$ spiro bicyclic carbocyclylene that is attached to L and M through two adjacent carbons, wherein said spiro bicyclic carbocyclylene is optionally substituted with 1-4 $Z^1$ groups;

$T^{10}$ is $C_5$-$C_{12}$ fused bicyclic carbocyclylene that is attached to L and M through two adjacent carbons, wherein said fused bicyclic carbocyclylene is optionally substituted with 1-4 $Z^1$ groups;

$T^{11}$ is $C_5$-$C_{12}$ bridged bicyclic carbocyclylene that is attached to L and M through two adjacent carbons, wherein said bridged bicyclic carbocyclylene is optionally substituted with 1-4 $Z^1$ groups;

$T^{12}$ is $C_4$-$C_8$ carbocyclylene that is attached to L and M through two non-adjacent carbons, wherein said carbocyclylene is optionally substituted with 1-4 $Z^1$ groups;

$T^{13}$ is a 5-8 membered fused, bridged, or spiro bicyclic heterocyclene that is attached to L and M through two adjacent atoms, wherein said heterocyclene is optionally substituted with 1-4 $Z^1$ groups;

$T^{14}$ is $C_3$-$C_8$ carbocyclylene that is attached to L and M through two adjacent carbons, wherein said carbocyclylene is optionally substituted with 1-4 $Z^4$ groups;

$L^1$ is $C_1$-$C_8$ alkylene or $C_2$-$C_8$ alkenylene;

$L^2$ is $C_1$-$C_8$ alkylene or $C_2$-$C_8$ alkenylene wherein said $C_1$-$C_8$ alkylene is substituted with 1-4 halogens or said $C_2$-$C_8$ alkenylene is substituted with 1-4 halogens;

$L^3$ is $C_1$-$C_8$ alkylene or $C_2$-$C_8$ alkenylene wherein said $C_1$-$C_8$ alkylene is substituted with 1-4 $Z^4$ groups or said $C_2$-$C_8$ alkenylene is substituted with 1-4 $Z^4$ groups and wherein each is optionally substituted with 1-4 halogens;

$L^4$ is $C_1$-$C_8$ alkylene or $C_2$-$C_8$ alkenylene substituted with two geminal $C_1$-$C_4$ alkyl groups that come together to form a spiro $C_3$-$C_8$ carbocyclyl group, wherein $L^4$ is optionally substituted with 1-4 $Z^1$ groups;

$L^5$ is 2-8 membered heteroalkylene or 4-8 membered heteroalkenylene that is connected to ⊙ by an O, S or N atom and said heteroalkylene or heteroalkenylene is optionally substituted with 1-4 $Z^3$ groups;

$L^6$ is 2-8 membered heteroalkylene or 5-8 membered heteroalkenylene that is connected to ⊙ by a carbon atom and said heteroalkylene or heteroalkenylene is substituted with 1-4 halogen atoms and is optionally substituted with 1-4 $Z^4$ groups;

$L^7$ is 2-8 membered heteroalkylene or 4-8 membered heteroalkenylene that is connected to ⊙ by a carbon atom and said heteroalkylene or heteroalkenylene is optionally substituted with 1-4 $Z^4$ groups;

$L^8$ is $L^{8A}$-$L^{8B}$-$L^{8C}$ wherein $L^{8A}$ and $L^{8C}$ are each independently selected from $C_1$-$C_6$ alkylene, $C_1$-$C_6$ heteroalkylene, $C_2$-$C_6$ alkenylene or a bond and $L^{8B}$ is a 3- to 6-membered saturated or unsaturated ring containing 0 to 3 heteroatoms selected from N, O, or S, wherein $L^{8A}$ and $L^{8C}$ connect to $L^{8B}$ at two different ring atoms and $L^{8B}$ is optionally substituted with 1-4 $Z^1$ groups;

$L^9$ is $C_2$-$C_8$ alkynylene optionally substituted with 1-4 $Z^1$ groups;

$L^{10}$ is $C_1$-$C_8$ alkylene or $C_3$-$C_8$ alkenylene substituted with two geminal $Z^1$ groups that come together to form a spiro 4-8 membered heterocyclyl group, wherein $L^{10}$ is optionally substituted with 1-4 $Z^1$ groups;

$U^1$ is $C_6$-$C_{14}$ membered arylene optionally substituted with 1-4 W groups;

$U^2$ is $C_3$-$C_8$ membered carbocyclylene optionally substituted with 1-4 W groups;

$U^3$ is 4-14 membered heterocyclene optionally substituted with 1-4 W groups that are located on one or more ring atoms selected from C or N;

$U^4$ is 5 or 6 membered monocyclic heteroarylene containing 1, 2 or 3 heteroatoms independently selected from N, O, or S, wherein said heteroarylene is optionally substituted with 1-4 W groups that are located on one or more ring atoms selected from C or N;

$U^5$ is 8, 9 or 10 membered fused bicyclic heteroarylene containing 1, 2 or 3 heteroatom ring atoms independently selected from N, O, or S, wherein said heteroarylene is optionally substituted with 1-4 W groups that are located on one or more ring atoms selected from C or N;

$U^6$ is 11-14 membered fused tricyclic heteroarylene containing 1, 2, 3 or 4 heteroatom ring atoms independently selected from N, O, or S, wherein said heteroarylene is optionally substituted with 1-4 W groups that are located on one or more ring atoms selected from C or N;

$U^7$ is 8-10 membered fused bicyclic heteroarylene containing 4 heteroatom ring atoms independently selected from N, O, or S, wherein said heteroaryl is optionally substituted with 1-2 W groups that are located on one or more ring atoms selected from C or N;

W is independently $W^1$, $W^2$, $W^3$, $W^4$, $W^5$, $W^6$ or $W^7$;

$W^1$ is oxo, halogen, —$OR^6$, $C_1$-$C_6$ alkyl, —CN, —$CF_3$, —$SR^6$, —$C(O)_2R^6$, —$C(O)N(R^6)_2$, —$C(O)R^6$, —$N(R^6)C(O)R^6$, —$SO_2(C_1$-$C_6$ alkyl), —$S(O)(C_1$-$C_6$ alkyl), $C_3$-$C_8$ carbocyclyl, $C_3$-$C_8$ cycloalkoxy, $C_1$-$C_6$ haloalkyl, —$N(R^6)_2$, —$NR^6(C_1$-$C_6$ alkyl)$O(C_1$-$C_6$ alkyl), halo($C_1$-$C_6$ alkoxy), —$NR^6SO_2R^6$, —$SO_2N(R^6)_2$, —$NHCOOR^6$, —$NHCONHR^6$, $C_6$-$C_{10}$ aryl, 5-14 membered heteroaryl, 4-10 membered heterocyclyl or —O(4-10 membered heterocyclyl), wherein said $W^1$ alkyl, carbocyclyl, cycloalkoxy, haloalkyl, haloalkoxy, aryl, heteroaryl, or heterocyclyl is optionally substituted with 1-4 $Z^{1c}$ groups;

each $R^6$ is independently selected from H, $C_6$-$C_{10}$ aryl or $C_1$-$C_6$ alkyl, wherein said aryl or alkyl is optionally substituted with 1 to 4 substituents independently selected from halogen atoms, $C_1$-$C_6$ alkyl, $C_6$-$C_{10}$ aryl, $C_3$-$C_8$ carbocyclyl, 5-14 membered heteroaryl, 4-10 membered heterocyclyl, halo($C_1$-$C_6$ alkoxy), —OH, —O($C_1$-$C_6$ alkyl), —SH, —S($C_1$-$C_6$ alkyl), —$NH_2$, —NH($C_1$-$C_6$ alkyl), —N($C_1$-$C_6$ alkyl)$_2$, —C(O)($C_1$-$C_6$ alkyl), —$SO_2N(C_1$-$C_6$ alkyl)$_2$, —NHCOO($C_1$-$C_6$ alkyl), —NHCO($C_1$-$C_6$ alkyl), —NHCONH($C_1$-$C_6$ alkyl), —$CO_2(C_1$-$C_6$ alkyl), or —C(O)N($C_1$-$C_6$ alkyl)$_2$;

$W^2$ is $C_1$-$C_6$ alkoxy substituted with a 5-14 membered heteroaryl or $C_6$-$C_{10}$ aryl; wherein said heteroaryl or aryl is substituted with 1-4 $Z^1$ groups;

W³ is C₂-C₆ alkynyl substituted with an C₆-C₁₀ aryl, C₃-C₈ carbocyclyl, C₁-C₈ alkyl, C₁-C₆ haloalkyl, 4-10 membered heterocyclyl, or 5-14 membered heteroaryl; wherein said aryl, carbocyclyl, alkyl, haloalkyl, heterocyclyl, or heteroaryl is optionally substituted with 1-4 $Z^1$ groups;

W⁴ is —SF₅;

W⁵ is —O(C₂-C₆ alkyl)OR²² wherein R²² is an C₆-C₁₀ aryl, 5-14 membered heteroaryl or 4-10 membered heterocyclyl optionally substituted with 1-4 $Z^1$ groups;

W⁶ is —O(C₂-C₆ alkyl)NR¹⁶R²² wherein R²² is an C₆-C₁₀ aryl, 5-14 membered heteroaryl or 4-10 membered heterocyclyl optionally substituted with 1-4 $Z^1$ groups;

W⁷ is —O(5-14 membered heteroaryl); wherein said —O(5-14 membered heteroaryl) is optionally substituted with 1-4 $Z^1$ groups;

E¹ is C₂-C₆ alkenyl;

E² is C₁-C₆ alkyl;

E³ is C₁-C₆ haloalkyl;

E⁴ is C₂-C₆ haloalkenyl;

E⁵ is C₃-C₆ carbocyclyl;

E⁶ is C₁-C₆ alkyl substituted with —OCH₃, —OCD₃, —OCF₃, or —OCF₂H;

Q¹ is H, C₁-C₈ alkyl, C₃-C₈ carbocyclyl, C₆-C₁₀ aryl, 5-6 membered heteroaryl, or 5-6 membered heterocyclyl, wherein when Q¹ is not H, said Q¹ is optionally substituted with 1-3 substituents independently selected from halogen, —OR⁶, —SR⁶, —N(R⁶)₂, C₆-C₁₀ aryl, C₁-C₆ alkyl, C₁-C₆ haloalkyl, C₁-C₆ haloalkoxy, —CN, —CF₃, —SO₂(C₁-C₆ alkyl), —S(O)(C₁-C₆ alkyl), —NR⁶SO₂Z², —SO₂NR¹⁷R¹⁸, —NHCOOR¹⁶, —NHCOZ², —NHCONHR¹⁶, —CO₂R⁶, —C(O)R⁶, or —CON(R⁶)₂;

Q² s C₅-C₁₀ spiro bicyclic carbocyclyl optionally substituted with 1-4 $Z^1$ groups;

Q³ is C₅-C₁₀ fused bicyclic carbocyclyl optionally substituted with 1-4 $Z^1$ groups;

Q⁴ is C₅-C₁₀ bridged bicyclic carbocyclyl optionally substituted with 1-4 $Z^1$ groups;

Q⁵ is 4-membered heterocyclyl having 1 heteroatom selected from N, O or S wherein Q⁵ is optionally substituted with 1-4 alkyl or $Z^3$ groups;

Q⁶ is C₁-C₈ alkyl, C₃-C₈ carbocyclyl, C₆-C₁₀ aryl, 5-6 membered heteroaryl, or 5-6 membered heterocyclyl, wherein Q⁶ is substituted with 1 oxo group and with 0 to 3 substituents independently selected from halogen, —OR⁶, —SR⁶, —N(R⁶)₂, C₆-C₁₀ aryl, C₁-C₆ alkyl, C₁-C₆ haloalkyl, C₁-C₆ haloalkoxy, —NO₂, —CN, —CF₃, —SO₂(C₁-C₆ alkyl), —S(O)(C₁-C₆ alkyl), —NR⁶SO₂Z², —SO₂NR¹⁷R¹⁸, —NHCOOR¹⁶, —NHCOZ², —NHCONHR¹⁶, —CO₂R⁶, —C(O)R⁶, or —CON(R⁶)₂;

Q⁷ is C₃-C₈ carbocyclyl, wherein Q⁷ is substituted with 4-8 F atoms and each carbon of Q⁷ is substituted with 0-2 F atoms;

each $Z^1$ is independently oxo, halogen, C₁-C₈ alkyl, C₂-C₈ alkenyl, C₂-C₈ alkynyl, C₃-C₈ carbocyclyl, C₅-C₁₀ bicyclic carbocyclyl, C₁-C₈ haloalkyl, C₆-C₁₀ aryl, 5-14 membered heteroaryl, 4-10 membered heterocyclyl, —CN, —C(O)R¹⁶, —C(O)OR¹⁶, —C(O)NR¹⁷R¹⁸, —NR¹⁷R¹⁸, —NR¹⁶C(O)R¹⁶, —NR¹⁶C(O)NR¹⁷R¹⁸, —NR¹⁶S(O)₂R¹⁶, —NR¹⁶S(O)₂NR¹⁷R¹⁸, —NR¹⁶S(O)₂OR¹⁶, —OR¹⁶, —OC(O)R¹⁶, —OC(O)NR¹⁷R¹⁸, —SR¹⁶, —S(O)R¹⁶, —S(O)₂R¹⁶ or —S(O)₂NR¹⁷R¹⁸ wherein any alkyl, alkynyl, carbocyclyl, aryl, heteroaryl or heterocyclyl of $Z^1$ is optionally substituted with 1-4 $Z^{1a}$ groups;

each $Z^{1a}$ is independently oxo, halogen, C₂-C₈ alkenyl, C₂-C₈ alkynyl, C₃-C₈ carbocyclyl, C₅-C₁₀ bicyclic carbocyclyl, C₁-C₈ haloalkyl, C₆-C₁₀ aryl, 5-14 membered heteroaryl, 4-10 membered heterocyclyl, —CN, —C(O)R¹⁶, —C(O)OR¹⁶, —C(O)NR¹⁷R¹⁸, —NR¹⁷R¹⁸, —NR¹⁶C(O)R¹⁶, —NR¹⁶C(O)OR¹⁶, —NR¹⁶C(O)NR¹⁷R¹⁸, —NR¹⁶S(O)₂R¹⁶, —NR¹⁶S(O)₂NR¹⁷R¹⁸, —NR¹⁶S(O)₂OR¹⁶, —OR¹⁶, —OC(O)R¹⁶, —OC(O)NR¹⁷R¹⁸, —SR¹⁶, —S(O)R¹⁶, —S(O)₂R¹⁶ or —S(O)₂NR¹⁷R¹⁸ wherein any alkenyl, alkynyl, carbocyclyl, aryl, heteroaryl or heterocyclyl of $Z^{1a}$ is optionally substituted with 1-4 $Z^{1c}$ groups;

each R¹⁶ is independently H, C₁-C₈ alkyl, C₂-C₈ alkenyl, C₂-C₈ alkynyl, C₃-C₈ carbocyclyl, C₅-C₁₀ bicyclic carbocyclyl, C₆-C₁₀ aryl, 5-14 membered heteroaryl or 4-10 membered heterocyclyl, wherein any alkyl, alkenyl, alkynyl, carbocyclyl, aryl, heteroaryl or heterocyclyl of R¹⁶ is optionally substituted with 1-4 $Z^{1c}$ groups;

each $Z^{1c}$ is independently oxo, halogen, C₁-C₈ alkyl, C₃-C₈ carbocyclyl, C₅-C₁₀ bicyclic carbocyclyl C₁-C₈ haloalkyl, C₆-C₁₀ aryl, 5-14 membered heteroaryl, 4-10 membered heterocyclyl, —CN, —C(O)(C₁-C₈ alkyl), —C(O)O(C₁-C₈ alkyl), —C(O)N(C₁-C₈ alkyl)₂, —NH₂, —NH(C₁-C₈ alkyl), —N(C₁-C₈ alkyl)₂, —NHC(O)O(C₁-C₈ alkyl), —NHC(O)(C₁-C₈ alkyl), —NHC(O)NH(C₁-C₈ alkyl), —OH, —O(C₁-C₈ alkyl), C₃-C₈ cycloalkoxy, C₅-C₁₀ bicyclic carbocyclyloxy, —S(C₁-C₈ alkyl) or —S(O)₂N(C₁-C₈ alkyl)₂ wherein any alkyl, carbocyclyl, aryl, heteroaryl, heterocyclyl or cycloalkoxy portion of $Z^{1c}$ is optionally substituted with 1-4 halogen atoms or C₁-C₈ alkoxy groups;

R¹⁷ and R¹⁸ are each independently H, C₁-C₈ alkyl, C₂-C₈ alkenyl, C₂-C₈ alkynyl, C₃-C₈ carbocyclyl, C₅-C₁₀ bicyclic carbocyclyl, —C(O)R¹⁶, —C(O)OR¹⁶, C₆-C₁₀ aryl, 5-14 membered heteroaryl or 4-10 membered heterocyclyl, wherein any alkyl, alkenyl, alkynyl, carbocyclyl, aryl, heteroaryl or heterocyclyl of R¹⁷ or R¹⁸ is optionally substituted with 1-4 $Z^{1c}$ groups, or R¹⁷ and R¹⁸ together with the nitrogen to which they are attached form a 4-7 membered heterocyclyl group, wherein said 4-7 membered heterocyclyl group is optionally substituted with 1-4 $Z^{1c}$ groups;

each $Z^2$ is independently C₁-C₈ alkyl, C₃-C₈ carbocyclyl. C₅-C₁₀ bicyclic carbocyclyl, C₆-C₁₀ aryl, 5-14 membered heteroaryl, 4-10 membered heterocyclyl, —NR¹⁷R¹⁸ or —OR¹⁶ wherein any alkyl, carbocyclyl, aryl, heteroaryl or heterocyclyl portion of $Z^2$ is optionally substituted with 1-4 $Z^{2a}$a groups;

each $Z^{2a}$ is independently oxo, halogen, C₁-C₈ alkyl, C₂-C₈ alkynyl, C₃-C₈ carbocyclyl, C₅-C₁₀ bicyclic carbocyclyl, C₁-C₈ haloalkyl, C₆-C₁₀ aryl, 5-14 membered heteroaryl, 4-10 membered heterocyclyl, —(C₂-C₈ alkynyl)aryl, —(C₂-C₈ alkynyl)heteroaryl, —CN, —C(O)(C₁-C₆ alkyl), —C(O)O(C₁-C₆ alkyl), —C(O)N(C₁-C₆ alkyl)₂, —NH₂, —NH(C₁-C₆ alkyl), —N(C₁-C₆ alkyl)₂, —NHC(O)O(C₁-C₆ alkyl), —NHC(O)(C₁-C₆ alkyl), —NHC(O)NH(C₁-C₆ alkyl), —OH, —O(C₁-C₆ alkyl), halo(C₁-C₆ alkoxy), C₃-C₈ cycloalkoxy, —S(C₁-C₆ alkyl), or —SO₂N(C₁-C₆ alkyl)₂; wherein any alkyl, alkynyl, carbocyclyl, cycloalkoxy, aryl, heteroaryl or heterocyclyl portions of $Z^{2a}$ is optionally substituted with 1-4 halogen or C₁-C₆ alkoxy groups;

each $Z^3$ is independently oxo, halogen, C₂-C₈ alkenyl, C₂-C₈ alkynyl, C₃-C₈ carbocyclyl, C₅-C₁₀ bicyclic carbocyclyl, C₁-C₈ haloalkyl, C₆-C₁₀ aryl, 5-14 membered heteroaryl, 4-10 membered heterocyclyl, —CN, —C(O)OR$^{16}$, —C(O)NR$^{17}$R$^{18}$, —NR$^{17}$R$^{18}$, —NR$^{16}$C(O)NR$^{17}$R$^{18}$, —OR$^{16}$, —SR$^{16}$ or —SO$_2$R$^{16}$; wherein any alkenyl, alkynyl, carbocyclyl, aryl, heteroaryl or heterocyclyl portions of Z$^3$ is optionally substituted with 1-4 halogen; and each Z$^4$ is independently oxo, C$_2$-C$_8$ alkenyl, C$_2$-C$_8$ alkynyl, C$_3$-C$_8$ carbocyclyl, C$_5$-C$_{10}$ bicyclic carbocyclyl, C$_1$-C$_8$ haloalkyl, C$_6$-C$_{10}$ aryl, 5-14 membered heteroaryl, 4-10 membered heterocyclyl, —CN, —C(O)OR$^{16}$, —C(O)NR$^{17}$R$^{18}$, —NR$^{17}$R$^{16}$, —NR$^{16}$C(O)NR$^{17}$R$^{18}$, —OR$^{16}$, —SR$^{16}$ or —SO$_2$R$^{16}$, wherein any alkenyl, alkynyl, carbocyclyl, aryl, heteroaryl or heterocyclyl portions of Z$^4$ is optionally substituted with 1-4 halogen.

In another embodiment, a compound of Formula (II):

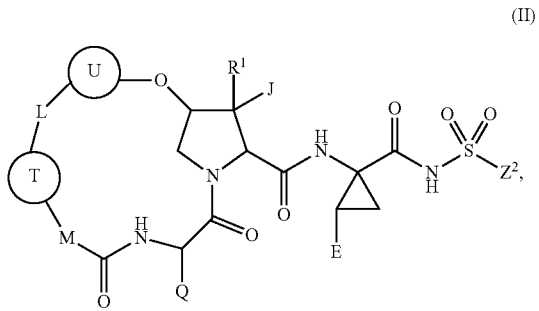

(II)

or a stereoisomer, or a mixture of stereoisomers, or a pharmaceutically acceptable salt thereof, is provided, wherein:

M is —O—;
J is J$^1$, J$^2$, J$^3$, J$^4$, J$^5$, J$^6$, J$^7$, J$^8$ or J$^9$;
⊙ is T$^1$, T$^2$, T$^3$, T$^4$, T$^5$, T$^7$, T$^8$, T$^9$, T$^{10}$, T$^{11}$, T$^{12}$, T$^{13}$ or T$^{14}$;
L is L$^1$, L$^2$, L$^3$, L$^4$, L$^5$, L$^6$, L$^7$, L$^8$, L$^9$ or L$^{10}$;
R$^1$ is H or F;
Q is Q$^1$, Q$^2$, Q$^3$, Q$^4$, Q$^5$, Q$^6$ or Q$^7$;
E is E$^1$, E$^2$, E$^3$, E$^4$, E$^5$, or E$^6$;
⊙ is U$^1$, U$^2$, U$^3$, U$^4$, U$^5$, U$^6$ or U$^7$;
J$^1$ is halogen;
J$^2$ is —OH and R$^1$ is H;
J$^3$ is —NR$^{17}$R$^{18}$ and R$^1$ is H;
J$^4$ is C$_1$-C$_8$ alkyl;
J$^5$ is C$_1$-C$_8$ alkyl optionally substituted with 1-4 Z$^3$ groups;
J$^6$ is C$_3$-C$_8$ carbocyclyl optionally substituted with 1-4 Z$^3$ groups;
J$^7$ is C$_6$-C$_{10}$ aryl, 5-14 membered heteroaryl, or 4-10 membered heterocyclyl, any of which are optionally substituted with 1-4 Z$^3$ groups;
J$^8$ is C$_1$-C$_8$ alkoxy optionally substituted with 1-4 Z$^3$ groups and R$^1$ is H;
J$^9$ is C$_3$-C$_8$ carbocyclyloxy optionally substituted with 1-4 Z$^3$ groups and R$^1$ is H;
T$^1$ is C$_3$-C$_8$ carbocyclylene that is attached to L and M through two adjacent carbons;
T$^2$ is C$_3$-C$_8$ carbocyclylene that is attached to L and M through two adjacent carbons, wherein said carbocyclylene is optionally substituted with 1-4 C$_1$-C$_8$ alkyl groups;
T$^3$ is C$_3$-C$_8$ carbocyclylene that is attached to L and M through two adjacent carbons, wherein said carbocyclylene is optionally substituted with 1-4 halogen atoms and said carbocyclylene is optionally substituted with 1-4 C$_1$-C$_6$ alkyl groups;
T$^4$ is C$_3$-C$_8$ carbocyclylene that is attached to L and M through two adjacent carbons, wherein said carbocyclylene is optionally substituted with a C$_1$-C$_8$ alkyl group, wherein said alkyl group is optionally substituted with 1-4 Z$^3$ groups;
T$^5$ is 4-10 membered heterocyclene that is attached to L and M through two adjacent carbons;
T$^7$ is 4-10 membered heterocyclene that is attached to M through a carbon atom and attached to L through a N atom, wherein said heterocyclene is optionally substituted with 1-4 Z$^1$ groups;
T$^8$ is 4-10 membered heterocyclene that is attached to L and M through two adjacent carbons, wherein said heterocyclene is optionally substituted with 1-4 Z$^1$ groups;
T$^9$ is C$_5$-C$_{12}$ spiro bicyclic carbocyclylene that is attached to L and M through two adjacent carbons, wherein said spiro bicyclic carbocyclylene is optionally substituted with 1-4 Z$^1$ groups;
T$^{10}$ is C$_5$-C$_{12}$ fused bicyclic carbocyclylene that is attached to L and M through two adjacent carbons, wherein said fused bicyclic carbocyclylene is optionally substituted with 1-4 Z$^1$ groups;
T$^{11}$ is C$_5$-C$_{12}$ bridged bicyclic carbocyclylene that is attached to L and M through two adjacent carbons, wherein said bridged bicyclic carbocyclylene is optionally substituted with 1-4 Z$^1$ groups;
T$^{12}$ is C$_4$-C$_8$ carbocyclylene that is attached to L and M through two non-adjacent carbons, wherein said carbocyclylene is optionally substituted with 1-4 Z$^1$ groups;
T$^{13}$ is a 5-8 membered fused, bridged, or spiro bicyclic heterocyclene that is attached to L and M through two adjacent atoms, wherein said heterocyclene is optionally substituted with 1-4 Z$^1$ groups;
T$^{14}$ is C$_3$-C$_8$ carbocyclylene that is attached to L and M through two adjacent carbons, wherein said carbocyclylene is optionally substituted with 1-4 Z$^4$ groups;
L$^1$ is C$_1$-C$_8$ alkylene or C$_2$-C$_8$ alkenylene;
L$^2$ is C$_1$-C$_8$ alkylene or C$_2$-C$_8$ alkenylene wherein said C$_1$-C$_8$ alkylene is substituted with 1-4 halogens or said C$_2$-C$_8$ alkenylene is substituted with 1-4 halogens;
L$^3$ is C$_1$-C$_8$ alkylene or C$_2$-C$_8$ alkenylene wherein said C$_1$-C$_8$ alkylene is substituted with 1-4 Z$^4$ groups or said C$_2$-C$_8$ alkenylene is substituted with 1-4 Z$^4$ groups and wherein each is optionally substituted with 1-4 halogens;
L$^4$ is C$_1$-C$_8$ alkylene or C$_2$-C$_8$ alkenylene substituted with two geminal C$_1$-C$_4$ alkyl groups that come together to form a spiro C$_3$-C$_8$ carbocyclyl group, wherein L$^4$ is optionally substituted with 1-4 Z$^1$ groups;
L$^5$ is 2-8 membered heteroalkylene or 4-8 membered heteroalkenylene that is connected to ⊙ by an O, S or N atom and said heteroalkylene or heteroalkenylene is optionally substituted with 1-4 Z$^3$ groups;
L$^6$ is 2-8 membered heteroalkylene or 5-8 membered heteroalkenylene that is connected to ⊙ by a carbon atom and said heteroalkylene or heteroalkenylene is substituted with 1-4 halogen atoms and is optionally substituted with 1-4 Z$^4$ groups;
L$^7$ is 2-8 membered heteroalkylene or 4-8 membered heteroalkenylene that is connected to ⊙ by a carbon atom and said heteroalkylene or heteroalkenylene is optionally substituted with 1-4 Z$^4$ groups;

$L^8$ is $L^{8A}$-$L^{8B}$-$L^{8C}$ wherein $L^{8A}$ and $L^{8C}$ are each independently selected from $C_1$-$C_6$ alkylene, $C_1$-$C_6$ heteroalkylene, $C_2$-$C_6$ alkenylene or a bond and $L^{8B}$ is a 3- to 6-membered saturated or unsaturated ring containing 0 to 3 heteroatoms selected from N, O, or S, wherein $L^{8A}$ and $L^{8C}$ connect to $L^{8B}$ at two different ring atoms and $L^{8B}$ is optionally substituted with 1-4 $Z^1$ groups;

$L^9$ is $C_2$-$C_8$ alkynylene optionally substituted with 1-4 $Z^1$ groups;

$L^{10}$ is $C_1$-$C_8$ alkylene or $C_3$-$C_8$ alkenylene substituted with two geminal $Z^1$ groups that come together to form a spiro 4-8 membered heterocyclyl group, wherein $L^{10}$ is optionally substituted with 1-4 $Z^1$ groups;

$U^1$ is $C_6$-$C_{14}$ membered arylene optionally substituted with 1-4 W groups; each $U^2$ is $C_3$-$C_8$ membered carbocyclylene optionally substituted 1-4 W groups;

each $U^3$ is 4-14 membered heterocyclene optionally substituted with 1-4 W groups that are located on one or more ring atoms selected from C or N;

$U^4$ is 5 or 6 membered monocyclic heteroarylene containing 1, 2 or 3 heteroatoms independently selected from N, O, or S, wherein said heteroarylene is optionally substituted with 1-4 W groups that are located on one or more ring atoms selected from C or N;

$U^5$ is 8, 9 or 10 membered fused bicyclic heteroarylene containing 1, 2 or 3 heteroatom ring atoms independently selected from N, O, or S, wherein said heteroarylene is optionally substituted with 1-4 W groups that are located on one or more ring atoms selected from C or N;

$U^6$ is 11-14 membered fused tricyclic heteroarylene containing 1, 2, 3 or 4 heteroatom ring atoms independently selected from N, O, or S, wherein said heteroarylene is optionally substituted with 1-4 W groups that are located on one or more ring atoms selected from C or N;

$U^7$ is 8-10 membered fused bicyclic heteroarylene containing 4 heteroatom ring atoms independently selected from N, O, or S, wherein said heteroaryl is optionally substituted with 1-2 W groups that are located on one or more ring atoms selected from C or N;

each W is independently $W^1$, $W^2$, $W^3$, $W^4$, $W^5$, $W^6$ or $W^7$;

each $W^1$ is oxo, halogen, —$OR^6$, $C_1$-$C_6$ alkyl, —CN, —$CF_3$, —$SR^6$, —$C(O)_2R^6$, —$C(O)N(R^6)_2$, —$C(O)R^6$, —$N(R^6)C(O)R^6$, —$SO_2(C_1$-$C_6$ alkyl), —$S(O)(C_1$-$C_6$ alkyl), $C_3$-$C_8$ carbocyclyl, $C_3$-$C_8$ cycloalkoxy, $C_1$-$C_6$ haloalkyl, —$N(R^6)_2$, —$NR^6(C_1$-$C_6$ alkyl)$O(C_1$-$C_6$ alkyl), halo($C_1$-$C_6$ alkoxy), —$NR^6SO_2R^6$, —$SO_2N(R^6)_2$, —$NHCOOR^6$, —$NHCONHR^6$, $C_6$-$C_{10}$ aryl, 5-14 membered heteroaryl, 4-10 membered heterocyclyl or —O(4-10 membered heterocyclyl), wherein said $W^1$ alkyl, carbocyclyl, cycloalkoxy, haloalkyl, haloalkoxy, aryl, heteroaryl, or heterocyclyl is optionally substituted with 1-4 $Z^{1c}$ groups;

each $R^6$ is independently selected from H, $C_6$-$C_{10}$ aryl or $C_1$-$C_6$ alkyl, wherein said aryl or alkyl is optionally substituted with 1 to 4 substituents independently selected from halogen atoms, $C_1$-$C_6$ alkyl, $C_6$-$C_{10}$ aryl, $C_3$-$C_8$ carbocyclyl, 5-14 membered heteroaryl, 4-10 membered heterocyclyl, halo($C_1$-$C_6$ alkoxy), —OH, —O($C_1$-$C_6$ alkyl), —SH, —S($C_1$-$C_6$ alkyl), —$NH_2$, —NH($C_1$-$C_6$ alkyl), —N($C_1$-$C_6$ alkyl)$_2$, —C(O)($C_1$-$C_6$ alkyl), —$SO_2N(C_1$-$C_6$ alkyl)$_2$, —NHCOO($C_1$-$C_6$ alkyl), —NHCO($C_1$-$C_6$ alkyl), —NHCONH($C_1$-$C_6$ alkyl), —$CO_2(C_1$-$C_6$ alkyl), or —C(O)N($C_1$-$C_6$ alkyl)$_2$;

each $W^2$ is $C_1$-$C_6$ alkoxy substituted with a 5-14 membered heteroaryl or $C_6$-$C_{10}$ aryl; wherein said heteroaryl or aryl is substituted with 1-4 $Z^{1c}$ groups;

each $W^3$ is $C_2$-$C_6$ alkynyl substituted with an $C_6$-$C_{10}$ aryl, $C_3$-$C_8$ carbocyclyl, $C_1$-$C_8$ alkyl, $C_1$-$C_6$ haloalkyl, 4-10 membered heterocyclyl, or 5-14 membered heteroaryl; wherein said aryl, carbocyclyl, alkyl, haloalkyl, heterocyclyl, or heteroaryl is optionally substituted with 1-4 $Z^1$ groups;

each $W^4$ is —$SF_5$;

each $W^5$ is —$O(C_2$-$C_6$ alkyl)$OR^{22}$ wherein $R^{22}$ is an $C_6$-$C_{10}$ aryl, 5-14 membered heteroaryl or 4-10 membered heterocyclyl optionally substituted with 1-4 $Z^1$ groups;

each $W^6$ is —$O(C_2$-$C_6$ alkyl)$NR^{16}R^{22}$ wherein $R^{22}$ is an $C_6$-$C_{10}$ aryl, 5-14 membered heteroaryl or 4-10 membered heterocyclyl optionally substituted with 1-4 $Z^1$ groups;

each $W^7$ is —O(5-14 membered heteroaryl); wherein said —O(5-14 membered heteroaryl) is optionally substituted with 1-4 $Z^1$ groups and 2 adjacent substituents of said —O(5-14 membered heteroaryl) may be taken together to form a 3- to 6-membered cyclic ring containing 0 to 3 heteroatoms independently selected from N, O, or S;

$E^1$ is $C_2$-$C_6$ alkenyl;

$E^2$ is $C_1$-$C_6$ alkyl;

$E^3$ is $C_1$-$C_6$ haloalkyl;

$E^4$ is $C_2$-$C_6$ haloalkenyl;

$E^5$ is $C_3$-$C_6$ carbocyclyl, $E^6$ is $C_1$-$C_6$ alkyl optionally substituted with —$OCH_3$,—$OCD_3$, —$OCF_3$, or —$OCF_2H$;

$Q^1$ is selected from H, $C_1$-$C_8$ alkyl, $C_3$-$C_8$ carbocyclyl, $C_6$-$C_{10}$ aryl, 5-6 membered heteroaryl, or 5-6 membered heterocyclyl groups, wherein when $Q^1$ is not H, said $Q^1$ is optionally substituted with 1-4 substituents independently selected from halogen, —$OR^6$, —$SR^6$, —$N(R^6)_2$, $C_6$-$C_{10}$ aryl, $C_1$-$C_6$ alkyl, $C_1$-$C_6$ haloalkyl, $C_1$-$C_6$ haloalkoxy, —$NO_2$, —CN, —$CF_3$, —$SO_2(C_1$-$C_6$ alkyl), —$S(O)(C_1$-$C_6$ alkyl), —$NR^6SO_2Z^2$, —$SO_2NR^{17}R^{18}$, —$NHCOOR^{16}$, —$NHCOZ^2$, —$NHCONHR^{16}$, —$CO_2R^6$, —$C(O)R^6$, and —$CON(R^6)_2$;

$Q^2$ is $C_5$-$C_{10}$ spiro bicyclic carbocyclyl optionally substituted with 1-4 $Z^1$ groups;

$Q^3$ is $C_5$-$C_{10}$ fused bicyclic carbocyclyl optionally substituted with 1-4 $Z^1$ groups;

$Q^4$ is $C_5$-$C_{10}$ bridged bicyclic carbocyclyl optionally substituted with 1-4 $Z^1$ groups;

$Q^5$ is 4-membered heterocyclyl having 1 heteroatom selected from N, O or S wherein $Q^5$ is optionally substituted with 1-4 $Z^3$ groups;

$Q^6$ is $C_1$-$C_8$ alkyl, $C_3$-$C_8$ carbocyclyl, $C_6$-$C_{10}$ aryl, 5-6 membered heteroaryl, or 5-6 membered heterocyclyl, wherein $Q^6$ is substituted with 1 oxo group and with 0 to 3 substituents independently selected from halogen, —$OR^6$, —$SR^6$, —$N(R^6)_2$, $C_6$-$C_{10}$ aryl, $C_1$-$C_6$ alkyl, $C_1$-$C_6$ haloalkyl, $C_1$-$C_6$ haloalkoxy, —$NO_2$, —CN, —$CF_3$, —$SO_2(C_1$-$C_6$ alkyl), —$S(O)(C_1$-$C_6$ alkyl), —$NR^6SO_2Z^2$, —$SO_2NR^{17}R^{18}$, —$NHCOOR^{16}$, —$NHCOZ^2$, —$NHCONHR^{16}$, —$CO_2R^6$, —$C(O)R^6$, or —$CON(R^6)_2$;

$Q^7$ is $C_3$-$C_8$ carbocyclyl, wherein $Q^7$ is substituted with 4-8 F atoms and each carbon of $Q^7$ is substituted with 0-2 F atoms;

each $Z^1$ is independently oxo, halogen, $C_1$-$C_8$ alkyl, $C_2$-$C_8$ alkenyl, $C_2$-$C_8$ alkynyl $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)R$^{16}$, —C(O)OR$^{16}$, —C(O)NR$^{17}$R$^{18}$, —NR$^{17}$R$^{18}$, —NR$^{16}$C(O)R$^{16}$, —NR$^{16}$C(O)NR$^{17}$R$^{18}$, —NR$^{16}$S(O)$_2$R$^{16}$, —NR$^{16}$S(O)$_2$NR$^{17}$R$^{18}$, —NR$^{16}$S(O)$_2$OR$^{16}$, —OR$^{16}$, —OC(O)R$^{16}$, —OC(O)NR$^{17}$R$^{18}$, —SR$^{16}$, —S(O)R$^{16}$, —S(O)$_2$R$^{16}$ or —S(O)$_2$NR$^{17}$R$^{18}$ wherein any alkyl, alkenyl, alkynyl, carbocyclyl, aryl, heteroaryl or heterocyclyl of $Z^1$ is optionally substituted with 1-4 $Z^{1a}$ groups;

each $Z^{1a}$ is independently oxo, halogen, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)R$^{16}$, —C(O)OR$^{16}$, —C(O)NR$^{17}$R$^{18}$, —NR$^{17}$R$^{18}$, —NR$^{16}$C(O)R$^{16}$, —NR$^{16}$C(O)OR$^{16}$, —NR$^{16}$C(O)NR$^{17}$R$^{18}$, —NR$^{16}$S(O)$_2$R$^{16}$, —NR$^{16}$S(O)$_2$NR$^{17}$R$^{18}$, —NR$^{16}$S(O)$_2$OR$^{16}$, —OR$^{16}$, —OC(O)R$^{16}$, —OC(O)NR$^{17}$R$^{18}$, —SR$^{16}$, —S(O)R$^{16}$, —S(O)$_2$R$^{16}$ or —S(O)$_2$NR$^{17}$R$^{18}$ wherein any alkenyl, alkynyl, carbocyclyl, aryl, heteroaryl or heterocyclyl of $Z^{1a}$ is optionally substituted with 1-4 $Z^{1c}$ groups;

each $R^{16}$ is independently H, $C_1$-$C_8$ alkyl, $C_2$-$C_8$ alkenyl. $C_2$-$C_8$ alkynyl, $C_3$-$C_8$ carbocyclyl, $C_5$-$C_{10}$ bicyclic carbocyclyl, $C_6$-$C_{10}$ aryl, 5-14 membered heteroaryl or 4-10 membered heterocyclyl, wherein any alkyl, alkenyl, alkynyl, carbocyclyl, aryl, heteroaryl or heterocyclyl of $R^{16}$ is optionally substituted with 1-4 $Z^{1c}$ groups;

each $Z^{1c}$ is independently oxo, halogen, $C_1$-$C_8$ alkyl, $C_3$-$C_8$ carbocyclyl, $C_5$-$C_{10}$ bicyclic carbocyclyl, $C_1$-$C_8$ haloalkyl $C_6$-$C_{10}$ aryl, 5-14 membered heteroaryl, 4-10 membered heterocyclyl, —CN, —C(O)($C_1$-$C_8$ alkyl), —C(O)O($C_1$-$C_8$ alkyl), —C(O)N($C_1$-$C_8$ alkyl)$_2$, —NH$_2$, —NH($C_1$-$C_8$ alkyl), —N($C_1$-$C_8$ alkyl)$_2$, —NHC(O)O($C_1$-$C_8$ alkyl), —NHC(O)($C_1$-$C_8$ alkyl), —NHC(O)NH($C_1$-$C_8$ alkyl), —OH, —O($C_1$-$C_8$ alkyl), $C_3$-$C_8$ cycloalkoxy, $C_5$-$C_{10}$ bicyclic carbocyclyloxy, —S($C_1$-$C_8$ alkyl) or —S(O)$_2$N($C_1$-$C_8$ alkyl)$_2$ wherein any alkyl, carbocyclyl, aryl, heteroaryl, heterocyclyl or cycloalkoxy portion of $Z^{1c}$ is optionally substituted with 1-4 halogen atoms or $C_1$-$C_6$ alkoxy groups;

$R^{17}$ and $R^{18}$ are each independently H, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, —C(O)R$^6$, —C(O)OR$^{16}$, $C_6$-$C_{10}$ aryl, 5-14 membered heteroaryl or 4-10 membered heterocyclyl, wherein any alkyl, alkenyl, alkynyl, carbocyclyl, aryl, heteroaryl or heterocyclyl of $R^{17}$ or $R^{18}$ is optionally substituted with 1-4 $Z^{1c}$ groups, or $R^{17}$ and $R^{18}$ together with the nitrogen to which they are attached form a 4-7 membered heterocyclyl group, wherein said 4-7 membered heterocyclyl group is optionally substituted with 1-4 $Z^{1c}$ groups;

each $Z^2$ is independently $C_1$-$C_8$ alkyl, $C_3$-$C_8$ carbocyclyl, $C_5$-$C_{10}$ bicyclic carbocyclyl, $C_6$-$C_{10}$ aryl, 5-14 membered heteroaryl, 4-10 membered heterocyclyl,—NR$^{17}$R$^{18}$ or —OR$^{16}$ wherein any alkyl, carbocyclyl, aryl, heteroaryl or heterocyclyl portion of $Z^2$ is optionally substituted with 1-4 $Z^{2a}$ groups;

each $Z^{2a}$ is independently oxo, halogen, $C_1$-$C_8$ alkyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —($C_2$-$C_8$ alkynyl)aryl, —($C_2$-$C_8$ alkynyl)heteroaryl, —CN, —C(O)($C_1$-$C_6$ alkyl), —C(O)O($C_1$-$C_6$ alkyl), —C(O)N($C_1$-$C_6$ alkyl)$_2$, —NH, —NH($C_1$-$C_6$ alkyl), —N($C_1$-$C_6$ alkyl)$_2$, —NHC(O)O($C_1$-$C_6$ alkyl), —NHC(O)($C_1$-$C_6$ alkyl), —NHC(O)NH($C_1$-$C_6$ alkyl), —OH, —O($C_1$-$C_6$ alkyl), halo($C_1$-$C_6$ alkoxy), $C_3$-$C_8$ cycloalkoxy, —S($C_1$-$C_6$ alkyl), or —SO$_2$N($C_1$-$C_6$ alkyl)$_2$; wherein any alkyl, alkynyl, carbocyclyl, cycloalkoxy, aryl, heteroaryl or heterocyclyl portions of $Z^{2a}$ is optionally substituted with 1-4 halogen or $C_1$-$C_6$ alkoxy groups;

each $Z^3$ is independently oxo, halogen, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)OR$^{16}$, —C(O)NR$^{17}$R$^{18}$, —NR$^{17}$R$^{18}$, —NR$^{16}$C(O)NR$^{17}$R$^{18}$, —OR$^{16}$, —SR$^{16}$ or —SO$_2$R$^{16}$; wherein any alkenyl, alkynyl, carbocyclyl, aryl, heteroaryl or heterocyclyl portions of $Z^3$ is optionally substituted with 1-4 halogen; and each $Z^4$ is independently oxo, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)OR$^{16}$, —C(O)NR$^{17}$R$^{18}$, —NR$^{17}$R$^{18}$, —NR$^{16}$C(O)NR$^{17}$R$^{18}$, —OR$^{16}$, —SR$^{16}$ or —SO$_2$R$^{16}$, wherein any alkenyl, alkynyl, carbocyclyl, aryl, heteroaryl or heterocyclyl portions of $Z^4$ is optionally substituted with 1-4 halogen.

In a further embodiment a compound of Formula (III):

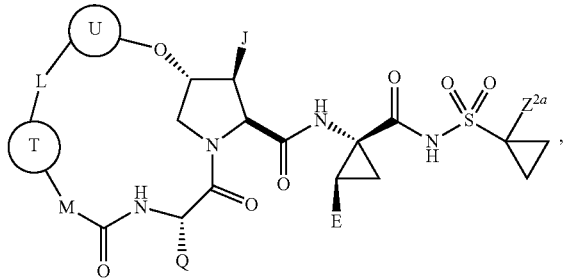

(III)

or a stereoisomer, or a mixture of stereoisomers, or a pharmaceutically acceptable salt thereof, is provided, wherein:

M is —O—;
J is $J^1$, $J^2$, $J^3$, $J^4$, $J^5$, $J^6$, $J^7$, $J^8$ or $J^9$;
⊙ is $T^1$, $T^2$, $T^3$, $T^4$, $T^5$, $T^7$, $T^8$, $T^9$, $T^{10}$, $T^{11}$, $T^{12}$, $T^{13}$ or $T^{14}$;
L is $L^1$, $L^2$, $L^3$, $L^4$, $L^5$, $L^6$, $L^7$, $L^8$, $L^9$ or $L^{10}$;
Q is $Q^1$, $Q^2$, $Q^3$, $Q^4$, $Q^5$ or $Q^7$;
E is $E^1$, $E^2$, $E^3$, or $E^4$;
⊙ is selected from $U^1$, $U^3$, $U^4$, $U^5$, $U^6$ or $U^7$;
$J^1$ is halogen;
$J^2$ is —OH;
$J^3$ is —NR$^{17}$R$^{18}$;
$J^4$ is $C_1$-$C_8$ alkyl.
$J^5$ is $C_1$-$C_8$ alkyl substituted with 1-4 $Z^3$ groups;
$J^6$ is $C_3$-$C_8$ carbocyclyl optionally substituted with 1-4 $Z^3$ groups;
$J^7$ is $C_6$-$C_{10}$ aryl, 5-14 membered heteroaryl, or 4-10 membered heterocyclyl any of which groups are optionally substituted with 1-4 $Z^3$ groups;
$J^8$ is $C_1$-$C_8$ alkoxy optionally substituted with 1-4 $Z^3$ groups;
$J^9$ is $C_1$-$C_8$ carbocyclyloxy optionally substituted with 1-4 $Z^3$ groups;

$T^1$ is $C_3$-$C_8$ carbocyclylene attached to L and M through two adjacent carbons;

$T^2$ is $C_3$-$C_8$ carbocyclylene attached to L and M through two adjacent carbons, wherein said carbocyclylene is substituted with 1-4 $C_1$-$C_8$ alkyl groups;

$T^3$ is $C_3$-$C_8$ carbocyclylene attached to L and M through two adjacent carbons, wherein said carbocyclylene is substituted with 1-4 halogen atoms and said carbocyclylene is optionally substituted with 1-4 $C_1$-$C_6$ alkyl groups;

$T^4$ is $C_3$-$C_8$ carbocyclylene that is attached to L and M through two adjacent carbons, wherein said carbocyclylene is substituted with a $C_1$-$C_8$ alkyl group, wherein said alkyl group is substituted with 1-4 $Z^3$ groups;

$T^5$ is 4-10 membered heterocyclene that is attached to L and M through two adjacent carbons;

$T^7$ is 4-10 membered heterocyclene that is attached to M through a carbon atom and attached to L through a N atom, wherein said heterocyclene is optionally substituted with 1-4 $Z^1$ groups;

$T^8$ is 4-10 membered heterocyclene that is attached to L and M through two adjacent carbons, wherein said heterocyclene is substituted with 1-4 $Z^1$ groups;

$T^9$ is $C_5$-$C_{12}$ spiro bicyclic carbocyclylene that is attached to L and M through two adjacent carbons, wherein said spiro bicyclic carbocyclylene is optionally substituted with 1-4 $Z^1$ groups;

$T^{10}$ is $C_5$-$C_{12}$ fused bicyclic carbocyclylene that is attached to L and M through two adjacent carbons, wherein said fused bicyclic carbocyclylene is optionally substituted with 1-4 $Z^1$ groups;

$T^{11}$ is $C_5$-$C_{12}$ bridged bicyclic carbocyclylene that is attached to L and M through two adjacent carbons, wherein said bridged bicyclic carbocyclylene is optionally substituted with 1-4 $Z^1$ groups;

$T^{12}$ is $C_4$-$C_8$ carbocyclylene that is attached to L and M through two non-adjacent carbons, wherein said carbocyclylene is optionally substituted with 1-4 $Z^1$ groups;

$T^{13}$ is a 5-8 membered fused, bridged, or spiro bicyclic heterocyclene that is attached to L and M through two adjacent atoms, wherein said heterocyclene is optionally substituted with 1-4 $Z^1$ groups;

$T^{14}$ is $C_3$-$C_8$ carbocyclylene that is attached to L and M through two adjacent carbons, wherein said carbocyclylene is substituted with 1-4 $Z^4$ groups;

$L^1$ is $C_1$-$C_8$ alkylene or $C_2$-$C_8$ alkenylene;

$L^2$ is $C_1$-$C_8$ alkylene or $C_2$-$C_8$ alkenylene wherein said $C_1$-$C_8$ alkylene or said $C_2$-$C_8$ alkenylene is substituted with 1-4 halogens;

$L^3$ is $C_1$-$C_8$ alkylene or $C_2$-$C_8$ alkenylene wherein said $C_1$-$C_8$ alkylene or said $C_2$-$C_8$ alkenylene and wherein said $C_1$-$C_8$ alkylene or said $C_2$-$C_8$ alkenylene is optionally substituted with 1-4 halogens;

$L^4$ is $C_1$-$C_8$ alkylene or $C_2$-$C_8$ alkenylene substituted with two geminal $C_1$-$C_4$ alkyl groups that come together to form a spiro $C_3$-$C_8$ carbocyclyl group, wherein $L^4$ is optionally substituted with 1-4 $Z^1$ groups;

$L^5$ is 2-8 membered heteroalkylene or 4-8 membered heteroalkenylene that is connected to ⊙ by an O, S or N atom and said heteroalkylene or heteroalkenylene is optionally substituted with 1-4 $Z^3$ groups;

$L^6$ is 2-8 membered heteroalkylene or 5-8 membered heteroalkenylene that is connected to ⊙ by a carbon atom and said heteroalkylene or heteroalkenylene is substituted with 1-4 halogen atoms and is optionally substituted with 1-4 $Z^4$ groups;

$L^7$ is 2-8 membered heteroalkylene or 4-8 membered heteroalkenylene that is connected to ⊙ by a carbon atom and said heteroalkylene or heteroalkenylene is optionally substituted with 1-4 $Z^4$ groups;

$L^8$ is $L^{8A}$-$L^{8B}$-$L^{8C}$ wherein $L^{8A}$ and $L^{8C}$ are each independently $C_1$-$C_6$ alkylene, $C_1$-$C_6$ heteroalkylene, $C_2$-$C_6$ alkenylene or a bond and $L^{8B}$ is a 3- to 6-membered saturated or unsaturated ring containing 0 to 3 heteroatoms selected from N, O, or S, wherein $L^{8A}$ and $L^{8C}$ connect to $L^{8B}$ at two different ring atoms and $L^{8B}$ is optionally substituted with 1-4 $Z^1$ groups;

$L^9$ is $C_2$-$C_8$ alkynylene optionally substituted with 1-4 $Z^1$ groups;

$L^{10}$ is $C_1$-$C_8$ alkylene or $C_3$-$C_8$ alkenylene substituted with two geminal $Z^1$ groups that come together to form a spiro 4-8 membered heterocyclyl group, wherein $L^{10}$ is optionally substituted with 1-4 $Z^1$ groups;

$U^1$ is a $C_6$-$C_{14}$ membered arylene optionally substituted with 1-4 W groups;

$U^3$ is a 4-14 membered heterocyclene optionally substituted with 1-4 W groups that are located on one or more ring atoms selected from C or N;

$U^4$ is a 5 or 6 membered monocyclic heteroarylene containing 1, 2 or 3 heteroatoms independently selected from N, O, or S, wherein said heteroarylene is optionally substituted with 1-4 W groups that are located on one or more ring atoms selected from C or N;

$U^5$ is a 8, 9 or 10 membered fused bicyclic heteroarylene containing 1, 2 or 3 heteroatom ring atoms independently selected from N, O, or S, wherein said heteroarylene is optionally substituted with 1-4 W groups that are located on one or more ring atoms selected from C or N;

$U^6$ is a 11-14 membered fused tricyclic heteroarylene containing 1, 2, 3 or 4 heteroatom ring atoms independently selected from N, O, or S, wherein said heteroarylene is optionally substituted with 1-4 W groups that are located on one or more ring atoms selected from C or N;

$U^7$ is a 8-10 membered fused bicyclic heteroarylene containing 4 heteroatom ring atoms independently selected from N, O, or S, wherein said heteroaryl is optionally substituted with 1-2 W groups that are located on one or more ring atoms selected from C or N;

each W is independently $W^1$, $W^2$, $W^3$, $W^4$, $W^6$ or $W^7$;

each $W^1$ is independently oxo, halogen, —$OR^6$, $C_1$-$C_6$ alkyl, —CN, —$CF_3$, —$SR^6$, —$C(O)_2R^6$, —$C(O)N(R^6)_2$, —$C(O)R^6$, —$N(R^6)C(O)R^6$, —$SO_2$($C_1$-$C_6$ alkyl), —$S(O)(C_1$-$C_6$ alkyl), $C_3$-$C_8$ carbocyclyl, $C_3$-$C_8$ cycloalkoxy, $C_1$-$C_6$ haloalkyl, —$N(R^6)_2$, —$NR^6$($C_1$-$C_6$ alkyl)O($C_1$-$C_6$ alkyl), halo($C_1$-$C_6$ alkoxy), —$NR^6SO_2R^6$, —$SO_2N(R^6)_2$, —$NHCOOR^6$, —$NHCONHR^6$, $C_6$-$C_{10}$ aryl, 5-14 membered heteroaryl, 4-10 membered heterocyclyl or —O(4-10 membered heterocyclyl), wherein said $W^1$ alkyl, carbocyclyl, cycloalkoxy, haloalkyl, haloalkoxy, aryl, heteroaryl, or heterocyclyl is optionally substituted with 1-4 $Z^{1c}$ groups;

each $R^6$ is independently H, $C_6$-$C_{10}$ aryl or $C_1$-$C_6$ alkyl, wherein said aryl or alkyl is optionally substituted with 1 to 4 substituents independently selected from halogen atoms, $C_1$-$C_6$ alkyl, $C_6$-$C_{10}$ aryl, $C_3$-$C_6$ carbocyclyl, 5-14 membered heteroaryl, 4-10 membered heterocyclyl, halo($C_1$-$C_6$ alkoxy), —OH, —O($C_1$-$C_6$ alkyl), —SH, —S($C_1$-$C_6$ alkyl), —$NH_2$, —NH($C_1$-$C_6$ alkyl), —N($C_1$-$C_6$ alkyl)$_2$, —C(O)($C_1$-$C_6$ alkyl), —$SO_2N(C_1$-

$C_6$ alkyl)$_2$, —NHCOO($C_1$-$C_6$ alkyl), —NHCO($C_1$-$C_6$ alkyl), —NHCONH($C_1$-$C_6$ alkyl), —CO$_2$($C_1$-$C_6$ alkyl), or —C(O)N($C_1$-$C_6$ alkyl)$_2$;

each $W^2$ is $C_1$-$C_6$ alkoxy substituted with a 5-14 membered heteroaryl or $C_6$-$C_{10}$ aryl; wherein said heteroaryl or aryl is substituted with 1-4 $Z^1$ groups;

each $W^3$ is $C_2$-$C_6$ alkynyl group substituted with a $C_6$-$C_{10}$ aryl, $C_3$-$C_8$ carbocyclyl, $C_1$-$C_8$ alkyl, $C_1$-$C_6$ haloalkyl, 4-10 membered heterocyclyl, or 5-14 membered heteroaryl group; wherein said aryl, carbocyclyl, alkyl, haloalkyl, heterocyclyl, or heteroaryl group is optionally substituted with 1-4 $Z^1$ groups;

each $W^4$ is —SF$_5$;

each $W^5$ is —O($C_2$-$C_6$ alkyl)OR$^{22}$ wherein R$^{22}$ is a $C_6$-$C_{10}$ aryl, 5-14 membered heteroaryl or 4-10 membered heterocyclyl group optionally substituted with 1-4 $Z^1$ groups;

each $W^6$ is —O($C_2$-$C_6$ alkyl)NR$^{16}$R$^{22}$ wherein R$^{22}$ is an aryl, heteroaryl or heterocyclyl group optionally substituted with 1-4 $Z^1$ groups;

each $W^7$ is —O(5-14 membered heteroaryl); wherein said —O(5-14 membered heteroaryl) is optionally substituted with 1-4 $Z^1$ groups and 2 adjacent substituents of said —O(5-14 membered heteroaryl) may be taken together to form a 3- to 6-membered cyclic ring containing 0 to 3 heteroatoms independently selected from N, O, or S;

$E^1$ is

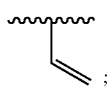

$E^2$ is

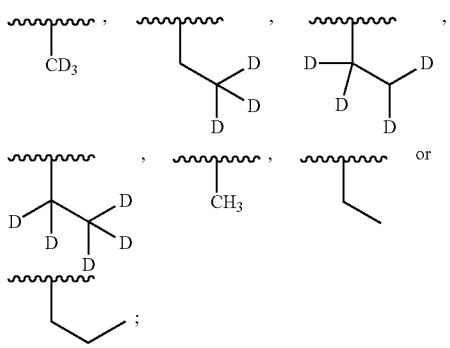

$E^3$ is

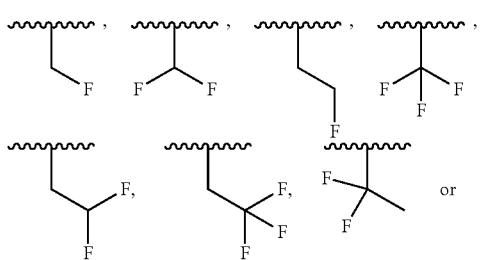

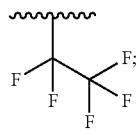

$E^4$ is

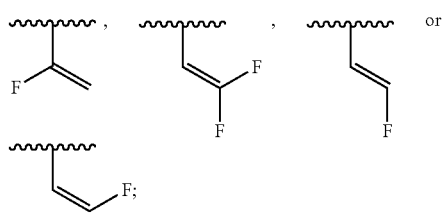

$Q^1$ is H, $C_1$-$C_8$ alkyl, $C_3$-$C_8$ carbocyclyl, $C_6$-$C_{10}$ aryl, 5-6 membered heteroaryl, or 5-6 membered heterocyclyl groups, wherein when $Q^1$ is not H, said $Q^1$ is optionally substituted with 1-4 substituents independently selected from halogen, —OR$^6$, —SR$^6$, —N(R$^6$)$_2$, $C_6$-$C_{10}$ aryl, $C_1$-$C_6$ alkyl, $C_1$-$C_6$ haloalkyl, $C_1$-$C_6$ haloalkoxy, —CN, —CF$_3$, —SO$_2$($C_1$-$C_6$ alkyl), —S(O)($C_1$-$C_6$ alkyl), —NR$^6$SO$_2$Z$^2$, —SO$_2$NR$^{17}$R$^{18}$, —NHCOOR$^{16}$, —NHCOZ$^2$, —NHCONHR$^{16}$, —CO$_2$R$^6$, —C(O)R$^6$ or —CON(R$^6$)$_2$;

$Q^2$ is $C_5$-$C_{10}$ spiro bicyclic carbocyclyl optionally substituted with 1-4 $Z^1$ groups;

$Q^3$ is $C_5$-$C_{10}$ fused bicyclic carbocyclyl optionally substituted with 1-4 $Z^1$ groups;

$Q^4$ is $C_5$-$C_{10}$ bridged bicyclic carbocyclyl optionally substituted with 1-4 $Z^1$ groups;

$Q^5$ is 4-membered heterocyclyl having 1 heteroatom selected from N, O or S wherein $Q^5$ is optionally substituted with 1-4 $Z^3$ groups;

$Q^7$ is $C_3$-$C_8$ carbocyclyl substituted with 4-8 F atoms and each carbon of $Q^7$ is substituted with 0-2 F atoms;

each $Z^1$ is independently oxo, halogen, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)R$^{16}$, —C(O)OR$^{16}$, —C(O)NR$^{17}$R$^{18}$, —NR$^{17}$R$^{18}$, —NR$^{16}$C(O)R$^{16}$, —NR$^{16}$C(O)NR$^{17}$R$^{18}$, —NR$^{16}$S(O)$_2$R$^{16}$, —NR$^{16}$S(O)$_2$NR$^{17}$R$^{18}$, —NR$^{16}$S(O)$_2$OR$^{16}$, —OR$^{16}$, —OC(O)R$^{16}$, —OC(O)NR$^{17}$R$^{18}$, —SR$^{16}$, —S(O)R$^{16}$, —S(O)$_2$R$^{16}$ or —S(O)$_2$NR$^{17}$R$^{18}$ wherein any alkyl, alkenyl, alkynyl, carbocyclyl, aryl, heteroaryl or heterocyclyl of $Z^1$ is optionally substituted with 1-4 $Z^{1a}$ groups;

each $Z^{1a}$ is independently oxo, halogen, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)R$^{16}$, —C(O)OR$^{16}$, —C(O)NR$^{17}$R$^{18}$, —NR$^{17}$R$^{18}$, —NR$^{16}$C(O)R$^{16}$, —NR$^{16}$C(O)OR$^{16}$, —NR$^{16}$C(O)NR$^{17}$R$^{18}$, —NR$^{16}$S(O)$_2$R$^{16}$, —NR$^{16}$S(O)$_2$NR$^{17}$R$^{18}$, —NR$^{16}$S(O)$_2$OR$^{16}$, —OR$^{16}$, —OC(O)R$^{16}$, —OC(O)NR$^{17}$R$^{18}$, —SR$^{16}$, —S(O)R$^{16}$, —S(O)$_2$R$^{16}$ or —S(O)$_2$NR$^{17}$R$^{18}$ wherein any alkenyl, alkynyl, carbocyclyl, aryl, heteroaryl or heterocyclyl of $Z^{1a}$ is optionally substituted with 1-4 $Z^{1c}$ groups;

each R$^{16}$ is independently H, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, $C_6$-$C_{10}$ aryl, 5-14 membered heteroaryl or 4-10 membered heterocyclyl, wherein any alkyl, alkenyl, alkynyl, carbocyclyl, aryl, heteroaryl or heterocyclyl of $R^{16}$ is optionally substituted with 1-4 $Z^{1c}$ groups;

each $Z^{1c}$ is independently oxo, halogen, $C_1$-$C_8$ alkyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)($C_1$-$C_8$ alkyl), —C(O)O($C_1$-$C_8$ alkyl), —C(O)N($C_1$-$C_8$ alkyl)$_2$, —NH$_2$, —NH($C_1$-$C_8$ alkyl), —N($C_1$-$C_8$ alkyl)$_2$, —NHC(O)O($C_1$-$C_8$ alkyl), —NHC(O)($C_1$-$C_8$ alkyl), —NHC(O)NH($C_1$-$C_8$ alkyl), —OH, —O($C_1$-$C_8$ alkyl), $C_3$-$C_8$ cycloalkoxy, $C_5$-$C_{10}$ bicyclic carbocyclyloxy, —S($C_1$-$C_8$ alkyl) or —S(O)$_2$N($C_1$-$C_8$ alkyl)$_2$ wherein any alkyl, carbocyclyl, aryl, heteroaryl, heterocyclyl or cycloalkoxy portion of $Z^{1c}$ is optionally substituted with 1-4 halogen atoms or $C_1$-$C_6$ alkoxy groups;

$R^{17}$ and $R^{18}$ are each independently H, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, —C(O)$R^{16}$, —C(O)O$R^{16}$, $C_6$-$C_{10}$ aryl, 5-14 membered heteroaryl or 4-10 membered heterocyclyl, wherein any alkyl, alkenyl, alkynyl, carbocyclyl, aryl, heteroaryl or heterocyclyl of $R^{17}$ or $R^{18}$ is optionally substituted with 1-4 $Z^{1c}$ groups, or $R^{17}$ and $R^{18}$ together with the nitrogen to which they are attached form a 4-7 membered heterocyclyl group, wherein said 4-7 membered heterocyclyl group is optionally substituted with 1-4 $Z^{1c}$ groups;

each $Z^2$ is independently $C_1$-$C_8$ alkyl, $C_3$-$C_8$ carbocyclyl, $C_5$-$C_{10}$ bicyclic carbocyclyl, $C_6$-$C_{10}$ aryl, 5-14 membered heteroaryl, 4-10 membered heterocyclyl, —NR$^{17}$R$^{18}$ or —OR$^{16}$ wherein any alkyl, carbocyclyl, aryl, heteroaryl or heterocyclyl portion of $Z^2$ is optionally substituted with 1-4 $Z^{2a}$ groups;

each $Z^{2a}$ is independently oxo, halogen, $C_1$-$C_8$ alkyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl. —($C_2$-$C_8$ alkynyl)aryl, —($C_2$-$C_8$ alkynyl)heteroaryl, —CN, —C(O)($C_1$-$C_6$ alkyl), —C(O)O($C_1$-$C_6$ alkyl), —C(O)N($C_1$-$C_6$ alkyl)$_2$, —NH$_2$, —NH($C_1$-$C_6$ alkyl), —N($C_1$-$C_6$ alkyl)$_2$, —NHC(O)O($C_1$-$C_6$ alkyl), —NHC(O)($C_1$-$C_6$ alkyl), —NHC(O)NH($C_1$-$C_6$ alkyl), —OH, —O($C_1$-$C_6$ alkyl), halo($C_1$-$C_6$ alkoxy), $C_3$-$C_8$ cycloalkoxy, —S($C_1$-$C_6$ alkyl), or —SO$_2$N($C_1$-$C_6$ alkyl)$_2$; wherein any alkyl, alkynyl, carbocyclyl, cycloalkoxy, aryl, heteroaryl or heterocyclyl portions of $Z^{2a}$ is optionally substituted with 1-4 halogen or $C_1$-$C_6$ alkoxy groups;

each $Z^3$ is independently oxo, halogen, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)OR$^{16}$, —C(O)NR$^{17}$R$^{18}$, —NR$^{17}$R$^{18}$, —NR$^{16}$C(O)NR$^{17}$R$^{18}$, —OR$^{16}$, —SR$^{16}$ or —SO$_2$R$^{16}$; wherein any alkenyl, alkynyl, carbocyclyl, aryl, heteroaryl or heterocyclyl portions of $Z^3$ is optionally substituted with 1-4 halogen; and each $Z^4$ is independently oxo, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)OR$^{16}$, —C(O)NR$^{17}$R$^{18}$, —NR$^{17}$R$^{18}$, —NR$^{16}$C(O)NR$^{17}$R$^{18}$, —OR$^{16}$, —SR$^{16}$ or —SO$_2$R$^{16}$, wherein any alkenyl, alkynyl, carbocyclyl, aryl, heteroaryl or heterocyclyl portions of $Z^4$ is optionally substituted with 1-4 halogen.

One embodiment provides a pharmaceutical composition comprising a compound of Formula I, II, III, or IV (such as any one of IVa-IVh), or a stereoisomer, or a mixture of stereoisomers, or a pharmaceutically acceptable salt thereof, and a pharmaceutically acceptable carrier.

One embodiment provides a method for treating a Flaviviridae viral infection (e.g., an HCV viral infection) in a patient in need thereof (e.g., mammal such as a human). The method includes administering a compound of Formula I, II, III, or IV (such as any one of IVa-IVh), or a stereoisomer, or a mixture of stereoisomers, or a pharmaceutically acceptable salt thereof, to the patient.

One embodiment provides a method for inhibiting the proliferation of the HCV virus, treating HCV or delaying the onset of HCV symptoms in a patient in need thereof (e.g., mammal such as a human). The method includes administering a compound of Formula I, II, III, or IV (such as any one of IVa-IVh) or a stereoisomer, or a mixture of stereoisomers, or a pharmaceutically acceptable salt thereof, to the patient.

One embodiment provides a compound of Formula I, II, III, or IV (such as any one of IVa-IVh) or a stereoisomer, or a mixture of stereoisomers, or a pharmaceutically acceptable salt thereof for use in medical therapy (e.g., for use in treating a Flaviviridae viral infection such as an HCV viral infection or in treating the proliferation of the HCV virus or delaying the onset of HCV symptoms in a patient in need thereof (e.g., mammal such as a human)).

One embodiment provides a compound of Formula I, II, III, or IV (such as any one of IVa-IVh), or a stereoisomer, or a mixture of stereoisomers, or a pharmaceutically acceptable salt thereof for use in the manufacture of a medicament for treating a Flaviviridae viral infection (e.g., an HCV viral infection) or the proliferation of the HCV virus or delaying the onset of HCV symptoms in a patient in need thereof (e.g., mammal such as a human).

One embodiment provides a compound of Formula I, II, III, or IV (such as any one of IVa-IVh), or a stereoisomer, or a mixture of stereoisomers, or a pharmaceutically acceptable salt thereof, for use in the prophylactic or therapeutic treatment of the proliferation of a Flaviviridae virus, an HCV virus or for use in the therapeutic treatment of delaying the onset of HCV symptoms.

One embodiment provides a compound of Formula I, II, III, or IV (such as any one of IVa-IVh) or a stereoisomer, or a mixture of stereoisomers, or a pharmaceutically acceptable salt thereof, for use in the prophylactic or therapeutic treatment of a Flaviviridae virus infection (e.g., an HCV virus infection).

One embodiment provides the use of a compound of Formula I, II, III, or IV (such as any one of IVa-IVh), or a stereoisomer, or a mixture of stereoisomers, or a pharmaceutically acceptable salt thereof, for the manufacture of a medicament for a Flaviviridae virus infection (e.g., an HCV virus infection) in a patient in need thereof (e.g., mammal such as a human).

One embodiment provides processes and intermediates disclosed herein that are useful for preparing compounds of Formula I, II, III, or IV (such as any one of IVa-IVh) or a stereoisomer, or a mixture of stereoisomers, or salts thereof.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Abbreviations

The following abbreviations are used throughout the specification, and have the following meanings:

° C.=degrees Celsius
Å=Angstrom
Ac=acetyl
AcOH=acetic acid
aq=aqueous
Ar=argon
atm=atmosphere
BEP=2-bromo-1-ethyl pyridinium tetrafluoroborate
Bis(diphenylphosphino)ferrocene)palladium(II) dichloride
Bn=benzyl
Boc=tert-butoxy carbonyl
$Boc_2O$=di-tert-butyl dicarbonate
bp=boiling point
Bs=4-bromophenylsulfonyl
Bu=butyl
calcd=calculated
CBS=Corey-Bakshi-Shibata
CBZ=Cbz=carboxybenzyl
CDI=1,1'-carbonyldiimidazole
cm=centimeter
COMU=(1-cyano-2-ethoxy-2-oxoethylidenaminooxy)dimethylamino-morpholino-carbenium hexafluorophosphate
DABCO=1,4-diazabicyclo[2.2.2]octane
DBU=1,8-diazabicycloundec-7-ene
DCE=1,2-dichloroethane
DCM=dichloromethane
DDQ=2,3-dichloro-5,6-dicyanobenzoquinone
DIAD=diisopropyl azodicarboxylate
dioxane=1,4-dioxane
DIPEA=N,N-diisopropyl-N-ethylamine
DMF=N,N-dimethylformamide
DMAP=4-dimethylaminopyridine
DMPU=1,3-dimethyl-3,4,5,6-tetrahydro-2(1H)-pyrimidinone
DMSO=dimethysulfoxide
dppf=1,1'-bis(diphenylphosphino)ferrocene
DSC=N,N'-disuccinimidyl carbonate
EA=EtOAc=ethyl acetate
$EC_{50}$=half maximal effective concentration
EDC=1-ethyl-3-(3-dimethylaminopropyl)carbodiimide
Et=ethyl
$Et_2O$=diethyl ether
EtOAc=ethyl acetate
EtOH=ethanol
equiv=equivalent
F-NMR=fluorine nuclear magnetic resonance spectroscopy
g=gram
h=hr=hour
HATU=O-(7-azabenzotriazol-1-yl)-N,N,N',N'-tetramethyl-uronium Hexafluorophosphate
HCV=hepatitis C virus
HEPES=hydroxyethyl piperazineethanesulfonic acid
Hex=hex=hexanes
HMDS=hexamethyldisilazane(azide)
HMPA=hexamethylphosphoramide
$^{1}$H-NMR=proton nuclear magnetic resonance spectroscopy
HOAc=acetic acid
HOBT=hydroxybenzotriazole
HPLC=high pressure liquid chromatography
Hz=Hertz
IPA=isopropyl alcohol
i=iso
J=coupling constant
KHMDS=potassium bis(trimethylsilyl)amide
L=liter
LCMS-ESI$^{+}$=liquid chromatography mass spectrometer (electrospray ionization)
LiHMDS=lithium bis(trimethylsilyl)amide
M=molar concentration (mol/L)
mCPBA=meta-chloroperoxyberzoic acid
Me=methyl
MeCN=ACN=acetonitrile
MeOH=methanol
MeTHF=2-methyltetrahydrofuran
mg=milligram
MHz=mega Hertz
mL=milliliter
mmol=millimole
min=minute
MTBE=methyl tert-butylether
Ms=methanesulfonyl
MsCl=methanesulfonyl chloride
MS=molecular sieves
MSA=methylsulfonic acid
n=normal
N=normal concentration
NCS=N-chlorosuccinimide
NMM=N-methylmorpholine
NMO=N-methylmorpholine-N-oxide
NMP=N-methylpyrrolidinone
o/n=overnight
PCR=polymerase chain reaction
Pf=9-phenyl-9H-fluoren-9-yl
PG=protecting group
PE=petroleum ether
Ph=phenyl
PhMe=toluene
pM=picomolar
PMB=4-methoxybenzyl
Pr=propyl
$Pd(dppf)Cl_2$=$PdCl_2(dppf)$=$PdCl_2dppf$=(1,1'-bis(diphenylphosphino)ferrocene)dichloropalladium(II)
$PPh_3$=triphenylphosphine
RetTime=retention time
rt=room temperature
sat=sat.=saturated
sec=secondary
$S_N1$=nucleophilic substitution unimolecular
$S_N2$=nucleophilic substitution bimolecular
$S_NAr$=nucleophilic substitution aromatic
t=tert=tertiary TBAF=tetra-n-butylammonium fluoride
TBS=TBDMS=tert-Butyldimethylsilyl
TBTU=O-(benzotriazol-1-yl)-N,N,N',N'-tetramethyluronium tetrafluoroborate
TEA=triethylamine
temp=temperature
TEMPO=(2,2,6,6-Tetramethylpiperidin-1-yl)oxyl
Tf=trifluoromethanesulfonyl
TFA=trifluoroacetic acid
THF=tetrahydrofuran
TIPS=triisoproylsilyl
TLC=thin layer chromatography
TMS=trimethylsilyl
TMSOTf=trimethylsilyl trifluoromethanesulfonate
TPAP=tetrapropylammonium perruthenate
Tr=triphenylmethyl
Ts=para-toluenesulfonyl
wt=weight
w/w=weight/weight ratio
Definitions Unless stated otherwise, the following terms and phrases as used herein are intended to have the following meanings:

When a cyclic group (e.g. cycloalkyl, carbocyclyl, bicyclic carbocyclyl, heteroaryl, heterocyclyl) is limited by a number or range of numbers, the number or numbers refer to the number of atoms making up the cyclic group, including any heteroatoms. Therefore, for example, a 4-8 membered heterocyclyl group has 4, 5, 6, 7 or 8 ring atoms.

"Alkenyl" refers to a straight or branched chain hydrocarbyl with at least one site of unsaturation, e.g., a (sp$^2$) carbon-(sp$^2$)carbon double bond. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=CH$_2$) and allyl (—CH$_2$CH=CH$_2$).

"Alkenylene" refers to an alkene having two monovalent radical centers derived by the removal of two hydrogen atoms from the same or two different carbon atoms of a parent alkene. Exemplary alkenylene radicals include, but are not limited to, 1,2-ethenylene (—CH=CH—) or prop-1-enylene (—CH$_2$CH=CH—).

"Alkoxy" is RO— where R is alkyl, as defined herein. Non-limiting examples of alkoxy groups include methoxy, ethoxy and propoxy.

"Alkyl" refers to a saturated, straight or branched chain hydrocarbyl radical. For example, an alkyl group can have 1 to 8 carbon atoms (i.e., ($C_1$-$C_8$) alkyl) or 1 to 6 carbon atoms (i.e., ($C_1$-$C_6$ alkyl) or 1 to 4 carbon atoms. Examples of alkyl groups include, but are not limited to, methyl, ethyl, propyl, isopropyl, butyl, isobutyl, t-butyl, pentyl, hexyl, heptyl, octyl, nonyl and decyl.

"Alkylene" refers to an alkyl having two monovalent radical centers derived by the removal of two hydrogen atoms from the same or two different carbon atoms of a parent alkane. Examples of alkylene radicals include, but are not limited to, methylene (—CH$_2$—), ethylene (—CH$_2$CH$_2$—), propylene (—CH$_2$CH$_2$CH$_2$—) and butylene (—CH$_2$CH$_2$CH$_2$CH$_2$—).

"Alkynyl" refers to a straight or branched chain hydrocarbon with at least one site of unsaturation, e.g., a (sp) carbon-(sp)carbon triple bond. For example, an alkynyl group can have 2 to 8 carbon atoms ($C_2$-$C_8$ alkyne) or 2 to 6 carbon atoms ($C_2$-$C_6$ alkynyl). Examples of alkynyl groups include, but are not limited to, acetylenyl (—C≡CH) and propargyl (—CH$_2$C≡CH) groups.

"Alkynylene" refers to an alkynyl having two monovalent radical centers derived by the removal of two hydrogen atoms from the same or two different carbon atoms of a parent alkyne. Typical alkynylene radicals include, but are not limited to, acetylene (—C≡C—), propargylene (—CH$_2$C≡C—), and 1-pentynylene (—CH$_2$CH$_2$CH$_2$C≡C—).

"Aryl" refers to a single all carbon aromatic ring or a multiple condensed all carbon ring system (e.g., a fused multicyclic ring system) wherein at least one of the rings is aromatic. For example, an aryl group can have 6 to 20 carbon atoms, 6 to 14 carbon atoms, or 6 to 12 carbon atoms. It is to be understood that the point of attachment of a multiple condensed ring system, as defined above, can be at any position of the ring system including an aromatic or a carbocyclyl portion of the ring. Examples of aryl groups include, but are not limited to, phenyl, naphthyl, tetrahydronaphthyl and indanyl.

"Arylene" refers to an aryl as defined herein having two monovalent radical centers derived by the removal of two hydrogen atoms from two different carbon atoms of a parent aryl. Typical arylene radicals include, but are not limited to, phenylene, e.g.,

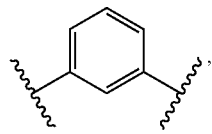

and naphthylene, e.g.,

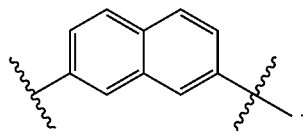 [SMILES: *c1ccc2ccc(*)cc2c1]

"Bicyclic carbocyclyl" refers to a 5-14 membered saturated or partially unsaturated bicyclic fused, bridged, or spiro ring hydrocarbon attached via a ring carbon. In a spiro bicyclic carbocyclyl, the two rings share a single common carbon atom. In a fused bicyclic carbocyclyl, the two rings share two common and adjacent carbon atoms. In a bridged bicyclic carbocyclyl, the two rings share three or more common, non-adjacent carbon atoms. Examples of bicyclic carbocyclyl groups include, but are not limited to spiro bicyclic carbocyclyl groups wherein two carbocyclyl rings share one common atom

fused bicyclic carbocyclyl groups wherein two carbocyclyl rings share two common atoms

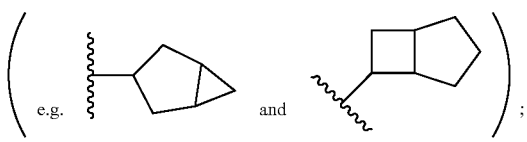

and bridged bicyclic carbocyclyl groups wherein two carbocyclyl rings share three or more (such as 3, 4, 5 or 6) common atoms

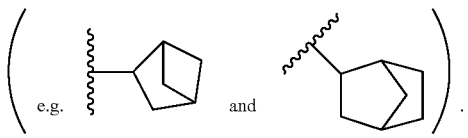

"Bicyclic carbocyclylene" refers to a bicyclic carbocyclyl, as defined above, having two monovalent radical centers derived from the removal of two hydrogen atoms from the same or two different carbon atom of a parent bicyclic carbocyclyl. Examples of bicyclic carbocyclylene groups include, but are not limited to, spiro bicyclic carbocyclylene groups wherein two carbocyclyl rings share one common atom

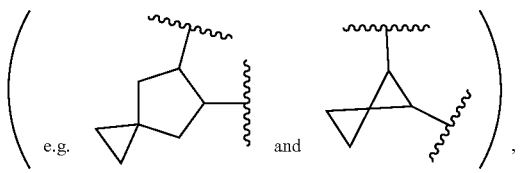

fused bicyclic carbocyclylene groups wherein two carbocyclyl rings share two common atoms

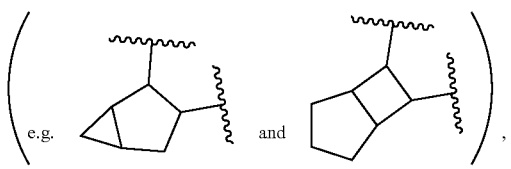

and bridged bicyclic carbocyclylene groups wherein two carbocyclyl rings share three or more (such as 3, 4, 5 or 6) common atoms

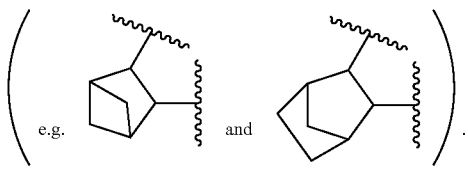

"Carbocyclyloxy" is RO— where R is carbocyclyl as defined herein.

"Bicyclic carbocyclyloxy" is RO— where R is bicyclic carbocyclyl, as defined herein.

"Carbocyclyl", and "carbocycle" refers to a hydrocarbyl group containing one saturated or partially unsaturated ring structure, attached via a ring carbon. In various embodiments, carbocyclyl refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Carbocyclylene" (as well as "carbocyclene") refers to a carbocyclyl, as defined herein, having two monovalent radical centers derived by the removal of two hydrogen atoms from the same or two different carbon atoms of a parent carbocyclyl. Examples of carbocyclene include, but are not limited to, cyclopropylene, cyclobutylene, cyclopentylene and cyclohexylene.

"Carbocyclylalkyl" refers to a hydrocarbyl group containing one saturated or partially unsaturated ring structure attached to an alkyl group, attached via a ring carbon or an alkyl carbon. In various embodiments, carbocyclylalkyl refers to a saturated or a partially unsaturated $C_1$-$C_{12}$ carbocyclylalkyl moiety, examples of which include cyclopropylalkyl, cyclobutylalkyl, cyclopropylethyl, and cyclopropylpropyl.

"Carbocyclylalkylene" refers to a carbocyclylalkyl, as defined herein, having two monovalent radical centers derived by the removal of two hydrogen atoms from the same or two different carbon atoms of a parent cycloalkylalkyl. Examples of cycloalkylene include, but are not limited to, cyclopropylmethylene and cyclopropylmethylene.

"Cycloalkyl" refers to a hydrocarbyl group containing one saturated ring structure, attached via a ring carbon. In various embodiments, cycloalkyl refers to a saturated $C_3$-$C_{12}$ cyclic moiety, examples of which include cyclopropyl, cyclobutyl, cyclopentyl, cyclohexyl, cycloheptyl and cyclooctyl.

"Cycloalkoxy" is RO— where R is cycloalkyl, as defined herein.

"Direct bond" refers a covalent bond between two atoms.

"Halo" or "halogen" refers to chloro (—Cl), bromo (—Br), fluoro (—F) or iodo (—I).

"Haloalkenyl" refers to alkenyl group, as defined herein, substituted with one or more halogen atoms.

"Haloalkoxy" refers to alkoxy, as defined herein, substituted with one or more halogen atoms.

"Haloalkyl" refers to an alkyl group, in which one or more hydrogen atoms of the alkyl group is replaced with a halogen atom. Examples of haloalkyl groups include, but are not limited to, —$CF_3$, —$CHF_2$, —$CFH_2$ and —$CH_2CF_3$.

"Haloalkylene" refers to alkylene group, as defined herein, substituted with one or more halogen atoms.

"Heteroalkyl" refers to an alkyl group, as defined herein, in which one or more carbon atoms is replaced with an oxygen, sulfur, or nitrogen atom.

"Heteroalkylene" refers to an alkylene group, as defined herein, in which one or more carbon atoms is replaced with an oxygen, sulfur, or nitrogen atom.

"Heteroalkenyl" refers to an alkenyl group, as defined herein, in which one or more carbon atoms is replaced with an oxygen, sulfur, or nitrogen atom.

"Heteroalkenylene" refers to heteroalkenyl group, as defined above, having two monovalent radical centers derived by the removal of two hydrogen atoms from the same or two different atoms of a parent heteroalkenyl group.

"Heteroaryl" refers to a single aromatic ring that has at least one atom other than carbon in the ring, wherein the atom is selected from the group consisting of oxygen, nitrogen and sulfur; the term also includes multiple condensed ring systems that have at least one such aromatic ring. For example, heteroaryl includes monocyclic, bicyclic or tricyclic ring having up to 6 atoms in each ring, wherein at least one ring is aromatic and contains from 1 to 4 heteroatoms in the ring selected from the group consisting of oxygen, nitrogen and sulfur. The rings of the multiple condensed ring system can be connected to each other via fused, spiro and bridged bonds when allowed by valency requirements. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazolyl, pyrrolyl, pyridazinyl, pyrazinyl, quinolinyl, isoquinolinyl, quinoxalinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroarylene" refers to a heteroaryl, as defined above, having two monovalent radical centers derived by the removal of two hydrogen atoms from the same or two different carbon atoms or the removal of a hydrogen from one carbon atom and the removal of a hydrogen atom from one nitrogen atom of a parent heteroaryl group. Non-limiting examples of heteroarylene groups are:

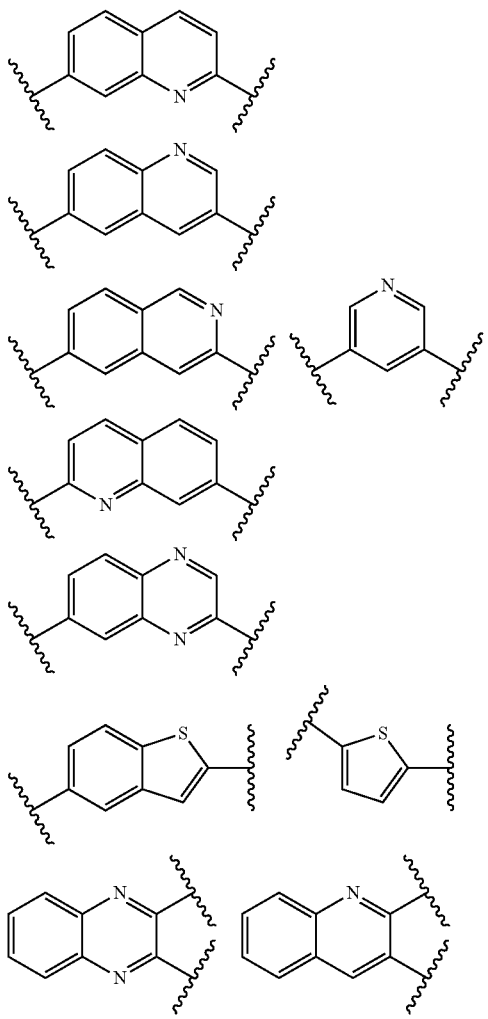

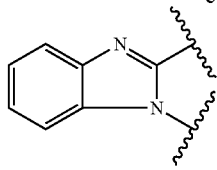

"Heterocyclyl" refers to a saturated or partially unsaturated monocyclic, bicyclic or tricyclic group of 2 to 14 ring-carbon atoms and, in addition to ring-carbon atoms, 1 to 4 heteroatoms selected from nitrogen, oxygen and sulfur. Bi- or tricyclic heterocyclyl groups may have fused, bridged, or spiro ring connectivity. In various embodiments the heterocyclic group is attached to another moiety through carbon or through a heteroatom. Examples of heterocyclyl include without limitation azetidinyl, oxazolinyl, isoxazolinyl, oxetanyl, tetrahydropyranyl, tetrahydrothiopyranyl, tetrahydroisoquinolinyl, 1,4-dioxanyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, chromanyl, dihydropyranoquinoxalinyl, tetrahydroquinoxalinyl, tetrahydroquinolinyl, dihydropyranoquinolinyl and tetrahydrothienyl and N-oxides thereof. A spiro bicyclic heterocyclyl group refers to a bicyclic heterocyclyl group wherein the two rings of the bicyclic heterocyclyl group share one common atom. A fused bicyclic bicyclic heterocyclyl group refers to a bicyclic heterocyclyl group wherein the two rings of the bicyclic heterocyclyl group share two common atoms. A bridged bicyclic heterocyclyl group refers to a bicyclic heterocyclyl group wherein the two rings of the bicyclic heterocyclyl group share three or more (such as 3, 4, 5 or 6) common atoms.

"Heterocyclene" refers to a heterocyclyl, as defined herein, having two monovalent radical centers derived from the removal of two hydrogen atoms from the same or two different carbon atoms, through a carbon and a heteroatom, or through two heteroatoms of a parent heterocycle.

"Prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

The term "optionally substituted" refers to a moiety wherein all substituents are hydrogen or wherein one or more of the hydrogens of the moiety are replaced by non-hydrogen substituents; that is to say the moiety that is optionally substituted is either substituted or unsubstituted.

"Leaving group" (LG) refers to a moiety of a compound that is active towards displacement or substitution in a chemical reaction. Examples of in which such as displacement or substitution occur include, but are not limited to, nucleophilic substitution bimolecular ($S_N2$), nucleophilic substitution unimolecular ($S_N1$), nucleophilic aromatic substitution ($S_NAr$), and transition metal catalyzed cross-couplings. Examples of leaving groups include, but are not limited to, a halogen atom (e.g. —Cl, —Br, —I) and sulfonates (e.g. mesylate (—OMs), tosylate (—OTs) or triflate (—OTf)). The skilled artisan will be aware of various chemical leaving groups and strategies for activation and will appreciate the appropriate moiety that will act as leaving groups, based on the particular chemical reaction, the functionality that the group is attached to, and the chemical reagents used to affect the displacement or substitution reaction. As a non-limiting example, in some situations, a halogen atom (e.g. —Cl, —Br, or —I) serves as a leaving group in a reaction catalyzed by a transition metal (e.g. Pd catalyzed Suzuki coupling between an aryl halide and aryl boronic acid) and another reagents such as a base.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their mirror image partner.

"Isomers" are different compounds that have the same molecular formula. Isomers include stereoisomers, enantiomers and diastereomers.

"Diastereoisomers" are stereoisomers that have at least two asymmetric atoms, but which are not mirror-images of each other.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

The term "stereoisomers" refers to compounds which have identical chemical constitution, but differ with regard to the arrangement of the atoms or groups in space.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

Tautomers

The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Isotopes

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be replaced by —CD$_3$.

Specific values listed below for radicals, substituents, and ranges are for illustration only; they do not exclude other defined values or other values within defined ranges for the radicals and substituents.

Protecting Groups

In certain embodiments, protecting groups include prodrug moieties and chemical protecting groups. Protecting groups may be represented by the abbreviation "PG."

"Protecting group" ("PG") refers to a moiety of a compound that masks or alters the properties of a functional group or the properties of the compound as a whole. Chemical protecting groups and strategies for protection/deprotection are well known in the art. See e.g. Peter G. M, Wuts and Theodora W. Greene, *Protective Groups in Organic Synthesis*, 4$^{th}$ edition; John Wiley & Sons, Inc.; New Jersey, 2007. See also Kocienski, P. J. *Protecting Groups*, 3$^{rd}$ edition: Georg Thieme Verlag Stuttgart. New York. 2005, in particular Chapter 1, Protecting Groups: An Overview, pages 1-48, Chapter 2, Carbonyl Protecting Groups, pages 49-118, Chapter 3, Diol Protecting Groups, pages 119-186, Chapter 4, Hydroxyl Protecting Groups, pages 187-364, Chapter 5, Thiol Protecting Groups, pages 365-392. Protecting groups are often utilized to mask the reactivity of certain functional groups, to assist in the efficiency of desired chemical reactions, e.g., making and breaking chemical bonds in an ordered and planned fashion.

Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

In certain embodiments, protecting groups are optionally employed to prevent side reactions with the protected group during synthetic procedures. Selection of the appropriate groups to protect, when to do so, and the nature of the chemical protecting group "PG" is dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Salts and Hydrates

Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein each X is independently selected from H or a $C_1$-$C_4$ alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of Formula I, II, III or IV, (such as any one of IVa-IVh) or a stereoisomer, or a mixture of stereoisomers, or another compound disclosed herein. All salts, whether or not derived from a physiologically acceptable acid or base, are within the scope of the present invention.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines Finally, it is to be understood that the compositions herein comprise compounds disclosed herein in their un-ionized, as well as zwitterionic form, and combinations with stoichiometric amounts of water as in hydrates.

Embodiments

In certain embodiments, A is —C(O)—, 6-10 membered arylene, or 5-6 membered heteroarylene group, wherein said arylene or heteroarylene is optionally substituted with 1-4 halogens or haloalkyl groups. In some embodiments, A is —C(O)—.

In certain embodiments, M is —O— or a bond. In some embodiments, M is —O—.

In certain embodiments, G is —$CO_2H$ or —$CONHSO_2Z^2$. In some embodiments, G is —$CONHSO_2Z^2$. In some embodiments, G is —$CONHSO_2Z^2$ and $Z^2$ is cyclopropyl optionally substituted with methyl.

In certain embodiments, G is:

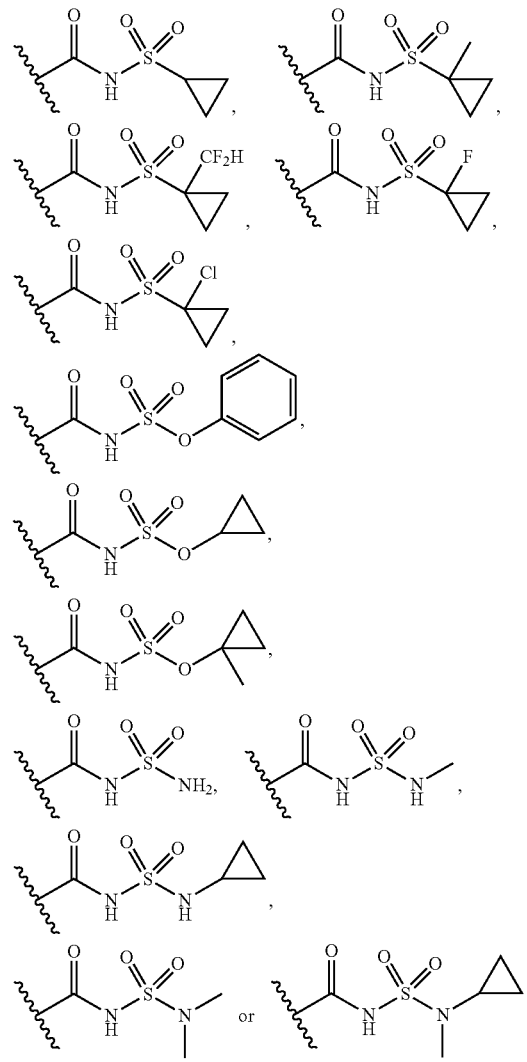

In some embodiments, G is:

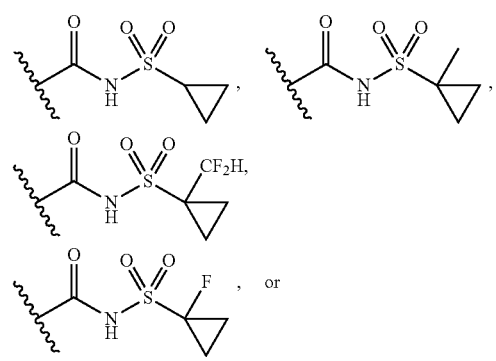

-continued

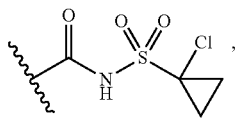

In certain embodiments, $Z^2$ is:

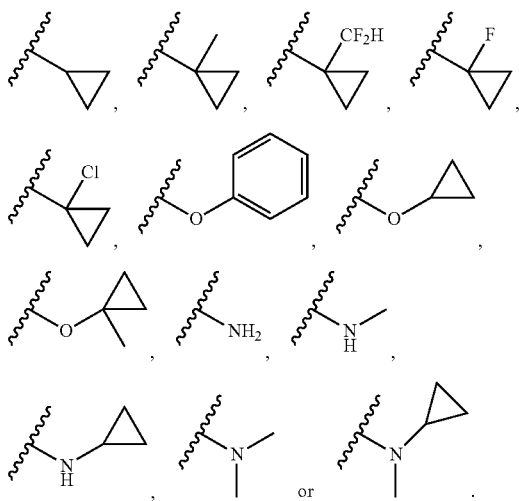

In certain embodiments, $Z^2$ is:

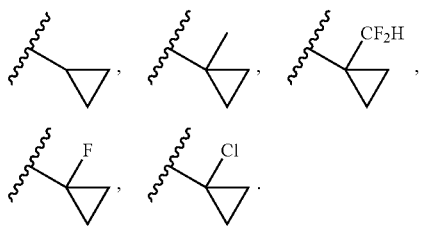

In certain embodiments, $Z^{2a}$ is hydrogen, halogen or methyl. In some embodiments, $Z^{2a}$ is:

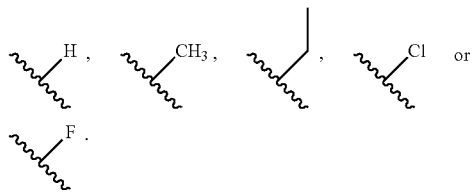

In other embodiments, $Z^{2a}$ is

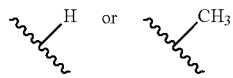

or (i.e., hydrogen or methyl).

In other embodiments, $Z^{2a}$ is

In still more embodiments, $Z^{2a}$ is

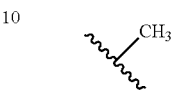

(i.e., methyl).

In certain embodiments, one of $R^3$, $R^4$, and $R^5$ is $Z^1$ and the other two are H. In some embodiments, $R^3$, $R^4$ and $R^5$ are each H.

In certain embodiments, X is —OC(O)—, —O—, or a direct bond. In some embodiments, X is —O—.

In certain embodiments, X is —OC(O)—, —O—, or a direct bond. In certain other embodiments, X is —O—.

In certain embodiments, ⊙ is $C_3$-$C_6$ carbocyclylene that is attached to L and to the remainder of the compound of Formula I, II, III, or IV (such as IVa-IVh) through two adjacent carbons, wherein said $C_3$-$C_5$ carbocyclylene is optionally substituted with $C_1$-$C_4$ alkyl or $C_1$-$C_3$ haloalkyl.

In certain embodiments, ⊙ is $C_3$-$C_6$ carbocyclylene that is attached to L and to the remainder of the compound of Formula I, II, III, or IV (such as any one of IVa-IVh) through two adjacent carbons, wherein the $C_3$-$C_5$ carbocyclylene is optionally substituted with methyl, ethyl or trifluoromethyl. In some embodiments, ⊙ is $C_3$-$C_6$ carbocyclylene that is attached to L and to the remainder of the compound of Formula I, II, III, or IV (such as any one of IVa-IVh) through two adjacent carbons.

In certain embodiments, ⊙ is $C_3$-$C_6$ cycloalkyl that is attached to L and to the remainder of the compound of Formula I, II, III, or IV (such as any one of IVa-IVh) through two adjacent carbons, wherein the $C_3$-$C_5$ cycloalkyl is optionally substituted with methyl, ethyl or trifluoromethyl.

In some embodiments, ⊙ is $C_3$-$C_6$ cycloalkyl that is attached to L and to the remainder of the compound of Formula I, II, III, or IV (such as any one of IVa-IVh) through two adjacent carbons.

In certain embodiments, ⊙ is cyclopropyl optionally substituted with methyl or trifluoromethyl.

In certain embodiments, ⊙ is $C_6$-$C_8$ bridged bicyclic carbocyclylene or $C_6$-$C_8$ bridged fused carbocyclylene that is attached to L and to the remainder of the compound of Formula I, II, III, or IV (such as any one of IVa-IVh) through two adjacent carbons.

In certain embodiments, ⊙ is $C_6$-$C_8$ bridged bicyclic cycloalkyl or $C_6$-$C_8$ bridged fused cycloalkyl that is attached to L and to the remainder of the compound of Formula I, II, III or IV (such as any one of IVa-IVh) through two adjacent carbons.

In some embodiments, ⊙ is $T^1$, $T^2$, $T^3$, $T^4$, $T^5$, $T^8$, $T^9$, $T^{10}$, $T^{11}$, or $T^{12}$. In certain embodiments, ⊙ is $T^1$, $T^2$, $T^3$, $T^4$, $T^9$, $T^{10}$, $T^{11}$ or $T^{14}$. In some embodiments, ⊙ is $T^1$, $T^2$, or $T^3$, optionally substituted with 1-4 $Z^1$ groups which are the same or different.

In some embodiments, $T^1$ is

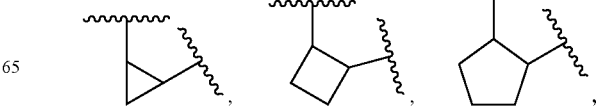

-continued
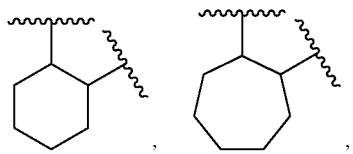
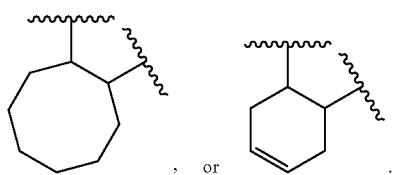
In some embodiments, T² is
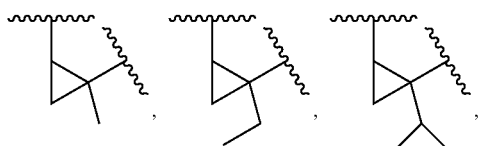
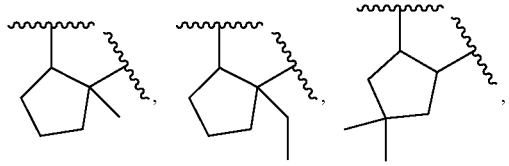
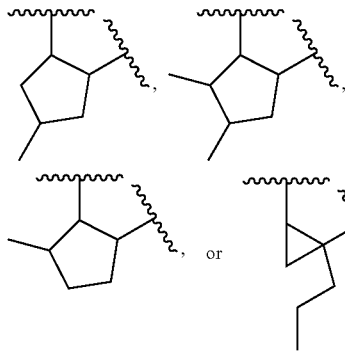
In some embodiments, T³ is
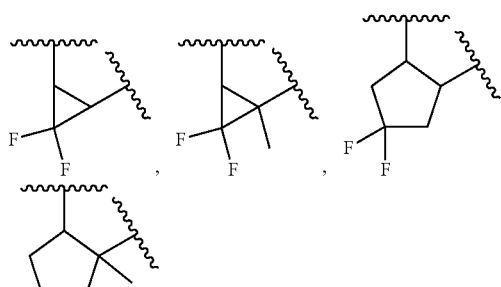
In some embodiments, T⁴ is
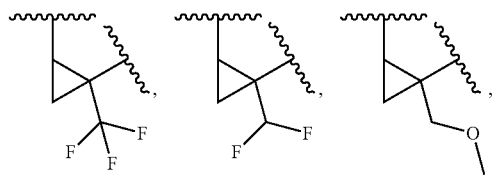
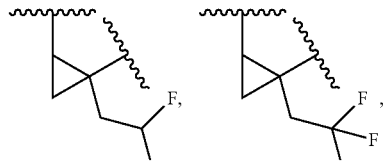
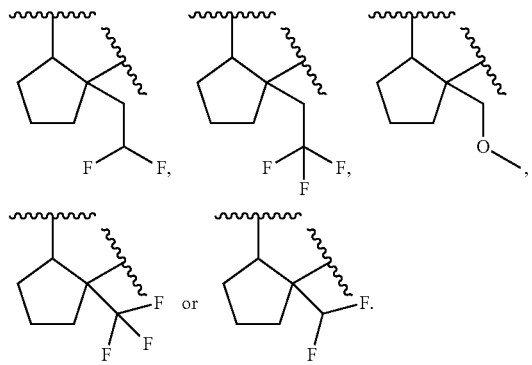
In some embodiments, T⁵ is
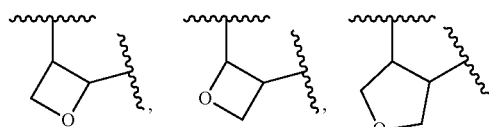
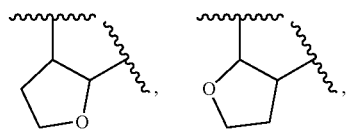
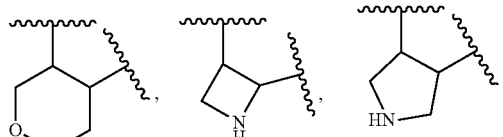
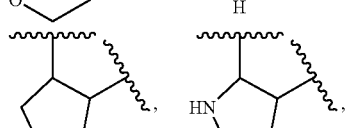
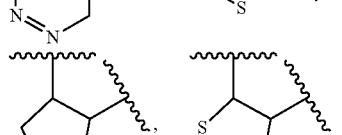

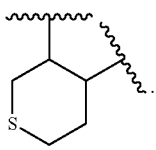
In some embodiments, $T^8$ is
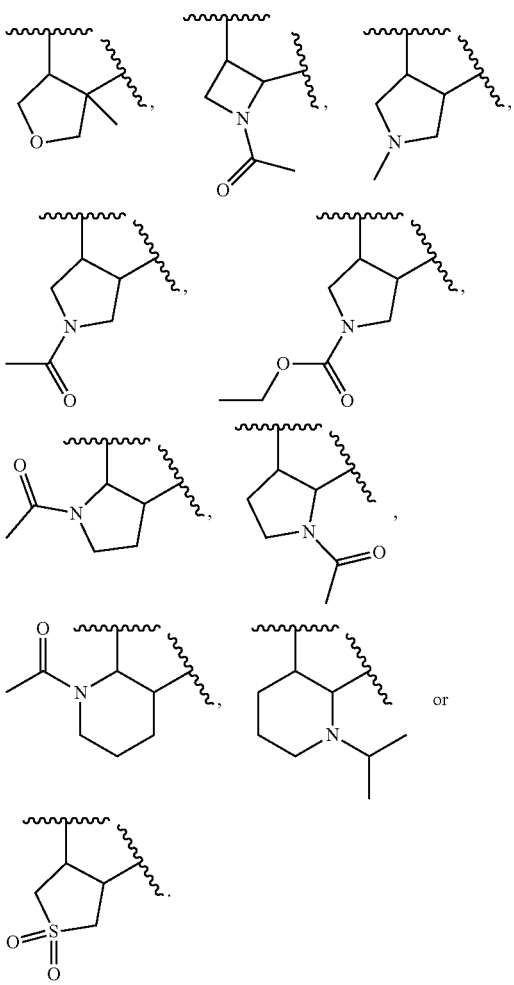
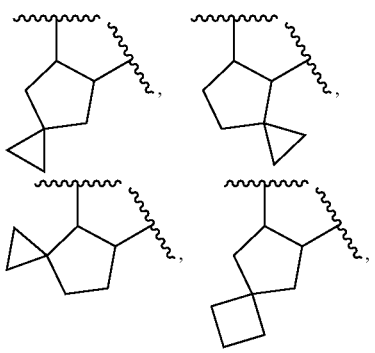
In some embodiments, $T^9$ is
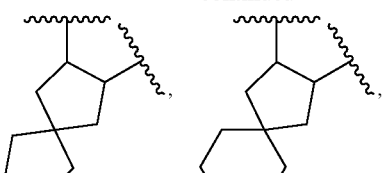
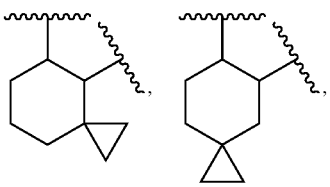
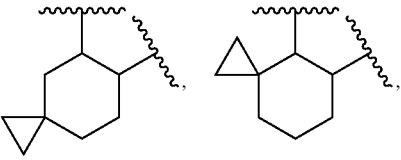
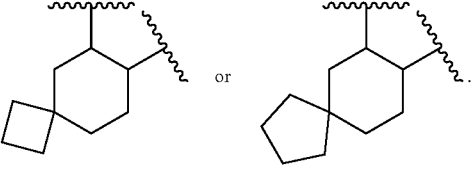
In some embodiments, $T^{10}$ is
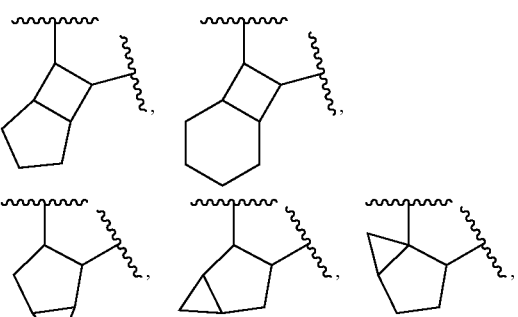
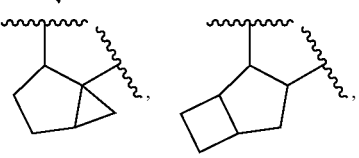
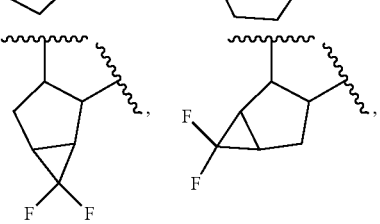

-continued
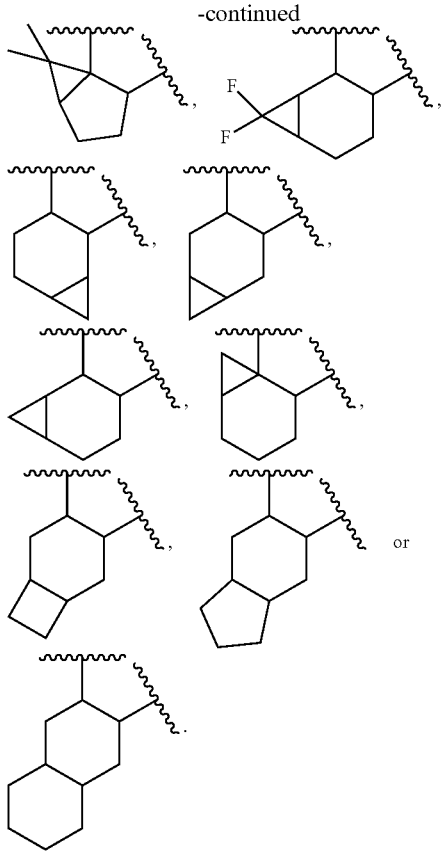
In some embodiments, T$^{11}$ is
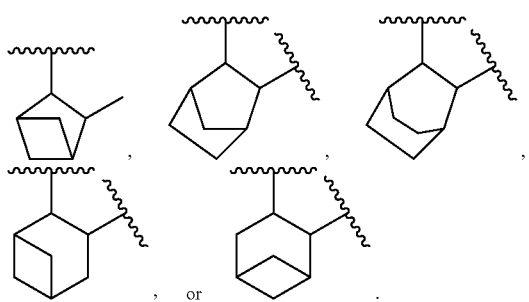
In some embodiments, T$^{12}$ is
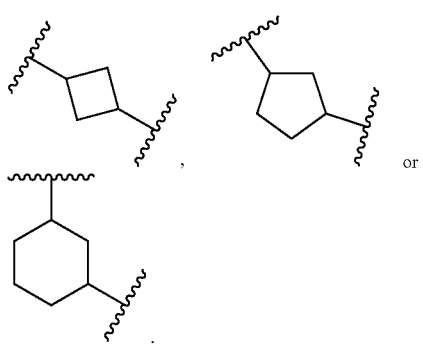
In other embodiments, ⊙ is
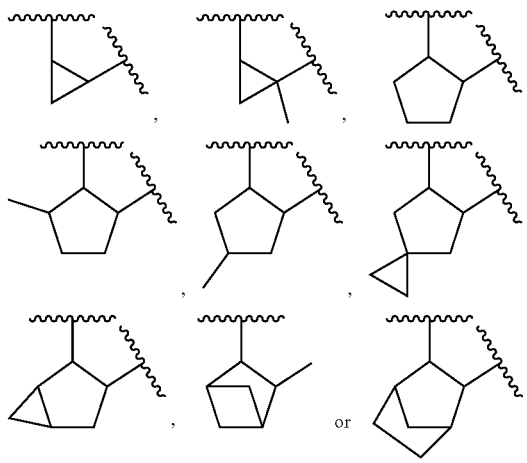
In certain embodiments, T$^1$ is:
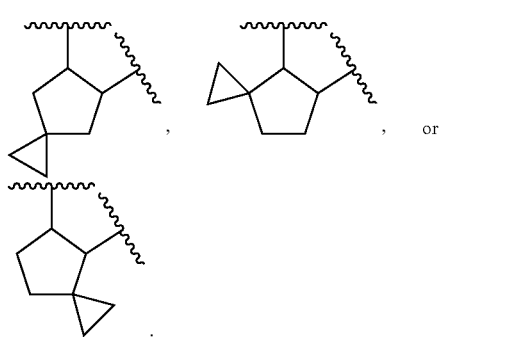
In certain embodiments, T$^2$ is:
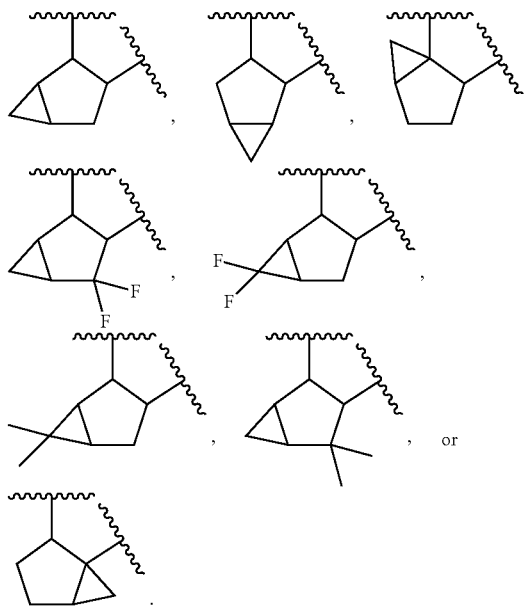

In certain embodiments, $T^3$ is:

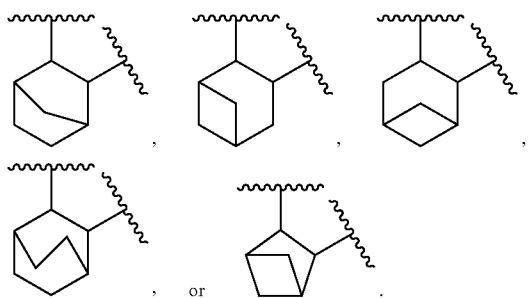

, or .

In certain embodiments, ⊙ is $T^2$, which is optionally substituted with 1-4 $Z^1$ groups, which are the same or different.

In certain embodiments, $T^2$ is:

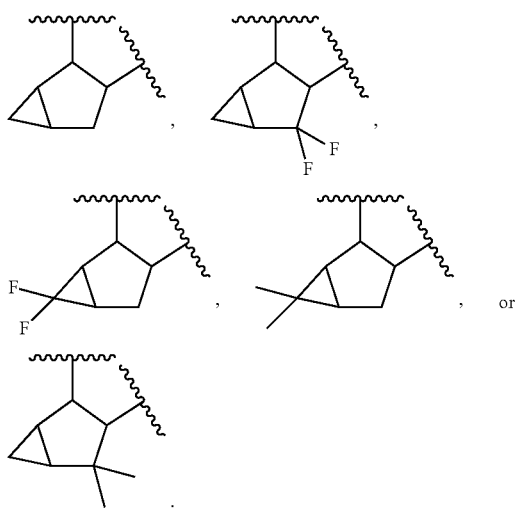

, or .

In certain embodiments, ⊙ is

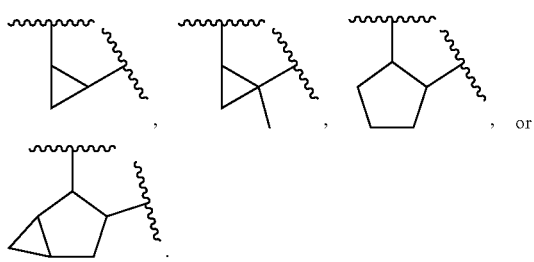

, or .

In other embodiments, ⊙ is

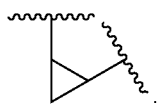 [SMILES: *C1CC1* ; "."]

In other embodiments, ⊙ is

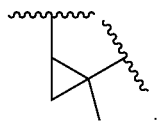 [SMILES: *C1CC1(*)C ; "."]

In other embodiments, ⊙ is

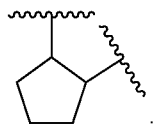 [SMILES: *C1CCCC1* ; "."]

.

In certain embodiments, $T^2$ is:

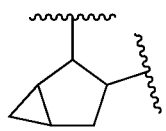

.

In certain embodiments, $T^2$ is:

.

In certain embodiments, $T^2$ is:

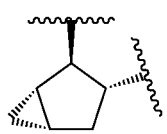 [SMILES: *[C@@H]1[C@H]2C[C@H]2C[C@H]1*]

(a stereoisomer of bicyclo[3.1.0]hexanylene).

In certain embodiments, J is $J^1$, $J^4$, $J^5$ or $J^8$. In other embodiments, J is $J^4$. In certain embodiments, J is $J^5$.

In further embodiments, $J^4$ is

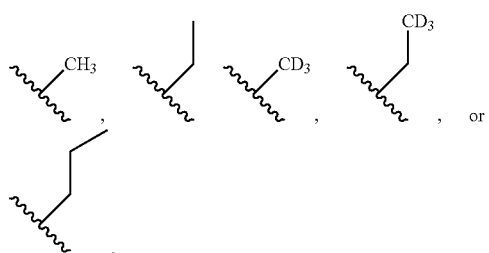

, or

In other embodiments, J is

.

In certain embodiments, J is

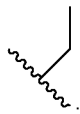

In certain embodiments, $J^5$ is

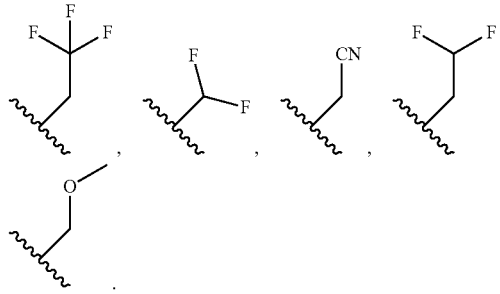

In certain embodiments, J is $C_1$-$C_3$ alkyl. In certain embodiments, J is methyl or ethyl. In further other embodiments, J is —$CH_2$—$CH_3$.

In some embodiments, L is $L^1$, $L^2$, $L^3$, $L^4$, $L^5$, $L^6$, $L^7$, $L^8$ or $L^9$. In one embodiment, L is $L^1$, $L^2$, $L^3$, $L^4$, $L^5$ or $L^6$. In certain embodiments, L is $L^1$ or $L^2$.

In some embodiments, L is $C_3$-$C_6$ alkylene, substituted with 1-4 halogens.

In some embodiments, L is $C_5$ alkylene, substituted with two halogens. In some embodiments, the halogens of L are each fluoro.

In certain embodiments, L is:

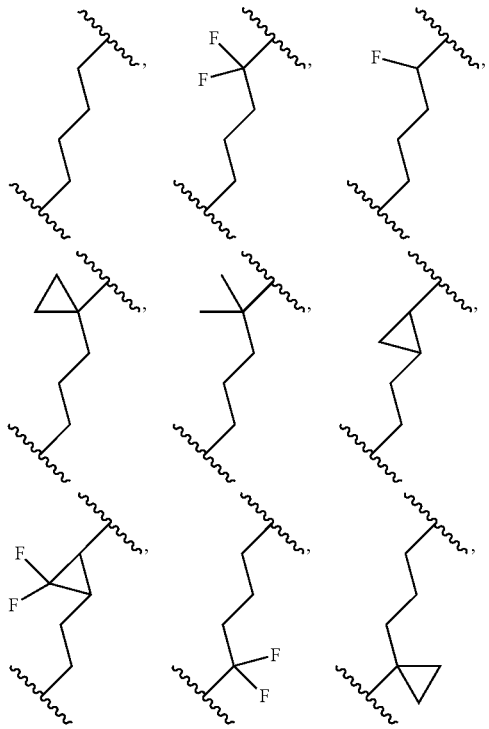

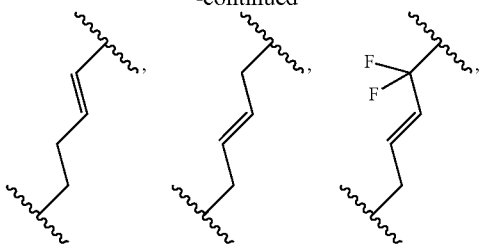

In certain other embodiments, L is

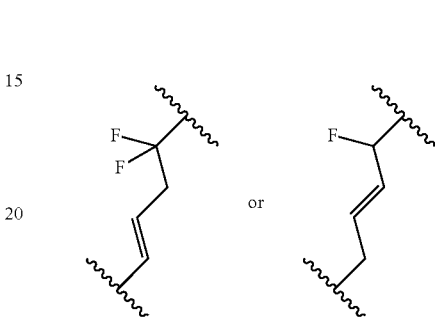

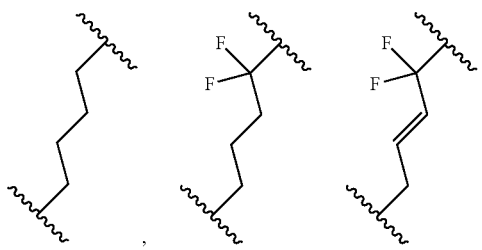

or

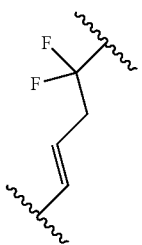

In some embodiments, $L^1$ is:

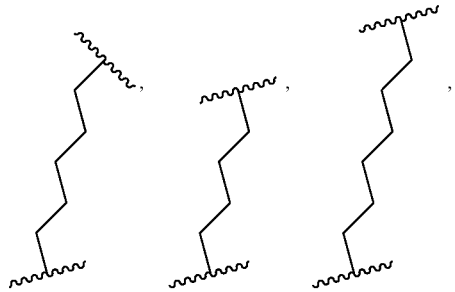

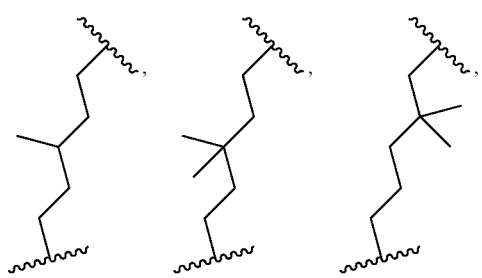
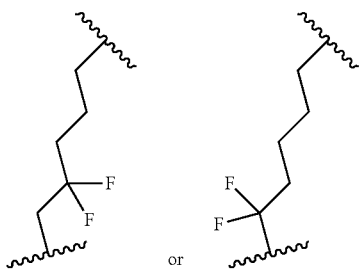
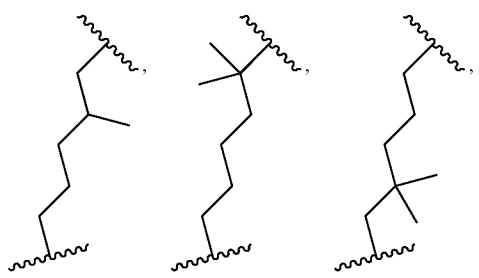
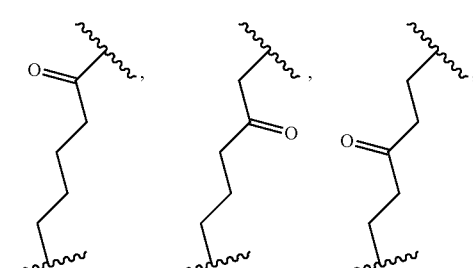
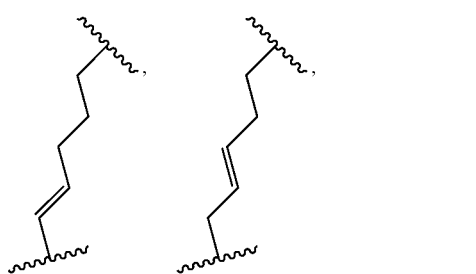
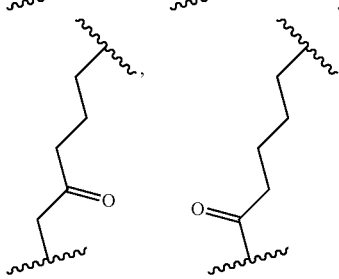
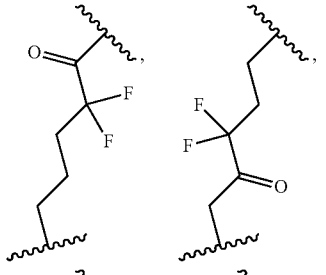
In some embodiments, $L^2$ is:
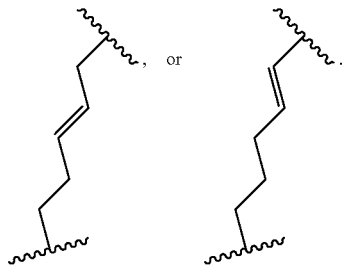
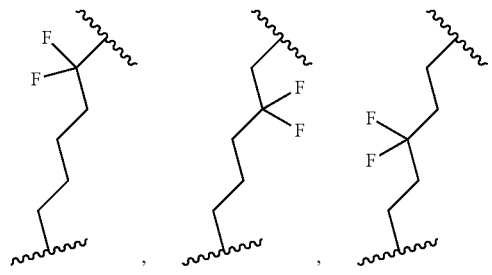
In some embodiments, $L^3$ is:
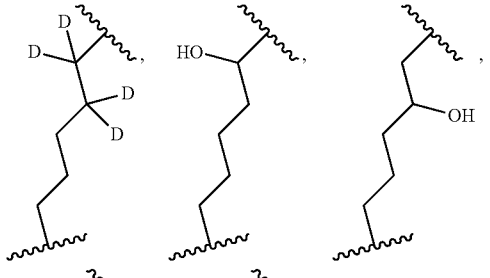
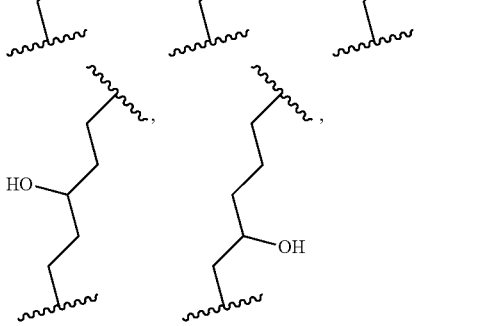

-continued
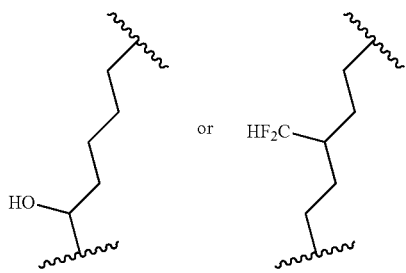
In some embodiments, $L^4$ is
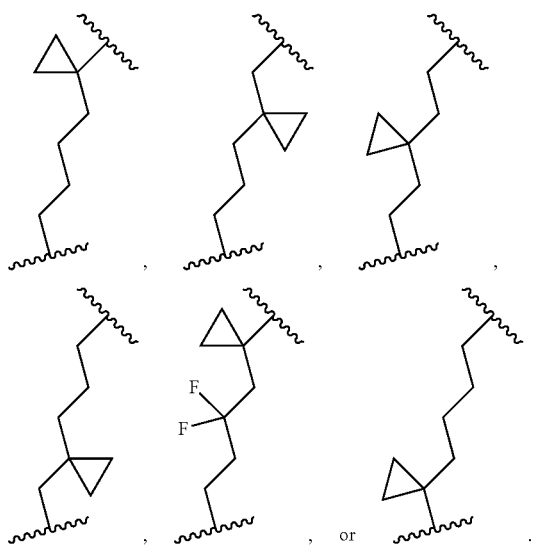
In some embodiments, $L^5$ is
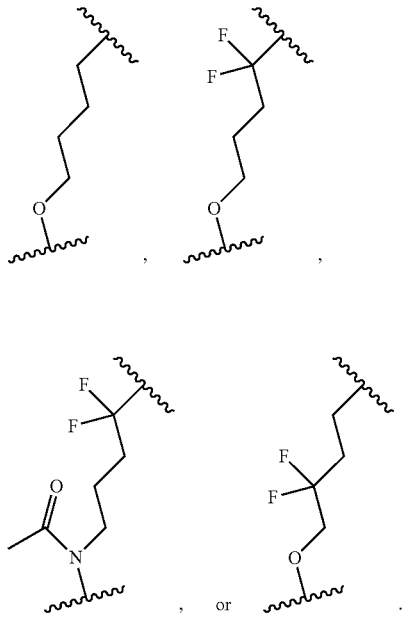
In some embodiments, $L^6$ is
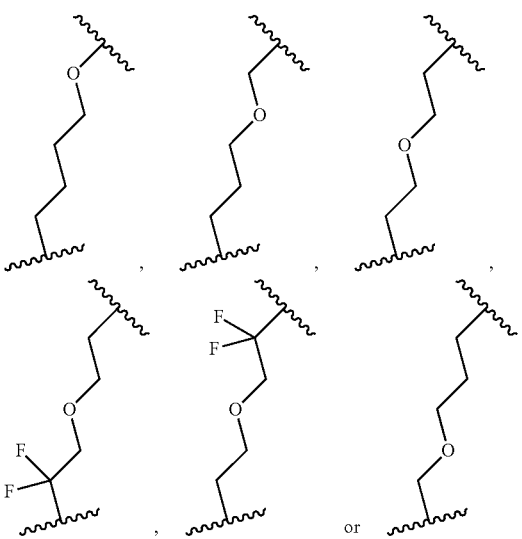
In some embodiments, $L^7$ is
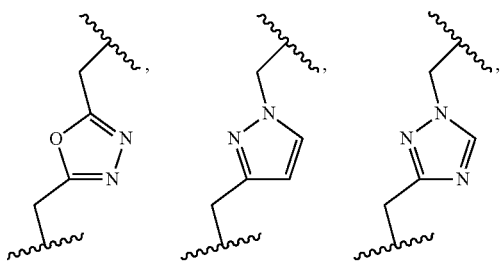
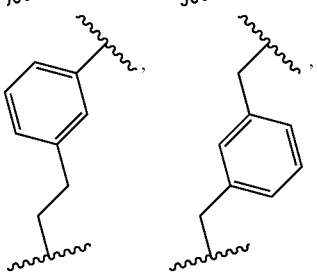
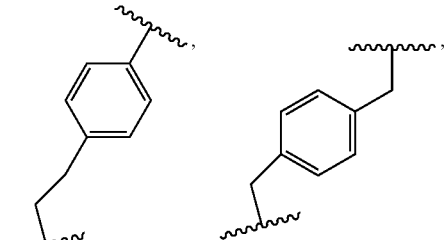
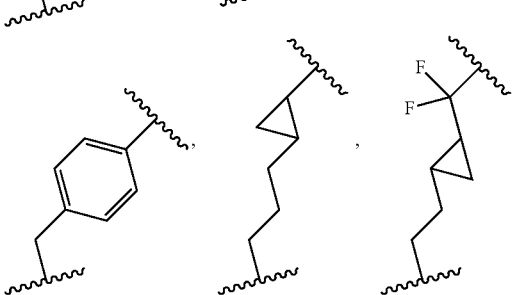

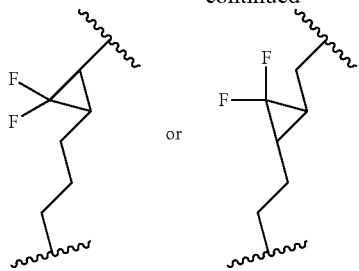
In some embodiments, $L^8$ is
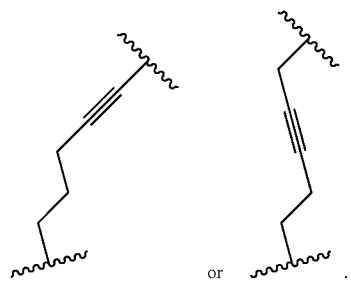 [SMILES: *C#CCCC* ; *CC#CCC* ; "."]
In some embodiments, $L^9$ is
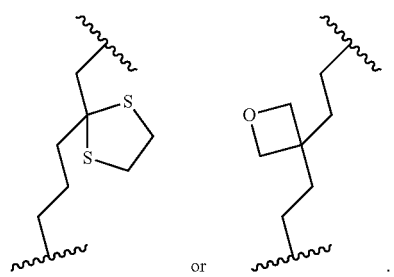 [SMILES: *CCCC1(C*)SCCS1 ; *CCC1(CC*)COC1 ; "or" ; "."]
In other embodiments, L is
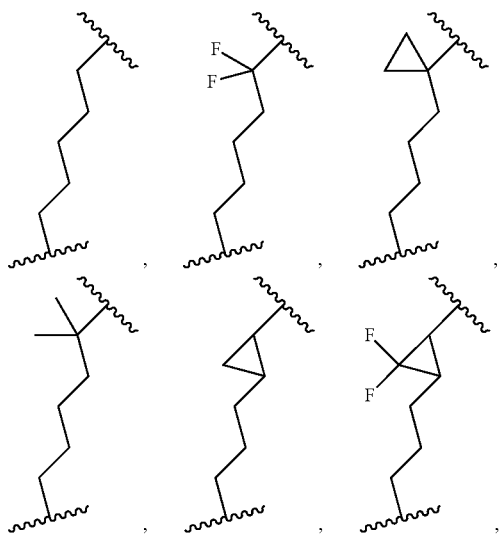
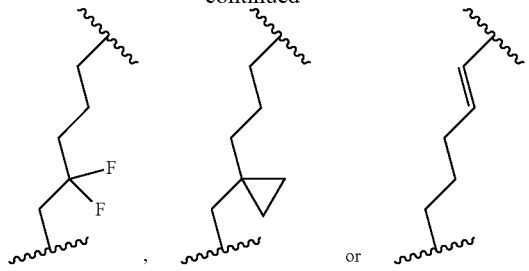
In further embodiments, L is
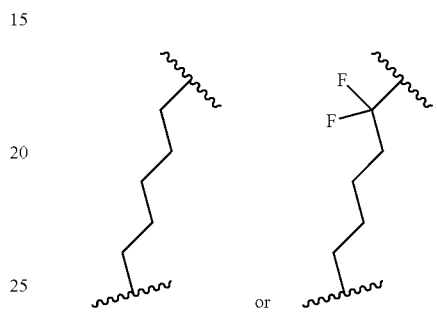
In further embodiments, L is
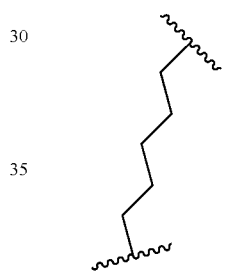
In still more embodiments, L is
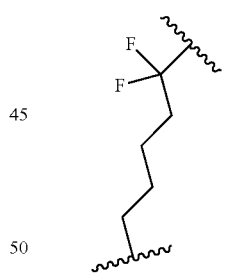
In other embodiments, L is
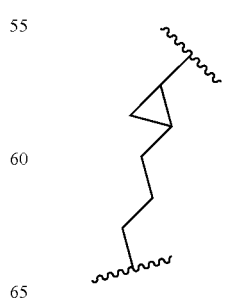
In some embodiments, Q is $Q^1$, $Q^2$, $Q^3$, $Q^4$, $Q^5$ or $Q^7$ In some embodiments, $Q^1$ is

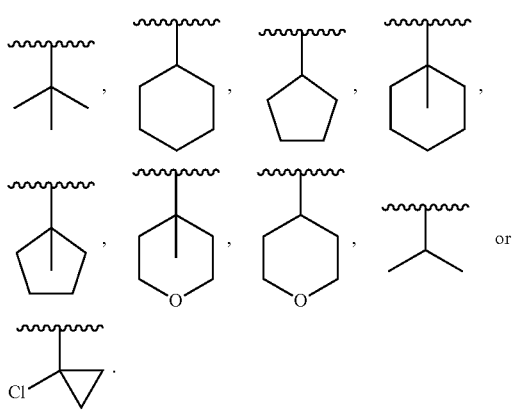

In some embodiments, $Q^2$ is

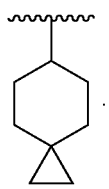

In some embodiments, $Q^3$ is

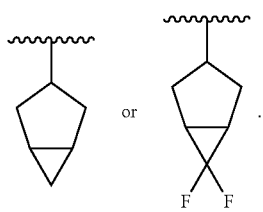 [SMILES: *C1CC2CC2C1 ; *C1CC2C(C1)C2(F)F]

In some embodiments, $Q^4$ is

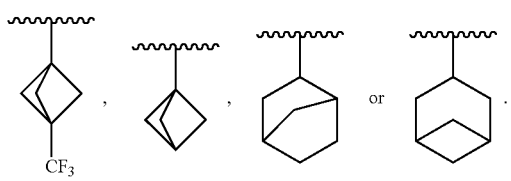 [SMILES: *C12CC(C(F)(F)F)(C1)C2 ; *C12CC(C1)C2 ; *C1CC2CCC1C2 ; *C1CC2CC(C1)C2]

In some embodiments, $Q^5$ is

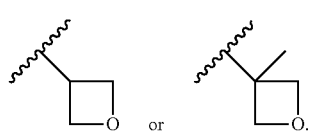

In some embodiments, $Q^7$ is

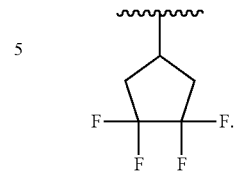

In other embodiments, Q is

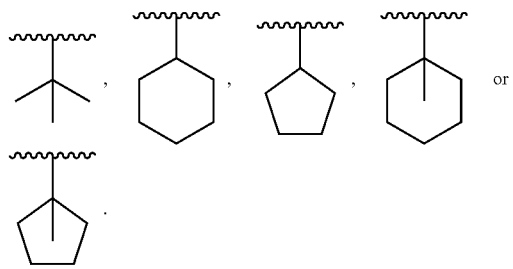

In certain embodiments, Q is $Q^1$. In certain other embodiments, Q is $C_1$-$C_4$ alkyl or C3-6 carbocyclyl. In further embodiments, Q is

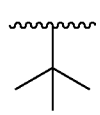 [SMILES: *C(C)(C)C]

(i.e., t-butyl). In some embodiments, Q is t-butyl or $C_5$-$C_6$ cycloalkyl.

In certain embodiments, E is $E^1$, $E^2$, $E^3$, or $E^4$. In certain embodiments, E is $E^3$.

In certain embodiments, E is $C_1$-$C_3$ alkyl optionally substituted with 1-3 halogen atoms. In certain embodiments, E is difluoromethyl.

In other embodiments, E is

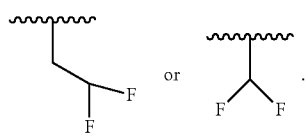

In other embodiments, E is

In other embodiments, E is

In other embodiments, E is

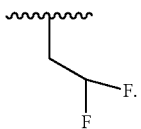 [SMILES: *CC(F)F]

In other embodiments, E is

In certain embodiments, ⊙ is bicyclic heteroaryl, optionally substituted with 1-4 W groups which are the same or different.

In certain other embodiments, ⊙ is

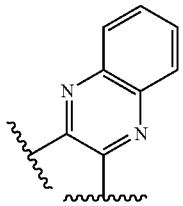 [SMILES: *c1nc2ccccc2nc1*]

optionally substituted with 1-4 W groups, which are the same or different.

In certain embodiments, ⊙ is substituted with one W group.

In some embodiments, ⊙ is $U^1$, $U^3$, $U^4$, $U^5$ or $U^6$, wherein each $U^1$, $U^3$, $U^4$, $U^5$ or $U^6$ is optionally substituted with 1-3 W at any substitutable position, and each W is independently $W^1$, $W^2$, $W^3$, $W^4$, $W^5$, $W^6$ or $W^7$.

In certain embodiments, $W^1$ is oxo, halogen, —$OR^6$, $C_1$-$C_6$ alkyl, —CN, —$CF_3$, —$SR^6$, —$C(O)_2R^6$, —C(O)N($R^6$)$_2$, —C(O)$R^6$, —N($R^6$)C(O)$R^6$, —$SO_2$($C_1$-$C_6$ alkyl), —S(O)($C_1$-$C_6$ alkyl), $C_3$-$C_8$ carbocyclyl, $C_3$-$C_8$ cycloalkoxy, $C_1$-$C_6$ haloalkyl, —N($R^6$)$_2$, —$NR^6$($C_1$-$C_6$ alkyl)O($C_1$-$C_6$ alkyl), halo($C_1$-$C_6$ alkoxy), —$NR^6SO_2R^6$, —$SO_2$N($R^6$)$_2$, —$NHCOOR^6$, —$NHCONHR^6$, $C_6$-$C_{10}$ aryl, 5-14 membered heteroaryl, 4-10 membered heterocyclyl or —O(4-10 membered heterocyclyl), wherein said $W^1$ alkyl, carbocyclyl, cycloalkoxy, haloalkyl, haloalkoxy, aryl, heteroaryl, or heterocyclyl is optionally substituted with 1-4 $Z^{1c}$ groups.

In certain embodiments, each $R^6$ is independently H, $C_6$-$C_{10}$ aryl or $C_1$-$C_6$ alkyl, wherein said aryl or alkyl is optionally substituted with 1 to 4 substituents independently selected from halogen atoms, $C_1$-$C_6$ alkyl, $C_6$-$C_{10}$ aryl, $_3$-$C_8$ carbocyclyl, 5-14 membered heteroaryl, 4-10 membered heterocyclyl, halo($C_1$-$C_6$ alkoxy), —OH, —O($C_1$-$C_6$ alkyl), —SH, —S($C_1$-$C_6$ alkyl), —$NH_2$, —NH($C_1$-$C_6$ alkyl), —N($C_1$-$C_6$ alkyl)$_2$, —C(O)($C_1$-$C_6$ alkyl), —$SO_2$N($C_1$-$C_6$ alkyl)$_2$, —NHCOO($C_1$-$C_6$ alkyl), —NHCO($C_1$-$C_6$ alkyl), —NHCONH($C_1$-$C_6$ alkyl), —$CO_2$($C_1$-$C_6$ alkyl), or —C(O)N($C_1$-$C_6$ alkyl)$_2$.

In certain embodiments, $W^2$ is $C_1$-$C_6$ alkoxy substituted with a 5-14 membered heteroaryl or $C_6$-$C_{10}$ aryl; wherein said heteroaryl or aryl is substituted with 1-4 $Z^{1c}$ groups.

In certain embodiments, $W^3$ is a $C_2$-$C_8$ alkynyl group substituted with a $C_6$-$C_{10}$ aryl, $C_3$-$C_8$ carbocyclyl, $C_1$-$C_8$ alkyl, $C_1$-$C_6$ haloalkyl, 4-10 membered heterocyclyl, or 5-14 membered heteroaryl group; wherein said aryl, carbocyclyl, alkyl, haloalkyl, heterocyclyl, or heteroaryl group is optionally substituted with 1-4 $Z^{1c}$ groups.

In some embodiments, $W^4$ is —$SF_5$.

In some embodiments, $W^5$ is —O($C_2$-$C_6$ alkyl)$OR^{22}$ wherein $R^{22}$ is a $C_6$-$C_{10}$ aryl 5-14 membered heteroaryl or 4-10 membered heterocyclyl group that is optionally substituted with 1-4 $Z^{1c}$ groups.

In certain embodiments, W is hydrogen, —O($C_1$-$C_3$) alkyl, halogen or cyano.

In certain embodiments, W is methoxy.

In some embodiments, $U^1$ is

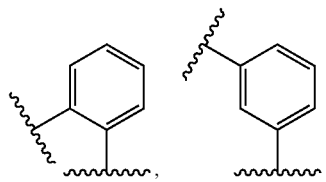

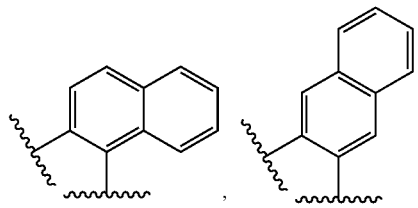

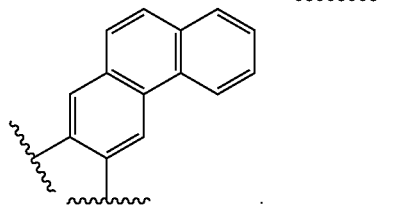

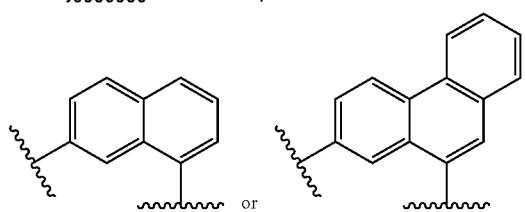

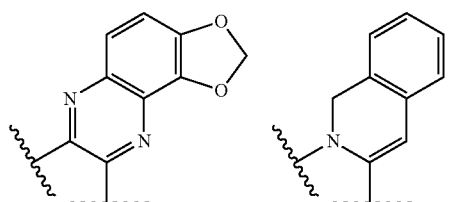 or 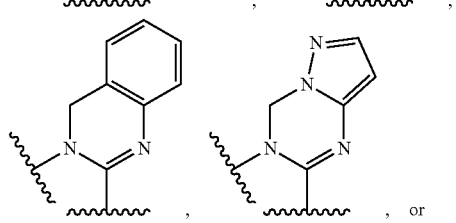

wherein each $U^1$ is optionally substituted with 1-2 $Z^1$ groups.

In some embodiments, $U^3$ is

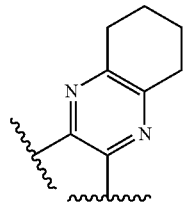
wherein each U³ is optionally substituted with 1-2 Z¹ groups.
In some embodiments, U⁴ is
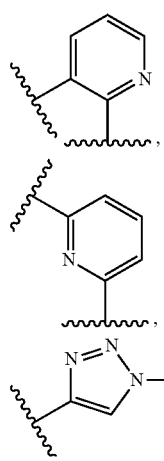
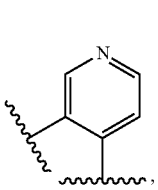
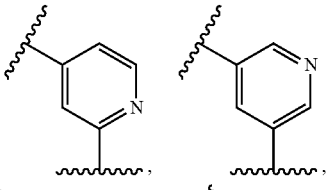
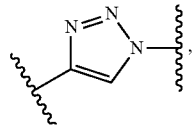
wherein each U⁴ is optionally substituted with 1-2 Z¹ groups.
In some embodiments, U⁵ is
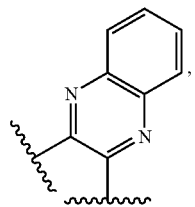
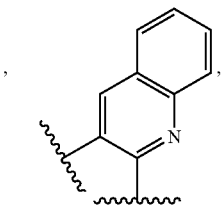
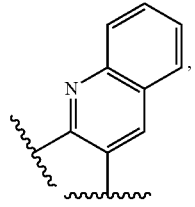
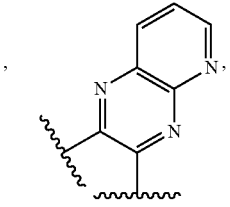
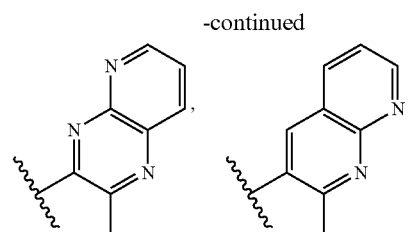
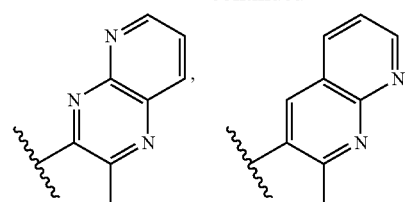
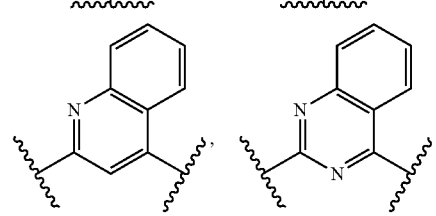
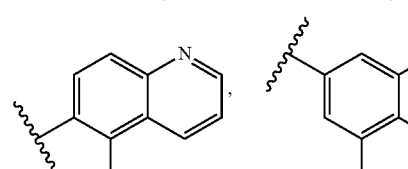
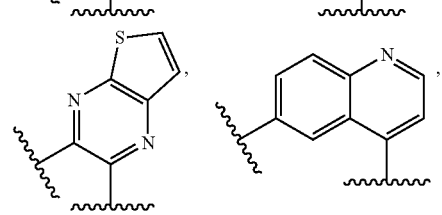
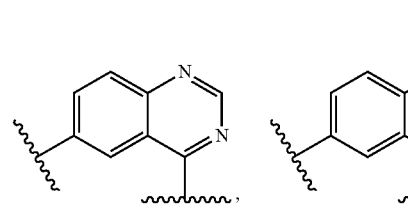
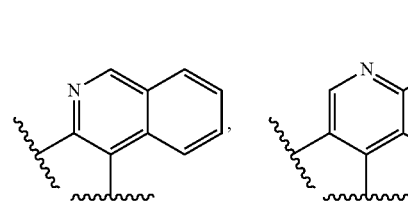
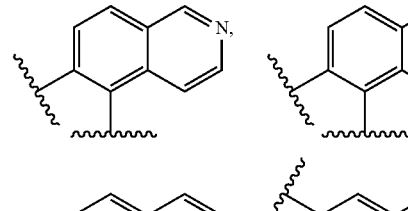
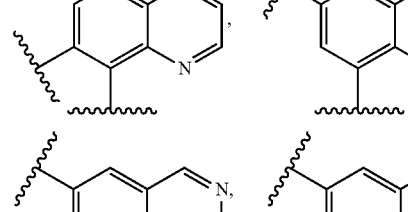
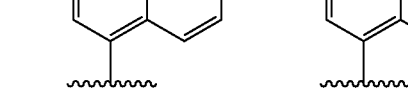

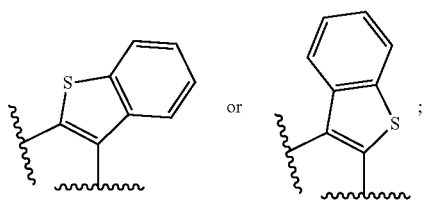

wherein each U⁵ is optionally substituted with 1-2 Z¹ groups.

In some embodiments, U⁶ is

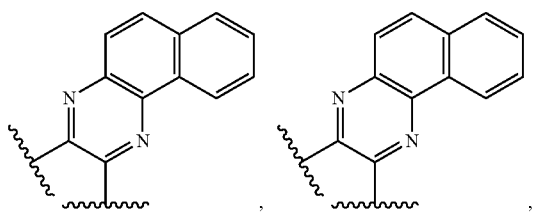

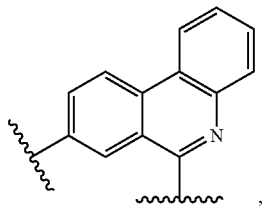

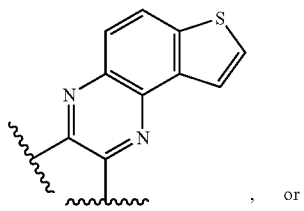

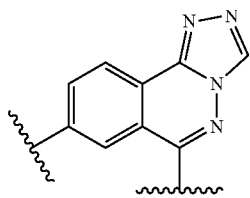, or

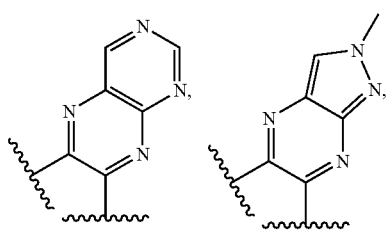

wherein each U⁶ is optionally substituted with 1-2 Z¹ groups.

In some embodiments, U⁷ is

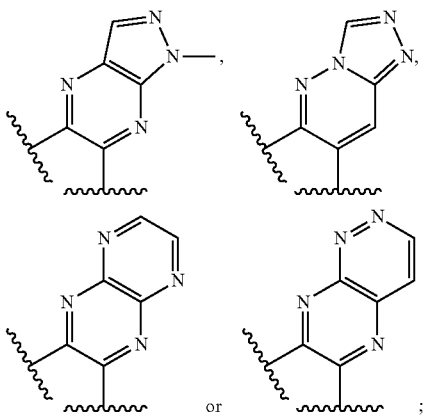

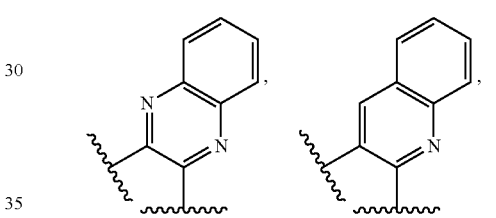

or 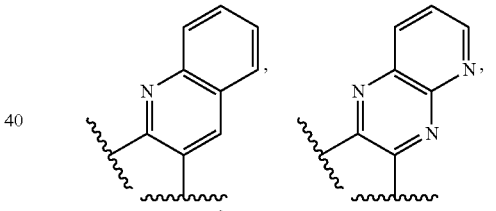;

wherein each U⁷ is optionally substituted with 1-2 Z¹ groups.

In other embodiments, ☺ is optionally substituted with one or two W at any substitutable position, and each W is independently W¹, W², W³, W⁴, W⁵, W⁶ or W⁷ wherein ☺ is

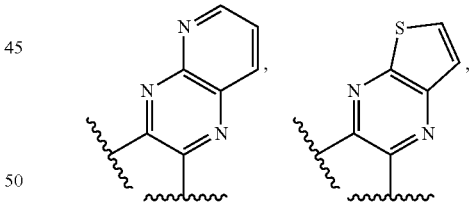

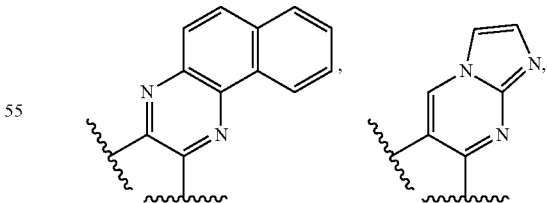

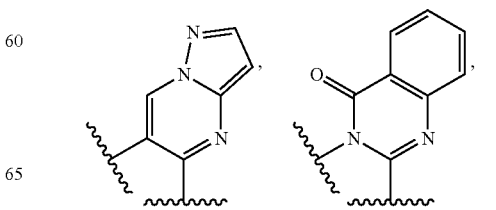

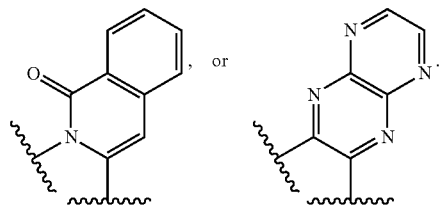
In other embodiments, ⊙ is optionally substituted with one W at any substitutable position, and each W is independently $W^1$, $W^2$, $W^3$, $W^4$, $W^5$, $W^6$ or $W^7$ wherein ⊙ is
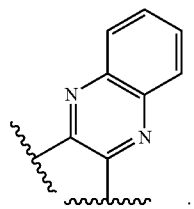 [SMILES: *c1nc2ccccc2nc1*]
In other embodiments, each W is independently $W^1$, $W^2$, $W^3$, $W^4$, $W^5$, $W^6$ or $W^7$.
In some embodiments, $W^1$ is
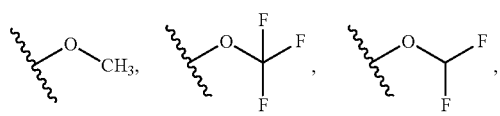
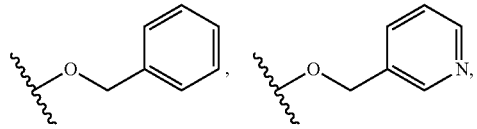
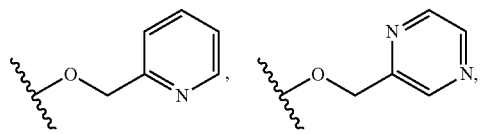
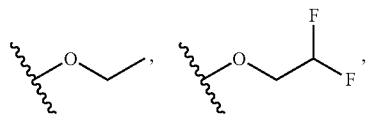
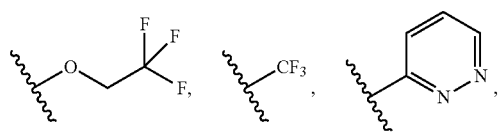
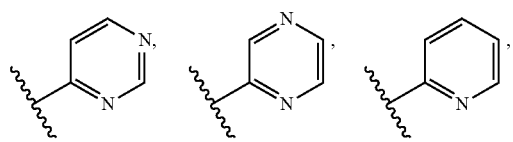
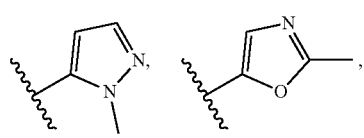
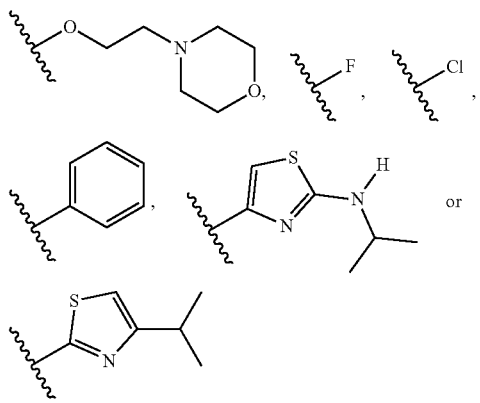
In some embodiments, $W^2$ is
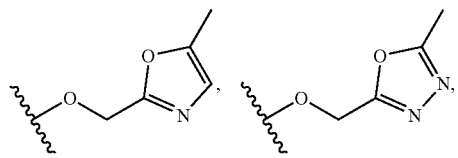
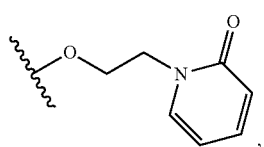
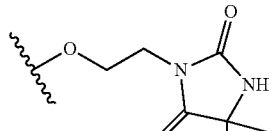
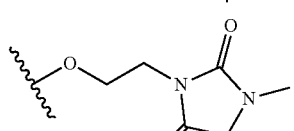
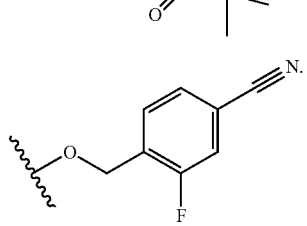
In some embodiments, $W^3$ is
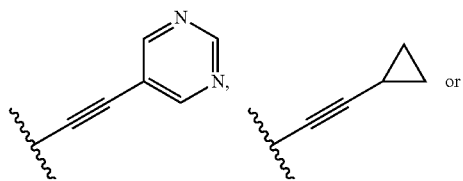

-continued

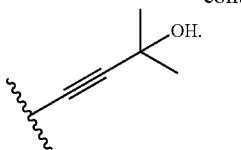

In some embodiments, $W^5$ is

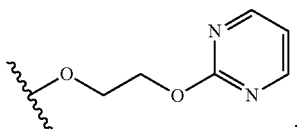 [SMILES: *OCCOc1ncccn1]

In some embodiments, $W^6$ is

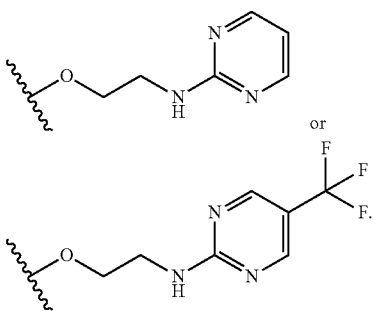

or

In some embodiments, $W^7$ is

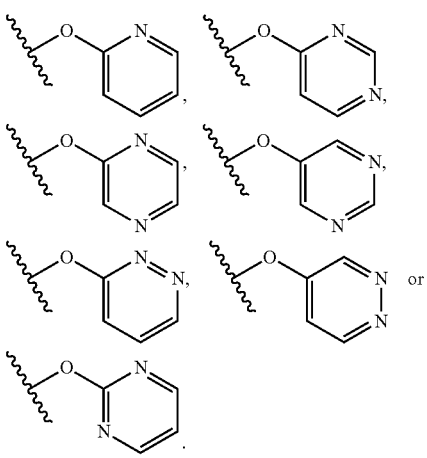

or

In other embodiments, W is

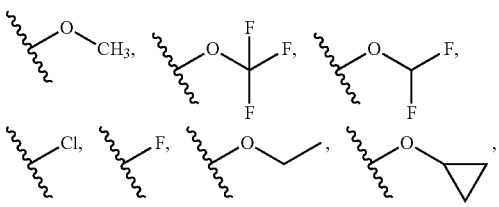

-continued

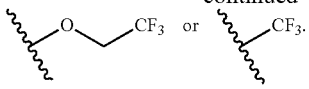

In certain embodiments, each W is independently halogen or $C_1$-$C_4$ alkoxy.

In a specific embodiment, J is methyl or ethyl; E is substituted with 1-2 halogen atoms; L is substituted with 1-2-halogen atoms, and T is unsubstituted.

In a further embodiment, J is methyl or ethyl; E is $C_1$-$C_3$ haloalkyl; L is $C_5$-alkyl or $C_5$-alkenyl.

In another embodiment, a compound of Formula (IV):

(IV)

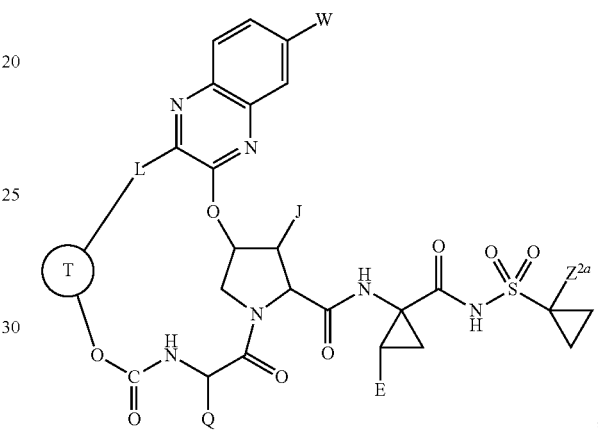

or a stereoisomer, or a mixture of stereoisomers, or a pharmaceutically acceptable salt thereof, is provided, wherein:

J is $C_1$-$C_4$ alkyl or $C_3$-$C_6$ carbocyclyl, wherein $C_1$-$C_4$ alkyl or $C_3$-$C_6$ carbocyclyl is optionally substituted with halogen, —OH, aryl or cyano;

⊙ is $C_3$-$C_5$ carbocyclylene that is attached to L and to the remainder of the compound through two adjacent carbons, wherein said $C_3$-$C_5$ carbocyclylene is optionally substituted with $C_1$-$C_4$ alkyl, $C_1$-$C_3$ haloalkyl, halogen, —OH, or cyano, or ⊙ is $C_5$-$C_8$ bicyclic carbocyclylene that is attached to L and to the remainder of the compound through two adjacent carbons, ⊙ or is $C_3$-$C_6$ carbocyclylene that is attached to L and to the remainder of the compound of Formula IV through two adjacent carbons, wherein said $C_3$-$C_6$ carbocyclene is optionally substituted with $C_1$-$C_4$ alkyl or $C_1$-$C_3$ haloalkyl;

L is $C_3$-$C_6$ alkylene, $C_3$-$C_6$ alkenylene or —$(CH_2)_3$-cyclopropylene-optionally substituted with 1-4 halogen, —OH, or cyano;

Q is $C_2$-$C_4$ alkyl or $C_3$-$C_6$ carbocyclyl optionally substituted with $C_1$-$C_3$ alkyl, halogen, —OH, or cyano;

E is $C_1$-$C_3$ alkyl or $C_2$-$C_3$ alkenyl, optionally substituted with $C_1$-$C_3$ alkyl, halogen, —OH, or cyano;

W is H, —OH, —O($C_1$-$C_3$)alkyl, —O($C_1$-$C_3$)haloalkyl, halogen or cyano; and $Z^{2a}$ is H or $C_1$-$C_3$ alkyl, halogen, —OH, or cyano.

In a further embodiment of Formula (IV), J is $C_1$-$C_3$ alkyl.

In a further embodiment of Formula (IV), J is methyl or ethyl.

In a further embodiment of Formula (IV), ⊙ is $C_3$-$C_6$ carbocyclylene that is attached to L and to the remainder of the compound of Formula IV through two adjacent carbons, wherein said $C_3$-$C_6$ carbocyclene is optionally substituted with $C_1$-$C_4$ alkyl or $C_1$-$C_3$ haloalkyl.

In a further embodiment of Formula (IV), ⊙ is $C_3$-$C_6$ carbocyclylene that is attached to L and to the remainder of the compound of Formula IV through two adjacent carbons, wherein the $C_3$-$C_6$ carbocyclene is optionally substituted with methyl, ethyl or trifluoromethyl.

In a further embodiment of Formula (IV), ⊙ is cyclopropylene.

In a further embodiment of Formula (IV), ⊙ is $C_6$-$C_8$ bridged bicyclic carbocyclylene or $C_6$-$C_8$ fused bicyclic carbocyclylene that is attached to L and to the remainder of the compound of Formula IV through two adjacent carbons.

In a further embodiment of Formula (IV), L is $C_3$-$C_6$ alkylene, substituted with 1-4 halogens. In another embodiment of Formula (IV), L is $C_5$ alkylene, substituted with two halogens. In some embodiments, the halogens are each fluoro.

In a further embodiment of Formula (IV), L is $C_3$-$C_6$ alkylene.

In a further embodiment of Formula (IV), L is $C_5$ alkylene.

In a further embodiment of Formula (IV), Q is t-butyl or $C_5$-$C_6$ carbocyclyl.

In a further embodiment of Formula (IV), Q is t-butyl.

In a further embodiment of Formula (IV), E is $C_1$-$C_3$ alkyl optionally substituted with 1-3 halogen atoms.

In a further embodiment of Formula (IV), E is difluoromethyl.

In a further embodiment of Formula (IV), W is hydrogen, —O($C_1$-$C_3$)alkyl, halogen or cyano.

In a further embodiment of Formula (IV), W is methoxy.

In a further embodiment of Formula (IV), $Z^{2a}$ is hydrogen or methyl.

In a further embodiment of Formula (IV), $Z^{2a}$ is methyl.

There is further provided a compound selected from the group consisting of:

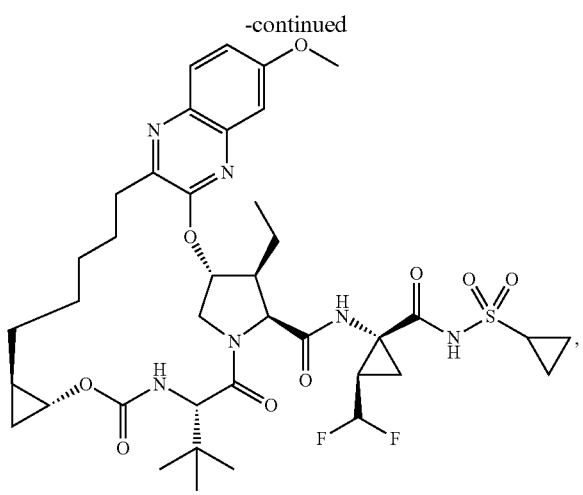

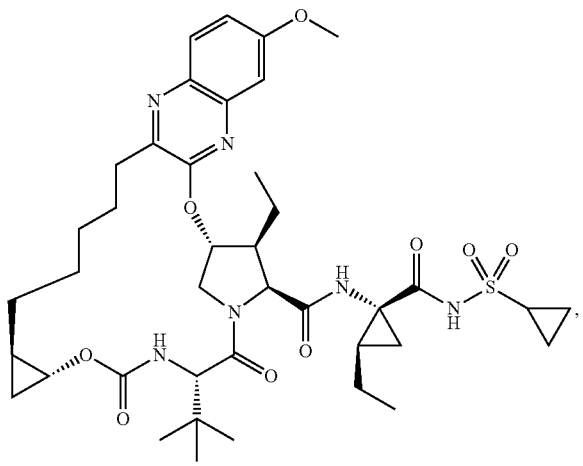

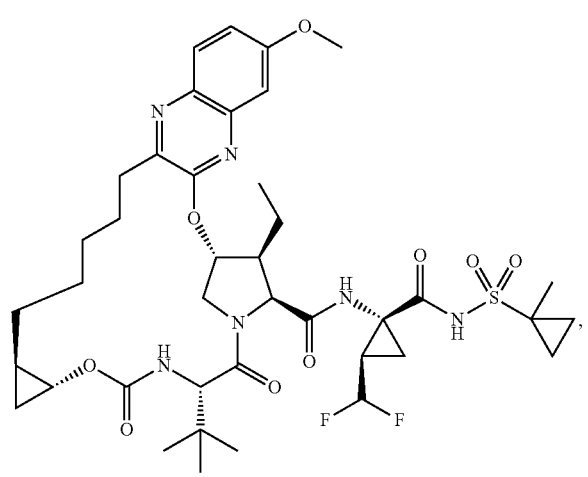

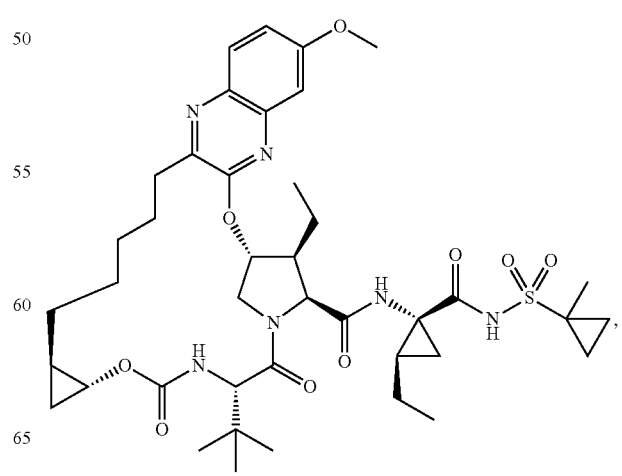

65
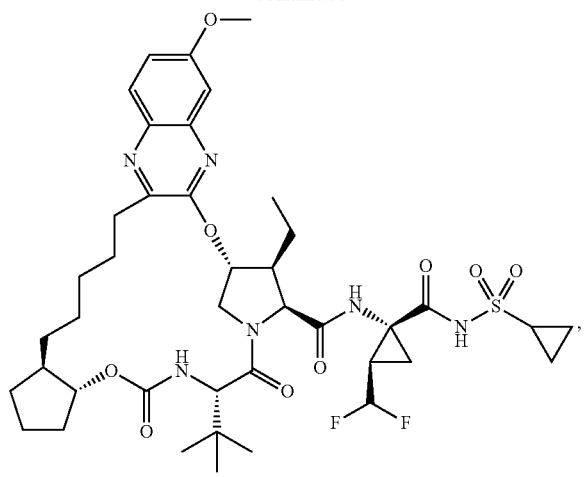
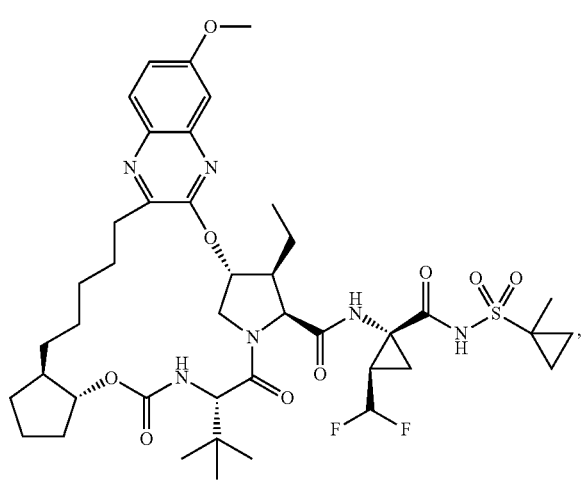
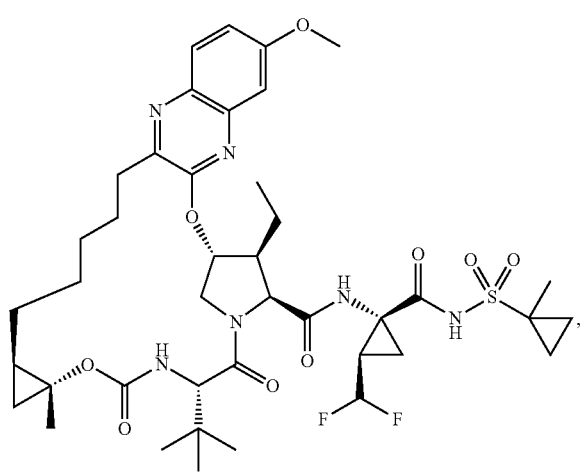
66
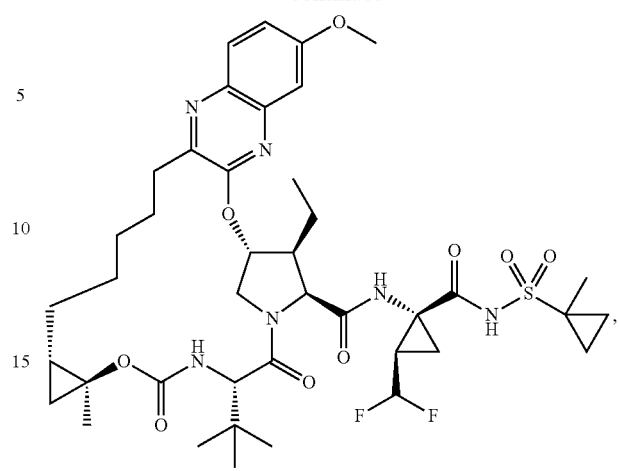
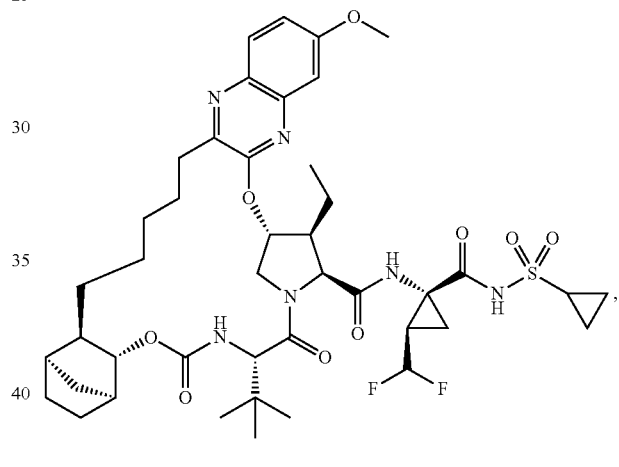
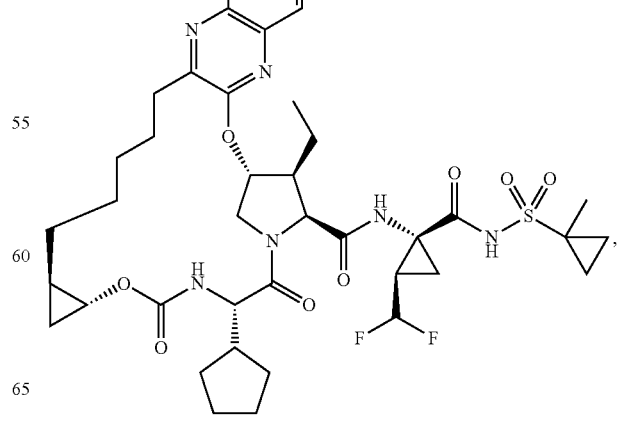

67
-continued
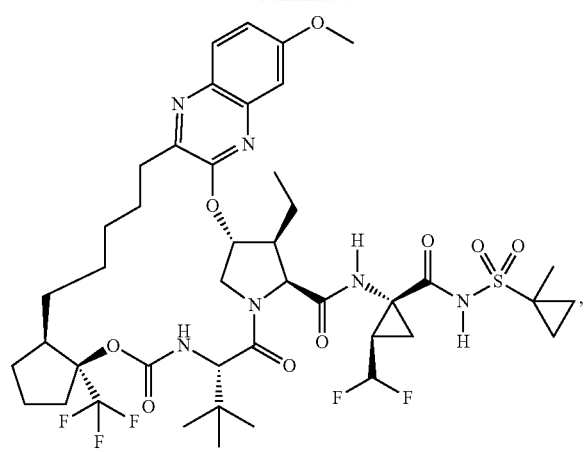
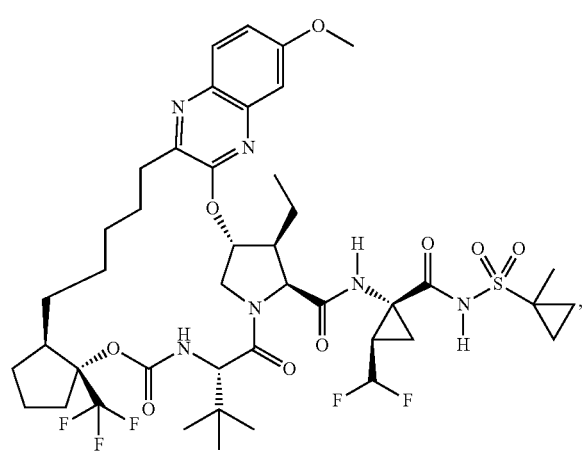
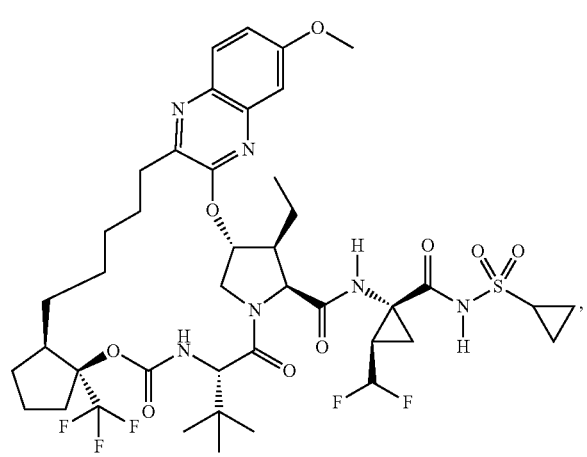
68
-continued
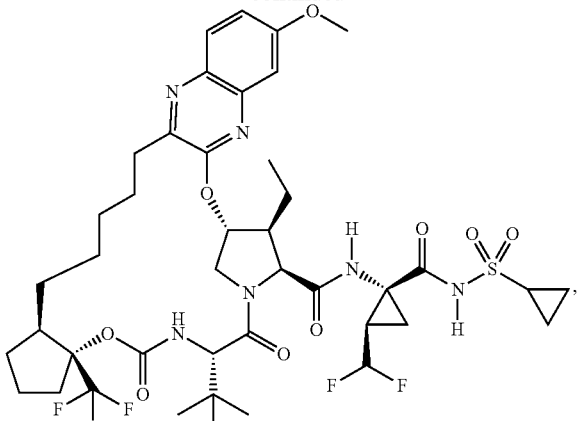
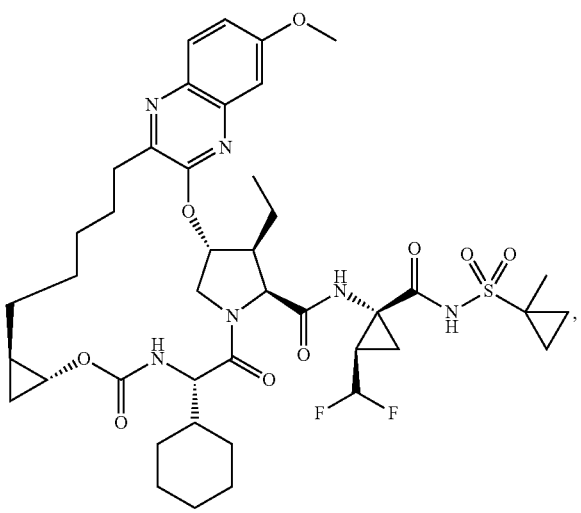

69
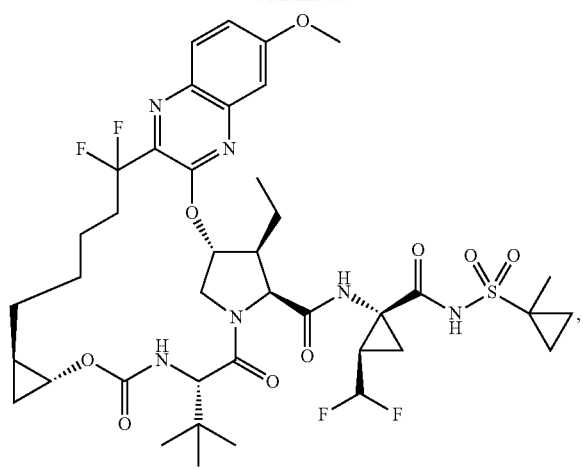
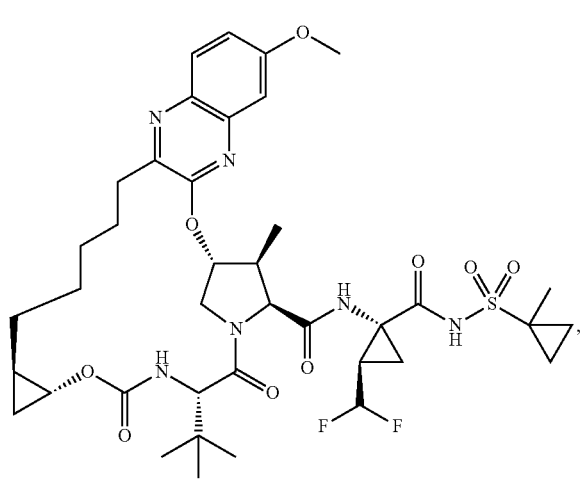
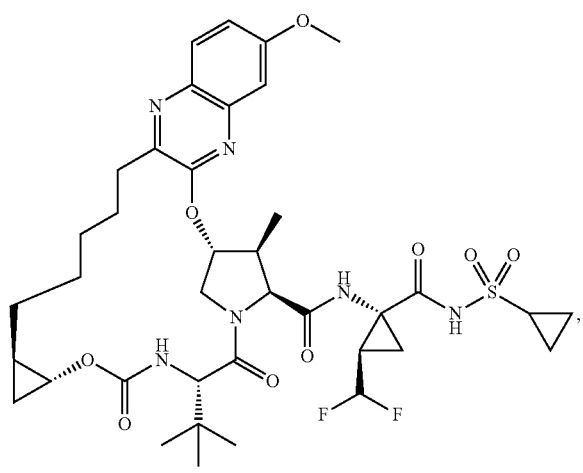
70
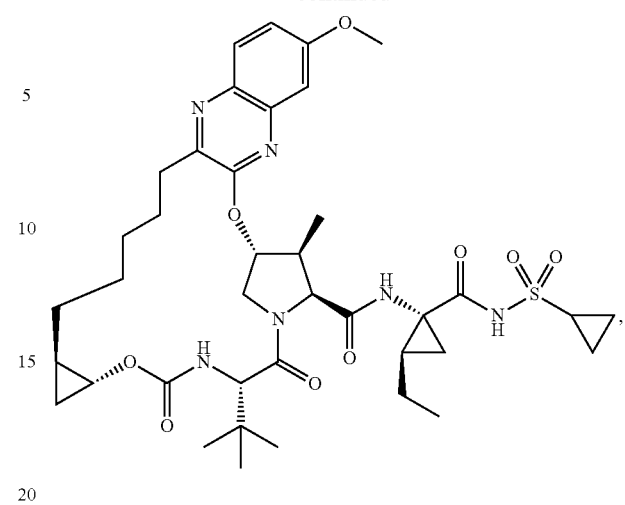
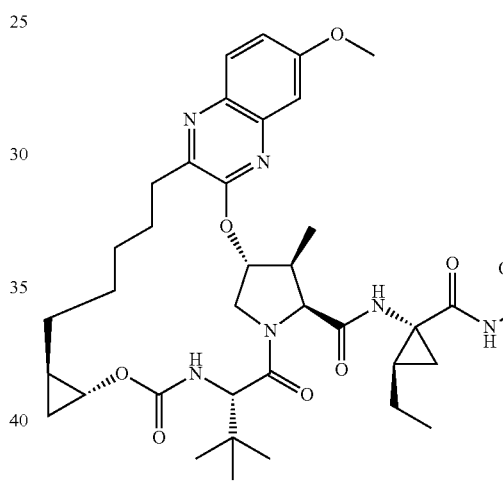
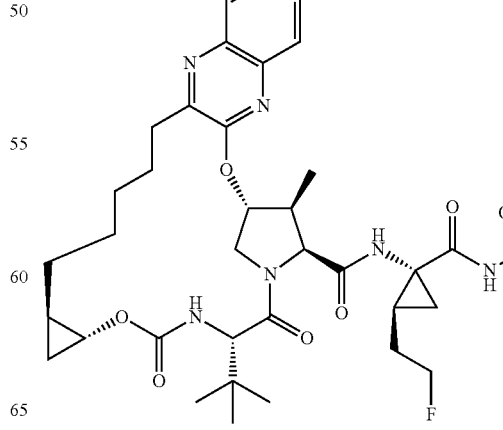

71 -continued
72 -continued
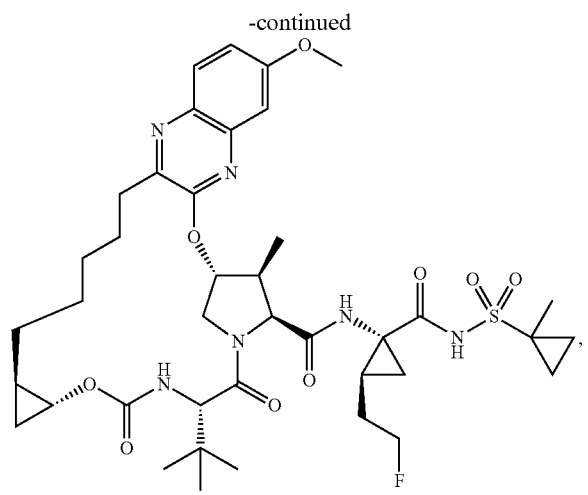
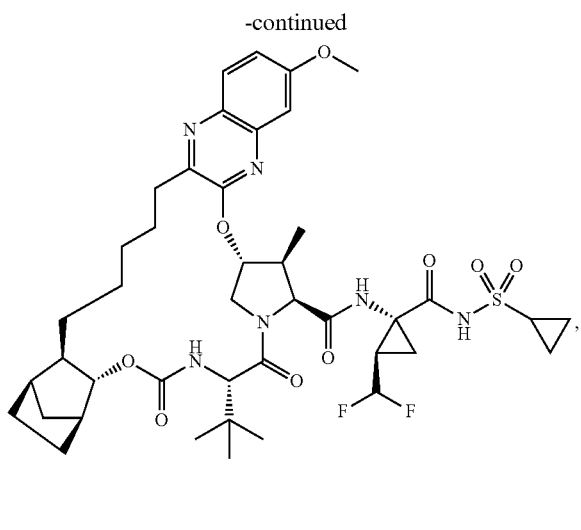
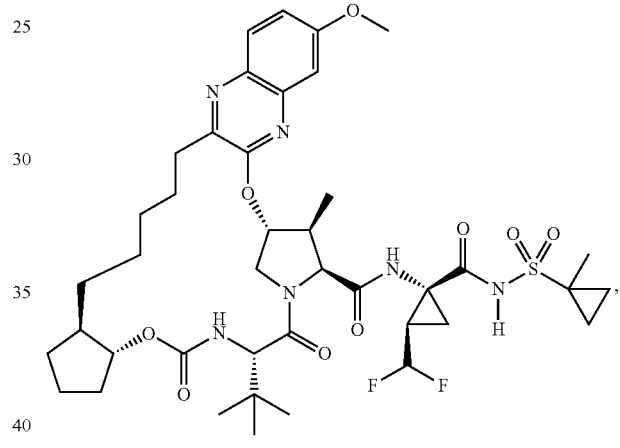
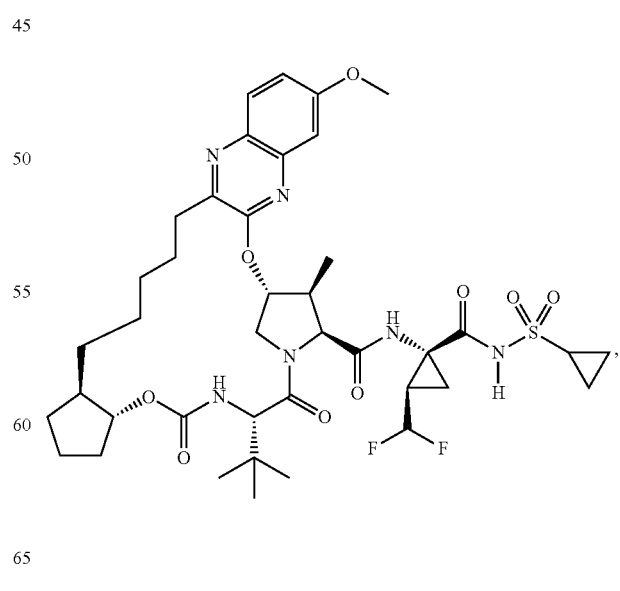

73
-continued
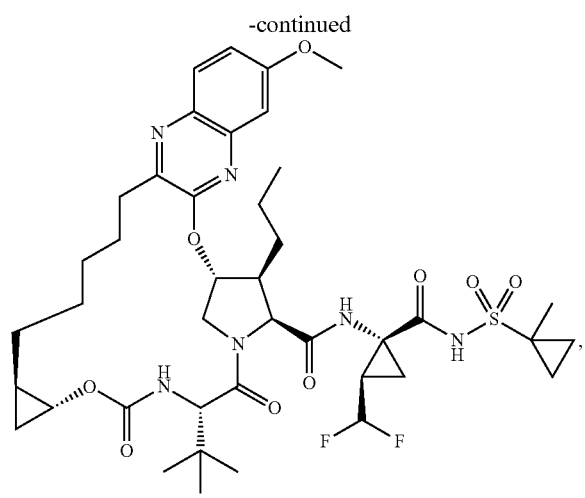
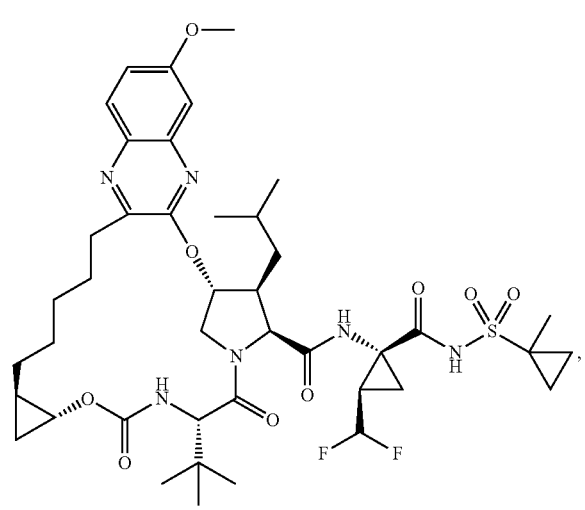
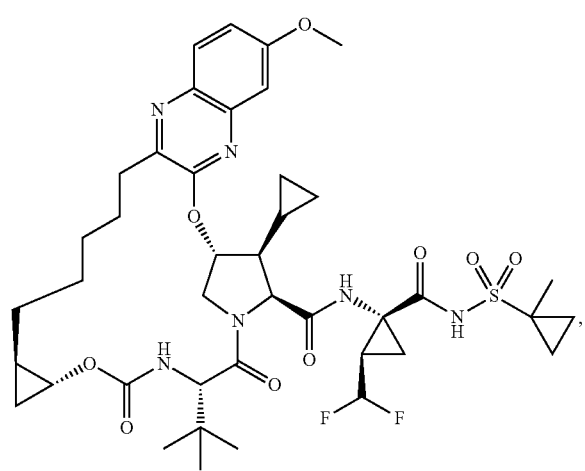
74
-continued
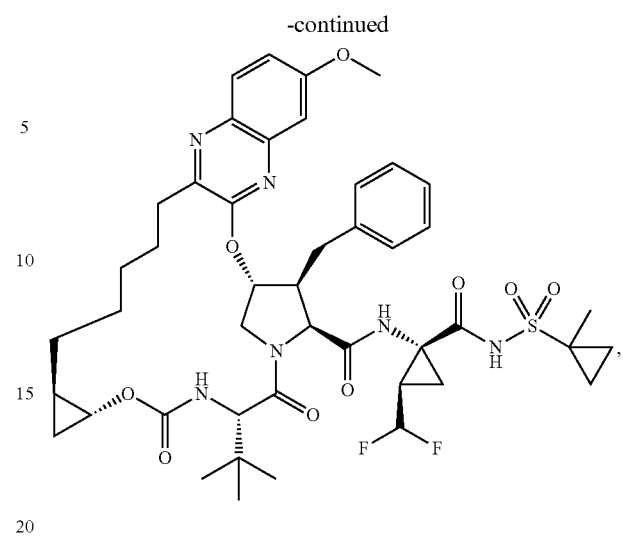
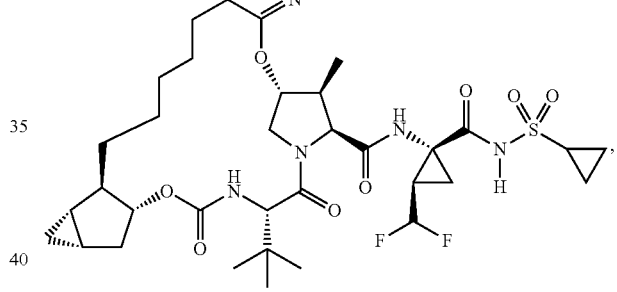
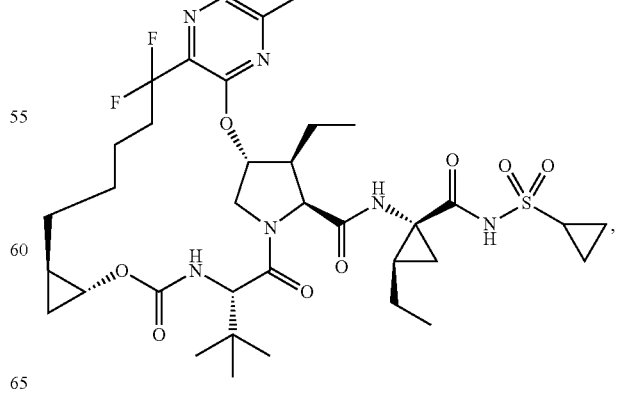

75
-continued
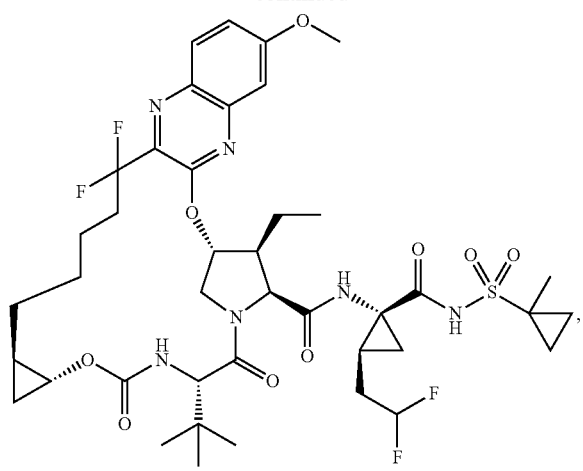
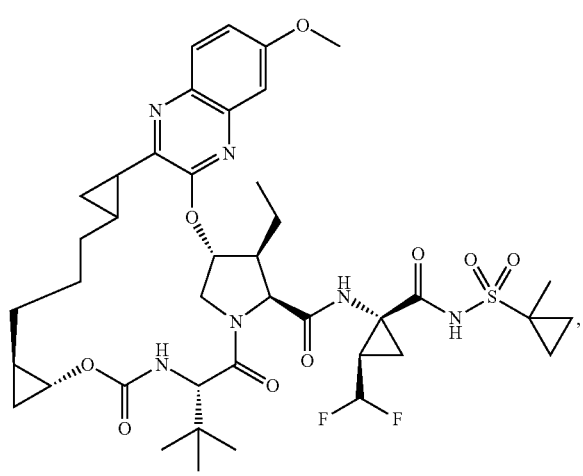
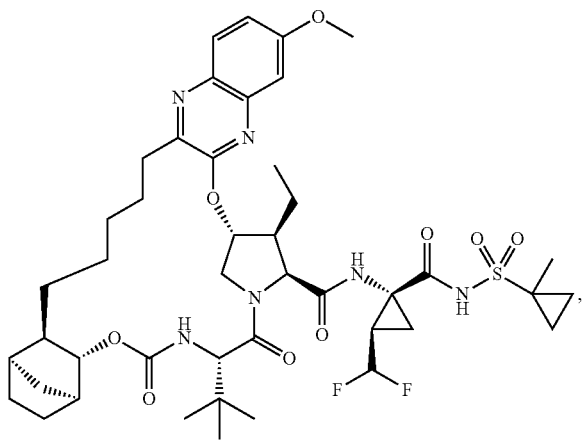
76
-continued
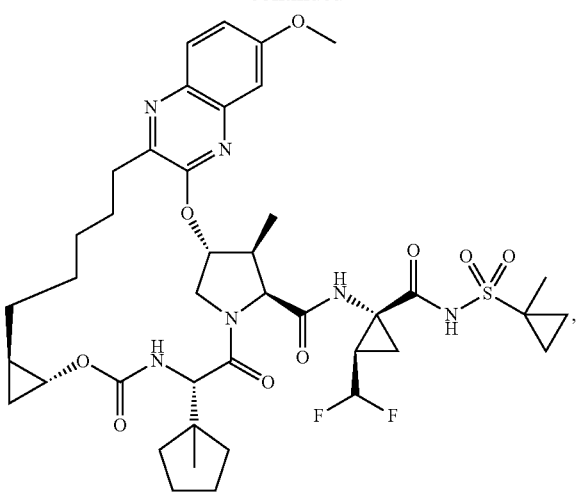
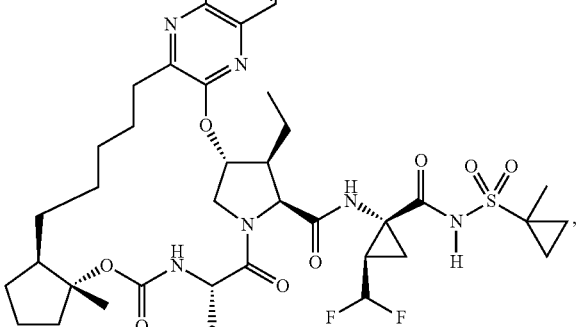
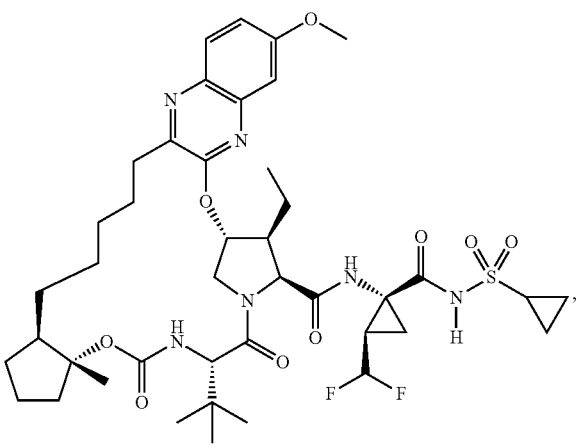

77
-continued
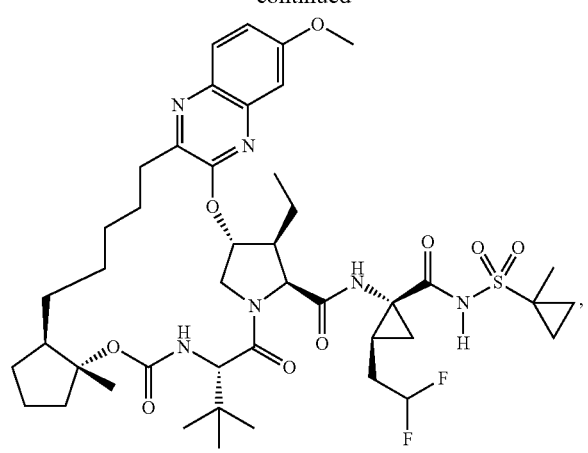
78
-continued
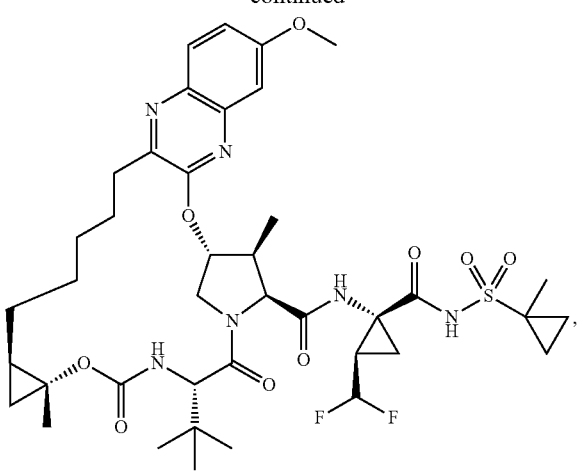
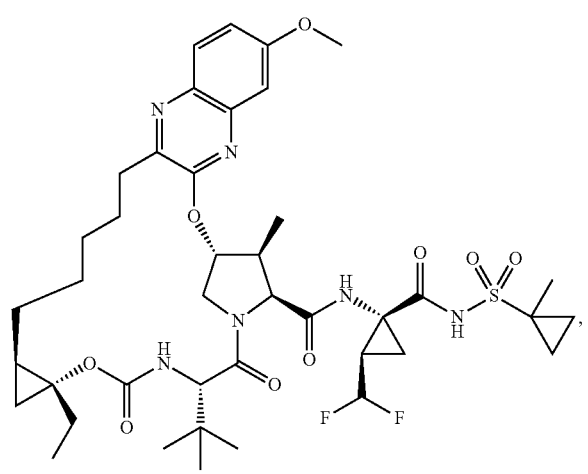
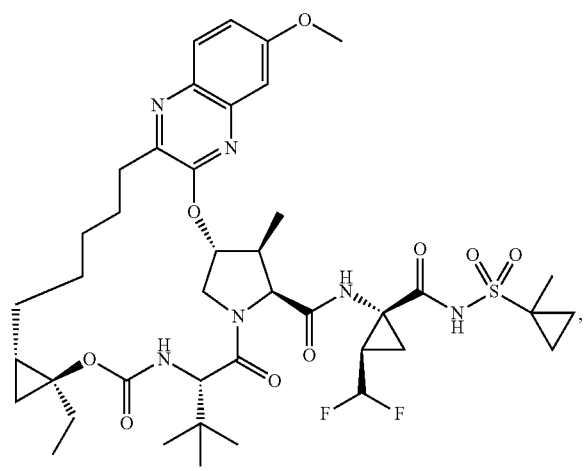 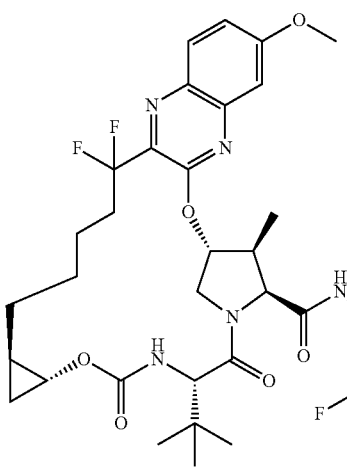

79
-continued
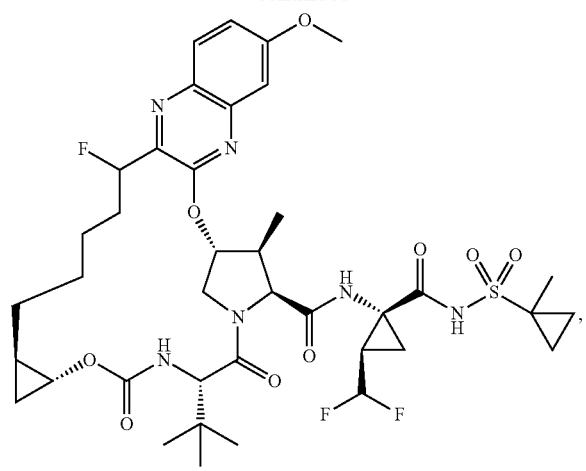
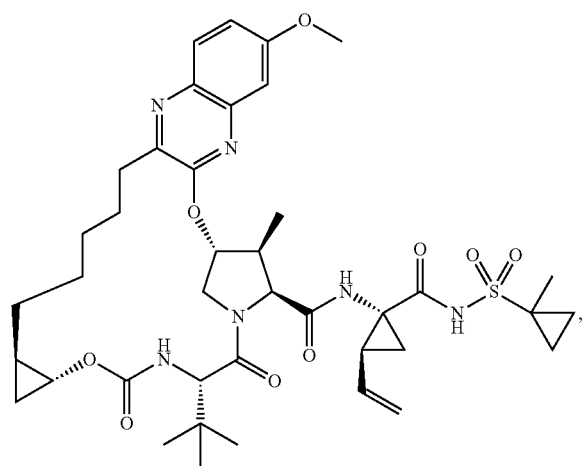
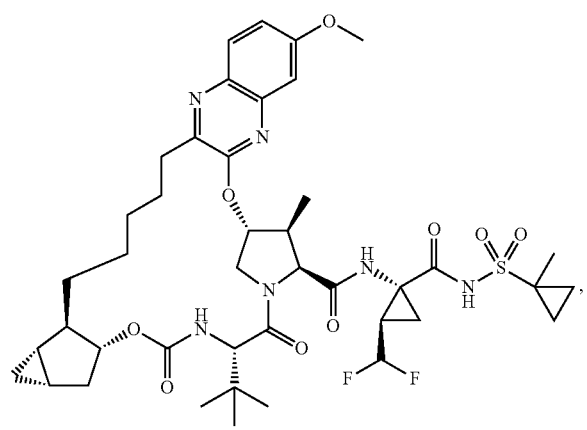
80
-continued
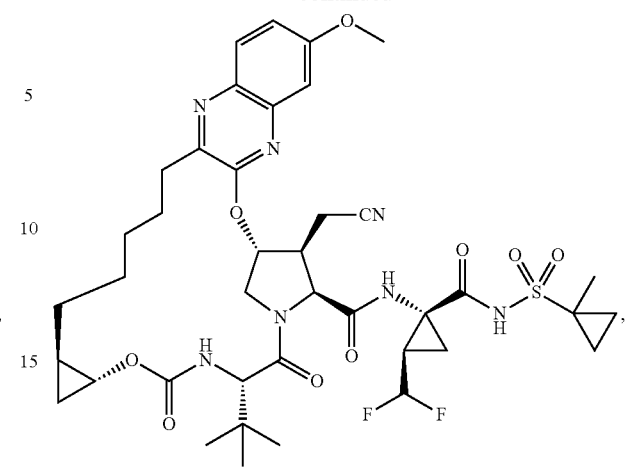
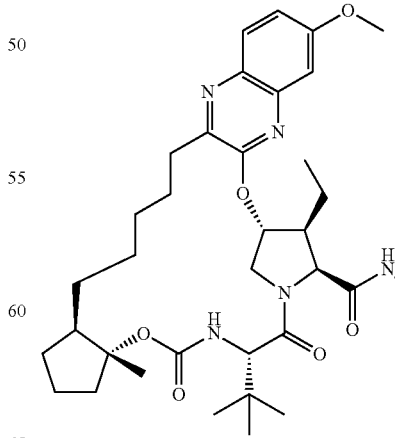

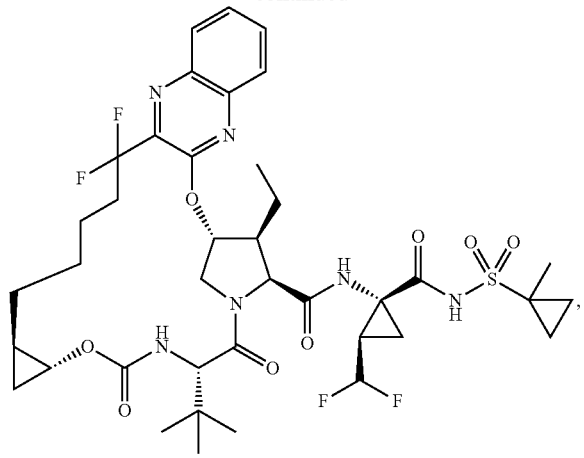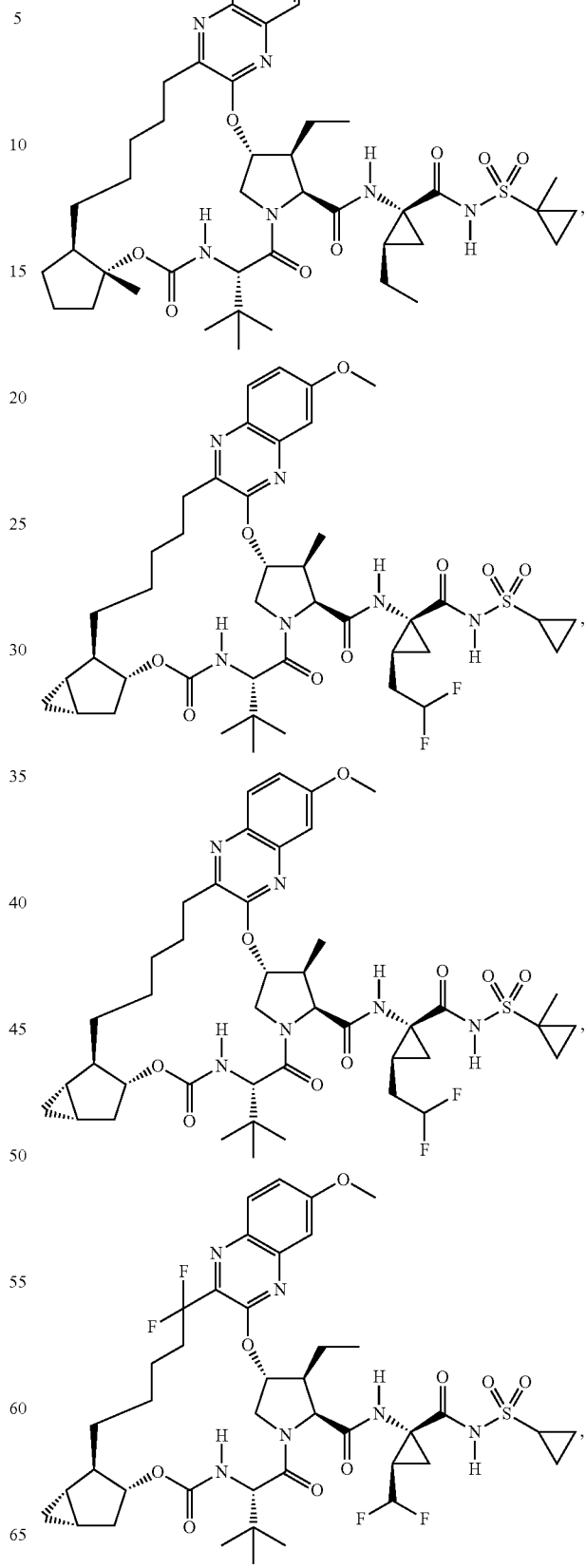

83
-continued
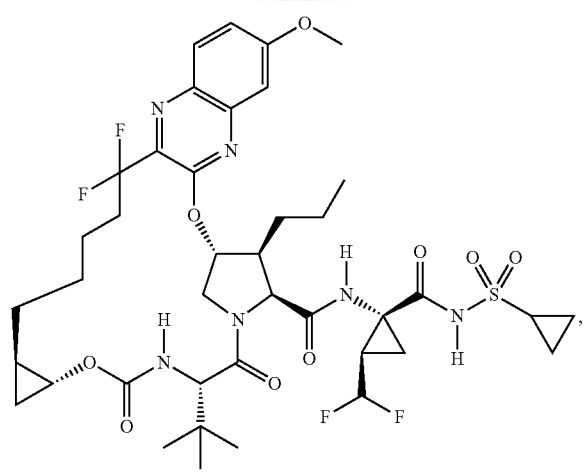
84
-continued
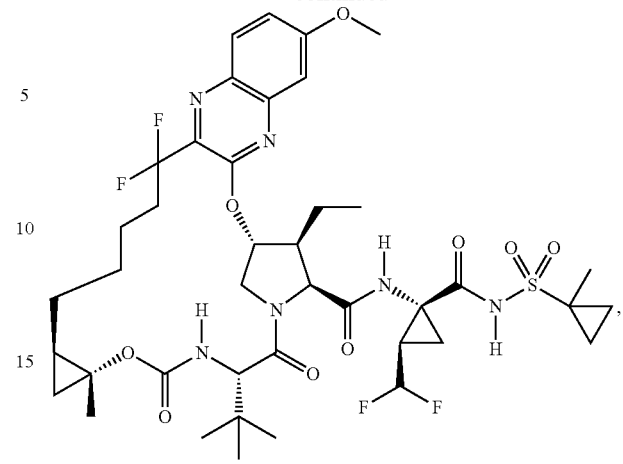
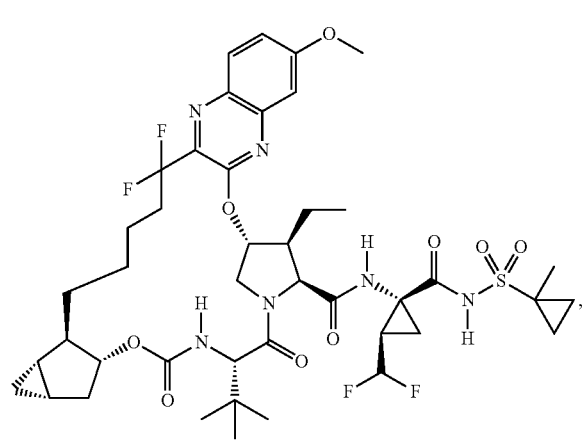
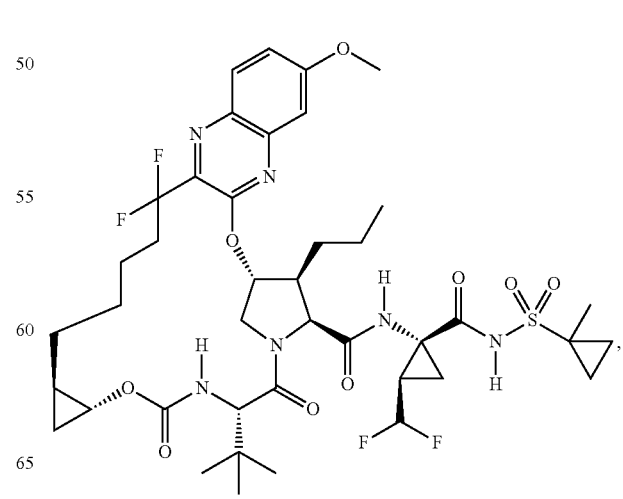

85
-continued
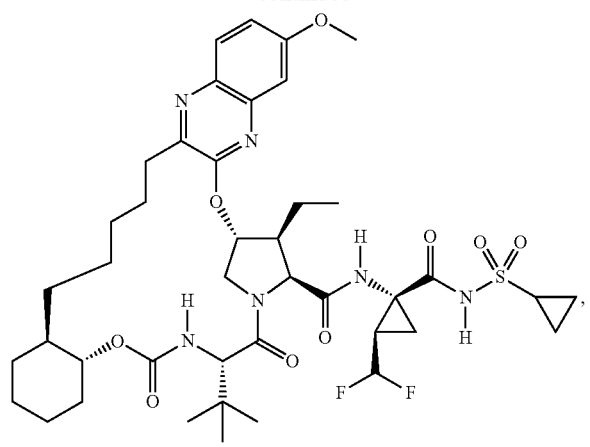
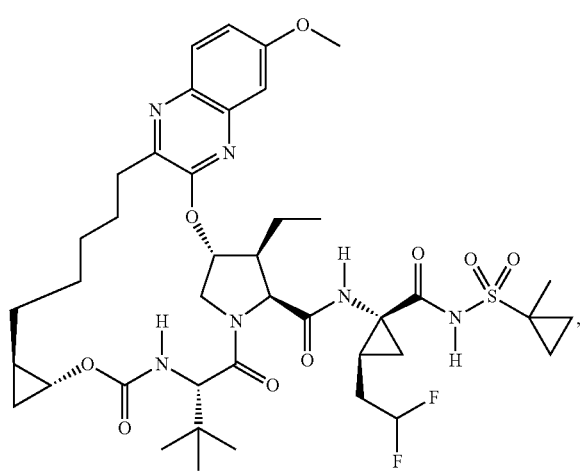
86
-continued
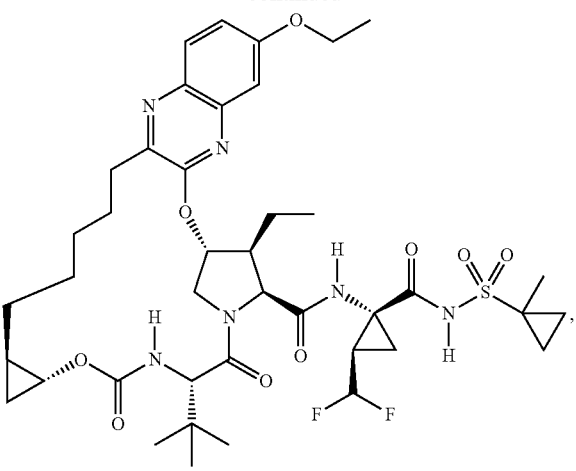
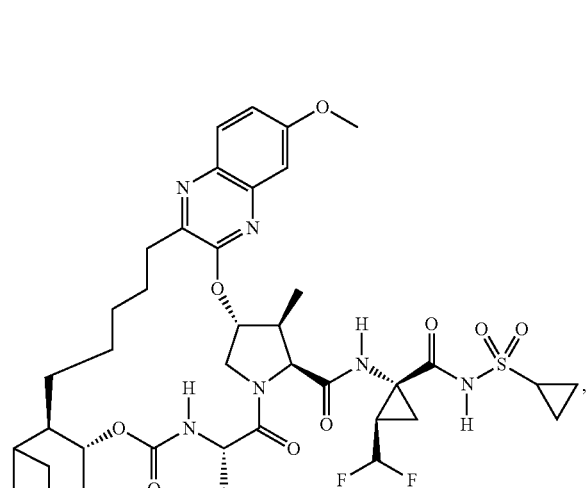

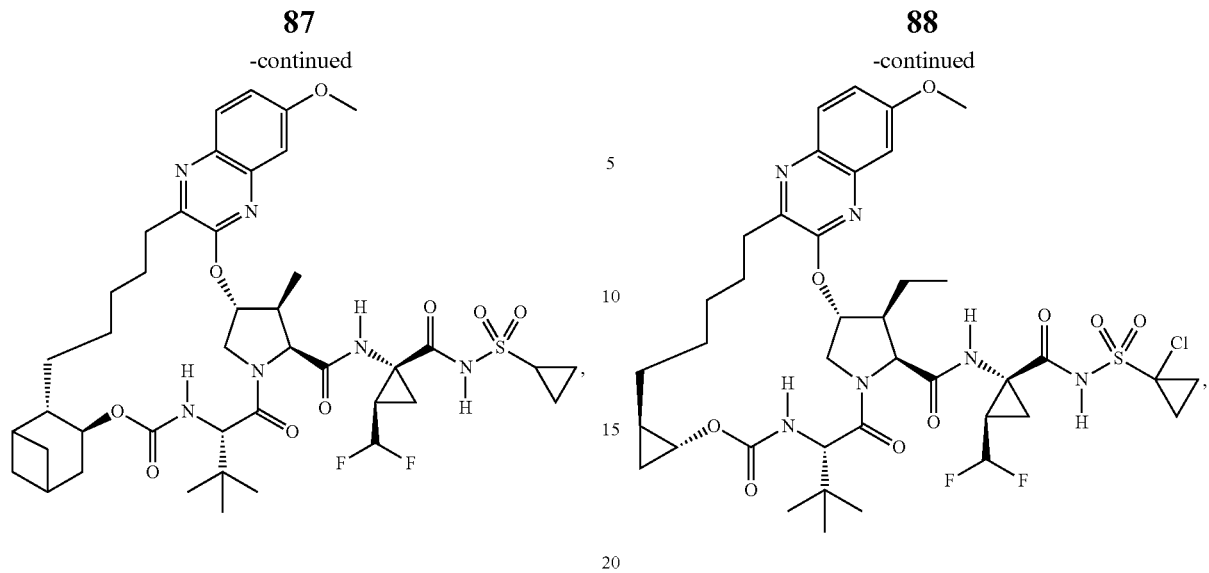
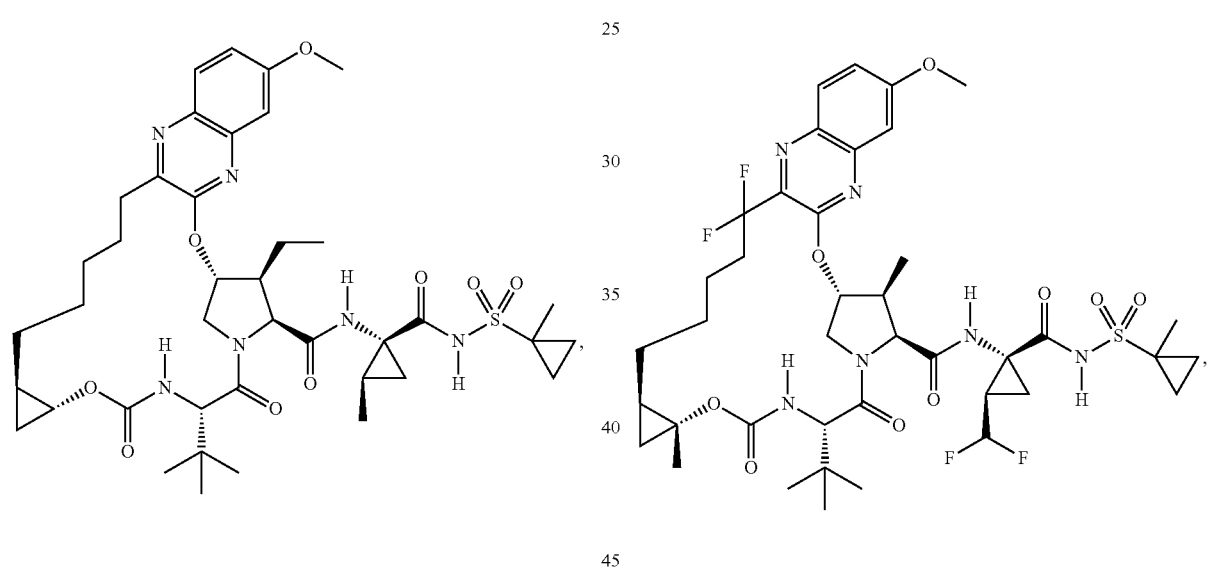
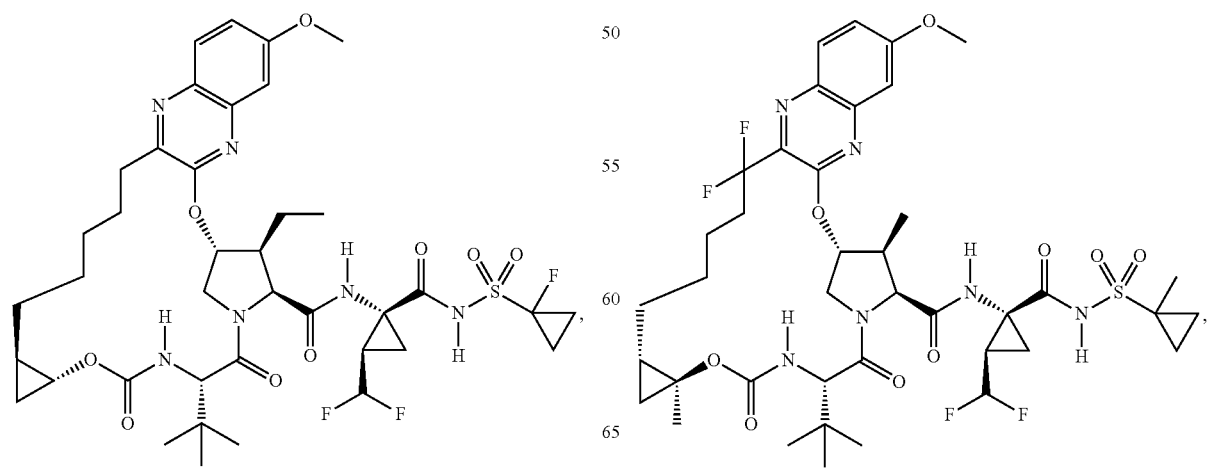

89
-continued
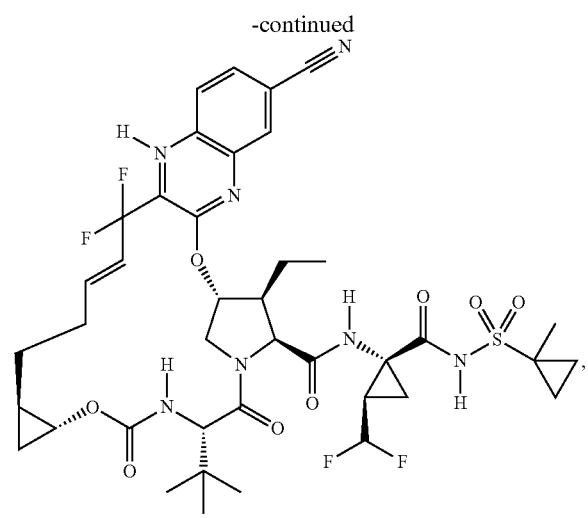
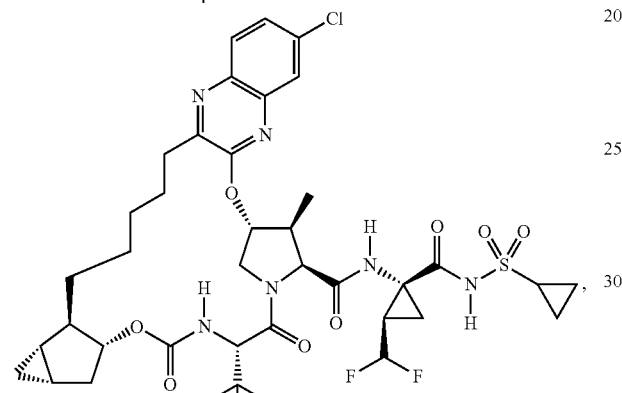
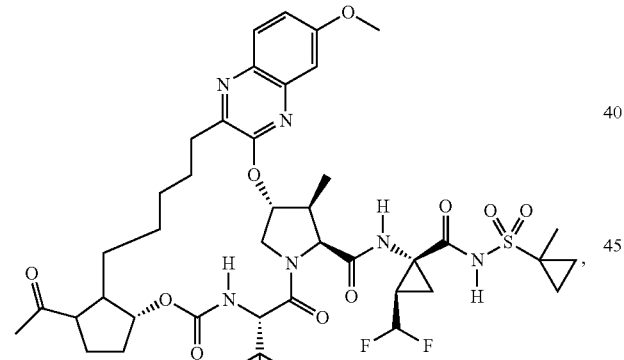
90
-continued
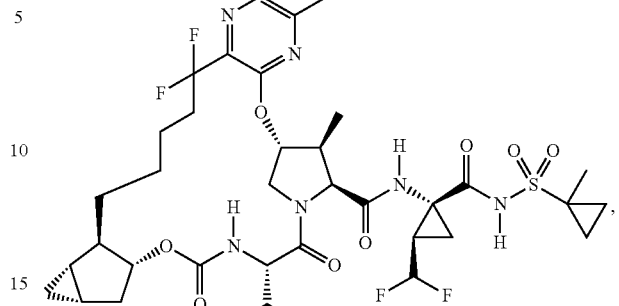
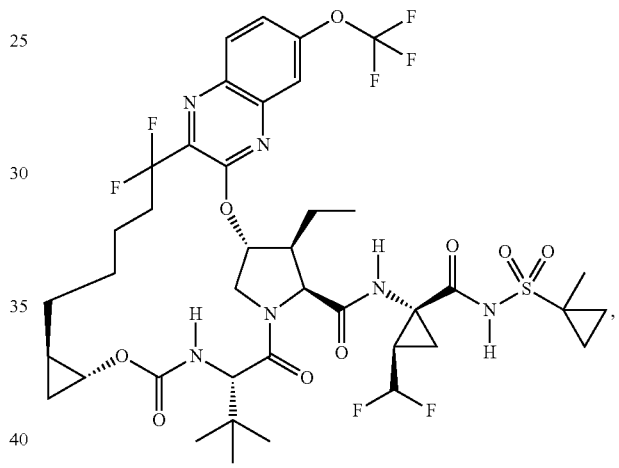
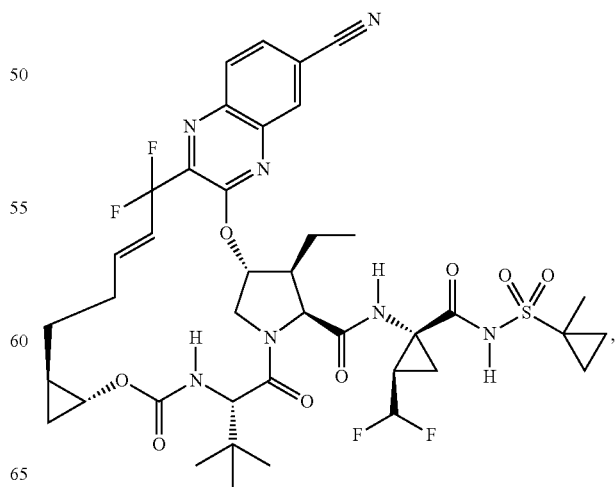

91
92
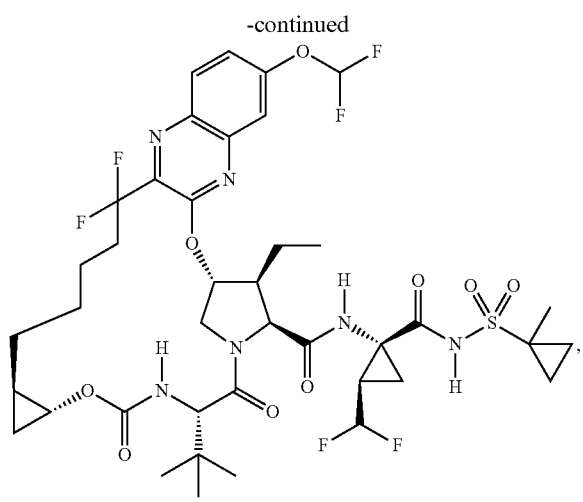
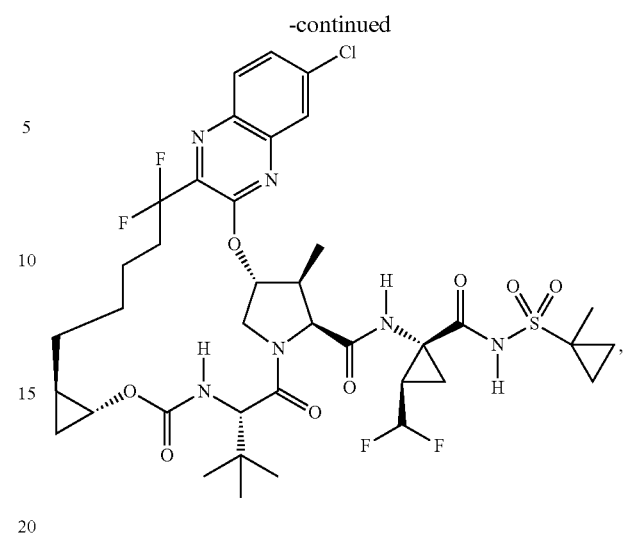
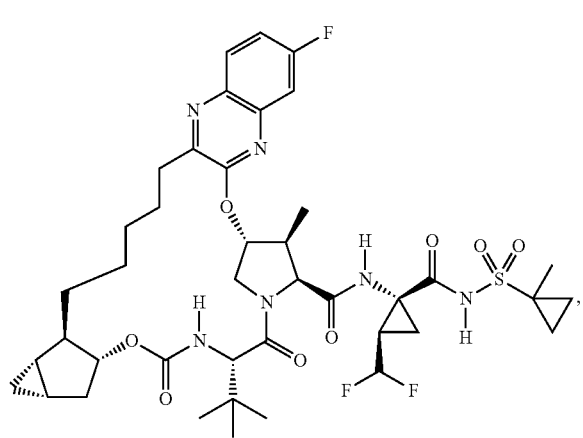
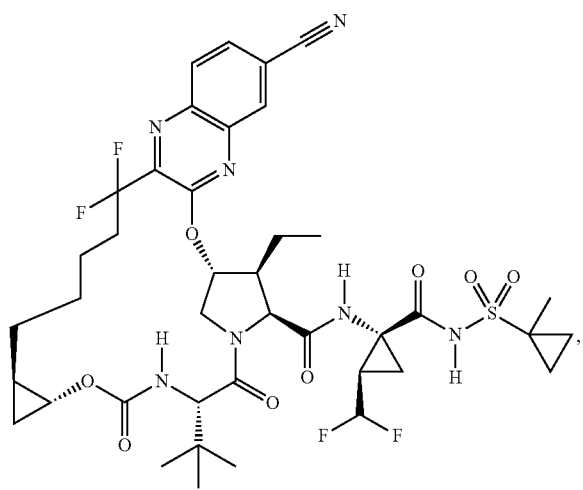
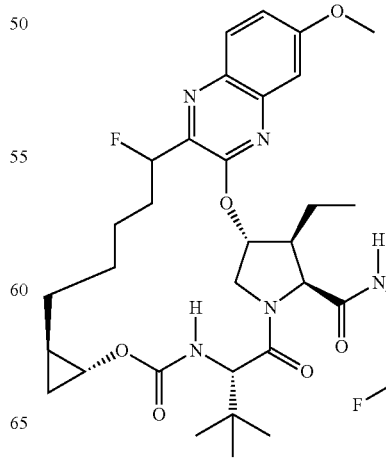

93
-continued
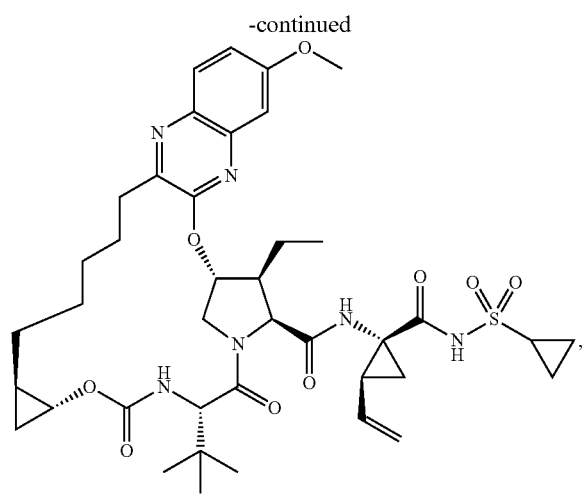
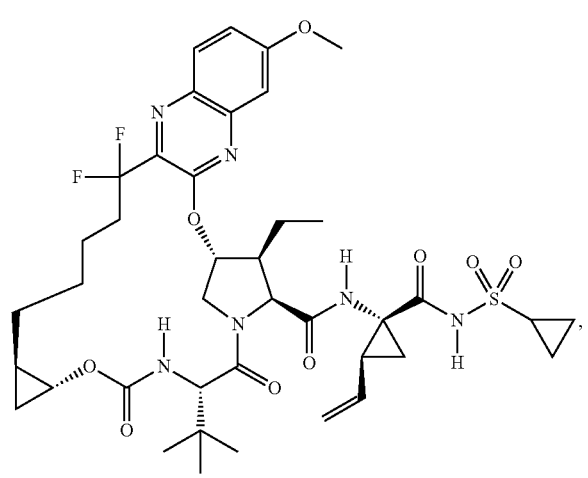
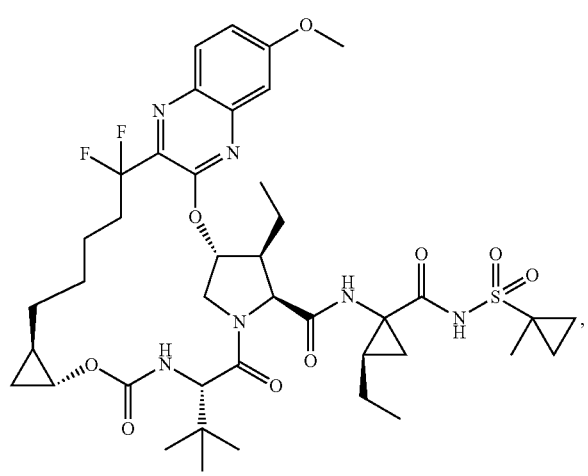
94
-continued
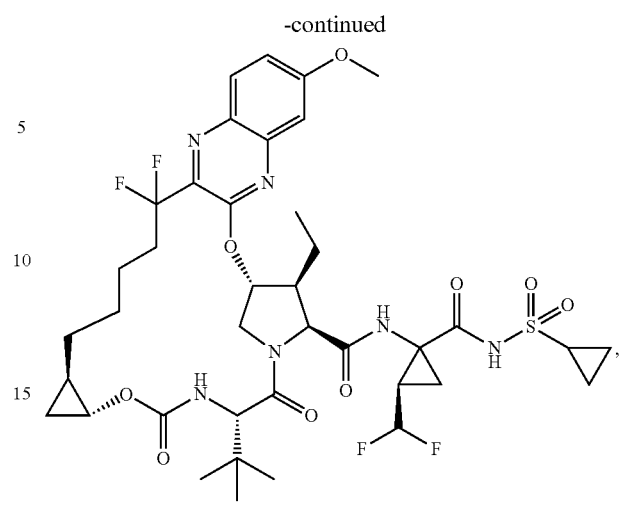
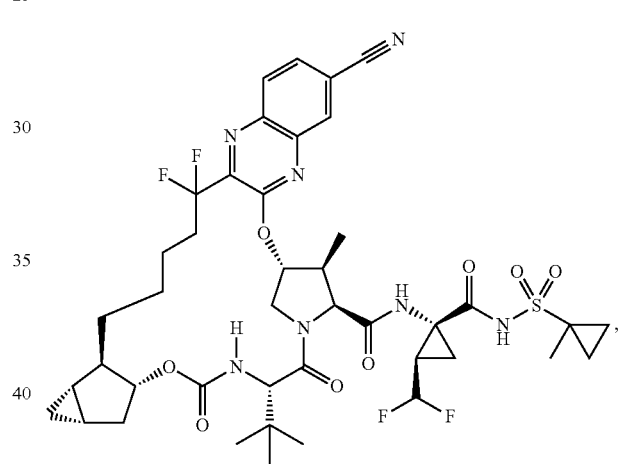
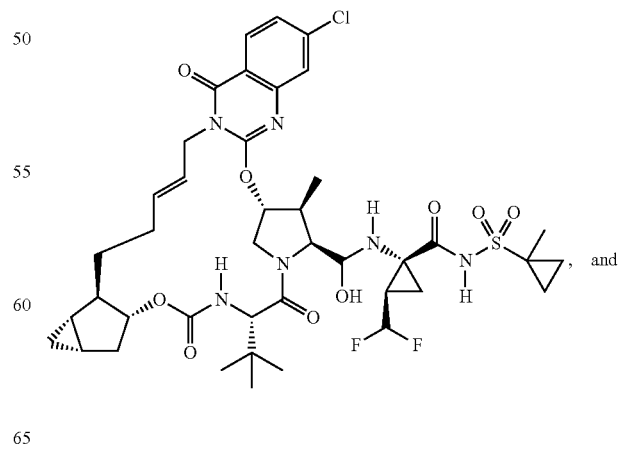
, and -continued

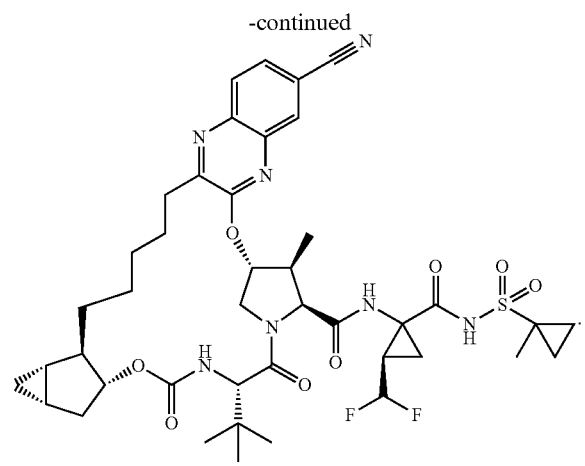

In one embodiment, a compound of Formula IVa, or a pharmaceutically acceptable salt thereof, is provided:

(IVa)

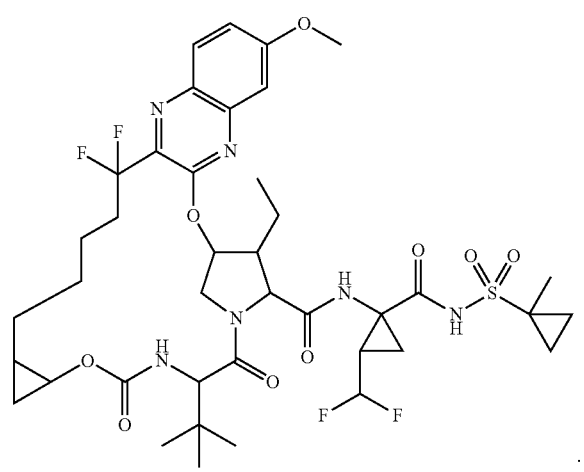

In one embodiment, a compound of Formula IVb: or a pharmaceutically acceptable salt thereof, is provided:

(IVb)

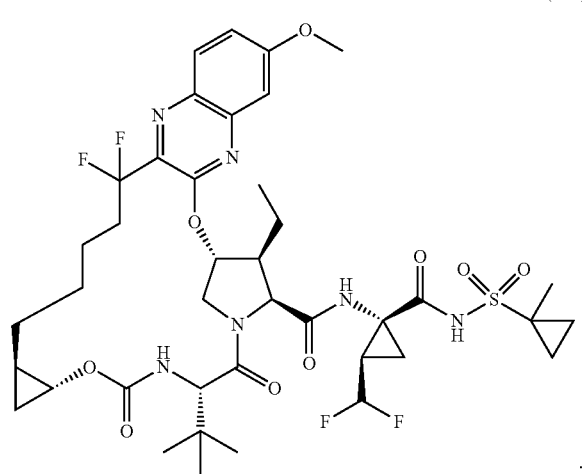

In one embodiment, a compound of Formula IVc. or a pharmaceutically acceptable salt thereof, is provided (IVc)

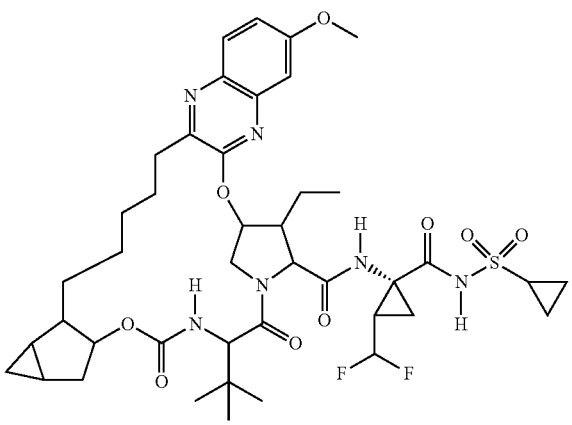

In one embodiment, a compound of Formula IVd, or a pharmaceutically acceptable salt thereof, is provided:

(IVd)

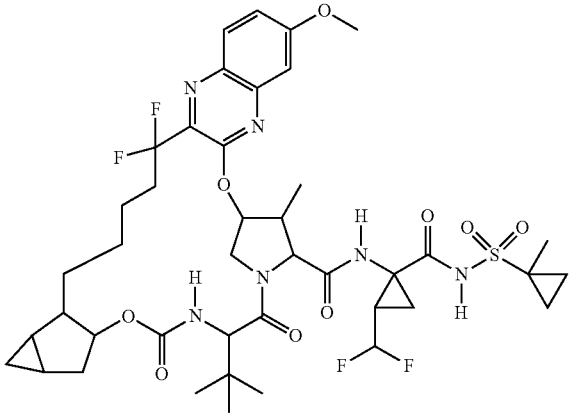

In one embodiment, a compound of Formula IVe, or a pharmaceutically acceptable salt thereof, is provided:

(IVe)

In one embodiment, a compound of Formula IVf, or a pharmaceutically acceptable salt thereof, is provided:

(IVf)

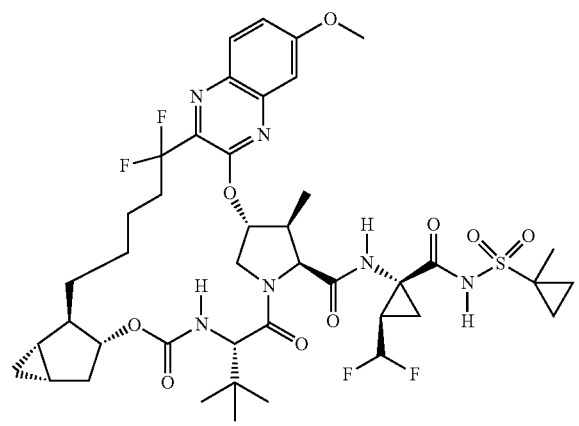

In one embodiment, a compound of Formula IVg, or a pharmaceutically acceptable salt thereof, is provided:

(IVg)

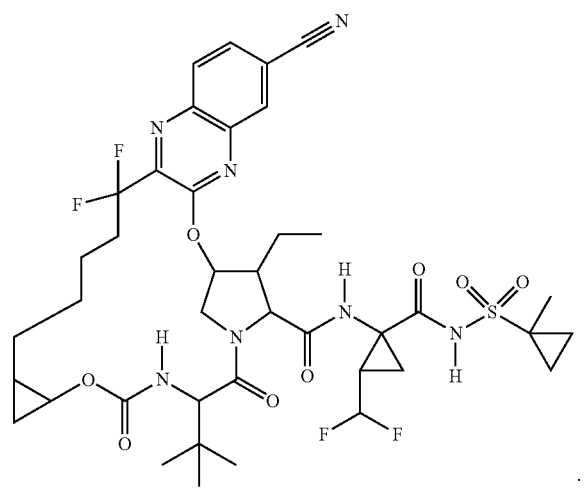

In one embodiment, a compound of Formula IVh, or a pharmaceutically acceptable salt thereof, is provided:

(IVh)

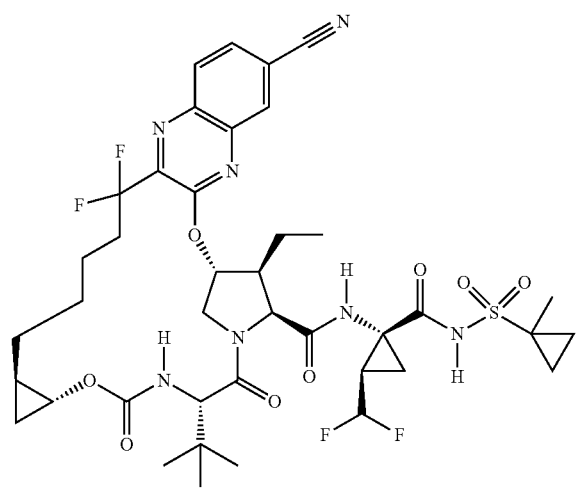

In one embodiment, a compound of any one of Formula IVa, IVb, IVc, IVd, IVe, IVf, IVg, or IVh, or a stereoisomer, or a mixture of stereoisomers, or a pharmaceutically acceptable salt thereof, is provided.

Methods of Treatment

One embodiment provides a method for treating a Flaviviridae viral infection (e.g., an HCV viral infection) in a patient in need thereof (e.g., a mammal such as a human). The method includes administering a compound of Formula I, II III or IV (such as any one of IVa-IVh), or a stereoisomer, or a mixture of stereoisomers, or a pharmaceutically acceptable salt thereof, to the patient.

One embodiment provides a method for inhibiting the proliferation of the HCV virus, treating HCV infection or delaying the onset of HCV symptoms in a patient in need thereof (e.g., a mammal such as a human). The method includes administering a compound of Formula I, II, III or IV (such as any one of IVa-IVh), or a stereoisomer, or a mixture of stereoisomers, or a pharmaceutically acceptable salt thereof, to the patient.

One embodiment provides a compound of Formula I, II, III or IV (such as any one of IVa-IVh), or a stereoisomer, or a mixture of stereoisomers, or a pharmaceutically acceptable salt thereof for use in medical therapy (e.g., for use in treating a Flaviviridae viral infection (e.g., an HCV viral infection) or the proliferation of the HCV virus or delaying the onset of HCV symptoms in a patient (e.g., a mammal such as a human).

One embodiment provides a compound of Formula I, II, III, or IV (such as any one of IVa-IVh) or a stereoisomer, or a mixture of stereoisomers, or a pharmaceutically acceptable salt thereof for use in the manufacture of a medicament for treating a Flaviviridae viral infection (e.g., an HCV viral infection) or the proliferation of the HCV virus or delaying the onset of HCV symptoms in a patient in need thereof (e.g., mammal such as a human).

One embodiment provides a compound of Formula I, II, III, or IV (such as any one of IVa-IVh), or a stereoisomer, or a mixture of stereoisomers, or a pharmaceutically acceptable salt thereof, for use in the prophylactic or therapeutic treatment of the proliferation of a Flaviviridae virus, an HCV virus or for use in the therapeutic treatment of delaying the onset of HCV symptoms.

One embodiment provides a compound of Formula I, II, III or IV (such as any one of IVa-IVh) or a stereoisomer, or a mixture of stereoisomers, or a pharmaceutically acceptable salt thereof, for use in the prophylactic or therapeutic treatment of a Flaviviridae virus infection (e.g., an HCV virus infection).

One embodiment provides the use of a compound of Formula I, II, III or IV (such as any one of IVa-IVh), or a stereoisomer, or a mixture of stereoisomers, or a pharmaceutically acceptable salt thereof, for the manufacture of a medicament for a Flaviviridae virus infection (e.g., an HCV virus infection) in a mammal (e.g., a human).

In certain embodiments, a method of treating chronic hepatitis C infection is provided. The method includes administering to a patient in need thereof, a compound of Formula I, II III or IV (such as any one of IVa-IVh), or a stereoisomer, or a mixture of stereoisomers, or a pharmaceutically acceptable salt thereof, to the patient.

In certain embodiments, a method of treating hepatitis C infection in treatment-naïve patients is provided. The method includes administering to a treatment-naïve patient, a compound of Formula I, II III or IV (such as any one of IVa-IVh), or a stereoisomer, or a mixture of stereoisomers, or a pharmaceutically acceptable salt thereof.

In certain embodiments, a method of treating hepatitis C infection in treatment-experienced patients is provided. The method includes administering to a treatment-experienced patient, a compound of Formula I, II III or IV (such as any one of IVa-IVh), or a stereoisomer, or a mixture of stereoisomers, or a pharmaceutically acceptable salt thereof.

In certain embodiments, a method of treating hepatitis C infection in an interferon ineligible or an interferon intolerant patient is provided. The method includes administering, a compound of Formula I, II III or IV (such as any one of IVa-IVh), or a stereoisomer, or a mixture of stereoisomers, or a pharmaceutically acceptable salt thereof, to the patient.

In certain embodiments, the methods of treatment described herein include administering the compound of Formula I, II III or IV (such as any one of IVa-IVh), or a stereoisomer, or a mixture of stereoisomers, or a pharmaceutically acceptable salt thereof, to the patient for a fixed period of duration. In some embodiments, the fixed period of duration is 4 weeks, 6 weeks, 8 weeks, 10 weeks or 12 weeks. In other embodiments, the fixed period of duration is not more than 12 weeks.

In some embodiments, the compound is administered for about 12 weeks. In further embodiments, the compound is administered for about 12 weeks or less, for about 10 weeks or less, for about 8 weeks or less, for about 6 weeks or less, or for about 4 weeks or less.

The compound may be administered once daily, twice daily, once every other day, two times a week, three times a week, four times a week, or five times a week.

In certain embodiments, the methods of treatment described herein includes administering a compound of Formula I, II III or IV (such as any one of IVa-IVh), or a stereoisomer, or a mixture of stereoisomers, or a pharmaceutically acceptable salt thereof, to is infected with HCV genotype (GT) 1, 2, 3, 4, 5, or 6 (i.e., a method for treating a GT 1, 2, 3, 4, 5, or 6 HCV infection).

One embodiment provides a method for treating an HCV infection in a patient in need thereof (e.g., a mammal such as a human), wherein the patient is infected with HCV genotype 1. The method includes administering a compound of Formula I, II III or IV (such as any one of IVa-IVh), or a stereoisomer, or a mixture of stereoisomers, or a pharmaceutically acceptable salt thereof, to the patient.

One embodiment provides a method for treating an HCV infection in a patient in need thereof (e.g., a mammal such as a human), wherein the patient is infected with HCV genotype 2. The method includes administering a compound of Formula I, II III or IV (such as any one of IVa-IVh), or a stereoisomer, or a mixture of stereoisomers, or a pharmaceutically acceptable salt thereof, to the patient.

One embodiment provides a method for treating an HCV infection in a patient in need thereof (e.g., a mammal such as a human), wherein the patient is infected with HCV genotype 3. The method includes administering a compound of Formula I, II III or IV (such as any one of IVa-IVh), or a stereoisomer, or a mixture of stereoisomers, or a pharmaceutically acceptable salt thereof, to the patient.

One embodiment provides a method for treating an HCV infection in a patient in need thereof (e.g., a mammal such as a human), wherein the patient is infected with HCV genotype 4. The method includes administering a compound of Formula I, II III or IV (such as any one of IVa-IVh), or a stereoisomer, or a mixture of stereoisomers, or a pharmaceutically acceptable salt thereof, to the patient.

One embodiment provides a method for treating an HCV infection in a patient in need thereof (e.g., a mammal such as a human), wherein the patient is infected with HCV genotype 5. The method includes administering a compound of Formula I, II III or IV (such as any one of IVa-IVh), or a stereoisomer, or a mixture of stereoisomers, or a pharmaceutically acceptable salt thereof, to the patient.

One embodiment provides a method for treating an HCV infection in a patient in need thereof (e.g., a mammal such as a human), wherein the patient is infected with HCV genotype 6. The method includes administering a compound of Formula I, II III or IV (such as any one of IVa-IVh), or a stereoisomer, or a mixture of stereoisomers, or a pharmaceutically acceptable salt thereof, to the patient.

In the methods of treatment described herein, the administering step includes administering a therapeutically effective amount of a compound of Formula I, II III or IV (such as any one of IVa-IVh), or a stereoisomer, or a mixture of stereoisomers, or a pharmaceutically acceptable salt thereof, to the patient in need of treatment.

In certain embodiments, methods of inhibiting the activity of HCV are provided. Such methods include the step of treating a sample suspected of containing HCV with a compound or composition disclosed herein.

In one embodiment, compounds disclosed herein act as inhibitors of HCV, as intermediates for such inhibitors or have other utilities as described below.

In certain embodiments, compounds binding in the liver may bind with varying degrees of reversibility.

In one embodiment, a method for treating HCV includes adding a compound disclosed herein to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of conditions associated with HCV activation in animals or in humans.

Pharmaceutical Formulations

"Pharmaceutically-acceptable" means suitable for use in pharmaceutical preparations, generally considered as safe for such use, officially approved by a regulatory agency of a national or state government for such use, or being listed in the U. S. Pharmacopoeia or other generally recognized pharmacopoeia for use in animals, and more particularly in humans.

"Pharmaceutically-acceptable carrier" refers to a diluent, adjuvant, excipient, or carrier, or other ingredient which is pharmaceutically-acceptable and with which a compound of the invention is administered.

The compounds of this invention are formulated with conventional carriers (e.g., inactive ingredient or excipient material), which will be selected in accordance with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipient, etc.) which constitutes one or more accessory ingredients. In general the formulations are prepared by uniformly and intimately bringing into association the active ingredient with liquid carriers or finely divided solid carriers or both, and then, if necessary, shaping the product.

In certain embodiments, formulations suitable for oral administration are presented as discrete units such as capsules, cachets or tablets each containing a predetermined amount of the active ingredient.

In certain embodiments, the pharmaceutical formulations include one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight, weight). In some embodiments, the pharmaceutical compositions described herein contain about 1 to 800 mg, 1 to 600 mg, 1 to 400 mg, 1 to 200 mg, 1 to 100 mg or 1 to 50 mg of the compound of Formula I, II, III or IV (such as any one of IVa-IVh), or a stereoisomer, or a mixture of stereoisomers, or a pharmaceutically acceptable salt thereof. In some embodiments, the pharmaceutical compositions described herein contain not more than about 400 mg of the compound of Formula I, II, III or IV (such as any one of IVa-IVh), or a stereoisomer, or a mixture of stereoisomers, or a pharmaceutically acceptable salt thereof. In some embodiments, the pharmaceutical compositions described herein contain about 100 mg of the compound of Formula I, II, III, or IV (such as any one of IVa-IVh), or a stereoisomer, or a mixture of stereoisomers, or a pharmaceutically acceptable salt thereof.

It should be understood that in addition to the ingredients particularly mentioned above the formulations disclosed herein may include other agents conventional in the art having regard to the type of formulation in question, for example those suitable for oral administration may include flavoring agents.

Veterinary compositions comprising at least one active ingredient as above defined together with a veterinary carrier are further provided.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of Formulas I, II, III, or IV (such as any one of IVa-IVh) (herein referred to as the active ingredients), or a pharmaceutically acceptable salt thereof, are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally. Accordingly, in one embodiment, the pharmaceutical compositions described herein are oral dosage forms. In certain embodiments, the pharmaceutical compositions described herein are oral solid dosage forms.

One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

Combination Therapy

In yet another embodiment, the present application discloses pharmaceutical compositions comprising a compound of Formulas I, II, III, or IV (such as any one of IVa-IVh), or a pharmaceutically acceptable salt thereof, in combination with at least one additional therapeutic agent (i.e., active ingredient), and a pharmaceutically acceptable carrier or excipient. In certain embodiments, additional therapeutic agents include additional antiviral agents.

The additional therapeutic agent used in combination with the compounds described herein includes, without limitation, any agent having a therapeutic effect when used in combination with the compound of the present invention. Such combinations are selected based on the condition to be treated, cross-reactivities of ingredients and pharmaco-properties of the combination. For example, in certain embodiments, the therapeutic agent used in combination with the compounds of Formulas I, II, III, or IV (such as any one of IVa-IVh) include, without limitation, one of more of the following: interferons, ribavirin analogs, NS3 protease inhibitors, NS5a inhibitors, NS5b inhibitors, alpha-glucosidase 1 inhibitors, hepatoprotectants, non-nucleoside inhibitors of HCV, nucleoside analogues, and other drugs for treating HCV infection. In some embodiments, the additional therapeutic agents include, without limitation, NS3 protease inhibitors, NS5a inhibitors, and/or NS5b inhibitors. In some embodiments, a pharmaceutical composition including a compound of Formulas I, II, III, or IV (such as any one of IVa-IVh), or a pharmaceutically acceptable salt thereof and one or more of an NS3 protease inhibitor, an NS5a inhibitor, and/or an NS5b inhibitor is provided. In some embodiments, a pharmaceutical composition including a compound of Formulas I, II, III, or IV (such as any one of IVa-IVh), or a pharmaceutically acceptable salt thereof and one or more of an NS5a inhibitor and/or an NS5b inhibitor is provided. In certain embodiments, pharmaceutical compositions is provided which includes a compound of Formulas I, II, III, or IV (such as any one of IVa-IVh) and one or more additional antiviral agents, wherein the additional antiviral agent is not an interferon, ribavirin, or a ribavirin analogue. In further embodiments, pharmaceutical compositions is provided which includes a compound of Formulas I, II, III, or IV (such as any one of IVa-IVh), or a stereoisomer, or a mixture of stereoisomers, and one or more additional antiviral agents, wherein the additional antiviral agent is not ribavirin or a ribavirin analogue.

In certain embodiments, the compounds disclosed herein are combined with one or more other active ingredients (e.g., one or more additional antiviral agents) in a unitary dosage form for simultaneous or sequential administration to a patient. The combination therapy may be administered as a simultaneous or sequential regimen. When administered sequentially, the combination is administered in two or more administrations. In certain embodiments, the active ingredients are: (1) co-formulated and administered or delivered simultaneously in a combined pharmaceutical composition; (2) delivered by alternation or in parallel as separate pharmaceutical composition; or (3) by some other regimen. When delivered in alternation therapy, the active ingredients are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Exemplary interferons include, without limitation, pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmune.

Exemplary ribavarin analogs include, without limitation, ribavirin (Rebetol, Copegus), levovirin VX-497, and taribavirin (Viramidine).

Exemplary NS5A inhibitors include, without limitation, ledipasvir (GS-5885). GS-5816, JNJ-47910382, daclatasvir (BMS-790052), ABT-267, MK-8742, EDP-239, IDX-719, PPI-668, GSK-2336805, ACH-3102, A-831, A-689, AZD-2836 (A-831), AZD-7295 (A-689), and BMS-790052.

Exemplary NS5B inhibitors include, without limitation, polymerase inhibitor is sofosbuvir (GS-7977), tegobuvir (GS-9190), GS-9669, TMC647055, ABT-333, ABT-072, setrobuvir (ANA-598), filibuvir (PF-868554), VX-222, IDX-375, IDX-184, IDX-102, BI-207127, valopicitabine (NM-283), R1626, PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A848837, GL59728, A-63890, A-48773, A-48547, BC-2329, BMS-791325, and BILB-1941.

Exemplary NS3 protease inhibitors include, without limitation, GS-9451, GS-9256, simeprevir (TMC-435), ABT-450, boceprevir (SCH-503034), narlaprevir (SCH-900518), vaniprevir (MK-7009), MK-5172, danoprevir (ITMN-191), sovaprevir (ACH-1625), necepravir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061.

Exemplary alpha-glucosidase 1 inhibitors include, without limitation, celgosivir (MX-3253), Miglitol, and UT-231B.

Exemplary hepatoprotectants include, without limitation, IDN-6556, ME 3738, MitoQ, and LB-84451.

Exemplary non-nucleoside inhibitors of HCV include, without limitation, benzimidazole derivatives, benzo-1,2,4-thiadiazine derivatives, and phenylalanine derivatives.

Exemplary nucleoside analogues include, without limitation, ribavirin, viramidine, levovirin, a L-nucleoside, or isatoribine and said interferon is α-interferon or pegylated interferon.

Exemplary other drugs for treating HCV infection include, without limitation, imiquimod, 852A, GS-9524, ANA-773, ANA-975, AZD-8848 (DSP-3025), PF-04878691, and SM-360320, cyclophillin inhibitors (e.g., DEBIO-025, SCY-635, or NIM811) or HCV IRES inhibitors (e.g., MCI-067); emericasan (IDN-6556), ME-3738, GS-9450 (LB-84451), silibilin, or MitoQ, BAS-100, SPI-452, PF-4194477, TMC-41629, GS-9350, GS-9585, and roxythromycin.

Additional exemplary other drugs for treating HCV infection include, without limitation, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811.

Still further exemplary other drugs for treating HCV infection include, without limitation, thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18. VGX-410C, EMZ-702, AVI 4065, BMS-650032, Bavituximab, MDX-1106 (ONO-4538), Oglufanide, FK-788, VX-497 (merimepodib), DEBIO-025, ANA-975 (isatoribine), XTL-6865, or NIM811.

General Synthetic Procedures

The schemes, procedures, and examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

The following schemes describe methods that are useful for preparing compounds disclosed herein.

$L_F$ is a "linker fragment," (that is to say, a precursor to L) wherein an attached unsaturated carbon-carbon bond (e.g. alkene or alkyne) at the portion of $L_F$ distal to ☉ facilitates, as a non-limiting example, a metal catalyzed reaction that results in the connection of $L_F$ to U to form an L group. Non-limiting examples of metal catalyzed reactions that result in such a connection include Ru catalyzed ring closing metathesis or a Pd catalyzed cross coupling reaction (e.g. Negishi, Heck, or Sonagashira couplings).

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents used in nuclear magnetic resonance experiments. $CDCl_3$, deuterochloroform; $CD_3OD$, perdeuteromethanol; $CD_3CN$, perdeuteroacetonitrile; $d_6$-DMSO, perdeuterodimethylsulfoxide. Mass spectra were obtained using Thermo Scientific or Agilent Technologies mass spectrometers equipped with electrospray ionisation (ESI). Masses are reported as ratios of mass to charge (m/z) of, for example, an ion of the compound (represented by $[M]^+$), an ion formed from the compound with another ion, such as a hydrogen ion (represented by $[M+H]^+$), a sodium ion (represented by $[M+Na]^+$), an ion formed from the compound by losing an ion, such as the deprotonated compound (represented by $[M-H]^-$), etc. Analytical HPLC measurements were performed on Agilent Technologies Series 1100 HPLC using Phenomenex Kinetex C18, 2.6 um 100 Å, 4.6×100 mm column with an elution program of 2% Solvent B for 0.55 min, gradient to 98% solvent B over 8 min which is maintained at 98% solvent B for 0.40 min before returning to 2% solvent B over 0.02 min and maintaining at 2% solvent B for 2.03 min at a flow rate of 1.5 mL/min (Solvent A=MiliQ filtered $H_2O$+0.1% TFA, Solvent B=MeCN+0.1% TFA). The term "thin layer chromatography (TLC)" refers to silica gel chromatography using silica gel 60 $F_{254}$ plates. The retention factor ("$R_f$") of a compound is the distance travelled by a compound divided by the distance travelled by the solvent front on a TLC plate. Terms such as "early eluting" and "late eluting" refer to the order in which a compound elutes or is recovered from a solid stationary phase/liquid solvent mobile phase based chromatography method (e.g. normal phase silica gel chromatography or reverse phase high pressure liquid chromatography (HPLC)).

Scheme 1

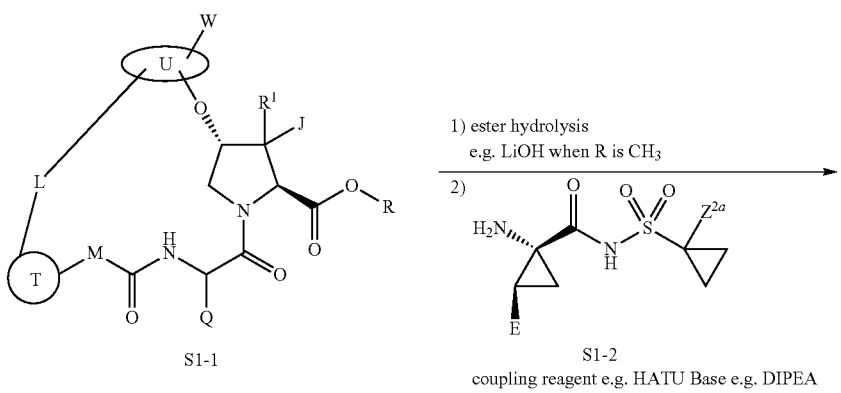

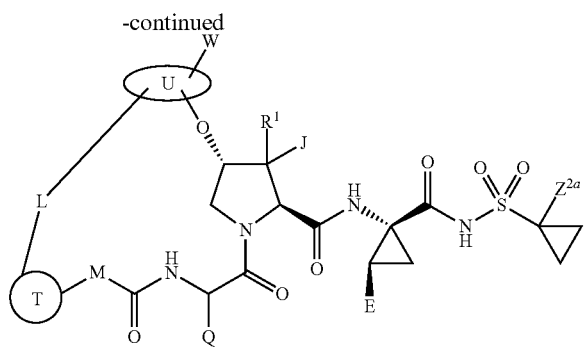

S1-3

Where: R = alkyl

Scheme 1 demonstrates a general route to S1-3, where J, $R^1$, R, M, L T, U, W and Q are as defined herein, $Z^{2a}$ is as defined in Formula IV or III, or is H or $Z^{2a}$ as defined in Formula I or II. In scheme 1, ester intermediate S1-1 is hydrolyzed with a base such as lithium hydroxide when R is $C_1$-$C_3$ alkyl (e.g., methyl), or with acid such as trifluoroacetic acid when R is tert-butyl. The product of the ester hydrolysis is then coupled to an intermediate S1-2 through a coupling reaction (e.g. using a peptide coupling agent such as HATU and a base such as DIPEA) to generate compounds of the general structure S1-3.

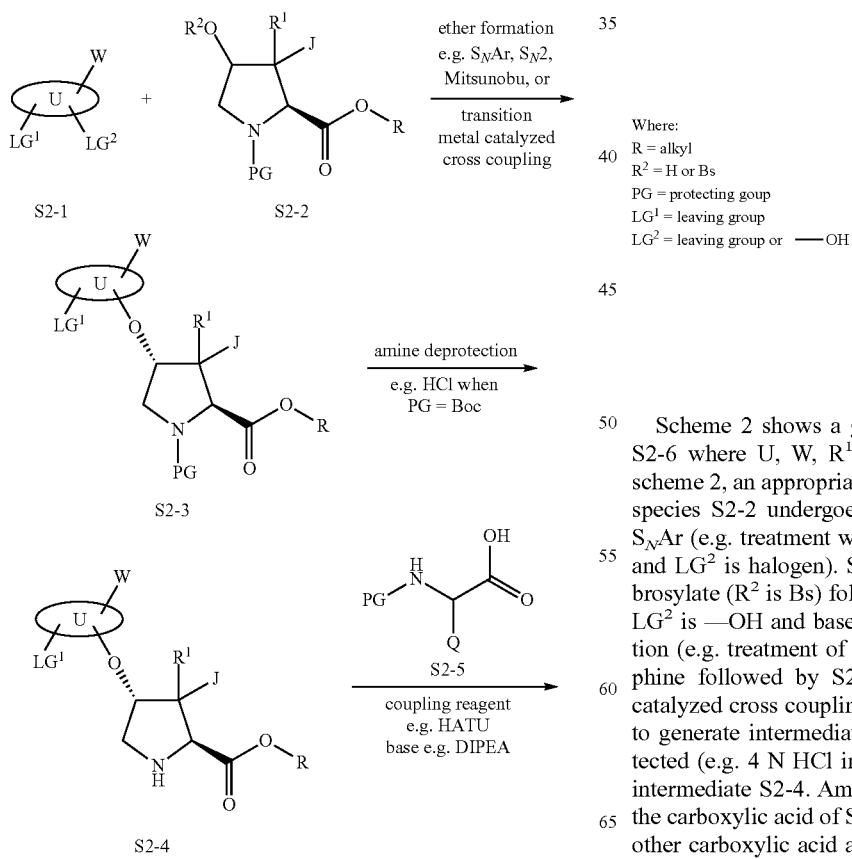

Scheme 2

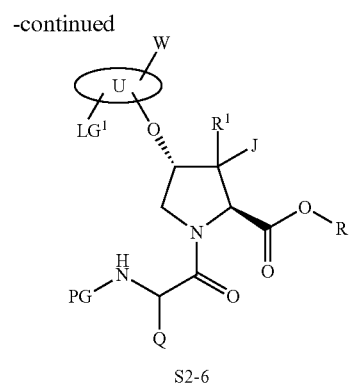

S2-6

Where:
R = alkyl
$R^2$ = H or Bs
PG = protecting goup
$LG^1$ = leaving group
$LG^2$ = leaving group or ——OH Scheme 2 shows a general synthesis of an intermediate S2-6 where U, W, $R^1$, J, and Q are as defied herein. In scheme 2, an appropriately substituted and protected proline species S2-2 undergoes an etherification reaction such as $S_N Ar$ (e.g. treatment with $Cs_2CO_3$ and S2-1 where $R^2$ is H and $LG^2$ is halogen), $S_N 2$ (e.g. preconversion of S2-2 to a brosylate ($R^2$ is Bs) followed by treatment with S2-1 where $LG^2$ is —OH and base such as DABCO), Mitsunobu reaction (e.g. treatment of S2-2 with DIAD and triphenylphosphine followed by S2-1 where $LG^2$ is —OH) or metal catalyzed cross coupling reaction ($LG^2$ is halogen, $R^2$ is H) to generate intermediate S2-3. Intermediate S2-3 is deprotected (e.g. 4 N HCl in dioxane when PG is Boc) to make intermediate S2-4. Amide bond formation via activation of the carboxylic acid of S2-5 using peptide coupling agents or other carboxylic acid activation methods prior to treatment of S2-4 provides intermediate S2-6.

Scheme 3

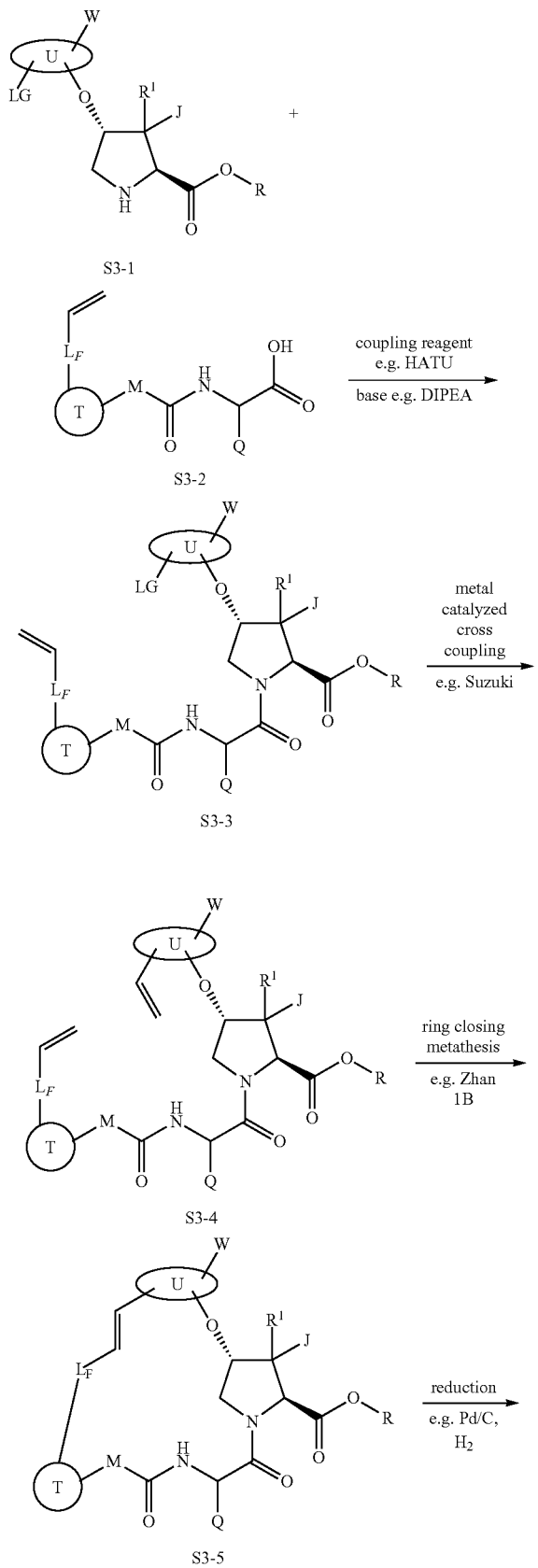

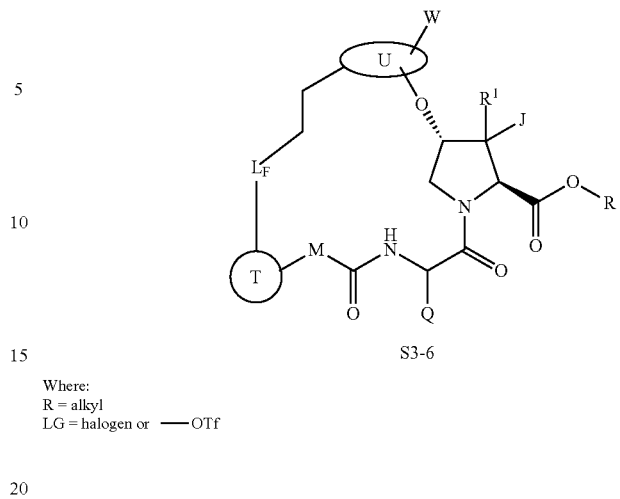

Where:
R = alkyl
LG = halogen or —OTf

Scheme 3 shows a general synthesis of intermediate S3-6 where $L_F$-CH$_2$—CH$_2$ is L, and U, W, R$^1$, J, Q, M, T, and L are as defied herein. In scheme 3, an intermediate S3-1 is coupled via amide bond formation reaction to an intermediate S3-2 to provide intermediate S3-3. Metal catalyzed cross-coupling (e.g. Suzuki reaction using potassium vinyltrifluoroborate, Et$_3$N, Pd(dppf)Cl$_2$) to give S3-4, followed by ring closing metathesis (e.g. Zhan 1B) to give S3-5, followed by reduction of the double bond (e.g. H$_2$, 10% Pd/C) provides intermediate S3-6.

Scheme 4

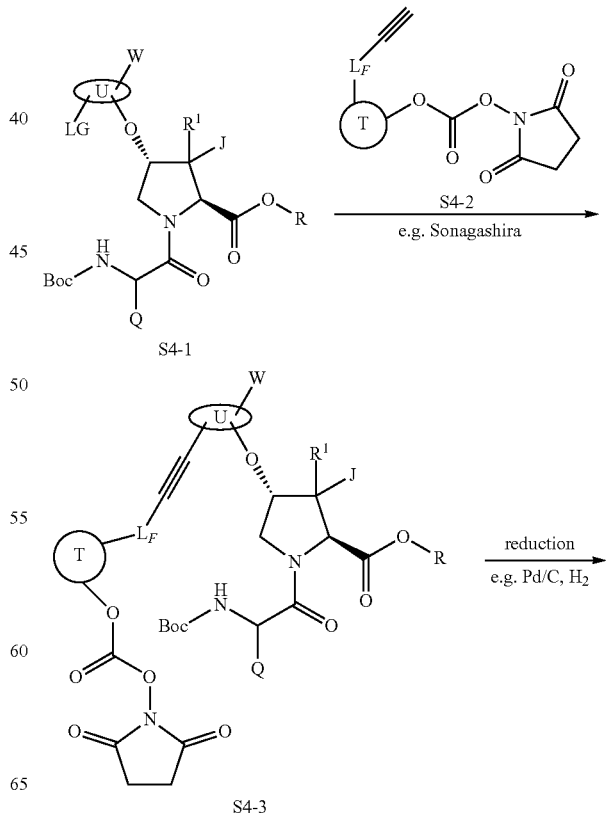

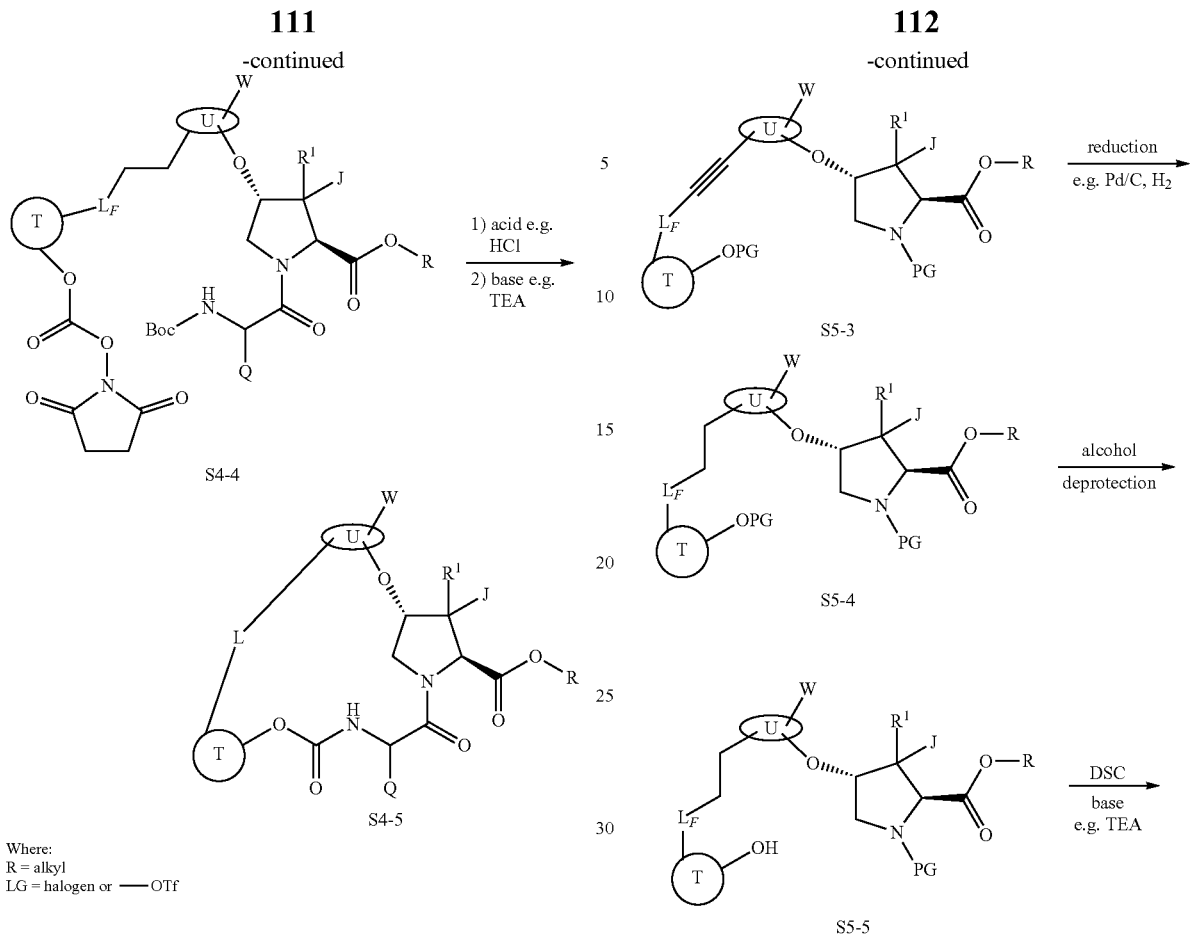

S4-4

S4-5

Where:
R = alkyl
LG = halogen or —OTf

Scheme 4 shows a general synthesis of an intermediate S4-5 where $L_F\text{-CH}_2\text{—CH}_2$ is L, and U, W, $R^1$, J, Q, Q and L are as defied herein. In scheme 4, intermediate S4-1 is protected with a protecting group such as Boc. S4-1 undergoes a transition metal catalyzed cross coupling (e.g. Sonogashira coupling) to an intermediate S4-2 to provide intermediate S4-3. The triple bond of intermediate S4-3 is reduced to a single bond by hydrogenation (e.g. $H_2$, catalytic 10% Pd/C) to give intermediate S4-4. Deprotection of the Boc-amine followed by coupling under basic conditions (e.g. triethylamine) provides intermediate S4-5.

Scheme 5

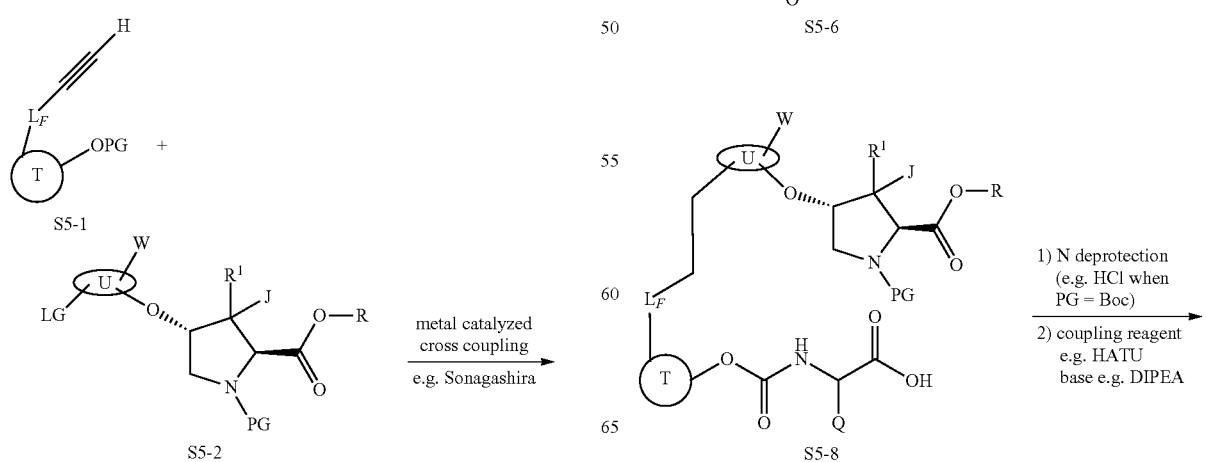

-continued

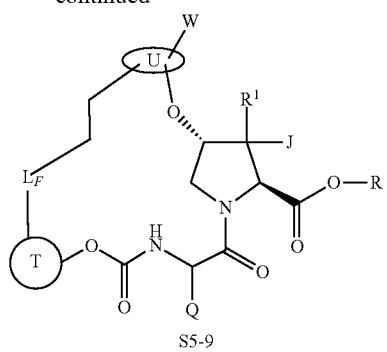

S5-9

Where:
LG = halogen, —OTf
R = alkyl
PG = protecting group

Scheme 5 shows a general synthesis of an intermediate S5-9 where $L_F\text{-}CH_2\text{---}CH_2$ is L, and U, W, $R^1$, J, Q, T and L are as defied herein. In scheme 5 intermediate S5-1 undergoes a metal catalyzed cross coupling (such as Sonogashira reaction) with an intermediate S5-2 to provide intermediate S5-3, The triple bond of intermediate S5-3 is reduced to a single bond under appropriate conductions such as by hydrogenation (e.g. using $H_2$ over catalytic 10% Pd/C) to give intermediate S5-4. Deprotection of the alcohol to provide S5-5, followed by activation (e.g. DSC under basic conditions, e.g. triethylamine) provides intermediate S5-6. Coupling of S5-6 and S5-7 under basic conditions provides S5-8. Deprotection of the proline nitrogen (e.g. HCl in dioxane when PG=Boc) followed by a macrolactamization (e.g. coupling agent such as HATU under basic conditions) provides intermediate S5-9.

Scheme 6

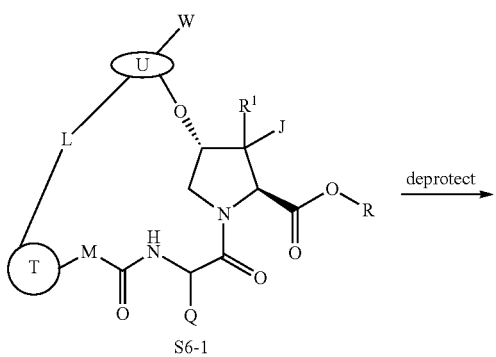

S6-1

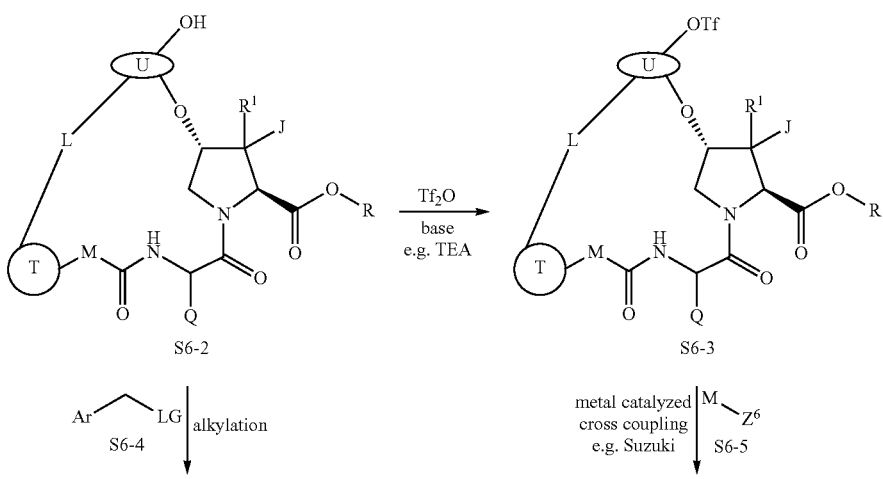

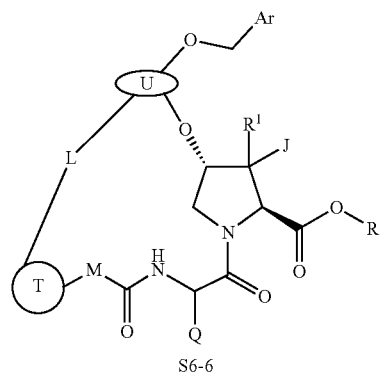

S6-6

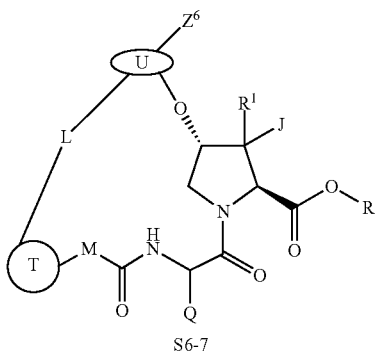

S6-7

Where:
R = alkyl
PG = protecting group
LG = halogen, —OMs, —OTf
Ar = aryl, heteroaryl ring
W = —OPG
$Z^6$ = alkyl, aryl, heteroaryl, heteroalkyl Scheme 6 shows a general synthesis of the intermediates S6-6 and S6-7 where U, $R^1$, J, Q, M, T and L are as defied herein. In scheme 6 intermediate S6-1, W is OPG, where PG is a protecting group. S6-1 is first deprotected to give intermediate S6-2. Alkylation of intermediate S6-2 with an appropriate electrophile such as S6-4 provides intermediate S6-6. Reaction of S6-2 with triflic anhydride provides S6-3, which then undergoes metal catalyzed cross coupling with an appropriate nucleophilic coupling partner such as S6-5 (e.g. Sonagashira or Suzuki reaction) to provide intermediate S6-7.

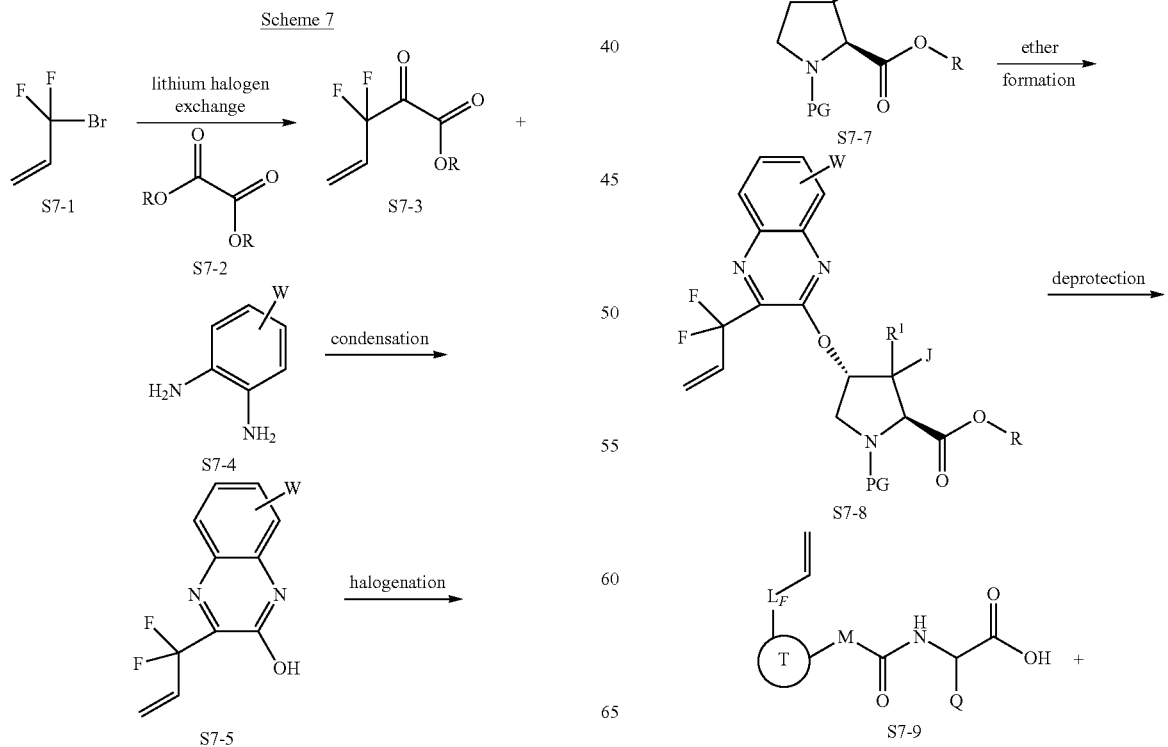

-continued

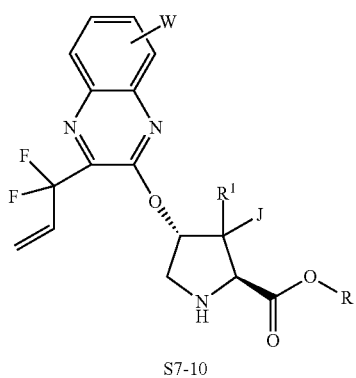

S7-10 coupling reagent
e.g. HATU
⟶
Base
e.g. DIPEA

-continued

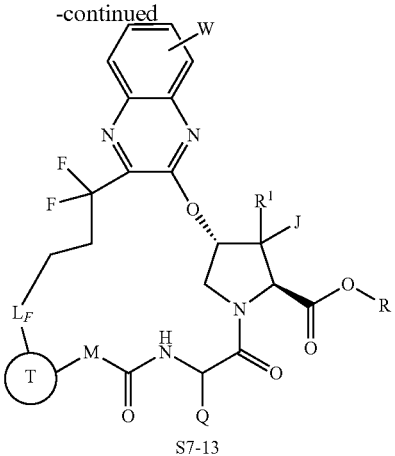

S7-13

Where:
R = alkyl
PG = protecting group
LG = halogen

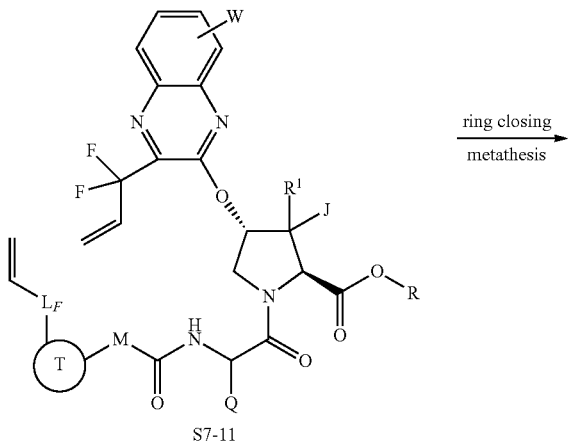

S7-11 ring closing
metathesis
⟶

Scheme 7 shows a general synthesis of intermediate S7-13 where $L_F$-$CH_2$—$CH_2$—$CF_2$ is L, and W, $R^1$, J, Q, M, and T are as defied herein. In S7-13, L is $C_1$-$C_3$ alkyl. In Scheme 7, intermediate S7-1 first undergoes lithium halogen exchange and then is treated with intermediate S7-2 to generate intermediate S7-3, which is then condensed with intermediate S7-4 to provide quinoxaline intermediate S7-5. Halogenation of S7-5 (e.g. $POCl_3$) provides intermediate S7-6. Intermediate S7-6 is attached via an ether formation to intermediate S7-7 through an $S_NAr$ reaction (e.g. $Cs_2CO_3$) to generate intermediate S7-8. Deprotection of the N-PG of intermediate S7-8 provides S7-10. An amide bond coupling reaction of intermediate S7-9 and intermediate S7-10 (e.g. EDC and HOBT, or HATU, NMM, DIPEA) provides intermediate S7-11. Ring closing metathesis of S7-11 generates intermediate S7-12. Reduction of the double bond (e.g. hydrogenation over palladium on carbon) provides intermediate S7-13.

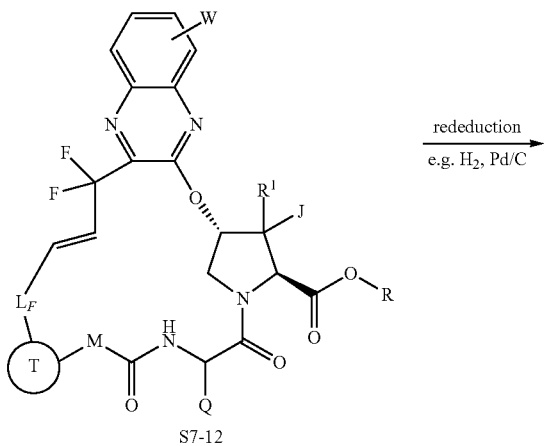

S7-12 rereduction
e.g. $H_2$, Pd/C
⟵

Scheme 8

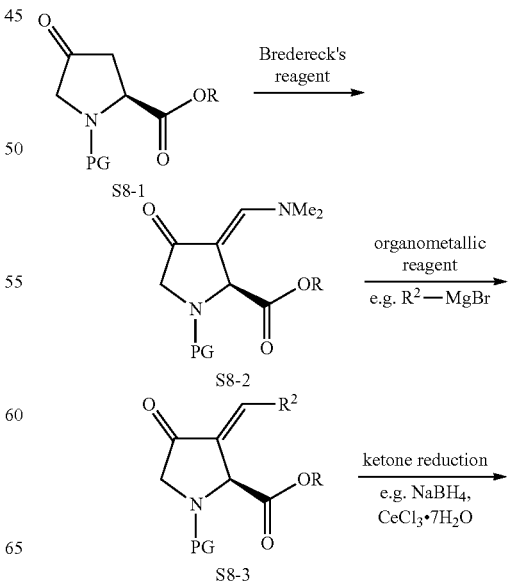

119

-continued

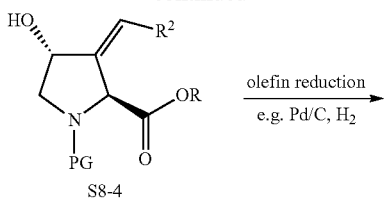

S8-4

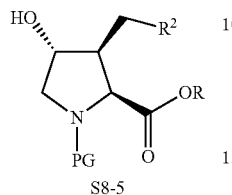

S8-5

Where:
PG = Boc, Pf, etc
R = alkyl
R² = alkyl, aryl, heteroaryl

Scheme 8 shows a general syntheses of intermediate S8-5 wherein an appropriately protected 4-oxo proline S8-1 is reacted with Bredereck's reagent to generate enaminone S8-2. Addition of an organometallic species provides enone S8-3, which undergoes reduction to hydroxyl intermediate S8-4 in a stereoselective manner (e.g. Luche reduction or CBS reduction). Subsequent olefin reduction gives 3-substituted hydroxy proline intermediate S8-5.

Scheme 9

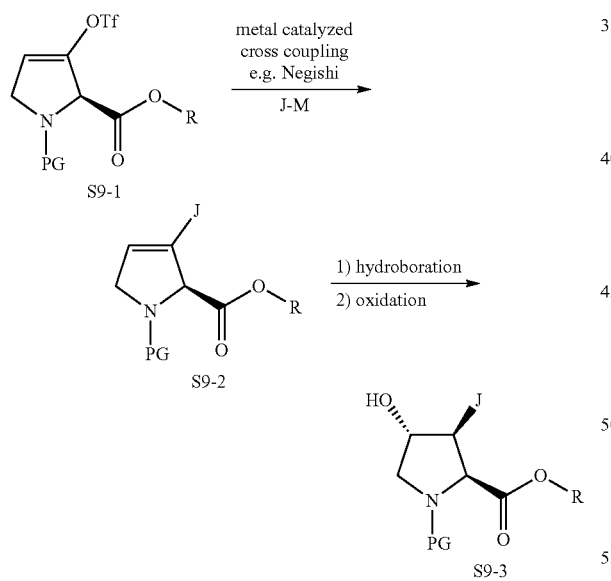

Where:
PG = protecting group
R = alkyl

Scheme 9 shows a general synthesis of intermediate S9-3 wherein a vinyl triflate S9-1 (prepared for example, by methods in Kamenecka, T. M., et al. *Tetrahedron Letters*, 2001, 8571) undergoes metal catalyzed cross coupling (e.g. Negishi coupling) to generate intermediate S9-2. Hydroboration and subsequent oxidation of intermediate S9-2 provides intermediate S9-3.

120

Scheme 10

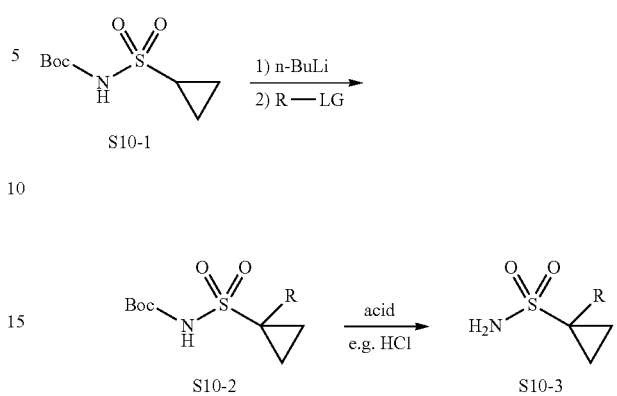

Where:
R = alkyl, haloalkyl, heteroalkyl
LG = halogen, ―OTf, etc.

Scheme 10 shows a general synthesis of substituted sulfonamide intermediate S10-3. Tert-butyl cyclopropylsulfonylcarbamate 810-1 is deprotonated (e.g. n-BuLi) and reacted with an electrophile (e.g. alkyl halide) to give the protected substituted sulfonamide intermediate 510-2, which is then deprotected (e.g. 4 N HCl in dioxane) to provide intermediate S10-3.

Scheme 11

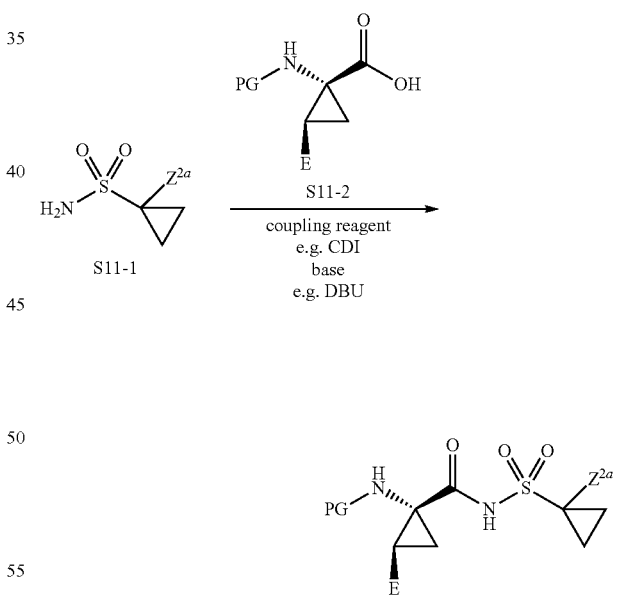

Where:
PG = Boc, etc.

Scheme 11 shows a general synthesis of an intermediate S11-3 where E is as defined herein. In Scheme 11, a sulfonamide S11-1 is coupled to a protected amino acid S11-2 using a coupling agent such as CDI and a base such as DBU, Scheme 12
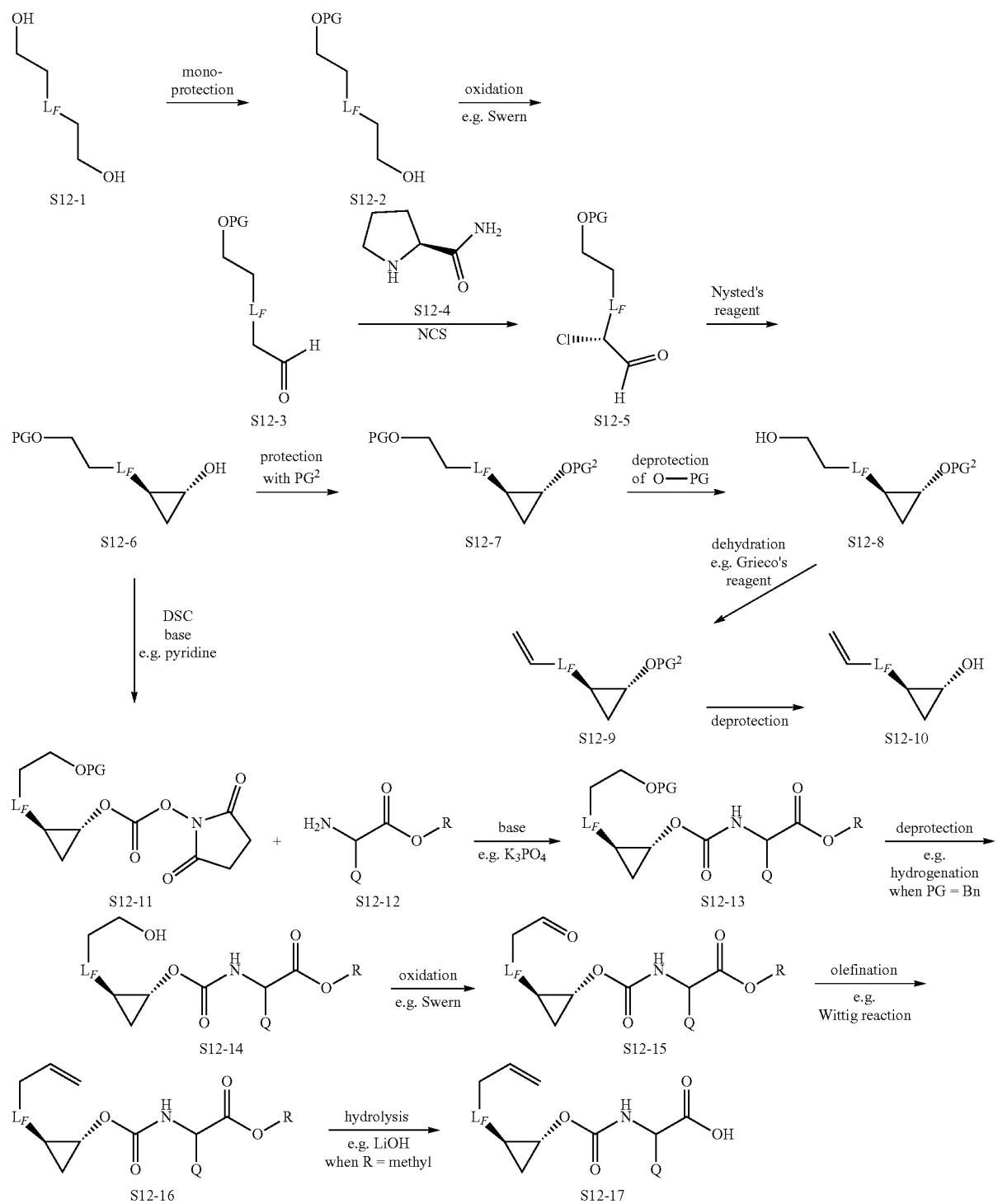
Where:
PG = protecting group
PG² = protecting group orthogonal to PG
R = alkyl
Scheme 12 shows a general synthesis of intermediates S12-10 and S12-17, where $L_F$ is $C_1$-$C_3$ alkylene. In Scheme 12, both syntheses begin with the monoprotection of intermediate S12-1 to produce S12-2, followed by oxidation (e.g.

Swern oxidation) to provide intermediate S12-3. Enantioselective alpha chlorination (e.g. organocatalyst S12-4 and NCS) provides chloroaldehyde S12-5. Reaction of S12-5 with a bis-zinciomethane derivative (e.g. Nysted's reagent) provides cyclopropane intermediate S12-6. Intermediate S12-6 is orthogonally protected to provide intermediate S12-7. Deprotection of —OPG of S12-7 provides intermediate S12-8, which is subsequently dehydrated (e.g. Grieco's reagent) to intermediate S12-9 and finally O-PG$^2$ is removed to afford intermediate S12-10, Intermediate S12-6 is alternatively be activated (e.g. DSC and a base such as pyridine) to provide intermediate S12-11 which is coupled to intermediate S12-12 to provide carbamate intermediate S12-13. Intermediate S12-13 is deprotected to give intermediate S12-14, which is then oxidized (e.g. Swern oxidation) to provide aldehyde intermediate S12-15. Olefination (e.g. Wittig reaction) of intermediate S12-15 provides intermediate S12-16. Ester hydrolysis (e.g. LiOH when R is methyl, TFA when R=tert-butyl) affords intermediate S12-17.

ditions gives ester intermediate S13-4. Ester hydrolysis (e.g. LiOH when R=methyl or TFA when R=tert-butyl) provides intermediate S13-5.

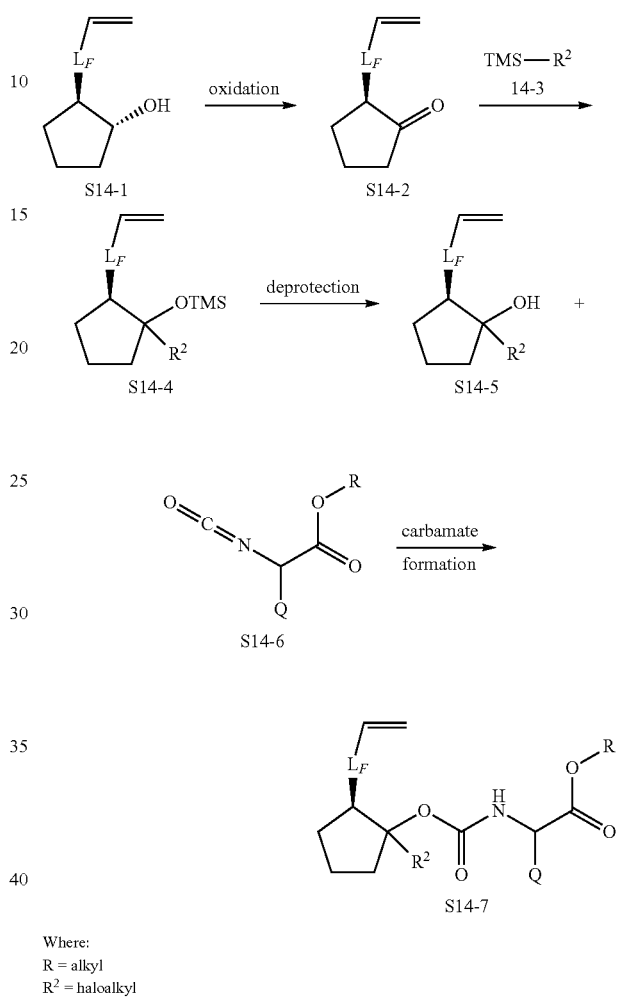

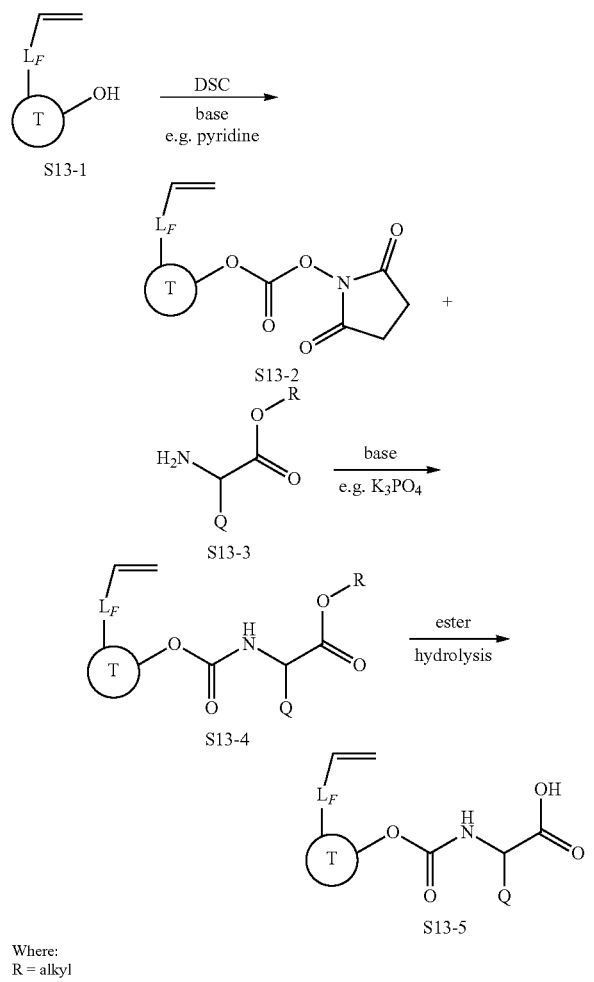

Where:
R = alkyl

Scheme 13 shows a general synthesis of intermediate S13-5 where Q and T are as defined herein and $L_F$ is $C_1$-$C_3$ alkylene. Activation of intermediate S13-1 (e.g. DSC) followed by carbamate formation between intermediate S13-2 and amino acid ester intermediate S13-3 under basic con- Where:
R = alkyl
R$^2$ = haloalkyl Scheme 14 shows a general synthesis of intermediate S14-7 where Q is as defined herein and $L_F$ is $C_1$-$C_3$ alkylene. Oxidation of intermediate S14-1 (e.g. Dess-Martin periodinane) produces ketone S84-2. Treatment of S14-2 with S14-3 (e.g. R$^2$ is —CF$_3$) in the presence of suitable reagent (such as CsF) provides intermediate S14-4. Deprotection of S14-4 (e.g. TBAF) provides S14-5, which is then added to an isocyanate S14-6 to give intermediate S14-7.

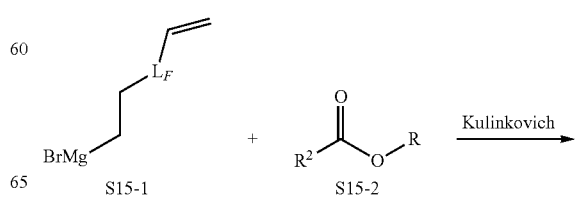

-continued

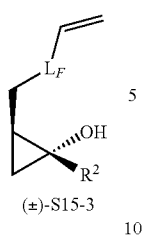

Where:
R = alkyl
R² = alkyl, cycloalkyl

Scheme 15 shows a general synthesis of an intermediate (±)-S15-3, generated from the Kulinkovich reaction of a Grignard reagent S15-1 and an ester S15-2, according to standard procedures as described in Kulinkovich, O. G. and Kananovich, D. G., *Eur. J. Org Chem.* 2007, 2007, 2121.

Scheme 16

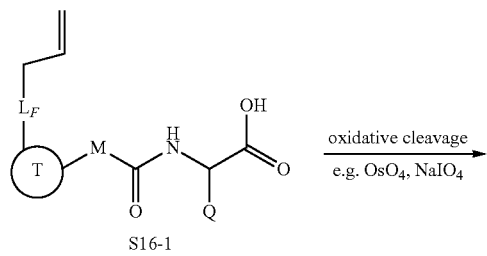

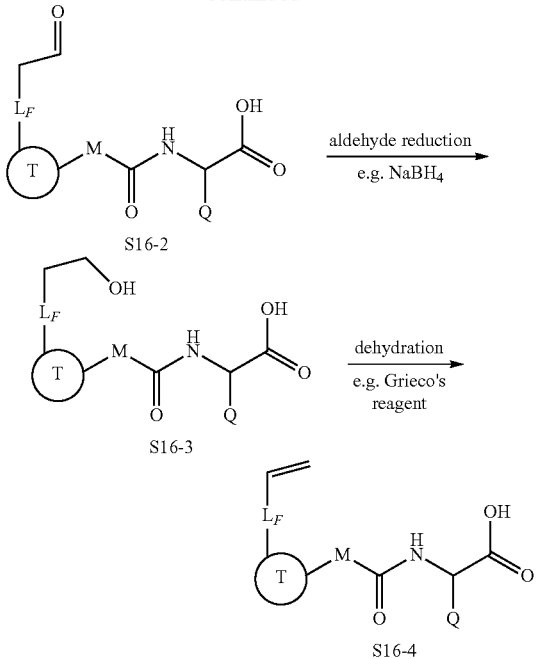

Scheme 16 shows a general synthesis of an intermediate S16-4 where Q, M, and T are as defined herein and $L_F$ is $C_1$-$C_3$ alkylene. In Scheme 16, olefin S16-1 undergoes oxidative cleavage (e.g. $OsO_4$, $NaIO_4$) to aldehyde S16-2, which is then reduced to alcohol S16-3 (e.g. $NaBH_4$) and finally is dehydrated (e.g. Greico elimination) to afford intermediate S16-4.

Scheme 17

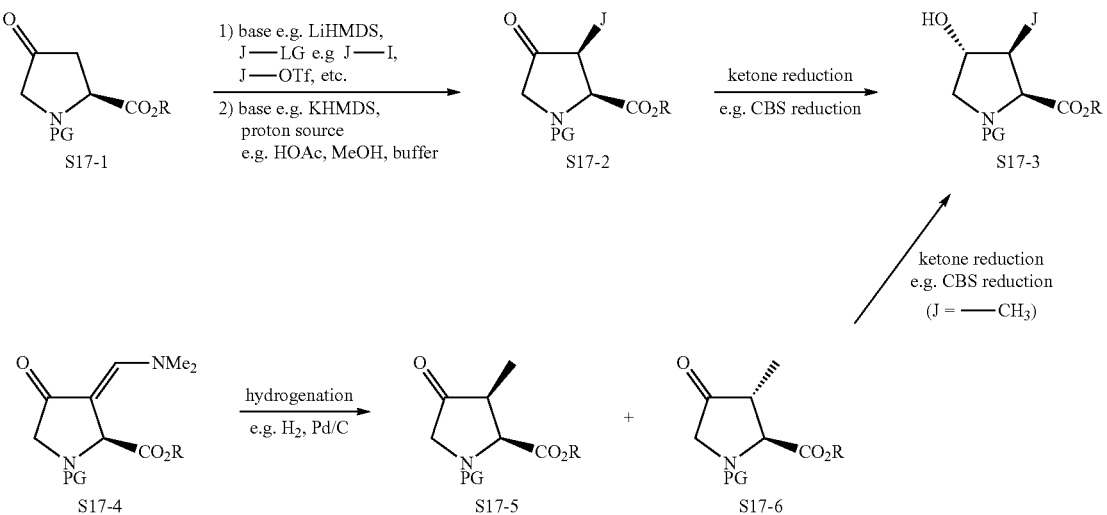

Where:
PG = Pf, Tr, Boc
R = alkyl, benzyl

Scheme 17 shows two general synthetic strategies for producing intermediate S17-3 where J is as defined herein. In Scheme 17, an appropriately protected 4-oxo proline S17-1 is deprotonated and alkylated (e.g. LiHMDS followed by J-LG). A second deprotonation with base followed by re-protonation at low temperature generates stereoenriched intermediate S17-2, based on a described protocol (Blanco, M-J. et. al. *J. Org. Chem.* 1999, 64, 8786). Reduction of the ketone in a stereoselective manner (e.g. CBS reduction) provides alcohol S17-3. Where J is methyl, Scheme 17 shows an alternative general synthesis wherein intermediate S17-4 is hydrogenated to generate a mixture of S17-5 and S17-6. Ketone reduction of S17-5 in a stereoselective manner (e.g. CBS reduction) provides intermediate S17-3, where J is methyl.

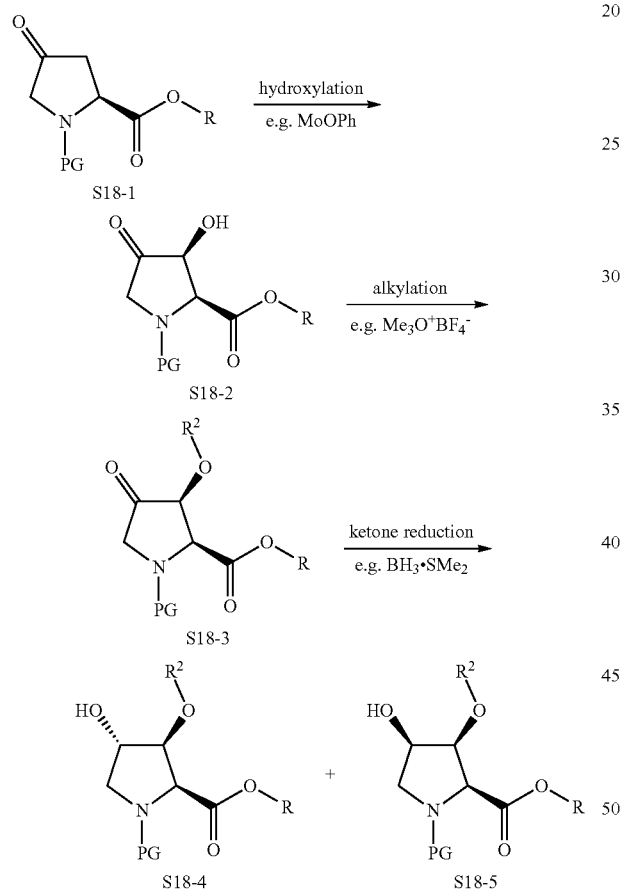

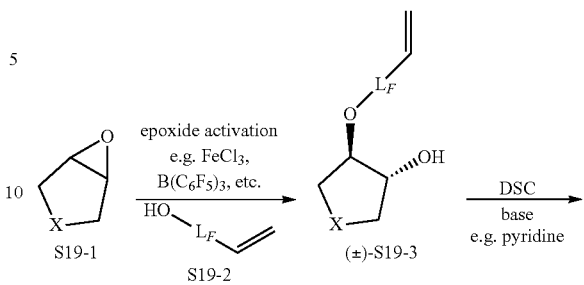

Scheme 18 shows a general synthesis of intermediates S18-4 and S18-5, wherein an appropriately protected 4-oxo proline S18-1 is hydroxylated in a stereoselective manner (e.g. MoOPh) to provide intermediate S18-2, which is subsequently reacted with an alkylating agent (e.g. trimethyloxonium tetrafluoroborate) to afford intermediate S18-3. Reduction of the ketone (e.g. BH$_3$.SMe$_2$ complex) provides intermediates S18-4 and S18-5.

Scheme 19 shows a general synthesis of an intermediate S19-7 where Q is as defined herein and L$_F$ is C$_1$-C$_3$ alkylene. In Scheme 19, an epoxide intermediate S19-1 is converted to the (±)-trans-intermediate S19-3. Activation of the alcohol intermediate (±)-S19-3 (e.g. DSC) produces carbonate (±)-S19-4, which is treated with intermediate S19-5 to afford carbamate intermediate S19-6 Intermediate S19-6 then undergoes ester hydrolysis (e.g. LiOH when R=methyl or TFA when R=tert-butyl) to provide intermediate S19-7.

Scheme 20

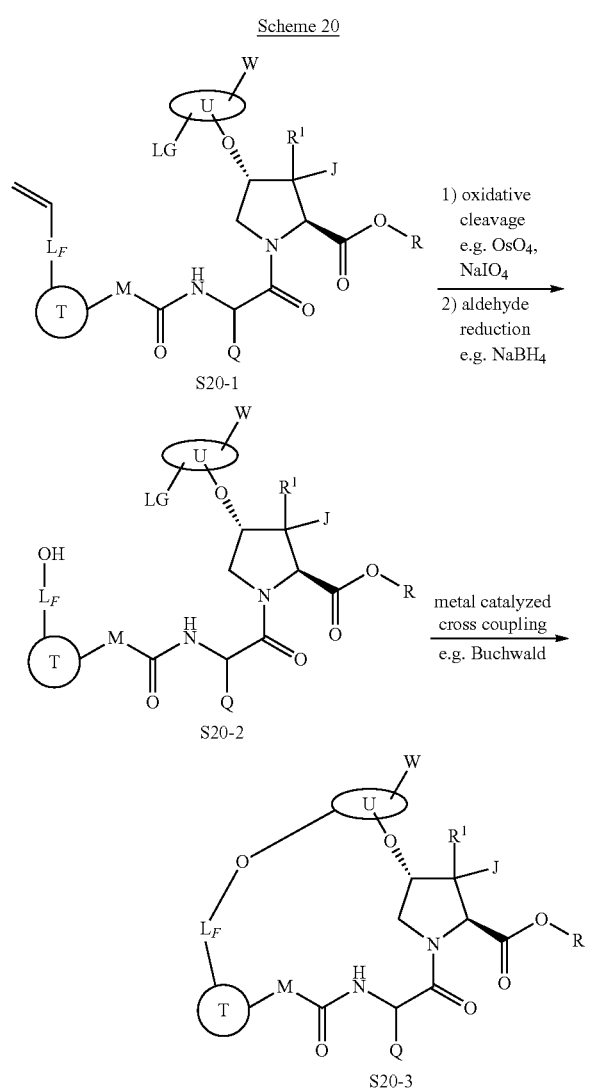

Where:
R = alkyl
LG = leaving group
PG = protecting group

Scheme 20 shows a general synthesis of an intermediate S20-3 where $L_F$-O is F, and U, W, $R^1$, J, Q, M, T and L are as defied herein. In scheme 20, intermediate S20-1 first undergoes oxidative cleavage of an olefin (e.g. $OsO_4$, $NaIO_4$) and subsequent reduction of the resultant aldehyde (e.g. $NaBH_4$) to provide intermediate S20-2. Transition metal catalyzed cross coupling provides intermediate S20-3.

Scheme 21

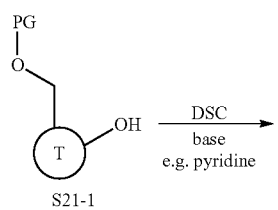

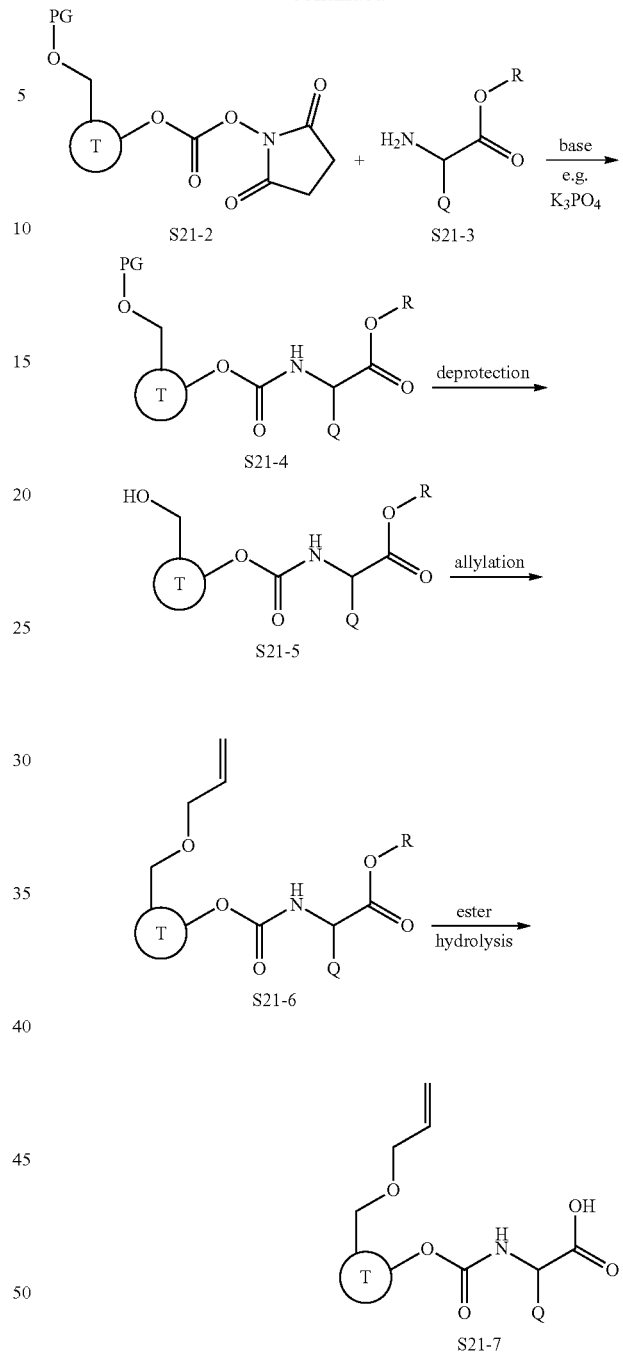

Where:
R = alkyl
PG = protecting group

Scheme 21 shows a general synthesis of an intermediate S21-7 where Q and T are as defined herein. In Scheme 21, activation of mono-protected diol S21-1 (e.g. DSC) followed by coupling with amino ester intermediate S21-3 provides carbamate intermediate S21-4. Intermediate S21-4 is then deprotected to unmask the alcohol functionality (intermediate S21-5) which is then allylated to provide intermediate S21-6. Intermediate S21-6 then undergoes ester hydrolysis (e.g. LiOH when R=methyl or TFA when R=tert-butyl) to provide intermediate S21-7.

Scheme 22

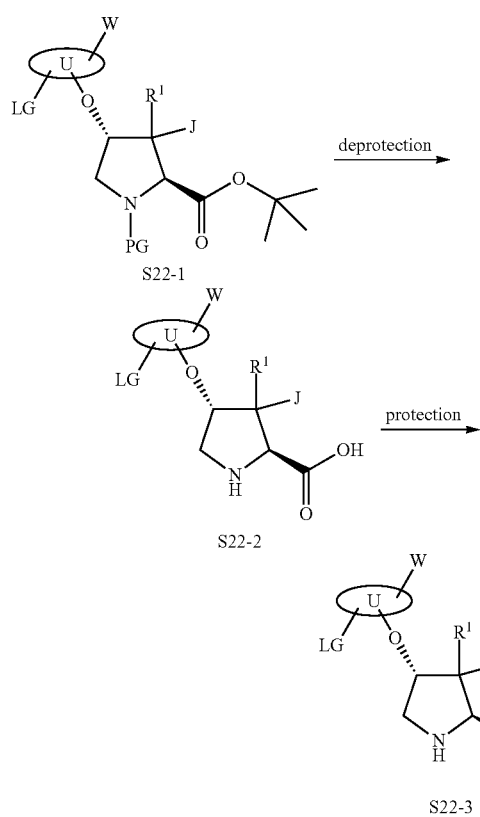

Where:
PG = protecting group
LG = leaving group

Scheme 22 shows a general synthesis of an intermediate S22-3 where U, W, R¹, J, and Q are as defied herein. In scheme 22 intermediate S22-1 is globally deprotected to provide amino acid intermediate S22-2. The acid functionality of intermediate S22-2 is then converted to a base-labile carboxylic acid ester (e.g. methyl ester), intermediate S22-3.

PREPARATION OF SELECTED INTERMEDIATES

Preparation of Intermediate A1

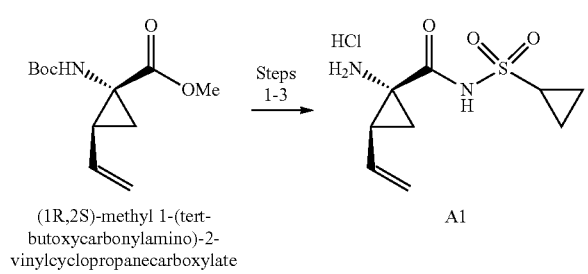

(1R,2S)-methyl 1-(tert-butoxycarbonylamino)-2-vinylcyclopropanecarboxylate

A1

Steps 1-3. Preparation of Intermediate A1: Intermediate A1 was prepared using the procedure detailed in Example 2.12 of International Patent Publication No. WO 20081064066 (hereinafter "WO '066") (p. 75-76) substituting (1R,2S)-methyl 1-(tert-butoxycarbonylamino)-2-vinyl-cyclopropane-carboxylate (prepared according to Beaulieu, P. L., et al., *J. Org. Chem.* 2005, 70, 5869) for (1R,2S)-ethyl 1-(tert-butoxycarbonylamino)-2-vinylcyclopropane-carboxylate.

Preparation of Intermediate A2

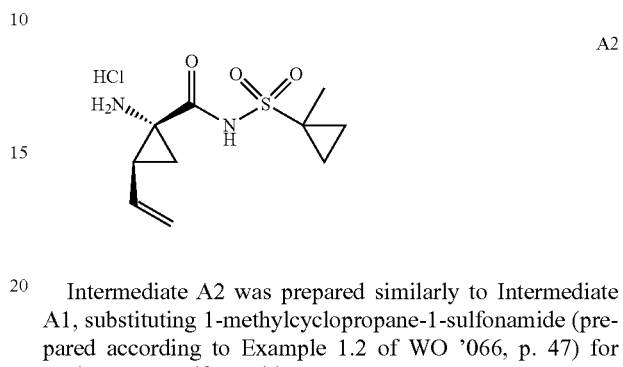

A2

Intermediate A2 was prepared similarly to Intermediate A1, substituting 1-methylcyclopropane-1-sulfonamide (prepared according to Example 1.2 of WO '066, p. 47) for cyclopropanesulfonamide.

Preparation of Intermediate A3

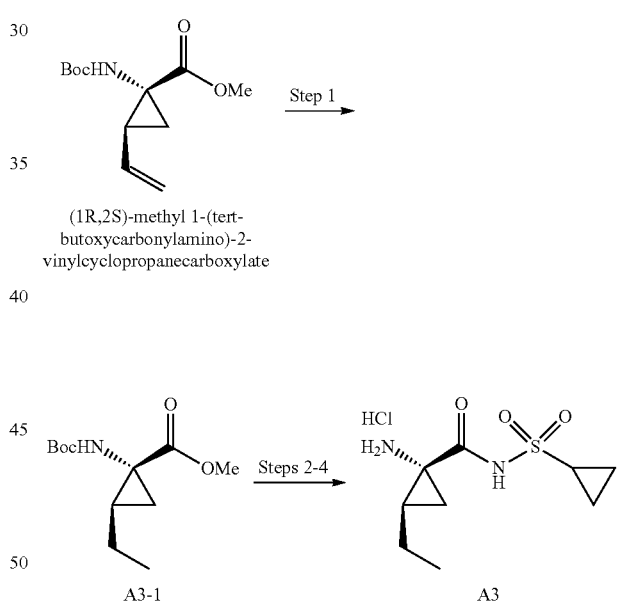

Step 1. Preparation of A3-1: Cyclopropane ester A3-1 was prepared from (1R,2S)-methyl 1-(tert-butoxycarbonylamino)-2-vinylcyclopropanecarboxylate (prepared according to Beaulieu, P L, et al., *J. Org. Chem.* 2005, 70, 5869) using the procedure detailed in Example 26 of International Patent Publication No. WO 2009/005677 (hereinafter "WO '677") (p. 176).

Steps 2-4. Preparation of Intermediate A3: Intermediate A3 was prepared similarly to (1R,2S)-1-amino-N-(cyclopropylsulfonyl)-2-vinylcyclopropanecarboxamide hydrochloride of Example 2.12 of WO '066 (p. 75-76) substituting A3-1 for (1R,2S)-ethyl 1-(tert-butoxycarbonylamino)-2-vinylcyclopropane-carboxylate.

Preparation of Intermediate A4

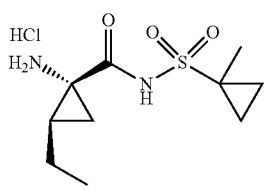

Intermediate A4 was prepared similarly to Intermediate A3, substituting 1-methylcyclopropane-1-sulfonamide (prepared according to Example 1.2 of WO '066, p. 47) for cyclopropanesulfonamide.

Preparation of Intermediate A5

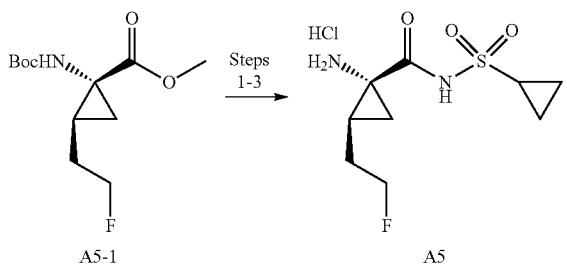

Steps 1-3. Preparation of Intermediate A5: Intermediate A5 was prepared similarly to (1R,2S)-1-amino-N-(cyclopropylsulfonyl)-2-vinylcyclopropane-carboxamide hydrochloride of Example 2.12 of WO '066 (p. 75-76) substituting A5-1 (prepared according to Example 104 of WO '677, p. 265) for (1R,2S)-ethyl 1-(tert-butoxycarbonylamino)-2-vinylcyclopropanecarboxylate.

Preparation of Intermediate A6

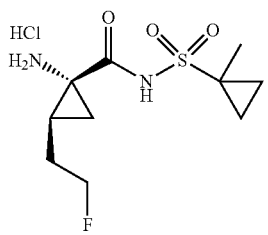

Intermediate A6 was prepared similarly to Intermediate A5, substituting 1-methylcyclopropane-1-sulfonamide (prepared according to Example 1.2 of WO '066, p. 47) for cyclopropanesulfonamide.

Preparation of Intermediate A7

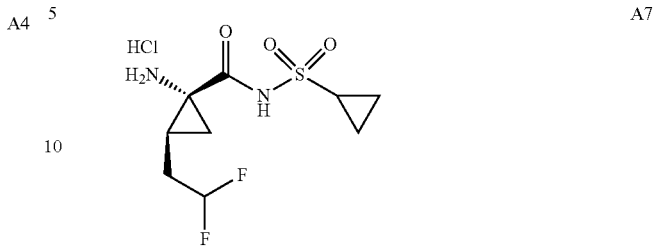

Intermediate A7 was prepared according to Example 97.1.6 of U.S. Patent Publication No. 2009/274652 (hereinafter "US '652"), p. 72-73.

Preparation of Intermediate A8

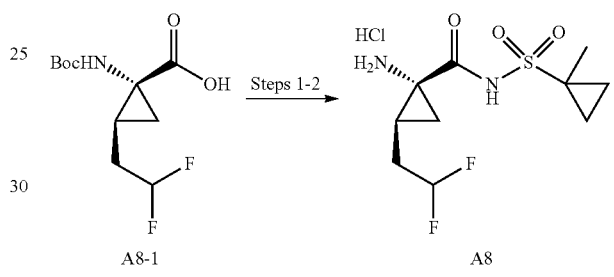

Steps 1-2. Preparation of Intermediate A8: Intermediate A8 was prepared similarly to (1R,2S)-1-amino-N-(cyclopropylsulfonyl)-2-vinylcyclopropane-carboxamide hydrochloride of Example 2.12 of WO '066 (p. 75-76) substituting A8-1 (prepared according to the procedure detailed in Example 97.1.4 of US '652, p. 72-3) for (1R,2S)-1-(tert-butoxycarbonylamino)-2-vinylcyclo-propanecarboxylic acid and substituting 1-methylcyclopropane-1-sulfonamide (prepared according to Example 1.2 of WO '066, p. 47) for cyclopropanesulfonamide. A8-1 $^1$H NMR (400 MHz, CDCl$_3$) δ 9.22 (br s, 1H), 6.05-5.75 (m, 1H), 5.38 (br s, 1H), 2.04 (m, 2H), 1.68 (m, 2H), 1.61 (m, 3H), 1.52 (m, 9H), 1.42 (m, 1H), 1.28 (m, 1H), 0.85 (m, 2H).

Preparation of Intermediate A9

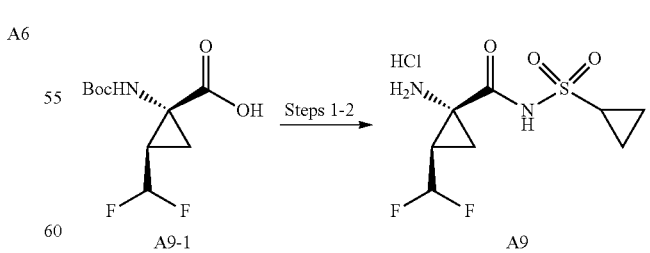

Step 1-2. Preparation of Intermediate A9: Intermediate A5 was prepared similarly to (1R,2S)-1-amino-N-(cyclopropylsulfonyl)-2-vinylcyclopropane-carboxamide hydrochloride of Example 2.12 of WO '066 (p. 75-76) substituting A9-1 (prepared according to Example 1, Steps 1L-1O of International Patent Publication No. WO 2009/134987, p. 75-77) for (1R,2S)-1-(terbutoxycarbonylamino)-2-vinylcyclopropanecarboxylic acid.

Preparation of Intermediate A10

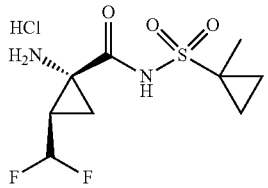

Intermediate A10 was prepared similarly to Intermediate A5, substituting 1-methylcyclopropane-1-sulfonamide (prepared according to Example 1.2 of WO '066, p. 47) for cyclopropanesulfonamide.

Preparation of Intermediate A11

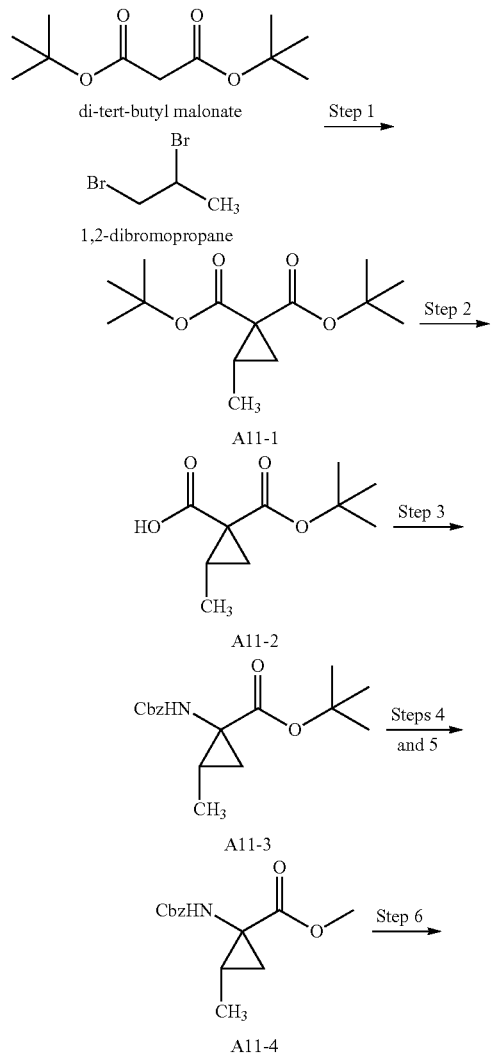

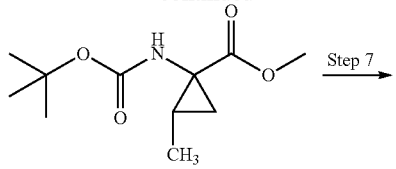

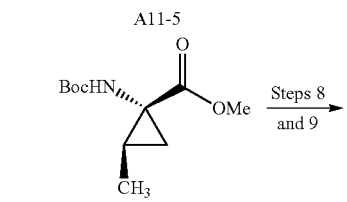

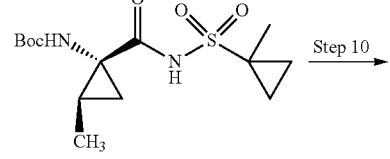

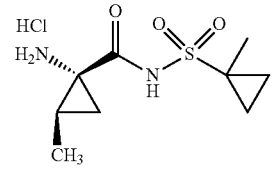

Step 1. Preparation of A11-1: To a solution of NaOH (46.2 g, 50% w/w in water) at rt was added BnEt$_3$NCl (10.5 g, 46 mmol), di-tert-butyl malonate (10 g, 46 mmol) and 1,2-dibromopropane (14 g, 69.3 mmol). The mixture was stirred at rt overnight and was extracted with DCM (3×100 mL). The organic layers were washed with water (80 mL) and brine (50 mL), dried over anhydrous Na$_2$SO$_4$. Concentration in vacuo produced A11-1 that was used subsequently without further purification. $^1$H NMR (400 MHz, CDCl$_3$) δ 1.83-1.62 (m, 1H); 1.42 (s, 9H); 1.40 (s, 9H); 1.24-1.05 (m, 2H); 1.03-1.02 (d, 3H).

Step 2. Preparation of A11-2: To a mixture of t-BuOK (175 g, 1.56 mol) in ether (1.2 L) at 0° C. was added water (3.4 mL) followed by addition of diester A11-1 (91 g, 0.35 mol). The mixture was stirred at rt for three days, then quenched with ice-water. The aqueous layer was extracted with ether (2×400 mL), acidified with critic acid, and then extracted with EA (3×400 mL). The combined ethyl acetate extracts were washed with water (2×100 mL), brine (200 mL), dried over anhydrous Na$_2$SO$_4$, and concentrated in vacuo to produce A11-2 that was used subsequently without further purification. $^1$H NMR (400 MHz, DMSO-d$_6$) δ 12.60 (s, 1H); 1.70-1.64 (s, 1H); 1.37 (s, 9H); 1.19-1.13 (m, 1H); 1.03-1.00 (m, 4H).

Step 3. Preparation of A11-3: To a mixture A11-2 (33.5 g, 0.17 mol) and triethylamine (70 mL) in THF (200 mL) at 0° C. was added ethyl chloroformate (22 mL). The mixture was stirred at 0° C. for 1 h. To the mixture at 0° C. was added sodium azide (54 g, 0.83 mol, 4.9 eq) in water (100 mL), the mixture was stirred for 40 min. The mixture was extracted with EA (2×400 mL), washed with water (100 mL), brine (100 mL), dried over anhydrous Na$_2$SO$_4$ and concentrated in vacuo to produce a residue that was taken up in toluene (100 mL) and treated with benzyl alcohol (50 mL). The mixture was then heated at 70° C. for 2 h, cooled to rt, adjusted to pH 8 with sodium bicarbonate, and then extracted with ether (3×200 mL). The aqueous layer was then adjusted to pH 5 with 1 N HCl and extracted with EA (2×300 mL), The combined ethyl acetate extracts were washed with water (100 mL), brine (80 mL), dried over anhydrous Na$_2$SO$_4$, and concentrated in vacuo to give CBZ protected amine A11-3 (16 g) that is used subsequently without further purification. $^1$H NMR (400 MHz. DMSO-d$_6$) δ 7.85 (s, 1H); 7.28-7.15 (m, 5H); 4.97-5.03 (m, 2H); 1.33 (s, 9H); 1.33-1.17 (m, 2H); 1.10 (d, J=6.8 Hz, 3H); 0.90-1.00 (m, 1H).

Steps 4 and 5. Preparation of A11-4: To a solution of Cbz protected amine A11-3 (16 g, 52 mmol) in DCM (250 mL) was added dropwise TFA (250 mL, 3.24 mol) at rt and the mixture stirred at rt overnight. The mixture was concentrated in vacuo, adjusted to pH 8~9 using aqueous sodium carbonate and washed with ether (3×80 mL). The aqueous phase was then adjusted to pH 5~6 using 1 N HCl and extracted with EA (2×300 mL). The combined ethyl acetate phases were washed with water (80 mL), brine (80 mL), dried over anhydrous Na$_2$SO$_4$ and concentrated to give 13 g as a slightly yellow oil that was used in the next step without further purification. This material (8.0 g, 32 mmol) was taken up in methanol (200 mL), treated with thionyl chloride (15 mL) at 0° C. then stirred at rt overnight. The resulting mixture was concentrated in vacuo and purified by flash chromatography on silica (eluent PE/EA 10:1-5:1) to give methyl ester A11-4 (6 g). $^1$H NMR (400 MHz, DMSO-d$_6$) δ 7.97 (s, 1H); 7.37-7.26 (m, 5H); 4.99 (s, 2H); 3.61 (s, 3H); 1.48-1.45 (m, 1H); 1.17-1.08 (m, 2H); 1.06-1.04 (d, 3H).

Step 6. Preparation of A11-5: Cbz carboxamide A11-4 (36 g, 0.15 mol), Boc$_2$O (40 g, 0.18 mol), and Pd/C (3.6 g, 10% w/w) were combined in methanol under H$_2$ and stirred at 32° C. overnight. The reaction mixture was filtered to remove the catalyst, additional Boc$_2$O (40 g, 0.18 mol) and Pd/C (3.6 g, 10% w/w) were added and the reaction placed under a H$_2$ atmosphere with stirring at rt for a weekend. The reaction mixture was filtered to remove the catalyst, concentrated in vacuo and purified by flash chromatography on silica (eluent PE/EA 20:1-10:1) to produce Boc protected amine A11-5. $^1$H NMR (400 MHz, DMSO-d$_6$) δ 7.48 (s, 1H), 3.59 (s, 3H), 1.43-1.41 (m, 1H), 1.34 (s, 9H), 1.21-1.18 (m, 1H), 1.07-1.01 (m, 4H).

Step 7. Preparation of A11-6: To a solution of NaH$_2$PO$_4$ (1.9 g) in water (160 mL) at 40° C. was added Alcalase (2.4 U/g, 16 mL). The mixture was adjusted with 50% aqueous sodium hydroxide to pH 8. A11-5 (2.80 g) in DMSO (32 mL) was added to the buffer dropwise over 30 min. The mixture was stirred at 40° C. and maintained at pH 8 with addition of 50% NaOH for 19 h. The mixture was cooled to rt, with ether (3×100 mL) and the organic phase washed with sat. NaHCO$_3$ (2×40 mL), water (2×40 mL), brine (40 mL), dried over anhydrous Na$_2$SO$_4$, filtered and concentrated in vacuo to produce A11-6. $^1$H NMR (300 MHz, DMSO-d$_6$) δ 5.18 (br s, 1H); 3.71 (s, 3H); 1.43-1.18 (m, 2H); 1.34 (s, 9H); 1.07-1.01 (m, 4H). Analysis of the product using chromega-Chiral CC3 column (0.46 cm I.D.×25 cm L, 3 µL injection, 80/20 hexane/IPA, 1 mL/min, 34° C., 220 nM UV detection) determined the enantiomeric excess was 99.4% (desired RT=5.238 min, undesired RT=6.745 min).

Steps 8 and 9. Preparation of A11-7: Solid LiOH.H$_2$O (19.1 g, 455 mmol) is taken up in 50 mL MeOH/50 mL water at rt. Once all LiOH has dissolved, methyl ester A11-6 (10.4 g, 45.5 mmol) is taken up in 100 mL THF added to reaction mixture and stirred vigorously overnight. The resulting solution is diluted with water (150 mL), adjusted to pH~3 with 12 M HCl and extracted with EtOAc. The combined organic layers are washed with brine, dried over anhydrous MgSO$_4$ and concentrated in vacuo to produce a fine white powder (9.2 g). This material (1.5 g, 7 mmol) is taken up in THF (30 mL) and treated with CDI (1.47 g, 9.1 mmol). The resulting solution was heated to 65° C. for 2 h, cooled to rt and treated with DBU (2.1 mL, 13.9 mmol) and 1-methylcyclopropane-1-sulfonamide (1.4 g, 10.5 mmol). The resulting solution is stirred at rt overnight. Addition of 1 M HCl is used to adjust the pH~1 prior to removing the majority of THF in vacuo. The resulting slurry is extracted with EtOAc and the combined organics washed with brine, dried over anhydrous MgSO$_4$ and concentrated in vacuo to produce 2.29 g of acyl sulfonamide A11-7. LCMS-ESI$^+$ (m/z): [M+Na]$^+$ calcd for C$_{14}$H$_{24}$N$_2$NaO$_5$S: 355.41; found: 355.84.

Step 10. Preparation of Intermediate A11. Acyl sulfonamide A11-7 (0.25 g, 0.75 mmol) in dioxane (1 mL) is treated with HCl (4 M in dioxane, 2.8 mL, 11.2 mmol) at rt. After 4 h, the reaction is concentrated in vacuo to produce 0.20 g of Intermediate A-11 that is used subsequently without additional purification. $^1$H NMR (400 MHz, CD$_3$OD) δ 1.87-1.84 (m, 0.5 H); 1.77-1.65 (m, 1.5H); 1.58-1.46 (m, 2H); 1.54 (d, J=8 Hz, 3H), 1.34-1.26 (m, 3+1H); 1.02-0.92 (m, 1H); 0.83-0.77 (m, 1H).

Preparation of Intermediate A12

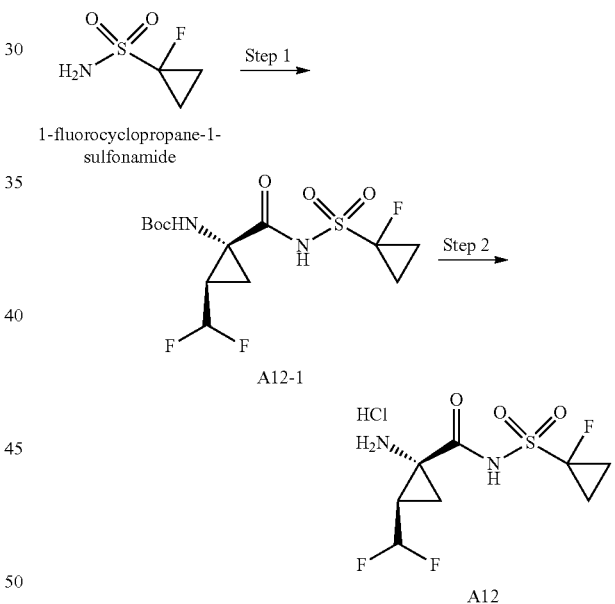

Step 1. Preparation of A12-1: A vessel containing a solution of carboxylic acid A9-1 (1 g, 4 mmol) in THF (15 mL) was treated with CDI (0.84 g, 5.2 mmol), sealed and heated to 75° C. for 2 h. The clear tan colored solution is divided in half and used subsequently without further purification for the remainder of Step 1 in the preparation of Intermediate A12 as well as the preparation of Intermediate A13 as detailed below. This solution is treated with 1-fluorocyclopropane-1-sulfonamide (0.42 g, 3 mmol; prepared according to Steps 1, 4, and 9 of Example 7 of International Patent Publication No. WO 2009/14730, p. 107-110) and DBU (0.6 mL, 4 mmol) and allowed to stir overnight at rt. The solution was acidified to pH~1 with 1 M HCl and concentrated in vacuo to remove the majority of THF. The aqueous layer was extracted with EtOAc and the combined organics washed with brine, dried over anhydrous MgSO₄ and concentrated in vacuo to dryness to afford 0.73 g of the A12-1 that was used without further purification.

Step 2. Preparation of Intermediate A12: Acyl sulfonamide A12-1 (0.25 g, 0.67 mmol) was taken up in 1 mL dioxane and treated with HCl (4 M in dioxane, 2.5 mL, 11 mmol). The reaction was stirred at rt for 2 h and concentrated in vacuo to dryness to afford a quantitative yield of Intermediate A12. ¹H NMR (400 MHz, CD₃OD) δ 6.04 (td, $J_{H-F}$=55.6 Hz, J=5.2 Hz, 1H); 2.25-2.14 (m, 1H); 1.78-1.62 (m, 2H); 1.52-1.38 (m, 4H).

Preparation of Intermediate A13

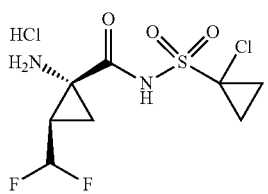

A13

Intermediate A13 was prepared similarly to Intermediate A12, substituting 1-chlorocyclopropane-1-sulfonamide (prepared according to Li, J, et al. *Synlett*, 2006, 5, pp. 725-728) for 1-chlorocyclopropane-1-sulfonamide in Step 1. ¹H NMR (400 MHz, CD₃OD) δ 6.03 (td, $J_{H-F}$=54.8 Hz. J=6 Hz, 1H); 2.32-2.18 (m, 1H); 2.06-1.92 (m, 2H); 1.80-1.68 (m, 2+1H); 1.56-1.44 (m, 1H); 1.44-1.37 (m, 1H).

Preparation of Intermediate B1

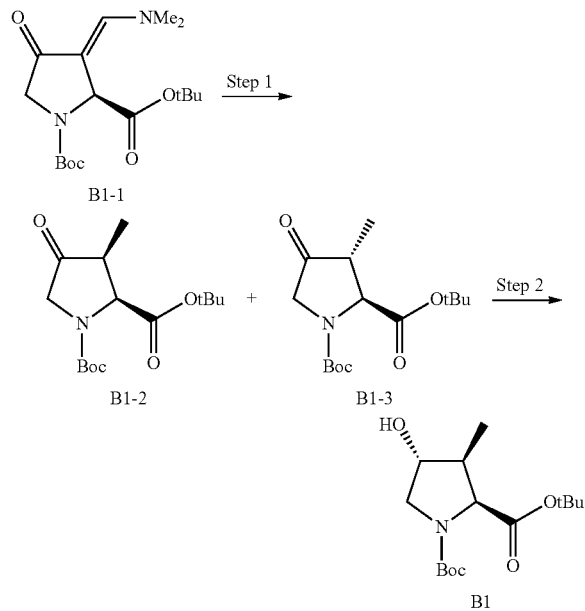

Steps 1 and 2. Preparation of Intermediate B1: Enaminone B1-1 (40 g, 11.8 mmol, prepared according to Camplo, M., et al. *Tetrahedron* 2005, 61, 3725) was dissolved in acetone (120 mL) and the reaction vessel was purged with Ar. Pd/C (10 wt. % Pd, 820 mg) was added in a single portion and the reaction vessel was purged twice with H₂. The reaction was stirred under 1 atm H₂ at rt for 15 h and was then filtered through a pad of Celite with acetone. The filtrate was concentrated and filtered through a plug of silica gel with 30% EtOAc in hexanes to afford a ~2:1 mixture of ketones B1-2 and B1-3 (3.48 g) as a white solid. This mixture (3.37 g, 11.3 mmol) was dissolved in THF (100 mL) under Ar. A 1 M solution of (R)-(+)-2-methyl-CBS-oxazaborolidine in toluene (11.3 mL, 11.3 mmol) was added in a single portion and the resulting solution was cooled to −78° C. A 1 M solution of BH₃.SMe₂ in CH₂Cl₂ (11.3 mL) was then added dropwise over 5 min. The resulting solution was stirred for 20 min and was removed from the cold bath. After an additional 15 min, the reaction was placed in a water bath at ambient temperature. After an additional 7 min, the reaction was quenched by dropwise addition of MeOH (20 mL). After stirring an additional 2.5 h. the reaction mixture was concentrated, dissolved in EtOAc (300 mL), and washed with 0.2 M HCl (200 mL). The phases were separated, and the aqueous phase was extracted with EtOAc (100 mL) The combined organic phase was filtered to remove solids, dried over Na₂SO₄, filtered, and concentrated. The crude residue was dissolved in CH₂Cl₂ and was concentrated onto 20 g silica gel. Purification by silica gel chromatography (25 to 40% EtOAc in hexanes) provided partial separation of Intermediate B1 from other diastereomeric products. Mixed fractions were pooled and concentrated onto 9 g silica gel. Purification by silica gel chromatography provided Intermediate B1 contaminated with minor diastereomeric components as a white solid (1.96 g). ¹H NMR (400 MHz, CDCl₃, rotamers observed) δ 4.25-4.15 (m, 1H), 4.13-4.04 (m, 1H), 3.91-3.79 (m, 1H), 3.28-3.09 (m, 1H), 2.41-2.23 (m, 1H), 2.04 (bs, 1H), 1.51-1.39 (m, 18H), 1.09-1.01 (m, 3H).

Preparation of Intermediate B2

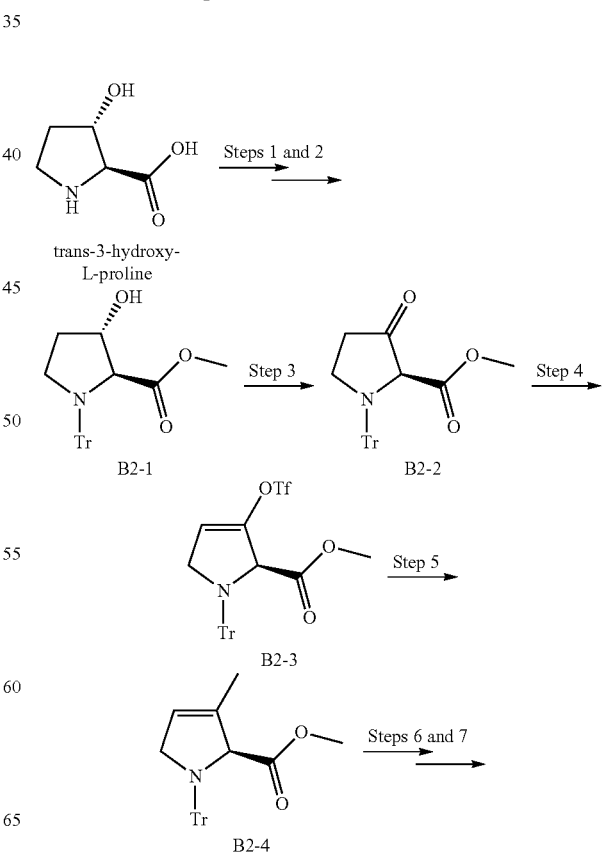

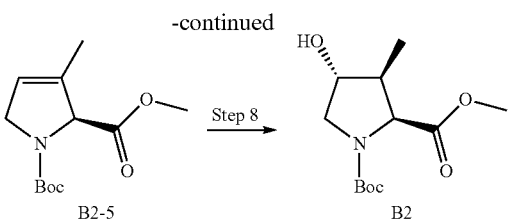

Steps 1 and 2. Preparation of B2-1: trans-3-Hydroxy-L-proline (571 mg, 4.35 mmol, Chem-Impex International, Inc.) was suspended in MeOH and cooled to 0° C. Thionyl chloride (1.6 mL, 22 mmol) was added over 5 min and the solution was warmed to rt. After stirring for 24 h, the reaction mixture was concentrated under reduced pressure to afford the methyl ester, which was carried on without further purification. The crude ester was suspended in DCM (22 mL) and treated with TEA (1.3 mL, 9.57 mmol). The stirred mixture was cooled to 0° C. and trityl chloride (1.21 g, 4.35 mmol) was added. The reaction mixture was allowed to gradually come to rt o/n, and then poured into saturated aqueous NaHCO$_3$. The aqueous layer was extracted three times with DCM. The combined organics were dried over Na$_2$SO$_4$, filtered and concentrated under reduced pressure. The crude residue was purified by silica gel chromatography (25% to 50% EtOAc/Hex to afford alcohol B2-1 (1.27 g).

Step 3. Preparation of B2-2: Alcohol B2-1 (1.23 g, 3.18 mmol) and 2 g 4 Å MS were suspended in DCM (16 mL) and treated with NMO (560 mg, 4.78 mmol) and TPAP (76 mg, 0.218 mmol). After stirring for 30 min, the mixture was filtered over a short pad of silica and eluted off with 50% EtOAc/Hex. The filtrate was concentrated and the crude residue was purified by silica gel chromatography (10% to 30% EtOAc/Hex to afford ketone B2-2 (0.99 g).

Step 4. Preparation of B2-3: LiHMDS (1.0 M in THF, 5.8 mL, 5.8 mmol) was added to THF (22 mL) and the stirred solution was cooled to −78° C. A rt solution of ketone B2-2 (2.14 g, 5.55 mmol) in THF (6 mL) was added dropwise by cannula over 5 min. The flask that had contained B2-2 was then rinsed with THF (4 mL) and the rinsing was added dropwise by cannula to the reaction mixture. After 35 min, N-(5-chloro-2-pyridyl)bis(trifluoromethanesulfonimide) (2.40 g, 6.11 mmol) in THF (6 mL) was added to the reaction mixture dropwise by syringe over 5 min. After another 1 h, the reaction mixture was warmed to rt. Following an additional 30 min, the reaction was quenched by addition of 20 mL H$_2$O and diluted with Et$_2$O. The organic solution was washed with 10% NaOH and dried over K$_2$CO$_3$ filtered and concentrated under reduced pressure. The crude residue was loaded onto a silica column that had been pre-equilibrated with 1% TEA/Hex. The material was purified by silica gel chromatography (0% to 15% EtOAc/Hex doped with 1% TEA) to afford enol triflate B2-3 (1.89 g).

Step 5. Preparation of B2-4: Enol triflate B2-3 (957 mg, 1.85 mmol) was dissolved in THF (9 mL) and treated with Pd(PPh$_3$)$_4$ (107 mg, 0.0925 mmol) and dimethyl zinc (2.0 M in PhMe, 1.9 mL, 3.7 mmol). The reaction mixture was stirred at rt for 5 h, then more dimethyl zinc (2.0 M in PhMe, 1.9 mL, 3.7 mmol) was added and the reaction was heated to 50° C. for 15 min. After cooling to rt, the mixture was diluted with Et$_2$O. The organic solution was washed with 10% NaOH twice, then dried over MgSO$_4$, filtered and concentrated under reduced pressure. The crude B2-4 residue was carried on without further purification.

Steps 6 and 7. Preparation of B2-5: Compound B2-4 (1.85 mmol theoretical) was dissolved in 1:1 MeOH/DCM (20 mL) and treated with HCl (4.0 M in dioxane, 2 mL, 8.0 mmol). After stirring for 2 h at rt, the reaction mixture was concentrated and the crude material was carried on without further purification. The crude product amine hydrochloride was treated with Boc$_2$O (2.02 g, 9.25 mmol), DCM (18 mL), MeOH (1.8 mL) and TEA (0.52 mL, 3.7 mmol). After stirring for 2 h at rt, the reaction mixture was diluted with EtOAc and washed with 10% HCl, saturated aqueous NaHCO$_3$ and brine. The organic solution was dried over MgSO$_4$, filtered and concentrated under reduced pressure. The residue was purified by silica gel chromatography (15% to 40% EtOAc/Hex) to afford carbamate B2-5 (331 mg). LCMS-ESI$^+$ (m/z): [M+H]$^+$ calcd for C$_{12}$H$_{20}$NO$_4$: 242.14; found: 243.26.

Step 8. Preparation of Intermediate B2: Carbamate B2-5 (345 mg, 1.43 mmol) was dissolved in THF (7 mL) and cooled to 0° C. BH$_3$.SMe$_2$ complex (2.0 M in THF, 0.79 mL, 1.58 mmol) was added dropwise and the reaction mixture was allowed to come to rt gradually. After 15 h, the reaction was quenched by dropwise addition of H$_2$O (added until bubbling ceased), then cooled to 0° C. Hydrogen peroxide (30% w/w in H$_2$O, 0.73 mL, 7.2 mmol) and NaOH (2.0 M in H$_2$O, 0.86 mL, 1.72 mmol) were added in quick succession and the stirred mixture was heated to 50° C. for 35 min. The mixture was then diluted with Et$_2$O and washed successively with H$_2$O, saturated aqueous NaHCO$_3$ and brine, then dried over MgSO$_4$, filtered and concentrated under reduced pressure. Intermediate B2 was used in subsequent reactions without further purification. LCMS-ESI$^+$ (m/z): [M+H]$^+$ calcd for C$_{12}$H$_{22}$NO$_5$: 260.15; found: 259.99.

Preparation of Intermediate B3

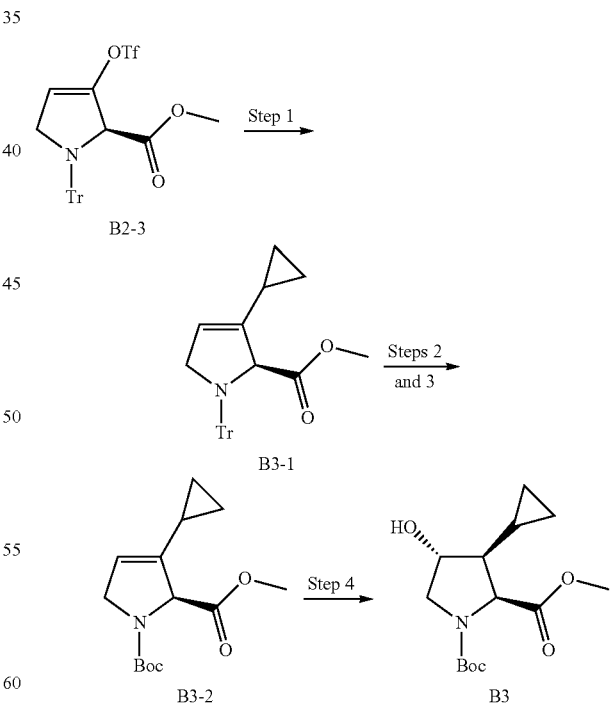

Step 1. Preparation of B3-1: Enol triflate B2-3 (91 mg, 0.176 mmol) was dissolved in THF (1.7 mL) and treated with cyclopropyl zinc bromide (0.5 M in THF, 1.7 mL, 0.85 mmol) and Pd(PPh$_3$)$_4$ (20 mg, 0.018 mmol). The stirred reaction mixture was heated to 50° C. for 2 h then cooled to rt and diluted with EtOAc. The organic solution was washed successively with saturated aqueous NaHCO$_3$ and brine, then dried over MgSO$_4$, filtered and concentrated under reduced pressure. The crude residue was purified by silica gel chromatography (0% to 20% EtOAc/Hex) to afford cyclopropane B3-1 (43 mg). LCMS-ESI$^+$ (m/z): [M−Tr+H]$^+$ calcd for C$_9$H$_{14}$NO$_2$: 168.10; found: 168.04.

Steps 2 and 3. Preparation of B3-2: Vinyl cyclopropane B3-1 (43 mg, 0.11 mmol) was dissolved in 1:1 MeOH/DCM (10 mL) and treated with HCl (4.0 M in dioxane, 1 mL, 4.0 mmol). After stirring for 1.5 h at rt, the reaction mixture was concentrated and the crude material was carried on without further purification. The crude product of step 2 was treated with Boc$_2$O (229 mg, 1.05 mmol), DMAP (13 mg, 0.105 mmol), DCM (5 mL) and TEA (0.293 mL, 2.10 mmol). After stirring for 5 h at rt, the reaction mixture was diluted with EtOAc and washed with 10% HCl, saturated aqueous NaHCO$_3$ twice and brine. The organic solution was dried over MgSO$_4$, filtered and concentrated under reduced pressure. The residue was purified by silica gel chromatography (10% to 30% EtOAc/Hex) to afford carbamate B3-2 (20 mg). LCMS-ESI$^+$ (m/z): [M-(t-Bu)+H]$^+$ calcd for C$_{10}$H$_{14}$NO$_4$: 212.09; found: 211.91.

Step 4. Preparation of Intermediate B3: Carbamate B3-2 (152 mg, 0.569 mmol) was dissolved in THF (5.7 mL) and cooled to 0° C. BH$_3$.SMe$_2$ complex (2.0 M in THF, 0.31 mL, 0.63 mmol) was added dropwise and the reaction mixture was allowed to come to rt gradually. After 20 h, the reaction was quenched by dropwise addition of H$_2$O (added until bubbling ceased), then cooled to 0° C. Hydrogen peroxide (30% w/w in H$_2$O, 0.29 mL, 2.85 mmol) and NaOH (2.0 M in H$_2$O, 0.43 mL, 0.86 mmol) were added in quick succession and the stirred mixture was heated to 50° C. for 30 min. The mixture was then diluted with Et$_2$O and washed successively with H$_2$O, saturated aqueous NaHCO$_3$ and brine, then dried over MgSO$_4$, filtered and concentrated under reduced pressure. Intermediate B3 was carried on without further purification. LCMS-ESI$^+$ (m/z): [M-(t-Bu)+H]$^+$ calcd for C$_{10}$H$_{16}$NO$_5$: 230.10; found: 230.03.

Preparation of Intermediate B4

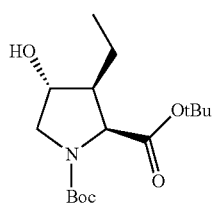

B4

(2S,3S,4R)-di-tert-butyl 3-ethyl-4-
hydroxypyrrolidine-1,2-dicarboxylate

Intermediate B4 ((2S,3S,4R)-di-tert-butyl 3-ethyl-4-hydroxypyrrolidine-1,2-dicarboxylate) was prepared according to Camplo. M., et al. *Tetrahedron* 2005, 61, 3725.

Preparation of Intermediate B5

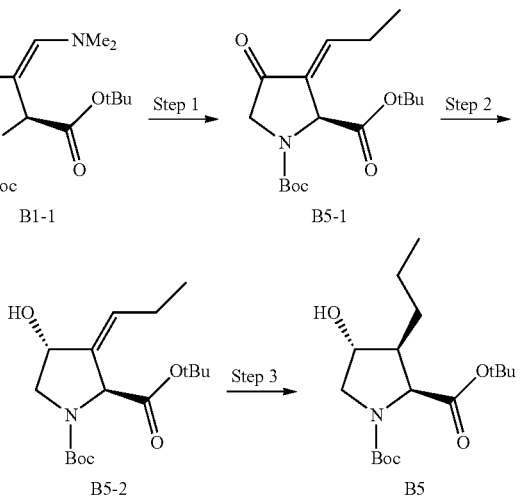

Step 1. Preparation of enone B5-2: To a solution of B1-1 in tetrahydrofuran (7.35 mL) was added ethylmagnesium bromide (3 M in diethyl ether, 1.47 mL 4.41 mmol) via syringe at −78° C. under an argon atmosphere. After 2.5 h, the reaction mixture was allowed to warm to rt over 30 min at which point the reaction mixture was diluted with saturated aqueous ammonium chloride solution (20 mL). The resulting mixture was extracted with ethyl acetate (20 mL twice), and the combined organic extracts were dried over anhydrous sodium sulfate and were concentrated in vacuo. The crude residue was purified by silica gel chromatography (0-100% ethyl acetate/hexanes gradient) to afford intermediate B5-1 (308.8 mg) as a colorless oil. LCMS-ESI$^+$ (m/z): [M+H]$^+$ calcd for C$_{17}$H$_{28}$NO$_5$: 326.2; found: 326.2.

Step 2. Preparation of B5-2: To a solution of enone B5-1 (308 mg, 0.95 mmol) in methanol (4.7 mL) was added cerium(III) chloride heptahydrate (566 mg, 1.52 mmol) at rt under an argon atmosphere. The resulting mixture was cooled to −78° C., and sodium borohydride (57.7 mg, 1.52 mmol) was added as a solid. After 1 h, the reaction mixture was warmed to 0° C. and saturated aqueous ammonium chloride (20 mL) was added. The resulting mixture was extracted with ethyl acetate (20 mL twice), and the combined organic extracts were dried over anhydrous sodium sulfate and were concentrated in vacuo to afford allylic alcohol B5-2 (319.3 mg) as a colorless oil, which was used directly in the next step without purification. LCMS-ESI$^+$ (m/z) [M+H]$^+$ calcd for C$_{17}$H$_{29}$NO$_5$: 328.2; found: 328.2.

Step 3, Preparation of Intermediate B5: To a solution of alcohol B5-2 (319 mg, 0.98 mmol) in ethanol (4.9 mL) was added Pd/C (10%, 103.9 mg, 0.097 mmol) at rt under an argon atmosphere. The atmosphere was replaced with hydrogen and the reaction mixture was stirred vigorously at rt. After 16 h, the reaction mixture was diluted with ethyl acetate (25 mL) and was filtered through a pad of Celite with ethyl acetate washings (10 mL three times). The filtrate was concentrated in vacuo to afford Intermediate B5 (188 mg), which was used directly in the next step without purification. LCMS-ESI$^+$ (m/z): [M+H]$^+$ calcd for C$_{17}$H$_{32}$NO$_5$: 330.2; found: 330.3.

Preparation of Intermediate B6

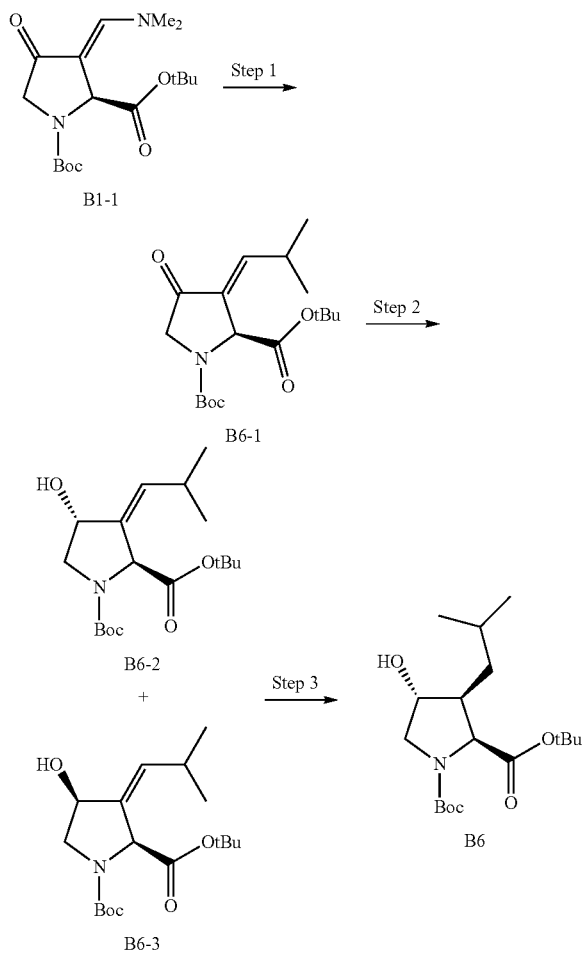

Step 1. Preparation of B6-1: A solution of isopropylmagnesium bromide (2.9 M in MeTHF, 3.2 mL, 9.3 mmol) was added dropwise to a cooled solution of B1-1 (1.02 g, 3.00 mmol) in 60 mL of ether at −78° C. under argon. Reaction mixture was warmed to room temperature and stirred for 3 hours. Reaction mixture was quenched with sat. aqueous NH$_4$Cl and extracted three times with ether Combined organics were washed with sat. aqueous NaHCO$_3$ and brine, dried (MgSO$_4$), filtered, and concentrated under reduced pressure. The resulting residue was purified by silica gel chromatography (0-30% ethyl acetate in hexanes) to yield B6-1 (743 mg) as a light yellow oil. $^1$H NMR (400 MHz, CDCl$_3$): δ 6.60 (dd, J=10.8, 2.4 Hz, 1H), 5.14 and 5.06 (rotamers, d, J=2.4 Hz, 1H), 3.96 (m, 2H), 2.91 (m, 1H), 1.46 (s, 9H), 1.27 (s, 9H), 1.04 (d, J=8.8 Hz, 6H).

Step 2. Preparation of B6-2 and B6-3: CeCl$_3$.7H$_2$O (1.32 g, 3.50 mmol) was added to a solution of B6-1 (740 mg, 2.18 mmol) in 47 mL of methanol at room temperature under argon. After cooling to −78° C., sodium borohydride (127 mg, 3.34 mmol) was added slowly portionwise. After two hours, reaction mixture was warmed to 0° C. After fifteen minutes, reaction mixture was quenched with sat. aqueous NH$_4$Cl and extracted three times with ethyl acetate. Combined organics were washed with brine, dried (MgSO$_4$), filtered and concentrated under reduced pressure to yield a ~3:1 mixture of B6-2 (major) and B6-3 (minor) as a colorless film (738 mg), which was used in the next step without further purification. $^1$H NMR (400 MHz, CDCl$_3$): δ 5.68-5.48 (m, 1H), 4.90-4.31 (m, 2H), 4.05-3.15 (m, 2H), 2.90-2.61 (m, 1H), 1.50-1.39 (br s, 18H), 1.02 (d, J=9.2 Hz, 6H).

Step 3. Preparation of Intermediate B6: The ~3:1 mixture of B6-2 and B6-3 (341 mg, 1.00 mmol) was dissolved in 28 mL of ethyl acetate. Palladium on carbon (10 wt %, 109 mg, 0.11 mmol) was then added and mixture was hydrogenated under an atmosphere of hydrogen for nineteen hours. Mixture was then filtered over Celite, washing with ethyl acetate, and filtrate was concentrated under reduced pressure. The resulting residue was purified by silica gel chromatography (0-50% ethyl acetate in hexanes) to yield Intermediate B6 (141 mg) as a colorless oil. $^1$H NMR (400 MHz, CDCl$_3$). δ 4.31-4.17 (m, 2H), 3.97-3.85 (m, 1H), 3.21-3.07 (m, 1H), 2.35-2.18 (m, 1H), 1.92-1.78 (m, 1H), 1.47-1.37 (m, 18H), 1.35-1.19 (m, 2H), 0.94 (d, J=8.8 Hz, 6H).

Preparation of Intermediate B7

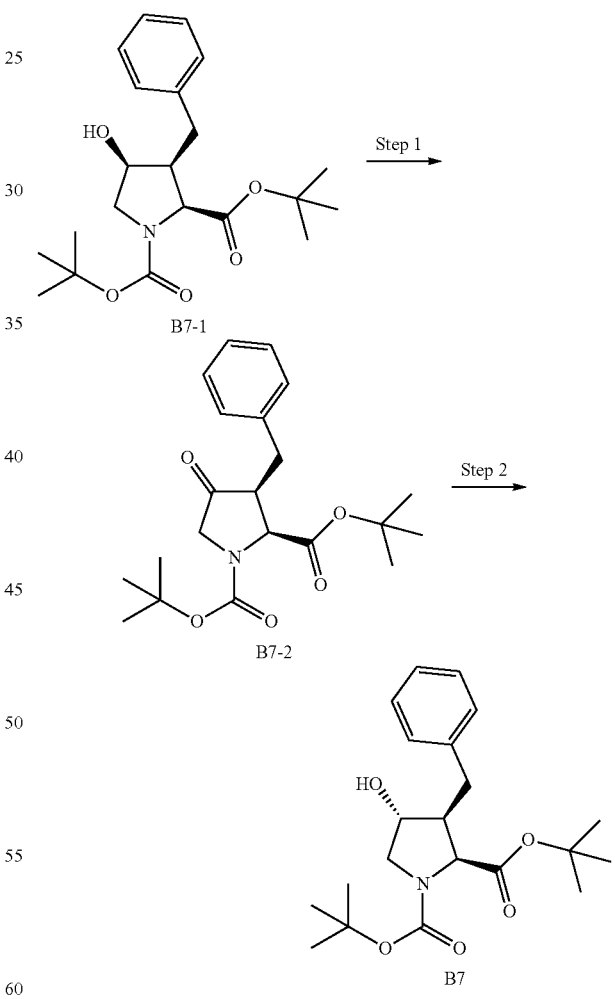

Step 1. Preparation of B7-2: To a solution of alcohol B7-1 (500 mg, 1.33 mmol; prepared according to Barreling, P., et al. *Tetrahedron* 1995, 51, 4195) in DCM (6.65 mL) was added Dess-Martin periodinane (564 mg, 1.33 mmol) at rt under an argon atmosphere. After 2 h, the reaction mixture was purified directly by silica gel chromatography (0-100% ethyl acetate/hexanes gradient) to afford ketone B7-2 (431 mg) as a colorless oil. LCMS-ESI⁺ (m/z): [M+H]° calcd for $C_{21}H_{30}NO_5$: 376.2; found: 376.2.

Step 2. Preparation of Intermediate B7: To a solution of intermediate B7-2 (410 mg, 1.09 mmol) and (R)-(+)-2-methyl-CBS-oxazaborolidine (Aldrich, 1 M in toluene, 1.09 mL, 1.09 mmol) in THF (5.45 mL) was added $BH_3$.THF (1 M in toluene, 2.18 mL, 2.18 mmol) at −78° C. under an argon atmosphere. After 1 h, the reaction mixture was quenched with saturated aqueous ammonium chloride solution (15 mL) and the resulting mixture was allowed to warm to rt. The phases where separated and the aqueous phase was extracted twice (20 mL) with DCM. The combined organic layers were dried over anhydrous sodium sulfate, and were concentrated in vacuo. The crude residue was purified by silica gel chromatography (0-100% ethyl acetate/hexanes gradient) to afford Intermediate B7 (390.9 mg, 4:1 diastereomeric mixture) as a colorless oil. LCMS-ESI⁺ (m/z): [M+H]⁺ calcd for $C_{21}H_{32}NO_5$: 378.2; found: 378.5.

Preparation of Intermediate B8

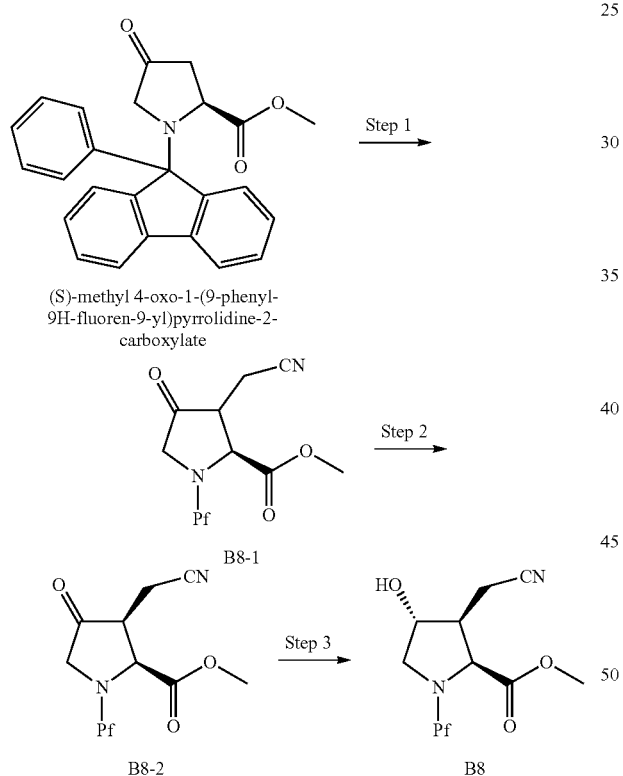

Step 1. Preparation of B8-1. n-BuLi (0.44 mL, 1.1 mmol, 2.5 M in hexane) was added to a cold (−78° C.) solution of (S)-methyl 4-oxo-1-(9-phenyl-9H-fluoren-9-yl)pyrrolidine-2-carboxylate (383 mg, 1 mmol, prepared as described in Sardina, F. J., Blanco, M.-J. *J Org. Chem.* 1996, 61, 4748) in THF/HMPA (3.8 mL/0.4 mL). The resulting solution was stirred at −78° C. to −50° C. for 1.5 h, and then bromoacetonitrile (0.2 mL, 3 mmol) was added. The reaction mixture was stirred while the temperature was allowed to reach −10° C. (4 h) To the reaction mixture was charged with saturated aqueous NH₄Cl (1 mL) and EtOAc (15 mL). The organic layer was separated, and the aqueous layer was extracted with EtOAc (10 mL). Both organic layers were combined, washed with H₂O and brine, and dried over Na₂SO₄. The organic layer was concentrated and purified via silica gel chromatography to afford diastereomeric mixture B8-1 (170 mg) as colorless oil.

Step 2. Preparation of B8-2. KHMDS (0.4 mL, 0.4 mmol, 1 M in THF) was added to a cold (−78° C.) solution of B8-1 (140 mg, 0.33 mmol) in THF/DMPU (1.5 mL/0.75 mL). The resulting solution was stirred at −78° C. for 1.5 h. Then HOAc (0.1 mL) was added. To the reaction mixture was charged with saturated aqueous NH₄Cl (1 mL) and EtOAc (15 mL). The organic layer was separated, and the aqueous layer was extracted with EtOAc (10 mL). Both organic layers were combined, washed with H₂O and brine, and dried over Na₂SO₄. The organic layer was concentrated and purified via silica gel chromatography to afford ketone B8-2 (120 mg) as colorless oil.

Step 3. Preparation of Intermediate B8. To an oven-dried, nitrogen-flushed flask was added $BH_3$.THF (0.28 mL, 0.28 mmol) followed by (R)-(+)-2-methyl-CBS-oxazaborolidine (0.012 mL, 0.03 mmol, 1.0 M in toluene). A solution of B8-2 (120 mg, 0.28 mmol) in THF (0.5 mL) was added dropwise. The reaction mixture was stirred at rt for 60 min, and then quenched by addition of 1.0 M aqueous HCl (0.2 mL). EtOAc (20 mL) was added and organic phase washed with sat. aqueous NaHCO₃ and brine, and dried over Na₂SO₄. The organic layer was concentrated and purified via silica gel chromatography to afford Intermediate B8 (100 mg) as colorless oil. LCMS-ESI⁺ (m/z): [M]⁺ calcd for $C_{27}H_{24}N_2O_3$: 424.49; found: 424.77.

Preparation of Intermediate C1

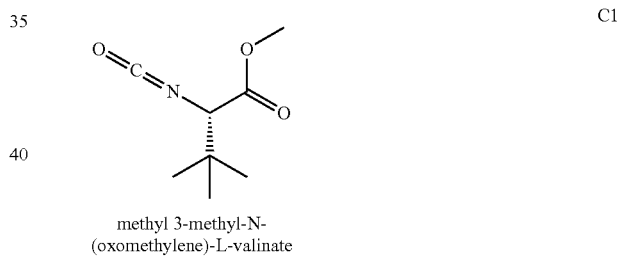

Methyl 3-methyl-N-(oxomethylene)-L-valinate (Intermediate C1) was prepared according to Step 3 of Intermediate B1 of International Patent Publication No. WO 2010/11566 (hereinafter "WO'566"), p 14.

Preparation of Intermediate C2

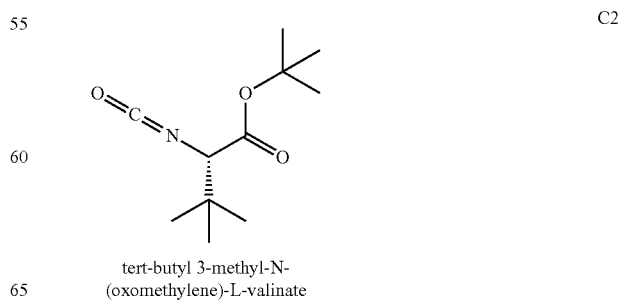

Intermediate C2 (tert-butyl 3-methyl-N-(oxomethylene)-L-valinate) was prepared in a similar fashion to Intermediate C1, substituting tert-butyl 3-methyl-L-valinate (Bachem AG) for methyl 3-methyl-L-valinate in Step 3 of intermediate B1 of WO'566, p 14.

Preparation of Intermediate D1

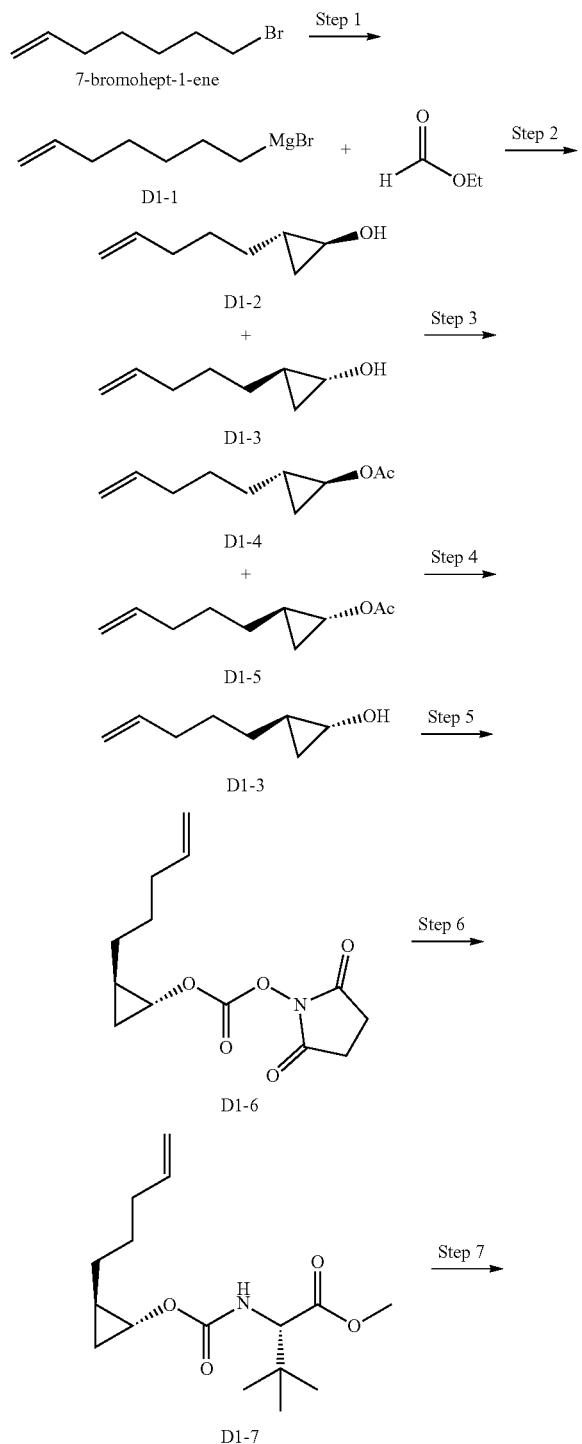

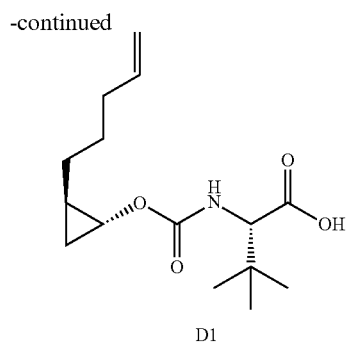

D1

Steps 1 and 2. Preparation of trans-cyclopropanol mixture D1-2 and D1-3: THF (1000 mL) was introduced in a three neck round bottomed flask containing Mg (32.2 g, 1.34 mol). A solution of 7-bromohept-1-ene (216 g, 1.22 mol) in THF (600 mL) was introduced to an addition funnel. One crystal of iodine and 20 mL of 7-bromohept-1-ene solution were added to the reaction. The solution was heated to reflux, and the remainder of the 7-bromohept-1-ene solution was added drop wise. After the addition was complete, the mixture was refluxed for an additional 2 h then allowed to cool to rt to produce a solution of Grignard reagent D1-1, which was then added dropwise to a solution of ethyl formate (30 g, 0.41 mol) and Ti(Oi-Pr)$_4$ (115.2 g, 0.41 mol) in THF (1200 mL) at rt. After stirring overnight, the mixture was poured into 1600 mL of 10% aqueous H$_2$SO$_4$ and extracted with MTBE (1500 mL three times). The combined organic layers were washed with brine, dried over MgSO$_4$, filtered and concentrated in vacuo. The residue was purified by silica gel chromatography to afford 31.0 g of a mixture of trans-cyclopropyl alcohols D1-2 and D1-3 as a yellow oil. $^1$H NMR: (400 MHz, CDCl$_3$): δ 5.77-5.70 (m, 1H), 4.96-4.86 (m, 2H), 3.15-3.12 (m, 1H), 2.03-1.98 (m, 2H), 1.75 (br s, 1H), 1.45-1.37 (m, 2H), 1.20-1.15 (m, 1H), 1.06-1.01 (m, 1H), 0.89-0.82 (m, 1H), 0.63-0.59 (m, 1H), 0.24 (q, J=6.0 Hz, 1H).

Step 3. Preparation of cyclopropyl acetate mixture D1-4 and D1-5: To a 1000 mL round bottom flask was added trans-cyclopropyl alcohol mixture D1-2 and D1-3 (60.3 g, 0.48 mol), 700 mL of DCM and TEA (62.9 g, 0.62 mol) prior to cooling the solution in an acetone/ice bath to an internal temp of <5° C. Acetyl chloride (41.3 g, 0.53 mol) was added dropwise to the solution over a 30 min period while maintaining an internal temp <10° C. The resulting slurry was then warmed to rt and stirred for 2 h. The reaction mixture was diluted with 350 mL of water. The biphasic mixture was transferred to a separatory funnel and the aqueous layer removed. The organic layer was washed with 480 mL of 2 N aqueous HCl and then with 500 mL of sat. aqueous NaHCO$_3$ prior to drying over MgSO$_4$. The solvent was removed in vacuo. The residue was purified by silica gel chromatography to afford a mixture D1-4 and D1-5 (56.3 g) as a yellow oil. TLC Information (PE/EtOAc=5/1) R$_f$ (starting material)=0.4: R$_f$ (product)=0.8.

Step 4. Preparation of D1-3: To a 1000 mL round-bottom flask was added a solution of mixture D1-4 and DI-5 (39 g, 0.23 mol) in 680 mL of MTBE saturated with aqueous 0.1 M pH 7 phosphate buffer. The flask was placed in an ice bath to maintain an internal temperature of approximately 10° C. throughout the hydrolysis reaction which was initiated by the addition of 3.0 g of Novozyme 435. The reaction was aged at 10° C. for approximately 6 h until conversion had reached about 40%. The reaction mixture was filtered, and the solid immobilized enzyme was washed three times with 200 mL of MTBE. The resulting MTBE solution was concentrated in vacuo. The residue was purified by silica gel chromatography to afford D1-3 (11.3 g) as a yellow oil. $^1$H NMR: (400 MHz, CDCl$_3$) δ 5.80-5.75 (m, 1H), 5.02-4.91 (min, 2H), 3.20-3.17 (m, 1H), 2.09-2.03 (m, 3H), 1.50-1.43 (m, 2H), 1.26-1.22 (m, 1H), 1.17-1.08 (m, 1H), 1.07-0.89 (m, 1H), 0.70-0.65 (m, 1H), 0.32-0.27 (m, 1H).

Step 5. Preparation of D1-6: Cyclopropanol D1-3 (17.7 g, 0.140 mol) was dissolved in 300 mL of MeCN at 0° C. To the solution was added DSC (72.0 g, 0.280 mol) and TEA (42.42 g, 0.420 mol). The reaction mixture was warmed to 40° C. and stirred overnight and then concentrated in vacuo. The residue was purified by silica gel chromatography to afford D1-6 (25.8 g) as a yellow solid. $^1$H NMR: (400 MHz, CDCl$_3$) δ 5.84-5.77 (m, 1H), 5.05-4.96 (m, 2H), 4.09-4.03 (d, J=24 Hz, 1H), 2.86 (s, 4H), 2.12-2.06 (m, 2H), 1.58-1.51 (m, 2H), 1.33-1.27 (m, 3H), 1.09 (m, 1H), 0.68-0.62 (m, 1H).

Step 6. Preparation of D1-7: To a solution of D1-6 (10 g, 0.0374 mol) in THF (374 mL) was added L-tert-leucine methyl ester hydrochloride (10.2 g, 0.056 mol) and TEA (11.3 g, 0.112 mol), The solution was stirred overnight at 40° C. The mixture was concentrated in vacuo. The residue was diluted with EtOAc and washed with water and brine, dried over anhydrous sodium sulfate, filtered and concentrated in vacuo. The residue was purified by silica gel chromatography to afford D1-7 (10.2 g) as a yellow oil. LCMS-ESI$^+$ (m/z): [M+H]$^+$ calcd for C$_{16}$H$_{28}$NO$_4$: 298.2; found: 298.0.

Step 7. Preparation of Intermediate D1: A solution of D1-7 (20 g, 0.067 mol) in 2:1 mixture of MeOH/H$_2$O (447 mL/223 mL) was treated with LiOH.H$_2$O (11.3 g, 0.269 mol) and then heated at 60° C. for 4 h. The reaction mixture was cooled, concentrated to half volume and extracted with MTBE. Then the aqueous solution was acidified with aqueous 1 N HCl (400 mL) and extracted with EtOAc (400 mL×3), the combined organic layers were washed with brine, dried over Na$_2$SO$_4$, filtered and concentrated to afford Intermediate D1 (18 g). $^1$H NMR: (400 MHz, CDCl$_3$) δ 10.5-9.4 (br, 1H), 5.82-5.71 (m, 1H), 5.20-5.17 (m, 1H), 4.99-4.91 (m, 2H), 4.19-4.16 (m, 1H), 3.86-3.68 (m, 1H), 2.09-2.03 (m, 2H), 1.53-1.32 (m, 2H), 1.30-1.20 (m, 2H), 1.18-1.13 (m, 1H), 1.11-0.99 (s, 9H), 0.80-0.75 (m, 1H), 0.49-0.47 (m, 1H).

Preparation of Intermediate D2

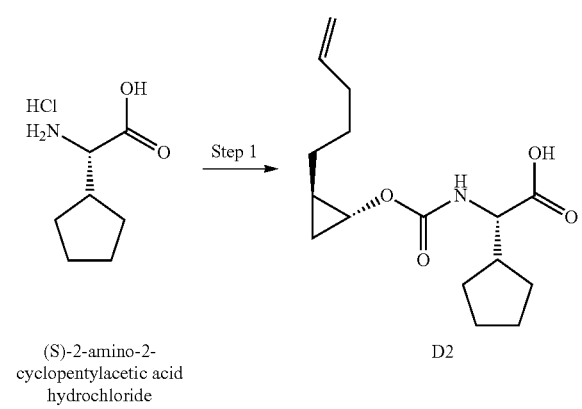 [SMILES: Cl ; N[C@H](C(=O)O)C1CCCC1 ; C=CCCC[C@@H]1C[C@H]1OC(=O)N[C@H](C(=O)O)C1CCCC1 ; "D2"]

(S)-2-amino-2-cyclopentylacetic acid hydrochloride

D2

Step 1. Preparation of Intermediate D2: To a suspension of D1-6 (600 mg, 2.25 mmol) and (S)-2-amino-2-cyclopentylacetic acid hydrochloride salt (386 mg, 2.7 mmol, Betapharma Inc.) in THF (20 mL) were added distilled water (6 mL) and triethylamine (0.94 mL, 6.74 mmol). The homogeneous solution was allowed to stir for ~18 h. The THF was evaporated and the aqueous residue was diluted with water (20 mL). The mixture was basified with 1 N NaOH (pH>10) and then washed twice (20 mL) with ethyl acetate. The aqueous phase was then acidified with 1 N HCl (pH<2) and the resulting solution was extracted twice (20 mL) with ethyl acetate. The combined organic phase was dried over anhydrous MgSO$_4$ and concentrated to afford Intermediate D2 (500 mg) as a brown oil. This was used without purification in a subsequent step. LCMS-ESI$^+$ (m/z): [M+H]$^+$ calcd for C$_{16}$H$_{26}$NO$_4$: 296.2, found: 296.3.

Preparation of Intermediate D3

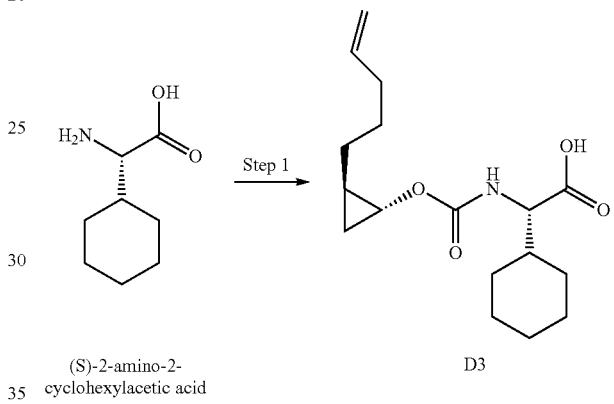

(S)-2-amino-2-cyclohexylacetic acid

D3

Step 1. Preparation of Intermediate D3: To a suspension of D1-6 (800 mg, 3 mmol) and (S)-2-amino-2-cyclohexylacetic acid (519 mg, 3.3 mmol; Alfa Aesar) in water (15 mL) was added K$_3$PO$_4$ (1.27 g, 6 mmol). The homogeneous solution was allowed to stir at rt for 5 h. To the reaction mixture was charged with water (15 mL) and EtOAc (15 mL). The organic layer was separated, and the aqueous layer was extracted with EtOAc (10 mL). Organic layers were combined, washed with 1 N HCl, H$_2$O and brine, and dried over Na$_2$SO$_4$. Concentration of the organic solution afforded Intermediate D3 (850 mg) as an oil that was used subsequently without further purification. LCMS-ESI$^+$ (m/z): [M+H]$^+$ calcd for C$_{17}$H$_{28}$NO$_4$: 310.4; found: 310.3.

Preparation of Intermediate D4

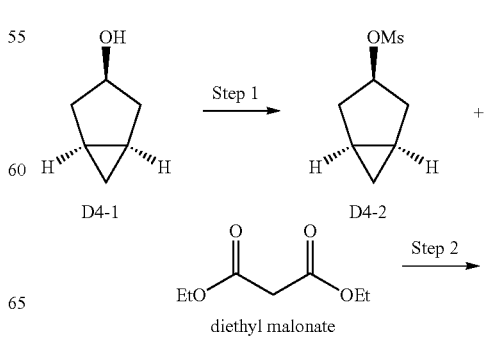

diethyl malonate

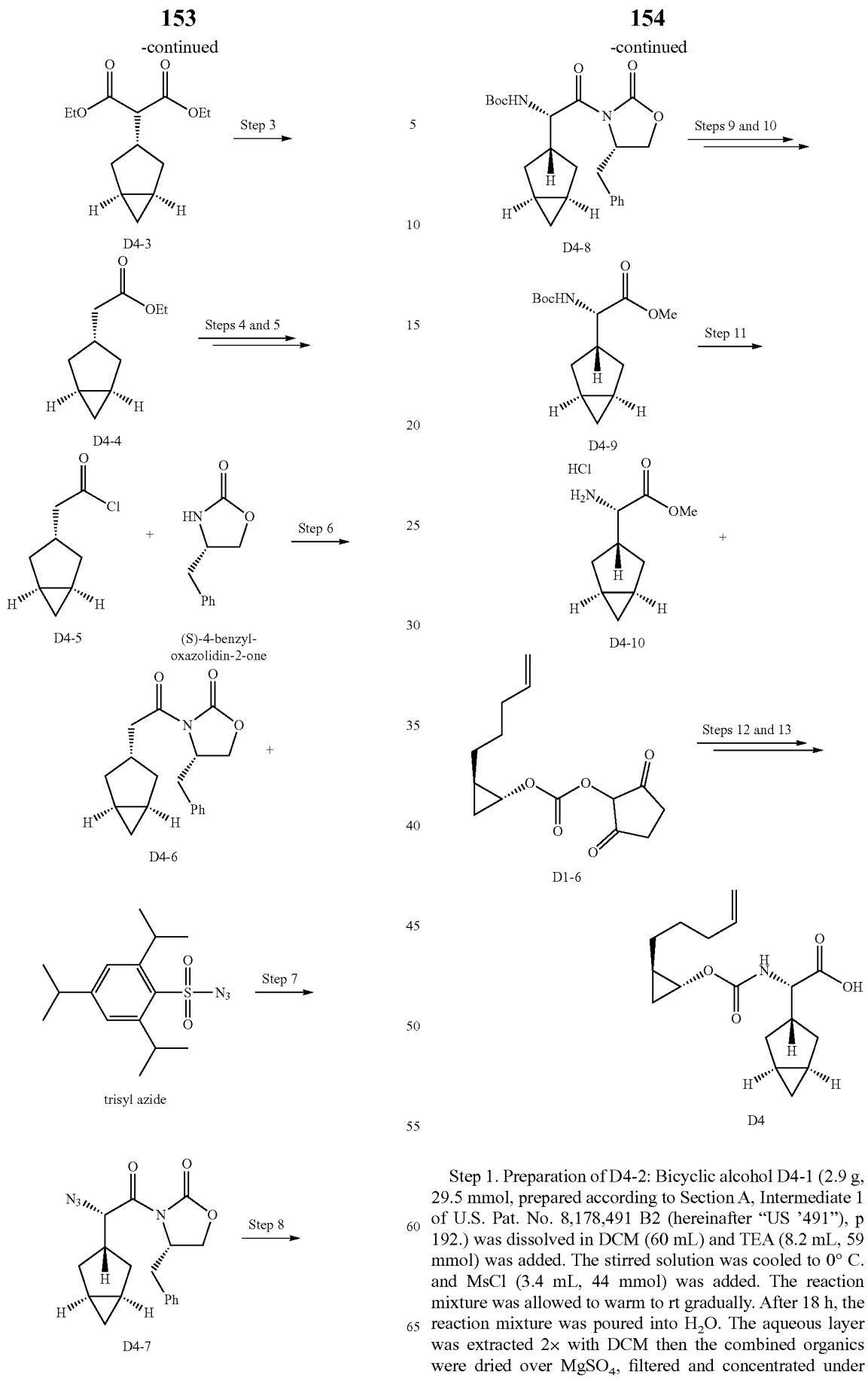

Step 1. Preparation of D4-2: Bicyclic alcohol D4-1 (2.9 g, 29.5 mmol, prepared according to Section A, Intermediate 1 of U.S. Pat. No. 8,178,491 B2 (hereinafter "US '491"), p 192.) was dissolved in DCM (60 mL) and TEA (8.2 mL, 59 mmol) was added. The stirred solution was cooled to 0° C. and MsCl (3.4 mL, 44 mmol) was added. The reaction mixture was allowed to warm to rt gradually. After 18 h, the reaction mixture was poured into H₂O. The aqueous layer was extracted 2× with DCM then the combined organics were dried over MgSO₄, filtered and concentrated under reduced pressure. The crude material was purified by silica gel chromatography (20% to 50% EtOAc/Hex) to afford D4-2 (3.73 g).

Step 2. Preparation of D4-3: NaH (1.69 g, 42.3 mmol) was suspended in 100 mL THF and the mixture was cooled to 0° C. Diethyl malonate (6.4 mL, 47 mmol) was added dropwise over 4 min and the stirred mixture was warmed to rt. After another hour, mesylate D4-2 (3.73 g, 21.2 mmol) in 20 mL THF was added and the reaction mixture was heated to reflux for 15 h. After this period, the reaction mixture was cooled to rt and poured into saturated aqueous $NaHCO_3$. The aqueous layer was extracted 2× with EtOAc. Then, the organics were dried over $MgSO_4$, filtered and concentrated under reduced pressure. The crude material was purified by silica gel chromatography (0% to 15% EtOAc/Hex) to afford D4-3 (4.64 g).

Step 3. Preparation of D4-4: Malonate D4-3 (4.64 g, 19.3 mmol) was dissolved in 20 mL DMSO then NaCl (1.24 g, 21.2 mmol) and water (0.694 mL, 38.6 mmol) were added. The stirred mixture was heated to 170° C. for 48 h then cooled to rt and diluted with $Et_2O$. The organic solution was washed with $H_2O$ twice, then brine, dried over $MgSO_4$, filtered and concentrated under reduced pressure. The crude material was purified by silica gel chromatography (5% to 15% EtOAc/Hex) to afford D44 (2.83 g).

Steps 4 and 5. Preparation of D4-5: A solution of ethyl ester D4-4 (2.83 g, 16.8 mmol) and LiOH (1 M in $H_2O$, 34 mL, 34 mmol) in EtOH (68 mL) was stirred at rt o/n then concentrated under reduced pressure to remove EtOH. The remaining material was diluted with $H_2O$ and washed twice with DCM. The aqueous phase was acidified to pH 1-2 with 10% HCl and then extracted three times with DCM. This DCM solution was dried over $MgSO_4$, filtered and concentrated under reduced pressure. The resulting crude carboxylic acid was dissolved in DCM (100 mL) and treated with DMF (5 drops). Oxalyl chloride (2.2 mL, 25 mmol) was added carefully. After stirring o/n, the reaction mixture was concentrated under reduced pressure to afford D4-5, which was carried on without further purification.

Step 6. Preparation of D4-6. (S)-4-Benzyl-2-oxazolidinone (3.57 g, 20.2 mmol) was dissolved in THF (80 mL) and cooled to −78° C. n-BuLi (1.6 M in hexane, 12.6 mL, 20.2 mmol) was added dropwise over 7 min and the reaction mixture was allowed to stir at −78° C. for 30 min. This solution, containing the lithiated oxazolidinone was then added by cannula to a −78° C. solution of acid chloride D4-5 (16.8 mmol) in THF (80 mL) over 6 min. After stirring at −78° C. for an additional 30 min, the reaction mixture was quenched by addition of 1 M aqueous $NaHSO_4$. The aqueous phase was extracted with EtOAc and the organic layer was dried over $MgSO_4$, filtered and concentrated under reduced pressure. The crude material was purified by silica gel chromatography (10% to 40% EtOAc/Hex) to afford D4-6 (4.32 g). LCMS-ESI$^+$ (m/z): [M+H]$^+$ calcd for $C_{15}H_{22}NO_3$: 300.16; found: 300.14.

Step 7. Preparation of D4-7: A solution of KHMDS (0.5 M in PhMe, 3.4 mL, 1.7 mmol) in THF (5 mL) was cooled to −78° C. and a separate −78° C. solution of oxazolidinone D4-6 (465 mg, 1.55 mmol) in THF (5 mL) was added dropwise by cannula. After 30 min, a −78° C. solution of trisyl azide (576 mg, 1.86 mmol) in THF (5 mL) was added by cannula. Three min later, the reaction was quenched by addition of AcOH (0.41 mL, 7.13 mmol) and the reaction mixture was heated to 30° C. for 2 h. After cooling, the mixture was poured into brine. The aqueous layer was extracted three times with DCM. The combined organics were dried over $MgSO_4$, filtered and concentrated under reduced pressure. The crude material was purified by silica gel chromatography (4% to 25% EtOAc/Hex) to afford azide D4-7 (367 mg). LCMS-ESI$^+$ (m/z): [M+H]$^+$ calcd for $C_{18}H_{21}N_4O_3$: 341.16 found: 341.10.

Step 8. Preparation of D4-8: Azide D4-7 (367 mg, 1.08 mmol) and di-tert-butyl dicarbonate (471 mg, 2.16 mmol) were dissolved in EtOAc (20 mL). 10% Pd/C (197 mg) was added and the atmosphere replaced with $H_2$. The suspension was stirred under 1 atm $H_2$ for 20 h, then filtered over Celite and concentrated under reduced pressure. The crude residue was purified by silica gel chromatography (15% to 30% EtOAc/Hex) to afford D4-8 (376 mg). LCMS-ESI$^+$ (m/z): [M-(t-Bu)+H]$^+$ calcd for $C_{19}H_{23}N_2O_5$: 359.16; found: 359.43.

Steps 9 and 10. Preparation of D4-9: Carbamate D4-8 (376 mg, 0.907 mmol) was dissolved in THF (9 mL) and cooled to 0° C. $H_2O_2$ (30% in $H_2O$, 0.463 mL, 4.54 mmol) and LiOH (1 M in $H_2O$, 2.7 mL, 2.7 mmol) were added. The reaction was allowed to stir at 0° C. for another 2 h and was then concentrated under reduced pressure. The resulting concentrate was poured into $H_2O$ and the aqueous solution was washed twice with $Et_2O$, then acidified to pH 1-2 and extracted three times with DCM. The combined extracts were dried over $MgSO_4$, filtered and concentrated under reduced pressure. The resulting crude residue was dissolved in DCM (8 mL) and MeOH (1 mL) and treated with trimethylsilyldiazomethane (2 M in hexane, 0.9 mL, 1.8 mmol). After stirring for 40 min at rt, the reaction was quenched by addition of 10% AcOH/MeOH and concentrated under reduced pressure. The residue was purified by silica gel chromatography (4% to 25% EtOAc/Hex) to afford D4-9 (167 mg). $^1$H NMR (400 MHz, CDCl$_3$) δ 4.98 (d, J=7.8 Hz, 1H), 4.22 (t, J=7.0 Hz, 1H), 3.70 (s, 3H), 1.89 (m, 1H), 1.77-1.46 (m, 4H), 1.42 (s, 9H), 1.22 (m, 2H), 0.28 (dd, J=7.2 Hz, 13.3 Hz, 1H), 0.13 (d, J=3.7 Hz, 1H).

Step 11. Preparation of D4-10: Carbamate D4-9 (223 mg, 0.828 mmol) was dissolved in DCM (4 mL) and treated with HCl (4.0 M in dioxane, 1 mL, 4.0 mmol). After stirring at rt for 17 h, the reaction mixture was concentrated under reduced pressure to afford amine hydrochloride salt D4-10, which was carried on without purification. LCMS-ESI$^+$ (m/z): [M+H]$^+$ calcd for $C_9H_{16}NO_2$: 170.12; found: 170.04.

Steps 12 and 13. Preparation of Intermediate D4: Amine hydrochloride salt D4-10 (0.828 mmol, theoretical) in $H_2O$ (1.4 mL) was treated with a freshly prepared solution of D1-6 (1.35 mmol) in DMF (1.4 mL). $K_3PO_4$ (703 mg, 3.31 mmol) was added and the reaction mixture was stirred for 2 h at rt After dilution with EtOAc, the organic layer was washed with 10% aqueous HCl and brine, then dried over $MgSO_4$, filtered and concentrated under reduced pressure. The residue was purified by silica gel chromatography (0% to 25% EtOAc/Hex) to afford the expected carbamate (239 mg). LCMS-ESI$^+$ (m/z): [M+H]$^+$ calcd for $C_{18}H_{28}NO_4$: 322.20; found: 323.00. This material (239 mg, 0.744 mmol) was dissolved in MeOH and treated with LiOH (1.0 M in $H_2O$, 5.0 mL, 5.0 mmol). After stirring at rt for 1 h, the MeOH was removed under reduced pressure. The aqueous solution was acidified to pH 1-2 with 10% aqueous HCl and was extracted three times with DCM. The combined organics were dried over $MgSO_4$, filtered and concentrated under reduced pressure to afford Intermediate D4 (229 mg) LCMS ESI$^+$ (m/z): [M+H]$^+$ calcd for $C_{17}H_{26}NO_4$: 308.2; found: 307.9.

Preparation of Intermediate D5

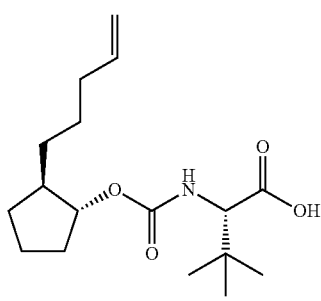

D5

Intermediate D5 was prepared according to the procedure detailed in Li. H., et al *Synlett* 2011, 10, 1454.

Preparation of Intermediate Mixture D6

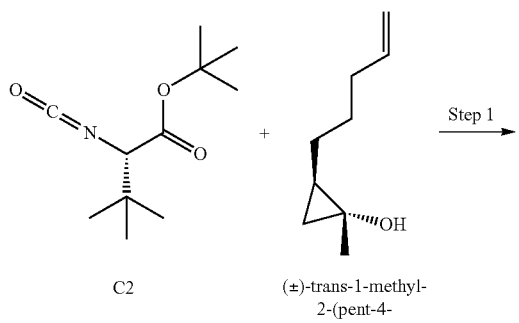

C2    (±)-trans-1-methyl-2-(pent-4-enyl)cyclopropanol

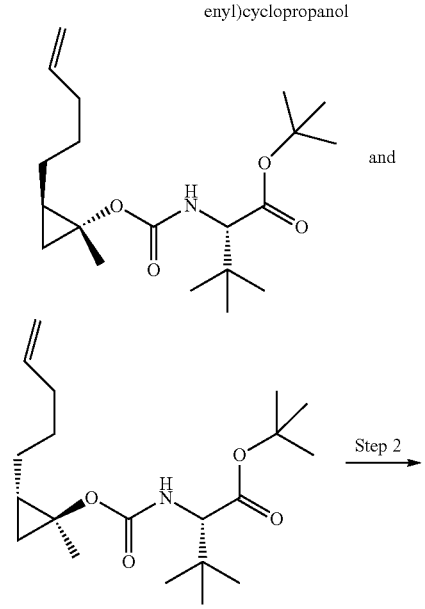

D6-1

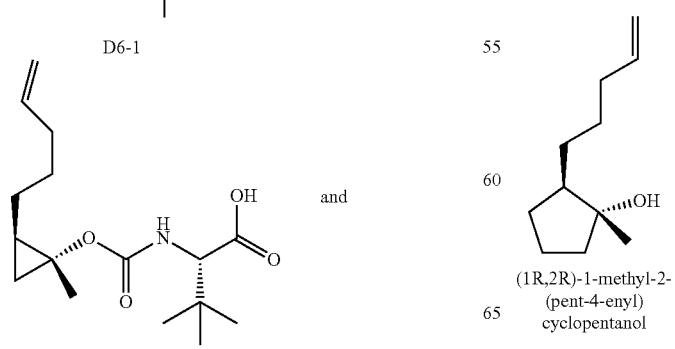

and

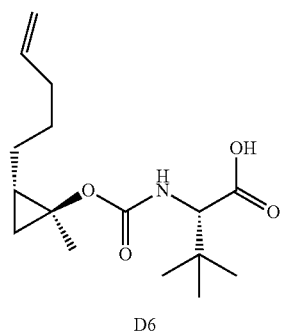

D6

Step 1. Preparation of diastereomeric carbamate mixture D6-1: Intermediate C2 (1.34 g, 6.31 mmol), (±)-trans-1-methyl-2-(pent-4-enyl)cyclopropanol (590 mg, 4.208 mmol; prepared according to procedure for Intermediate C3, WO02011014487, p. 36), DMAP (514 mg, 4.21 mmol), and DIPEA (2.93 mL, 16.83 mmol) were combined in toluene (14 mL). The reaction was heated at 90° C. for 18 h. The reaction was diluted with Et$_2$O (25 mL) and 1 N aqueous HCl (75 mL), stirred well, and organics were removed. The aqueous layer was extracted three times with ether (50 mL), the organics were combined, washed with brine, dried over MgSO$_4$, filtered, and concentrated to give a crude oil, which was purified via silica gel chromatography to give 1:1 diastereomeric mixture D6-1 as a clear oil (820 mg). LCMS-ESI$^+$ (m/z): [M+Na]$^+$ calcd for C$_{20}$H$_{35}$NNaO$_4$: 376.3; found: 376.2.

Step 2: Preparation of diastereomeric Intermediate mixture D6. The diastereomeric mixture D6-1 was taken up in DCM (2 mL) and treated with TFA (2 mL) at room temperature. After 1.5 h, the reaction was concentrated in vacuo and co-evaporated with chloroform repeatedly to remove residual TFA and purified via silica gel chromatography to give 1:1 diastereomeric mixture of Intermediate D6 as a brown oil, (536 mg) LCMS-ESI$^+$ (m/z): [M+Na]$^+$ calcd for C$_{16}$H$_{27}$NNaO$_4$: 320.2; found: 320.1.

Preparation of Intermediate D7

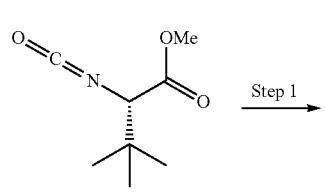

(1R,2R)-1-methyl-2-(pent-4-enyl)cyclopentanol

C1

Step 1

159
-continued

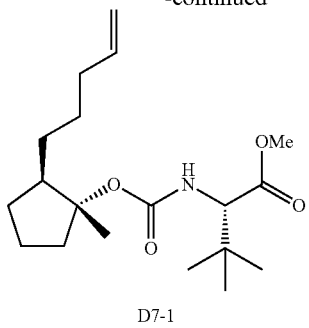

D7-1

Step 2 →

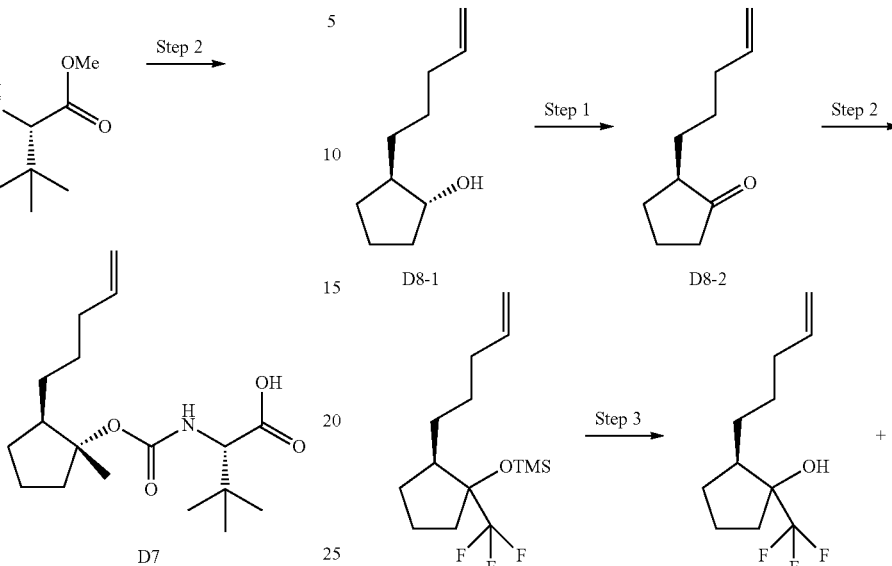

D7

Step 1. Preparation of D7-1: (1R,2R)-1-methyl-2-(pent-4-enyl)cyclopentanol (220.9 mg, 1.313 mmol, prepared according to procedure for Intermediate B26. International Patent Publication No. WO 2008/057209 (hereinafter "WO '209") p 45) and Intermediate C1 (337.1 mg, 1.969 mmol) were treated with DIPEA (0.91 mL, 5.252 mmol) and DMAP (160.4 mg, 1.313 mmol) in toluene (4.4 mL). The mixture was heated at 85° C. for 21 h. The solution was diluted with ether (80 mL). The solution was washed with 1 N aqueous HCl (30 mL) and brine (30 mL) successively. Obtained organic layer was dried over Na₂SO₄. After removal of drying agent by a filtration, the solvent was removed under reduced pressure. The residue was purified by silica gel chromatography (13% ethyl acetate in hexanes) to give D7-1 (249.5 mg, 0.735 mmol) as colorless oil. $^1$H NMR (300 MHz, CDCl₃, rotamers expressed as total H value×fraction present) δ 5.76-5.92 (m, 1H), 5.12 (d, J=9.6 Hz, 1H), 5.02 (d, J=16.8 Hz, 1H), 4.96 (d, J=9.6 Hz, 1H), 4.13 (d, J=9.6 Hz, 1H), 3.81 (s, 3×4/10H), 3.73 (s, 3×6/10H), 1.80-2.15 (m, 7H), 1.04-1.74 (m, 6H), 1.36 (s, 3H), 1.04 (s, 9×4/10H), 0.97 (s, 9×6/10H).

Step 2. Preparation of Intermediate 07: Ester D7-1 (249.5 mg, 0.735 mmol) was treated with 2 M aqueous LiOH aqueous solution (2 mL, 4.0 mmol) in MeOH/THF (4 mL/4 mL) at rt for 25 h. The reaction mixture was then treated with 1 N aqueous HCl (5 mL) and aqueous brine (25 mL) to slightly acidify. The mixture was extracted three times with CH₂Cl₂ (30 mL). The organic layer was washed with aqueous brine (30 mL). Obtained organic layer was dried over Na₂SO₄. After removal of drying agent by filtration, the solvent was removed under a reduced pressure to give intermediate D7 (191.2 mg, 0.587 mmol) as a colorless oil which was used subsequently without further purification. $^1$H NMR (300 MHz, CDCl₃) δ 9.00 (br s, 1H), 5.72-5.90 (m, 1H), 5.12 (d, J=9.6 Hz, 1H), 5.00 (d, J=16.8 Hz, 1H), 4.94 (d, J=9.6 Hz, 1H), 4.13 (d, J=9.6 Hz, 1H), 1.80-2.16 (m, 7H), 1.04-1.74 (m, 6H), 1.35 (s, 3H), 1.02 (s, 9H).

160

Preparation of Intermediate Mixture D-8

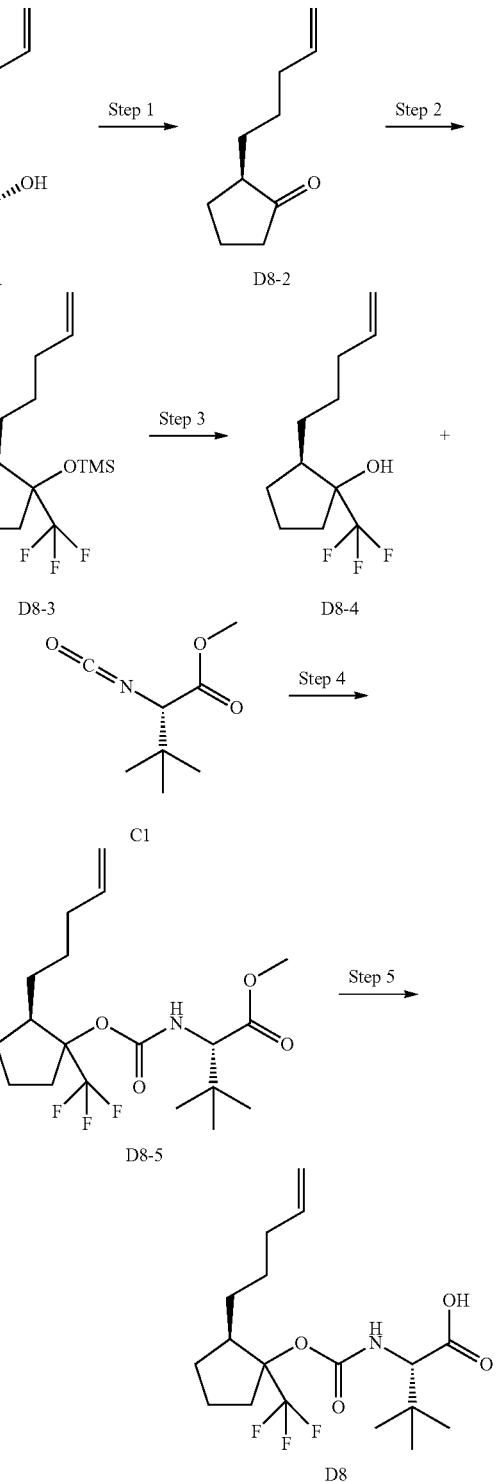

Step 1. Preparation of D8-2: To a solution of intermediate D8-1 (500 mg, 3.24 mmol, prepared according to WO '209, p. 36) in DCM (6.65 mL) was added Dess-Martin periodinane (1.37 g, 3.24 mmol) at rt under an argon atmosphere. After 6 h, the reaction mixture was filtered through a pad of Celite and was directly purified by silica gel chromatography (0-100% ethyl acetate/hexanes gradient) to afford ketone D8-2 (252 mg) as a colorless oil. $^1$H NMR (400 MHz, CDCl$_3$) δ 5.81 (ddt, J=16.9, 10.2, 6.6 Hz, 1H), 5.05-4.92 (m, 2H), 2.38-1.93 (m, 7H), 1.87-1.68 (m, 2H), 1.60-1.37 (m, 3H), 1.35-1.20 (m, 1H).

Step 2. Preparation of diastereomeric mixture D8-3: To a solution of ketone D8-2 (385 mg, 2.53 mmol) and TMSCF$_3$ (749 μL, 5.07 mmol) in THF (2.3 mL) was added CsF (7.0 mg, 46 μmol) at rt under an argon atmosphere. After 2.5 h, the reaction mixture was diluted with water (10 mL) and the resulting mixture was extracted twice with DCM (10 mL). The combined organic layers were dried over anhydrous sodium sulfate, and were concentrated in vacuo. The crude residue was purified by silica gel chromatography (0-100% ethyl acetate/hexanes gradient) to afford silyl ether D8-3 (714 mg, 1:1 diastereomeric mixture) as a colorless oil. $^1$H NMR (400 MHz, CDCl$_3$) δ 5.67 (ddt, J=13.3, 10.1, 6.7 Hz, 1H), 4.91-4.76 (m, 2H), 2.02-1.00 (m, 13H), 0.00 (s, 9H).

Step 3. Preparation of diastereomeric mixture D8-4: To a solution of D8-3 (700 mg, 2.38 mmol) in THF (11.9 mL) was added TBAF (1 M in THF, 2.38 mL, 2.38 mmol) at rt under an argon atmosphere. After 30 min. the reaction mixture was diluted with dichloromethane (100 mL). The resulting mixture was washed with saturated aqueous sodium bicarbonate solution (75 mL), was dried over anhydrous sodium sulfate, and was concentrated in vacuo. The crude residue was purified by silica gel chromatography (0-100% ethyl acetate/hexanes gradient) to afford alcohol D8-4 (418 mg, 1:1 diastereomeric mixture) as a colorless oil. $^1$H NMR (400 MHz, CDCl$_3$) δ 5.81 (dt, J=16.8, 6.6 Hz, 1H), 5.09-4.88 (m, 2H), 2.20-1.91 (m, 4H), 1.86-1.08 (m, 10H).

Step 4. Preparation of diastereomeric mixture D8-5: A solution of D8-4 (380 mg, 1.72 mmol), Intermediate C1 (295.7 mg, 1.72 mmol), DIPEA (1.20 mL, 6.88 mmol), and DMAP (210 mg, 1.72 mmol) in toluene (8.6 mL) was heated to 85° C. under an argon atmosphere. After 20 h, the reaction mixture was allowed to cool to rt and was diluted with ethyl acetate (100 mL). The resulting mixture was washed with 1 N HCl solution (50 mL), saturated aqueous sodium bicarbonate solution (50 mL), and brine (50 mL). The organic layer was dried over anhydrous sodium sulfate, and was concentrated in vacuo. The crude residue was purified by silica gel chromatography (0-100% ethyl acetate/hexanes gradient) to afford carbamate D8-5 (550 mg, 1:1 diastereomeric mixture) as a colorless oil. $^1$H NMR (400 MHz, CDCl$_3$) δ 5.81 (ddt, J=16.7, 9.8, 6.6 Hz, 1H), 5.37 (d, J=9.4 Hz, 1H), 5.06-4.89 (m, 2H), 4.16-4.07 (m, 1H), 3.75 (s, 3H), 2.84-2.29 (m, 2H), 2.27-1.89 (m, 3H), 1.85-1.12 (m, 8H), 0.98 (s, 9H).

Step 5. Preparation of diastereomeric intermediate mixture D8. To a solution of carbamate D8-5 (500 mg, 1.27 mmol) in DCE (6.4 mL) was added trimethyltin hydroxide (2.30 g, 12.7 mmol) at rt under an argon atmosphere, and the resulting mixture was heated to 65° C. After 21 h, the reaction mixture allowed to cool to rt and was diluted with 1 N HCl solution (50 mL). The resulting mixture was extracted with ethyl acetate (2×50 mL). The combined organic extracts were dried over anhydrous sodium sulfate and were concentrated in vacuo to afford Intermediate D8 (575 mg, 1:1 diastereomeric mixture) as a colorless oil, which was used subsequently without further purification. $^1$H NMR (400 MHz, CDCl$_3$) δ 5.90-5.71 (m, 1H), 5.32 (d, J=9.3 Hz, 1H), 5.07-4.89 (m, 2H), 4.16 (d, J=9.8 Hz, 1H), 2.83-2.30 (m, 2H), 2.27-1.87 (m, 3H), 1.83-1.12 (m, 8H), 1.04 (s, 9H).

Preparation of Intermediate Mixture D9 and D10

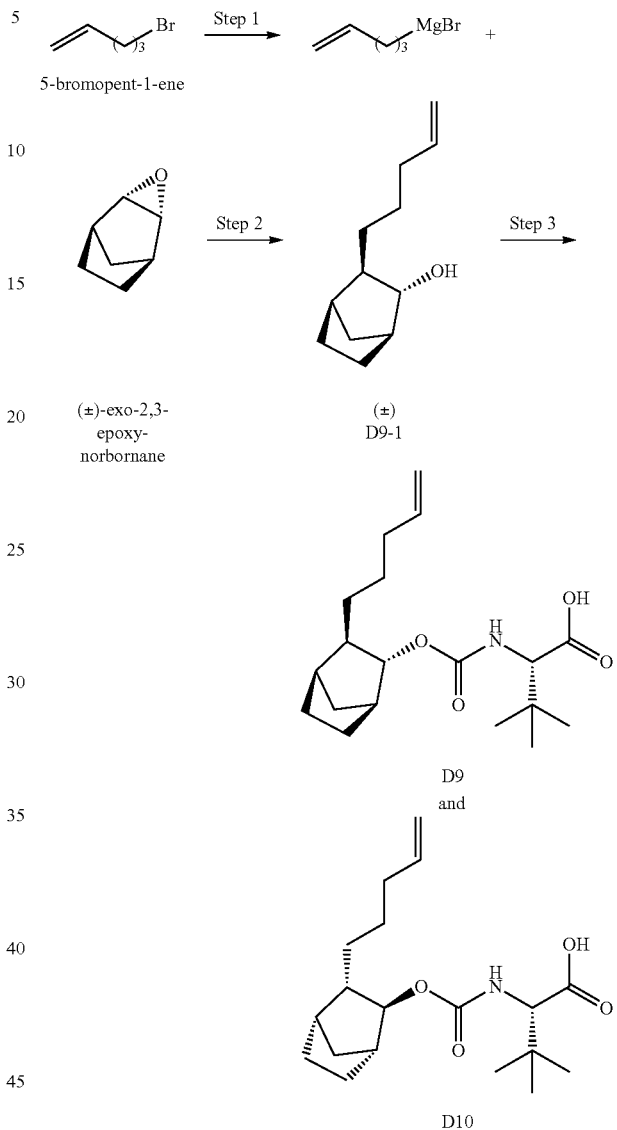

Steps 1 and 2: Preparation of racemate D9-1: Magnesium metal (1.32 g, 54.3 mmol) was added to a 2-neck flask fitted with a reflux condenser and the vessel was flushed with Ar. THF (42 mL) was added followed by iodine (ca. 5 mg). The stirred suspension was heated to 45° C. and 5-bromopent-1-ene was added (1.2 g, 8.1 mmol) in one portion. After stirring several minutes, additional 5-bromopent-1-ene (5.5 g, 37 mmol) was added at a rate sufficient to maintain gentle reflux. The resulting mixture was stirred at 50° C. for 15 min and was then cooled to ambient temperature and used immediately in the following step. A suspension of CuI (630 mg, 3.3 mmol) in THF (24 mL) under Argon was cooled to −5° C. An aliquot of pent-4-enylmagnesium bromide (ca. 0.95 M, 20 mL, 19 mmol) prepared in step 1 was added over 5 min, and the resulting mixture was stirred for an additional 15 min. The reaction mixture was then cooled to −20° C. and (±)-exo-2,3-epoxynorbornane (1.5 g, 14 mmol) was added as a solution in THF (5 mL) over 1 min. Two additional portions of THF (2.5 mL each) were used to ensure complete transfer, and the resulting mixture was stirred for 20 min. The reaction was then removed from the cold bath and warmed to rt. After stirring an additional 1.75 h, the reaction was quenched with saturated aqueous NH₄Cl (5 mL) and was filtered with EtOAc (100 mL) and H₂O (100 mL) through Celite. The phases were separated, and the organic phase was dried over Na₂SO₄, filtered, and concentrated to afford (±)-D9-1 as a colorless residue (813 mg), $^1$H NMR (300 MHz, CDCl₃) δ 5.90-5.67 (m, 1H), 5.04-486 (m, 2H), 3.12 (s, 1H), 2.20-1.92 (m, 5H), 1.69-1.57 (m, 1H), 1.55-1.12 (m, 9H), 1.03-0.84 (m, 1H).

Step 3. Preparation of diastereomeric Intermediate mixture D9 and D10: Alcohol mixture (±)-D9-1 (813 mg, 4.51 mmol) was dissolved in DMF (4.5 mL). Pyridine (370 µL, 4.5 mmol) was added followed by DSC (1.5 g, 5.8 mmol). The reaction mixture was heated to 45° C. and was stirred for 4 h. The reaction mixture was then cooled to 0° C. and water (4.5 mL) was added dropwise over 2 min. The reaction mixture was stirred for 5 min and was removed from the cold bath. After an additional 5 min, the reaction mixture was cooled to 0° C. and L-tert-leucine (835 mg, 6.37 mmol) and K₃PO₄ (2.70 g, 12.7 mmol) were added. The mixture was stirred for 10 min and was removed from the cold bath. After stirring an additional 24 h, the mixture was diluted with EtOAc (30 mL), acidified with 1 M aqueous HCl (15 mL), and diluted with 0.2 M aqueous HCl (15 mL). The phases were separated, and the organic phase was washed with 0.2 M aqueous HCl (2×20 mL), dried over Na₂SO₄, filtered, and concentrated to afford diastereomeric Intermediate mixture D9 and D10 (1.64 g). LCMS-ESI⁺ (m/z): [M−H]⁻ calcd for C₁₉H₃₀NO₄: 336.2; found: 336.0.

Preparation of Intermediate D11

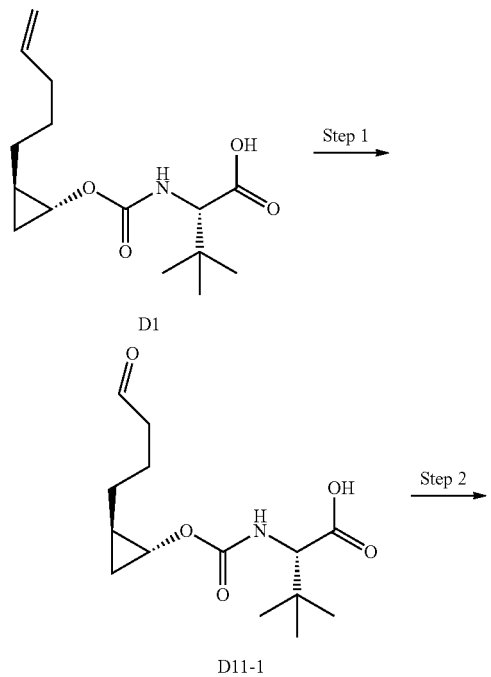

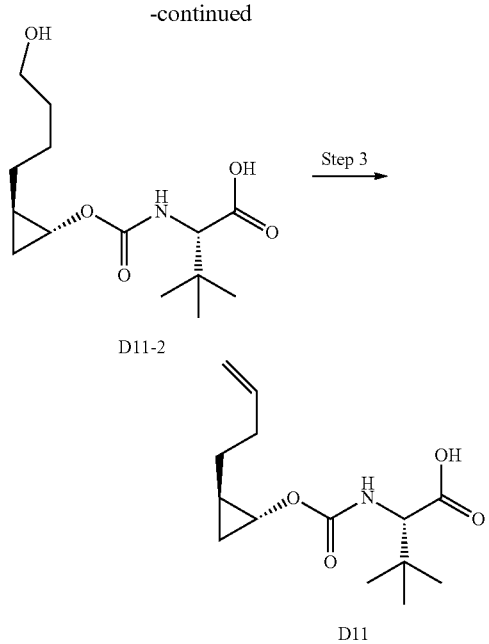

Step 1. Preparation of D11-1: To a mixture of D1 (1.0 g, 3.53 mmol), sodium periodate (2.26 g, 10.59 mmol) in 24 mL THF and 12 mL water was added Os EnCat™ 40 (0.25 mmol/g loading, 282 mg, 0.071 mmol, Sigma-Aldrich). The mixture was stirred for 3 days. Water (50 mL) was added and the mixture was filtered. The filter cake was washed with water (total volume 400 mL) and ethyl acetate (total volume 600 mL). The filtrate layers were separated. The organic phase was dried over sodium sulfate, filtered and concentrated to give D11-1 (1.56 g) which was used without further purification. LCMS-ESI⁺ (m/z): [M+H]⁺ calcd for C₁₄H₂₄NO₅: 286.2 found: 286.1.

Step 2. Preparation of D11-2: To a solution of D11-1 (3.05 g, 10.7 mmol) in MeOH (50 mL) at 0° C. was added sodium borohydride in portions (809 mg, 21.4 mmol). The reaction mixture was stirred at rt for 6 h. The mixture was diluted with 50 mL ethyl acetate and 50 mL brine and the layers were separated. The organic phase was extracted with two 25 mL portions of ethyl acetate. The combined organic phase was dried over sodium sulfate, filtered and concentrated. The crude product mixture was purified by silica gel chromatography (EtOAc in hexanes: 10% to 100%) to give D11-2 (380 mg). LCMS-ESI⁺ (m/z): [M+H]⁺ calcd for C₁₄H₂₆NO₅: 288.2; found: 288.1.

Step 3. Preparation of Intermediate D11: To a solution of D11-2 (283 mg, 0.98 mmol) in THF (2.8 mL) at 0° C. was added 1-nitro-2-selenocyanatobenzene (336 mg, 1.47 mmol) and tributylphosphine (363 µL, 1.47 mmol). The cooling bath was removed and the mixture was stirred for 25 minutes at rt. The reaction was again cooled to 0° C. and was treated with 30% hydrogen peroxide solution (0.665 mL, 5.85 mmol) and stirred for 1 h at rt and then heated at 60° C. for 1 h. The reaction was diluted with EtOAc and the desired product was extracted into aqueous sodium bicarbonate. The bicarbonate extract was acidified with 2 N HCl and extracted with ethyl acetate. The organic phase was dried over sodium sulfate and concentrated to give Intermediate D11 (136 mg). LCMS-ESI⁺ (m/z): [M+H]⁺ calcd for C₁₄H₂₄NO₄: 270.2; found: 270.1.

Preparation of Intermediate Mixture D12 and D13

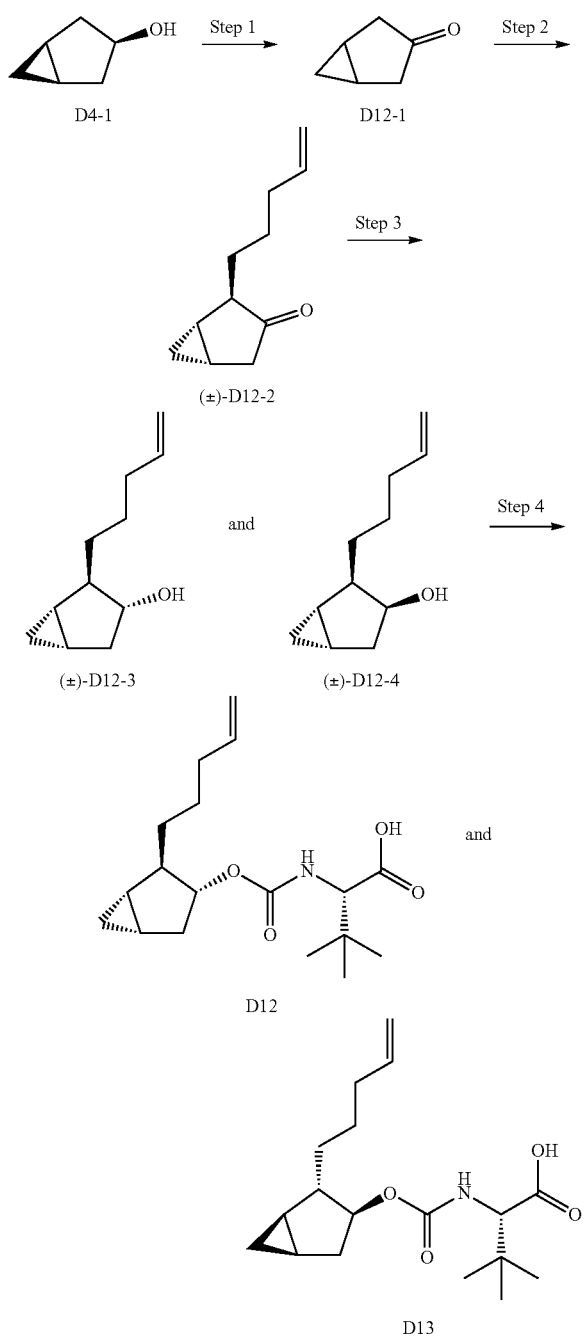

Step 1: Preparation of D12-1: To a solution of K₂Cr₂O₇ (121 g, 0.41 mol) in H₂O (1.5 L) was added dropwise H₂SO₄ (143 g, 1.46 mol) at rt and the mixture was stirred for 1 h. The mixture was then cooled to 0° C. and D4-1 (80 g, 0.814 mol; prepared according to Section A, Intermediate 1 of US '491, p 192.) in MTBE (1.5 L) was added dropwise. The reaction mixture was stirred at rt for 2 h. The aqueous phase was extracted with MTBE (3×500 mL), dried over MgSO₄, filtered, and concentrated in vacuo. The crude product was purified by distillation (20 mmHg, bp: 60-62° C.) to provide D12-1 as a pale yellow liquid (60 g). $^1$H NMR (400 MHz, CDCl₃) δ 2.57-2.63 (m, 2H), 2.14-2.19 (d, J=20 Hz, 2H), 1.52-1.57 (m, 2H), 0.89-0.94 (m, 1H), −0.05--0.02 (m, 1H).

Step 2: Preparation of (±)-D12-2: Under Ar, a mixture of THF (4.4 mL) and HMPA (1.8 mL) was cooled to −78° C. A 1 M solution of LiHMDS in THF (2.2 mL, 2.2 mmol) was added. Ketone D12-1 (202 mg, 2.10 mmol) was added as a solution in THF (2 mL) over 1 min, washing with additional THF (2×1 mL) to ensure complete transfer. After 25 min, 5-iodopent-1-ene (prepared according to Jin, J. et. al. *J. Org. Chem.* 2007, 72, 5098-5103) (880 mg, 4.5 mmol) was added over 30 s by syringe. After 10 min, the reaction was placed in a cold bath at −45° C. and was warmed to −30° C. over 1.5 h. The reaction was quenched with saturated aqueous NH₄Cl (15 mL) and was diluted with EtOAc (30 mL) and H₂O (15 mL). The phases were separated, and the aqueous phase was extracted with EtOAc (30 mL). The combined organics were dried over Na₂SO₄, filtered, and concentrated to afford a crude residue that was purified by silica gel chromatography (0% to 15% EtOAc in hexanes) to provide (+/−)-D12-2 a colorless oil (162 mg). $^1$H NMR (400 MHz, CDCl₃) 5.82-5.67 (m, 1H), 5.03-4.87 (m, 2H), 2.61-2.51 (m, 1H), 2.11 (d, J=19.1 Hz, 1H), 2.08-1.99 (m, 3H), 1.61-1.40 (m, 5H), 1.36-1.28 (m, 1H), 0.92-0.81 (m, 1H), −0.03--0.11 (m, 1H).

Step 3: Preparation of (±)-D12-3 and (±)-D12-4: A solution of (±)-D12-2 (142 mg, 0.865 mmol) in THF (4 mL) was cooled to −78° C. A 1 M THF solution of LiBHEt₃ (1.3 mL, 1.3 mmol) was added dropwise over 30 s. The reaction was stirred 15 min and was removed from the cold bath. After warming to rt (15 min), the reaction was quenched with saturated aqueous NH₄Cl (1 mL). The resulting mixture was diluted with Et₂O (20 mL) and H₂O (20 mL). The phases were separated, and the aqueous phase was extracted with Et₂O (20 mL). The combined organics were dried over MgSO₄, filtered, and concentrated to a crude residue. Purification by silica gel chromatography (0% to 10% EtOAc in hexanes) provided 133 mg of a mixture of diastereomers (±)-D12-3 and (±)-D12-4. The combined material from two experiments (253 mg) was further purified by silica gel chromatography (0% to 15% EtOAc in hexanes) to provide (±)-D12-3 (150 mg) and (±)-D12-4 (58 mg) as colorless oils. $^1$H NMR for (±)-D12-3 (300 MHz, CDCl₃) δ 5.91-5.69 (m, 1H), 5.07-4.88 (m, 2H), 3.97 (d, J=6.7 Hz, 1H) 2.19-1.99 (m, 3H), 1.84-1.73 (m, 1H), 1.62 (d, J=14.1 Hz, 1H), 1.54-1.40 (m, 2H), 1.32-1.17 (m, 3H), 1.16-1.06 (m, 1H), 0.60-0.43 (m, 2H). $^1$H NMR for (±)-D12-4 (300 MHz, CDCl₃) δ 5.95-5.73 (m, 1H), 5.09-4.88 (m, 2H), 4.05-3.86 (m, 1H), 2.17-1.84 (m, 4H), 1.72-1.34 (m, 5H), 1.28-1.08 (m, 3H), 0.49-0.36 (m, 1H), 0.21-0.11 (m, 1H).

Step 4. Preparation of diastereomeric Intermediate mixture D12 and D13: A mixture of (±)-D12-3 (150 mg, 0.90 mmol) was dissolved in DMF (1.0 mL). Pyridine (75 μL, 0.92 mmol) and DSC (302 mg, 1.18 mmol) were added, and the reaction was stirred at 45° C. for 21.5 h. The reaction was then placed in an ice water bath and H₂O (1.0 mL) was added dropwise via syringe over 1 min. The mixture was removed from the cold bath and allowed to stir 5 min. The mixture was re-cooled in an ice water bath and L-tert-leucine (154 mg, 1.17 mmol) was added followed by K₃PO₄ (502 mg, 2.36 mmol). The reaction mixture was removed from the cold bath and allowed to stir at rt for 24 h. The mixture was then diluted with EtOAc (40 mL) and 1 M aqueous HCl (20 mL). The phases were separated, and the aqueous phase was extracted with EtOAc (30 mL). The combined organic phase was washed with 0.2 M aqueous HCl (2×20 mL), dried over MgSO₄, filtered, and concentrated to afford diastereomeric intermediate mixture D12 and D13 (300 mg) as a colorless oil. LCMS-ESI⁻ (m/z): [M–H]⁻ calcd for $C_{18}H_{28}NO_4$: 322.2; found: 322.0).

Preparation of Intermediate D12

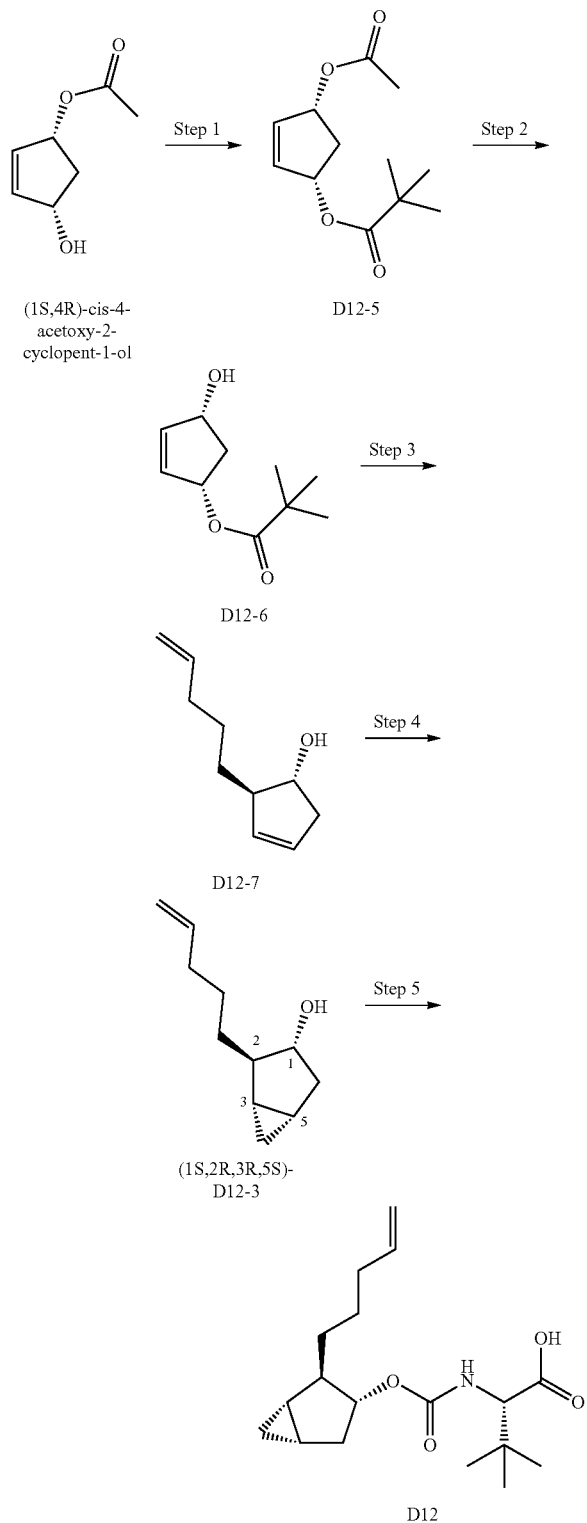

Step 1: Preparation of D12-5: To a solution of (1S,4R)-cis-4-acetoxy-2-cyclopent-1-ol (Aldrich, 10 g, 70.4 mmol), triethylamine (48.8 mL, 350 mmol), and DMAP (4.29 g, 35.2 mmol) in dichloromethane (352 mL) was added pivaloyl chloride (10.8 mL, 87.75 mmol) dropwise via syringe at 0° C. under an argon atmosphere. After 2 h. the reaction mixture was diluted with saturated aqueous sodium bicarbonate solution (500 mL), and extracted with dichloromethane (2×500 mL). The combined organic extracts were dried over anhydrous sodium sulfate and were concentrated in vacuo to afford D12-5 (15.0 g) as a colorless oil. ¹H NMR (300 MHz, CDCl₃) δ 6.08 (br s, 2H), 5.54 (td, J=8.0, 4.1 Hz, 2H), 2.88 (dt, J=14.9, 7.5 Hz, 1H), 2.07 (s, 3H), 1.69 (dt, J=14.7, 4.1 Hz, 1H), 1.20 (s, 9H).

Step 2: Preparation of D12-6: To a solution of D12-5 (15.0 g, 70.4 mmol) in methanol (352 mL) was added potassium carbonate (9.73 g, 70.4 mmol) at rt under an argon atmosphere. After 5 h, the reaction mixture was filtered and was concentrated in vacuo. The residue was dissolved into ethyl acetate (500 mL) and the resulting mixture was washed with water (500 mL) and brine (500 mL), dried over anhydrous sodium sulfate, and concentrated in vacuo. The crude residue was purified by silica gel chromatography (0-100% ethyl acetate/hexanes) to afford D12-6 (12.0 g) as a colorless oil. ¹H NMR (300 MHz, CDCl₃) δ 6.11 (br d, J=5.5 Hz, 1H), 5.97 (br d, J=5.6 Hz, 1H), 5.48 (br s, 1H), 4.73 (br s, 1H), 2.82 (dt, J=14.6, 7.3 Hz, 1H), 1.67 (s, 1H), 1.61 (dt, J=14.5, 4.0 Hz, 1H), 1.20 (s, J=3.8 Hz, 9H).

Step 3: Preparation of D12-7: To a solution of copper(I) cyanide (5.10 g, 57.0 mmol) in diethyl ether (95 mL) was added pent-4-enylmagnesium bromide (Novel Chemical Solutions, 0.5 M in THF, 114 mL, 57.0 mmol) dropwise via cannula over a 30 min period at 0° C. under an argon atmosphere. After 10 min, a solution of D12-6 (3.50 g, 19.0 mmol) in diethyl ether (10 mL) was added slowly via cannula. The reaction mixture was then allowed to slowly warm to rt. After 16 h, the resulting mixture was quenched with saturated aqueous ammonium chloride solution (400 mL) and the resulting mixture was extracted into ethyl acetate (2×400 mL). The combined organic phases were washed with brine (400 mL), dried over anhydrous sodium sulfate, and concentrated in vacuo. The crude residue was purified by silica gel chromatography (0-100% ethyl acetate/ hexanes) to afford D12-7 (2.4 g) as a colorless oil. ¹H NMR (400 MHz, CDCl₃) δ 5.80 (ddt, J=16.9, 10.2, 6.7 Hz, 1H), 5.69 (dd, J=5.8, 1.7 Hz, 1H), 5.65 (d, J=7.2 Hz, 1H); 5.00 (dd, J=17.1, 1.3 Hz, 1H), 4.94 (d, J=10.2 Hz, 1H), 4.12-4.05 (m, 1H), 2.69 (ddd, J=17.2, 6.4, 1.5 Hz, 1H), 2.54-2.45 (m, 1H), 2.24 (d, J=17.2 Hz, 1H), 1.69 (br s, 1H), 1.52-1.19 (m, 6H).

Step 4: Preparation of (1S,2R,3R,5S)-D12-3: To a solution of D12-7 (20 mg, 0.13 mmol), and diethyl zinc (1 M in hexanes, 132 μL, 0.132 mmol) in diethyl ether (0.66 mL) was added diiodomethane (21 μL, 0.26 mmol) at rt under an argon atmosphere After 2 h, the reaction mixture was quenched with 1 N aqueous HCl solution (0.66 mL). After 5 min, the resulting yellow mixture was diluted with saturated aqueous sodium bicarbonate solution (5 mL) and the resulting mixture was extracted with dichloromethane (3×5 mL). The combined organic extracts were dried over anhydrous sodium sulfate solution, and were concentrated in vacuo. The crude residue was purified by silica gel chromatography (0-100% ethyl acetate/hexanes) to afford (1S,2R, 3R,5S)-D12-3 (10 mg) as a colorless oil. ¹H NMR (400 MHz, CDCl₃) δ 5.83 (ddt, J=16.9, 10.2, 6.7 Hz, 1H), 5.02 (d, J=17.2 Hz, 1H), 4.96 (d, J=11.3 Hz, 1H), 4.00 (d, J=6.7 Hz, 1H), 2.19-2.02 (m, 3H), 1.82 (t, J=7.2 Hz, 1H), 1.64 (d, J=14.2 Hz, 1H), 1.55-1.42 (m, 2H), 1.38-1.20 (m, 4H), 1.19-1.08 (m, 1H), 0.62-0.47 (m, 2H).

Step 5: Preparation of Intermediate D12: Alcohol (1S,2R,3R,5S)-D12-3 (0.450 g, 2.7 mmol) was taken up in DMF (2.7 mL) and treated subsequently with DSC (0.92 g, 3.52 mmol) and pyridine (0.22 mL, 2.8 mmol). The reaction was then heated to 50° C. o/n. The reaction was then cooled to 0° C. and water (5.5 mL) was added dropwise over 1 min. The resulting opaque suspension was stirred at rt for 10 min before recooling to 0° C. The reaction was then treated subsequently with L-tert-leucine (0.462 g, 3.5 mmol) and $K_3PO_4$ (1.5 g, 7.0 mmol) and allowed to warm to rt overnight with vigorous stirring. The resulting opaque suspension was diluted with EtOAc and 1 M aqueous HCl. Additional HCl (12 M) was added dropwise to adjust the pH~3. The aqueous layer was extracted with EtOAc and the combined organics were washed with brine and dried over anhydrous $MgSO_4$. Following concentration in vacuo, Intermediate D12 was obtained (1.72 g) as a viscous, colorless oil that is contaminated with small amounts of DMF and EtOAc. The material was used in subsequent reactions without further purification. LCMS-ESI+ (m/z): [M+H]+ calcd for $C_{18}H_{30}NO_4$: 324.2; found 324.7.

Preparation of Intermediate D14

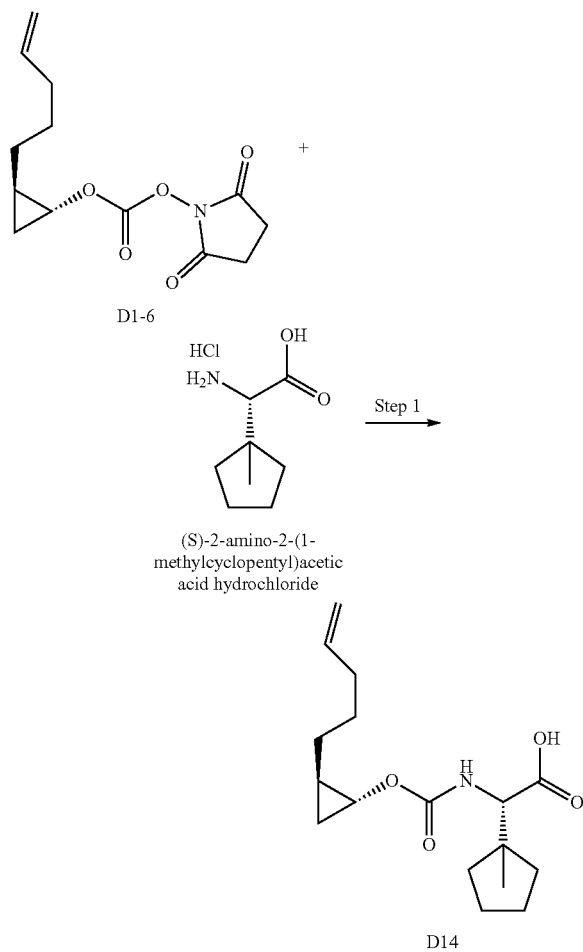

Step 1. Preparation of Intermediate D14. Carbonate D1-6 (862 mg, 3.23 mmol) was treated with (S)-2-amino-2-(1-methylcyclopentyl)acetic acid hydrochloride (750 mg, 3.87 mmol, prepared according to Robl, J. A., et al. *J. Med. Chem.*, 2004, 47, 2587), THF (28 mL), $H_2O$ (8.4 mL) and TEA (1.4 mL, 9.7 mmol) The reaction mixture was stirred for 16 h and the THF was removed in vacuo. The remaining material was diluted with $H_2O$ and the pH adjusted to ~10-12 by addition of 10% aqueous NaOH The aqueous phase was washed twice with EtOAc and then acidified to pH~1-2 with 10% aqueous HCl. The acidic solution was extracted 3× with EtOAc. The combined extractions were dried over anhydrous $MgSO_4$, filtered and concentrated in vacuo. The initial EtOAc washings (of the basic aqueous solution) were washed with 10% aqueous HCl, dried over $MgSO_4$ filtered and concentrated in vacuo. The combined concentrates were purified by silica gel chromatography (50% to 100% EtOAc/Hex) to afford Intermediate D14 (980 mg). LCMS-ESI+ (m/z): [M+H]+ calcd for $C_{17}H_{28}NO_4$: 310.2; found 310.0.

Preparation of Intermediate Mixture D15

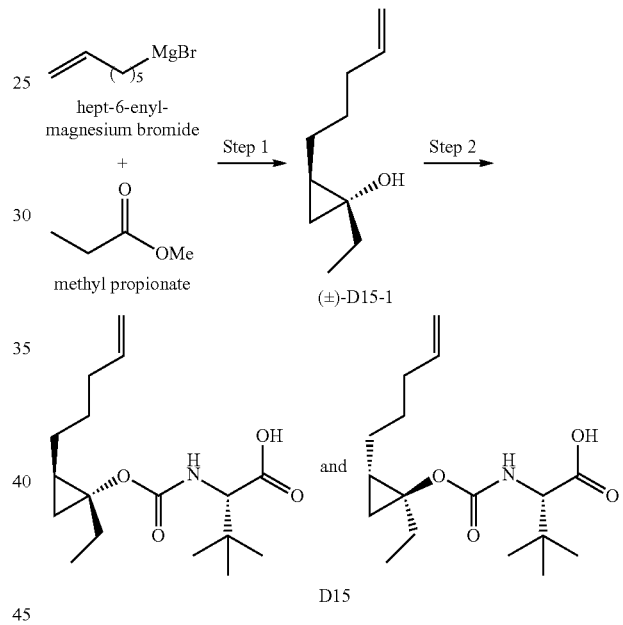

Step 1. Preparation of (±)-D15-1: To a solution of titanium (IV) isopropoxide (11.3 g, 40.0 mmol) in THF (160 mL) was added methyl magnesium bromide (3 M in $Et_2O$, 20 mL, 60.0 mmol) dropwise via syringe at rt under an argon atmosphere. After 10 min, the reaction mixture was cooled to 0° C. and a solution of methyl propionate (3.80 mL, 40.0 mmol) in THF (10 mL) was added slowly via syringe. After 5 min, hept-6-enylmagnesium bromide (Novel Chemical Solutions, 0.5 M in THF 160 mL, 80 mmol) was added dropwise via addition funnel over 1 h After 2.5 h, the reaction mixture was quenched with 10% aqueous sulfuric acid (100 mL) and the resulting mixture was extracted with diethyl ether (2×200 mL). The organic phase was dried over anhydrous sodium sulfate and was concentrated in vacuo. The crude residue was purified by silica gel chromatography (0-100% ethyl acetate/hexanes) to afford (±)-D15-1 (3.03 g, 50%) as a colorless oil. $^1$H NMR (300 MHz, $CDCl_3$) δ 5.77 (ddt, J=16.9, 10.2, 6.7 Hz, 1H), 5.03-4.86 (m, 2H), 2.04 (q, J=6.1 Hz, 2H), 1.75-1.14 (m, 6H), 1.04 (t, J=7.4 Hz, 3H), 1.01-0.91 (m, 1H), 0.89-0.71 (m, 2H), 0.02 (t, J=5.5 Hz, 1H).

Step 2. Preparation of diastereomeric intermediate mixture D15: Racemic alcohol mixture (±)-D15-1 (2.00 g, 13.0 mmol) was dissolved in DMF (13.0 mL). Pyridine (1.05 mL, 13.0 mmol) was added followed by DSC (4.00 g, 15.6 mmol). The reaction mixture was heated to 50° C. and was stirred for 20 h. The reaction mixture was then cooled to rt and water (13 mL) was added dropwise over 2 min. L-tert-leucine (2.17 g, 13.0 mmol) and K$_3$PO$_4$ (8.28 g, 39.0 mmol) were then added and the reaction mixture was warmed to 50° C. After 5 h, the reaction mixture was allowed to cool to rt and was diluted with water (500 mL). The resulting mixture was washed with dichloromethane (100 mL) The aqueous phase was then acidified to pH 2 with 2 N aqueous HCl solution, and was extracted with DCM (2×400 mL). The combined organic extracts were dried over anhydrous sodium sulfate and were concentrated under reduced pressure to afford diastereomeric Intermediate mixture D15 (4.5 g) as a pale orange oil, which was used subsequently without further purification.

Preparation of Intermediate D16

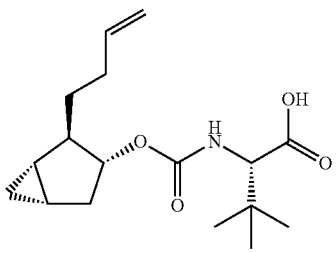

D16

Intermediate D16 was prepared in a similar fashion to the preparation of Intermediate D12, substituting but-3-enyl-magnesium bromide for pent-4-enylmagnesium bromide in Step 3. LCMS-ESI$^+$ (m/z): [M+H]$^+$ calcd for C$_{17}$H$_{28}$NO$_4$: 310.2; found 310.8.

Preparation of Intermediate D17

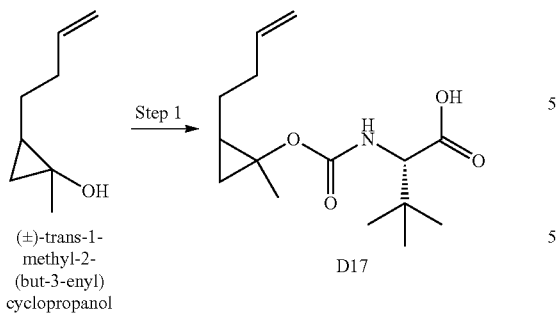

(±)-trans-1-methyl-2-(but-3-enyl)cyclopropanol

D17

Step 1. Preparation of intermediate mixture D17. (±)-trans-1-methyl-2-(but-3-enyl)cyclopropanol (900 mg, 0.13 mmol), prepared according to procedure for Intermediate B2, International Patent Publication No. WO 2012/40040 (hereinafter "WO '040"), p. 38, was dissolved in DMF (6 mL). Pyridine (577 µL, 7.13 mmol) was added followed by DSC (2.37 g, 9.27 mmol). The reaction mixture was heated to 40° C. and was stirred for 18 h. The reaction mixture was then cooled to 0° C. and water (6 mL) was added dropwise over 5 min. The reaction mixture was stirred for 5 min and was removed from the cold bath. After an additional 5 min, the reaction mixture was cooled to 0° C. and L-tert-leucine (1.21 g, 9.27 mmol) and K$_3$PO$_4$ (4.69 g, 22.1 mmol) were added. The mixture was stirred for 10 min and was removed from the cold bath. After stirring an additional 6 h, the mixture was diluted with EtOAc (30 mL), acidified with 1 M aqueous HCl (25 mL), and diluted with 0.2 M aqueous HCl (25 mL). The phases were separated, and the organic phase was washed with 0.2 M aqueous HCl (2×20 mL), dried over Na$_2$SO$_4$, filtered, and concentrated to afford diastereomeric carbamate mixture D17 (2.10 g) LCMS-ESI$^+$ (m/z): [M+Na]$^+$ calcd for C$_{15}$H$_{25}$NNaO$_4$: 306.2; found: 306.1.

Preparation of Intermediate D18

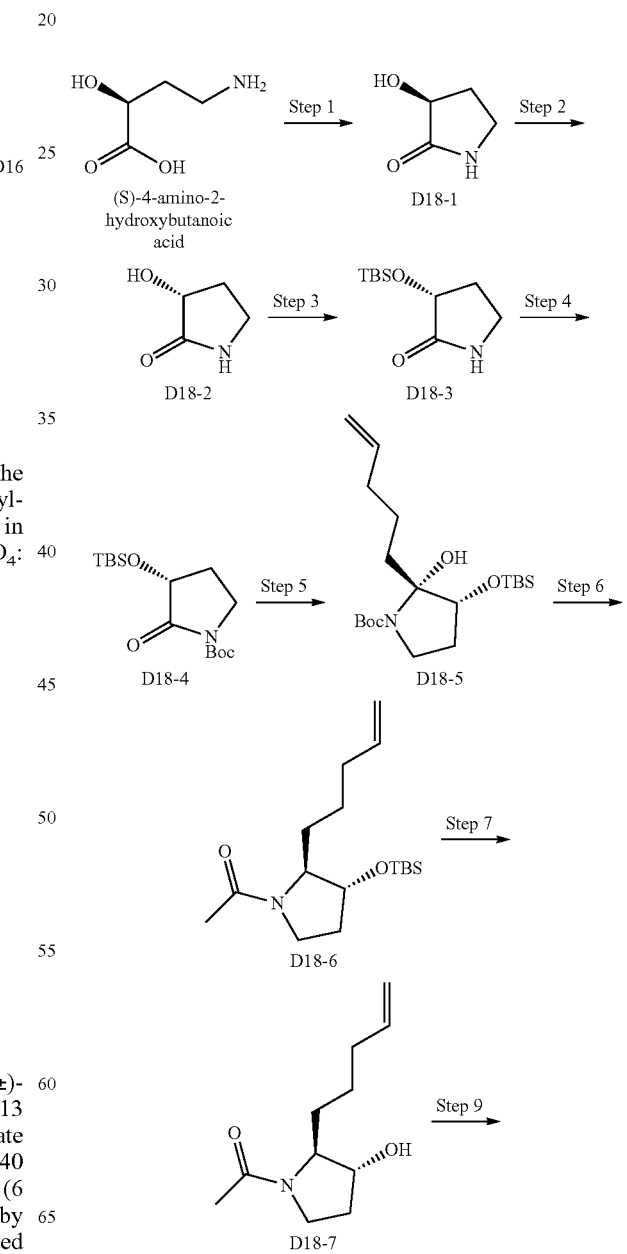

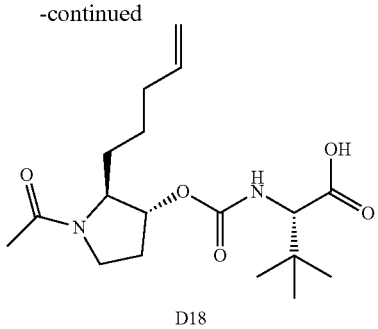

D18

Step 1. Preparation of D18-1: (Prepared according to WO2011013141) To a solution of (S)-4-amino-2-hydroxybutanoic acid (15 g, 126 mmol) in methanol (95 mL) was added concentrated sulfuric acid (8 mL), and the reaction was heated to reflux. After 18 h, the resulting mixture was allowed to cool to room temperature and was concentrated in vacuo. The residue was slurried with ethyl acetate (95 mL) and D18-1 was collected by vacuum filtration. $^1$H NMR (400 MHz, CDCl$_3$) δ 5.69 (br s, 1H), 4.31 (ddd, J=9.2, 8.1, 2.2 Hz, 1H), 3.49 (d, J=5.6 Hz, 1H), 3.41 (tt, J=9.2, 1.7 Hz, 1H), 3.33 (td, J=9.4, 6.5 Hz, 1H), 2.81 (br s, 1H), 2.59-2.48 (m, 1H), 2.09 (dq, J=12.9, 9.1 Hz, 1H).

Step 2. Preparation of D18-2: To a solution of D18-1 (4.5 g, 44 mmol), 4-nitrobenzoic acid (8.19 g, 49 mmol), and triphenylphosphine (22.4 g, 132 mmol) in tetrahydrofuran (220 mL) was added diisopropyl azodicarboxylate (12.1 mL, 61.6 mmol) dropwise via syringe at 23° C. under an argon atmosphere. After 20 h, the resulting cloudy orange reaction mixture was concentrated in vacuo and methanol (200 mL) followed by potassium carbonate (15 g, 109 mmol) were added and the reaction was stirred at 23° C. After an additional 5 h, the resulting mixture was diluted with chloroform (200 mL) and was filtered. The filtrate was concentrated in vacuo and the crude residue was taken up into water (150 mL) and 1 N aqueous hydrochloric acid solution (50 mL). The aqueous layer was washed with ethyl acetate (3×200 mL) to remove organic by-products, and was concentrated in vacuo to crude afford D18-2 that was used directly in the next step. $^1$H NMR (300 MHz, CD$_3$OD) δ 4.28 (t, J=8.4 Hz, 1H), 3.43-3.20 (m, 1H), 2.56-2.39 (m, 1H), 1.96 (dq, J=12.7, 8.7 Hz, 1H).

Step 3. Preparation of D18-3: To a solution of crude D18-2 (5 g, 49.5 mmol) and imidazole (3.4 g, 49.5 mmol) in DMF (247 mL) was added TBSCl (7.5 g, 49.5 mmol) at 0° C. under an argon atmosphere. The resulting mixture was allowed to warm to 23° C. After 7 h, additional imidazole (7 g, 102 mmol) and TBSCl (16 g, 106 mmol) were added sequentially After an additional 16 h, the resulting mixture was diluted with 1 N aqueous hydrochloric acid solution (1 L) and was extracted with ethyl acetate (1 L). The organic layer was split and was washed with brine (1 L), was dried with anhydrous sodium sulfate, and was concentrate in vacuo. The crude residue was purified by silica gel chromatography (0-100% ethyl acetate/hexanes gradient) to afford D18-3. $^1$H NMR (300 MHz, CDCl$_3$) δ 5.99 (s, 1H), 4.26 (t, J=7.7 Hz, 1H), 3.44-3.33 (m, 1H), 3.30-3.19 (m, 1H), 2.45-2.29 (m, 1H), 2.11-1.95 (m, 1H), 0.91 (s, 9H), 0.02 (s, 3H), 0.00 (s, 3H).

Step 4. Preparation of D18-4: To a solution of D18-3 (1.00 g, 4.65 mmol), DMAP (57.8 mg, 0.465 mmol), and triethylamine (1.29 mL, 9.3 mmol) in dichloromethane (23.3 mL) was added di-tert-butyl dicarbonate (1.5 g, 6.97 mmol) at 23° C. under and argon atmosphere. After 20 h, the reaction mixture was purified directly by silica gel chromatography (0-100% ethyl acetate/hexanes gradient) to afford D18-4. $^1$H NMR (400 MHz, CDCl$_3$) δ 4.31 (dd, J=9.4, 7.9 Hz, 1H), 3.79 (ddd, J=11.0, 8.9, 2.2 Hz, 1H), 3.53-3.41 (m, 1H), 2.34-2.21 (m, 1H), 1.92 (dq, J=12.2, 9.2 Hz, 1H), 1.53 (s, 9H), 0.91 (s, 9H), 0.17 (s, 3H), 0.13 (s, 3H).

Step 5. Preparation of D18-5: To a solution of D18-4 (700 mg, 2.22 mmol) in tetrahydrofuran (11.1 mL) was added pent-4-enylmagnesium bromide (Novel Chemical Solutions, 0.5 M in 2-MeTHF, 4.89 mL, 2.44 mmol) at −78° C. dropwise via syringe under an argon atmosphere. After 1 h, the reaction mixture was quenched with saturated aqueous ammonium chloride solution (50 mL) and was allowed to warm to room temperature. The resulting mixture was extracted with ethyl acetate (2×100 mL), and the combined organic extracts were washed with brine (100 mL), were dried over anhydrous sodium sulfate and were concentrated in vacuo. The crude residue was purified by silica gel chromatography (0-100% ethyl acetate/hexanes gradient) to afford D18-5. $^1$H NMR (400 MHz, CDCl$_3$) δ 5.77-5.62 (m, 1H), 4.95 (d, J=15.8 Hz, 1H), 4.92 (d, J=10.2 Hz, 1H), 4.26 (app t, J=8.4 Hz, 1H), 3.77-3.69 (m, 1H), 3.41 (td, J=10.4, 6.7 Hz, 1H), 2.48 (t, J=7.4 Hz, 2H), 2.28-2.17 (m, 1H), 1.91-1.78 (m, 2H), 1.77-1.65 (m, 1H), 1.60 (quin, J=7.3 Hz, 2H), 1.47 (s, 9H), 0.85 (s, 9H), 0.11 (s, 3H), 0.07 (s, 3H).

Step 6. Preparation of D18-6: To a solution of D18-5 (740 mg, 1.92 mmol) and triethylsilane (6.10 mL, 38.4 mmol) in dichloromethane (9.6 mL) was added boron trifluoride diethyl etherate (308 µL, 2.50 mmol) at −78° C. dropwise via syringe under an argon atmosphere. After 1 h, the reaction mixture was allowed to warm to room temperature. After an additional 4 h, the reaction was quenched with saturated aqueous ammonium chloride solution (10 mL), and was diluted with saturated sodium bicarbonate solution (50 mL). The resulting mixture was extracted with ethyl acetate (50 mL), and the organic layer was dried over anhydrous sodium sulfate and was concentrated in vacuo to afford crude free amine which was used directly in the next step. To a solution of the crude free amine, and triethylamine (535 µL, 3.84 mmol) in tetrahydrofuran (9.6 mL) was added acetic anhydride (146.5 µL, 1.55 mmol) at room temperature under an argon atmosphere. After 1 h, the resulting mixture was concentrated in vacuo and the crude residue was purified by silica gel chromatography (0-100% ethyl acetate/hexanes gradient) to afford D18-6 (2:1 diastereomeric mixture favoring desired 1-((2S,3R)-3-(tert-butyldimethylsilyloxy)-2-(pent-4-enyl)pyrrolidin-1-yl) ethanone diastereomer). $^1$H NMR (400 MHz, CDCl$_3$, Minor diastereomer denoted by *) δ 5.80-5.64 (m, 1H, 1H*), 5.01-4.82 (m, 2H, 2H*), 4.10 (d, J=4.2 Hz, 1H*), 4.04 (d, J=3.7 Hz, 1H), 3.82 (dd, J=10.3, 4.0 Hz, 1H), 3.66-3.56 (m, 1H*), 3.55-3.29 (m, 2H, 1H*), 3.24-3.16 (m, 1H*), 2.37-2.25 (m, 1H*), 2.08-1.88 (m, 2H, 1H*), 2.03 (s, 3H*), 2.00 (s, 3H), 1.81-1.61 (m, 2H, 2H*), 1.50-1.01 (m, 4H, 4H*), 0.85 (s, 9H*), 0.80 (s, 9H), 0.10 (s, 3H*), 0.09 (s, 3H*), 0.00 (br s, 6H).

Step 7. Preparation of D18-7: To a solution of D18-6 (338 mg, 1.08 mmol) in tetrahydrofuran (21 mL) was added TBAF (1M in tetrahydrofuran, 21 mL, 21 mmol) at 0° C. under an argon atmosphere. After 17 h, the reaction mixture was concentrated in vacuo and was directly purified by silica gel chromatography (0-100% ethyl acetate/hexanes gradient) to afford D18-7 (102 mg, 2:1 diastereomeric mixture favoring desired 1 1-((2S,3R)-3-hydroxy-2-(pent-4-enyl) pyrrolidin-1-yl)ethanone diastereomer). $^1$H NMR (400 MHz, CDCl$_3$ Minor diastereomer denoted by *) δ 5.84-5.70

(m, 1H, 1H*), 5.06-4.91 (m, 2H, 2H*), 4.25 (d, J=3.7 Hz, 1H*), 4.20 (d, J=3.7 Hz, 1H), 3.98 (dd, J=9.2, 4.2 Hz, 1H), 3.76-3.68 (m, 1H*), 3.67-3.59 (m, 1H, 1H*), 3.55-3.46 (m, 1H, 2H*), 3.02-2.94 (m, 1H), 2.22-1.85 (m, 2H, 2H*), 2.10 (s, 3H*), 2.07 (s, 3H), 1.82-1.59 (m, 2H, 2H*), 1.55-1.13 (m, 4H, 4H*).

Step 8. Preparation of D18-8: To a solution of D18-7 (102 mg, 0.518 mmol) and pyridine (8 μL, 0.104 mmol) was added DSC (159.2 mg, 0.621 mmol) at room temperature, and the resulting mixture was heated to 45° C. After 16 h, the reaction mixture was allowed to cool to room temperature and water (518 μL), L-tert-leucine (86.5 mg, 0.518 mmol), and K_3PO_4 (330 mg, 1.55 mmol) were sequentially added, and the resulting mixture was heated to 50° C. After 6 h, the reaction mixture was allowed to cool to room temperature and was diluted with 1N aqueous hydrochloric acid solution (10 mL). The resulting mixture was extracted with dichloromethane (2×10 mL), and the combined organic extracts were dried over anhydrous sodium sulfate and were concentrated in vacuo to afford D18-8 (2:1 diastereomeric mixture favoring the desired (S)-2-(((2S,3R)-1-acetyl-2-(pent-4-enyl)pyrrolidin-3-yloxy)carbonylamino)-3,3-dimethylbutanoic acid). $^1$H NMR (400 MHz, CDCl_3, Minor diastereomer denoted by *) δ 5.85-5.65 (m, 1H, 1H*), 5.39 (d, J=9.3 Hz, 1H*), 5.34 (d, J=9.2 Hz, 1H), 5.07-4.87 (m, 3H, 3H*), 4.16-4.03 (m, 1H, 1H*), 3.83-3.45 (m, 3H, 3H*), 2.30-1.95 (m, 8H), 2.30-1.95 (m, 2H, 3H*), 1.82-1.65 (m, 2H, 1H*), 2.11 (s, 3H), 2.09 (s, 3H*), 1.58-1.13 (m, 4H, 4H*), 1.01 (br s, 9H, 9H*).

Preparation of Intermediate Mixture D19

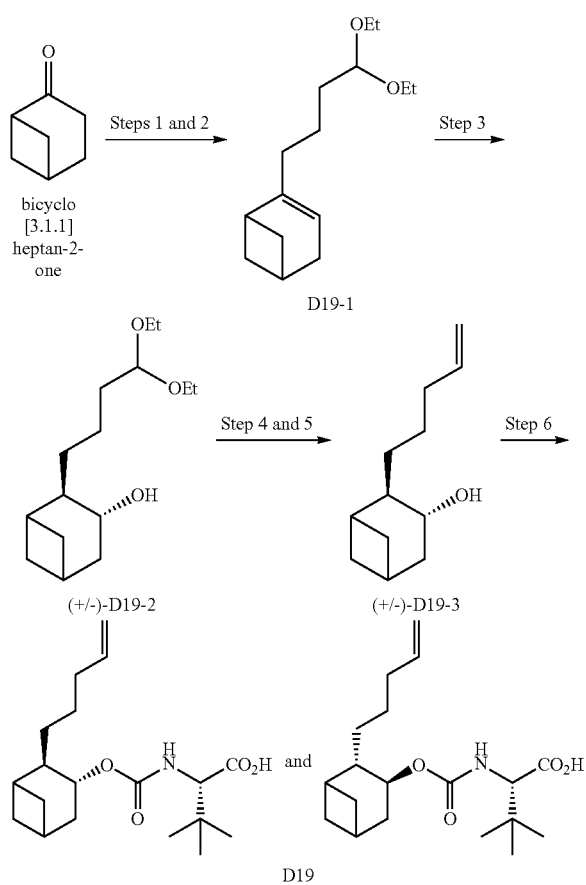

Steps 1 and 2: Preparation of D19-1: A 1.0 M THF solution of KHMDS (10 mL, 10 mmol) was diluted with THF (10 mL) under Ar and the resulting solution was cooled to −78° C. in a CO_2:acetone bath. Bicyclo[3.1.1]heptan-2-one (1.0 g, 9.1 mmol, see: Yin, et, al. J. Org. Chem. 1985, 50, 531) was added as a solution in THF (5 mL) over 2 min, washing with additional THF (2×2.5 mL) to ensure complete transfer. The resulting mixture was stirred for 30 min, and N-(5-Chloro-2-pyridyl)bis(trifluoromethanesulfonimide) (3.8 g, 9.7 mmol) was added as a solution in THF (10 mL) over 2 min, washing with additional THF (2×2.5 mL). The resulting mixture was stirred for 5 min and removed from the cold bath. After stirring an additional 30 min, the reaction was diluted with Et_2O (70 mL) and 1 M aqueous HCl (50 mL). The phases were separated, and the organic phase was washed with 1 M aqueous NaOH (2×30 mL). The combined organic phase was dried over MgSO_4, filtered and concentrated to afford a crude residue. This was filtered through a plug of silica with 30% EtOAc in hexanes to afford a crude residue of (1.24 g) that was used directly in the following step. Step 2: To a solution of 3-butenal diethyl acetal (1.4 mL, 8.3 mmol) under Ar cooled in an ice water bath was added a 0.5 M THF solution of 9-borabicyclo[3.3.3.1]nonane (15.9 mL, 7.95 mmol) over 3 min. The reaction was stirred for 20 h, with the cold bath being allowed to expire overnight. A 3 M aqueous solution of NaOH (2.9 mL, 8.7 mmol) was then added, and, after stirring 20 min, the resulting solution was transferred in its entirety to a flask containing the product from Step 1 (ca. 5.16 mmol) and PdCl_2(dppf) CH_2Cl_2 (420 mg, 0.51 mmol). The resulting mixture was heated to 60° C. After stirring 14 h, the reaction mixture was diluted with Et_2O (50 mL) and H_2O (50 mL). The phases were separated, and the organic phase was dried over MgSO_4, filtered, and concentrated. Purification by silica gel chromatography (0% to 10% EtOAc in hexanes following pre-equilibration with 1% Et_3N in EtOAc) provided intermediate D19-1. $^1$H NMR (300 MHz, CDCl_3) 5.36-5.28 (m, 1H), 4.59 (t, J=5.6 Hz, 1H), 3.73-3.58 (m, 2H), 3.54-3.39 (m, 2H), 2.72-2.60 (m, 1H), 2.45-2.34 (m, 3H), 2.23-2.08 (m, 4H), 1.89-1.76 (m, 2H), 1.67 (dt, J=16.1, 6.9 Hz, 2H), 1.58-1.47 (m, 2H), 1.23 (t, J=7.0 Hz, 6H).

Step 3: Preparation of D19-2: A solution of olefin D19-1 (660 mg, 2.77 mmol) in THF (25 mL) was cooled in an ice water bath. BH_3.Me_2S was then added as a 1 M solution in CH_2Cl_2 (2.9 mL, 2.9 mmol) over 1 min. The resulting solution was stirred for 2 h in the ice water bath and was then allowed to warm to r.t. After stirring an additional 3 h, the reaction mixture was re-cooled in an ice water bath and was diluted with 2 M aqueous NaOH (7 mL) followed by 30% aqueous H_2O_2 (7 mL). The resulting mixture was stirred an additional 16 h as the cold bath was allowed to gradually expire. The mixture was partitioned between Et_2O (100 mL) and H_2O (50 mL), the phases were separated, and the organic phase was washed with 0.5 M aqueous NaOH (50 mL). The organic phase was dried over MgSO_4, filtered, and concentrated to afford a crude residue that was purified by silica gel chromatography (15% to 40% EtOAc in hexanes) to afford 570 mg of Intermediate D19-2. $^1$H NMR (300 MHz, CDCl_3) δ 4.60 (t, J=5.6 Hz, 1H), 3.76-3.60 (m, 3H), 3.58-3.42 (m, 2H), 2.39-2.05 (m, 4H), 1.91-1.48 (m, 9H), 1.43-1.35 (m, 1H), 1.25 (t, J=7.0 Hz, 6H), 1.06-0.98 (m, 1H).

Steps 4 and 5: Preparation of D19-3: Acetal D19-2 (360 mg, 1.4 mmol) was dissolved in THF (8 mL) and H_2O (2 mL). para-Toluenesulfonic acid monohydrate (40 mg, 0.2 mmol) was added and the resulting solution was stirred 16 h at r.t. The reaction was diluted with Et$_2$O (50 mL) and H$_2$O (30 mL) and the phases were separated. The aqueous phase was extracted with Et$_2$O (30 mL) and the combined organic phase was washed with saturated aqueous NaHCO$_3$ (15 mL). The organic phase was dried over MgSO$_4$, filtered, and concentrated to afford a crude residue that was used immediately in the following step. Step 5: Methyl triphenylphosphonium bromide (1.66 g, 4.6 mmol) was suspended in THF (40 mL) under Ar and was cooled via a CO$_2$/acetone bath to −78° C. A 1 M solution of NaHMDS in THF (4.2 mL, 4.2 mmol) was added in dropwise fashion and the resulting yellow suspension was stirred for 5 min. The mixture was removed from the cold bath and stirring continued an additional 30 min. The mixture was then re-cooled to −78° C. and the crude residue from the previous step (ca. 1.4 mmol) was added as a solution in THF (5 mL) over 5 min, washing with additional THF (2×2.5 mL) to ensure complete transfer. The resulting mixture was stirred for 5 min and was then placed in an ice water bath and stirred an additional 1 h. The reaction was quenched with saturated aqueous NH$_4$Cl (20 mL) and was diluted with Et$_2$O (30 mL) and H$_2$O (20 mL). The phases were separated and the organic phase was dried over MgSO$_4$, filtered, and concentrated onto 5 g silica gel. Purification by silica gel chromatography (10% to 30% EtOAc in hexanes) provided 019-3. $^1$H NMR (300 MHz, CDCl$_3$) δ 6.01-5.81 (m, 1H), 5.22-5.05 (m, 2H), 3.79-3.66 (m, 1H), 2.43-2.25 (m, 2H), 2.24-2.04 (m, 4H), 1.83-1.16 (m, 10H).

Step 6: Intermediate 019-3 (270 mg, 1.5 mmol) was dissolved in DMF (2.0 mL). Pyridine (125 µL, 1.5 mmol) and DSC (500 mg, 1.9 mmol) were added, and the reaction was stirred at 45° C. for 15 h. The reaction was then placed in an ice water bath and H$_2$O (2.0 mL) was added dropwise over 30 s. The mixture was removed from the cold bath and allowed to stir 10 min. The mixture was re-cooled in an ice water bath and L-tert-leucine (259 mg, 1.97 mmol) was added followed by K$_3$PO$_4$ (835 mg, 3.93 mmol). The reaction mixture was removed from the cold bath and allowed to stir at r.t. for 5.25 h. The mixture was then diluted with EtOAc (40 mL), 1 M aqueous HCl (20 mL), and H$_2$O (15 mL). The phases were separated, and the aqueous phase was extracted with EtOAc (30 mL). The combined organic phase was washed with 0.2 M aqueous HCl (2×25 mL), dried over Na$_2$SO$_4$, filtered, and concentrated to afford a mixture of diastereomers D19 (505 mg) as a colorless oil. LCMS-ESI$^+$ (m/z) [M+H]$^+$ calcd for C$_{19}$H$_{32}$NO$_4$: 338.2; found: 337.8.

Preparation of Intermediate E1

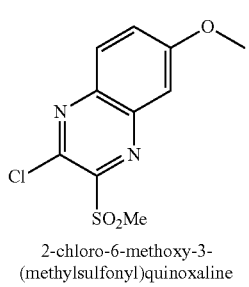

E1

2-chloro-6-methoxy-3-(methylsulfonyl)quinoxaline

Intermediate E1 (2-chloro-6-methoxy-3-(methylsulfonyl) quinoxaline) was prepared according to Mahata, P. K., et al. *Org. Lett.* 2005, 7, 2169.

Preparation of Intermediate E2

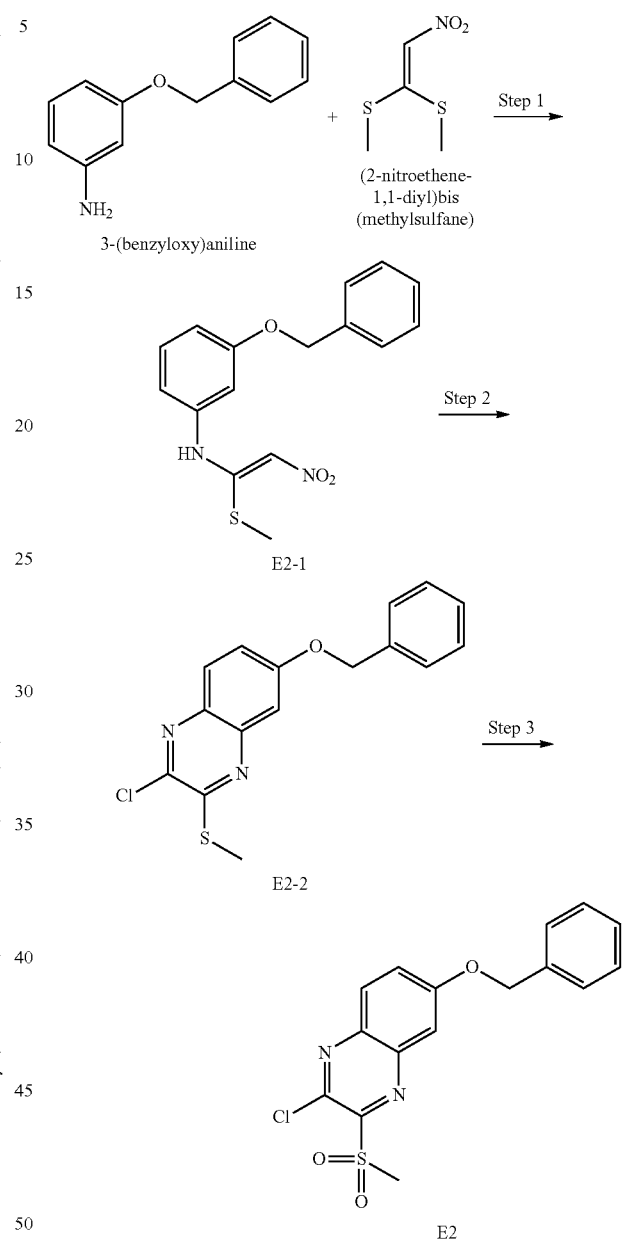

Step 1. Preparation of E2-1: In a round bottom flask, 3-(benzyloxy)aniline (4.025 g, 20.20 mmol) and 1,1-bis (methylthio)-2-nitroethylene (3.338 g, 20.20 mmol) in ethanol (40 mL) was refluxed for 24 h with constant stirring. The reaction mixture was then cooled in an ice bath and diluted with ether (150 mL). The mixture was filtered and washed with ether to afford E2-1 (3.32 g) as a yellow solid which was used directly in the following in step. LCMS-ESI$^+$ (m/z): [M+H]$^+$ calcd for C$_{16}$H$_{17}$N$_2$O$_3$S: 317.1; found: 317.1.

Step 2. Preparation of E2-2: To a suspension of E2-1 (3.32 g, 10.49 mmol) in 25 mL MeCN, POCl$_3$ (2.93 mL, 31.5 mmol) was added dropwise over 15 min with constant stirring. The reaction mixture was warmed to 80° C. and stirred for 5 h. The reaction was then cooled to ambient temperature and neutralized with ice cold saturated aqueous NaHCO$_3$ solution, extracted three times with CH$_2$Cl$_2$ (100 mL), washed with water, brine and dried over anhydrous Na$_2$SO$_4$. The solvent was removed under reduced pressure. The crude material was eluted through a plug of silica with CH$_2$Cl$_2$. The solvent was removed under reduced pressure and the solid was washed with MeCN to afford E2-2 (1.56 g) as an off white solid. LCMS-ESI$^+$ (m/z): [M+H]$^+$ calcd for C$_{16}$H$_{14}$ClN$_2$OS: 317.1; found: 317.3.

Step 3. Preparation of Intermediate E2. A solution of mCPBA (1.87 g, 10.83 mmol) in CH$_2$Cl$_2$ (40 mL) was added dropwise to a stirred solution of E2-2 (1.56 g, 4.92 mmol) in CH$_2$Cl$_2$ (40 mL) at 0° C. over a period of 30 min. The reaction mixture was further stirred at ambient temperature for 5 h. It was then poured into ice could saturated aqueous NaHCO$_3$ and partitioned with CH$_2$Cl$_2$. The organic layer was then washed subsequently with water, brine and dried over anhydrous Na$_2$SO$_4$. The solvent was removed under reduced pressure and the crude material was purified by normal phase chromatography with CH$_2$Cl$_2$ to provide the title compound Intermediate E2 as a pale yellow solid. LCMS-ESI$^+$ (m/z): [M+H]$^+$ calcd for C$_{16}$H$_{14}$ClN$_2$O$_3$S: 349.0; found: 349.0.

Preparation of Intermediate E3

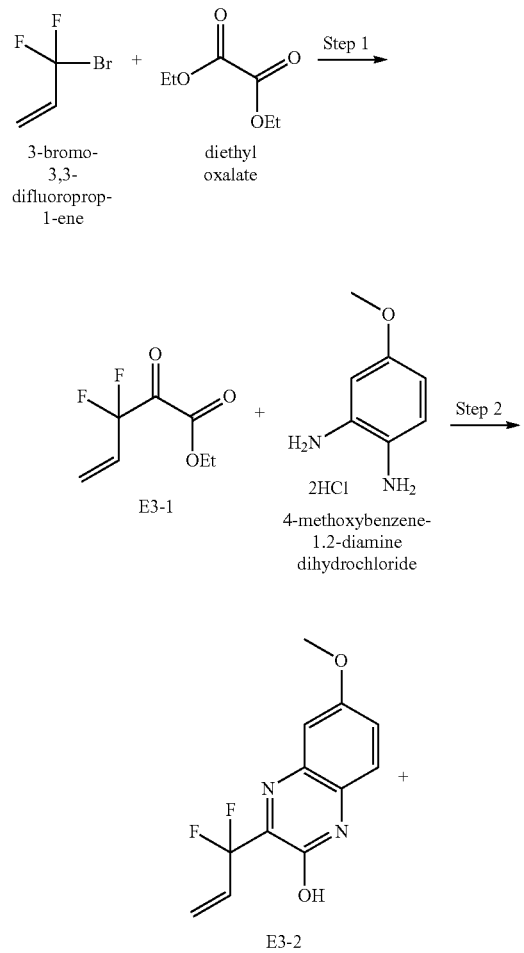

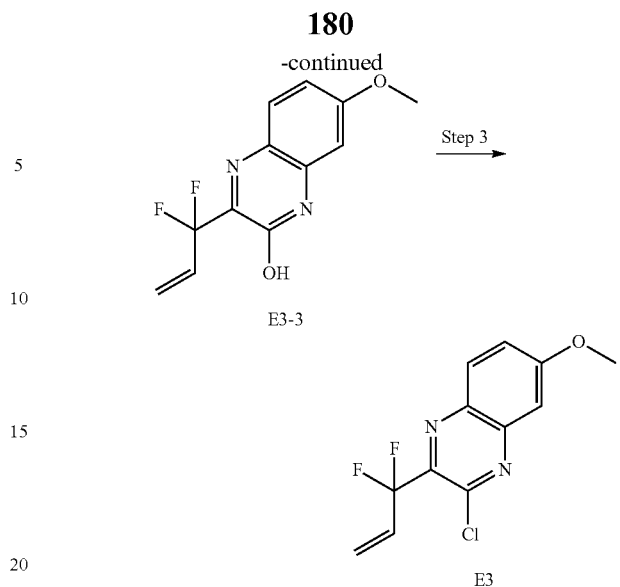

Step 1. Preparation of E3-1: To a solution of 3-bromo-3,3-difluoroprop-1-ene (25.0 g, 159 mmol) and diethyl oxalate (21.6 mL, 159 mmol) in THF (380 mL), diethyl ether (90 mL) and n-pentane (90 mL) at −100° C. was added dropwise n-butyllithium (2.5 M in hexane, 67 mL, 167.6 mmol) over 30 min. The reaction mixture was stirred at −95° C. for 1 h and −78° C. for 2 h, and quenched with aq. NH$_4$Cl (11 g in 150 mL of water). The mixture was extracted with ether (three times). The organic layers were washed with 1 N aqueous HCl, brine, and dried over Na$_2$SO$_4$, and concentrated to give the crude residue, which was purified by silica gel chromatography (EtOAc in hexanes: 0% to 40%) to give E3-1 (7.0 g). $^1$H NMR (300 MHz, CDCl$_3$) δ 5.98-6.18 (m, 1H), 5.78 (dd, J=0.9 Hz, 13 Hz, 1H), 5.60 (dd, J=0.9 Hz, 11 Hz, 1H), 4.38 (q, J=6.9 Hz, 2H), 1.37 (t, J=7.2 Hz, 3H).

Step 2. Preparation of E3-2 and E3-3: To a solution of E3-1 (14.0 g, 78.6 mmol) and 4-methoxybenzene-1,2-diamine dihydrochloride (15.08 g, 71.4 mmol) in EtOH (360 mL) at rt was added triethylamine (19.9 mL, 142.8 mmol). The reaction mixture was stirred at rt overnight. The mixture was concentrated. Slurrying in dichloromethane (30 mL) and filtering gave some separation of regioisomers with E3-2 as the precipitating species. (16.5 g total yield from filtration and subsequent chromatography). $^1$H NMR (400 MHz, CDCl$_3$) δ 11.940 (br s, 1H), 7.850 (d, J=9 Hz, 1H), 6.985 (dd, J=3 Hz, 9 Hz, 1H), 6.754 (d, J=2 Hz, 1H), 6.625-6.498 (m, 1H), 5.907 (dt, J=17, 2 Hz, 1H), 5.601 (d, J=11 Hz, 1H), 3.938 (s, 3H). The mixture was slurried, filtered, and concentrated once more, then was purified by silica gel chromatography (EtOAc in hexanes: 5% to 34%) to give E3-3 (2.07 g) as the first eluting component. $^1$H NMR (400 MHz. CDCl$_3$) δ 12.05 (br s, 1H), 7.850 (d, J=9 Hz, 1H), 6.986 (dd, J=3 Hz, 9 Hz, 1H), 6.761 (d, J=3 Hz, 1H), 6.597-6.526 (m, 1H), 5.91 (dt, J=17, 2 Hz, 1H), 5.601 (d, J=11 Hz, 1H), 3.939 (s, 3H).

Step 3. Preparation of Intermediate E3: A solution of E3-3 (2.07 g, 8.2 mmol in 1 mL DMF was treated with POCl$_3$ (0.8 mL) and heated at 65° C. for 2.5 h. The reaction was diluted with EtOAc and quenched by pouring into ice water. The organic phase was washed subsequently with saturated aqueous sodium bicarbonate and brine, dried over sodium sulfate and concentrated to give 2.1 g of Intermediate E3. $^1$H NMR (400 MHz, CDCl$_3$) δ 8.028 (d, J=10 Hz, 1H), 7.46 (dd, J=3 Hz, 9 Hz, 1H), 7.32 (d, J=3 Hz, 1H), 6.549-6.478 (m, 1H), 5.86 (dt, J=17, 2 Hz, 1H), 5.67 (d, J=11 Hz, 1H), 3.981 (s, 3H).

Preparation of Intermediate E4

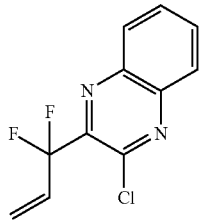

E4

Intermediate E4 (2-chloro-3-(1,1-difluoroallyl)quinoxaline) was prepared in a similar fashion to Intermediate E3, substituting 1,2-diaminobenzene for 4-methoxybenzene-1,2-diamine dihydrochloride in Step 2.

Preparation of Intermediate E5

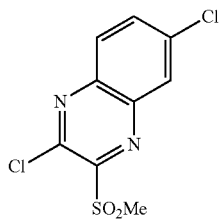

E5

Intermediate E5 (2,6-dichloro-3-(methylsulfonyl)quinoxaline) was prepared according to Mahata. P. K., et al. *Org. Lett.* 2005, 7, 2169.

Preparation of Intermediate E6

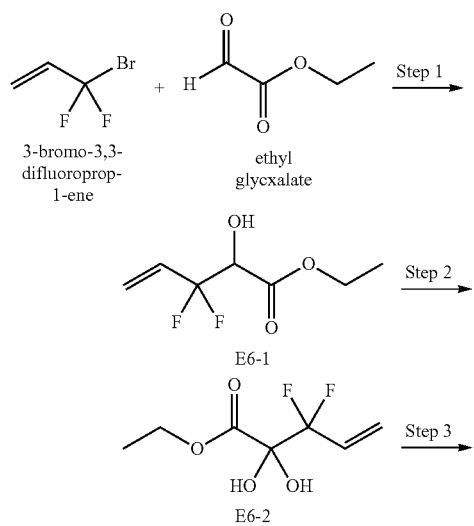

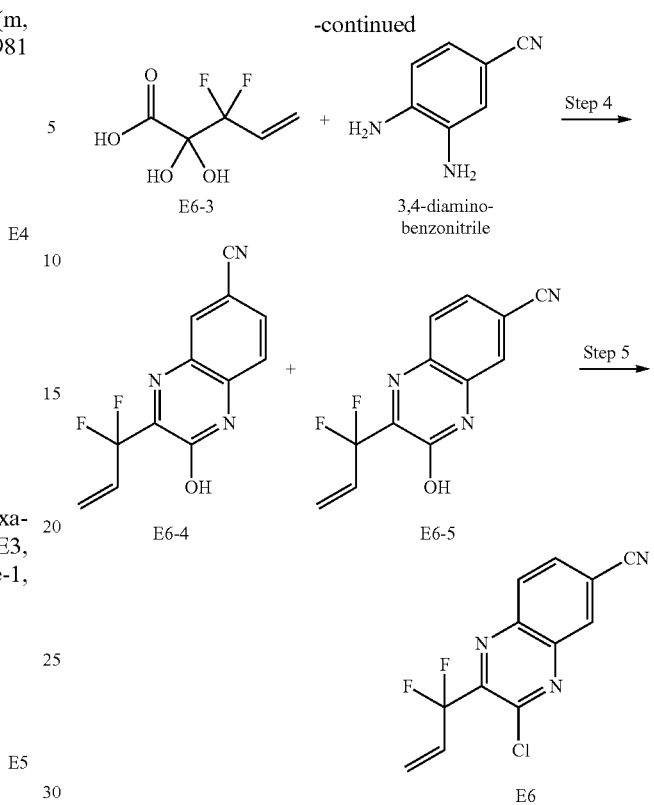

Step 1. Preparation of E6-1: A 1-L 3-necked round-bottom flask was charged with a solution of 3-bromo-3,3-difluoroprop-1-ene (25 g, 159.3 mmol) in DMF (360 mL) and water (90 mL). The resulting solution was treated with ethyl 2-oxoacetate (33 mL, 1 M in toluene), and in (25 g). The reaction mixture was stirred overnight at rt and then extracted with 3×300 mL of ether. The organic layers were combined, washed with 1×100 mL of saturated aqueous NH$_4$Cl and 1×100 mL of brine, dried over anhydrous Na$_2$SO$_4$ and concentrated in vacuo to afford E6-1 that was used subsequently without additional purification.

Step 2. Preparation of E6-2. To hydroxyester E6-1 (58.1 g, 323 mmol) was added DCM (700 mL) in a 2 L 3-neck flask equipped with overhead stirring and an internal temperature probe. Then TEMPO (5.4 g, 35 mmol), buffer solution (prepared by dissolving 4.2 g NaHCO$_3$ and 0.53 g Na$_2$CO$_3$ per 100 mL water, 700 mL, 7v), and NaOCl (Clorox 6.15% wt, 422 mL, 395 mmol) were sequentially added to the flask at 20° C. After 2 h the organic layer was separated and the aqueous phase extracted with ethyl acetate (2×300 mL). The combined organic layers were dried over anhydrous Na$_2$SO$_4$ and concentrated in vacuo to afford E6-2. $^1$H-NMR (300 MHz, CDCl$_3$) δ 5.98-6.18 (m, 1H), 5.78 (dd, J=0.9 Hz, 13 Hz, 1H) 5.60 (dd, J=0.9 Hz, 11 Hz, 1H), 4.38 (q, J=6.9 Hz, 2H), 1.37 (t, J=7.2 Hz, 3H).

Step 3. Preparation of E6-3. To a solution of ethyl 3,3-difluoro-2,2-dihydroxypent-4-enoate E6-2 (57.4 g, 292 mmol) in THF (725 mL) and water (131 mL) was added LiOH.H$_2$O (22 g, 529 mmol) at 20° C. After 2.5 h, the reaction mixture was concentrated in vacuo. The solid residue was suspended in water (300 mL) and the resulting mixture was acidified to pH=1 with concentrated aqueous hydrochloric acid solution. The resulting mixture was stirred until all solids were dissolved (~1.5 h), and then sodium chloride was added until the solution was saturated. The resulting solution was extracted with MTBE (2×500 mL) and ethyl acetate (2×500 mL), and the combined organic layers were dried over anhydrous Na$_2$SO$_4$ and were concentrated in vacuo. The crude orange solid residue was suspended into DCM (100 mL) and was stirred until the solids were finely distributed before hexanes (75 mL) were slowly added via addition funnel. The resulting solids were collected by vacuum filtration through a medium fritted funnel and washed with 1:1 dichloromethane/hexanes (2×10 mL) to afford the desired product. $^1$H-NMR (400 MHz, DMSO-d$_6$) δ 13.17 (bs, 1H), 6.18-6.01 (m, 1H), 5.64-5.52 (m, 2H).

Step 4. Preparation of E6-4 and E6-5: A solution of E6-3 (0.5 g, 3.3 mmol) in EtOH (12 mL) was treated with 3,4-diaminobenzonitrile (0.47 g, 3.5 mmol). The reaction mixture was heated at 80° C. for 1 h, then concentrated in vacuo. The resulting residue was absorbed on silica gel, then was purified by column chromatography to give E6-4 (0.5 g) as the first eluting component. $^1$H-NMR (400 MHz, CD$_3$OD) δ 8.01 (d, 1H), 7.65 (dd, 2H), 6.49 (m, 1H), 5.80 (dt, 1H), 5.60 (d, 1H). E6-5 (0.2 g) was recovered as the second eluting component $^1$H-NMR (400 MHz, CD$_3$OD) δ 8.25 (d, 1H), 7.87 (dd, 1H), 7.41 (d, 1H), 6.49 (m, 1H), 5.80 (dt, 1H), 5.59 (d, 1H).

Step 5. Preparation of Intermediate E6: A solution of E6-4 (0.5 g, 2 mmol in 4.5 mL DMF was treated with POCl$_3$ (3 mL) and heated at 65° C. for 3 h. The reaction was diluted with EtOAc and quenched by pouring into ice water. The organic phase was washed subsequently with saturated aqueous NaHCO$_3$ and brine, dried over anhydrous Na$_2$SO$_4$ and concentrated in vacuo to give 0.48 g of Intermediate E6 (3-chloro-2-(1,1-difluoroallyl)quinoxaline-6-carbonitrile). $^1$H-NMR (400 MHz, CD$_3$OD) δ 8.52 (s, 1H), 8.30 (d, 1H), 8.13 (dd, 1H), 6.55 (m, 1H), 584 (dt, 1H), 5.72 (d, 1H).

Preparation of Intermediate E7

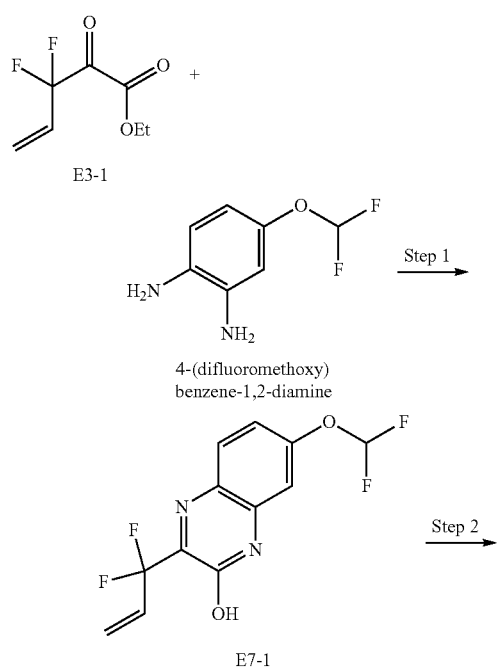

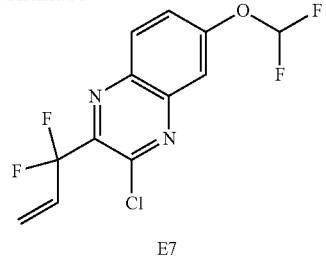

Step 1. Preparation of E7-1: To a solution of E3-1 (1.84 g 10.93 mmol) and 4-(difluoromethoxy)benzene-1,2-diamine (1.90 g, 10.93 mmol, prepared according to Reference Example 30y of WO2003035065, p. 511) in DMF (40 mL) at rt was added DIPEA (9.5 mL, 54.65 mmol) and HATU (6.23 g, 16.4 mmol). The reaction mixture was stirred at room temperature for 24 h, diluted with ethyl acetate (100 mL), washed with water (100 mL) and brine (50 mL). The mixture was concentrated in vacuo. Purification via silica gel chromatography (EtOAc in hexanes: 20% to 60%) provided E7-1 (800 mg) as the later eluting fraction of two with the similar mass spectra. LCMS-ESI$^+$ (m/z): [M+H]$^+$ calcd for C$_{12}$H$_9$F$_4$N$_2$O: 289.2; found: 289.0.

Step 2: Preparation of Intermediate E7: Hydroxyquinoxaline E7-1 (800 mg, 2.8 mmol), POCl$_3$ (1.65 mL, 3.0 mmol) and DMF (10 mL) are combined at rt and then heated to 65° C. for 2.5 h at which time additional POCl$_3$ (0.2 mL, 0.36 mmol) was added. The reaction was heated an additional 3 h at 65° C. then cooled to rt. The reaction was quenched by addition of cold water (30 mL), and taken up into ethyl acetate (50 mL), washed with saturated aqueous Na$_2$CO$_3$ (100 mL) followed by brine (50 mL), and dried over anhydrous MgSO$_4$. The resulting solution was concentrated in vacuo to give Intermediate E7 (859 mg) which was used subsequently without further purification. LCMS-ESI$^+$ (m/z): [M+H]$^+$ calcd for C$_{12}$H$_8$ClF$_4$N$_2$O: 307.0; found: 307.0.

Preparation of Intermediate E8

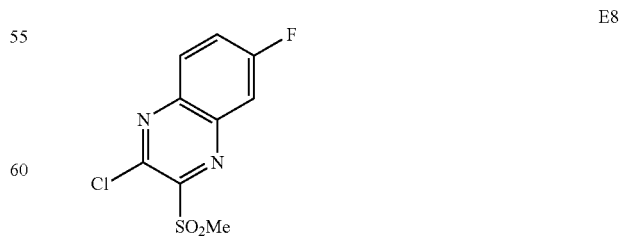

Intermediate E8 (2-chloro-6-fluoro-3-(methylsulfonyl)quinoxaline) was prepared according to Mahata, P. K., et al. *Org. Lett.* 2005, 7, 2169.

185

Preparation of Intermediate E9

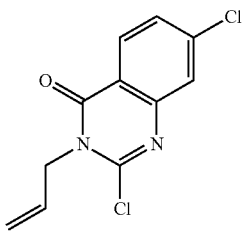

E9

2,7-dichloro-3-(prop-2-en-1-yl)quinazolin-4(3H)-one (intermediate E9) was prepared according to Step 3 of Intermediate 05 of WO '040 p 53-4.

PREPARATION OF EXAMPLES

Example 1

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

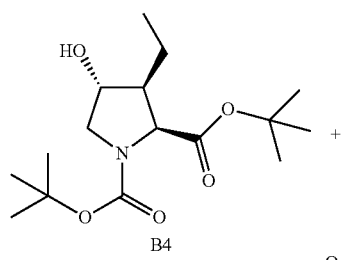

B4

+

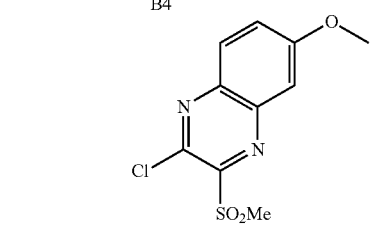

E1

Step 1 →

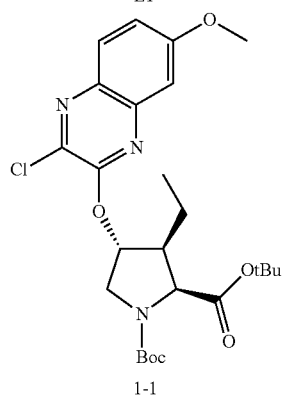

1-1

Step 2 →

186

-continued

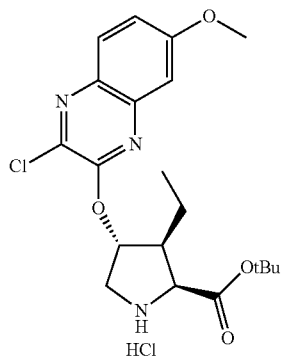

1-2

+

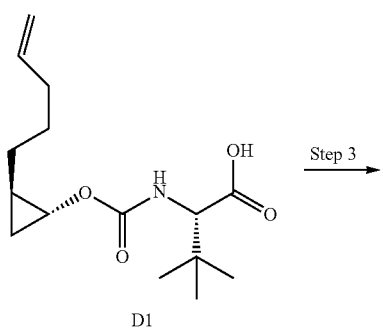

D1

Step 3 →

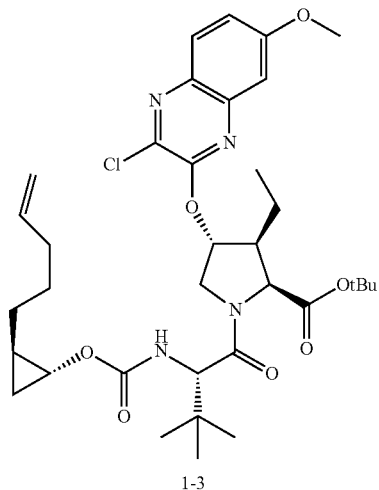

1-3

Step 4 →

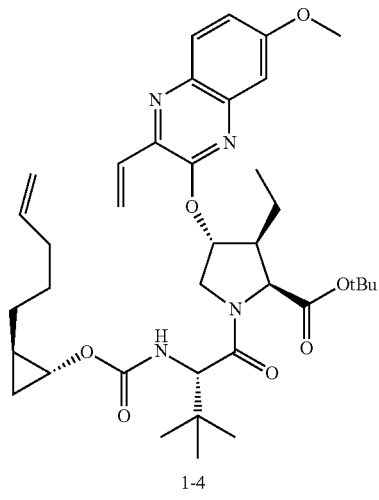

1-4

Step 5 →

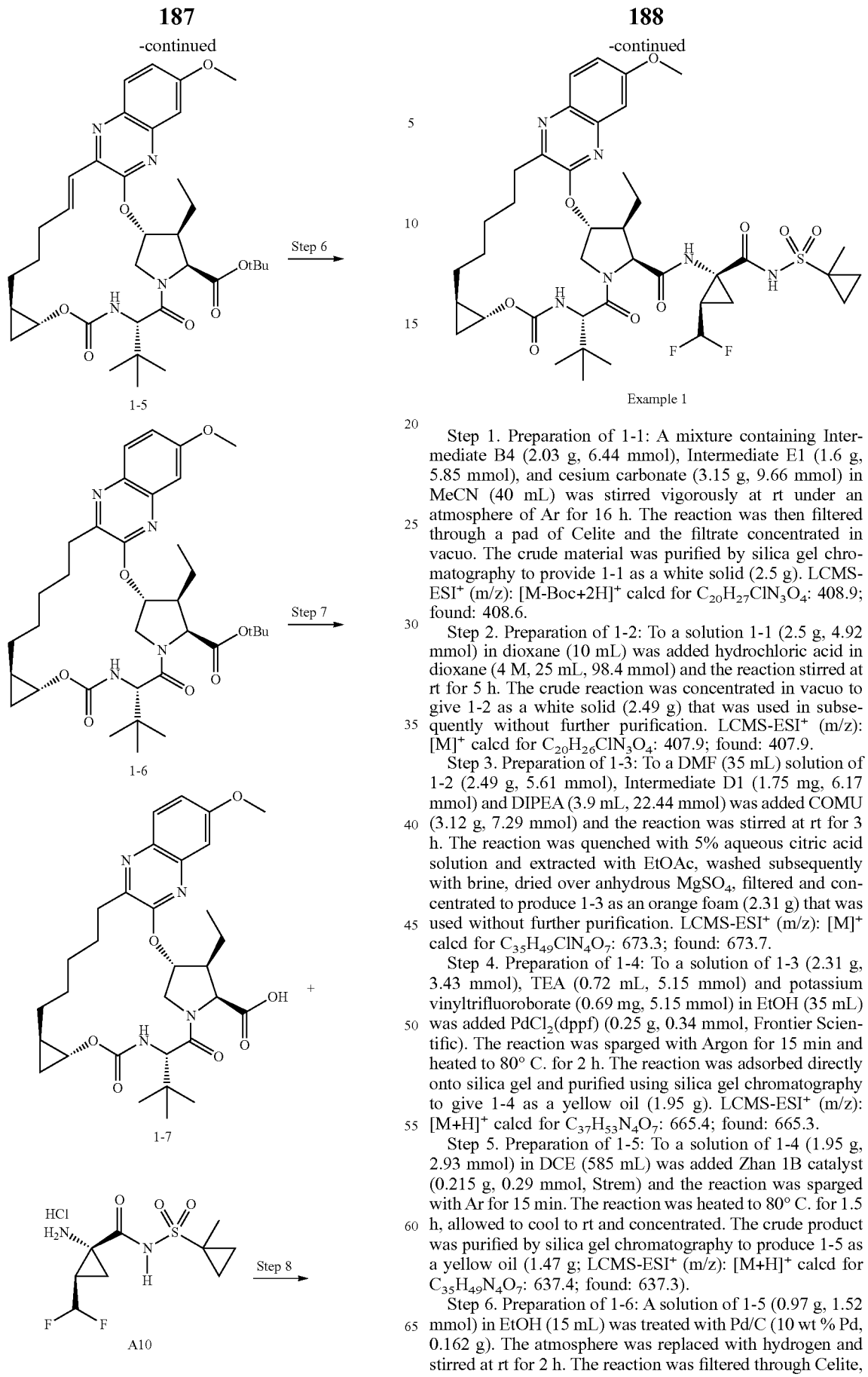

Step 1. Preparation of 1-1: A mixture containing Intermediate B4 (2.03 g, 6.44 mmol), Intermediate E1 (1.6 g, 5.85 mmol), and cesium carbonate (3.15 g, 9.66 mmol) in MeCN (40 mL) was stirred vigorously at rt under an atmosphere of Ar for 16 h. The reaction was then filtered through a pad of Celite and the filtrate concentrated in vacuo. The crude material was purified by silica gel chromatography to provide 1-1 as a white solid (2.5 g). LCMS-ESI$^+$ (m/z): [M-Boc+2H]$^+$ calcd for $C_{20}H_{27}ClN_3O_4$: 408.9; found: 408.6.

Step 2. Preparation of 1-2: To a solution 1-1 (2.5 g, 4.92 mmol) in dioxane (10 mL) was added hydrochloric acid in dioxane (4 M, 25 mL, 98.4 mmol) and the reaction stirred at rt for 5 h. The crude reaction was concentrated in vacuo to give 1-2 as a white solid (2.49 g) that was used in subsequently without further purification. LCMS-ESI$^+$ (m/z): [M]$^+$ calcd for $C_{20}H_{26}ClN_3O_4$: 407.9; found: 407.9.

Step 3. Preparation of 1-3: To a DMF (35 mL) solution of 1-2 (2.49 g, 5.61 mmol), Intermediate D1 (1.75 mg, 6.17 mmol) and DIPEA (3.9 mL, 22.44 mmol) was added COMU (3.12 g, 7.29 mmol) and the reaction was stirred at rt for 3 h. The reaction was quenched with 5% aqueous citric acid solution and extracted with EtOAc, washed subsequently with brine, dried over anhydrous MgSO$_4$, filtered and concentrated to produce 1-3 as an orange foam (2.31 g) that was used without further purification. LCMS-ESI$^+$ (m/z): [M]$^+$ calcd for $C_{35}H_{49}ClN_4O_7$: 673.3; found: 673.7.

Step 4. Preparation of 1-4: To a solution of 1-3 (2.31 g, 3.43 mmol), TEA (0.72 mL, 5.15 mmol) and potassium vinyltrifluoroborate (0.69 mg, 5.15 mmol) in EtOH (35 mL) was added PdCl$_2$(dppf) (0.25 g, 0.34 mmol, Frontier Scientific). The reaction was sparged with Argon for 15 min and heated to 80° C. for 2 h. The reaction was adsorbed directly onto silica gel and purified using silica gel chromatography to give 1-4 as a yellow oil (1.95 g). LCMS-ESI$^+$ (m/z): [M+H]$^+$ calcd for $C_{37}H_{53}N_4O_7$: 665.4; found: 665.3.

Step 5. Preparation of 1-5: To a solution of 1-4 (1.95 g, 2.93 mmol) in DCE (585 mL) was added Zhan 1B catalyst (0.215 g, 0.29 mmol, Strem) and the reaction was sparged with Ar for 15 min. The reaction was heated to 80° C. for 1.5 h, allowed to cool to rt and concentrated. The crude product was purified by silica gel chromatography to produce 1-5 as a yellow oil (1.47 g; LCMS-ESI$^+$ (m/z): [M+H]$^+$ calcd for $C_{35}H_{49}N_4O_7$: 637.4; found: 637.3).

Step 6. Preparation of 1-6: A solution of 1-5 (0.97 g, 1.52 mmol) in EtOH (15 mL) was treated with Pd/C (10 wt % Pd, 0.162 g). The atmosphere was replaced with hydrogen and stirred at rt for 2 h. The reaction was filtered through Celite, the pad washed with EtOAc and concentrated to give 1-6 as a brown foamy solid (0.803 g) that was used subsequently without further purification. LCMS-ESI⁺ (m/z): [M+H]⁺ calcd for $C_{35}H_{51}N_4O_7$: 639.4; found: 639.3.

Step 7. Preparation of 1-7: To a solution of 1-6 (0.803 g, 1.26 mmol) in DCM (10 mL) was added TFA (5 mL) and stirred at rt for 3 h. An additional 2 mL TFA was added and the reaction stirred for another 1.5 h. The reaction was concentrated to a brown oil that was taken up in EtOAc (35 mL). The organic solution was washed with water. After separation of the layers, sat. aqueous NaHCO₃ was added with stirring until the aqueous layer reached a pH~7-8. The layers were separated again and the aqueous extracted with EtOAc twice. The combined organics were washed with 1 M aqueous citric acid, brine, dried over anhydrous MgSO₄, filtered and concentrated to produce 1-6 as a brown foamy solid (0.719 g) that was used subsequently without further purification. LCMS-ESI⁺ (m/z): [M+H]⁺ calcd for $C_{31}H_{43}N_4O_7$: 583.3; found: 583.4.

Step 8. Preparation of Example 1: To a solution of 1-7 (0.200 g, 0.343 mmol), Intermediate A10 (0.157 g, 0.515 mmol), DMAP (0.063 g, 0.51 mmol) and DIPEA (0.3 mL, 1.72 mmol) in DMF (3 mL) was added HATU (0.235 g, 0.617 mmol) and the reaction was stirred at rt o/n. The reaction was diluted with MeCN and purified directly by reverse phase HPLC (Gemini, 30-100% MeCN/H₂O+0.1% TFA) and lyophilized to give Example 1 (118.6 mg) as a solid TFA salt. Analytic HPLC RetTime: 8.63 min. LCMS-ESI⁺ (m/z): [M+H]⁺ calcd for $C_{40}H_{55}F_2N_6O_9S$: 833.4; found: 833.5. ¹H NMR (400 MHz, CD₃OD) δ 9.19 (s, 1H); 7.80 (d, J=8.8 Hz, 1H) 7.23 (dd, J=8.8, 2.4 Hz, 1H); 7.15 (d, J=2.4 Hz, 1H); 5.89 (d, J=3.6 Hz, 1H); 5.83 (td, $J_{H-F}$=55.6 Hz, J=6.4 Hz, 1H); 4.56 (d, J=7.2 Hz, 1H); 4.40 (s, 1H) 4.38 (ap d, J=7.2 Hz, 1H); 4.16 (dd, J=12, 4 Hz, 1H); 3.93 (s, 3H); 3.75 (m, J=7.2, 4 Hz, 1H); 3.00-2.91 (m, 1H); 2.81 (td, J=12, 4.4 Hz, 1H); 2.63-2.54 (m, 1H); 2.01 (br s, 2H); 1.88-1.64 (m, 3H); 1.66-1.33 (m, 11H) 1.52 (s, 3H); 1.24 (t, J=7.2 Hz, 3H); 1.10 (s, 9H); 1.02-0.96 (m, 2H); 0.96-0.88 (m, 2H); 0.78-0.68 (m, 1H); 0.55-0.46 (m, 1H).

Example 2

Preparation of (1aR,5S,8S,9S,10R,22aR)-5-tert-butyl-N-[(1R,2R)-1-[(cyclopropylsulfonyl)carbamoyl]-2-(difluoromethyl)cyclopropyl]-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 2

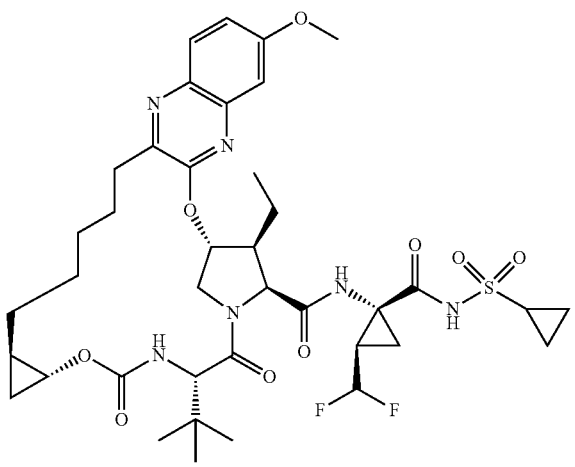

Example 2 was prepared in a similar fashion to Example 1, substituting Intermediate A9 for Intermediate A10 in Step 8. Example 2 was isolated (37.9 mg) in approximately 85% purity as a TFA salt. Analytic HPLC RetTime: 8.54 min. LCMS-ESI⁺ (m/z): [M+H]⁺ calcd for $C_{39}H_{53}F_2N_6O_9S$: 819.35; found: 819.51. ¹H NMR (400 MHz, CDCl₃) δ 10.26 (s, 1H); 7.90 (d, J=9.2 Hz, 1H); 7.26 (dd, J=9.2, 2.4 Hz, 1H); 7.10 (d, J=2.4 Hz, 1H); 6.68 (br s, 1H); 6.01 (td, $J_{H-F}$=55.6 Hz, J=6.8 Hz, 1H); 5.87 (d, J=3.6 Hz, 1H); 5.38 (d, J=10 Hz, 1H); 4.50-4.40 (m, 3H); 4.10 (dd, J=12, 3.6 Hz, 1H); 3.95 (s, 3H); 3.79-3.72 (m, 1H); 2.96-2.82 (m, 3H); 2.63-2.56 (m, 1H); 2.14 (t, J=6.8 Hz, 1H); 1.98-1.86 (m, 1H); 1.84-1.28 (m, 13H); 1.23 (t, J=7.2 Hz, 3H); 1.16-0.92 (m, 3H); 1.09 (s, 9H); 0.74-0.64 (m, 1H), 0.48 (q, J=6.4 Hz, 1H).

Example 3

Preparation of (1aR,5S,8S,9S,10R,22aR)-5-tert-butyl-N-{(1R,2R)-1-[(cyclopropylsulfonyl)carbamoyl]-2-ethylcyclopropyl}-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 3

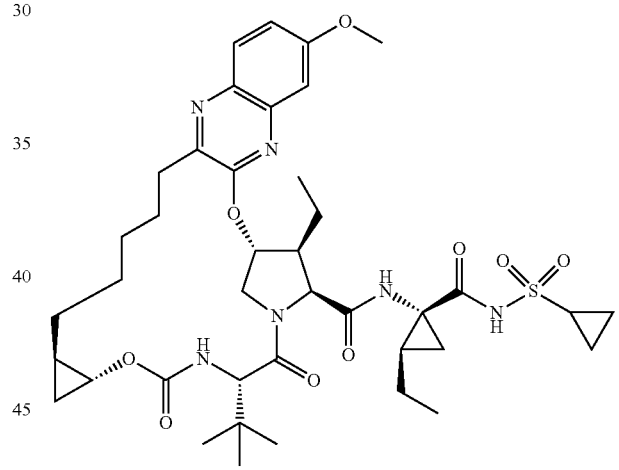

Example 3 was prepared in a similar fashion to Example 1, substituting Intermediate A3 for Intermediate A10 in Step 8. Example 3 was isolated (0.035 g) in approximately 88% purity as a TFA salt. Analytic HPLC RetTime: 8.63 min. LCMS-ESI⁺ (m/z): [M+H]⁺ calcd for $C_{40}H_{57}N_6O_9S$: 797.4; found 797.5. ¹H NMR (400 MHz, CD₃OD) δ 8.98 (s, 1H); 7.80 (d, J=9.2 Hz, 1H); 7.23 (d, J=9.2, 2.8 Hz, 1H); 7.15 (d, J=2.8 Hz, 1H); 5.89 (d, J=3.6 Hz, 1H); 4.58 (d, J=7.6 Hz, 1H); 4.41-4.32 (m, 2H); 4.16 (dd, J=12.4, 3.6 Hz, 1H); 3.93 (s, 3H); 3.74 (dt, J=6.8, 2.8 Hz, 1H); 3.20-2.91 (m, 2H); 2.86-2.76 (m, 1H); 2.61-2.53 (m, 1H); 1.88-1.68 (m, 4H); 1.66-1.34 (m, 9H); 1.34-1.20 (m, 5H); 1.18-1.04 (m, 3H); 1.10 (s, 9H); 1.00-0.92 (m, 7H); 0.79-0.69 (m, 1H); 0.50 (br d, J=7.2 Hz, 1H).

Example 4

Preparation of (1aR,5S,8S,9S,10R,22aR)-5-tert-butyl-9-ethyl-N-[(1R,2R)-2-ethyl-1-{[(1-methylcyclopropyl)sulfonyl]carbamoyl}cyclopropyl]-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 4

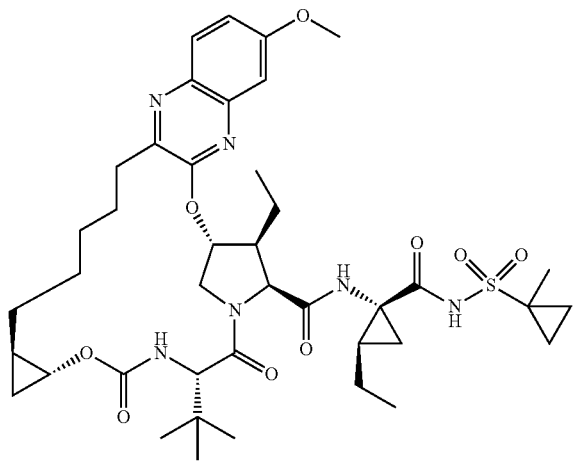

Example 4 was prepared in a similar fashion to Example 1, substituting Intermediate A4 for Intermediate A10 in Step 8. Example 4 was isolated (0.018 g) in approximately 88% purity as a TFA salt. Analytic HPLC RetTime: 8.75. LCMS-ESI$^+$ (m/z): [M+H]$^+$ calcd for $C_{41}H_{59}N_6O_9S$: 811.4; found: 811.6. $^1$H NMR (400 MHz, CD$_3$OD) δ 8.91 (s, 1H); 7.80 (d, J=9.2 Hz, 1H); 7.23 (dd, J=9.2, 2.8 Hz, 1H); 7.16 (d, J=2.8 Hz, 1H); 5.90 (d, J=3.6 Hz, 1H); 4.59 (d, J=6.8 Hz, 1H); 4.38 (s, 1H); 4.37 (d, J=11.6 Hz, 1H), 4.16 (dd, J=11.6, 6.8 Hz, 1H), 3.93 (s, 3H); 3.74 (dt, J=6.8, 3.6 Hz, 1H); 3.10-2.91 (m, 1H); 2.90-2.7 (m, 1H); 2.63-2.55 (m, 1H); 1.86-1.69 (m, 3H); 1.65-1.36 (m, 13H); 1.52 (s, 3H); 1.24 (t, J=7.2 Hz, 3H), 1.16-1.06 (m, 2H); 1.10 (s, 9H); 1.02-0.85 (m, 7H); 0.79-0.68 (m, 1H); 0.50 (br d, J=6.8 Hz, 1H).

Example 5

Preparation of (3aR,7S,10S,11S,12R,24aR)-7-tert-butyl-N-[(1R,2R)-1-[(cyclopropylsulfonyl)carbamoyl]-2-(difluoromethyl)cyclopropyl]-11-ethyl-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide

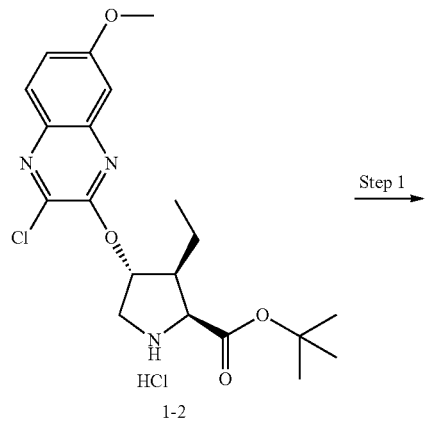

Step 1 →

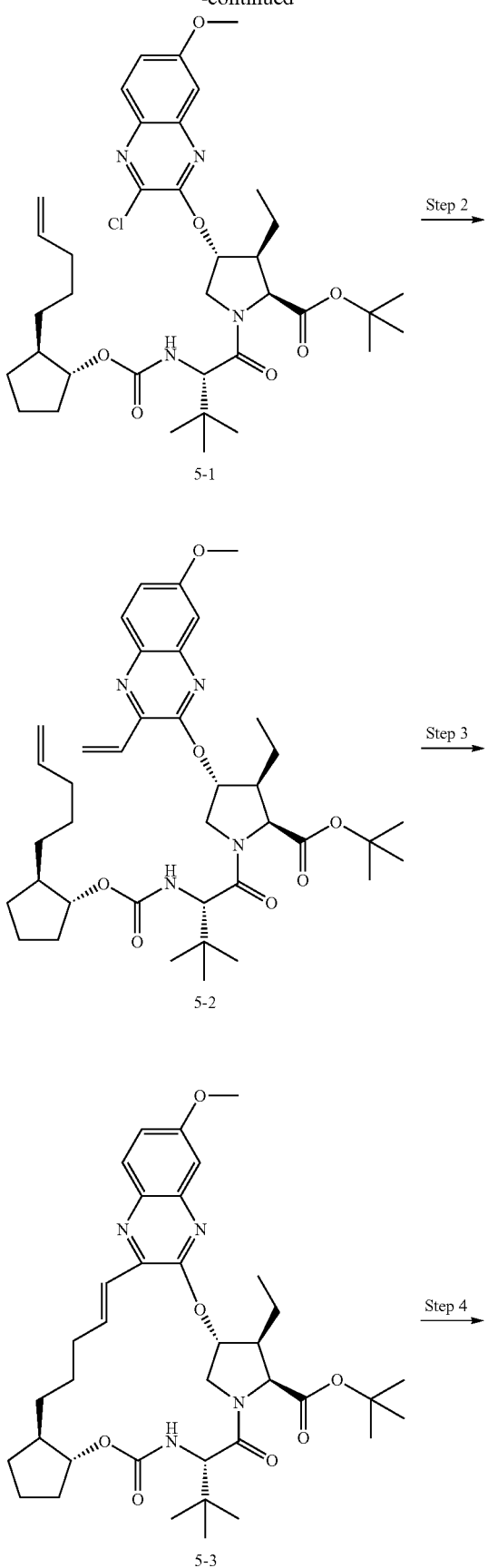

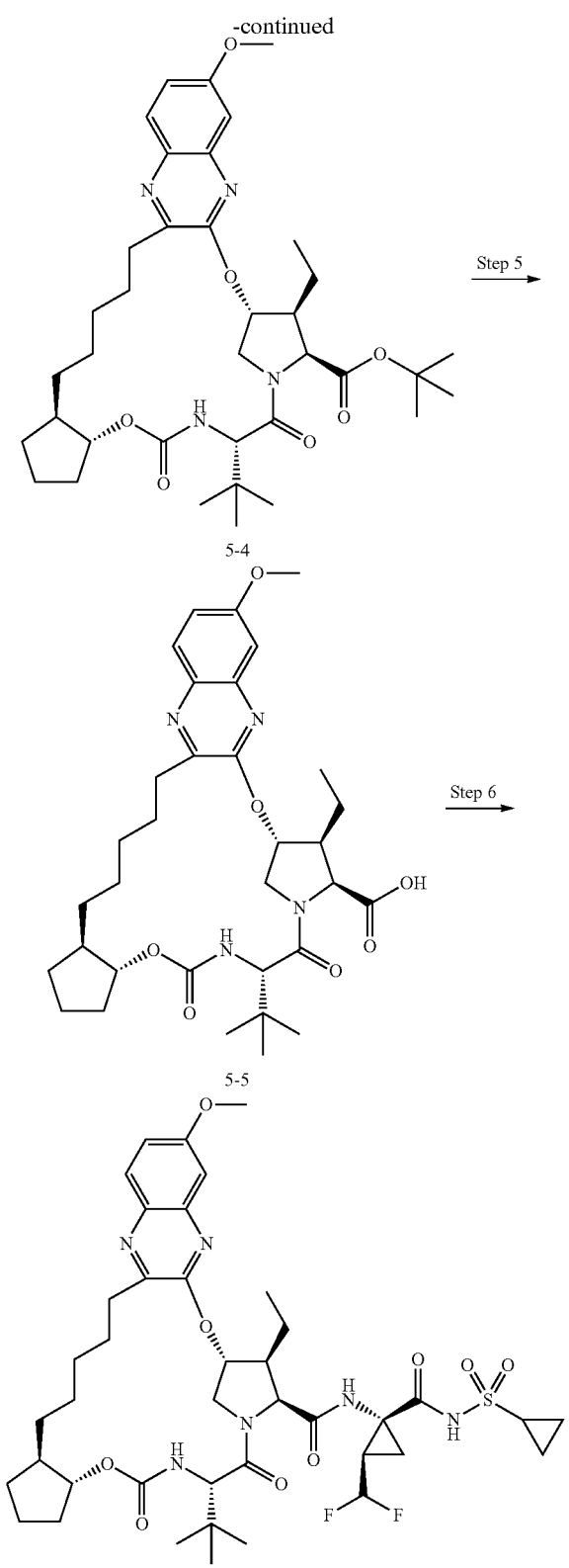

Step 1. Preparation of 5-1: HATU (555 mg, 1.46 mmol, Oakwood) and DIPEA (1.10 mL, 6.35 mmol) were added to a mixture of 1-2 (533 mg, 1.20 mmol) and Intermediate D5 (414 mg, 1.33 mmol) in 12 mL of DMF under argon. After stirring overnight, the reaction mixture was poured into water and extracted three times with ethyl acetate. Combined organics were washed with water and brine, dried (MgSO$_4$), filtered, and concentrated under reduced pressure. The resulting residue was purified by silica gel chromatography (0-35% ethyl acetate in hexanes) to yield 5-1 (713 mg) as a white solid. LCMS-ESI$^+$ (m/z): [M+H]$^+$ calcd for C$_{37}$H$_{54}$ClN$_4$O$_7$: 701.36; found: 701.58.

Step 2. Preparation of 5-2: Pd(dppf)Cl$_2$.CH$_2$Cl$_2$ (94 mg, 0.115 mmol, Strem) was added to a deoxygenated mixture of 5-1 (710 mg, 1.01 mmol), potassium vinyltrifluoroborate (213 mg, 1.59 mmol), and triethylamine (0.210 mL, 1.52 mmol) in 11 mL of EtOH at room temperature. Reaction mixture was heated at 78° C. under argon for one hour. After cooling to room temperature, reaction mixture was poured into water and extracted three times with ethyl acetate. Combined organics were washed with water and brine, dried (MgSO$_4$), filtered, and concentrated under reduced pressure to yield 5-2 (699 mg), which was used in the next step without further purification. LCMS-ESI$^+$ (m/z): [M+H]$^+$ calcd for C$_{39}$H$_{57}$N$_4$O$_7$: 693.41; found: 693.47.

Step 3. Preparation of 5-3: A mixture of 5-2 (699 mg, 1.01 mmol) and Zhan 1B catalyst (81 mg, 0.111 mmol, Strem) in 200 mL of DCE was deoxygenated under argon for 25 minutes. The mixture was then heated at 95° C. for 45 minutes. Reaction mixture was heated at 95° C. for 10 additional minutes, was cooled to room temperature, and then concentrated under reduced pressure. The resulting residue was purified by silica gel chromatography (0-30% ethyl acetate in hexanes) to yield 5-3 (336 mg) as a light brown solid. LCMS-ESI$^+$ (m/z): [M+H]$^+$ calcd for C$_{37}$H$_{53}$N$_4$O$_7$: 665.38; found: 665.53.

Step 4. Preparation of 5-4: Palladium on carbon (10 wt. % Pd, 102 mg, 0.096 mmol) was added to a solution of 5-3 (330 mg, 0.497 mmol) in 8 mL of ethanol and 3.5 mL of ethyl acetate. Mixture was stirred under an atmosphere of hydrogen for 100 minutes and was then filtered over Celite, washing with ethyl acetate. Filtrate was concentrated under reduced pressure to yield 5-4 (64 mg) as a light yellow-brown solid film, which was used in the next step without further purification. LCMS-ESI$^+$ (m/z): [M+H]$^+$ calcd for C$_{37}$H$_{55}$N$_4$O$_7$: 667.40; found: 667.52.

Step 5. Preparation of 5-5: TMSOTf (0.53 mL, 2.91 mmol) was added dropwise to a solution of 5-4 (329 mg, 0.494 mmol) in 10 mL of dichloromethane under argon at room temperature. After one hour, an additional 0.3 mL of TMSOTf was added. After an additional hour, reaction mixture was concentrated under reduced pressure. The resulting film was taken up in 12 mL of toluene and concentrated under reduced pressure. This process was repeated a second time to yield 5-5 (301 mg), which was used in the next step without further purification. LCMS-ESI$^+$ (m/z): [M+H]$^+$ calcd for C$_{33}$H$_{47}$N$_4$O$_7$: 611.34; found: 611.46.

Step 6. Preparation of Example 5: HATU (129 mg, 0.339 mmol) and DIPEA (0.22 mL, 1.27 mmol) were added to a mixture of 5-5 (134 mg, 0.22 mmol) and Intermediate A9 (95 mg, 0.328 mmol) in 6.6 mL of MeCN under argon. After stirring for 5 h, reaction mixture was poured into water and extracted three times with ethyl acetate. Combined organics were washed with water and brine, dried (MgSO$_4$), filtered, and concentrated under reduced pressure. The resulting residue was purified by reverse phase preparatory HPLC (15-100% acetonitrile in water, with 0.1% trifluoroacetic acid buffer) to yield Example 5 (43 mg) as a light yellow solid, trifluoroacetic acid salt, after lyophilization. Analytic HPLC RetTime: 9.11 min. LCMS-ESI$^+$ (m/z): [M+H]$^+$ calcd for C$_{41}$H$_{57}$F$_2$N$_6$O$_9$S: 847.38; found: 847.62. $^1$H NMR (400 MHz, CD$_3$OD): δ 9.31 (s, 1H), 7.80 (d, J=9.2 Hz, 1H), 7.23

(dd, J=15.4, 2.8 Hz, 1H), 7.19 (d, J=2.8 Hz, 1H), 5.87 (td, $J_{H-F}$=56 Hz, J=6 Hz, 1H), 5.87-5.83 (m, 1H), 4.59 (d, J=7.6 Hz, 1H), 4.38 (s, 1H), 4.23-4.14 (m, 2H), 3.93 (s, 3H), 3.06-2.94 (m, 2H), 2.77-2.67 (m, 1H), 2.65-2.58 (m, 1H), 2.07-2.01 (m, 2H), 1.98-1.74 (m, 4H), 1.72-1.52 (m, 4H), 1.50-1.20 (m, 12H), 1.18-1.02 (m, 8H), 1.06 (s, 9H).

Example 6

Preparation of (3aR,7S,10S,11S,12R,24aR)-7-tert-butyl-N-[(1R,2R)-2-(difluoromethyl)-1-{[(1-methyl-cyclopropyl)sulfonyl]carbamoyl}cyclopropyl]-11-ethyl-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide

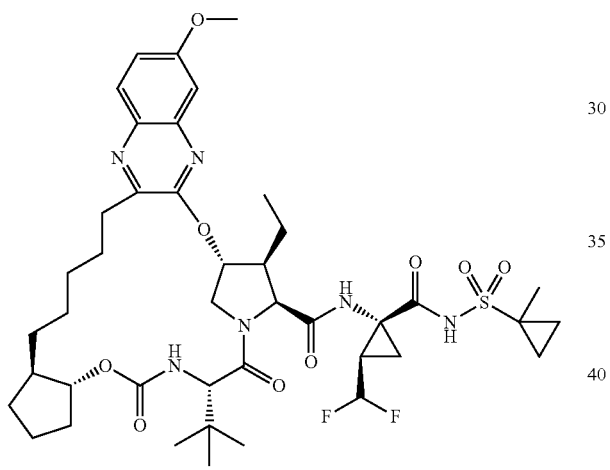

Example 6

Example 6 was prepared in a similar fashion to Example 5, substituting Intermediate A10 for Intermediate A9 in Step 6. Example 6 was isolated (29 mg) as a white solid. Analytic HPLC RetTime: 9.26 min. LCMS-ESI+ (m/z): [M+H]+ calcd for $C_{42}H_{59}F_2N_6O_9S$: 861.40; found: 861.20. $^1$H NMR (400 MHz, CDCl$_3$) δ 9.91 (s, 1H), 7.82 (d, J=12 Hz, 1H), 7.18 (d, J=12 Hz 1H), 7.13-7.06 (m, 1H), 6.48 (s, 1H), 5.95 (td, $J_{H-F}$=56 Hz. J=6 Hz, 1H), 5.82 (d, J=4.4 Hz, 1H), 5.33 (d, J=10 Hz, 1H), 4.95-4.91 (m, 1H), 4.38-4.31 (m, 2H), 4.10-3.88 (m, 2H), 3.98 (s, 3H), 2.98-2.89 (m, 1H), 2.67-2.59 (m, 1H), 2.05-1.65 (m, 4H), 1.64-1.21 (m, 12H), 1.40 (s, 3H), 1.17-0.80 (m, 12H), 1.09 (s, 9H).

Example 7

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-14-methoxy-1a-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

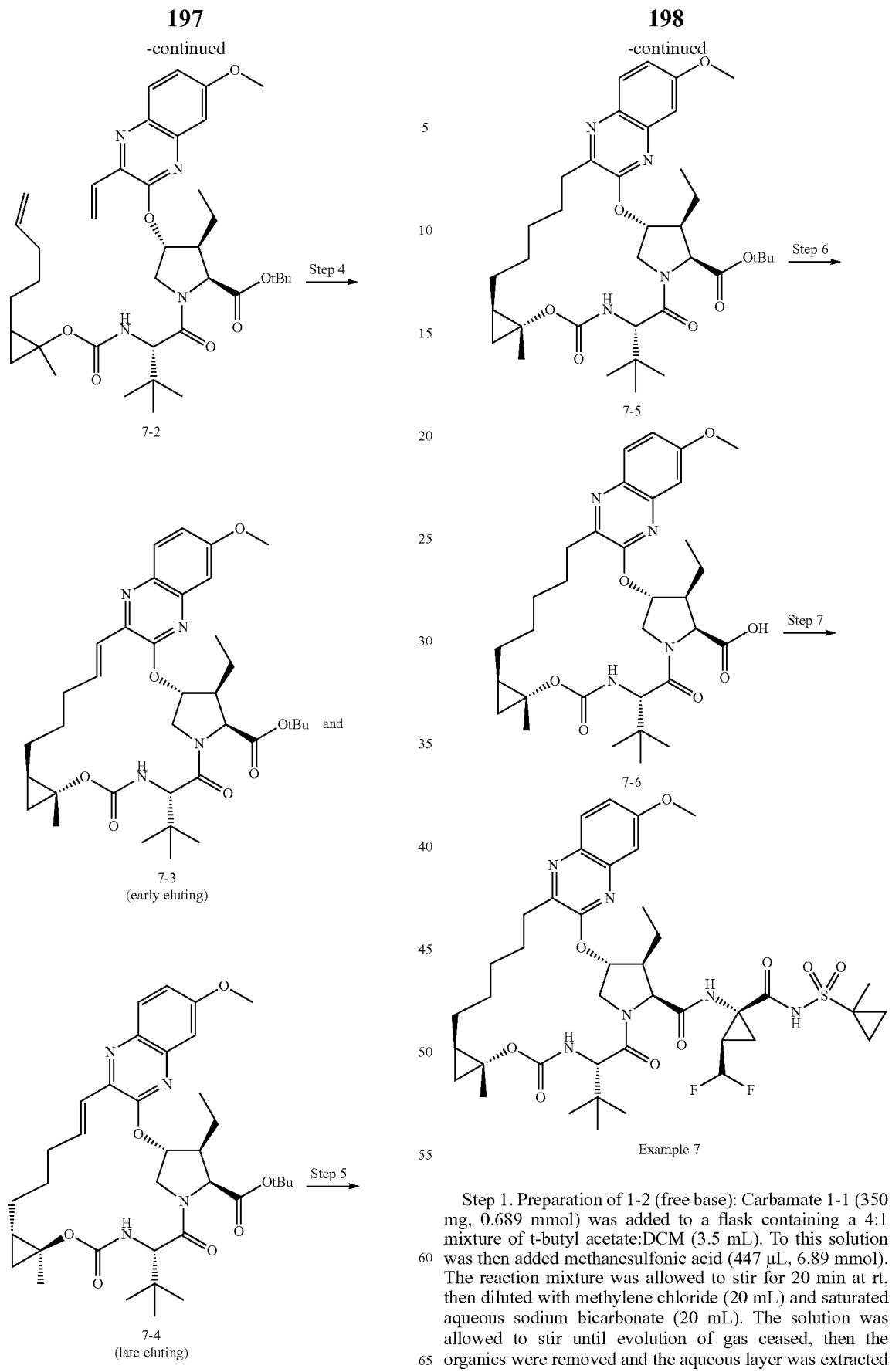

Step 1. Preparation of 1-2 (free base): Carbamate 1-1 (350 mg, 0.689 mmol) was added to a flask containing a 4:1 mixture of t-butyl acetate:DCM (3.5 mL). To this solution was then added methanesulfonic acid (447 μL, 6.89 mmol). The reaction mixture was allowed to stir for 20 min at rt, then diluted with methylene chloride (20 mL) and saturated aqueous sodium bicarbonate (20 mL). The solution was allowed to stir until evolution of gas ceased, then the organics were removed and the aqueous layer was extracted twice with methylene chloride (20 mL). The combined organics were then washed with brine, dried over Na$_2$SO$_4$, filtered, and concentrated in vacuo. The resulting white solid 1-2 (free base, 280 mg) was used in the subsequent reaction without further purification. LCMS-ESI⁺ (m/z): [M+H]⁺ calcd for $C_{20}H_{27}ClN_3O_4$: 408.2; found: 408.1.

Step 2. Preparation of mixture 7-1: Amine 1-2 (281 mg, 0.689 mmol) was combined with diastereomeric Intermediate mixture D6 (266 mg, 0.895 mmol), DIPEA (600 µL, 3.45 mmol) and DMF (2 mL). HATU (340 mg, 0.895 mmol) was then added to the reaction mixture, which was stirred at 40° C. for 5 h. Reaction mixture was then diluted with water (10 mL) and taken up into methylene chloride (10 mL). Organics were separated and aqueous layer was extracted once with methylene chloride (10 mL). Combined organics were then washed with brine, dried over MgSO₄, filtered, and concentrated in vacuo. Crude residue was then purified via silica gel chromatography to give 7-1 as a 1:1 diastereomeric mixture (280 mg). LCMS-ESI⁺ (m/z): [M+H]⁺ calcd for $C_{36}H_{52}ClN_4O_7$: 687.4; found: 687.3.

Step 3. Preparation of 7-2: Pd(dppf)Cl₂ (29 mg, 0.0407 mmol) was added to a degassed mixture of 7-1 (280 mg, 0.407 mmol), potassium vinyltrifluoroborate (55 mg, 0.733 mmol), and triethylamine (91 µL, 0.651 mmol) in 2 mL of ethanol at room temperature. Reaction mixture was heated at 80° C. under N₂ for one hour. After cooling to room temperature, reaction mixture was diluted with toluene (10 mL), concentrated in vacuo to a small volume of solvent, and rediluted in toluene (1 mL). Mixture was then loaded directly onto a silica column and purified by silica gel chromatography to afford 7-2 as a 1:1 diastereomeric mixture which was carried on to the next step without concentrating fully to dryness. LCMS-ESI⁺ (m/z): [M+H]⁺ calcd for $C_{38}H_{55}N_4O_7$: 679.4; found: 679.4.

Step 4. Preparation of 7-3 and 7-4: Diastereomeric mixture 7-2 (276 mg, 0.407 mmol) and Zhan 1B catalyst (32 mg, 0.0407 mmol, Strem) were dissolved in 80 mL of DCE and degassed under N₂ for 25 minutes. The mixture was then heated to 100° C. for 1 h. Reaction was then cooled to room temperature and concentrated in vacuo. The resulting residue was purified via silica gel chromatography (0% to 30% ethyl acetate in hexanes) to yield single diastereomers 7-3 (20 mg, early eluting fraction) and 7-4 (25 mg, late eluting fraction) as light brown residues. Early eluting fraction: LCMS-ESI⁺ (m/z): [M+H]⁺ calcd for $C_{36}H_{55}N_4O_7$: 651.4; found: 651.3. Late eluting fraction: LCMS-ESI⁺ (m/z): [M+H]⁺ calcd for $C_{36}H_{51}N_4O_7$: 651.4; found: 651.3.

Step 5. Preparation of 7-5: Palladium on carbon (10% w/w, 25 mg) was added to a solution of 7-3 (20 mg, 0.0307 mmol) in a 1:1 mixture of ethyl acetate and dioxane (2 mL). Mixture was stirred under an atmosphere of hydrogen for 30 min and was then filtered through a plug of Celite, and washed with ethyl acetate. Filtrate was concentrated under reduced pressure to yield 7-5 (16 mg) as a light brown film, which was used in the next step without further purification. LCMS-ESI⁺ (m/z): [M+H]⁺ calcd for $C_{36}H_{53}N_4O_7$: 653.4; found: 653.4.

Step 6. Preparation of 7-6: Intermediate 7-5 (16 mg, 0.023 mmol) was dissolved in 2 M HCl in dioxane (2 mL) and heated at 80° C. for 1.5 h via microwave reactor. Reaction mixture was then concentrated in vacuo to give 7-6 (15 mg) as a brown residue, which was used in the subsequent step without further purification. LCMS-ESI⁺ (m/z): [M+H]⁺ calcd for $C_{32}H_{44}N_4O_7$: 597.3; found: 597.3.

Step 7. Preparation of Example 7: HATU (11.9 mg, 0.031 mmol) and DIPEA (22 µL, 0.126 mmol) were added to a mixture of 7-6 (15 mg, 0.025 mmol) and A10 (11.5 mg, 0.0377 mmol) in 1 mL of DMF. After stirring overnight at room temperature, reaction mixture was poured into water, acidified to pH 1 with 1 N aqueous HCl, and extracted three times with methylene chloride (15 mL). Combined organics were washed with water, brine, dried over MgSO₄, filtered, and concentrated under reduced pressure. The resulting residue was purified by reverse phase prep HPLC (5-100% acetonitrile in water, with 0.1% trifluoroacetic acid buffer) followed by silica gel chromatography to afford Example 7 (4.3 mg) as a white solid film. Analytic HPLC RetTime: 9.07 min. LCMS-ESI⁺ (m/z): [M+H]⁺ calcd for $C_{41}H_{57}F_2N_6O_9S$: 847.4; found: 847.4. ¹H NMR (400 MHz, CDCl₃) δ 9.88 (s, 1H), 7.83 (d, J=9.1 Hz, 1H), 7.20 (dd, J=9.1 Hz, 2.8 Hz, 1H), 7.07 (d, J=2.7 Hz, 1H), 6.56 (s, 1H), 5.98 (td. $J_{H\text{-}F}$=55.7, J=6.7 Hz, 1H), 5.95 (d, J=9.6, 1H), 5.32 (d, J=9.6 Hz, 1H), 4.45 (dd, J=13.0 Hz, 9.6 Hz, 2H), 4.32 (d, J=9.7 Hz, 1H), 4.13 (dd, J=15.5 Hz, 8.8 Hz, 1H), 3.93 (s, 3H), 2.99-2.84 (m, 1H), 2.82-2.68 (m, 1H), 2.62-2.47 (m 1H), 2.16-2.02 (m, 1H) 2.00-1.85 (m, 1H) 1.84-1.69 (m, 1H); 1.70-1.15 (m, 11H), 1.52 (s, 3H), 1.50 (s, 3H), 1.20 (t, J=7.3 Hz, 3H), 1.14-0.77 (m, 5H) 1.09 (s, 9H), 0.11 (m, 1H).

Example 8

Preparation of (1aS,5S,8S,9S,10R,22aS)-5-tert-butyl-N-[(1R,2R)-2-(difluoromethyl)-1-{[(1-methylcyclopropyl)sulfonyl]carbamoyl}cyclopropyl]-9-ethyl-14-methoxy-1a-methyl-3,6-dioxo-1,1a,3,4,5,6,9,10, 18,19,20,21,22,22a-tetradecahydro-8H-7,10-methanocyclopropa[18,19][1,10,3,6] dioxadiazacyclononadecino[11,12-b]quinoxaline-8-carboxamide Example 8

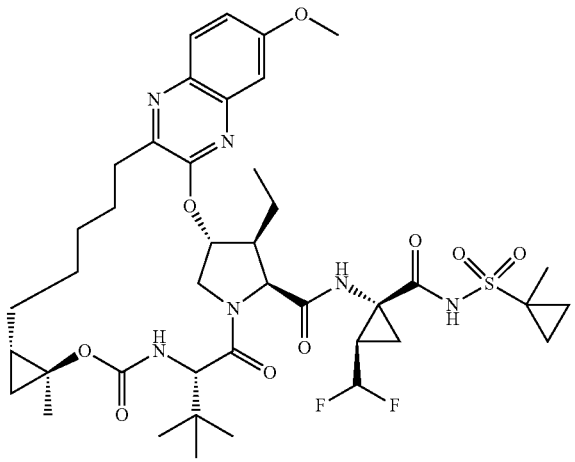

Example 8 was prepared in a similar fashion to Example 7, substituting late eluting 7-4 for early eluting 7-3 in Step 5. Example 7 was isolated (2.9 mg) as a white solid. Analytic HPLC RetTime: 9.09 min. LCMS-ESI⁺ (m/z): [M+H]⁺ calcd for $C_{41}H_7F_2N_6O_9S$: 847.4; found: 847.4.

Examples 9 and 10

Preparation of (7S,10S,11S,12R)-7-tert-butyl-N-[(1R,2R)-2-(difluoromethyl)-1-{[(1-methylcyclopropyl)sulfonyl]carbamoyl}cyclopropyl]-11-ethyl-16-methoxy-5,8-dioxo-3aR-(trifluoromethyl)-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide and (7S,10S,11S,12R)-7-tert-butyl-N-[(1R,2R)-2-(difluoromethyl)-1-{[(1-methylcyclopropyl)sulfonyl]carbamoyl}cyclopropyl]-11-ethyl-16-methoxy-5,8-dioxo-3aS-(trifluoromethyl)-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide.

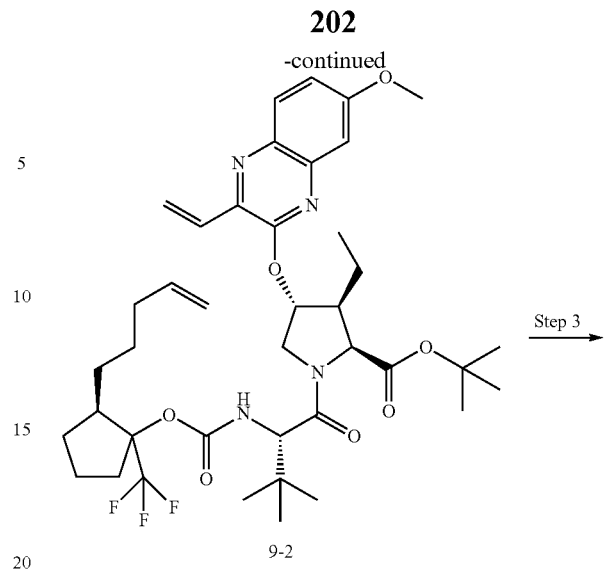

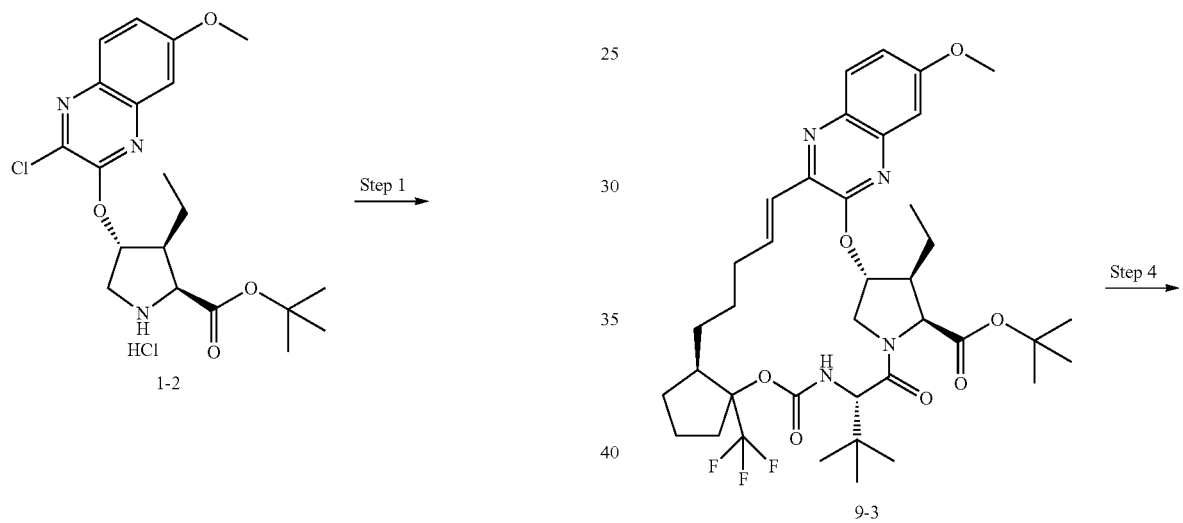

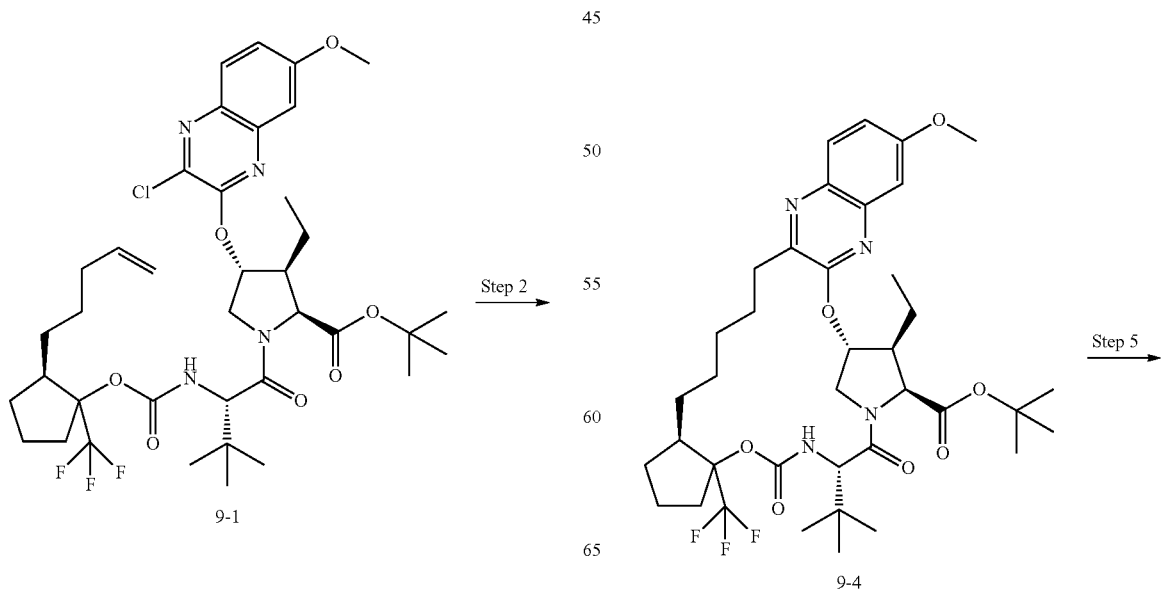

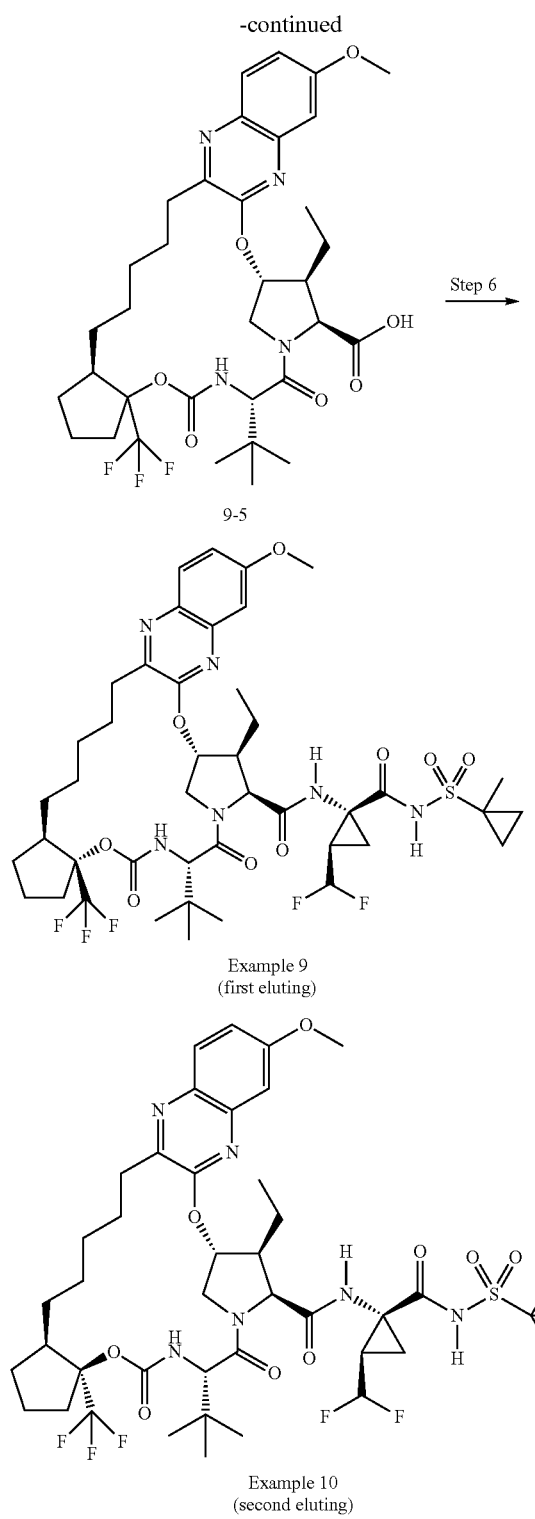

9-5

Example 9
(first eluting)

Example 10
(second eluting)

Step 1. Preparation of 9-1: To a solution of Intermediate D8 (322 mg, 0.85 mmol) and 1-2 (316 mg, 0.78 mmol) in MeCN (3.9 mL) was added HATU (323 mg, 0.85 mmol) followed by DIPEA (678 µL, 390 mmol) at rt under an argon atmosphere. After 2 h, the reaction mixture was allowed to coo to re was concentrated in vacuo, and the crude residue was purified by silica gel chromatography (0-100% ethyl acetate/hexanes gradient) to afford amide 9-1 (476 mg, 1:1 diastereomeric mixture) as a colorless oil. LCMS-ESI$^+$ (m/z): [M+H]$^+$ calcd for $C_{38}H_{53}ClF_3N_4O_7$: 769.4; found: 769.5.

Step 2. Preparation of 9-2. To a solution of 9-1 (470 mg, 612 µmol) in TEA (128 µL, 918 µmol), and potassium vinyltrifluoroborate (123 mg, 918 µmol) in EtOH (3.06 mL) was added PdCl2(dppf) (50 mg, 61 µmol). The reaction mixture was deoxygenated with argon for 10 min and heated to 78° C. After 1 h. the reaction mixture was allowed to cool to rt and was concentrated in vacuo. The crude residue was purified by silica gel chromatography (0-100% ethyl acetate/hexanes gradient) to afford vinyl quinoxaline 9-2 (329 mg, 1:1diasteromeric mixture) as a yellow oil. LCMS-ESI$^+$ (m/z): [M+H]$^+$ calcd for $C_{40}H_{56}F_3N_4O_7$: 761.4; found: 761.6.

Step 3. Preparation of 9-3: To a solution of 9-2 (329 mg, 485 µmol) in DCE (97 mL) was added Zhan 1B catalyst (35 mg, 49 µmol, Strem) and the reaction mixture was deoxygenated for 10 minutes with argon. The reaction mixture was then heated to 100° C. After 30 min, the reaction mixture was allowed to cool to rt and was concentrated in vacuo. The crude residue was purified by silica gel chromatography (0-100% ethyl acetate/hexanes gradient) to afford macrocycle 9-3 (301 mg, 7:4 diastereomeric mixtures) as a light yellow oil. LCMS-ESI$^+$ (m/z): [M+H]$^+$ calcd for $C_{38}H_{52}F_3N_4O_7$: 733.4; found: 733.5.

Step 4. Preparation of 9-4: To a solution of 9-3 (300 mg, 410 µmol) in ethanol (2.00 mL) was added Pd/C (10 wt % Pd, 43 mg, 41 µmol) at rt under an argon atmosphere. The atmosphere of the reaction was replaced with hydrogen gas and the reaction mixture stirred vigorously at rt After 30 min, the reaction mixture was diluted with ethyl acetate (10 mL) and filtered through a pad of Celite with ethyl acetate washings (3×5 mL). The filtrate was concentrated in vacuo to afford macrocycle 9-4 (295 mg, 7:4 diastereomeric mixture), which was used directly in the next step without further purification. LCMS-ESI$^+$ (m/z): [M+H]$^+$ calcd for $C_{38}H_{54}F_3N_4O_7$: 735.4; found: 735.5.

Step 5. Preparation of 9-5: To a solution of 9-4 (295 mg, 401 µmol) in DCM (2 mL) was added TMSOTf (72.6 µL, 401 mmol) at rt under an argon atmosphere. After 1.5 h, additional TMSOTf (362.9 µL, 2.00 mmol) was added. After 1 h, additional TMSOTf (362.9 µL, 2.00 mmol) was added. After 2 h, the reaction mixture was added slowly to a 0.25 N aqueous NaOH solution (precooled to 0° C., 3 mL). The resulting mixture was diluted with 1 N aqueous HCl solution (5 mL), and was extracted with DCM (3×5 mL). The combined organic extracts were dried over anhydrous sodium sulfate and were concentrated to afford carboxylic acid 9-5 (353 mg, 7:4 diastereomeric mixture) as a tan solid, which was used directly in the next step without further purification. LCMS-ESI$^+$ (m/z): [M+H]$^+$ calcd for $C_{34}H_{45}F_3N_4O_7$: 679.3; found: 679.5.

Step 6. Preparation of Example 9 and Example 10: To a solution of acid 9-5 (150 mg, 220 µmol) and Intermediate A10 (101 mg, 330 µmol) in MeCN (1.1 mL) was added HATU (127 mg, 330 µmol) followed by DIPEA (191 µL, 1.10 mmol) at rt under an argon atmosphere. After 1 h, the reaction mixture was concentrated in vacuo, and the crude residue was purified by silica gel chromatography (0-100% ethyl acetate/hexanes gradient). The fractions containing the desired product were combined and were repurified by silica gel chromatography (0-50% acetone/hexanes gradient) to afford the first eluting Example 9 (40 mg) as a white powder and the second eluting Example 10 (70 mg) as a white powder First eluting Example 9: Analytic HPLC RetTime: 9.42 min. LCMS-ESI$^+$ (m/z): [M+H]+ calcd for $C_{43}H_{58}F_5N_6O_9S$: 929.4; found: 929.5. $^1$H NMR (400 MHz, CDCl$_3$) δ 9.83 (s, 1H), 7.92 (d, J=9.1 Hz, 1H), 7.19 (dd, J=9.0, 2.6 Hz, 1H), 7.13 (d, J=2.6 Hz, 1H), 5.99 (br s, 1H), 5.96 (td, $J_{H-F}$ 55.5, J=6.6 Hz, 1H), 5.70 (d, J=10.0 Hz, 1H), 4.63 (d, J=6.6 Hz, 1H), 4.38 (d, J=10.0 Hz, 1H), 4.22-4.04 (m, 2H), 3.96 (s, 3H), 3.12-2.89 (m, 1H), 2.71-2.51 (m, 2H), 2.17 (s, 3H), 2.15-1.82 (m, 4H), 1.83-1.34 (m, 8H), 1.36-0.98 (m, 12H), 1.26 (s, 9H), 0.92-0.79 (m, 4H). Second eluting Example 10: Analytic HPLC RetTime: 9.55 min. LCMS-ESI+ (m/z): [M+H]+ calcd for $C_{43}H_{58}F_5N_6O_9S$: 929.4; found: 929.5. $^1$H NMR (400 MHz, CDCl$_3$) δ 9.61 (s, 1H), 7.91 (d, J=9.1 Hz, 1H), 7.23 (dd, J=9.0, 3.0 Hz, 1H), 7.18 (d, J=2.7 Hz, 1H), 5.98-5.91 (m, 1H), 5.83 (td, $J_{H-F}$ 55.5, J=6.6 Hz, 1H), 5.33 (d, J=9.8 Hz, 1H), 4.72-4.63 (m, 1H), 4.46-4.38 (m, 1H), 4.32 (d, J=10.0 Hz, 1H), 4.25-4.14 (m, 1H), 3.97 (s, 3H), 3.73 (br d, J=7.6 Hz, 1H), 3.23-3.07 (m, 1H), 2.86-2.37 (m, 2H), 2.14-1.79 (m, 2H), 1.78-1.38 (m, 8H), 1.51 (s, 3H), 1.35-1.08 (m, 8H), 1.25 (s, 9H), 1.05 (br s, 3H), 0.93-0.68 (m, 6H).

Examples 11 and 12

Preparation of (7S,10S,11S,12R)-7-tert-butyl-N-[(1R,2R)-1-[(cyclopropylsulfonyl)carbamoyl]-2-(difluoromethyl)cyclopropyl]-1-ethyl-16-methoxy-5,8-dioxo-3aR-(trifluoromethyl)-1,2,3,3a,5,6,7,8,11,12,20,21,22,23,24,24a-hexadecahydro-1OH-9,12-methanocyclopenta[18,19][1,10,3,6]dioxadiazacyclononadecino[11,12-b]quinoxaline-10-carboxamide and (7S,10S,11S,12R)-7-tert-butyl-N-[(1R,2R)-1-[(cyclopropylsulfonyl)carbamoyl]-2-(difluoromethyl)cyclopropyl]-11-ethyl-16-methoxy-5,8-dioxo-3aS-(trifluoromethyl)-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide Example 11

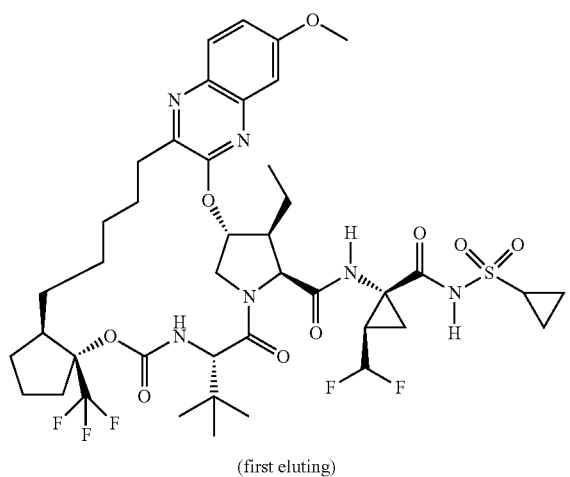

(first eluting)

Example 12

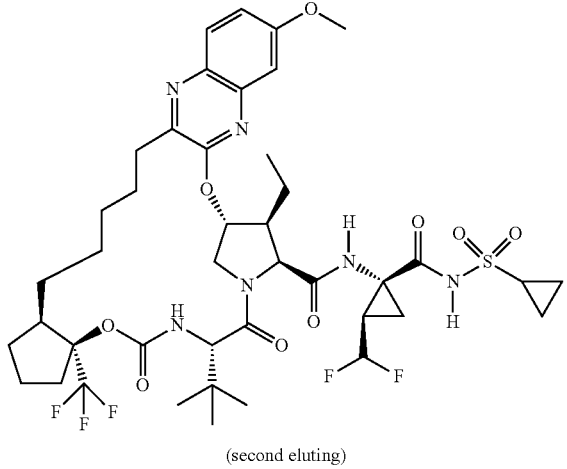

(second eluting)

Preparation of Example 11 and Example 12: To a solution of acid 9-5 (150 mg, 220 μmol) and Intermediate A9 (96 mg, 330 μmol) in MeCN (1.1 mL) was added HATU (127 mg, 330 μmol) followed by DIPEA (191 μL, 1.10 mmol) at rt under an argon atmosphere. After 1 h, the reaction mixture was concentrated in vacuo, and the crude residue was purified by silica gel chromatography (0-50% acetone/hexanes gradient). The fractions containing the desired product were combined and were repurified by silica gel chromatography (0-50% acetone/hexanes gradient) to afford the first eluting Example 11 (29 mg) as a white powder and the second eluting Example 12 (60.2 mg) as a white powder, First eluting Example 11: Analytic HPLC RetTime 9.44 min. LCMS-ESI+ (m/z): [M+H]+ calcd $C_{42}H_{56}F_5N_6O_9S$: 915.4; found: 915.6. $^1$H NMR (400 MHz, CDCl$_3$) δ 10.17 (br s, 1H), 7.83 (d, J=9.1 Hz, 1H), 7.21 (dd, J=9.1, 2.7 Hz, 1H), 7.17-7.07 (m, 1H), 5.99 (br s, 1H), 5.97 (td, $J_{H-F}$ 55.5, J=6.6 Hz, 1H), 5.82 (d, J=9.8 Hz, 1H), 4.55 (d, J=7.2 Hz, 1H), 4.39 (d, J=10.0 Hz, 1H), 4.20-4.03 (m, 2H), 3.95 (s, J=5.9 Hz, 3H), 2.97-2.82 (m, 2H), 2.79-2.49 (m, 3H), 2.24-1.81 (m, 8H), 1.80-1.11 (m, 12H), 1.10-0.98 (m, 4H), 1.07 (s, 9H), 0.95-0.81 (m, 3H). Second eluting Example 12: Analytic HPLC RetTime: 9.48 min. LCMS-ESI+ (m/z): [M+H]+ calcd $C_{42}H_{56}F_5N_6O_9S$: 915.4; found: 915.6. $^1$H NMR (400 MHz, CDCl$_3$) δ 10.07 (s, 1H), 7.93 (d, J=9.6 Hz, 1H), 7.28-7.20 (m, 1H), 7.16 (s, 1H), 6.17-5.68 (m, 3H), 4.67-4.55 (m, 1H), 4.37-4.23 (m, 2H), 4.17-4.05 (m, 1H), 3.97 (s, 3H), 3.75-3.66 (m, 1H), 3.22-3.04 (m, 1H), 3.02-2.31 (m, 6H), 2.30-1.83 (m, 10H), 1.85-1.13 (m, 13H), 1.06 (s, 9H), 0.95-0.79 (m, 1H).

Example 13
Preparation of (1R,4S,4aR,8S,11S,12S,13R,25aR)-8-tert-butyl-N-[(1R,2R)-1-[(cyclopropylsulfonyl)carbamoyl]-2-(difluoromethyl)cyclopropyl]-12-ethyl-17-methoxy-6,9-dioxo-2,3,4,4a,6,7,8,9,12,13,21,22,23,24,25,25a-hexadecahydro-1H,11H-1,4:10,13-dimethanoquinoxalino[2,3-k][1,10,3,6]benzodioxadiazacyclononadecine-11-carboxamide
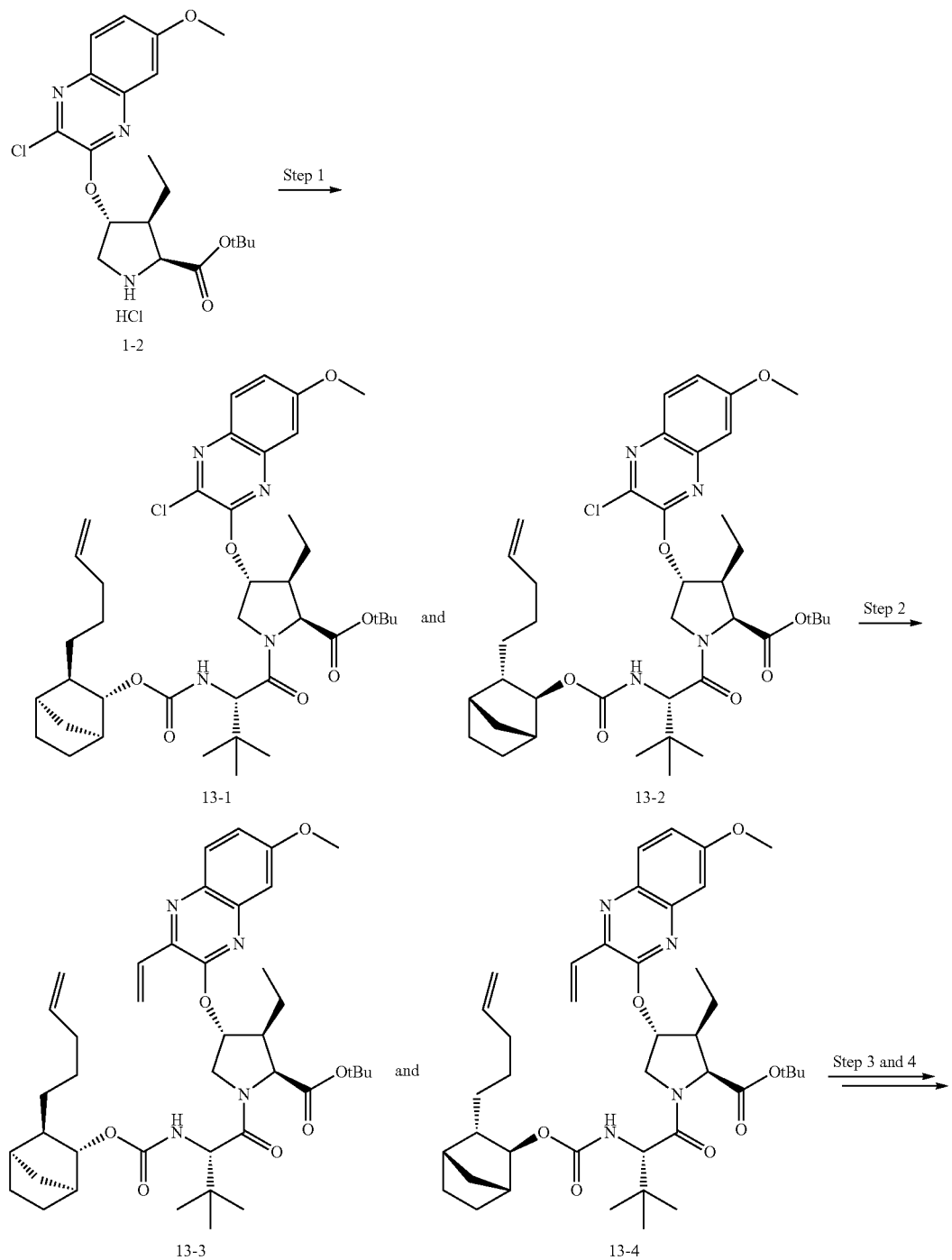

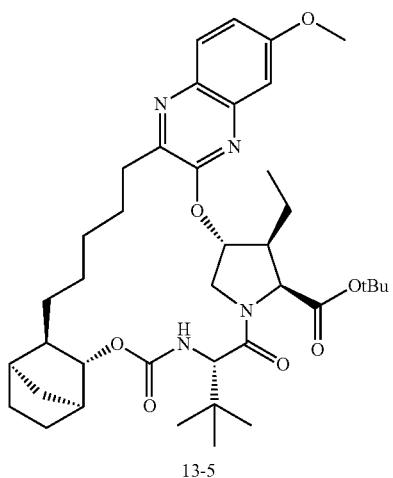

13-5

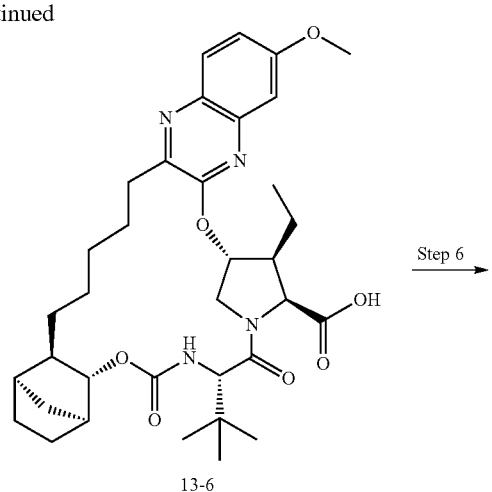

13-6

Step 5 → Step 6 →

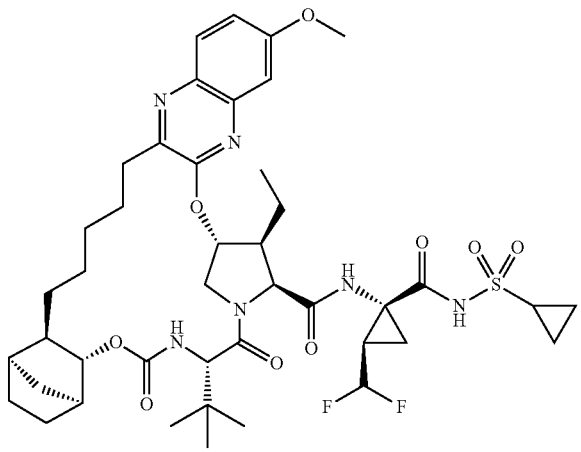

Example 13

Step 1. Preparation of diastereomer mixture 13-1 and 13-2: To a solution of 1-2 (354 mg, 0.87 mmol), Intermediate mixture D9 and D10 (323 mg, 0.96 mmol) and BEP (263 mg, 0.96 mmol; TCI America) was added DIPEA (0.45 mL, 2.61 mmol) and the reaction was stirred at 50° C. for 2 h. The reaction was quenched with sat. aqueous NaHCO₃ solution and extracted with EtOAc, the organic phase was washed with brine, dried over magnesium sulfate and concentrated. The crude product was purified by silica gel chromatography (0-30% EtOAc/hexanes) to yield an inseparable mixture of diastereomers 13-1 and 13-2 (338 mg). LCMS-ESI⁺ (m/z): [M+H]⁺ calcd for $C_{39}H_{56}ClN_4O_7$: 727.38, found: 727.46.

Step 2. Preparation of diastereomer mixture 13-3 and 13-4: To a solution of the mixture of 13-1 and 13-2 (338 mg, 0.46 mmol), TEA (0.10 mL, 0.69 mmol) and potassium vinyltrifluoroborate (93 mg, 0.69 mmol) in EtOH (30 mL) was added PdCl₂(dppf) (38 mg, 0.046 mmol, Strem Chemicals). The reaction was deoxygenated with N₂ for 10 min and heated to 80° C. for 1 h. The reaction was quenched with sat. aqueous NaHCO₃ solution and extracted with EtOAc, washed subsequently with brine, dried over magnesium sulfate and concentrated. The residue was purified using silica gel chromatography to give an inseparable mixture of diastereomers 13-3 and 13-4 (285 mg). LCMS-ESI + (m/z): [M+H]+ calcd for $C_{41}H_{59}N_4O_7$: 719.44; found: 719.70.

Step 3 and 4. Preparation of 13-5: To a solution of the diastereomeric mixture 13-3 and 13-4 (285 mg, 0.40 mmol) in DCE (100 mL) was added Zhan 1B catalyst (30 mg, 0.04 mmol, Strem) and the reaction was deoxygenated for 30 minutes with N₂. The reaction was heated to 100° C. for 45 min, allowed to cool to rt and concentrated. The crude product was purified by silica gel chromatography to produce macrocyclic olefin product (125 mg; LCMS-ESI⁺ (m/z): [M+H]⁺ calcd for $C_{39}H_{55}N_4O_7$: 691.41; found: 691.58) that was taken up in EtOH (6 mL) and treated with Pd/C (10%, 120 mg). The atmosphere was replaced with hydrogen and stirred at rt for 1.5 h. The reaction was filtered over Celite, washed with EtOAc and concentrated to give 13-5 as an oil (125 mg) that was used subsequently without further purification. LCMS-ESI⁺ (m/z): [M+H]⁺ calcd for $C_{39}H_{57}N_4O_7$: 693.42; found: 693.46.

Step 5. Preparation of 13-6: To a solution of 13-5 (50 mg, 0.072 mmol) in DCM (4 mL) was added TFA (1 mL) and stirred at rt for 6 h. The reaction was diluted with EtOAc, washed with H₂O, aqueous pH 7 buffer, dried over magnesium sulfate, and concentrated to give 13-6 as a residue that was used subsequently without further purification. LCMS-ESI⁺ (m/z): [M+H]⁺ calcd for $C_{35}H_{49}N_4O_7$: 637.36; found: 637.40.

Step 6. Preparation of Example 13: To a solution of 13-6 (46 mg, 0.072 mmol), Intermediate A9 (28 mg, 0.11 mmol), TBTU (34 mg, 0.10 mmol) and DMAP (13 mg, 0.11 mmol) in DCM (5 mL) was added DIPEA (0.038 mL, 0.22 mmol) and the reaction was stirred at rt for 16 h. The reaction was quenched with water, diluted with EtOAc, washed with sat. aqueous NaHCO₃, brine, dried over magnesium sulfate, and concentrated. The crude material was purified by reverse phase HPLC (Gemini, 30-85% MeCN/H₂O+0.1% TFA) and lyophilized to give Example 13 (14.5 mg) as a TFA salt. Analytic HPLC RetTime: 9.39 min. LCMS-ESI⁺ (m/z): [M+H]⁺ calcd for $C_{43}H_{59}F_2N_6O_9S$: 873.40; found: 873.42. ¹H NMR (400 MHz, CD₃OD) δ 9.28 (s, 1H), 7.82 (d, J=9.2 Hz, 1H), 7.26 (dd, J=6.4, 2.8 Hz, 1H), 7.19 (d, J=2.8 Hz, 1H), 6.04-5.74 (m, 2H), 5.50 (s, 1H), 4.55 (d, J=7.6 Hz, 1H), 4.47 (s, 1H), 4.26-4.16 (m, 2H), 3.94 (s, 3H), 3.03-2.95 (m, 2H), 2.78-2.66 (m, 2H), 2.17 (br, 2H), 2.05 (s, 3H), 1.90-1.85 (m, 1H), 1.76-1.74 (m, 2H), 1.61-1.21 (m, 20H), 1.15-1.11 (m, 2H), 1.08 (s, 9H), 0.93-0.90 (m, 1H).

Example 14

Preparation of (1aR,5S,8S,9S,10R,22aR)-5-cyclopentyl-N-[(1R,2R)-2-(difluoromethyl)-1-{[(1-methylcyclopropyl)sulfonyl]carbamoyl}cyclopropyl]-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

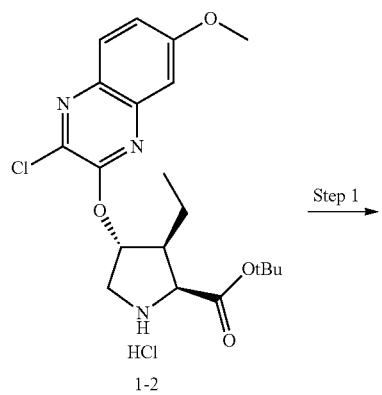

1-2

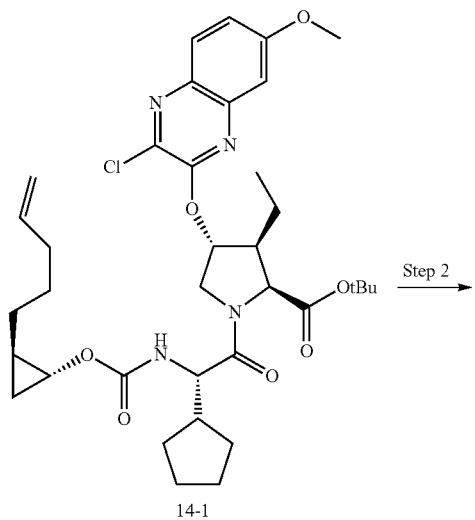

14-1

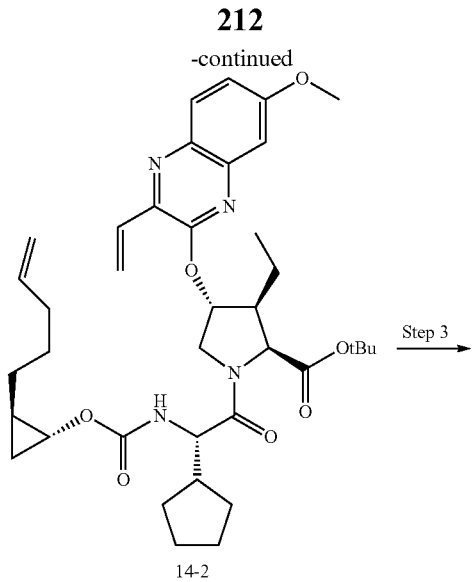

14-2

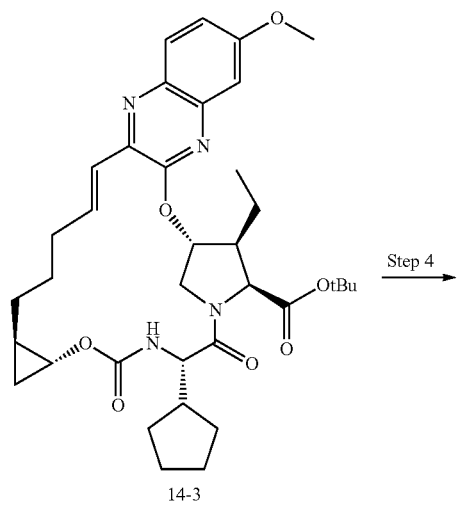

14-3

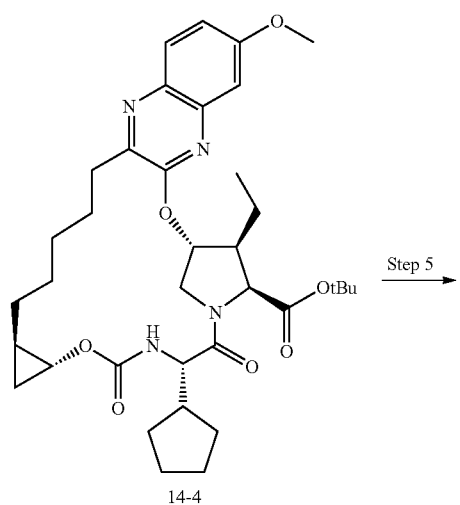

14-4

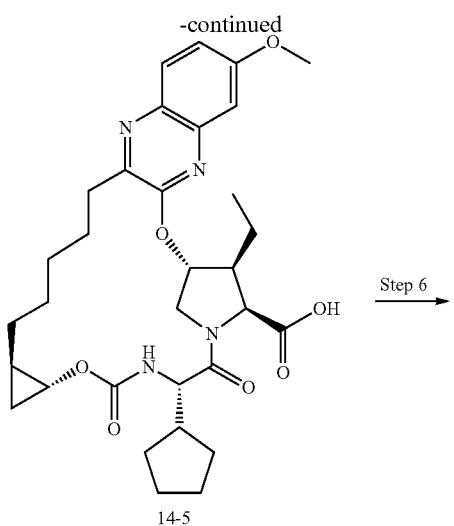

14-5

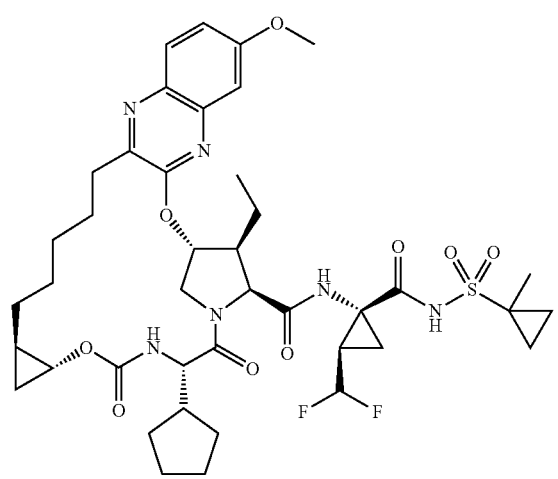

Example 14

Step 1. Preparation of 14-1: To a solution of 1-2 (223 mg, 0.50 mmol) and Intermediate D2 (221 mg, 0.75 mmol) in acetonitrile (5 mL) was added HATU (306 mg, 0.80 mmol) followed by DIPEA (0.43 mL, 2.5 mmol) at room temperature. After 19 h, solvent was removed under reduced pressure and the resulting residue was diluted with ethyl acetate (15 mL). The resulting solution was washed with 1 M aqueous HCl (10 mL). The aqueous layer was extracted with ethyl acetate (2×10 mL) and combined organic layer was washed with brine (15 mL), dried over anhydrous magnesium sulfate and concentrated. The resulting crude residue was purified via silica gel chromatography (0-100% ethyl acetate/hexanes gradient) to afford 14-1 (173 mg) as colorless oil. LCMS-ESI$^+$ (m/z): [M+H]$^+$ calcd for $C_{36}H_{50}ClN_4O_7$: 685.33; found: 685.49.

Step 2. Preparation of 14-2: To a solution of 14-1 (173 mg, 0.25 mmol) in EtOH (3 mL) was added potassium vinyltrifluoroborate (51 mg, 0.38 mmol), PdCl$_2$(dppf) (21 mg, 0.025 mmol) and TEA (0.053 mL, 0.38 mmol) sequentially and the resulting mixture was heated to 80° C. After 1 h, additional potassium vinyltrifluoroborate (17 mg, 0.12 mmol) was added and continued stirring at 80° C. After 2.5 h, additional potassium vinyltrifluoroborate (8 mg, 0.06 mmol) was added and the reaction was stirred for additional 10 minutes at 80° C. The reaction was cooled to room temperature, diluted with ethyl acetate (20 mL), and washed with brine (20 mL). Aqueous layer was extracted with ethyl acetate (10 mL), and the combined organic layer was dried over anhydrous magnesium sulfate and concentrated to afford 14-2 as a residue which was used it without purification in the next step. LCMS-ESI$^+$ (m/z): [M+H]$^+$ calcd for $C_{38}H_{53}N_4O_7$: 677.38; found 677.50.

Step 3. Preparation of 14-3: To a solution of 14-2 in deoxygenated DCE (0.006 M) was added Zhan 1B catalyst (18 mg, 0.025 mmol, Strem) and the reaction was deoxygenated for another 10 minutes with Ar. The reaction was heated to 100° C. After 1.5 h, Zhan 1B catalyst (9 mg, 0.012 mmol) was added and the reaction was stirred for another 30 min. The reaction mixture was allowed to cool to rt and concentrated to 4-5 mL volume. This was directly purified by silica gel chromatography to afford 14-3 as a brown oil (70 mg). LCMS-ESI$^+$ (m/z): [M+H]$^+$ calcd for $C_{36}H_{49}N_4O_7$: 649.35, found: 649.50.

Step 4. Preparation of 14-4: To a solution of 14-3 (70 mg, 0.11 mmol) in EtOH (5 mL) was added Pd/C (10 wt % Pd, 12 mg) under argon. The atmosphere was replaced with hydrogen and the reaction was stirred at rt for 16 h. The reaction was filtered over Celite, washed with EtOH and concentrated to give 14-4 as a brown oil that was used subsequently without further purification. LCMS-ESI$^+$ (m/z): [M+H]$^+$ calcd for $C_{36}H_{51}N_4O_7$: 651.37; found: 651.60.

Step 5. Preparation of 14-5: To a solution of 14-4 (70 mg, 0.11 mmol) in DCM (3 mL) was added TMSOTf (0.103 mL, 0.53 mmol) and the reaction was stirred at rt for 1 h. The reaction was concentrated to afford 14-5 which was used it for the next step without purification. LCMS-ESI$^+$ (m/z): [M+H]$^+$ calcd for $C_{32}H_{43}N_4O_7$: 595.31; found: 595.43, Step 6. Preparation of Example 14: To a solution of 14-5 (36.8 mg, 0.06 mmol) and Intermediate A10 (28 mg, 0.09 mmol) in acetonitrile (1.5 mL) was added HATU (38 mg, 0.1 mmol) followed by DIPEA (0.065 mL, 0.37 mmol) at room temperature. After 20 minutes, the reaction mixture was directly purified by reverse phase HPLC (Gemini 5u C18 110 Å column, 15-100% MeCN/H$_2$O+0.1% TFA) and lyophilized to afford Example 14 as a yellow solid (24 mg) as a TFA salt. Analytic HPLC RetTime: 9.03 min. LCMS-ESI$^+$ (m/z): [M+H]$^+$ calcd for $C_{41}H_{55}F_2N_6O_9S$: 845.4; found: 845.6. $^1$H NMR (400 MHz, CD$_3$OD) δ 9.31 (s, 1H), 7.80 (d, J=9.1 Hz, 1H), 7.23 (dd, J=91, 2.8 Hz, 1H), 7.16 (d, J=2.7 Hz, 1H), 6.03-5.66 (m, 2H), 4.53 (dd, J=13.2, 9.6 Hz, 2H), 4.18 (dd, J=17.2, 7.1 Hz, 2H), 3.92 (s, 3H), 3.68 (dt, J=6.8, 2.8 Hz, 1H), 3.13 (quin, J=1.7 Hz, 1H), 3.02-2.92 (m, 1H), 2.85-2.78 (m, 1H), 2.62-2.55 (m, 1H), 2.30-2.17 (m, 1H), 2.02 (s, 2H), 1.97-1.86 (m, 3H), 1.86-1.79 (m, 1H), 1.80-1.41 (m, 17H), 1.40-1.28 (m, 3H), 1.22 (t, J=7.4 Hz, 3H), 1.03-0.87 (m, 4H), 0.76-0.68 (m, 1H), 0.51-0.44 (m, 1H).

Example 15

Preparation of (1aR,5S,8S,9S,10R,22aR)-5-cyclopentyl-N-[(1R,2R)-1-[(cyclopropylsulfonyl)carbamoyl]-2-(difluoromethyl)cyclopropyl]-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

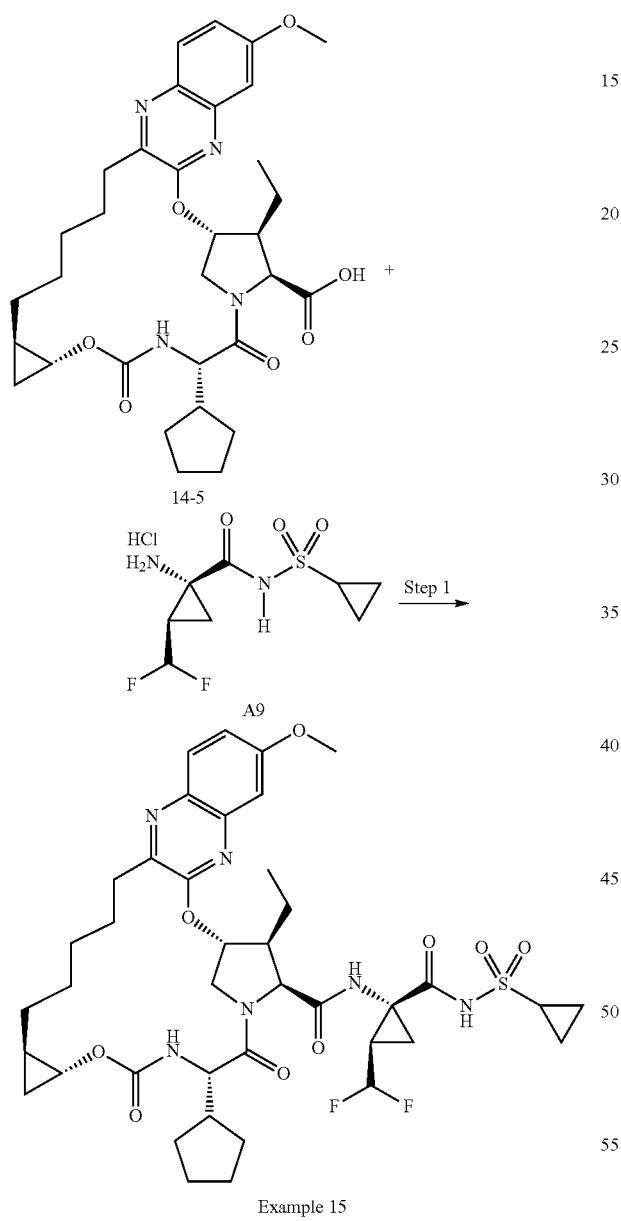

as a TFA salt. Analytic HPLC RetTime: 8.89 min. LCMS-ESI+ (m/z): [M+H]+ calcd for $C_{40}H_{53}F_2N_6O_9S$: 831.4; found: 831.6. $^1$H NMR (400 MHz, CD$_3$OD) δ 9.32 (s, 1H), 7.79 (d, J=9.1 Hz, 1H), 7.23 (dd, J=9.1, 2.8 Hz, 1H), 7.16 (d, J=2.8 Hz, 1H), 6.03-5.66 (m, 2H), 4.53 (t, J=10.0 Hz, 2H), 4.22-4.14 (m, 2H), 3.92 (s, 3H), 3.67 (dt, J=6.5, 2.9 Hz, 1H), 3.13 (quin, 1.6 Hz, 1H), 3.04-2.92 (m, 3H), 2.85-2.77 (m, 1H), 2.63-2.55 (m, 1H), 2.26-2.19 (m, 1H), 2.05-2.02 (m, 2H), 1.99-1.86 (m, 3H), 1.84-1.42 (m, 12H), 1.41-1.25 (m, 4H), 1.22 (t, J=7.2 Hz, 3H), 1.15-1.03 (m, 3H), 1.01-0.90 (m, 2H), 0.76-0.68 (m, 1H), 0.49-0.45 (m, 1H).

Example 16

Preparation of (1aR,5S,8S,9S,10R,22aR)-5-cyclohexyl-N-[(1R,2R)-2-(difluoromethyl)-1-{[(1-methylcyclopropyl)sulfonyl]carbamoyl}cyclopropyl]-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

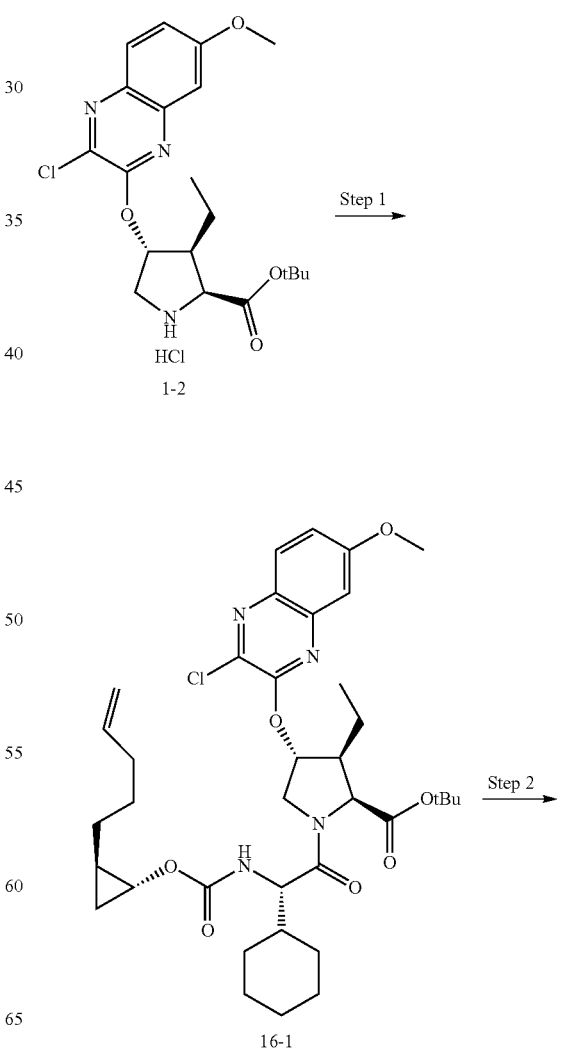

Step 1. Preparation of Example 15. To a solution of 14-5 (27 mg, 0.045 mmol) and Intermediate A9 (20 mg, 0.067 mmol) in acetonitrile (1.3 mL) was added HATU (27 mg, 0.072 mmol) followed by DIPEA (0.047 mL, 0.27 mmol) at room temperature. After 20 minutes, the reaction mixture was directly purified by reverse phase HPLC (Gemini 5u C18 110 Å column, 15-100% MeCN/H$_2$O+0.1% TFA) and lyophilized to afford Example 15 as a yellow solid (18.6 mg)

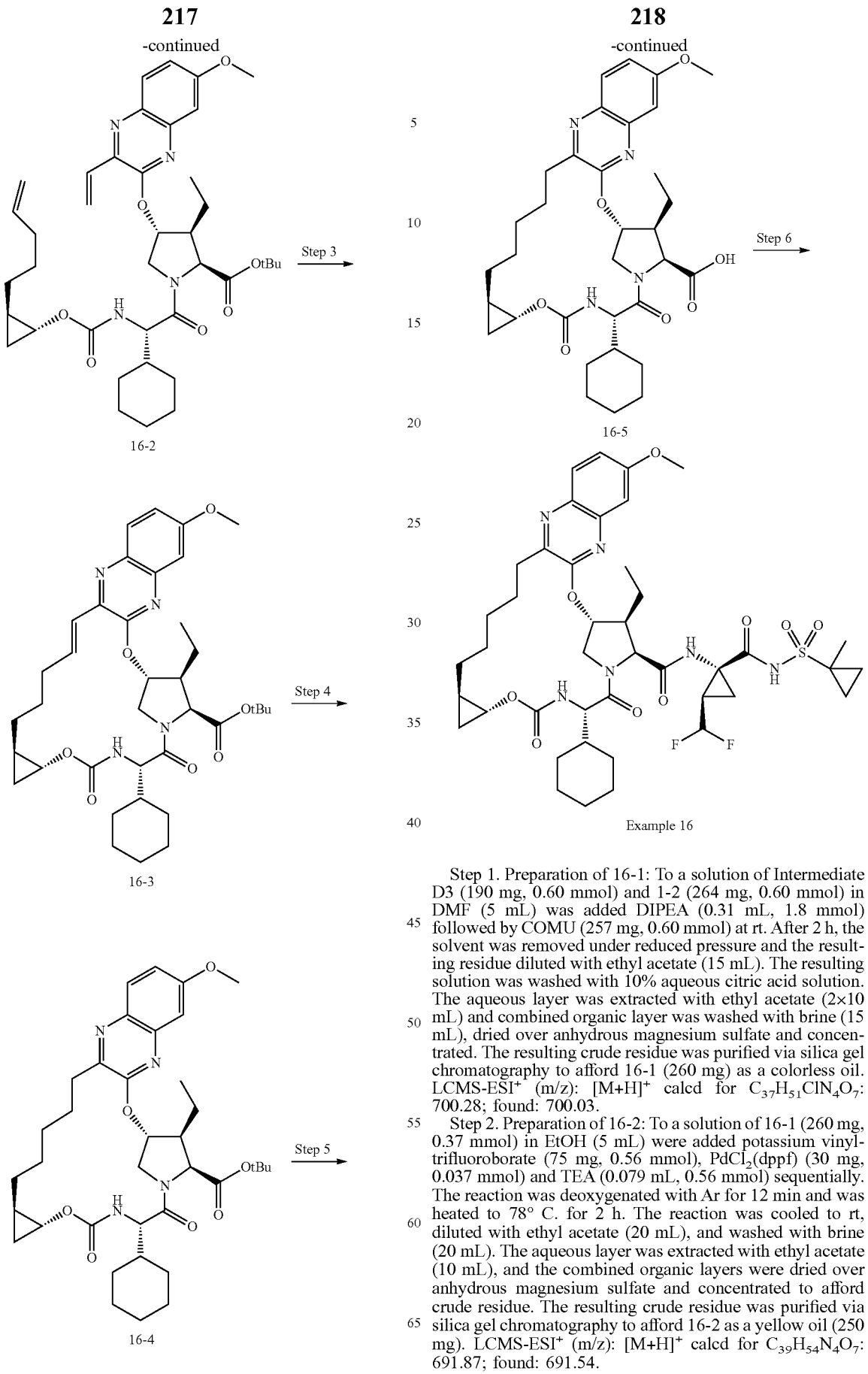

Example 16

Step 1. Preparation of 16-1: To a solution of Intermediate D3 (190 mg, 0.60 mmol) and 1-2 (264 mg, 0.60 mmol) in DMF (5 mL) was added DIPEA (0.31 mL, 1.8 mmol) followed by COMU (257 mg, 0.60 mmol) at rt. After 2 h, the solvent was removed under reduced pressure and the resulting residue diluted with ethyl acetate (15 mL). The resulting solution was washed with 10% aqueous citric acid solution. The aqueous layer was extracted with ethyl acetate (2×10 mL) and combined organic layer was washed with brine (15 mL), dried over anhydrous magnesium sulfate and concentrated. The resulting crude residue was purified via silica gel chromatography to afford 16-1 (260 mg) as a colorless oil. LCMS-ESI$^+$ (m/z): [M+H]$^+$ calcd for $C_{37}H_{51}ClN_4O_7$: 700.28; found: 700.03.

Step 2. Preparation of 16-2: To a solution of 16-1 (260 mg, 0.37 mmol) in EtOH (5 mL) were added potassium vinyltrifluoroborate (75 mg, 0.56 mmol), PdCl$_2$(dppf) (30 mg, 0.037 mmol) and TEA (0.079 mL, 0.56 mmol) sequentially. The reaction was deoxygenated with Ar for 12 min and was heated to 78° C. for 2 h. The reaction was cooled to rt, diluted with ethyl acetate (20 mL), and washed with brine (20 mL). The aqueous layer was extracted with ethyl acetate (10 mL), and the combined organic layers were dried over anhydrous magnesium sulfate and concentrated to afford crude residue. The resulting crude residue was purified via silica gel chromatography to afford 16-2 as a yellow oil (250 mg). LCMS-ESI$^+$ (m/z): [M+H]$^+$ calcd for $C_{39}H_{54}N_4O_7$: 691.87; found: 691.54.

Step 3. Preparation of 16-3: To a solution of 16-2 (250 mg, 0.36 mmol) in deoxygenated DCE (0.005 M) was added Zhan 1B catalyst (26 mg, 0.036 mmol, Strem) and the reaction was deoxygenated for another 10 minutes with Ar. The reaction was heated to 70° C. for 2 h. The reaction mixture was allowed to cool to rt and concentrated. The resulting residue was directly purified by silica gel chromatography to afford 16-3 as a yellow oil (250 mg), LCMS-ESI$^+$ (m/z): [M+H]$^+$ calcd for C$_{37}$H$_{50}$N$_4$O$_7$: 663.82; found: 663.42.

Step 4. Preparation of 16-4: To a solution of 16-3 (200 mg, 0.3 mmol) in EtOAc (10 mL) was added Pd/C (10 wt % Pd, 100 mg) under argon. The atmosphere was replaced with hydrogen and the reaction was stirred at rt for 1.5 h. The reaction was filtered over Celite, washed with EtOH and concentrated to give 16-4 as an oil (180 mg) that was used subsequently without further purification. LCMS-ESI$^+$ (m/z): [M+H]$^+$ calcd for C$_{37}$H$_{52}$N$_4$O$_7$: 665.83; found: 665.36.

Step 5. Preparation of 16-5: To a solution of 16-4 (165 mg, 0.25 mmol) in DCM (5 mL) was added TFA (2 mL) and the reaction was stirred at rt for 4 h. The solvent was removed under reduced pressure the reaction was diluted with ethyl acetate (15 mL). The resulting solution was washed with sat. aqueous NaHCO$_3$ and concentrated to afford 16-5 which was used in the next step without further purification. LCMS-ESI$^+$ (m/z): [M+H]$^+$ calcd for C$_{33}$H$_{44}$N$_4$O$_7$: 609.73; found: 609.47.

Step 6. Preparation of Example 16: To a solution of 16-5 (70 mg, 0.12 mmol) and Intermediate A10 (65 mg, 0.21 mmol) in DCM (1 mL) was added DIPEA (0.08 mL, 0.46 mmol) followed by HATU (88 mg, 0.23 mmol). The reaction was stirred at room temperature for 3 h. The reaction was diluted with EtOAc and washed with aqueous NH$_4$Cl and brine. The crude material was purified by reverse phase HPLC (Gemini column, 58-98% MeCN/H$_2$O+0.1% TFA) and lyophilized to afford Example 16 (40 mg) as a TFA salt. Analytic HPLC RetTime: 9.21 min. LCMS-ESI$^+$ (m/z): [M+H]$^+$ calcd for C$_{42}$H$_{56}$F$_2$N$_6$O$_9$S: 859.99; found: 859.60. $^1$H NMR (400 MHz, CD$_3$OD) δ 9.28 (s, 1H), 7.76 (d, J=9.2 Hz, 1H), 7.18 (d, J=9.2 Hz, 1H), 7.10 (s, 1H), 5.97-5.82 (m, 2H), 4.88 (m, 2H), 4.51-4.46 (m, 3H), 4.19-4.11 (m, 3H), 3.90 (s, 3H), 3.70-3.29 (m, 6H), 2.97-2.52 (m, 3H), 2.06-1.41 (m, 20H), 1.39-1.17 (m, 4H), 1.09-0.89 (m, 4H), 0.65 (m, 1H), 0.46-0.44 (m, 1H).

Example 17

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

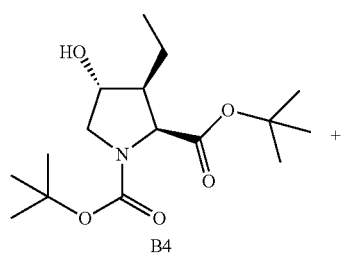

B4

+

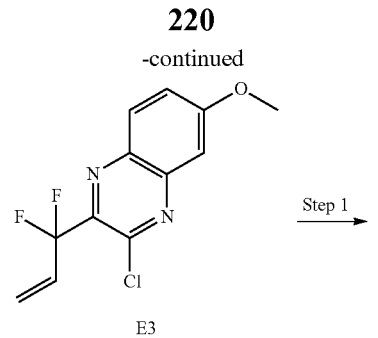

E3

Step 1

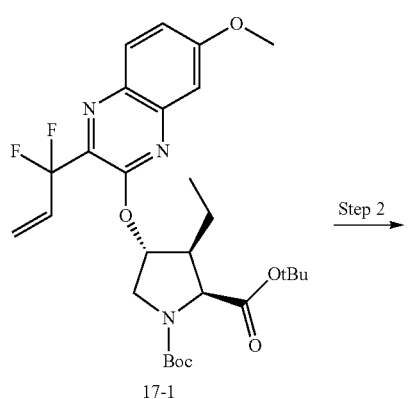

17-1

Step 2

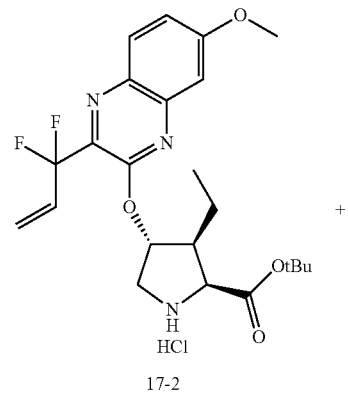

17-2

+

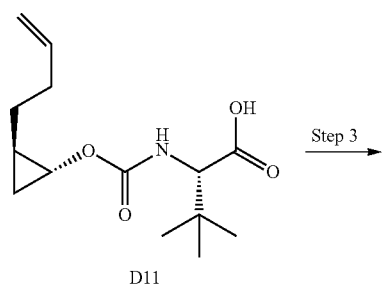

D11

Step 3

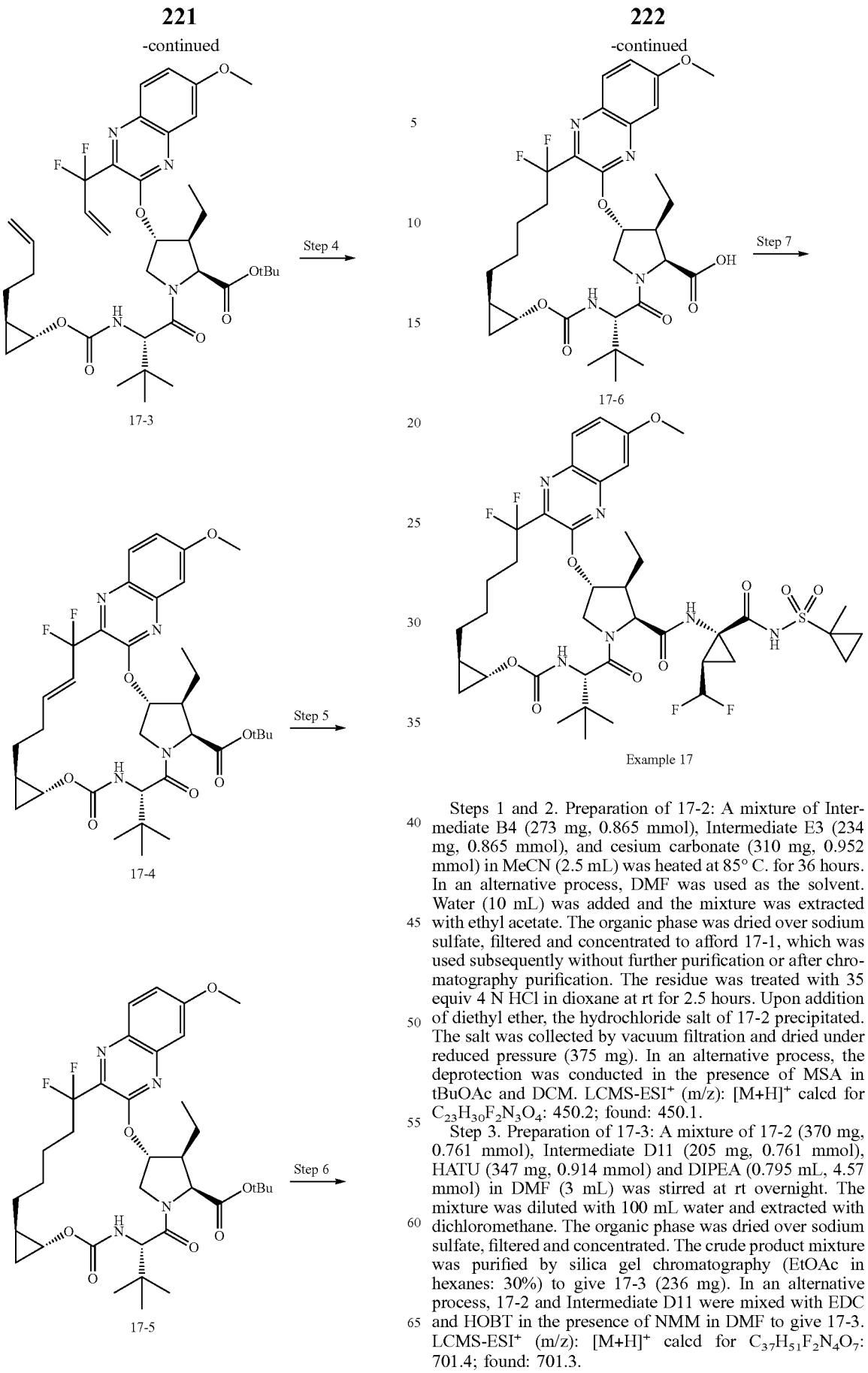

Example 17

Steps 1 and 2. Preparation of 17-2: A mixture of Intermediate B4 (273 mg, 0.865 mmol), Intermediate E3 (234 mg, 0.865 mmol), and cesium carbonate (310 mg, 0.952 mmol) in MeCN (2.5 mL) was heated at 85° C. for 36 hours. In an alternative process, DMF was used as the solvent. Water (10 mL) was added and the mixture was extracted with ethyl acetate. The organic phase was dried over sodium sulfate, filtered and concentrated to afford 17-1, which was used subsequently without further purification or after chromatography purification. The residue was treated with 35 equiv 4 N HCl in dioxane at rt for 2.5 hours. Upon addition of diethyl ether, the hydrochloride salt of 17-2 precipitated. The salt was collected by vacuum filtration and dried under reduced pressure (375 mg). In an alternative process, the deprotection was conducted in the presence of MSA in tBuOAc and DCM. LCMS-ESI$^+$ (m/z): [M+H]$^+$ calcd for $C_{23}H_{30}F_2N_3O_4$: 450.2; found: 450.1.

Step 3. Preparation of 17-3: A mixture of 17-2 (370 mg, 0.761 mmol), Intermediate D11 (205 mg, 0.761 mmol), HATU (347 mg, 0.914 mmol) and DIPEA (0.795 mL, 4.57 mmol) in DMF (3 mL) was stirred at rt overnight. The mixture was diluted with 100 mL water and extracted with dichloromethane. The organic phase was dried over sodium sulfate, filtered and concentrated. The crude product mixture was purified by silica gel chromatography (EtOAc in hexanes: 30%) to give 17-3 (236 mg). In an alternative process, 17-2 and Intermediate D11 were mixed with EDC and HOBT in the presence of NMM in DMF to give 17-3. LCMS-ESI$^+$ (m/z): [M+H]$^+$ calcd for $C_{37}H_{51}F_2N_4O_7$: 701.4; found: 701.3.

Step 4. Preparation of 17-4: A solution of 17-3 (236 mg, 0.34 mmol) in DCE (67 mL) was deoxygenated with argon for 40 minutes. Zhan 1B catalyst (25 mg, 0.034 mmol, Strem) was added and the reaction was heated in a 100° C. oil bath for 40 minutes. Solvent was removed under reduced pressure and the residue was purified by silica gel chromatography (EtOAc in hexanes: 5% to 65%) to give the 17-4 (229 mg). LCMS-ESI$^+$ (m/z): [M–F]$^+$ calcd for $C_{35}H_{46}FN_4O_7$: 653.3; found: 653.2.

Step 5. Preparation of 17-5: A solution of 17-4 (229 mg, 0.34 mmol) in 50 mL ethanol was hydrogenated at 1 atm hydrogen gas over 220 mg of 10% wt Pd/C (wet) for 2.5 hours. Filtration through Celite and concentration under reduced pressure gave a crude residue of 17-5 (184 mg). In an alternative process, 17-4 was hydrogenated at hydrogen gas in the presence of Rh. LCMS-ESI$^+$ (m/z): [M+H]$^+$ calcd for $C_{35}H_{49}F_2N_4O_7$: 675.4; found: 675.3.

Step 6. Preparation of 17-6: Ester 17-5 (184 mg, 0.27 mmol) in 2 mL DCM was treated with 1 mL TFA and stirred at rt for 3 h. The reaction mixture was concentrated and then partitioned between water and ethyl acetate. The organic phase was washed with water, dried over anhydrous sodium sulfate, filtered and concentrated to give 17-6 (153 mg). LCMS-ESI$^+$ (m/z): [M+H]$^+$ calcd for $C_{31}H_{41}F_2N_4O_7$: 619.3; found: 619.2.

Step 7. Preparation of Example 17: A mixture of carboxylic acid 17-6 (153 mg, 0.247 mmol), Intermediate A10 (90 mg, 0.297 mmol), HATU (113 mg, 0.297 mmol), DMAP (45 mg, 0.37 mmol) and DIPEA (0.215 mL, 1.24 mmol) in DMF (1.5 mL) was stirred at rt for 40 minutes. The mixture was diluted with 2 N aqueous HCl (2 mL) and extracted with dichloromethane. The organic phase was dried over sodium sulfate, filtered and concentrated. The crude product mixture was purified by silica gel chromatography (EtOAc in hexanes: 30%-95%) to give Example 17 (95 mg) Analytic HPLC RetTime: 8.79 min. LCMS-ESI$^+$ (m/z): [M+H]$^+$ calcd for $C_{40}H_{53}F_4NO_9S$: 869.3; found: 869.2. $^1$H NMR (400 MHz, CDCl$_3$) δ 9.948 (br s, 1H), 7.99 (d, J=9.2 Hz, 1H), 7.29 (dd, J=8.8, 2.4 Hz, 1H), 7.09 (d, J=2.8 Hz, 1H), 6.57 (br s, 1H), 5.97 (td, J$_{H-F}$=52 Hz, J=6.8 Hz, 1H) 5.92 (d, J=3.6 Hz, 1H), 5.322 (d, J=9.6 Hz, 1H), 4.42 (ap d, J=7.2 Hz, 1H), 4.40 (ap s, 1H), 4.34 (ap d, J=10 Hz, 1H), 4.08 (dd, J=12.0, 3.6 Hz, 1H), 3.99-3.94 (m, 1H), 3.96 (s, 3H), 3.67 (m, 1H), 2.52 (m, 2H), 2.06 (m, 1H), 1.93 (m, 2H), 1.77 (m, 2H), 1.63 (m, 3H), 1.50 (s, 3H), 1.56-1.42 (m, 4H), 1.25 (m, 1H), 1.19 (t, J=7.2 Hz, 3H), 1.09 (s, 9H), 1.10-0.93 (m, 2H), 0.85 (m, 2H), 0.69 (m, 1H), 0.49 (m, 1H).

Example 18

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-14-methoxy-9-methyl-3,6-dioxo-1,1a,3,4,5,6,9,10,18,19,20,21,22,22a-tetradecahydro-8H-7,10-methanocyclopropa[18,19][1,10 3,6]dioxadiazacyclononadecino[11,12-b]quinoxaline-8-carboxamide

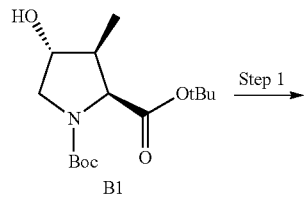

Step 1

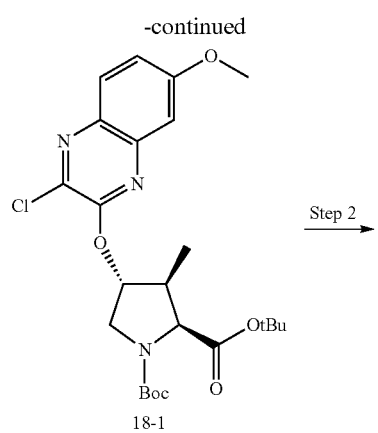

18-1

Step 2

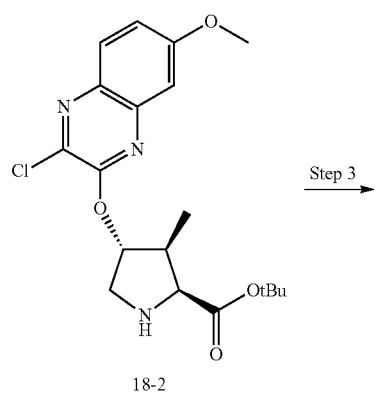

18-2

Step 3

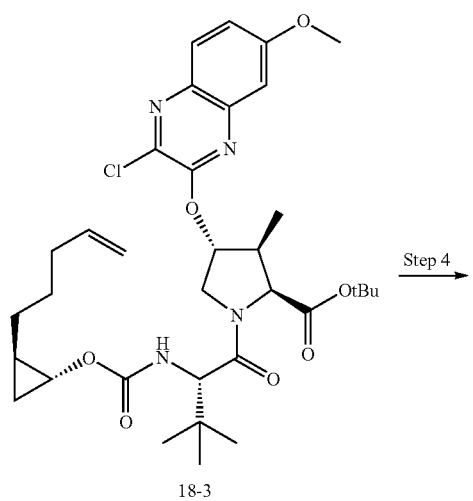

18-3

Step 4

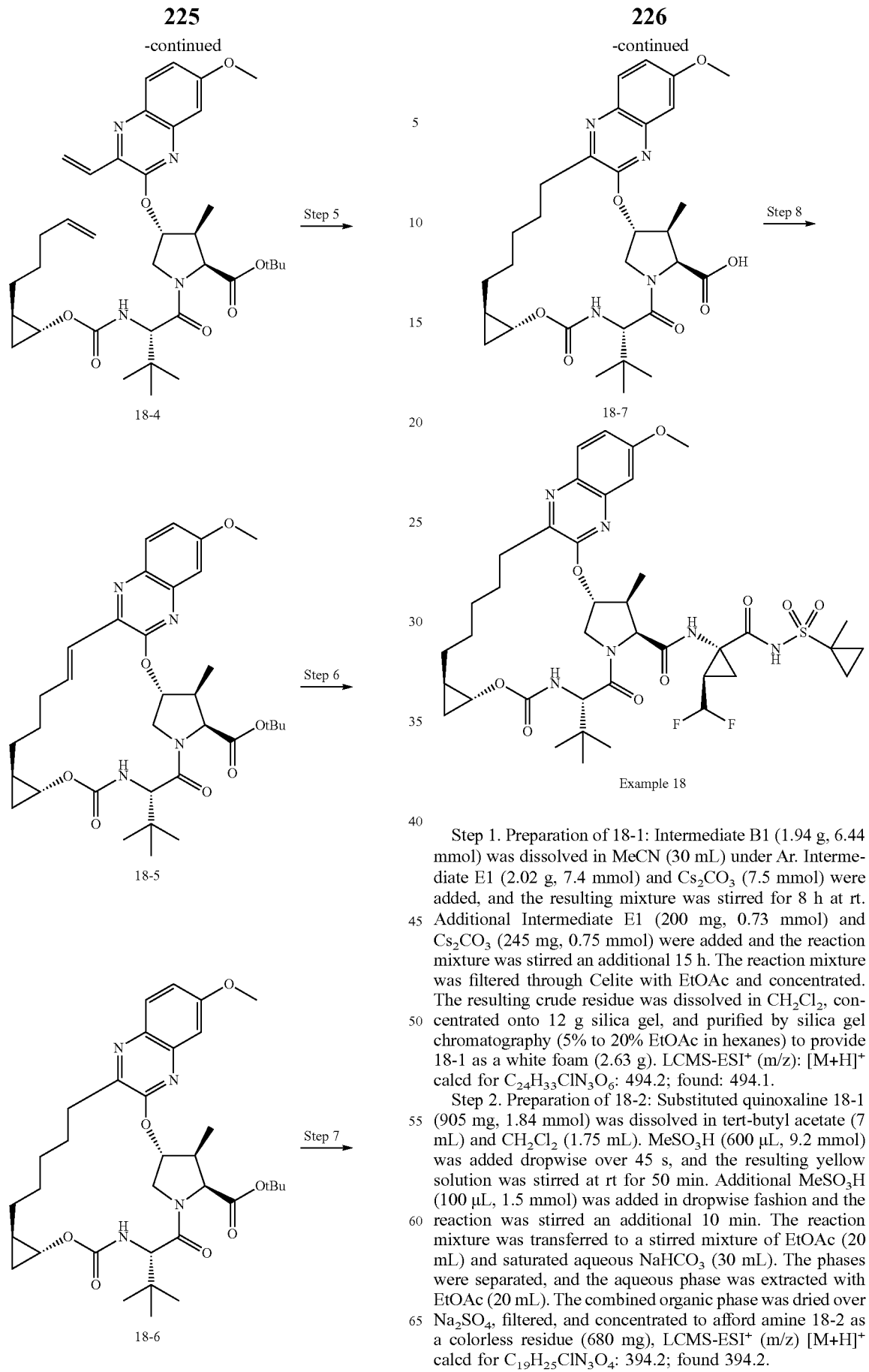

Example 18

Step 1. Preparation of 18-1: Intermediate B1 (1.94 g, 6.44 mmol) was dissolved in MeCN (30 mL) under Ar. Intermediate E1 (2.02 g, 7.4 mmol) and $Cs_2CO_3$ (7.5 mmol) were added, and the resulting mixture was stirred for 8 h at rt. Additional Intermediate E1 (200 mg, 0.73 mmol) and $Cs_2CO_3$ (245 mg, 0.75 mmol) were added and the reaction mixture was stirred an additional 15 h. The reaction mixture was filtered through Celite with EtOAc and concentrated. The resulting crude residue was dissolved in $CH_2Cl_2$, concentrated onto 12 g silica gel, and purified by silica gel chromatography (5% to 20% EtOAc in hexanes) to provide 18-1 as a white foam (2.63 g). LCMS-ESI$^+$ (m/z): [M+H]$^+$ calcd for $C_{24}H_{33}ClN_3O_6$: 494.2; found: 494.1.

Step 2. Preparation of 18-2: Substituted quinoxaline 18-1 (905 mg, 1.84 mmol) was dissolved in tert-butyl acetate (7 mL) and $CH_2Cl_2$ (1.75 mL). $MeSO_3H$ (600 μL, 9.2 mmol) was added dropwise over 45 s, and the resulting yellow solution was stirred at rt for 50 min. Additional $MeSO_3H$ (100 μL, 1.5 mmol) was added in dropwise fashion and the reaction was stirred an additional 10 min. The reaction mixture was transferred to a stirred mixture of EtOAc (20 mL) and saturated aqueous $NaHCO_3$ (30 mL). The phases were separated, and the aqueous phase was extracted with EtOAc (20 mL). The combined organic phase was dried over $Na_2SO_4$, filtered, and concentrated to afford amine 18-2 as a colorless residue (680 mg), LCMS-ESI$^+$ (m/z) [M+H]$^+$ calcd for $C_{19}H_{25}ClN_3O_4$: 394.2; found 394.2.

Step 3. Preparation of 18-3: Amine 18-2 (680 mg, 1.73 mmol) and Intermediate D1 (600 mg, 2.1 mmol) were dissolved in DMF (10 mL). DIPEA (925 µL, 5.30 mmol) was added followed by HATU (880 mg, 2.3 mmol). The reaction was stirred 110 min at rt and was diluted with saturated aqueous NaHCO$_3$ (30 mL) and EtOAc (30 mL). The phases were separated and the organic phase was washed with half-saturated brine (2×40 mL), dried over anhydrous Na$_2$SO$_4$, filtered and concentrated to a crude residue. Purification by silica gel chromatography (10% to 20% EtOAc in hexanes) provided 18-3 as a colorless residue (703 mg). LCMS-ESI$^+$ (m/z): [M+H]$^+$ calcd for C$_{34}$H$_{48}$ClN$_4$O$_7$: 659.3; found: 659.4.

Step 4. Preparation of 18-4: A stirred heterogeneous mixture of 18-3 (703 mg, 1.07 mmol), PdCl$_2$(dppf).CH$_2$Cl$_2$ (48 mg, 0.059 mmol) and potassium vinyltrifluoroborate (290 mg, 2.16 mmol) in EtOH (11 mL) was sparged with argon for 15 min. Triethylamine (320 µL, 2.3 mmol) was added and the mixture was heated to 75° C. for 70 min. The reaction mixture was cooled to ambient temperature and was diluted with EtOAc (40 mL) and half-saturated brine (30 mL), The phases were separated and the organic phase was dried over Na$_2$SO$_4$, filtered, and concentrated. Purification by silica gel chromatography (10% to 20% to 30% EtOAc in hexanes) provided 18-4 as a yellow residue (490 mg). LCMS-ESI$^+$ (m/z): [M+H]$^+$ calcd for C$_{36}$H$_{51}$N$_4$O$_7$: 651.4; found: 651.3.

Step 5. Preparation of 18-5: 18-4 (490 mg, 0.179 mmol) was dissolved in DCE (250 mL) and the solution was sparged with Ar for 15 min. Zhan 1B catalyst (66 mg, 0.090 mmol, Strem) was added as a solution in DCE (5 mL) and the resulting solution was stirred at 85° C. under Ar for 105 min. The reaction mixture was cooled to rt and was adsorbed onto silica gel (7.5 g). Purification by silica gel chromatography (10% to 30% EtOAc in hexanes) provided 18-5 as an amorphous residue (290 mg). LCMS-ESI$^+$ (m/z). [M+H]$^+$ calcd for C$_{34}$H$_{47}$N$_4$O$_7$: 623.3; found: 623.3.

Step 6: Preparation of 18-6: Olefin 18-5 (290 mg, 0.072 mmol) was dissolved in EtOAc (5.5 mL) and EtOH (5.5 mL) and the reaction vessel was purged with Ar. Pd/C (10 wt % Pd, 92 mg) was added in a single portion and the reaction vessel was purged twice with H$_2$. The reaction was stirred at rt under 1 atm H$_2$ for 1.5 h and was filtered through a pad of Celite and concentrated to afford a crude residue of 18-6 that was used without further purification (LCMS-ESI$^+$ (m/z): [M+H]$^+$ calcd for C$_{34}$H$_{49}$N$_4$O$_7$: 625.4; found: 625.0.

Step 7. Preparation of 18-7: 18-6 (0.466 mmol) was dissolved in CH$_2$Cl$_2$ (4.3 mL) under Ar. TMSOTf (210 µL, 1.16 mmol) was added dropwise over 30 s. The reaction was stirred 65 min and an additional portion of TMSOTf (50 µL, 0.28 mmol) was added. The reaction was stirred an additional 100 min and an additional portion of TMSOTf (100 µL, 0.55 mmol) was added. The reaction was stirred an additional 105 min and was concentrated in vacuo. The resulting crude residue was dissolved in CH$_2$C$_2$ (20 mL) and 0.2 M aqueous NaOH (10 mL) was added. The mixture was stirred for 5 min and was acidified with 1 M aqueous HCl (20 mL). The phases were separated, and the aqueous phase was extracted with CH$_2$Cl$_2$ (2×20 mL). The combined organic phase was dried over MgSO$_4$, filtered, and concentrated to afford 18-7 as a brown solid (273 mg). LCMS-ESI$^+$ (m/z): [M+H]$^+$ calcd for C$_{30}$H$_{41}$N$_4$O$_7$: 569.3; found: 568.9.

Step 8. Preparation of Example 18: To a suspension of acid 18-7 (28 mg, 0.049 mmol) and Intermediate A10 (26.5 mg, 0.087 mmol) in MeCN (1.3 mL) was added DIPEA (55 µL, 0.31 mmol). To the resulting solution was added HATU (30.5 mg, 0.080 mmol) The reaction was stirred at rt for 1 h and an additional portion of Intermediate A10 (3 mg, 0.01 mmol) was added After an additional 15 min, the reaction was diluted with EtOAc (30 mL) and 1 M aqueous HCl (20 mL). The phases were separated and the aqueous phase was extracted with EtOAc (30 mL). The combined organic phase was dried over Na$_2$SO$_4$, filtered, and concentrated to afford a crude residue. Purification by silica gel chromatography (10% to 40% acetone in hexanes) provided an amorphous residue that was lyophilized from water and MeCN to provide Example 18 as a white amorphous solid (26.4 mg). Analytic HPLC RetTime: 8.42 min. LCMS-ESI$^+$ (m/z): [M+H]$^+$ calcd for C$_{39}$H$_{53}$F$_2$N$_6$O$_9$S: 819.4; found: 819.1. $^1$H NMR (300 MHz, CDCl$_3$) δ 9.68 (s, 1H), 7.82 (d, J=9.1 Hz, 1H), 7.19 (dd, J=9.1, 2.8 Hz, 1H), 7.08 (d, J=2.6 Hz, 1H), 6.86 (s, 1H), 6.14-5.70 (m, 1H), 5.65 (d, J=9.9 Hz, 1H), 5.56-5.50 (m, 1H), 4.53-4.40 (m, 3H), 4.12 (dd, J=11.9, 4.3 Hz, 1H), 3.93 (s, 3H), 3.81-3.74 (m, 1H), 3.06-2.64 (m, 4H), 2.10-1.35 (m, 13H), 1.13 (d, J=7.5 Hz, 3H), 1.09 (s, 9H), 1.04-0.65 (m, 6H), 0.52-0.41 (m, 1H).

Example 19

Preparation of (1aR,5S,8S,9S,10R,22aR)-5-tert-butyl-N-[(1R,2R)-1-[(cyclopropylsulfonyl)carbamoyl]-2-(difluoromethyl)cyclopropyl]-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

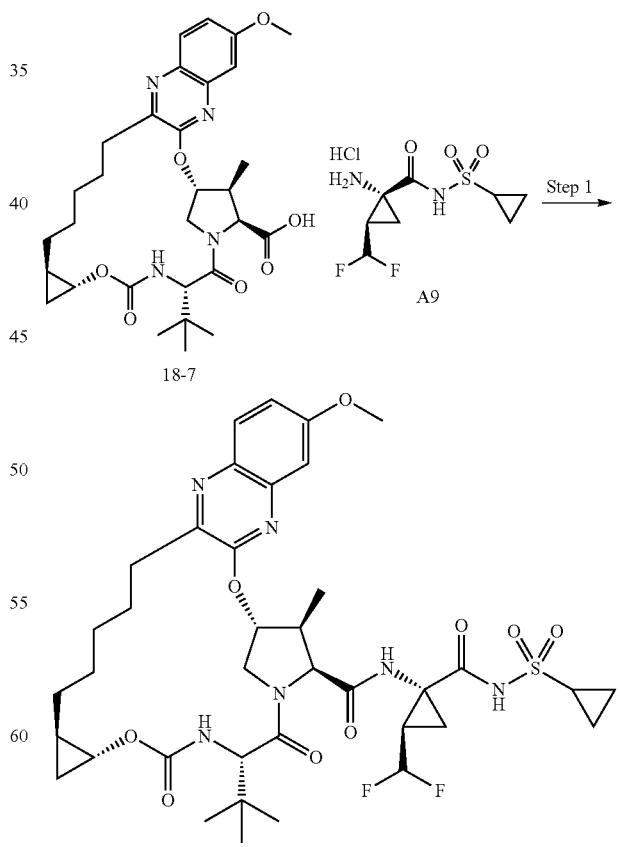

Example 19

Step 1. Preparation of Example 19: To a suspension of acid 18-7 (8.8 mg, 0.015 mmol) and Intermediate A9 (7.4 mg, 0.025 mmol) in MeCN (0.5 mL) was added DIPEA (14 µL, 0.08 mmol). To the resulting solution was added HATU (9.1 mg, 0.024 mmol). The reaction was stirred at rt for 1 h and an additional portion of Intermediate A9 (5 mg, 0.02 mmol) and HATU (5 mg, 0.01 mmol) were added. After an additional 1.5 h, the reaction was diluted with EtOAc (30 mL), 0.2 M aqueous HCl (10 mL), and brine (10 mL). The phases were separated and the aqueous phase was extracted with EtOAc (30 mL). The combined organic phase was dried over $Na_2SO_4$, filtered, and concentrated to afford a crude residue. Purification by silica gel chromatography (10% to 40% acetone in hexanes) provided a residue that was lyophilized from water and MeCN to provide Example 19 as a white amorphous solid (8.5 mg). Analytic HPLC RetTime: 8.69 min. LCMS-ESI$^+$ (m/z): [M+H]$^+$ calcd for $C_{38}H_{51}F_2N_6O_9S$: 805.3; found: 805.2. $^1$H NMR (300 MHz, $CDCl_3$) δ 10.12 (s, 1H), 7.83 (d, J=9.1 Hz, 1H), 7.19 (dd, J=9.1, 2.7 Hz, 1H), 7.09 (d, J=2.7 Hz, 1H), 6.77 (s, 1H), 6.25-5.76 (m, 1H), 5.57 (d, J=3.7 Hz, 1H), 5.51 (d, J=9.9 Hz, 1H), 4.49-4.37 (m, 3H), 4.13 (dd, J=12.2, 4.3 Hz, 1H), 3.94 (s, 3H), 3.79-3.72 (m, 1H), 3.01-2.69 (m, 4H), 2.13-2.06 (m, 1H), 2.01-1.22 (m, 9H), 1.14 (d, J=7.2 Hz, 3H), 1.09 (s, 9H), 1.06-0.82 (m, 6H), 0.76-0.62 (m, 1H), 0.54-0.41 (m, 1H).

Step 1. Preparation of Example 20: To a suspension of acid 18-7 (10 mg, 0.018 mmol) and Intermediate A3 (6.3 mg, 0.023 mmol) in MeCN (0.5 mL) was added DIPEA (15 µL, 0.086 mmol) To the resulting solution was added HATU (9.0 mg, 0.024 mmol). The reaction was stirred at rt for 2.5 h and an additional portion of intermediate A3 (6.5 mg, 0.024 mmol) was added. After an additional 45 min, the reaction was diluted with EtOAc (2 mL) and 1 M aqueous HCl (1.5 mL). The phases were separated and the aqueous phase was extracted with EtOAc (4×1.5 mL). The combined organic phase was dried over $Na_2SO_4$, filtered, and concentrated to afford a crude residue, Purification by silica gel chromatography (20% to 25% to 30% acetone in hexanes) provided a residue that was lyophilized from water and MeCN to provide Example 20 as a white amorphous solid (8.0 mg). Analytic HPLC RetTime: 8.40 min. LCMS-ESI$^+$ (m/z): [M+H]$^+$ calcd for $C_{39}H_{55}N_6O_9S$: 783.4; found: 783.2. $^1$H NMR (300 MHz, $CDCl_3$) δ 9.98 (s, 1H), 7.83 (d, J=9.1 Hz, 1H), 7.19 (dd, J=9.1, 2.8 Hz, 1H), 7.09 (d, J=2.7 Hz, 1H), 6.42 (s, 1H), 5.57 (d, J=3.8 Hz, 1H), 5.36 (d, J=9.9 Hz, 1H) 4.48-4.34 (m, 3H), 4.11 (dd, J=11.8, 4.1 Hz, 1H), 3.94 (s, 3H), 3.79-3.72 (m, 1H) 2.98-2.68 (m, 4H), 1.95-0.80 (m, 33H), 0.76-0.61 (m, 1H), 0.53-0.41 (m, 1H).

Example 20

Preparation of (1aR,5S,8S,9S,9S,10R,22aR)-5-tert-butyl-N-{(1R,2R)-1-[(cyclopropylsulfonyl)carbamoyl]-2-ethylcyclopropyl}-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 21

Preparation of (1aR,5S,8S,9S,10R,22aR)-5-tert-butyl-N-[(1R,2R)-2-ethyl-1-{[(1-methylcyclopropyl)sulfonyl]carbamoyl}cyclopropyl]-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

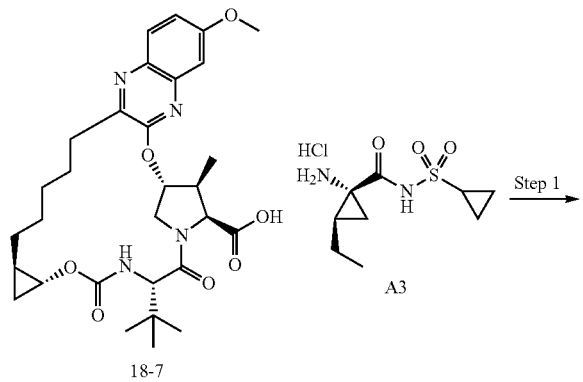

Example 20

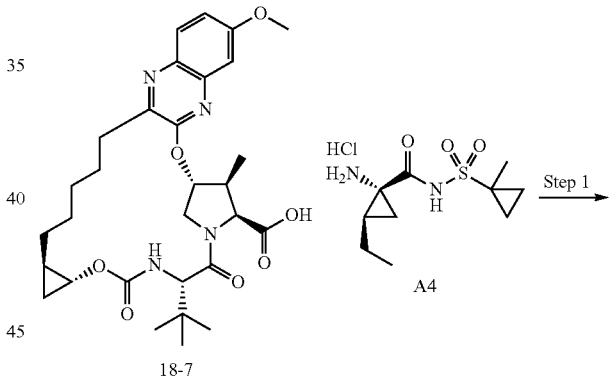

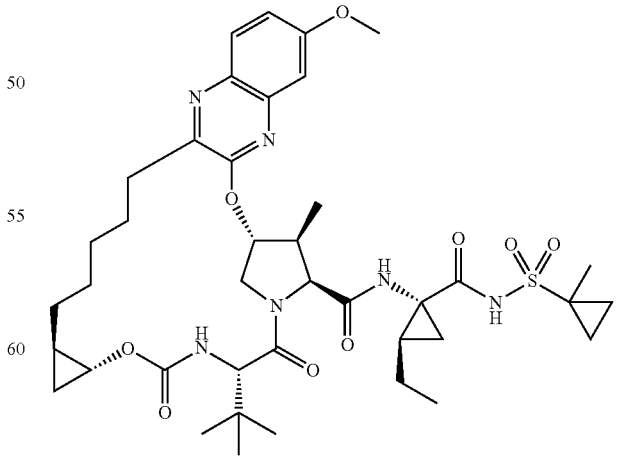

Example 21

Step 1. Preparation of Example 21: To a suspension of acid 18-7 (94.9 mg, 0.167 mmol) and Intermediate A4 (74.5 mg, 0.263 mmol) in MeCN (2.5 mL) was added DIPEA (180 µL, 1.0 mmol). To the resulting solution was added HATU (9.0 mg, 0.024 mmol). The reaction was stirred at rt for 110 min and additional portions of Intermediate A4 (31 mg, 0.11 mmol) and DIPEA (50 µL, 0.29 mmol) were added. After an additional 40 min, the reaction was diluted with EtOAc (30 mL), 0.2 M aqueous HCl (20 mL), and brine (10 mL), The phases were separated and the aqueous phase was extracted with EtOAc (20 mL). The combined organic phase was dried over $Na_2SO_4$, filtered, and concentrated to afford a crude residue. Purification by silica gel chromatography (10% to 40% acetone in hexanes) provided a residue that was lyophilized from water and MeCN to provide Example 21 as a white amorphous solid (102.1 mg). Analytic HPLC Ret-Time: 8.83 min. LCMS-ESI$^+$ (m/z): [M+H]$^+$ calcd for $C_{40}H_{57}N_6O_9S$: 797.4; found: 797.5. $^1$H NMR (400 MHz, CDCl$_3$) δ 9.76 (s, 1H), 7.80 (d, J=9.1 Hz, 1H), 7.17 (dd, J=9.1, 2.8 Hz, 1H), 7.07 (d, J=2.7 Hz, 1H), 6.92 (s, 1H), 5.58-5.42 (m, 2H), 4.48-4.36 (m, 3H), 4.09 (dd, J=11.8, 4.2 Hz, 1H), 3.92 (s, 3H), 3.79-3.74 (m, 1H), 2.97-2.66 (m, 4H), 1.80-0.88 (m, 33H), 0.84-0.77 (m, 1H), 0.77-0.61 (m, 2H), 0.52-0.40 (m, 1H).

Example 22

Preparation of (1aR,5S,8S,9S,10R,22aR)-5-tert-butyl-N-[(1R,2S)-1-[(cyclopropylsulfonyl)carbamoyl]-2-(2-fluoroethyl)cyclopropyl]-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

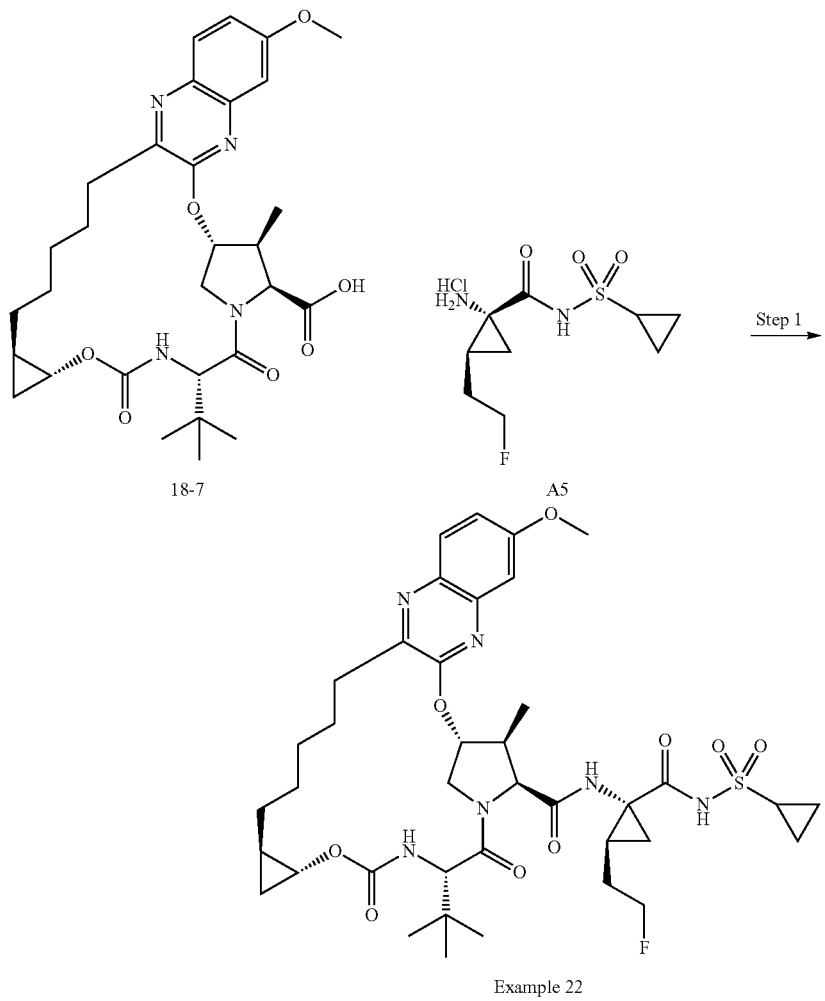

Example 22

Step 1. Preparation of Example 22: To a suspension of acid 18-7 (30.1 mg, 0.0529 mmol) and Intermediate A5 (35 mg, 0.12 mmol) in MeCN (0.5 mL) was added DIPEA (85 µL, 0.49 mmol). To the resulting solution was added HATU (34.5 mg, 0.0907 mmol). The reaction was stirred at rt for 90 min and was diluted with EtOAc (30 mL), 0.2 M aqueous HCl (20 mL), and brine (10 mL). The phases were separated and the aqueous phase was extracted with EtOAc (30 mL) The combined organic phase was dried over $Na_2SO_4$, filtered, and concentrated to afford a crude residue that was dissolved in $CH_2Cl_2$ and adsorbed onto 2 g silica gel. Purification by silica gel chromatography (15% to 55% acetone in hexanes) provided a residue that was lyophilized from water and MeCN to provide Example 22 as a white amorphous solid (35.5 mg). Analytic HPLC RetTime: 8.54 min. LCMS-ESI⁺ (m/z): [M+H]⁺ calcd for $C_{39}H_{54}FN_6O_9S$: 801.4; found: 801.3. ¹H NMR (400 MHz, CDCl₃) δ 9.95 (s, 1H), 7.82 (d, J=9.1 Hz, 1H), 7.19 (dd, J=9.1, 2.8 Hz, 1H), 7.08 (d, J=2.7 Hz, 1H), 6.68 (s, 1H), 5.56 (d, J=3.9 Hz, 1H), 5.43 (d, J=9.9 Hz, 1H), 4.57-4.29 (m, 5H), 4.12 (dd, J=11.8, 4.1 Hz, 1H), 3.93 (s, 3H), 3.78-3.71 (m, 1H), 2.97-2.67 (m, 4H), 2.12-1.25 (m, 14H), 1.15 (d, J=7.4 Hz, 3H), 1.10 (s, 9H), 1.06-0.89 (m, 4H), 0.76-0.62 (m, 1H), 0.53-0.42 (m, 1H).

Example 23

Preparation of (1aR,5S,8S,9S,10R,22aR)-5-tert-butyl-N-[(1R,2S)-2-(2-fluoroethyl)-1-{[(1-methylcyclopropyl)sulfonyl]carbamoyl}cyclopropyl]-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide stirred at rt for 75 min and an additional portion of Intermediate A6 (9 mg, 0.03 mmol) was added. After an additional 75 min the reaction was diluted with EtOAc (30 mL), 0.2 M aqueous HCl (20 mL), and brine (10 mL). The phases were separated and the aqueous phase was extracted with EtOAc (30 mL). The combined organic phase was dried over Na₂SO₄, filtered, and concentrated to afford a crude residue that was dissolved in CH₂Cl₂ and adsorbed onto 2 g silica gel. Purification by silica gel chromatography (15% to 55% acetone in hexanes) provided a residue that was lyophilized from water and MeCN to provide Example 23 as a white amorphous solid (37.1 mg). Analytic HPLC RetTime: 8.64 min. LCMS-ESI⁺ (m/z): [M+H]⁺ calcd for $C_{40}H_{56}FN_6O_9S$: 815.4; found: 8156. ¹H NMR (400 MHz, CDCl₃) δ 9.63 (s, 1H), 7.83 (d, J=9.1 Hz, 1H), 7.20 (dd, J=9.1, 2.8 Hz, 1H), 7.10 (d, J=2.7 Hz, 1H), 6.75 (s, 1H), 5.56 (d, J=3.9 Hz, 1H), 5.50 (d, J=10.0 Hz, 1H), 4.56-4.34 (m, 5H), 4.13 (dd, J=11.8,

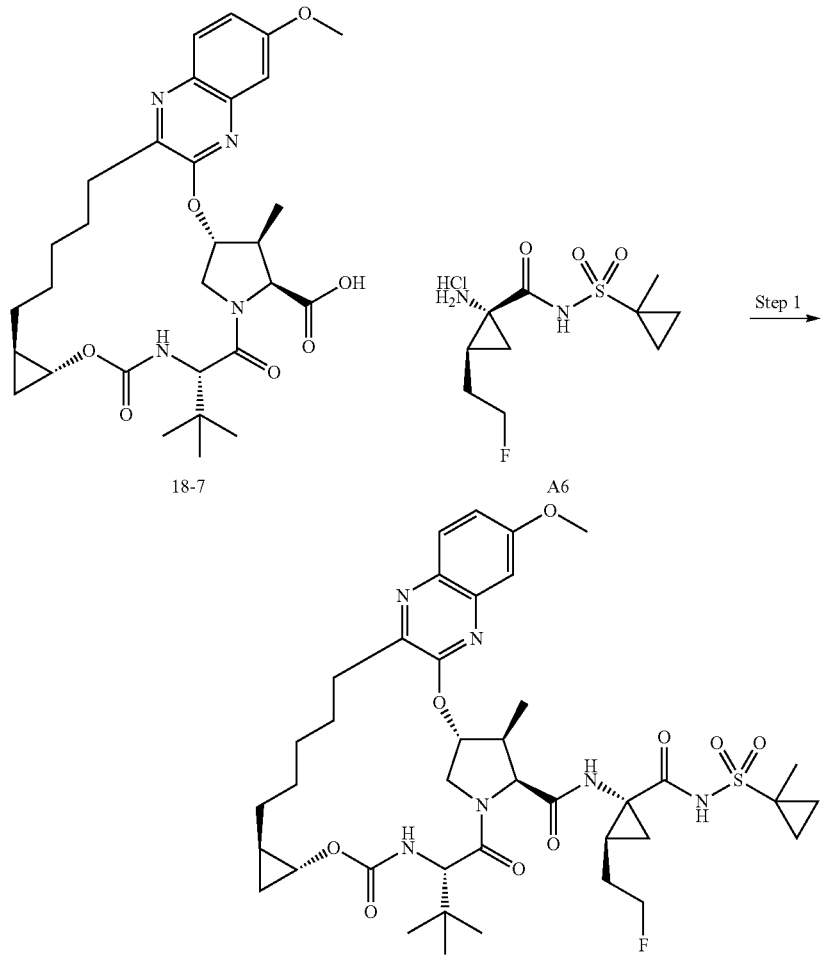

Step 1. Preparation of Example 23: To a suspension of acid 18-7 (30.5 mg, 0.0536 mmol) and Intermediate A6 (24.8 mg, 0.0824 mmol) in MeCN (0.5 mL) was added DIPEA (60 µL, 0.34 mmol). To the resulting solution was added HATU (32.3 mg, 0.0850 mmol). The reaction was 4.2 Hz, 1H), 3.95 (s, 3H), 3.82-3.75 (m, 1H), 2.98-2.70 (m, 4H), 2.07-2.00 (m, 1H), 2.00-1.93 (m, 1H), 1.88-1.44 (m, 12H), 1.32-1.26 (m, 1H), 1.17 (d, J=7.4 Hz, 3H), 1.12 (d, J=10.6 Hz, 9H), 1.07-0.83 (m, 4H), 0.81-0.65 (m, 2H), 0.52-0.44 (m, 1H).

Example 24

Preparation of (1aR,5S,8S,9S,10R,22aR)-5-tert-butyl-N-[(1R,2S)-1-[(cyclopropylsulfonoyl)carbamoyl]-2-(2,2-difluoroethyl)cyclopropyl]-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

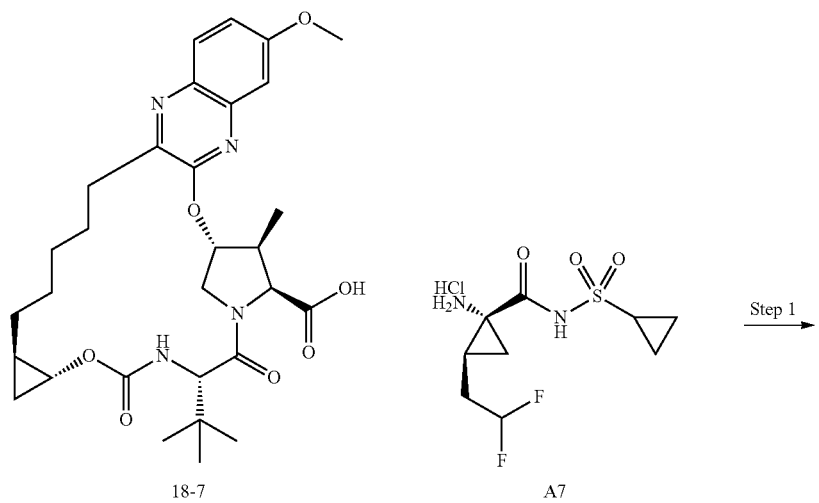

18-7        A7        Step 1

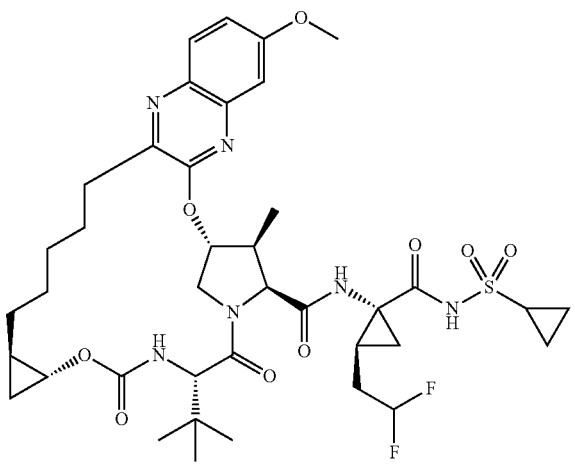

Example 24

Step 1. Preparation of Example 24: To a suspension of acid 18-7 (30.2 mg, 0.0531 mmol) and Intermediate A7 (25.9 mg, 0.0850 mmol) in MeCN (0.5 mL) was added DIPEA (60 µL, 0.34 mmol). To the resulting solution was added HATU (32 mg, 0.084 mmol). The reaction was stirred at rt for 75 min and an additional portion of Intermediate A7 (3.0 mg, 0.0098 mmol) was added. After an additional 30 min the reaction was diluted with EtOAc (30 mL), 0.2 M aqueous HCl (20 mL), and brine (10 mL). The phases were separated and the aqueous phase was extracted with EtOAc (30 mL). The combined organic phase was dried over $Na_2SO_4$, filtered, and concentrated to afford a crude residue that was dissolved in $CH_2Cl_2$ and adsorbed onto 2 g silica gel. Purification by silica gel chromatography (15% to 55% acetone in hexanes) provided a residue that was lyophilized from water and MeCN to provide Example 24 as a white amorphous solid (35.5 mg). Analytic HPLC RetTime: 8.62 min. LCMS-ESI$^+$ (m/z): [M+H]$^+$ calcd for $C_{39}H_{53}F_2N_6O_9S$: 819.4; found: 819.2. $^1$H NMR (400 MHz, CDCl$_3$) δ 9.99 (s, 1H), 7.82 (d, J=9.1 Hz, 1H), 7.19 (dd, J=9.1, 2.8 Hz, 1H), 7.08 (d, J=2.7 Hz, 1H), 6.69 (s, 1H), 5.99-5.64 (m, 1H), 5.56 (d, J=3.9 Hz, 1H), 5.40 (d, J=10.0 Hz, 1H), 4.47-4.39 (m, 3H), 4.14-4.08 (m, 1H), 3.93 (s, 3H), 3.78-3.72 (m, 1H), 2.96-2.67 (m, 4H), 2.29-2.16 (m, 2H), 1.83-1.24 (m, 12H), 1.15 (d, J=7.4 Hz, 3H), 1.09 (s, 9H), 1.05-0.82 (m, 4H), 0.74-0.63 (m, 1H), 0.53-0.42 (m, 1H).

Example 25

Preparation of (1aR,5S,8S,9S,10R,22aR)-5-tert-butyl-N-[(1R,2S)-2-(2,2-difluoroethyl)-1-{[(1-methylcyclopropyl)sulfonyl]carbamoyl}cyclopropyl]-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

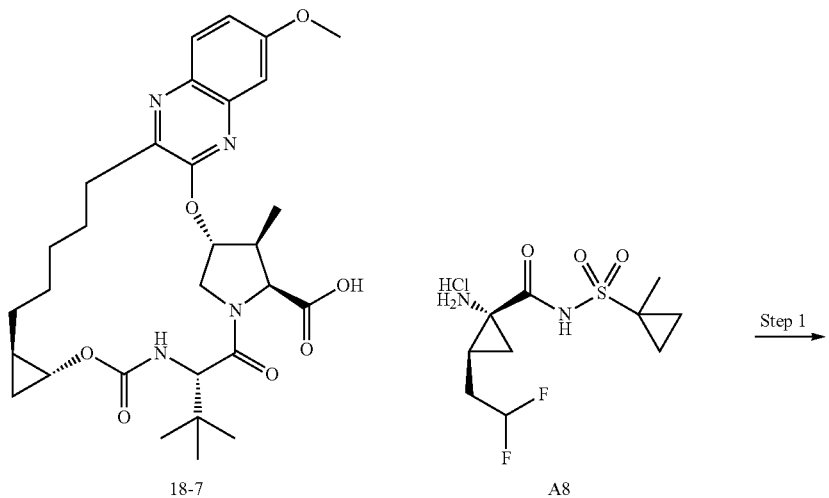

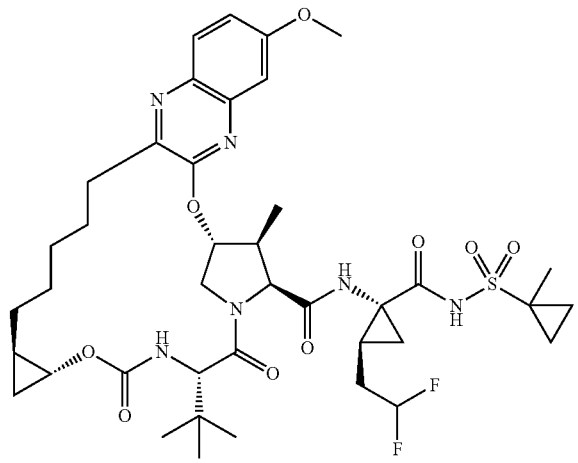

Example 25

Step 1. Preparation of Example 25: To a suspension of acid 18-7 (30.3 mg, 0.0532 mmol) and intermediate A8 (28.3 mg, 0.0887 mmol) in MeCN (0.5 mL) was added DIPEA (60 µL, 0.34 mmol). To the resulting solution was added HATU (32.4 mg, 0.0852 mmol). The reaction was stirred at rt for 2.5 h and was diluted with EtOAc (30 mL), 0.2 M aqueous HCl (20 mL), and brine (10 mL). The phases were separated and the aqueous phase was extracted with EtOAc (30 mL). The combined organic phase was dried over $Na_2SO_4$, filtered, and concentrated to afford a crude residue that was dissolved in $CH_2Cl_2$ and adsorbed onto 2 g silica gel. Purification by silica gel chromatography (15% to 55% acetone in hexanes) provided a residue that was lyophilized from water and MeCN to provide Example 25 as a white amorphous solid (33.9 mg). Analytic HPLC RetTime: 8.66 min. LCMS-ESI$^+$ (m/z): [M+H]$^+$ calcd for $C_{40}H_{55}F_2N_6O_9S$: 833.4; found: 833.4. $^1$H NMR (400 MHz, CDCl$_3$) δ 9.62 (s, 1H), 7.82 (d, J=9.1 Hz, 1H), 7.18 (dd, J=9.1, 2.8 Hz, 1H), 7.08 (d, J=2.7 Hz, 1H), 6.64 (s, 1H), 6.04-5.66 (m, 1H), 5.54 (d, J=4.0 Hz, 1H), 5.47 (d, J=10.0 Hz, 1H), 4.50-4.38 (m, 3H), 4.11 (dd, J=11.8, 4.2 Hz, 1H), 3.93 (s, 3H), 3.82-3.71 (m, 1H), 2.98-2.68 (m, 4H), 2.27-2.11 (m, 2H), 1.96-1.41 (m, 12H), 1.32 (dd, J=9.6, 5.4 Hz, 1H), 1.15 (d, J=7.4 Hz, 3H), 1.10 (s, 9H), 1.05-0.64 (m, 6H), 0.51-0.42 (m, 1H).

Example 26
Preparation of (1R,4S,4aR,8S,11S,12S,13R,25aR)-8-tert-butyl-N-[(1R,2R)-1-[(cyclopropylsulfonyl)carbamoyl]-2-(difluoromethyl)cyclopropyl]-17-methoxy-12-methyl-6,9-dioxo-2,3,4,4a,6,7,8,9,12,13,21,22,23,24,25,25a-hexadecahydro-1H,11H-1,4:10,13-dimethanoquinoxalino[2,3-k][1,10,3,6]benzodioxadiazacyclononadecine-11-carboxamide
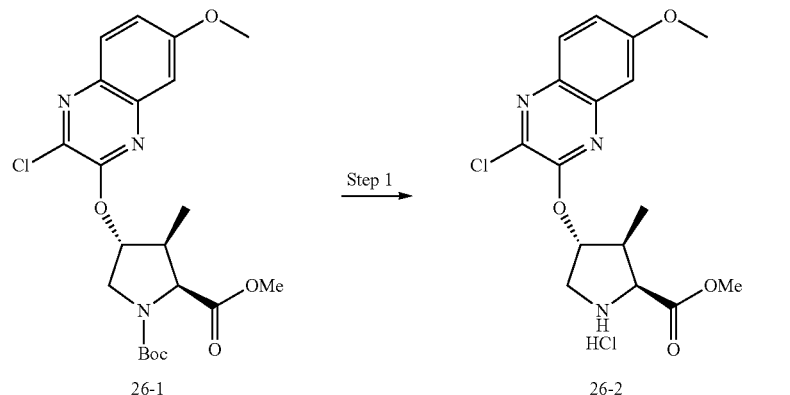
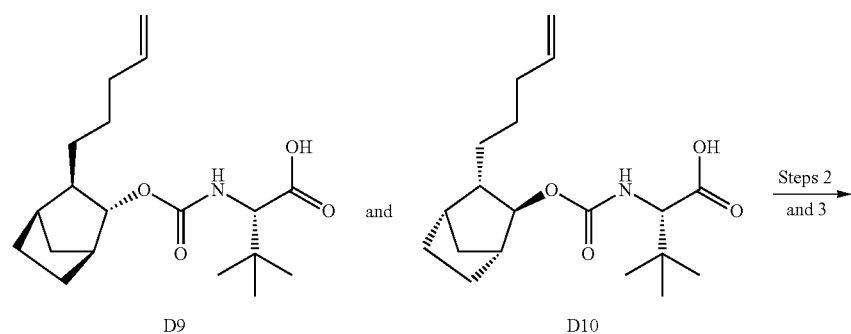
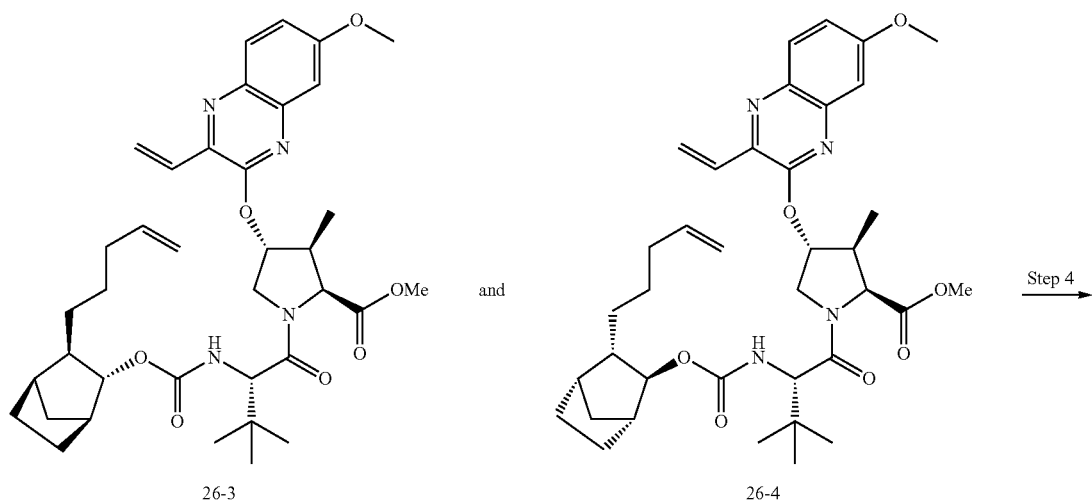

-continued

26-5

Steps 5 and 6 →

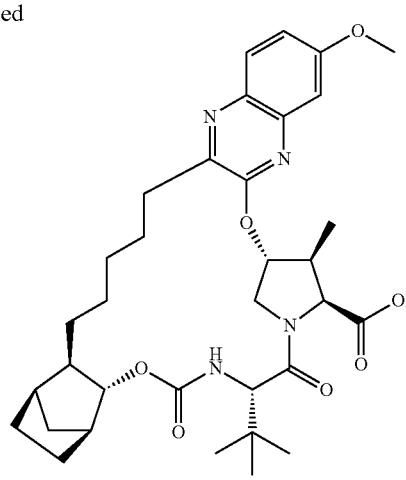

26-6

Step 7 →

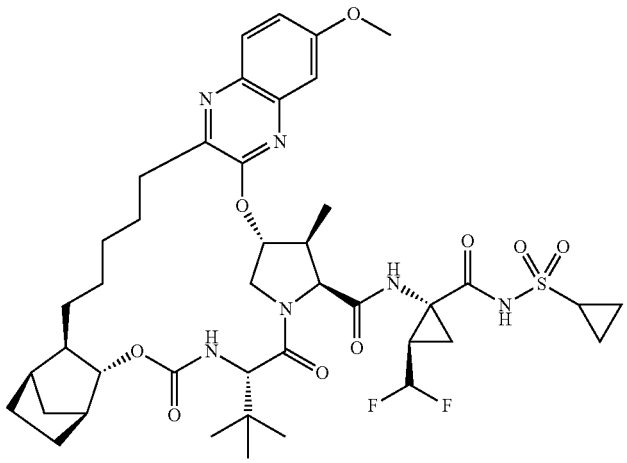

Example 26

Step 1. Preparation of 26-2: To a solution of 26-1 (311 mg, 0.710 mmol; prepared similarly to 18-1 of Example 18 substituting Intermediate B2 for Intermediate B1 in step 1) in dixane (1.8 mL) was added 4 M HCl in dioxane (1.8 mL, 7.2 mmol). The reaction was stirred for 15.5 h at rt and was than concentrated under reduced pressure to give 26-2 as a white amorphous solid that was used without further purification in the following step. LCMS-ESI$^+$ (m/z): [M+H]$^+$ calcd for $C_{16}H_{19}ClN_3O_4$: 352.1; found: 352.2.

Steps 2 and 3. Preparation of diastereomeric mixture 26-3 and 26-4: Amine hydrochloride 26-2 (0.710 mmol) was dissolved along with 1:1 mixture of Intermediate mixture D9 and D10 (266 mg, 0.788 mmol) and DIPEA (600 µL, 3.4 mmol) in DMF (4.5 mL). HATU (360 mg, 0.95 mmol) was added in one portion. The reaction was stirred 1.75 h at rt and was diluted with saturated aqueous NaHCO$_3$ (20 mL), water (10 mL) and EtOAc (30 mL). The phases were separated and the organic phase was washed twice with a mixture of water (30 mL) and brine (5 mL). The organic phase was dried over anhydrous Na$_2$SO$_4$, filtered and concentrated to a crude residue that was purified by silica gel chromatography (10% to 30% EtOAc in hexanes) to provide a colorless residue (380 mg; LCMS-ESI$^+$ (m/z): [M+H]$^+$ calcd for $C_{35}H_{48}ClN_4O_7$: 671.3; found: 671.6). A stirred heterogeneous mixture of this residue, PdCl$_2$(dppf).CH$_2$Cl$_2$ (35 mg, 0.043 mmol) and potassium vinyltrifluoroborate (156 mg, 1.16 mmol) in EtOH (7 mL) was sparged with argon for several minutes. Triethylamine (170 µL, 1.2 mmol) was added and the mixture was heated to 70° C. for 55 min. The reaction mixture was cooled to ambient temperature, diluted with EtOAc (40 mL), and washed with water (30 mL). The organics were dried over anhydrous Na$_2$SO$_4$, filtered and concentrated to afford a residue that was purified by silica gel chromatography (15% to 30% EtOAc in hexanes) to afford diastereomeric mixture 26-3 and 26-4 as a yellow residue (277 mg). LCMS-ESI$^+$ (m/z): [M+H]$^+$ calcd for $C_{37}H_{51}N_4O_7$: 663.4; found: 663.3.

Step 4. Preparation of 26-5: Diastereomeric mixture 26-3 and 26-4 (277 mg, 0.419 mmol) was dissolved in DCE (140 mL) and the solution was sparged with Ar for 15 min. Zhan 1B catalyst (37 mg, 0.050 mmol, Strem) was added and the resulting solution was stirred at 85° C. under Ar for 1.5 h. The reaction mixture was then concentrated and purified by silica gel chromatography (20% to 50% EtOAc in hexanes) to afford 26-5 as an amorphous residue (105 mg). LCMS-ESI$^+$ (m/z): [M+H]$^+$ calcd for $C_{35}H_{47}N_4O_7$: 635.3; found: 635.3.

Steps 5 and 6. Preparation of 26-6: To a solution of 26-5 (105 mg, 0.165 mmol) in 1:1 EtOAc:EtOH (4 mL) was added Pd/C (10 wt % Pd, 43 mg). The reaction vessel was purged twice with H$_2$ and was stirred at rt under 1 atm H$_2$ for 1 h. The reaction mixture was filtered through a pad of Celite and concentrated to afford a crude residue (106 mg; LCMS-ESI+ (m/z): [M+H]+ calcd for $C_{35}H_{49}N_4O_7$: 637.4; found: 637.3). This residue was then dissolved in THF (0.8 mL). MeOH (0.4 mL), water (0.4 mL) and LiOH.H$_2$O (67 mg, 1.6 mmol) were added and the mixture was stirred at 45° C. for 14.5 h. The reaction was quenched dropwise with 1 N aqueous HCl (1.3 mL) and was diluted with CH$_2$Cl$_2$ (30 mL) and 1 N aqueous HCl (20 mL). The phases were separated, and the aqueous phase was extracted with CH$_2$Cl$_2$ (30 mL). The combined organic phase was dried over MgSO$_4$, filtered and concentrated to afford 26-6 as a residue (93.8 mg) that was used directly in Step 7. LCMS-ESI+ (m/z): [M+H]+ calcd for $C_{34}H_{47}N_4O_7$: 623.3; found: 623.3.

Step 7. Preparation of Example 26: To a suspension of acid 26-6 (93.8 mg, 0.151 mmol) and Intermediate A9 (58 mg, 0.20 mmol) in MeCN was added DIPEA (120 µL, 0.69 mmol). To the resulting solution was added HATU (73.5 mg, 0.193 mmol). The reaction was stirred at rt for 100 min and an additional portion of Intermediate A9 (6 mg, 0.02 mmol) was added. After an additional 30 min, additional Intermediate A9 (9 mg, 0.03 mmol), HATU (9 mg, 0.02 mmol) and DIPEA (10 µL, 0.06 mmol) were added. The reaction was stirred for an additional 50 min and was diluted with EtOAc (25 mL), 0.2 M aqueous HCl (20 mL) and brine (10 mL). The phases were separated and the aqueous phase was extracted with EtOAc (25 mL). The combined organic phase was dried over Na$_2$SO$_4$, filtered, and concentrated to afford a crude residue. Purification by silica gel chromatography (25% to 40% acetone in hexanes) provided an amorphous residue that was lyophilized from water and MeCN to provide Example 26 as a white amorphous solid (113 mg). Analytic HPLC RetTime: 9.19 min. LCMS-ESI+ (m/z): [M+H]+ calcd for $C_{42}H_{57}F_2N_6O_9S$: 859.4; found: 859.2. $^1$H NMR (400 MHz, CDCl$_3$) δ 10.02 (s, 1H), 7.80 (d, J=9.1 Hz, 1H), 7.21-7.15 (m, 2H), 7.07 (d, J=2.7 Hz, 1H), 6.13-5.79 (m, 1H), 5.63 (d, J=10.1 Hz, 1H), 5.50-5.45 (m, 1H), 4.51 (d, J=10.1 Hz, 1H), 4.44 (d, J=7.4 Hz, 1H), 4.25 (s, 1H), 4.18-4.12 (m, 2H), 3.93 (s, 3H), 3.02-2.77 (m 3H), 2.66-2.57 (m, 1H), 2.18-0.90 (m, 36H).

Example 27

Preparation of (3aR,7S10S,1S,12R,24aR)-7-tert-butyl-N-[(1R,2R)-2-(difluoromethyl)-1-{[(1-methyl-cyclopropyl)sulfonyl]carbamoyl}cyclopropyl]-16-methoxy-11-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide

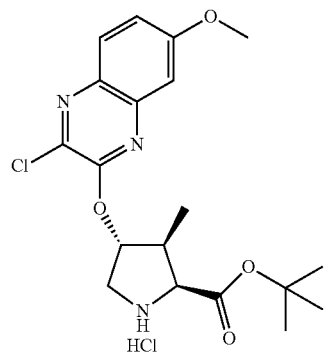

26-2

→ Step 1

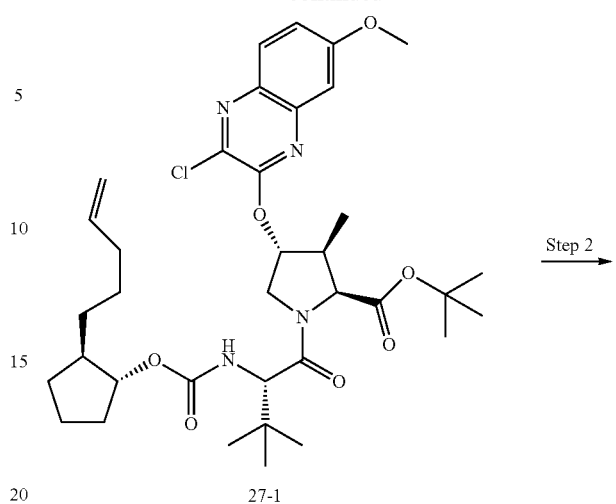

27-1

→ Step 2

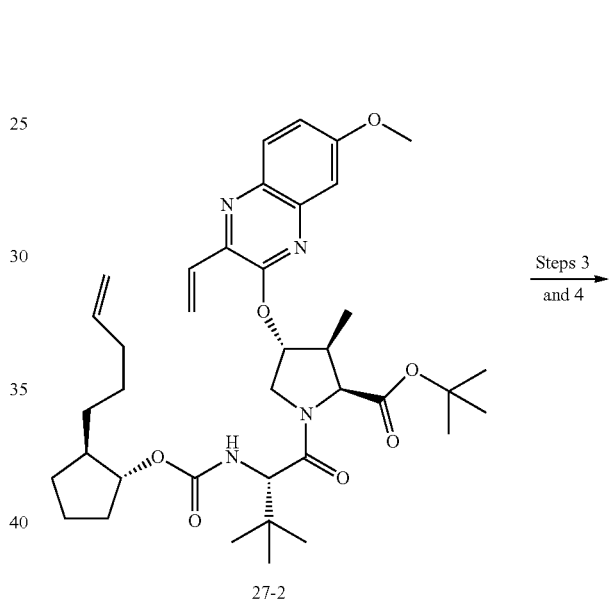

27-2

→ Steps 3 and 4

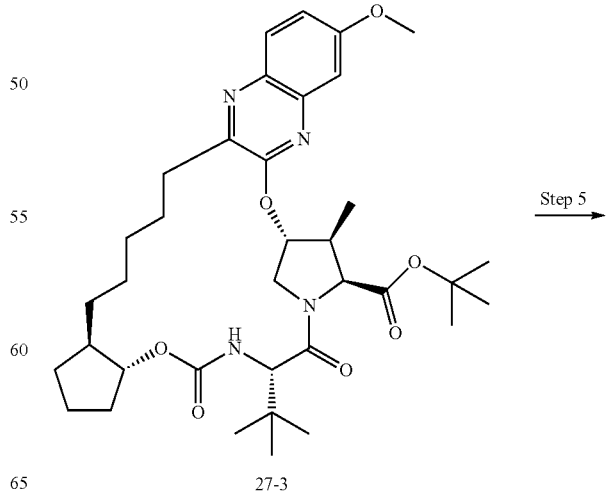

27-3

→ Step 5

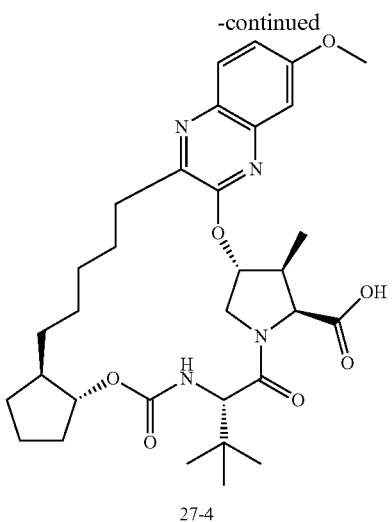

27-4

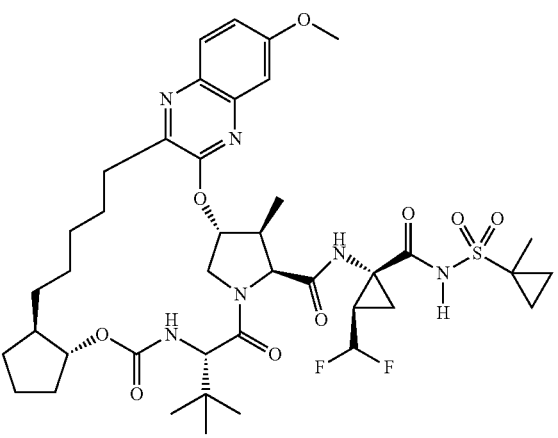

Example 27

Step 1. Preparation of 27-1: Amine hydrochloride 26-2 (217 mg, 0.504 mmol), was treated with BEP (207 mg, 0.756 mmol), Intermediate D5 (283 mg, 0.909 mmol), EtOAc (9 mL). NMP (1 mL) and DIPEA (0.44 mL, 2.5 mmol), then heated to 50° C. After 1.5 h, the reaction mixture was diluted with EtOAc. The organic solution was washed successively with saturated aqueous $NaHCO_3$ and brine, then dried over $MgSO_4$, filtered and concentrated under reduced pressure. The residue was purified by silica gel chromatography (9% to 40% EtOAc/Hex) to afford amide 27-1 (235 mg). LCMS-ESI$^+$ (m/z): [M+H]$^+$ calcd for $C_{36}H_{52}ClN_4O_7$: 687.35; found: 688.13.

Step 2. Preparation of 27-2: Amide 27-1 (235 mg, 0.342 mmol) was treated with potassium vinyltrifluoroborate (69 mg, 0.513 mmol), Pd(dppf).Cl$_2$.DCM (28 mg, 0.0342 mmol), EtOH (3.4 mL) and TEA (0.072 mL, 0.513 mmol), then heated to reflux. After 50 min, the reaction mixture was diluted with EtOAc and washed with $H_2O$ and brine. The organics were dried over $MgSO_4$, filtered and concentrated under reduced pressure. The residue was purified by silica gel chromatography (9% to 40% EtOAc/Hex) to afford vinyl quinoxaline 27-2 (219 mg). LCMS-ESI$^+$ (m/z): [M+H]$^+$ calcd for $C_{38}H_{55}N_4O_7$: 679.41; found: 679.49.

Steps 3 and 4. Preparation of 27-3: Vinyl quinoxaline 27-2 (219 mg, 0.323 mmol) was suspended in DCE (65 mL) and treated with Zhan 1B catalyst (41 mg, 0.065 mmol. Strem). The suspension was deoxygenated with bubbling $N_2$ for 17 min, then heated to reflux for 90 min. The reaction mixture was then filtered over Celite and concentrated under reduced pressure. The crude residue was purified by silica gel chromatography (15% to 50% EtOAc/Hex) to afford the desired macrocycle (165 mg; LCMS-ESI$^+$ (m/z): [M+H]$^+$ calcd for $C_{36}H_{51}N_4O_7$: 651.38; found 651.40). The macrocyclic product of step 3 was dissolved in EtOH (10 mL) and EtOAc (2 mL) and treated with 10 wt % Pd/C (95 mg). Hydrogen from a balloon was bubbled through the suspension for 1 min and the mixture was stirred under $H_2$ (1 atm) for an additional 1.5 h. The reaction mixture was filtered over Celite and concentrated under reduced pressure to afford the desired macrocycle 27-3 which was carried on without further purification. LCMS-ESI$^+$ (m/z) [M+H]$^+$ calcd for $C_{36}H_{53}N_4O_7$: 653.39; found: 653.32.

Step 5. Preparation of 27-4: The crude product of step 4 was dissolved in DCM and treated with TMSOTf (0.23 mL, 1.3 mmol). After stirring at rt for 1 h 15 min, the reaction mixture was concentrated under reduced pressure. The residue was redissolved in DCM and added by pipette to a separatory funnel containing 1 M aqueous NaOH. The mixture was agitated for 1 min, then acidified to pH 1~2 with 10% aqueous HCl. The aqueous layer was extracted three times with DCM and combined organics dried over $MgSO_4$, filtered and concentrated under reduced pressure. The crude material was purified by silica gel chromatography to afford carboxylic acid 27-4 (119 mg). LCMS-ESI$^+$ (m/z): [M+H]$^+$ calcd for $C_{32}H_{45}N_4O_7$: 597.33; found: 597.40.

Step 6. Preparation of Example 27: Carboxylic acid 27-4 (105 mg, 0.177 mmol) and Intermediate A10 (65 mg, 0.212 mmol) were treated with TBTU (68 mg, 0.212 mmol), DMAP (26 mg, 0.212 mmol), DCM (1.8 mL) and DIPEA (0.31 mL 1.8 mmol). The reaction mixture was stirred at rt for 30 min, then more amine A10 (40 mg, 0.131 mmol) was added and the reaction mixture was heated to reflux. After an additional 1.25 h, the mixture was concentrated under reduced pressure. The crude residue was purified by HPLC to afford Example 27 (80 mg) in approximately 90% purity as a TFA salt. Analytic HPLC RetTime: 9.06 min. LCMS-ESI$^+$ (m/z): [M+H]$^+$ calcd for $C_{41}H_{57}F_2N_6O_9S$: 847.39; found: 847.69. $^1$H NMR (400 MHz, CD$_3$OD) δ 9.23 (s, 1H), 7.87-7.72 (m, 1H), 7.31-7.14 (m, 2H), 5.84 (td, J=55.6, 6.5 Hz, 1H), 5.58 (d, J=22.6 Hz, 1H), 4.94-4.81 (m, 1H), 4.37 (d, J=15.8 Hz, 1H), 4.29-4.10 (m, 2H), 3.94 (s, 3H), 3.01 (ddd, J=15.1, 9.9, 5.3 Hz, 1H), 2.84 (p, J=7.4 Hz, 1H), 2.75 (ddd, J=13.3, 10.2, 6.0 Hz, 1H), 2.03 (d, J=9.0 Hz, 2H), 1.97-1.74 (m, 4H), 1.73-1.55 (m, 6H), 1.53 (s, 3H), 1.48-1.21 (m, 8H), 1.19-1.02 (m, 14H), 0.99-0.80 (m, 2H).

Example 28

Preparation of (3aR,7S,10S,11S,12R,24aR)-7-tert-butyl-N-[(1R,2R)-1-[(cyclopropylsulfonyl)carbamoyl]-2-(difluoromethyl)cyclopropyl]-16-methoxy-11-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide

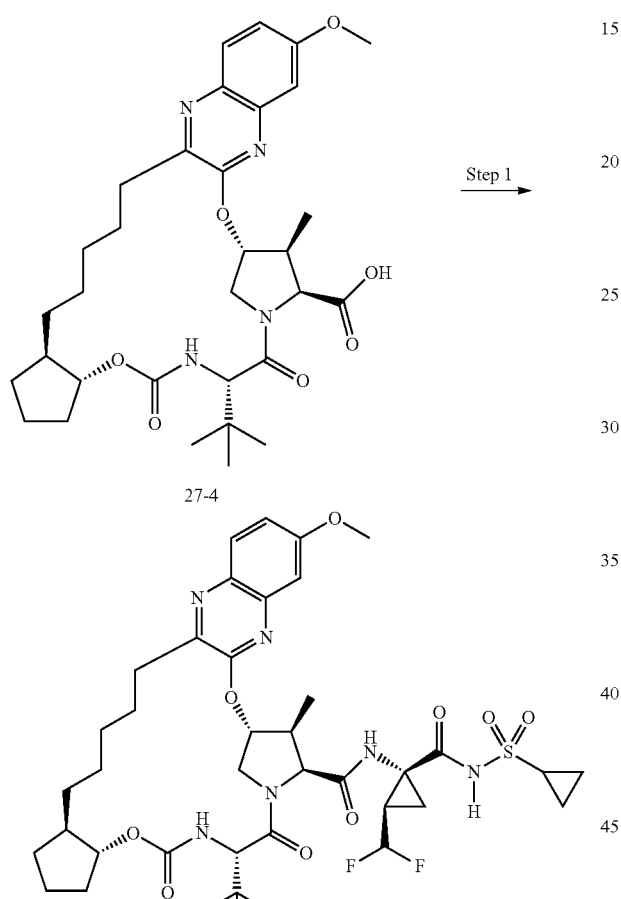

Example 28

Step 1. Carboxylic acid 27-4 (20 mg, 0.034 mmol) and Intermediate A9 (35 mg, 0.12 mmol) were treated with TBTU (22 mg, 0.067 mmol), DMAP (8 mg, 0.07 mmol), DCM (1 mL) and DIPEA (0.117 mL, 0.674 mmol). The reaction mixture was stirred at rt for 15 h, then concentrated under reduced pressure. The crude residue was purified by HPLC to afford Example 28 (22 mg) in approximately 90% purity as a TFA salt. Analytic HPLC RetTime: 8.90 min. LCMS-ESI+ (m/z): [M+H]+ calcd for $C_{40}H_{55}F_2N_6O_9S$: 833.37; found: 833.61. $^1$H NMR (400 MHz, CD$_3$OD) δ 9.23 (s, 1H), 7.79 (d, J=8.8 Hz, 1H), 7.34-7.10 (m, 2H), 5.86 (td, J=55.8, 6.5 Hz, 1H), 5.61 (s, 1H), 4.54 (t, J=9.7 Hz, 1H), 4.36 (d, J=16.5 Hz, 1H), 4.28-4.07 (m, 2H), 3.95 (d, J=17.8 Hz, 3H), 3.08-2.91 (m, 2H), 2.90-2.79 (m, 1H), 2.73 (ddd, J=13.3, 10.3, 6.0 Hz, 1H), 2.04 (s, 2H), 1.97-1.74 (m, 4H), 1.64 (ddd, J=18.7, 11.6, 4.0 Hz, 4H), 1.49-1.19 (m, 11H), 1.18-0.94 (m, 14H), 0.94-0.80 (m, 1H).

Example 29

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-14-methoxy-3,6-dioxo-9-propyl-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

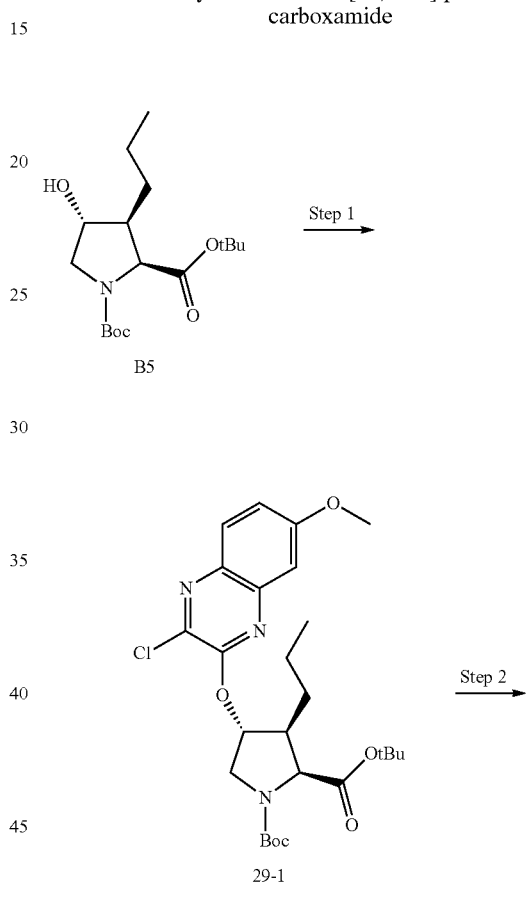

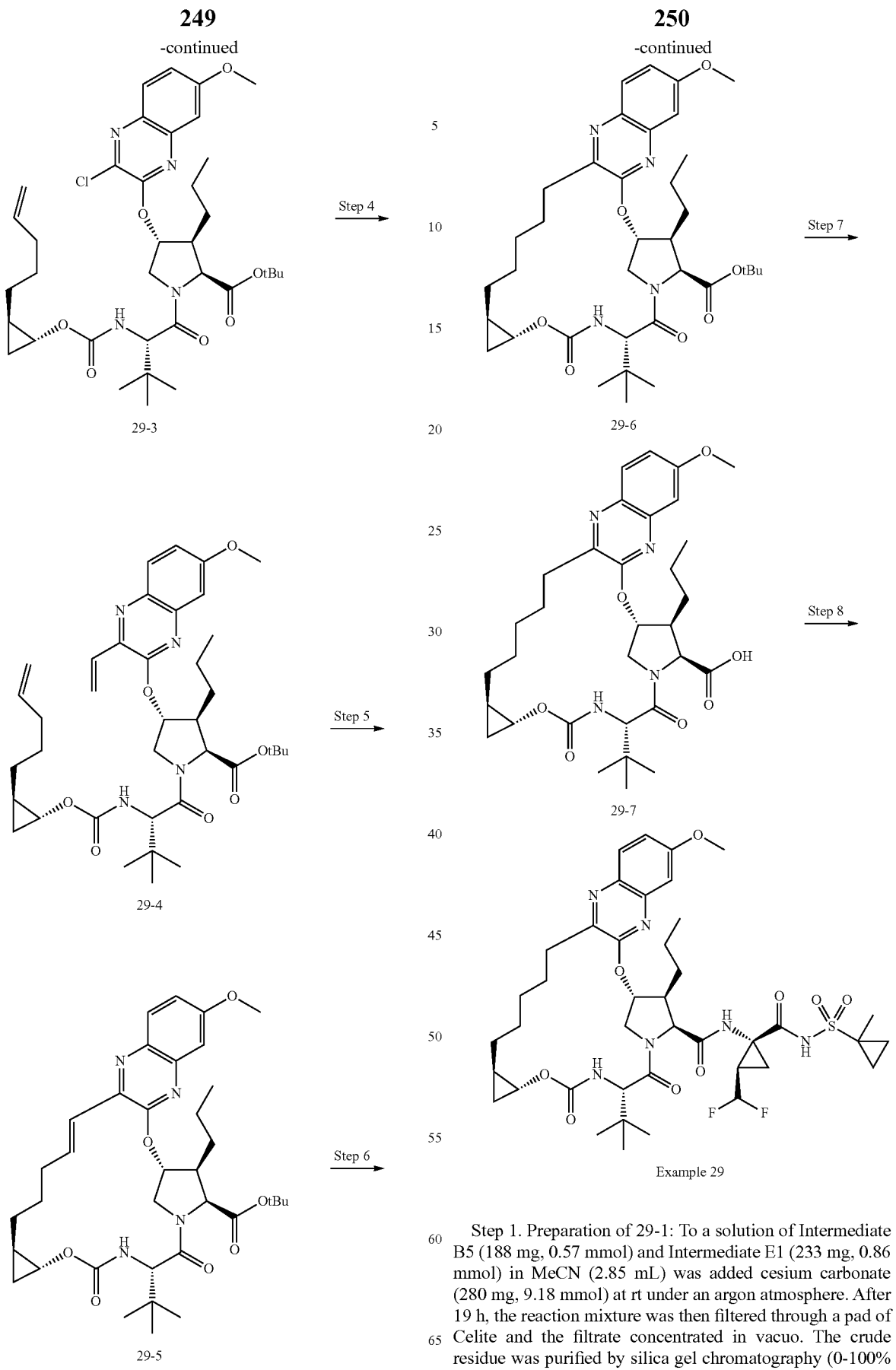

Step 1. Preparation of 29-1: To a solution of Intermediate B5 (188 mg, 0.57 mmol) and Intermediate E1 (233 mg, 0.86 mmol) in MeCN (2.85 mL) was added cesium carbonate (280 mg, 9.18 mmol) at rt under an argon atmosphere. After 19 h, the reaction mixture was then filtered through a pad of Celite and the filtrate concentrated in vacuo. The crude residue was purified by silica gel chromatography (0-100% ethyl acetate/hexanes gradient) to afford substituted quinoxaline 29-1 (240 mg) as a colorless oil, LCMS-ESI⁺ (m/z): [M+H]⁺ calcd for $C_{26}H_{37}ClN_3O_6$: 522.2; found: 522.3.

Step 2. Preparation of 29-2: To a solution 29-1 (240 mg, 0.46 mmol) in dioxane (1 mL) was added 4 M hydrochloric acid in dioxane (4 mL, 1 mmol) and the reaction stirred at rt. After 15 h, the reaction mixture was concentrated in vacuo to afford amine hydrochloride 29-2 (200 mg) as an off white solid, which was used directly in the next step without further purification. LCMS-ESI⁺ (m/z): [M+H]⁺ calcd for $C_{21}H_{29}ClN_3O_4$: 422.2; found: 422.2.

Step 3. Preparation of 29-3: To a solution of 29-2 (200 mg, 0.46 mmol) and Intermediate D1 (170 mg, 0.51 mmol) in MeCN (2.3 mL) was added HATU (192 mg, 0.51 mmol) followed by DIPEA (400 µL, 2.30 mmol) at rt under and argon atmosphere. After 1.5 h, the reaction mixture was concentrated in vacuo, and the crude residue was purified by silica gel chromatography (0-100% ethyl acetate/hexanes gradient) to afford amide 29-3 (67 mg) as a colorless oil. LCMS-ESI⁺ (m/z): [M+H]⁺ calcd for $C_{36}H_{52}ClN_4O_7$: 687.3; found: 687.5.

Step 4. Preparation of 29-4: To a solution of 29-3 (67 mg, 98 µmol), TEA (20 µL, 150 µmol) and potassium vinyltrifluoroborate (19.7 mg, 150 µmol) in EtOH (500 µL) was added PdCl₂(dppf) (8 mg, 9.8 µmol). The reaction mixture was deoxygenated with argon for 10 min and was heated to 78° C. After 40 min, the reaction mixture was allowed to cool to rt and was concentrated in vacuo. The crude residue was purified by silica gel chromatography (0-100% ethyl acetate/hexanes gradient) to afford vinyl quinoxaline 29-4 (40.2 mg) as a colorless oil. LCMS-ESI⁺ (m/z): [M+H]⁺ calcd for $C_{36}H_{55}N_4O_7$: 679.4; found: 679.6.

Step 5. Preparation of 29-5: To a solution of 29-4 (40 mg, 59 µmol) in DCE (11.8 mL) was added Zhan 1B catalyst (4 mg, 6 µmol, Strem) and the reaction mixture was degassed for 10 minutes with argon. The reaction mixture was then heated to 100° C. After 1 h, the reaction mixture was allowed to cool to rt and was concentrated in vacuo. The crude residue was purified by silica gel chromatography (0-100% ethyl acetate/hexanes gradient) to afford macrocycle 29-5 (31 mg) as a light yellow oil. LCMS-ESI⁺ (m/z): [M+H]⁺ calcd for $C_{36}H_{51}N_4O_7$: 651.4; found: 651.5.

Step 6. Preparation of macrocycle 29-6: To a solution of macrocycle 29-5 (31 mg, 47 µmol) in ethanol (500 µL) was added Pd/C (10 wt %, 5 mg, 5 µmol) at rt under an argon atmosphere. The reaction vessel was evacuated and refilled with 1 atm hydrogen gas (3×) and the reaction mixture was stirred vigorously at rt. After 1 h, the reaction mixture was diluted with ethyl acetate (10 mL) and was filtered through a pad of Celite with ethyl acetate washings (3×5 mL). The filtrate was concentrated in vacuo to afford macrocycle 29-6 (31 mg), which was used directly in the next step without further purification. LCMS-ESI⁺ (m/z): [M+H]⁺ calcd for $C_{36}H_{53}N_4O_7$: 653.4; found: 653.5.

Step 7. Preparation of 29-7: To a solution of 29-6 (31 mg, 47 µmol) in DCM (0.5 mL) was added TMSOTf (44 µL, 0.25 mmol) at rt under an argon atmosphere. After 25 min, the reaction mixture was concentrated in vacuo and was azeotropically dried from toluene (2×2 mL) to afford carboxylic acid 29-7 (35 mg) as a yellow oil, which was used directly in the next step without further purification. LCMS-ESI⁺ (m/z): [M+H]⁺ calcd for $C_{32}H_{45}N_4O_7$: 597.3; found: 597.4.

Step 8. Preparation of Example 29: To a solution of 29-7 (35 mg, 49 µmol) and Intermediate A10 (22 mg, 74 µmol) in MeCN (245 µL) was added HATU (28 mg, 74 µmol) followed by DIPEA (43 µL, 250 µmol) at rt under an argon atmosphere. After 3 h, the reaction mixture was concentrated in vacuo, was purified by preparatory HPLC (Gemini 5u C18 110 Å column, 5-100% MeCN/H₂O, 0.1% trifluoroacetic acid modifier) and was lyophilized to afford Example 29 (22.3 mg) as a white powder TFA salt. Analytic HPLC RetTime: 8.81 min. LCMS-ESI⁺ (m/z): [M+H]⁺ calcd for $C_{41}H_{56}F_2N_6O_9S$: 847.4; found: 847.5. ¹H, NMR (400 MHz, CDCl₃) δ 9.83 (d, J=9.4 Hz, 1H), 7.93 (d, J=9.1 Hz, 1H), 7.36 (d, J=9.1 Hz, 1H), 7.21 (d, J=11.0 Hz, 1H), 7.14 (s, 1H), 5.97 (td, $J_{H-F}$=55 Hz, J=7.2 Hz, 1H), 5.84 (br s, 1H), 5.41 (d, J=9.4 Hz, 1H) 4.66-4.34 (m, 3H), 4.13 (app d, J=11.8 Hz, 1H), 4.08 (s, 1H), 3.97 (s, 3H), 3.78-3.71 (m, 1H), 3.09-2.65 (m, 5H), 2.14-2.04 (m, 1H), 1.87-1.34 (m, 8H), 1.52 (s, 3H), 1.12 (s, 9H), 1.08-0.84 (m, 10H), 0.76-0.62 (m, 1H), 0.50 (dd, J=12.6, 6.6 Hz, 1H).

Example 30

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-14-methoxy-9-(2-methylpropyl)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

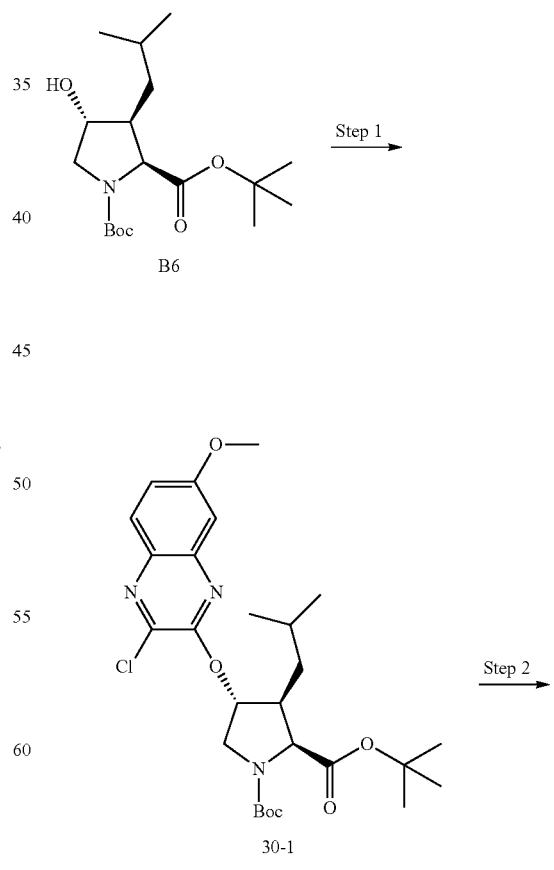

253
-continued
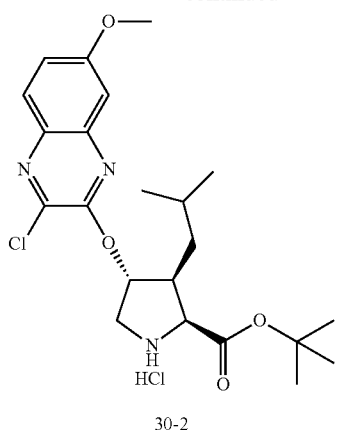
30-2
Step 3 →
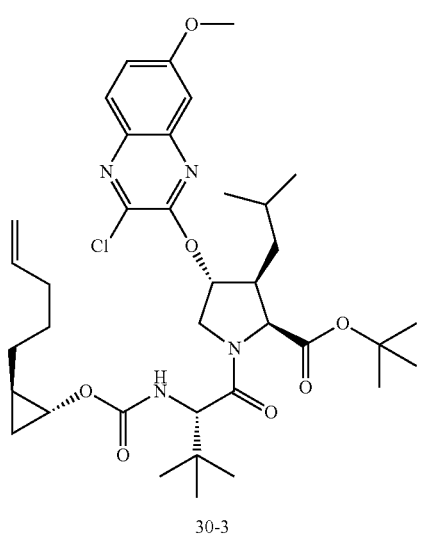
30-3
Step 4 →
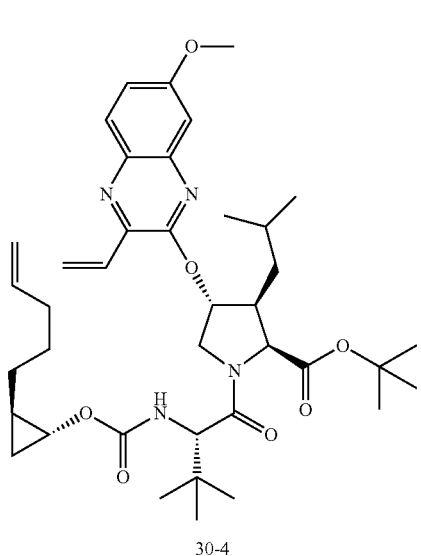
30-4
Step 5 →
254
-continued
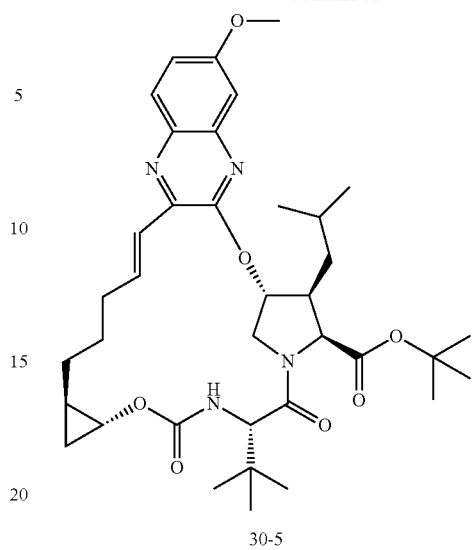
30-5
Step 6 →
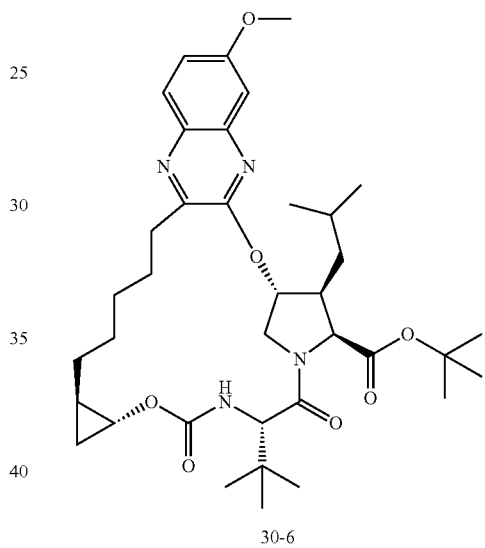
30-6
Step 7 →
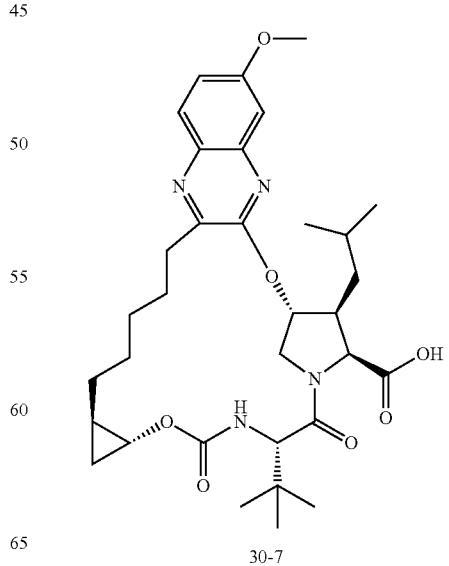
30-7
Step 8 →

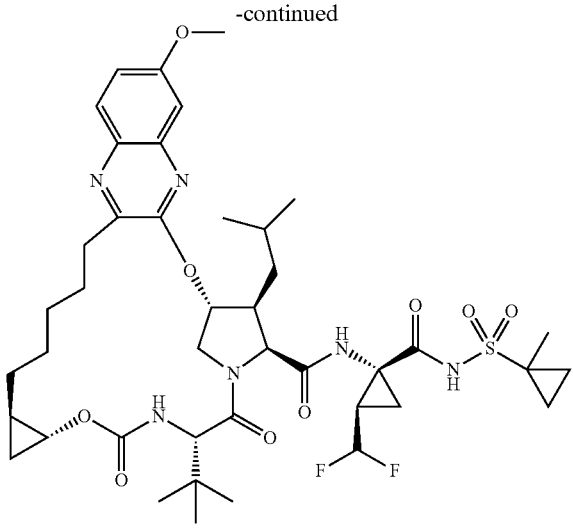

Example 30

Step 1. Preparation of 30-1: A mixture of Intermediate B6 (139 mg, 0.405 mmol), Intermediate E1 (170 mg, 0.625 mmol), and cesium carbonate (203 mg, 0.623 mmol) in 3.3 mL of acetonitrile was stirred at room temperature under argon overnight. Reaction mixture was filtered over Celite, washing with ethyl acetate, and filtrate was concentrated under reduced pressure. The resulting residue was purified by silica gel chromatography (0-30% ethyl acetate in hexanes) to yield 30-1 (170 mg) as a clear film. LCMS-ESI$^+$ (m/z): [M+H]$^+$ calcd for $C_{27}H_{39}ClN_3O_6$: 536.24; found: 536.31.

Step 2. Preparation of 30-2: A solution of hydrogen chloride in dioxane (4.0 M, 0.16 mL, 0.64 mmol) was added to a solution of 30-1 (168 mg, 0.314 mmol) in 3.3 mL of dioxane at room temperature. After thirty minutes, an additional 4 equivalents of HCl was added and mixture was stirred overnight. An additional 25 equivalents of HCl was then added. After thirty minutes, an additional 19 equivalents of HCl was added. After one hour, an additional 29 equivalents of HCl was added. After thirty minutes, reaction mixture was concentrated under reduced pressure to yield 30-2 (148 mg, 85% purity), which was used in the next step without further purification. LCMS-ESI$^+$ (m/z): [M+H]$^+$ calcd for $C_{22}H_{31}ClN_3O_4$ 436.19; found: 436.25.

Step 3. Preparation of 30-3: HATU (144 mg, 0.379 mmol, Oakwood) and DIPEA (0.28 mL, 1.58 mmol) were added to a mixture of 30-2 (148 mg, 0.315 mmol) and Intermediate D1 (99 mg, 0.348 mmol) in 3.5 mL of DMF under argon. After stirring overnight, reaction mixture was poured into water and extracted with ethyl acetate (3×). Combined organics were washed with water and brine, dried (MgSO$_4$), filtered, and concentrated under reduced pressure. The resulting residue was purified by silica gel chromatography (0-50% ethyl acetate in hexanes) to yield 30-3 (136 mg) as a white solid LCMS-ESI$^+$ (m/z): [M+H]$^+$ calcd for $C_{37}H_{54}ClN_4O_7$: 701.36; found: 701.47.

Step 4. Preparation of 30-4: Pd(dppf)$_2$Cl$_2$·CH$_2$C$_2$ (35 mg, 0.043 mmol) was added to a degassed mixture of 30-3 (135 mg, 0.193 mmol), potassium vinyltrifluoroborate (41 mg, 0.306 mmol), and triethylamine (0.040 mL, 0.289 mmol) in 2.1 mL of ethanol at room temperature. Reaction mixture was heated at 78° C. under argon for 45 minutes. After cooling to room temperature, reaction mixture was poured into water and extracted with ethyl acetate (three times). Combined organics were washed with water and brine, dried (MgSO$_4$), filtered, and concentrated under reduced pressure to yield 30-4 (133 mg), which was used in the next step without further purification. LCMS-ESI$^+$ (m/z): [M+H]$^+$ calcd for $C_{39}H_{57}N_4O_7$: 693.41; found: 693.48.

Step 5. Preparation of 30-5: A mixture of 30-4 (133 mg, 0.192 mmol) and Zhan 1B catalyst (16 mg, 0.022 mmol, Strem) in 38 mL of DCE was deoxygenated under argon for 25 minutes. The mixture was then heated at 95° C. for 50 minutes. After cooling to room temperature, reaction mixture was concentrated under reduced pressure. The resulting residue was purified by silica gel chromatography (0-50% ethyl acetate in hexanes) to yield 30-5 (70 mg) as a light yellow film. LCMS-ESI$^+$ (m/z). [M+H]$^+$ calcd for $C_{37}H_{53}N_4O_7$: 665.38; found: 665.50.

Step 6. Preparation of 30-6: Palladium on carbon (10 wt % Pd, 22 mg, 0.0208 mmol) was added to a solution of 30-5 (69 mg, 0.104 mmol) in 3 mL of ethanol. Mixture was then stirred under an atmosphere of hydrogen for 1 hour and then was filtered over Celite, washing with ethyl acetate. Filtrate was concentrated under reduced pressure to yield 30-6 (64 mg) as a light yellow-brown solid film, which was used in the next step without further purification. LCMS-ESI$^+$ (m/z): [M+H]$^+$ calcd for $C_{37}H_{55}N_4O_7$: 667.40; found: 667.43.

Step 7. Preparation of 30-7: TMSOTf (0.050 mL, 0.274 mmol) was added dropwise to a solution of 30-6 (30 mg, 0.045 mmol) in 1.2 mL of dichloromethane under argon at room temperature After 45 minutes, reaction mixture was concentrated under reduced pressure. The resulting film was taken up in 5 mL of toluene and concentrated under reduced pressure. This process was repeated a second time to yield 30-7 (27 mg), which was used in the next step without further purification. LCMS-ESI$^+$ (m/z): [M+H]$^+$ calcd for $C_{33}H_{47}N_4O_7$: 611.34; found: 611.41.

Step 8. Preparation of Example 30: HATU (28 mg, 0.074 mmol, Oakwood) and DIPEA (0.050 mL, 0.281 mmol) were added to a mixture of 30-7 (27 mg, 0.045 mmol) and Intermediate A10 (22 mg, 0.072 mmol) in 2.2 mL of acetonitrile under argon. After stirring overnight, reaction mixture was poured into water and extracted with ethyl acetate (3×). Combined organics were washed with water and brine, dried (MgSO$_4$), filtered, and concentrated under reduced pressure. The resulting residue was purified by silica gel chromatography (0-50% ethyl acetate in hexanes) and reverse phase prep HPLC (15-100% acetonitrile in water, with 0.1% trifluoroacetic acid buffer) to yield the trifluoroacetic acid salt of Example 30 (18 mg) as a light yellow solid, after lyophilization. Analytic HPLC RetTime: 8.96 min. LCMS-ESI$^+$ (m/z): [M+H]$^+$ calcd for $C_{42}H_{59}F_2N_6O_9S$: 861.40; found: 861.30. $^1$H NMR (400 MHz, CD$_3$OD): δ 9.17 (s, 1H), 7.80 (d, J=8.8 Hz, 1H), 7.23 (dd, J=8.8, 2.8 Hz, 1H), 7.14 (d, J=2.8 Hz, 1H), 5.81 (td, $J_{H-F}$=56 Hz, J=7.6 Hz, 1H); 5.77 (d, J=3.2 Hz, 1H), 4.55 (d. J=7.2 Hz, 1H), 4.39 (t, J=5.6 Hz, 2H), 4.16 (dd, J=11.8, 4 Hz, 1H), 3.91 (s, 3H), 3.79-3.71 (m, 1H), 2.98-2.90 (m, 1H), 2.84 (dd, J=12.6, 4.8 Hz, 1H), 279-2.72 (m, 1H), 2.06-1.91 (m, 3H), 1.77 (m, 3H), 1.64-1.44 (m, 6H), 1.51 (s, 3H), 1.44-1.32 (m, 3H), 1.15-1.07 (m, 1H), 1.10 (s, 9H), 1.06-0.96 (m, 3H), 1.04-1.01 (m, 6H), 0.93-0.89 (m, 2H), 0.79-0.68 (m, 1H), 0.52-0.47 (m, 1H).

Example 31
Preparation of (1aR,5S,8S,9S,10R,22aR)-5-tert-butyl-9-cyclopropyl-N-[(1R,2R)-2-(difluoromethyl)-1-{[(1-methylcyclopropyl)sulfonyl]carbamoyl}cyclopropyl]-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide
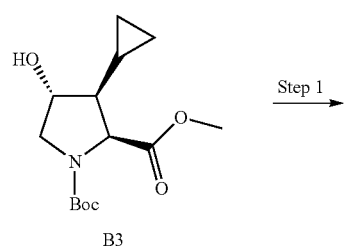
B3
Step 1 →
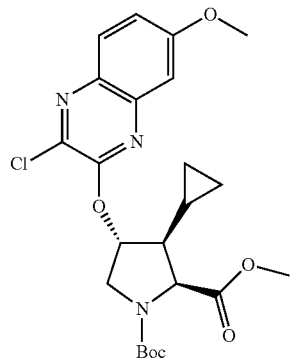
31-1
Step 2 →
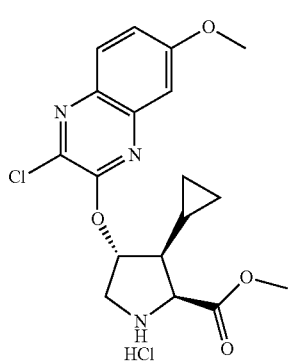
31-2
Step 3 →
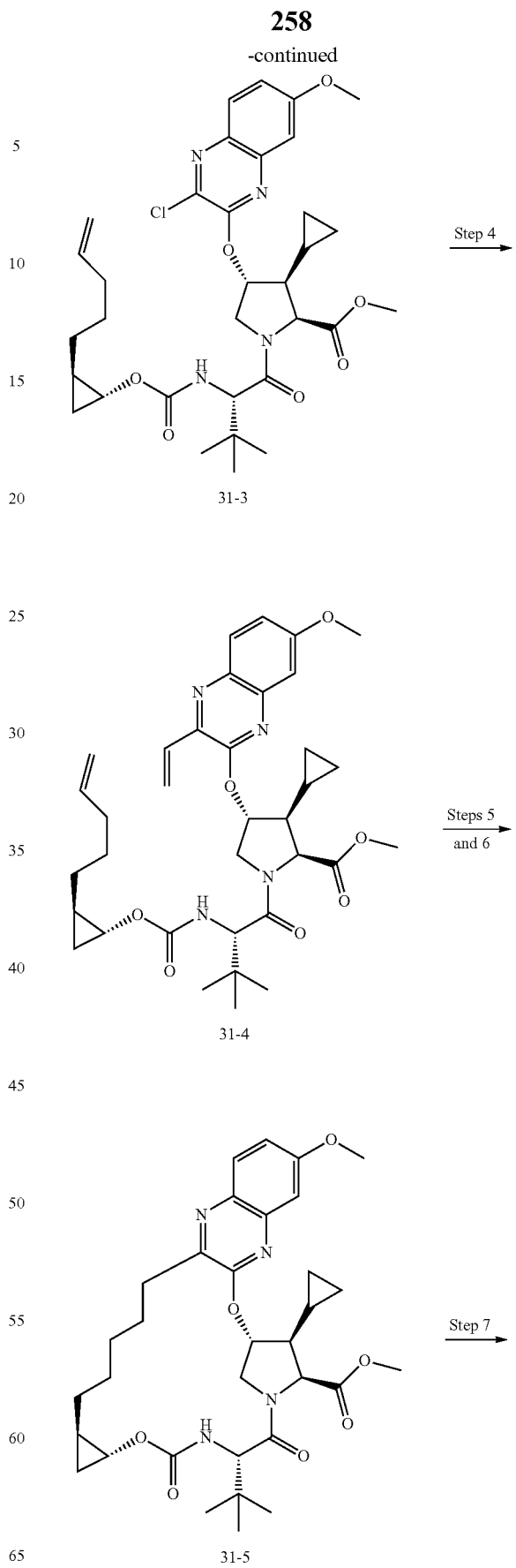
31-3
Step 4 →
31-4
Steps 5 and 6 →
31-5
Step 7 →

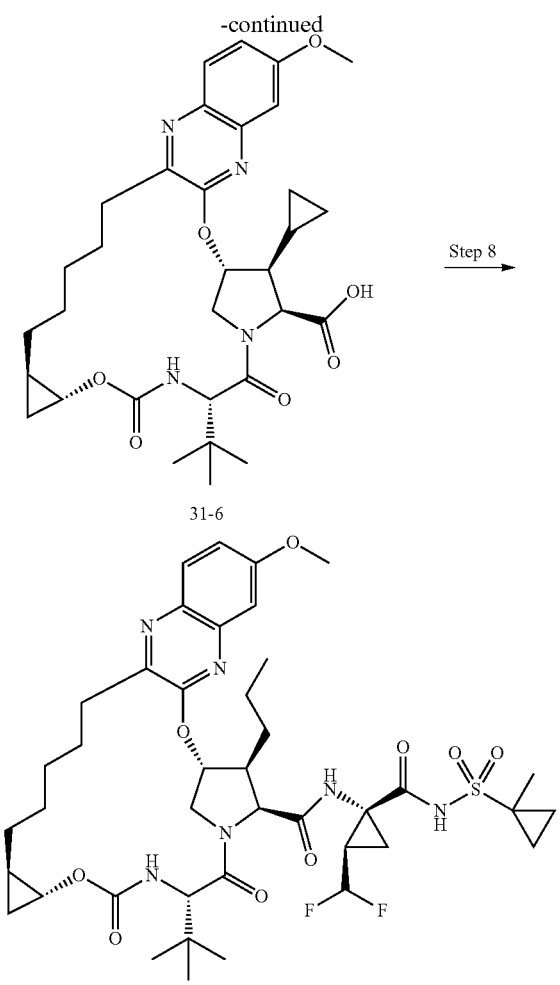

Example 31

Step 1. Preparation of 31-1: An unpurified sample of Intermediate B3 was treated with Intermediate E1 (217 mg, 0.797 mmol), MeCN (5.7 mL) and Cs$_2$CO$_3$ (371 mg, 1.14 mmol). After stirring at rt for 17 h, the reaction mixture was filtered over Celite and concentrated under reduced pressure. The crude residue was purified by silica gel chromatography (20% to 40% EtOAc/Hex) to afford quinoxaline 31-1 (143 mg). LCMS-ESI$^+$ (m/z): [M−Boc+2H]$^+$ calcd for C$_{18}$H$_{21}$ClN$_3$O$_4$: 378.12; found 378.59.

Step 2. Preparation of 31-2: Quinoxaline 31-1 (143 mg, 0.299 mmol) was dissolved in DCM (10 mL) and treated with HCl (4.0 M in dioxane, 5 mL, 20.0 mmol). After stirring for 2 h at rt, the reaction mixture was concentrated and the crude 31-2 was carried on without further purification.

Step 3. Preparation of 31-3: The crude amine hydrochloride 31-2 was treated with BEP (115 mg, 0.419 mmol), Intermediate D1 (120 mg, 0.423 mmol), EtOAc (9 mL), NMP (1 mL) and DIPEA (0.37 mL, 2.1 mmol), then heated to 50° C. After 1.5 h, the reaction mixture was diluted with Et$_2$O. The organic solution was washed successively with saturated aqueous NaHCO$_3$ and brine, then dried over MgSO$_4$, filtered and concentrated under reduced pressure. The residue was purified by silica gel chromatography (15% to 30% EtOAc/Hex) to afford amide 31-3 (166 mg). LCMS-ESI$^+$ (m/z): [M+H]$^+$ calcd for C$_{33}$H$_{44}$ClN$_4$O$_7$: 643.29; found: 643.48.

Step 4. Preparation of 31-4: Amide 31-3 (166 mg, 0.258 mmol) was treated with potassium vinyltrifluoroborate (52 mg, 0.387 mmol), Pd(dppf)C$_2$.DCM (21 mg, 0.0258 mmol), EtOH (2.6 mL) and TEA (0.054 mL), then heated to reflux. After 50 min. the reaction mixture was diluted with EtOAc and washed with H$_2$O and brine. The organics were dried over MgSO$_4$, filtered and concentrated under reduced pressure. The residue was purified by silica gel chromatography (15% to 40% EtOAc/Hex) to afford vinyl quinoxaline 31-4 (145 mg), LCMS-ESI$^+$ (m/z): [M+H]$^+$ calcd for C$_{35}$H$_{47}$N$_4$O$_7$: 635.34; found: 635.58.

Steps 5 and 6. Preparation of 31-5: Vinyl quinoxaline 31-4 (145 mg, 0.228 mmol) was suspended in DCE (46 mL) and treated with Zhan 1B catalyst (33 mg, 0.0456 mmol, Strem). The suspension was deoxygenated with bubbling N$_2$ for 22 min, then heated to reflux for 50 min. The reaction mixture was then filtered over Celite and concentrated under reduced pressure. The crude residue was purified by silica gel chromatography (25% to 35% EtOAc/Hex) to afford the desired macrocycle (54 mg; LCMS-ESI$^+$ (m/z): [M+H]$^+$ calcd for C$_{33}$H$_{43}$N$_4$O$_7$: 607.31; found: 607.67). The macrocyclic product of step 5 was dissolved in EtOH (10 mL) and treated with 10% Pd/C (45 mg). Hydrogen from a balloon was bubbled through the suspension for 1 min and hydrogenation (1 atm) was continued for an additional 1.5 h. The reaction mixture was filtered over Celite and concentrated under reduced pressure to afford the desired macrocycle 31-5 which was carried on without further purification. LCMS-ESI$^+$ (m/z): [M+H]$^+$ calcd for C$_{33}$H$_{45}$N$_4$O$_7$: 609.33; found: 609.95.

Step 7. Preparation of 31-6: The crude product 31-5 was dissolved in THF and treated with LiOH (1.0 M in H$_2$O, 5 mL, 5 mmol). After stirring at rt for 3 d, the reaction mixture was heated to reflux for 20 h. The mixture was then poured into H$_2$O and acidified to pH~1-2 with 10% HCl. The aqueous layer was extracted three times with DCM. The combined organics were dried over MgSO$_4$, filtered and concentrated under reduced pressure. The crude material was purified by silica gel chromatography (80% to 100% EtOAc/Hex) to afford carboxylic acid 31-6 (24 mg). LCMS-ESI$^+$ (m/z): [M+H]$^+$ calcd for C$_{32}$H$_{43}$N$_4$O$_7$: 595.31; found: 595.12.

Step 8. Preparation of Example 31: Carboxylic acid 31-6 (24 mg, 0.040 mmol) and Intermediate A10 (25 mg, 0.081 mmol) were treated with TBTU (23 mg, 0.081 mmol), DMAP (10 mg, 0.081 mmol), DCM (2 mL) and DIPEA (0.070 mL, 0.40 mmol). The reaction mixture was stirred at rt for 15 h then concentrated under reduced pressure. The crude residue was purified by HPLC to afford Example 31 (13 mg, 34%) in approximately 90% purity as a TFA salt. Analytic HPLC RetTime: 8.92 min. LCMS-ESI$^+$ (m/z): [M+H]$^+$ calcd for C$_{41}$H$_{55}$F$_2$N$_6$O$_9$S: 845.37; found: 845.67. $^1$H NMR (400 MHz, CD$_3$OD) δ 9.13 (s, 1H), 7.79 (d, J=9.1 Hz, 1H), 7.23 (dd, J=9.1, 2.7 Hz, 1H), 7.13 (d, J=2.7 Hz, 1H), 6.05-5.65 (m, 2H), 4.55 (d, J=7.0 Hz, 1H), 4.47 (d, J=11.7 Hz, 2H), 4.27 (dd, J=12.0, 3.7 Hz, 1H), 3.94 (s, 3H), 3.78 (dd, J=6.8, 2.8 Hz, 1H), 2.99-2.86 (m, 1H), 2.80 (td, J=13.2, 4.1 Hz, 1H), 1.98 (d, J=28.8 Hz, 2H), 1.92-1.67 (m, 4H), 1.65-1.41 (m, 10H), 1.33 (d, J=27.7 Hz, 3H), 1.20-1.06 (m, 9H), 1.04-0.84 (m, 6H), 0.82-0.62 (m, 3H), 0.61-0.41 (m, 2H), 0.06 (dd, J=9.2, 4.9 Hz, 1H).

Example 32
Preparation of (1aR,5S,8S,9S,10R,22aR)-9-benzyl-5-tert-butyl-N-[(1R,2R)-2-(difluoromethyl)-1-{[(1-methylcyclopropyl)sulfonyl]carbamoyl}cyclopropyl]-4-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide
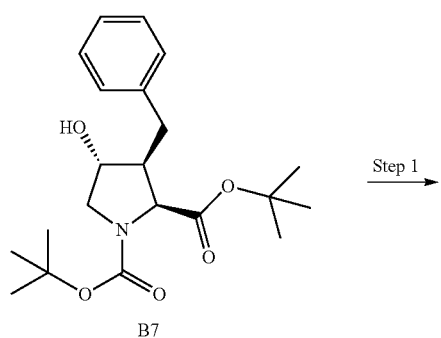
B7
Step 1 →
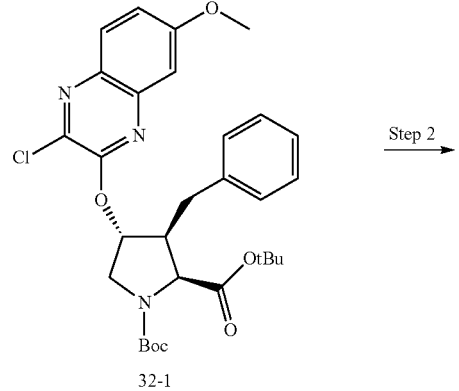
32-1
Step 2 →
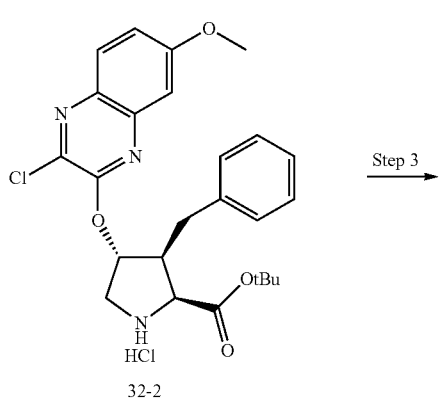
32-2
Step 3 →
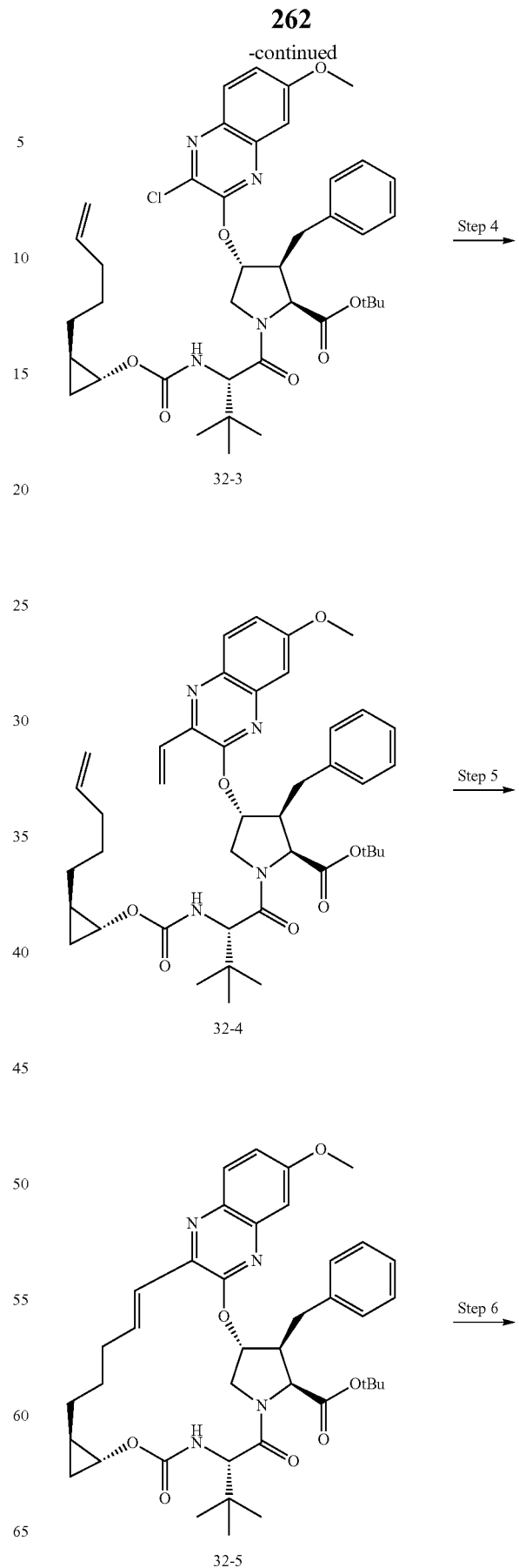

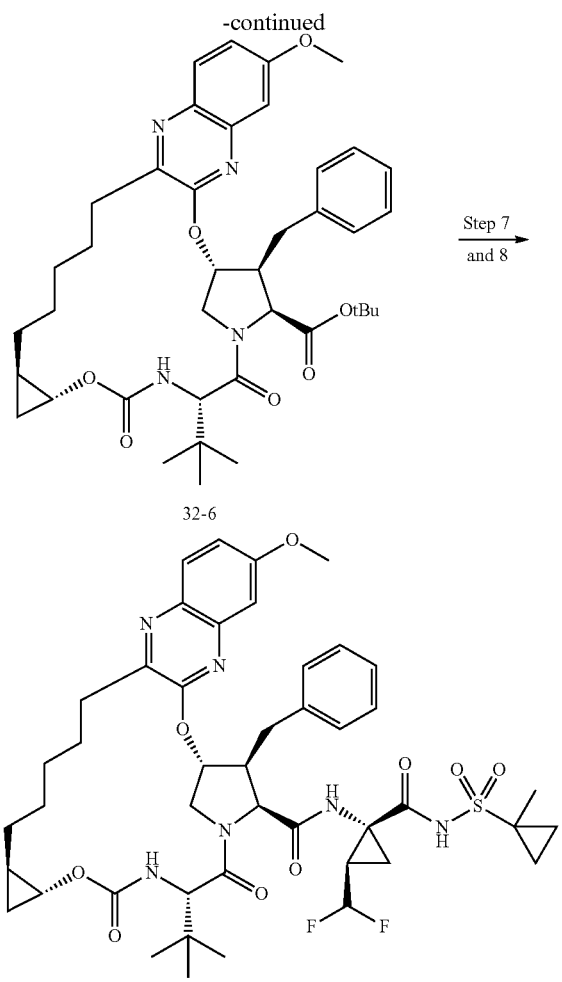

Example 32

Step 1. Preparation of 32-1: To a solution of Intermediate B7 (390 mg, 1.00 mmol) and Intermediate E1 (272 mg, 1.00 mmol) in MeCN (5 mL) was added cesium carbonate (390 mg, 1.00 mmol) at rt under an argon atmosphere. After 24 h, the reaction mixture was diluted with ethyl acetate (50 mL). The resulting mixture was washed with saturated aqueous sodium bicarbonate solution (50 mL) and brine (50 mL), was dried over anhydrous sodium sulfate, and was concentrated in vacuo. The crude residue was purified by silica gel chromatography (0-100% ethyl acetate/hexanes gradient) to afford quinoxaline 32-1 (550 mg) as a colorless oil. LCMS-ESI$^+$ (m/z): [M+H]$^+$ calcd for $C_{30}H_{37}ClN_3O_6$: 570.2; found: 570.2.

Step 2. Preparation of 32-2: To a solution of 32-1 (549 mg, 0.96 mmol) in dioxane (2 mL) was added 4 M hydrochloric acid in dioxane (2 mL, 1 mmol) and the reaction was stirred at rt. After 24 h, the reaction mixture was concentrated in vacuo to afford amine hydrochloride 32-2 (461 mg) as an off white solid, which was used directly in the next step without further purification. LCMS-ESI$^+$ (m/z). [M+H]$^+$ calcd for $C_{25}H_{29}ClN_3O_4$: 470.2; found: 470.2.

Step 3. Preparation of 32-3: To a solution of 32-2 (461 mg, 0.96 mmol) and Intermediate D1 (369 mg, 1.10 mmol) in MeCN (5 mL) was added HATU (418 mg, 1.10 mmol) followed by DIPEA (869 µL, 5.00 mmol) at rt under and argon atmosphere. After 24 h, the reaction mixture was concentrated in vacuo, and the crude residue was purified by silica gel chromatography (0-100% ethyl acetate/hexanes gradient) to afford 32-3 (202.6 mg) as a colorless oil. LCMS-ESI$^+$ (m/z): [M+H]$^+$ calcd for $C_{40}H_{52}ClN_4O_7$: 735.3; found: 735.4.

Step 4. Preparation of 32-4: To a solution of 32-3 (202 mg, 276 µmol), TEA (56 µL, 414 µmol) and potassium vinyltrifluoroborate (56 mg, 414 µmol) in EtOH (2.76 mL) was added PdCl$_2$(dppf) (22.5 mg, 27.6 µmol). The reaction mixture was degassed with argon for 10 min and was heated to 78° C. After 1 h, the reaction mixture was allowed to cool to rt and was concentrated in vacuo. The crude residue was purified by silica gel chromatography (0-100% ethyl acetate/hexanes gradient) to afford 32-4 (163 mg) as a yellow oil. LCMS-ESI$^+$ (m/z). [M+H]$^+$ calcd for $C_{42}H_{55}N_4O_7$: 727.4; found: 727.5.

Step 5. Preparation of 32-5: To a solution of 32-4 (163 mg, 220 µmol) in DCE (44 mL) was added Zhan 1B catalyst (16 mg, 22 µmol, Strem) and the reaction mixture was degassed for 10 minutes with argon. The reaction mixture was then heated to 100° C. After 45 min, the reaction mixture was allowed to cool to rt and was concentrated in vacuo. The crude residue was purified by silica gel chromatography (0-100% ethyl acetate/hexanes gradient) to afford 32-5 (125 mg) as a light yellow oil. LCMS-ESI$^+$ (m/z): [M+H]$^+$ calcd for $C_{40}H_{51}N_4O_7$: 699.4; found: 699.4.

Step 6. Preparation of 32-6: To a solution of macrocycle 32-5 (124 mg, 178 µmol) in ethanol (890 µL) was added Pd/C (10 wt % Pd, 19 mg, 18 µmol) at rt under an argon atmosphere. The reaction vessel was evacuated and refilled with hydrogen gas (3×) and the reaction mixture was stirred vigorously at rt under 1 atm H$_2$. After 2.5 h, the reaction mixture was diluted with ethyl acetate (5 mL) and was filtered through a pad of Celite with ethyl acetate washings (3×5 mL), The filtrate was concentrated in vacuo to afford 32-6 (139 mg), which was used directly in the next step without further purification. LCMS-ESI$^+$ (m/z): [M+H]$^+$ calcd for $C_{40}H_{53}N_4O_7$: 701.4; found: 701.5.

Steps 7 and 8. Preparation of Example 32: To a solution of 32-6 (124 mg, 178 µmol) in DCM (3 mL) was added TFA (2 mL) at rt under an argon atmosphere. After 3 h, the reaction mixture was concentrated in vacuo and was azeotropically dried from toluene (2×2 mL) to afford the desired carboxylic acid as a yellow oil, which was used directly in the next step without further purification. (126 mg; LCMS-ESI$^+$ (m/z): [M+H]$^+$ calcd for $C_{36}H_{45}N_4O_7$: 645.3; found: 645.4). To a solution of this carboxylic acid (120 mg, 178 µmol) and Intermediate A10 (119 mg, 392 µmol) in MeCN (1 mL) was added HATU (151 mg, 392 µmol) followed by DIPEA (155 µL, 890 µmol) at rt under an argon atmosphere After 30 min, the reaction mixture was concentrated in vacuo, and the crude residue was purified by silica gel chromatography (0-100% ethyl acetate/hexanes gradient). The fractions containing the desired product were combined, were repurified by preparatory HPLC (Gemini 5u C18 110 Å column, 5-100% MeCN/H$_2$O, 0.1% trifluoroacetic acid modifier) and were lyophilized to afford the TFA salt of Example 32 (23 mg) as a white powder. Analytic HPLC RetTime: 8.81 min. LCMS-ESI$^+$ (m/z): [M+H]$^+$ calcd for $C_{45}H_{57}F_2N_6O_9S$: 895.4; found: 895.6. $^1$H NMR (400 MHz, CD$_3$OD) δ 9.24 (s, 1H), 7.73 (d, J=9.1 Hz, 1H), 7.47-7.27 (m, 4H), 7.21-7.12 (m, 1H), 6.65 (d, J=2.9 Hz, 1H), 5.83 (td, $J_{H-F}$=55 Hz, J=7.2 Hz, 1H), 5.77 (br s, 1H), 4.63 (d, J=6.9 Hz, 2H), 4.50-4.28 (m, 3H), 3.93 (s, 2H), 3.79-3.71 (m, 1H), 3.11-2.99 (m, 1H), 2.97-2.85 (m, 1H), 2.82-2.61 (m, 3H), 1.92 (br s, 2H), 1.82-1.70 (m, 2H), 1.63-1.44 (m, 4H), 1.52 (s, 3H), 1.15 (s, 9H), 1.04 (br s, 2H), 1.02-0.96 (m, 2H), 0.95-0.88 (m, 4H), 0.78-0.66 (m, 1H), 0.56-0.46 (m, 1H).

Example 33
Preparation of (1aS,2aR,6S,9S,10S,11R,23aR, 23bS)-6-tert-butyl-N-[(1 S,2R)-1-[(cyclopropylsulfonyl)carbamoyl]-2-(difluoromethyl)cyclopropyl]-15-methoxy-10-methyl-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide
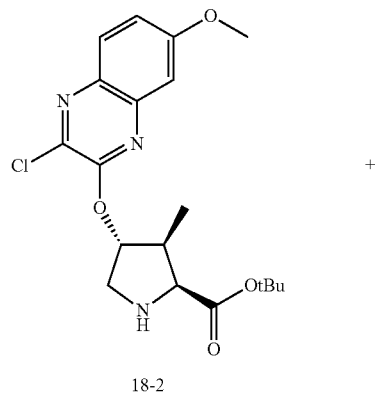
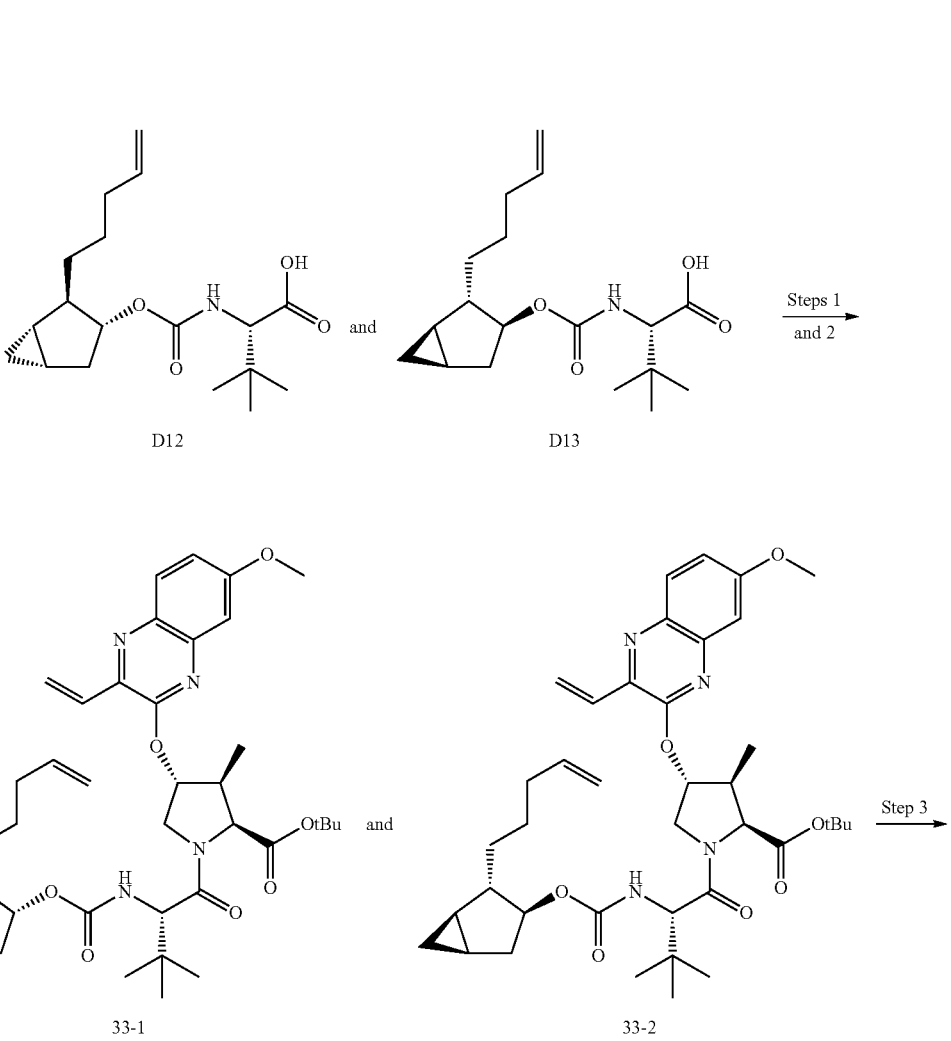

-continued

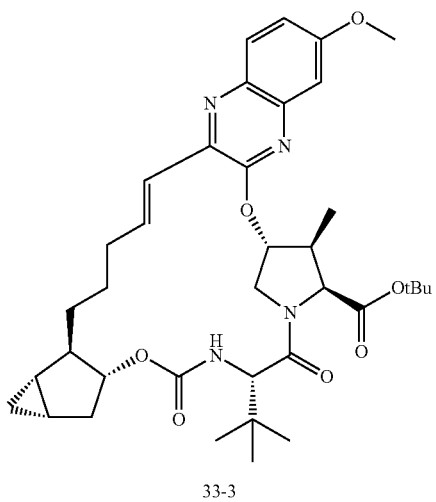

33-3

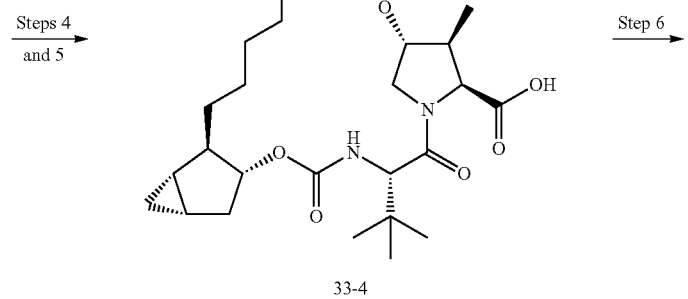

33-4

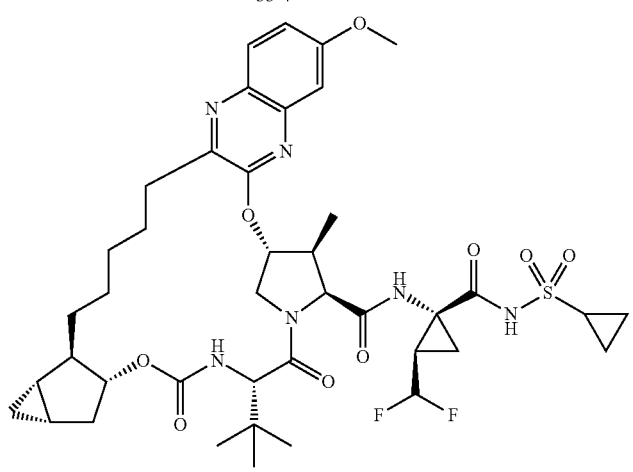

Example 33

Steps 1 and 2. Preparation of diastereomeric mixture 33-1 and 33-2: Quinoxaline 18-2 (220 mg, 0.56 mmol) was dissolved along with 1:1 diastereomer Intermediate mixture D12 and D13 (208 mg, 0.643 mmol) in MeCN (5 mL). DIPEA (280 µL, 1.6 mmol) and HATU (360 mg, 0.95 mmol) were added, and the reaction was stirred for 1.25 h at rt. The reaction was then diluted with EtOAc (30 mL), saturated aqueous NaHCO$_3$ (15 mL), H$_2$O (10 mL), and brine (10 mL). The phases were separated and the aqueous phase was extracted with EtOAc (30 mL). The organic phase was dried over anhydrous Na$_2$SO$_4$, filtered and concentrated to a crude residue that was dissolved in CH$_2$Cl$_2$ and adsorbed onto silica gel (5 g). Purification by silica gel chromatography (10% to 30% EtOAc in hexanes) provided a white foam (352 mg; LCMS-ESI$^+$ (m/z): [M+H]$^+$ calcd for C$_{37}$H$_{52}$ClN$_4$O$_7$: 699.4; found 699.1). A stirred heterogeneous mixture of this residue, PdCl$_2$(dppf).CH$_2$Cl$_2$ (30.7 mg, 0.0376 mmol) and potassium vinyltrifluoroborate (135 mg, 1.01 mmol) in EtOH (5 mL) was sparged with argon for several minutes. Triethylamine (160 µL, 1.1 mmol) was added and the mixture was heated to 75° C. for 1 h. The reaction mixture was cooled to ambient temperature and was diluted with EtOAc (30 mL), H$_2$O (15 mL) and brine (15 mL). The phases were separated, and the aqueous phase was extracted with EtOAc (30 mL) The organics were dried over anhydrous Na$_2$SO$_4$, filtered and concentrated to afford a crude residue that was dissolved in CH$_2$Cl$_2$ and adsorbed onto silica gel (3 g). Purification by silica gel chromatography (10% to 40% EtOAc in hexanes) produced inseparable mixture of 33-1 and 33-2 as a yellow residue (258 mg). LCMS-ESI$^+$ (m/z): [M+H]$^+$ calcd for C$_{39}$H$_{55}$N$_4$O$_7$: 691.4; found: 691.7.

Step 3: Preparation of 33-3: Diastereomeric mixture 33-1 and 33-2 (258 mg, 0.373 mmol) was dissolved in DCE (125 mL) and the solution was sparged with Ar for 10 min. Zhan 1B catalyst (41 mg, 0.056 mmol, Strem) was added as a solution in DCE (3.3 mL) and the resulting solution was stirred at 85° C. under Ar for 105 min. The reaction mixture was then concentrated onto 5 g silica gel and was purified by silica gel chromatography (0% to 25% EtOAc in hexanes) to afford macrocycle 33-3 as an amorphous residue (81.9 mg). LCMS-ESI$^+$ (m/z): [M+H]$^+$ calcd for C$_{37}$H$_{51}$N$_4$O$_7$: 663.4; found: 663.3.

Steps 4 and 5: Preparation of 33-4: To a solution of 33-3 (81.9 mg, 0.124 mmol) in 1:1 EtOAc:EtOH (4 mL) was added Pd/C (10 wt % Pd, 19 mg). The reaction vessel was purged twice with H$_2$ and was stirred at rt under 1 atm H$_2$ for 2.5 h. The reaction mixture was filtered through a pad of Celite and concentrated to afford a crude residue. This residue was dissolved in CH$_2$Cl$_2$ (1.2 mL) and TMSOTf (90 µL, 0.50 mmol) was added. The mixture was stirred at rt for 4.5 h. The reaction was then concentrated in vacuo and dissolved in CH$_2$Cl$_2$ (5 mL), 0.2 M aqueous NaOH (5 mL) was added and the biphasic mixture was stirred at rt for 5 min. The mixture was then acidified with 1 M aqueous HCl (20 mL) and was diluted with CH$_2$Cl$_2$ (20 mL). The phases were separated and the aqueous phase was extracted with CH$_2$Cl$_2$ (2×20 mL). The combined organic phase was dried over MgSO$_4$, filtered, and concentrated to afford 33-4 as a crude residue (76.1 mg). LCMS-ESI$^+$ (m/z): [M+H]$^+$ calcd for C$_{33}$H$_{45}$N$_4$O$_7$: 609.3; found: 608.9.

Step 6: Preparation of Example 33: To a suspension of acid 33-4 (43 mg, 0.072 mmol) and Intermediate A9 (40.9 mg, 0.14 mmol) in MeCN (800 μL) was added DIPEA (100 μL, 0.57 mmol). HATU (37 mg, 0.097 mmol) was added to the resulting solution, and the reaction was stirred at rt for 15 h. The reaction was then diluted with EtOAc (20 mL), 0.2 M aqueous HCl (10 mL) and brine (10 mL). The phases were separated and the aqueous phase was extracted with EtOAc (20 mL). The combined organic phase was dried over Na$_2$SO$_4$, filtered, and concentrated to afford a crude residue. This residue was dissolved in CH$_2$Cl$_2$ and was concentrated onto 2 g silica gel. Purification by silica gel chromatography (15% to 55% acetone in hexanes) provided an amorphous residue that was lyophilized from water and MeCN to provide Example 33 as a white amorphous solid (29.6 mg). Analytic HPLC RetTime: 9.07 min. LCMS-ESI$^+$ (m/z): [M+H]$^+$ calcd for C$_{41}$H$_{55}$F$_2$N$_6$O$_9$S: 845.4; found: 845.2. $^1$H NMR (400 MHz, CDCl$_3$) δ 10.21 (s, 1H), 7.82 (d, J=9.1 Hz, 1H), 7.19 (dd, J=9.1, 2.7 Hz, 1H), 7.09 (d, J=2.7 Hz, 1H), 6.79 (s, 1H), 6.21-5.76 (m, 1H) 5.65 (d, J=3.9 Hz, 1H), 5.29 (d, J=9.7 Hz, 1H), 4.99 (d, J=7.5 Hz, 1H), 4.47-4.29 (m, 4H), 4.16-4.09 (m, 1H), 3.93 (s, 3H), 2.99-2.85 (m, 2H), 2.80-2.64 (m, 2H), 2.24-2.16 (m, 1H), 2.13-2.05 (m, 1H), 2.01-0.95 (m, 29H), 0.56-0.45 (m, 1H), 0.45-0.35 (m, 1H).

Example 34

Preparation of (1aR,5S,8S,9S,10R,22aR)-5-tert-butyl-N-{(1R,2R)-1-[(cyclopropylsulfonyl)carbamoyl]-2-ethylcyclopropyl}-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 34

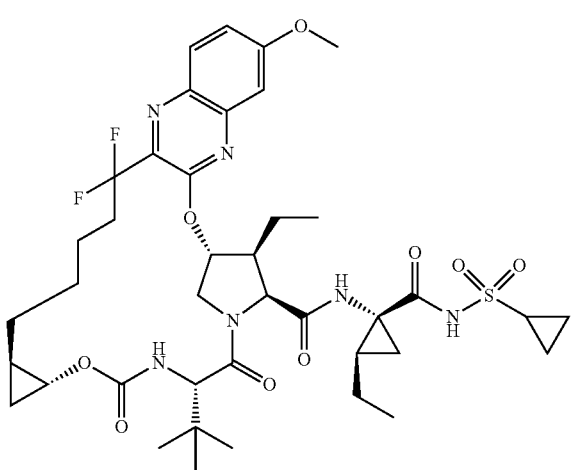

Example 34 was prepared in a similar fashion to Example 17, substituting Intermediate A3 for Intermediate A10 in Step 7. Example 34 was isolated (5.7 mg) in approximately 95% purity. Analytic HPLC RetTime: 8.81 min. LCMS-ESI$^+$ (m/z): [M+H]$^+$ calcd for C$_{40}$H$_{55}$F$_2$N$_6$O$_9$S: 833.4; found: 833.25. $^1$H NMR (400 MHz, CDCl$_3$) δ 10.027 (br s, 1H), 7.98 (d, J=8.8 Hz, 1H), 7.29 (dd, J=9.2, 2.8 Hz, 1H), 7.09 (d, J=2.8 Hz, 1H), 6.32 (br s, 1H), 5.92 (d, J=3.6 Hz, 1H), 5.30 (d, J=10.0 Hz, 1H), 4.42-4.33 (m, 3H), 4.08 (dd, J=11.6, 4.0 Hz, 1H), 3.96 (s, 3H), 3.65 (m, 1H), 2.93 (m, 1H), 2.51 (m, 2H), 2.02 (m, 1H), 1.86-1.40 (m, 11H) 1.34-1.14 (m, 7H), 1.09 (s, 9H), 1.10-0.82 (m, 6H), 0.72 (m, 1H), 0.48 (m, 1H).

Example 35

Preparation of (1aR,5S,8S,9S,10R,22aR)-5-tert-butyl-N-[(1R,2S)-2-(2,2-difluoroethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 35

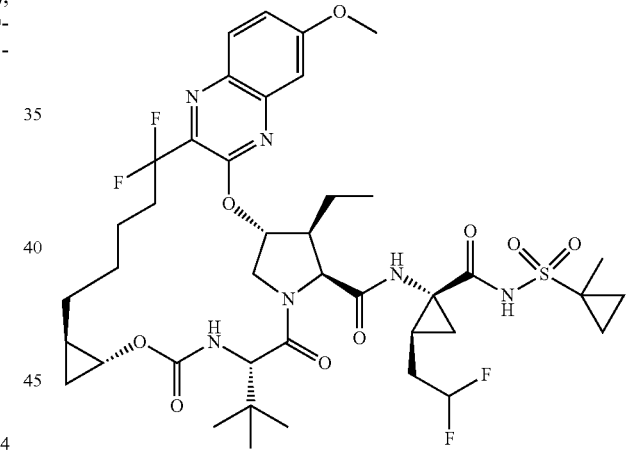

Example 35 was prepared in a similar fashion to Example 17, substituting Intermediate A8 for Intermediate A10 in Step 7. Example 35 was isolated (12.8 mg) in approximately 90% purity. Analytic HPLC RetTime: 8.78 min. LCMS-ESI (m/z). [M+H]$^+$ calcd for C$_{41}$H$_{55}$F$_4$N$_6$O$_9$S: 883.4; found: 8832 $^1$H NMR (400 MHz, CDCl$_3$) δ 9.69 (br s, 1H), 7.98 (d, J=9.2 Hz, 1H), 7.29 (dd, J=9.2, 2.8 Hz, 1H), 7.09 (d, J=2.8 Hz, 1H), 6.53 (br s, 1H), 5.91 (d, J=4.0 Hz, 1H), 5.84 (tt, J$_{H-F}$=56 Hz, J=3.6 Hz, 1H), 5.33 (d, J=6.4 Hz, 1H), 4.43 (m, 2H), 4.34 (ap d, J=9.6 Hz, 1H), 4.08 (dd, J=11.6, 4.0 Hz, 1H), 3.96 (s, 3H), 3.99-3.94 (m, 1H), 3.68 (m, 1H), 2.58-2.52 (m, 3H), 2.20 (m, 2H), 1.82-1.58 (m, 7H) 1.54-1.40 (m, 5H), 1.36-1.18 (m, 6H), 1.09 (s, 9H), 1.10-1.00 (m, 1H), 0.85 (m, 2H), 0.69 (m, 1H), 0.49 (m, 1H).

Example 36

Preparation of (1aR,5S,8S,9S,10R,21aR)-5-tert-butyl-N-[(1R,2R)-2-(difluoromethyl)-1-{[(1-methylcyclopropyl)sulfonyl]carbamoyl}cyclopropyl]-9-ethyl-14-methoxy-3,6-dioxo-1a,3,4,5,6,9,10,17b,18,18a,19,20,21,21a-tetradecahydro-1H,8H-7,10-methanodicyclopropa[13,14:18,19][1,10,3,6]dioxadiazacyclononadecino[11,12-b]quinoxaline-8-carboxamide

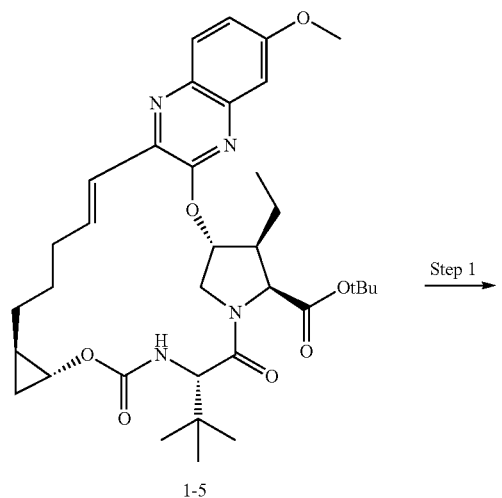

1-5

Step 1

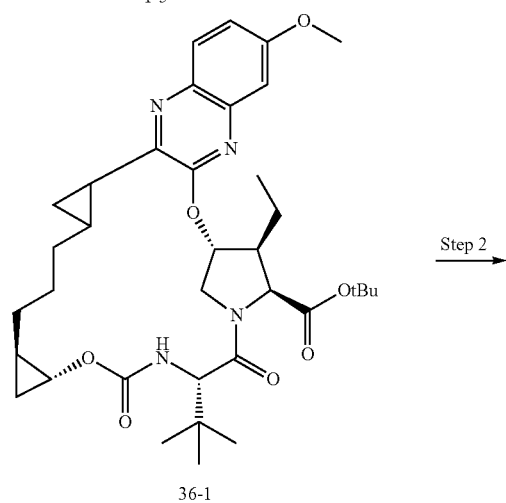

36-1

Step 2

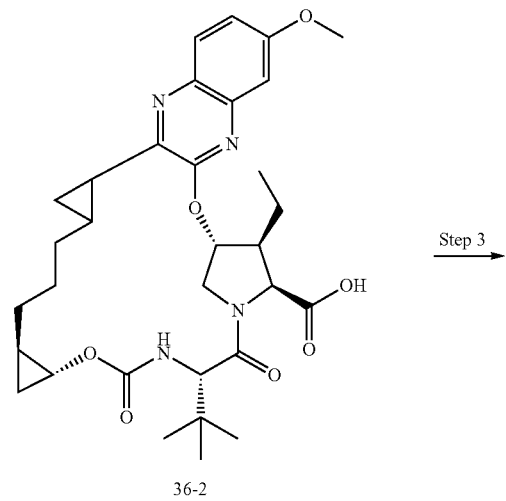

36-2

Step 3

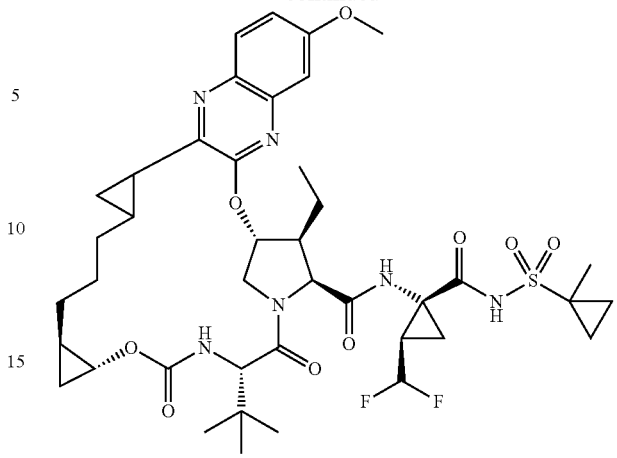

Example 36

Step 1. Preparation of 36-1: To a solution of trimethylsulfoxonium iodide (72 mg, 0.32 mmol) in DMSO/THF (1:1, 2 mL) was added sodium hydride (60%, 12 mg, 0.32 mmol) and stirred at rt for 2 h. Macrocycle 1-5 (103 mg, 0.16 mmol) was added dropwise in THF (3 mL). The mixture was heated to 65° C. and stirred for 16 h. After cooling to rt, the mixture was diluted with EtOAc/H$_2$O, extracted with EtOAc, dried over anhydrous MgSO$_4$, and concentrated in vacuo. The residue was purified by silica gel chromatography (0-25% EtOAc/hexanes) to give 36-1 (27 mg) as a residue. LCMS-ESI$^+$ (m/z): [M+H]$^+$ calcd for C$_{36}$H$_{51}$N$_4$O$_7$: 651.38; found: 651.52.

Step 2. Preparation of 36-2: To a solution of 36-1 (26 mg, 0.04 mmol) in DCM (1 mL) was added TMSOTf (0.036 mL, 0.2 mmol) and stirred at rt for 2 h. The reaction was pipetted into stirring 1 N NaOH (2 mL). After 10 min, the mixture was diluted with DCM and acidified to pH 3 with 1 N aqueous HCl. Following extraction of the aqueous layer with DCM, the combined organics were dried over anhydrous MgSO$_4$ and concentrated in vacuo. The residue was purified by silica gel chromatography (0-10% EtOAc/MeOH) to give 36-2 (24 mg) as a residue that was used without further purification. LCMS-ESI$^+$ (m/z): [M+H]$^+$ calcd for C$_{32}$H$_{43}$N$_4$O$_7$: 595.31; found: 595.43.

Step 3. Preparation of Example 36: To a solution of 36-2 (24 mg, 0.041 mmol), Intermediate A10 (16 mg, 0.053 mmol), TBTU (19 mg, 0.06 mmol) and DMAP (8 mg, 0.06 mmol) in DCM (2 mL) was added DIPEA (0.021 mL, 0.12 mmol) and the reaction was stirred at rt for 16 h. Additional Intermediate A10 (16 mg, 0.053 mmol), TBTU (19 mg, 0.06 mmol), DMAP (8 mg, 0.06 mmol), and DIPEA (0.021 mL, 0.12 mmol) were added and the reaction was stirred at rt for 4 h. The reaction was quenched with water, diluted with EtOAc, washed with sat. aqueous NaHCO$_3$, brine, dried over anhydrous MgSO$_4$ and concentrated in vacuo. The crude material was purified by reverse phase HPLC (Gemini, 45-85% MeCN/H$_2$O+0.1% TFA) and lyophilized to give Example 36 (3 mg) as a TFA salt. Analytic HPLC RetTime: 9.06 min. LCMS-ESI$^+$ (m/z): [M+H]$^+$ calcd for C$_{41}$H$_{55}$F$_2$N$_6$O$_9$S: 845.37; found: 845.43. $^1$H NMR (400 MHz, CD$_3$OD) δ 9.31 (s, 1H), 7.72 (d, J=10 Hz, 1H), 7.20-7.17 (m, 2H), 5.60-5.82 (m, 2H), 5.51 (s, 1H), 4.72 (d, J=7.2 Hz, 1H), 4.43 (d, J=11.6 Hz, 1H), 4.31 (s, 1H), 4.26-4.22 (dd, J=11.6, 4 Hz, 1H), 3.94 (s, 3H), 3.78 (m, 1H), 2.60 (m, 1H), 2.27 (m, 1H) 2.04 (s, 3H), 1.68 (m, 3H), 1.59 (m, 2H), 1.54-1.15 (m, 11H), 1.09 (s, 9H), 0.95-0.86 (m, 8H), 0.47 (m, 1H).

Example 37

Preparation of (1R,4S,4aR,8S,11 S, 12S,13R,25aR)-8-tert-butyl-N-[(1R,2R)-2-(difluoromethyl)-1-{[(1-methylcyclopropyl)sulfonyl]carbamoyl}cyclopropyl]-12-ethyl-17-methoxy-6,9-dioxo-2,3,4,4a,6,7,8,9,12,13,21,22,23,24,25,25a-hexadecahydro-1H,11H-1,4:10,13-dimethanoquinoxalino[2,3-k][1,10,3,6]benzodioxadiazacyclononadecine-11-carboxamide

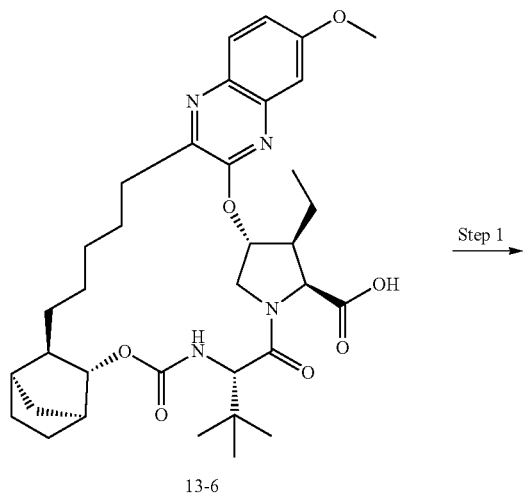

Step 1. Preparation of Example 37: To a solution of 13-6 (76 mg, 0.12 mmol), Intermediate A10 (44 mg, 0.14 mmol), HATU (55 mg, 0.14 mmol) and DMAP (21 mg, 0.18 mmol) in DMF (2 mL) was added DIPEA (0.11 mL, 0.6 mmol) and the reaction was stirred at rt for 16 h. Additional Intermediate A10 (44 mg, 0.14 mmol), HATU (55 mg, 0.14 mmol), DMAP (21 mg, 0.18 mmol), followed by DIPEA (0.11 mL, 0.6 mmol) was added and the reaction was stirred at 40° C. for 50 h. The reaction was quenched with water, diluted with EtOAc, washed with sat. aqueous NaHCO$_3$, brine, dried over anhydrous MgSO$_4$ and concentrated in vacuo. The crude material was purified by reverse phase HPLC (Gemini, 45-85% MeCN/H$_2$O+0.1% TFA) and lyophilized to give Example 37 (30 mg) as a TFA salt Analytic HPLC RetTime: 9.44 min. LCMS-ESI$^+$ (m/z): [M+H]$^+$ calcd for C$_{44}$H$_{81}$F$_2$N$_6$O$_9$S: 887.42; found: 887.50. $^1$H NMR (400 MHz, CD$_3$OD) δ 9.24 (s, 1H), 7.76 (d, J=9.2 Hz, 1H), 7.20 (dd, J=8.8, 2.4 Hz, 1H), 7.12 (m, 1H), 5.95-5.66 (m, 2H), 5.43 (s, 1H), 4.51 (d, J=7.6 Hz, 1H), 4.41 (s, 1H), 4.20-4.10 (m, 2H), 3.88 (s, 3H), 2.94-2.88 (m, 1H), 2.73-2.63 (m, 2H), 2.11 (br, 2H), 2.02-0.83 (m, 41H).

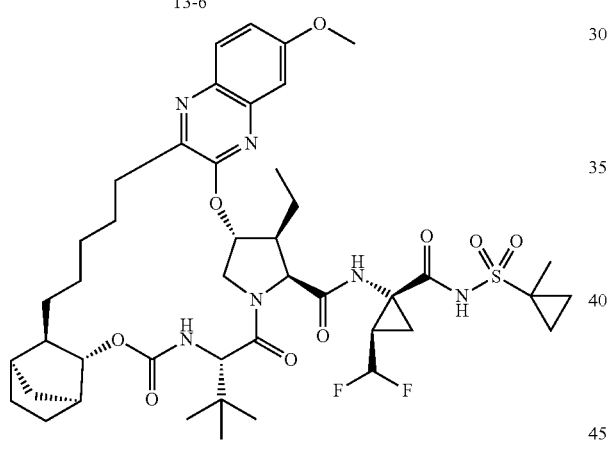

Example 37

Example 38

Preparation of (1aR,5S,8S,9S,10R,22aR)—N-[(1R,2R)-2-(difluoromethyl)-1-{[(1-methylcyclopropyl)sulfonyl]carbamoyl}cyclopropyl]-14-methoxy-9-methyl-5-(1-methylcyclopentyl)-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

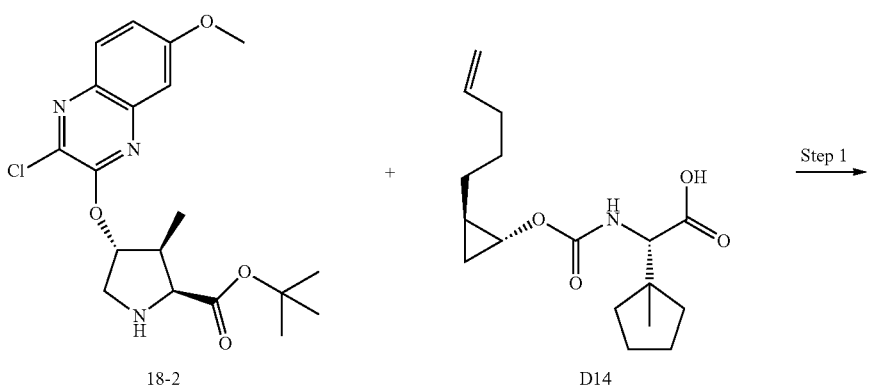

-continued
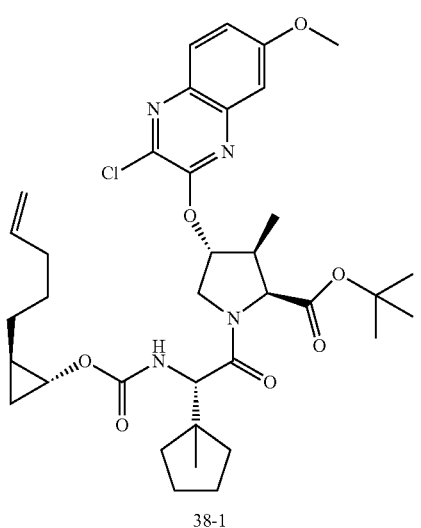
38-1
Step 2 →
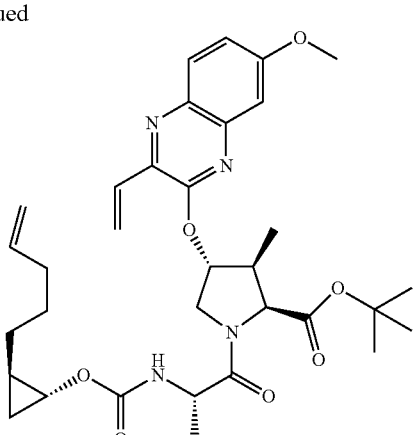
38-2
Steps 3 and 4 →
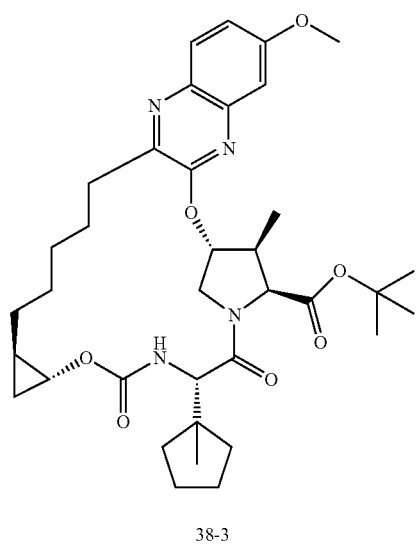
38-3
Step 5 →
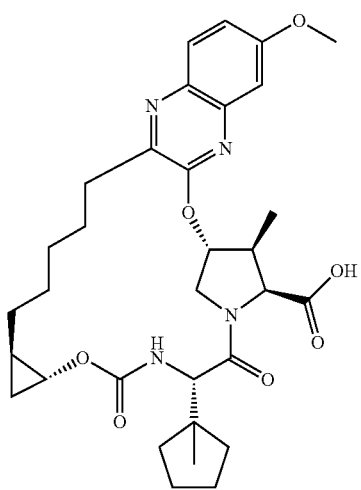
38-4
Step 6 →
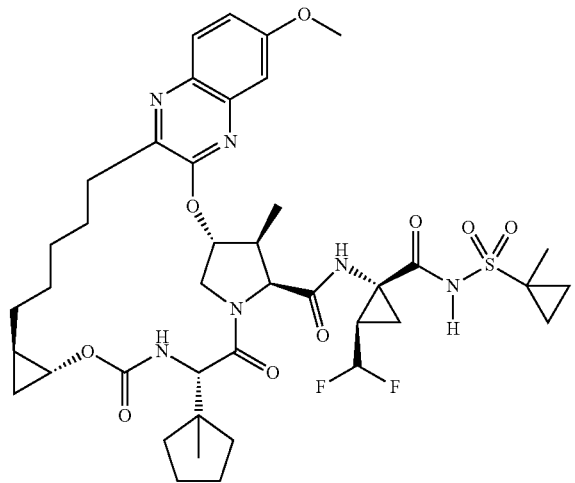
Example 38

Step 1. Preparation of 38-1: Amine 18-2 (192 mg, 0.487 mmol) was treated with BEP (246 mg, 0.898 mmol), Intermediate D14 (278 mg, 0.898 mmol), EtOAc (9 mL), NMP (1 mL) and DIPEA (0.42 mL, 2.4 mmol), then heated to 50° C. After 1 h. the reaction mixture was diluted with EtOAc. The organic solution was washed successively with sat. aqueous NaHCO$_3$ and brine, then dried over MgSO$_4$, filtered and concentrated in vacuo. The residue was purified by silica gel chromatography (15% to 35% EtOAc/Hex) to afford amide 38-1 (264 mg). LCMS-ESI$^+$ (m/z): [M+H]$^+$ calcd for C$_{36}$H$_{50}$ClN$_4$O$_7$: 685.34; found: 685.82.

Step 2. Preparation of 38-2: Amide 38-1 (264 mg, 0.385 mmol) was treated with potassium vinyltrifluoroborate (82 mg, 0.615 mmol), Pd(dppf)Cl$_2$.DCM (33 mg, 0.041 mmol), EtOH (4.0 mL) and TEA (0.086 mL, 0.62 mmol), then heated to reflux. After 55 min, the reaction mixture was diluted with EtOAc and washed with H$_2$O and brine. The organics were dried over anhydrous MgSO$_4$, filtered and concentrated in vacuo. The residue was purified by silica gel chromatography (15% to 30% EtOAc/Hex) to afford vinyl quinoxaline 38-2 (168 mg). LCMS-ESI$^+$ (m/z): [M+H]$^+$ calcd for C$_{38}$H$_{53}$N$_4$O$_7$: 677.39; found: 677.38.

Steps 3 and 4. Preparation of 38-3: Vinyl quinoxaline 38-2 (225 mg, 0.332 mmol) was suspended in DCE (66 mL) and treated with Zhan 1B catalyst (42 mg, 0.067 mmol, Strem). The suspension was degassed with bubbling N$_2$ for 28 min, then heated to reflux for 90 min. The reaction mixture was then filtered over Celite and concentrated in vacuo. The crude residue was purified by silica gel chromatography (15% to 30% EtOAc/Hex) to afford the desired macrocycle (168 mg; LCMS-ESI$^+$ (m/z): [M+H]$^+$ calcd for C$_{36}$H$_{49}$N$_4$O$_7$: 649.36; found: 649.33). The macrocycle was dissolved in EtOH (25 mL) and EtOAc (5 mL) and treated with Pd/C (10 wt % Pd, 95 mg). Hydrogen from a balloon was bubbled through the suspension for 1 min the reaction was stirred under an H$_2$ atmosphere for an additional 1.5 h. Upon completion, the reaction mixture was filtered over Celite and concentrated in vacuo to afford the desired macrocycle 38-3 which was carried on without further purification. LCMS-ESI$^+$ (m/z): [M+H]$^+$ calcd for C$_{36}$H$_{51}$N$_4$O$_7$: 651.38; found: 651.42.

Step 5. Preparation of 38-4: Unpurified 38-3 from the previous step was dissolved in DCM (10 mL) and treated with TMSOTf (0.23 mL, 1.3 mmol). After stirring at rt for 1 h 15 min, the reaction mixture was concentrated in vacuo. The residue was redissolved in DCM and pipetted into 1 M aqueous NaOH. The mixture was agitated for 1 min, then acidified to pH~1-2 with 10% aqueous HCl. The aqueous layer was extracted three times with DCM and combined organics dried over anhydrous MgSO$_4$, filtered and concentrated in vacuo. The crude material was purified by silica gel chromatography (0% to 20% MeOH/EtOAc) to afford carboxylic acid 38-4 (131 mg). LCMS-ESI$^+$ (m/z): [M+H]$^+$ calcd for C$_{32}$H$_{43}$N$_4$O$_7$: 595.31; found: 595.29.

Step 6. Preparation of Example 38: Carboxylic acid 38-4 (131 mg, 0.220 mmol) and Intermediate A10 (81 mg, 0.264 mmol) were treated with TBTU (85 mg, 0.264 mmol), DMAP (32 mg, 0.264 mmol), DCM (2.6 mL) and DIPEA (0.38 mL, 2.2 mmol). The reaction mixture was stirred at rt for 14 h, then concentrated under reduced pressure. The crude residue was purified by HPLC to afford Example 38 (74 mg) in approximately 90% purity as a TFA salt. Analytic HPLC RetTime: 8.93 min. LCMS-ESI$^+$ (m/z): [M+H]$^+$ calcd for C$_{41}$H$_{55}$F$_2$N$_6$O$_9$S: 845.37; found: 845.57. $^1$H NMR (400 MHz, CD$_3$OD) δ 9.12 (s, 1H), 7.77 (d, J=9.2 Hz, 1H), 7.20 (dd, J=9.0 Hz, 2.7 Hz, 1H), 7.16 (d, J=2.8 Hz, 1H), 5.81 (td, J=55.9, 6.6 Hz, 1H), 5.59 (d, =3.5 Hz, 1H), 4.52 (d, J=6.8 Hz, 1H), 4.50 (s, 1H), 4.40 (d, J=12.0 Hz, 1H), 4.18 (dd, J=11.9 Hz, 3.9 Hz, 1H), 3.93 (s, 3H), 3.74 (m, 1H), 2.97-2.90 (m, 1H), 2.85-2.75 (m, 2H), 2.01 (m, 2H), 1.85-1.41 (m, 21H), 1.12 (s, 3H), 1.08 (d, J=7.4 Hz, 3H), 0.96 (m 2H), 0.91 (t, J=4.3 Hz, 2H), 0.70 (m, 1H), 0.48 (m, 1H).

Example 39

Preparation of (3aR,7S,10S,11S,12R,24aR)-7-tert-butyl-N-[(1R,2R)-2-(difluoromethyl)-1-{[(1-methyl-cyclopropyl)sulfonyl]carbamoyl}cyclopropyl]-1-ethyl-16-methoxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide

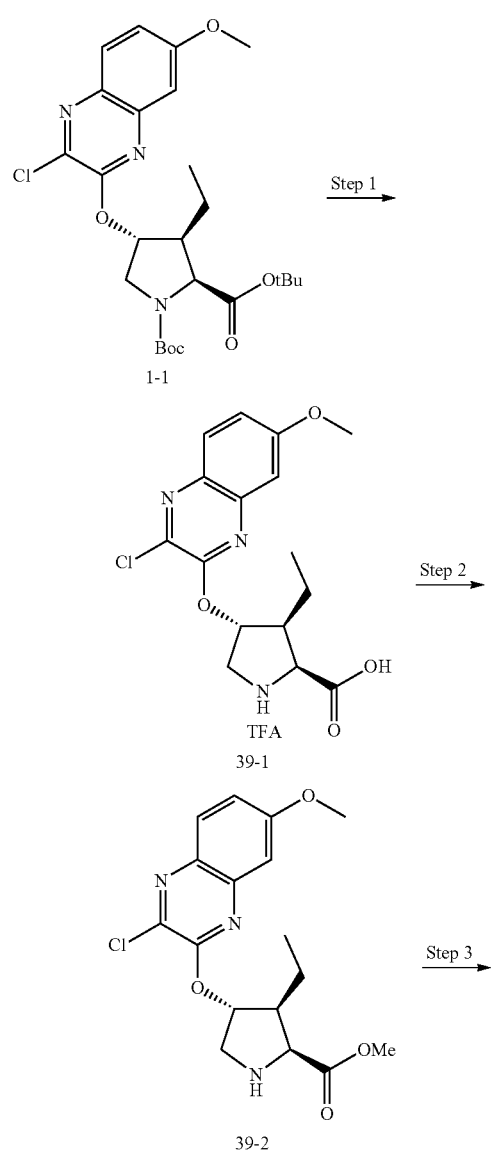

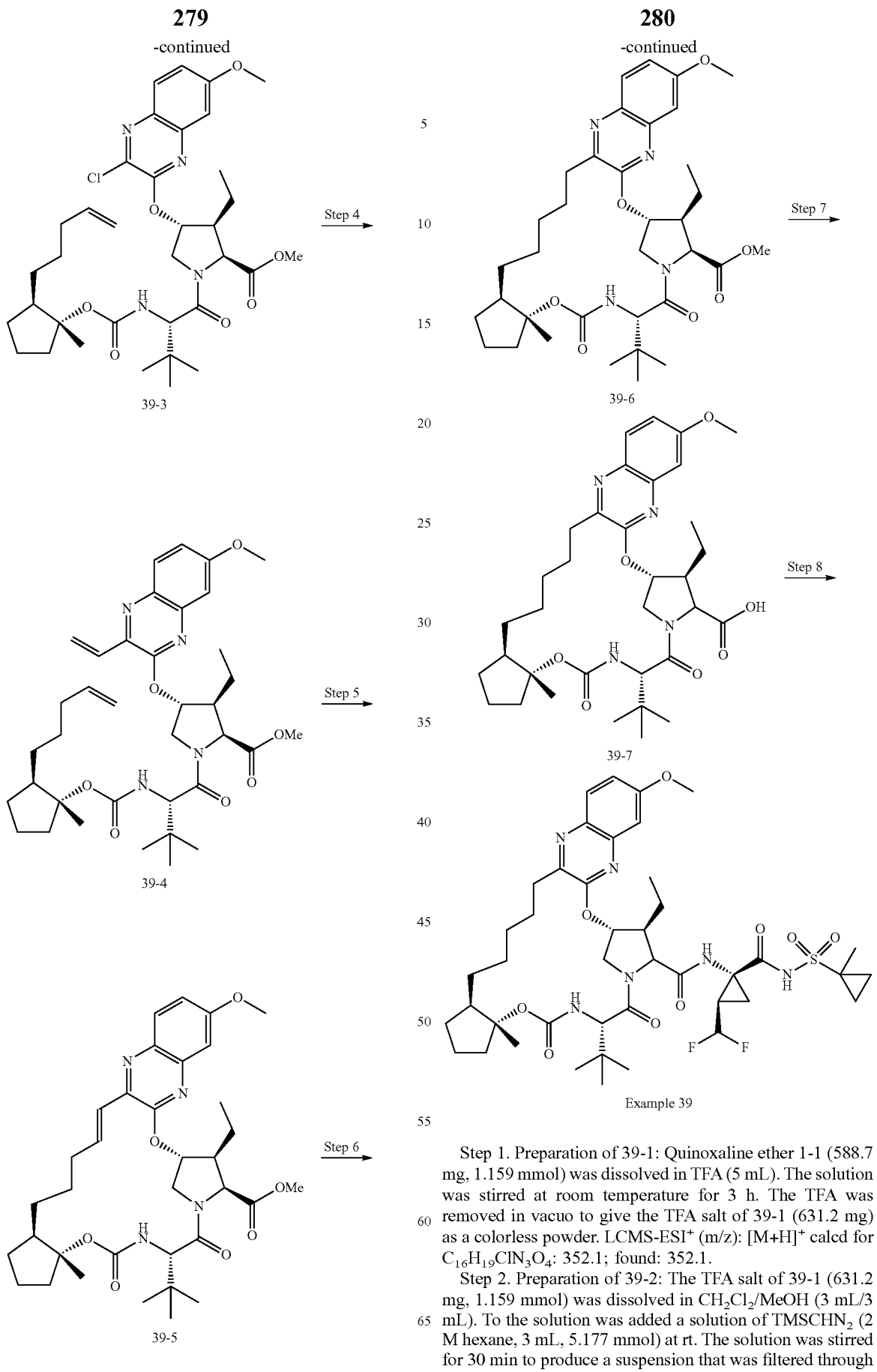

Example 39

Step 1. Preparation of 39-1: Quinoxaline ether 1-1 (588.7 mg, 1.159 mmol) was dissolved in TFA (5 mL). The solution was stirred at room temperature for 3 h. The TFA was removed in vacuo to give the TFA salt of 39-1 (631.2 mg) as a colorless powder. LCMS-ESI+ (m/z): [M+H]+ calcd for $C_{16}H_{19}ClN_3O_4$: 352.1; found: 352.1.

Step 2. Preparation of 39-2: The TFA salt of 39-1 (631.2 mg, 1.159 mmol) was dissolved in $CH_2Cl_2$/MeOH (3 mL/3 mL). To the solution was added a solution of $TMSCHN_2$ (2 M hexane, 3 mL, 5.177 mmol) at rt. The solution was stirred for 30 min to produce a suspension that was filtered through a fritted glass funnel to remove solids. The filtrate was concentrated in vacuo to afford a residue that was purified by silica gel chromatography (100% ethyl acetate) to produce methyl ester 39-2 (213.0 mg) as colorless crystals. LCMS-ESI+ (m/z): [M+H]+ calcd for $C_{17}H_{21}ClN_3O_4$: 366.1; found: 366.1.

Step 3. Preparation of 39-3: Intermediate D7 (191.2 mg, 0.587 mmol) and methyl ester 39-2 (414.1 mg, 1.132 mmol) were treated with HATU (860.0 mg, 2.264 mmol) and DIPEA (0.59 mL, 3.396 mmol) in DMF (8 mL) at rt for 4 h. The reaction was quenched with $H_2O$ (50 mL) and extracted with EtOAc (50 mL three times). The combined organics were washed with brine (50 mL) and dried over anhydrous $Na_2SO_4$. After removal of drying agent by filtration, the solvent was removed in vacuo. The residue was purified by silica gel chromatography (20% ethyl acetate in hexanes) to give the desired amide 39-3 (573.9 mg) as colorless oil. LCMS-ESI+ (m/z): [M+Na]+ calcd for $C_{33}H_{49}ClN_4NaO_7$: 695.3; found: 695.3.

Step 4. Preparation of 39-4: Amide 39-3 (573.9 mg, 0.8524 mmol), potassium trifluorovinylborate (171.3 mg, 1.279 mmol) and $PdCl_2dppf \cdot CH_2Cl_2$ (62.4 mg, 0.085 mmol) were treated with $Et_3N$ (0.18 mL, 1.279 mmol) in EtOH (8 mL) under a nitrogen atmosphere and gently refluxed for 30 min. The reaction was diluted with PhMe (30 mL) and the solvent was removed in vacuo. The residue was purified by silica gel chromatography (20% ethyl acetate in hexanes) to give the desired vinyl quinoxaline 39-4 (542.0 mg, 0.8152 mmol) as an orange foam. LCMS-ESI+ (m/z): [M+H]+ calcd for $C_{37}H_{52}N_4NaO_7$: 687.4; found: 687.3.

Step 5. Preparation of 39-5: The vinyl quinoxaline 39-4 (542.0 mg, 0.8152 mmol) was treated with Zhan 1b catalyst (59.8 mg, 0.08 mmol, Strem) in DCE (41 mL). The mixture was heated at 80° C. for 1 h. Additional Zhan 1b catalyst (59.8 mg, 0.08 mmol, Strem) was added and the mixture to heat at 80° C. for an additional 30 min. The solvent was removed in vacuo and the residue purified by silica gel chromatography (20% ethyl acetate in hexanes) to produce macrocycle 39-5 (401.0 mg, 0.6297 mmol) as an orange oil. LCMS-ESI+ (m/z): [M+H]+ calcd for $C_{35}H_{49}N_4O_7$; 637.4; found: 637.3.

Step 6. Preparation of 39-6: Macrocycle 39-5 (401.0 mg, 0.6297 mmol) was taken up in 1,4-dioxane (15 mL) and treated with Pd/C (10% wt Pd, 200.0 mg) and MgO (200.0 mg) stirred under an atmosphere of hydrogen. The mixture was stirred at rt for 1 h. The reaction mixture was filtered through Celite (5 g) using EtOAc (80 mL). The solvent was removed in vacuo to give macrocycle 39-6 (425.3 mg) as a pale orange oil. LCMS-ESI+ (m/z): [M+H]+ calcd for $C_{35}H_{51}N_4O_7$: 639.4; found: 639.3.

Step 7. Preparation of 39-7: Macrocycle 39-6 (74.8 mg, 0.110 mmol) was treated with 2 M aqueous LiOH aqueous solution (1.6 mL, 3.15 mmol) in MeOH/THF (4 mL/4 mL) at rt for 8 h, 50° C. for 2 h and then 60° C. for 3 h. The mixture was cooled to 0° C. using ice-water bath. To the mixture was added brine (30 mL). The whole was extracted with $CH_2Cl_2$ (30 mL three times). The organic layer was washed with brine (30 mL) and dried over anhydrous $Na_2SO_4$. After removal of the drying agent by filtration, the solvent was removed in vacuo to give carboxylic acid 39-7 (370.6 mg, 0.5932 mmol) as a colorless oil. LCMS-ESI+ (m/z): [M+H]+ calcd for $C_{34}H_{49}N_4O_7$: 625.4; found: 625.3.

Step 8. Preparation of Example 39: Carboxylic acid 39-7 (100.0 mg, 0.1601 mmol) and Intermediate A10 (73.2 mg, 0.2401 mmol) were treated with HATU (91.3 mg, 0.2401 mmol) and DIPEA (0.14 mL, 0.8005 mmol) in DMF (3 mL) at rt for 5 h. The reaction was quenched with $H_2O$ (30 mL) and extracted with EtOAc (30 mL three times). The organic layer was washed with brine (30 mL) and dried over anhydrous $Na_2SO_4$. After removal of the drying agent by filtration, the solvent was removed in vacuo. The residue was purified by silica gel chromatography (25 to 100% ethyl acetate in hexanes). Fractions containing desired product were concentrated in vacuo and the residue further purified by super critical fluid column chromatography (DAICEL Chiralpak IC 10×250 mm, 18.9 mL/min, 35% MeOH, 15 atm. 40° C.) to give Example 39 (80.5 mg, 0.0920 mmol, 57%) as a colorless powder. Analytic HPLC RetTime: 9.35 min. LCMS-ESI+ (m/z): [M+H]+ calcd for $C_{43}H_{61}F_2N_6O_9S$: 875.4; found: 875.4. 1H NMR (300 MHz, $CD_3OD$) δ 7.81 (d, J=9.6 Hz, 1H), 7.27 (s, 1H), 7.24 (d, J=9.6 Hz, 1H), 6.68 (d, J=9.6 Hz, 1H), 5.74-6.30 (m, 3H), 4.73 (d, J=7.2 Hz, 1H), 4.73 (d, J=7.2 Hz, 1H), 4.40-4.60 (m, 1H), 4.22 (d, J=9.6 Hz, 1H), 3.95 (s, 3H), 3.61 (q, J=7.2 Hz, 2H), 3.16-3.30 (m, 1H), 2.50-2.77 (m, 2H), 2.20-0.60 (m, 21H), 1.35 (s, 3H) 1.12 (t, J=7.2 Hz, 3H), 1.18 (s, 3H), 1.02 (s, 9H).

Example 40

Preparation of (3aR,7S,10S,11S,12R,24aR)-7-tert-butyl-N-[(1R,2R)-1-[(cyclopropylsulfonyl)carbamoyl]-2-(difluoromethyl)cyclopropyl]-11-ethyl-16-methoxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide

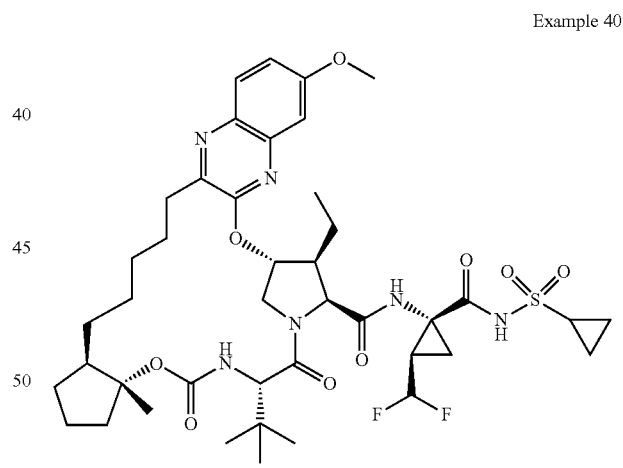

Example 40

Example 40 was prepared in a similar fashion to Example 39, substituting Intermediate A9 for Intermediate A10 in Step 8. Example 40 was isolated (70.9 mg) in approximately 92% purity. Analytic HPLC RetTime: 9.24 min. LCMS-ESI+ (m/z): [M+H]+ calcd for $C_{42}H_{59}F_2N_6O_9S$: 861.4; found: 861.4. 1H NMR (300 MHz, $CD_3OD$) δ 7.80 (d, J=9.6 Hz, 1H), 7.25 (s, 1H), 7.23 (d, J=9.6 Hz, 1H), 6.70 (d, J=9.6 Hz, 1H), 5.60-6.10 (m, 3H), 4.69 (d, J=7.2 Hz, 1H), 4.39 (dd, J=12.0, 6.0 Hz, 1H), 4.2 (d, J=9.6 Hz, 1H), 4.03-4.10 (m, 1H), 3.94 (s, 3H), 3.12-3.28 (m, 1H), 2.89-3.05 (m, 1H), 2.50-2.76 (m, 2H), 2.30-0.80 (m, 19H), 1.36 (s, 3H) 1.25 (t, J=7.2 Hz, 3H), 1.10 (s, 3H), 1.04 (s, 9H).

Example 41

Preparation of (3aR,7S,10S,11S,12R,24aR)-7-tert-butyl-N-[(1R,2S)-2-(2,2-difluoroethyl)-1-{[(1-methylcyclopropyl)sulfonyl]carbamoyl}cyclopropyl]-11-ethyl-16-methoxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide Example 41

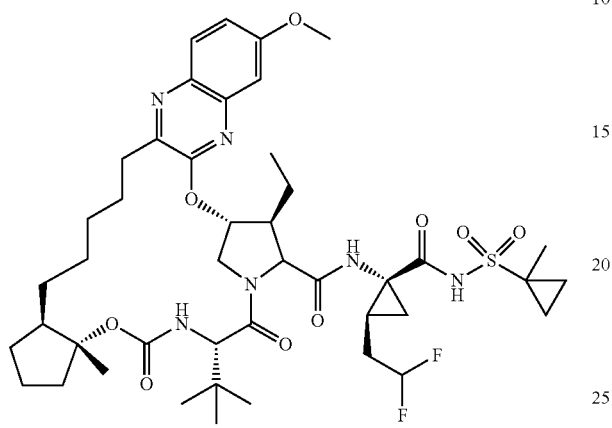

Example 41 was prepared in a similar fashion to Example 39, substituting Intermediate A8 for Intermediate A10 in Step 8. Example 41 was isolated (4.3 mg) in approximately 92% purity. Analytic HPLC RetTime: 9.36 min. LCMS-ESI$^+$ (m/z): [M+H]$^+$ calcd for $C_{42}H_{59}F_2N_6O_9S$: 889.4; found: 889.5. $^1$H NMR (300 MHz, $CD_3COCD_3$) δ 7.83 (d, J=7.83 Hz, 1H), 7.19-7.30 (m, 1H), 5.74-6.30 (m, 3H), 4.70 (d, J=7.2 Hz, 1H), 4.19 (dd, J=12.0, 6.0 Hz, 1H), 4.24 (d, J=9.6 Hz, 1H), 4.12 (d, J=12.0, 9.6 Hz, 1H), 3.96 (s, 3H), 3.10-3.26 (m, 1H), 2.56-2.80 (m, 2H), 2.30-0.80 (m, 25H), 1.54 (s, 3H), 1.42 (s, 3H), 1.12 (t, J=7.2 Hz, 3H), 1.06 (s, 9H).

Example 42 and Example 43

Preparation of (1aS,5S,8S,9S,10R,22aS)-5-tert-butyl-N-[(1R,2R)-2-(difluoromethyl)-1-{[(1-methylcyclopropyl)sulfonyl]carbamoyl}cyclopropyl]-1a-ethyl-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide and (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-1a-ethyl-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

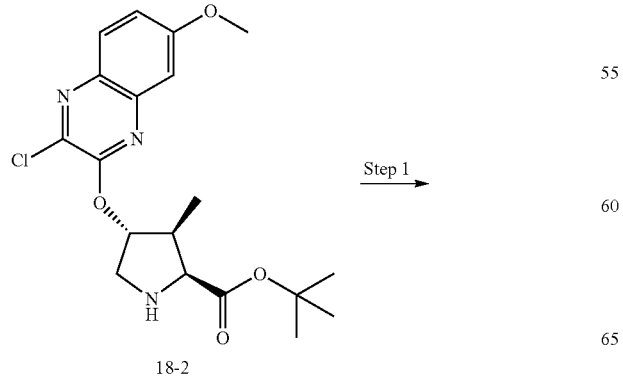

18-2

Step 1

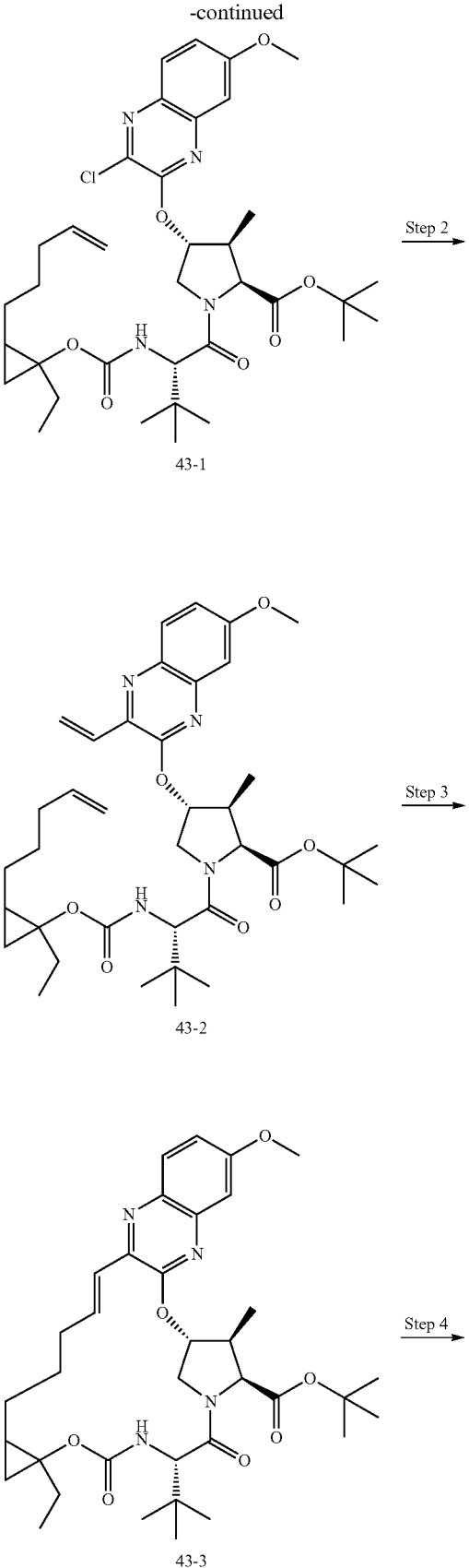

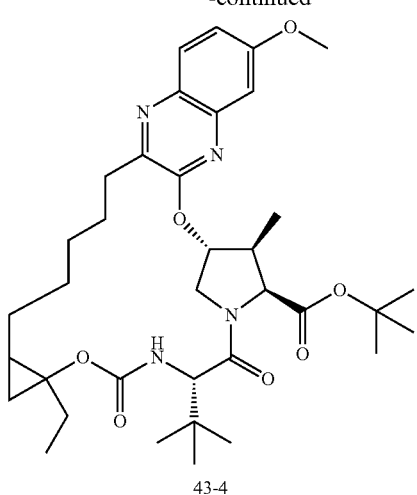

43-4

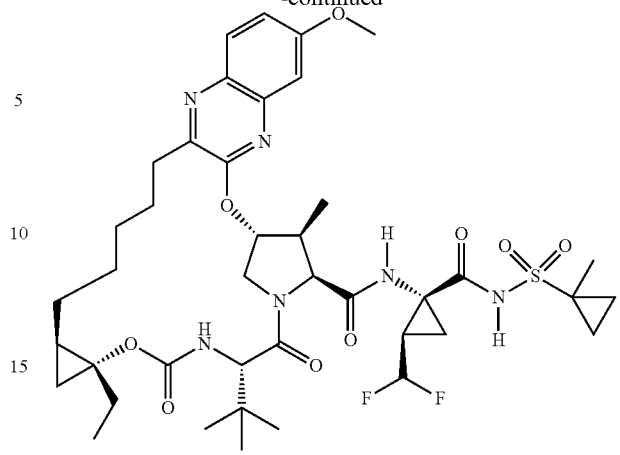

Example 43

Step 1. Preparation of 43-1: To a solution of Intermediate mixture D15 (281 mg, 0.81 mmol) and Intermediate 18-2 (290 mg, 0.74 mmol) in MeCN (3.7 mL) was added HATU (308 mg, 0.81 mmol) followed by DIPEA (640 µL, 3.68 mmol) at rt under an argon atmosphere. After 17 h, the reaction mixture was concentrated in vacuo, and the crude residue was purified by silica gel chromatography (0-100% ethyl acetate/hexanes) to afford 43-1 (121 mg, 1:1 diastereomeric mixture) as a colorless oil. LCMS-ESI$^+$ (m/z): [M+H]$^+$ calcd for $C_{36}H_{52}ClN_4O_7$: 687.3; found: 687.5.

Step 2. Preparation of 43-2: To a solution of diastereomeric mixture 43-1 (121 mg, 176 µmol), TEA (38 µL, 264 µmol) and potassium vinyltrifluoroborate (35.4 mg, 264 µmol) in EtOH (0.88 mL) was added PdCl$_2$(dppf) (14.4 mg, 17.6 µmol). The reaction mixture was degassed with argon for 10 min and heated to 78° C. After 25 min, the reaction mixture was allowed to cool to rt and was concentrated in vacuo. The crude residue was purified by silica gel chromatography (0-100% ethyl acetate/hexanes) to afford 43-2 (105 mg, 1.1 diastereomeric mixture) as a yellow oil. LCMS-ESI$^+$ (m/z): [M+H]$^+$ calcd for $C_{38}H_{55}N_4O_7$: 679.4; found: 679.5.

Step 3. Preparation of 43-3: To a solution of diastereomeric mixture 43-2 (105 mg, 155 µmol) in DCE (31 mL) was added Zhan 1B catalyst (11.3 mg, 15.5 µmol, Strem) and the reaction mixture was degassed for 10 minutes with argon. The reaction mixture was then heated to 100° C. After 15 min, the reaction mixture was allowed to cool to rt and was concentrated in vacuo. The crude residue was purified by silica gel chromatography (0-100% ethyl acetate/hexanes) to afford 43-3 (52.3 mg, 1:1 diastereomeric mixture) as a light yellow oil. LCMS-ESI$^+$ (m/z): [M+H]$^+$ calcd for $C_{36}H_{55}N_4O_7$: 651.4; found: 651.5.

Step 4. Preparation of 43-4: To a solution of diastereomeric mixture 43-3 (52 mg, 80 µmol) in ethanol (0.4 mL) was added Pd/C (10 wt % Pd, 9 mg, 8 µmol) at rt under an argon atmosphere. The atmosphere was replaced with hydrogen and the reaction mixture was stirred vigorously at rt. After 45 min, the reaction mixture was diluted with ethyl acetate (1 mL) and was filtered through a pad of Celite with ethyl acetate washings (3×1 mL). The filtrate was concentrated in vacuo to afford 43-4 (49 mg, 1:1 diastereomeric mixture), which was used directly in the next step without further purification. LCMS-ESI$^+$ (m/z): [M+H]$^+$ calcd for $C_{36}H_{52}N_4O_7$: 653.4; found: 653.6.

Step 5. Preparation of 43-5: To a solution of diastereomeric mixture 43-4 (49 mg, 67 µmol) in DCM (0.5 mL) was

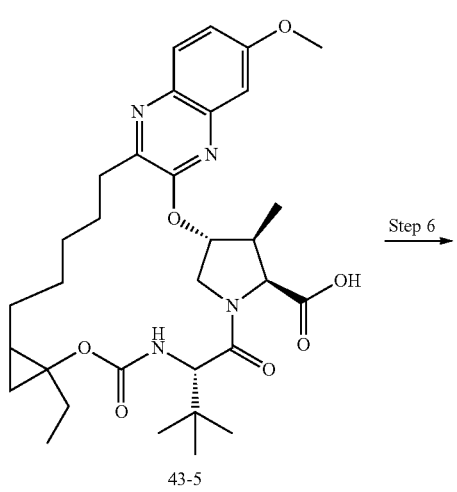

43-5

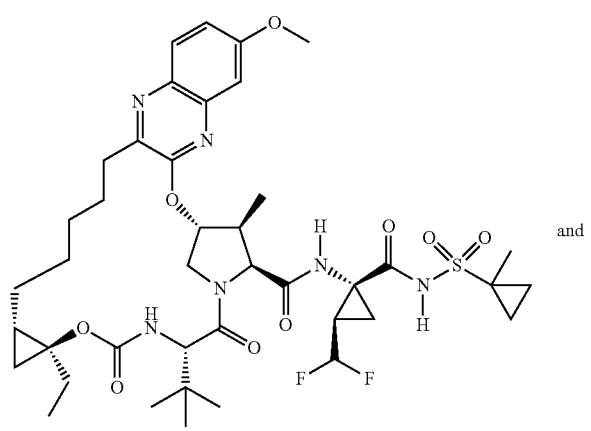

Example 42 and added TMSOTf (60 µL, 0.34 mmol) at rt under an argon atmosphere. After 3 h, the reaction mixture was added slowly to a 0.25 N aqueous NaOH solution (precooled to 0° C., 1 mL). The resulting mixture was diluted with 1 N aqueous HCl solution (5 mL), and was extracted with DCM (3×5 mL). The combined organic extracts were dried over anhydrous sodium sulfate and were concentrated to afford 43-5 (71 mg, 1:1 diastereomeric mixture) as a tan solid, which was used directly in the next step without further purification. LCMS-ESI+ (m/z): [M+H]+ calcd for $C_{32}H_{45}N_4O_7$: 597.3; found: 597.5.

Step 6. Preparation of Examples 42 and 43: To a solution of diastereomeric mixture 43-5 (71 mg, ~67 µmol) and Intermediate A10 (54 mg, 178 µmol) in MeCN (1.00 mL) was added HATU (69 mg, 178 µmol) followed by DIPEA (155 µL, 0.89 mmol) at rt under an argon atmosphere. After 1 h the reaction mixture was concentrated in vacuo, and the crude residue was purified by silica gel chromatography (0-100% ethyl acetate/hexanes). The fractions containing the desired product were combined and repurified by preparatory HPLC (Gemini 5u C18 110 Å column, 50-100% MeCN/H$_2$O, 0.1% trifluoroacetic acid modifier) and were lyophilized to afford Example 42 (10 mg) and Example 43 (10 mg) as off white powders. Example 42: Analytic HPLC RetTime: 9.04 min. [M+H]+ calcd for $C_{41}H_{57}F_2N_6O_9S$: 847.4; found: 847.6. $^1$H NMR (400 MHz, CD$_3$OD) δ 8.98 (s, 1H), 7.73 (d, J=8.4 Hz, 2H), 7.20-7.13 (m, 2H), 5.70 (td, J=55.8, 6.4 Hz, 1H), 5.65 (d, J=3.7 Hz, 1H), 5.44 (br s, 1H), 4.55-4.42 (m, 1H), 4.20-4.03 (m, 1H), 3.87 (s, 3H), 3.17-3.08 (m, 1H), 2.85-2.72 (m, 1H), 2.71-2.59 (m, 1H), 2.18-2.06 (m, 1H), 2.03-1.83 (m, 4H), 1.80-1.53 (m, 5H), 1.50 (br s, 3H), 1.46 (s, 3H), 1.40-1.31 (m, 1H), 1.33-1.09 (m, 5H), 1.06 (s, 9H), 1.05-0.95 (m, 6H), 0.92-0.73 (m, 3H), Example 43: Analytic HPLC RetTime: 9.17 min. [M+H]+ calcd for $C_{41}H_{57}F_2N_6O_9S$: 847.4; found: 847.6. $^1$H NMR (400 MHz, CD$_3$OD) δ 9.03 (s, 1H), 7.68 (d, J=9.5 Hz, 1H), 7.14-7.09 (m, 2H), 5.68 (td, $J_{H-F}$=55.5, 6.7 Hz, 1H), 5.59 (d, J=3.7 Hz, 1H), 4.45 (d, J=6.8 Hz, 1H), 4.29 (d, J=12.1 Hz, 1H), 4.12 (s, 1H), 4.08 (dd, J=12.1, 4.3 Hz, 1H), 3.82 (s, 3H), 2.90-2.79 (m, 1H), 2.79-2.70 (m, 1H), 2.66-2.56 (m, 1H), 2.43-2.31 (m, 1H), 1.95-1.85 (m, 2H), 1.75-1.62 (m, 1H), 1.61-1.42 (m, 5H), 1.44 (br s, 3H) 1.40 (s, 3H), 1.34-1.02 (m, 8H), 1.00 (s, 9H), 0.99-0.89 (m, 5H), 0.85-0.74 (m, 3H).

Example 44

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-14-methoxy-1a,9-dimethyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

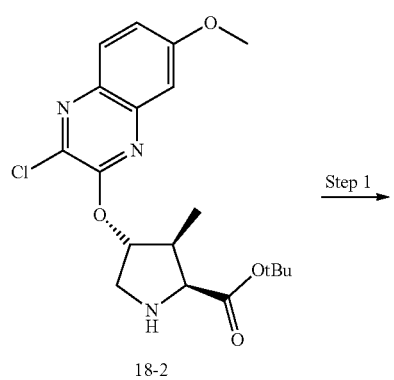

18-2

Step 1

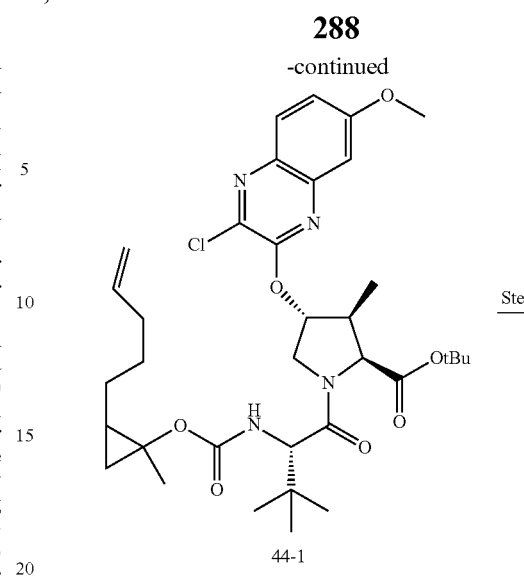

44-1

Step 2

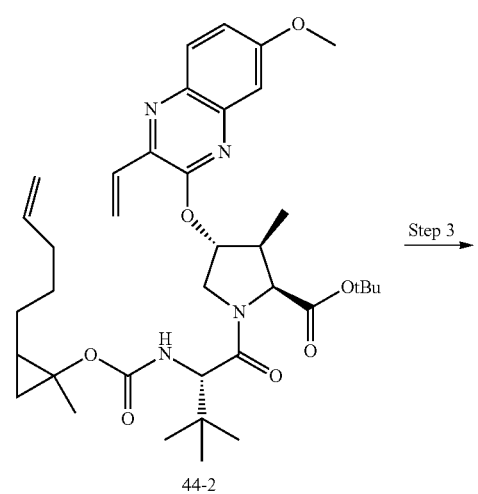

44-2

Step 3

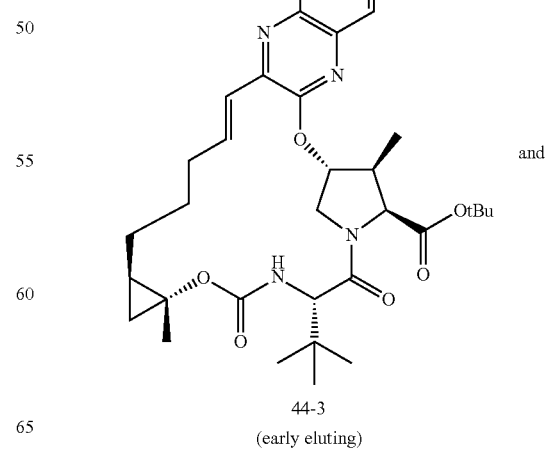

44-3
(early eluting)

and

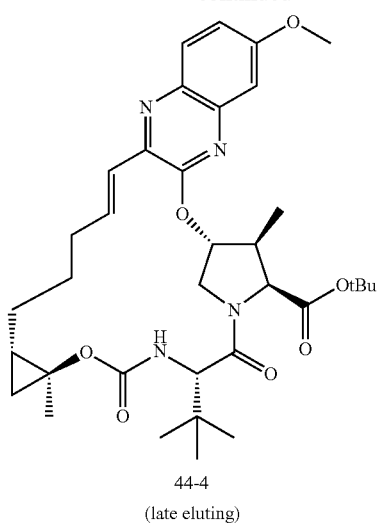

44-4
(late eluting)

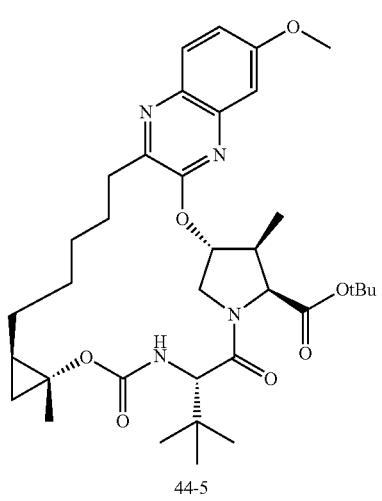

44-5

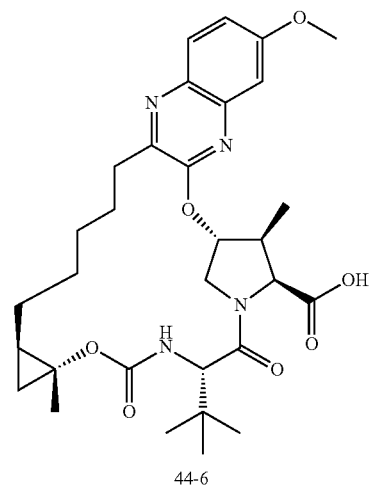

44-6

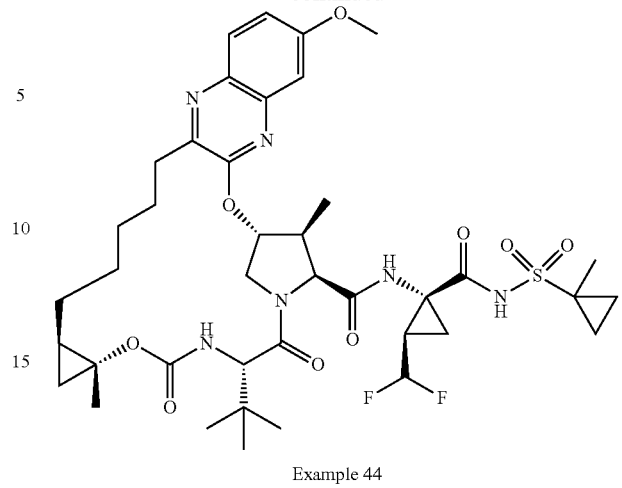

Example 44

Step 1. Preparation of 44-1: HATU (544 mg, 1.43 mmol, Oakwood) and DIPEA (0.83 mL, 4.76 mmol) were added to a mixture of 18-2 (429 mg, 1.09 mmol) and an Intermediate mixture D6 (395 mg, 1.33 mmol) in 12 mL of acetonitrile under argon. After stirring overnight, the reaction mixture was concentrated under reduced pressure and the resulting residue was purified by silica gel chromatography (0-30% ethyl acetate in hexanes) to produce 44-1 (545 mg; 1:1 mixture of diastereomers) as a white solid. LCMS-ESI$^+$ (m/z): [M+H]$^+$ calcd for $C_{35}H_{50}ClN_4O_7$: 673.33; found: 673.47.

Step 2. Preparation of 44-2: Pd(dppf)Cl$_2$.CH$_2$Cl$_2$ (74 mg, 0.091 mmol, Strem) was added to a deoxygenated mixture of 44-1 (542 mg, 0.805 mmol), potassium vinyltrifluoroborate (168 mg, 1.25 mmol), and triethylamine (0.170 mL, 1.21 mmol) in 9 mL of EtOH at room temperature. Reaction mixture was heated at 78° C. under argon for 75 minutes. After cooling to rt, 6 mL of toluene was added and reaction mixture was concentrated in vacuo. The resulting residue was purified by silica gel chromatography (0-35% ethyl acetate in hexanes) to yield 44-2 (438 mg; 1:1 mixture of diastereomers) as a yellow film. LCMS-ESI$^+$ (m/z): [M+H]$^+$ calcd for $C_{37}H_{53}N_4O_7$: 665.38; found: 665.55.

Step 3. Preparation of 44-3 and 44-4: A diastereomeric mixture 44-2 (437 mg, 0.658 mmol) and Zhan 1B catalyst (81 mg, 0.072 mmol, Strem) in 131 mL of DCE was deoxygenated under argon for 25 minutes. The mixture was then heated at 95° C. for 50 minutes. An additional 7 mg of Zhan 1B catalyst was added and reaction mixture was heated at 95° C. for 10 minutes. After cooling to room temperature, reaction mixture was concentrated in vacuo. The resulting residue was purified by silica gel chromatography (0-40% ethyl acetate in hexanes) to yield single diastereomers 44-3 (143 mg, early eluting component) as a light yellow film and 44-4 (118 mg, late eluting component) as a light yellow solid. Early eluting 44-3: LCMS-ESI$^+$ (m/z): [M+H]$^+$ calcd for $C_{35}H_{49}N_4O_7$: 637.35; found: 637.45. Late eluting 44-4: LCMS-ESI$^+$ (m/z): [M+H]$^+$ calcd for $C_{35}H_{49}N_4O_7$: 637.35; found: 637.59.

Step 4. Preparation of 44-5: Palladium on carbon (10 wt % Pd, 48 mg, 0.045 mmol) was added to a solution of 44-3 (143 mg, 0.225 mmol) in 6 mL of ethanol. The atmosphere was replaced with hydrogen and the reaction stirred for 90 minutes. The reaction mixture was filtered over Celite and washed with ethyl acetate. Filtrate was concentrated in vacuo to yield 44-5 (130 mg) as brown solid film, which was used in the next step without further purification. LCMS-ESI$^+$ (m/z): [M+H]$^+$ calcd for $C_{35}H_{51}N_4O_7$: 639.37; found: 639.53.

Step 5. Preparation of 44-6: TMSOTf (0.53 mL, 2.91 mmol) was added dropwise to a solution of 44-5 (130 mg, 1.27 mmol) in 3.8 mL of dichloromethane under argon at room temperature. After one hour, an additional 0.22 mL of TMSOTf was added. After an additional hour, 0.20 mL of TMSOTf was added. After 40 minutes, 0.25 mL of TMSOTf was added. After one hour, reaction mixture was taken up in 10 mL of dichloromethane and quenched by addition of 20 mL of 1 N aqueous HCl with stirring. Layers were separated and aqueous was extracted with dichloromethane (3×30 mL) Combined organics were washed with brine, dried over anhydrous $Na_2SO_4$, filtered, and concentrated in vacuo to yield 44-6 (113 mg) as an off white solid, which was used in the next step without further purification. LCMS-ESI$^+$ (m/z): [M+H]$^+$ calcd for $C_{31}H_{43}N_4O_7$: 583.31; found: 583.45.

Step 6. Preparation of Example 44: HATU (53 mg, 0.139 mmol) and DIPEA (0.080 mL, 0.459 mmol) were added to a mixture of 44-6 (51 mg, 0.088 mmol) and Intermediate A10 (49 mg, 0.161 mmol) in 1.5 mL of MeCN under argon. After stirring for overnight, an additional 13 mg of Intermediate A10 was added. After one hour, reaction mixture was taken up in 15 mL of ethyl acetate and poured into 20 mL of 1 N aqueous HCl. Layers were separated and aqueous was extracted three times with ethyl acetate. Combined organics were washed with water and brine, dried over anhydrous $Na_2SO_4$, filtered, and concentrated in vacuo. The resulting residue was purified by silica gel chromatography (0-40% ethyl acetate in hexanes) to yield Example 44 (41 mg) as an off white solid. Analytic HPLC RetTime: 8.86 min. LCMS-ESI$^+$ (m/z): [M+H]$^+$ calcd for $C_{40}H_{55}F_2N_6O_9S$: 833.36; found: 833.51. $^1$H NMR (400 MHz, $CD_3OD$): 7.79 (d, J=10 Hz, 1H), 7.28-7.21 (m, 2H), 6.77 (d, J=8.4 Hz, 1H), 5.81 (td, $J_{H-F}$=56 HZ, J=6.4 Hz, 1H), 5.73-5.70 (m, 1H), 4.56 (d, J=7.2 Hz, 1H), 4.40 (d, J=11.6 Hz, 1H), 4.26-4.16 (m, 2H), 3.93 (s, 3H), 3.05-2.91 (m, 1H), 2.90-2.82 (m, 1H), 2.77-2.68 (m, 1H), 2.06-1.94 (m, 2H), 1.88-1.74 (m, 1H), 1.72-1.58 (m, 3H), 1.58-1.44 (m, 4H), 1.53 (s, 3H), 1.51 (s, 3H), 1.43-1.36 (m, 1H), 1.12-1.02 (m, 2H), 1.09 (s, 9H), 1.07 (d, J=4 Hz, 3H), 1.00-0.94 (m, 2H), 0.92-0.84 (m, 3H), 0.16-0.11 (m, 1H).

Example 45

Preparation of (1aS,5S,8S,9S,10R,22aS)-5-tert-butyl-N-[(1R,2R)-2-(difluoromethyl)-1-{[(1-methylcyclopropyl)sulfonyl]carbamoyl}cyclopropyl]-14-methoxy-1a,9-dimethyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 45

Example 45 was prepared in a similar fashion to Example 44, substituting late eluting 44-4 for early eluting 44-3 in step 4. Example 45 was isolated (23 mg) as an off white solid. Analytic HPLC RetTime: 8.92 min. LCMS-ESI$^+$ (m/z): [M+H]$^+$ calcd for $C_{40}H_{55}F_2N_6O_9S$: 833.36; found: 833.54. $^1$H NMR (400 MHz, $CD_3OD$): 7.79 (d, J=9.2 Hz, 1H), 7.25-7.19 (m, 2H), 6.55 (d, J=5.2 Hz, 1H), 5.78 (td, $J_{H-F}$=61 Hz, J=6 Hz, 1H), 5.52-5.48 (m, 1H), 4.58 (d, J=6.4 Hz, 1H), 4.52 (d, J=12 Hz, 1H), 4.17-4.10 (m, 1H), 4.04 (d, J=6.4 Hz, 1H), 3.93 (s, 3H), 3.22-3.14 (m, 1H), 2.88-2.80 (m, 1H), 2.78-2.66 (m, 1H), 2.08-1.90 (m, 2H), 1.76-1.64 (m, 1H), 1.63-1.50 (m, 7H), 1.51 (s, 3H), 1.47-1.36 (m, 2H), 1.46 (s, 3H), 1.18-1.06 (m, 1H), 1.12 (s, 9H), 1.07 (m, 3H), 1.00-0.80 (m, 4H), 0.10-0.04 (m, 1H).

Example 46 and 47

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-18,18-difluoro-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide and (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-8-fluoro-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[1,12-b]quinoxaline-8-carboxamide

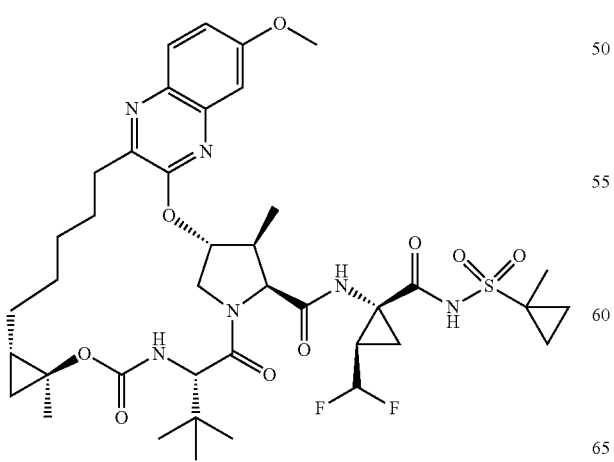

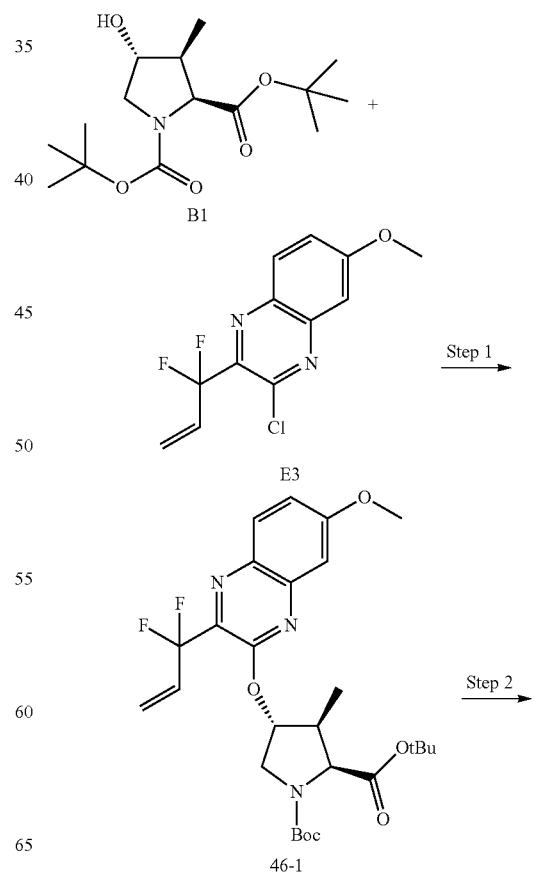

293
-continued
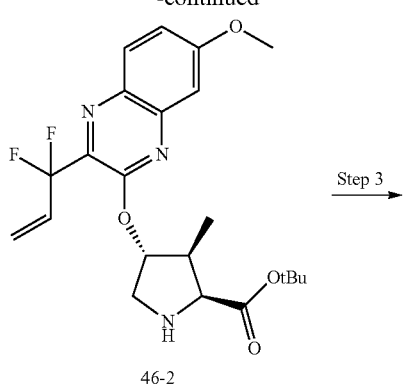
46-2
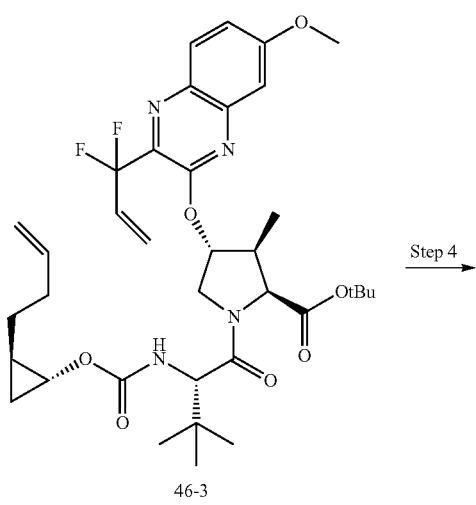
46-3
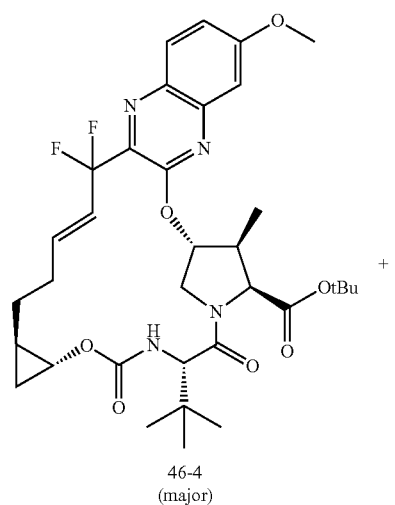
46-4
(major)
Step 3 →
Step 4 →
294
-continued
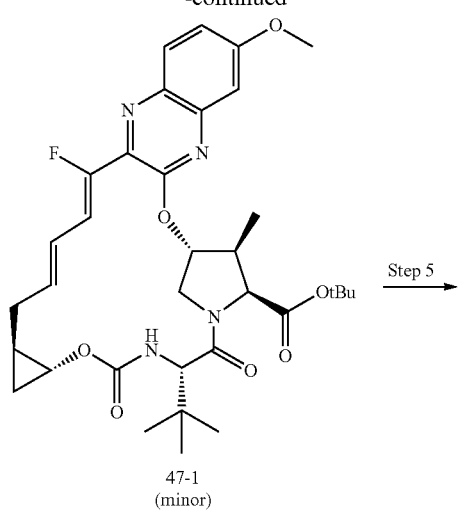
47-1
(minor)
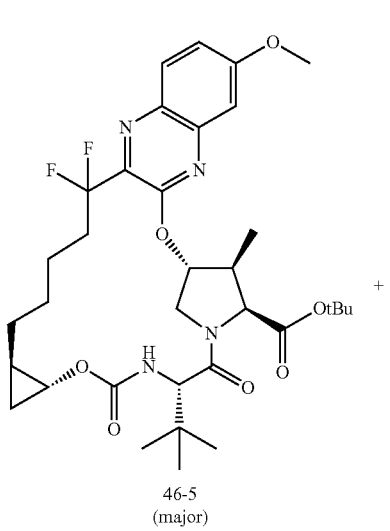
46-5
(major)
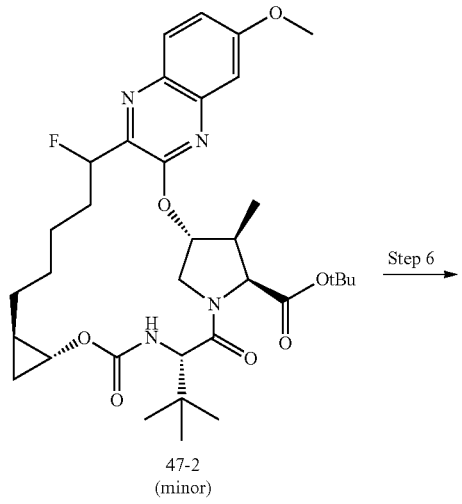
47-2
(minor)
Step 5 →
Step 6 →

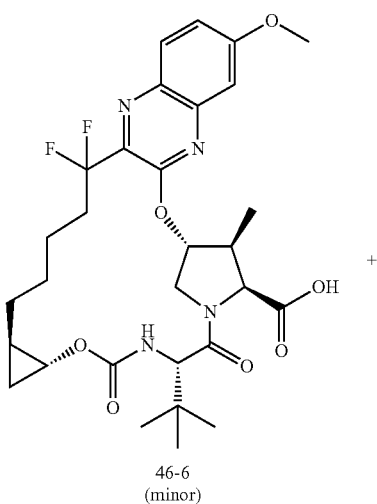

46-6
(minor)

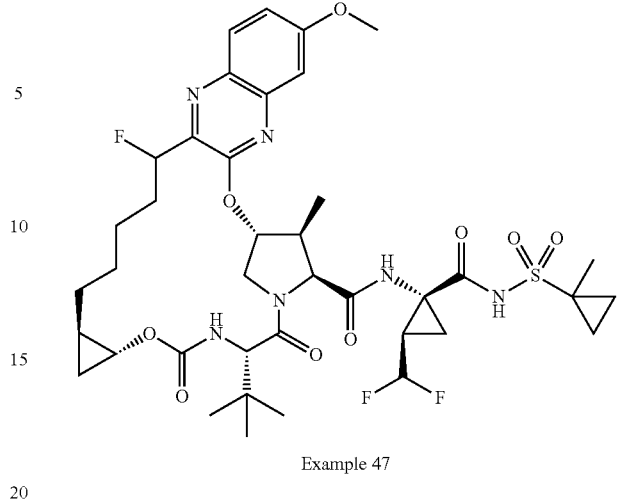

Example 47

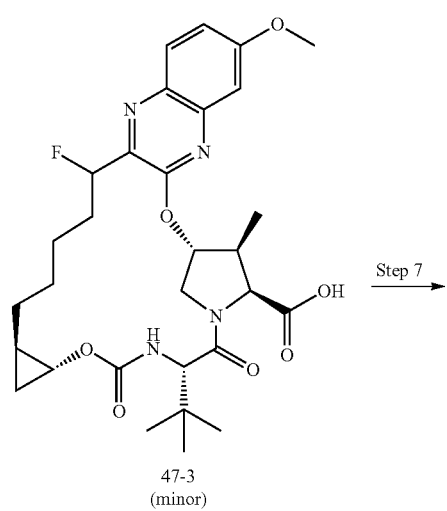

Step 7 →

47-3
(minor)

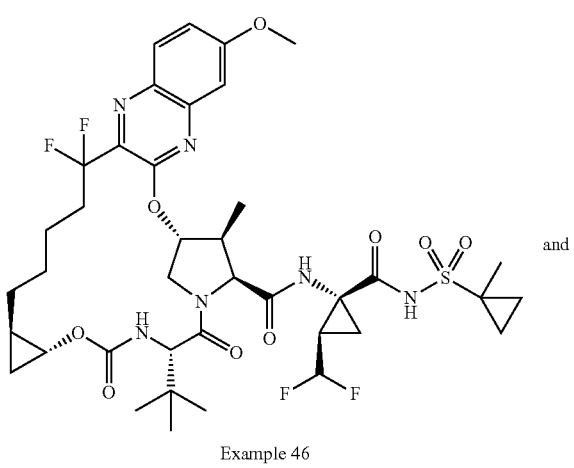

and

Example 46

Step 1. Preparation of 46-1: A mixture of Intermediate B1 (627 mg, 2.08 mmol), Intermediate E3 (548 mg, 1.91 mmol) and cesium carbonate (744 mg, 2.28 mmol) in 7 mL of DMF was stirred at 85° C. under argon for 36 hours. Reaction mixture was cooled to room temperature and poured into 30 mL of water and aqueous was extracted with ethyl acetate (3×30 mL). Combined organics were washed with water, brine, dried over anhydrous Na$_2$SO$_4$, filtered, and concentrated in vacuo. The resulting residue was purified by silica gel chromatography (0-30% ethyl acetate in hexanes) to yield 46-1 (891 mg) as a white solid. LCMS-ESI$^+$ (m/z): [M+H]$^+$ calcd for $C_{27}H_{36}F_2N_3O_6$: 536.25; found: 536.35.

Step 2. Preparation of 46-2: Quinoxaline ether 46-1 (478 mg, 0.893 mmol) was dissolved in 4.2 mL of tert-butyl acetate and 1.1 mL of dichloromethane at room temperature. MeSO$_3$H (0.30 mL, 4.67 mmol) was added dropwise and reaction mixture stirred at rt for 2 h. The reaction mixture was transferred to a stirred mixture of EtOAc (20 mL) and saturated aqueous NaHCO$_3$ (30 mL). The phases were separated, and the aqueous phase was extracted with EtOAc (2×20 mL). The combined organic phase was dried over anhydrous Na$_2$SO$_4$, filtered, and concentrated in vacuo to afford amine 46-2 as a yellow solid film (346 mg). LCMS-ESI$^+$ (m/z): [M+H]$^+$ calcd for $C_{22}H_{28}F_2N_3O4$: 436.20 found: 436.29.

Step 3. Preparation of 46-3: HATU (396 mg, 1.04 mmol, Oakwood) and DIPEA (0.57 mL, 3.29 mmol) were added to a mixture of 46-2 (345 mg, 0.793 mmol) and Intermediate D11 (260 mg, 0.965 mmol) in 9 mL of acetonitrile under argon. After stirring overnight, the reaction mixture was concentrated under reduced pressure and the resulting residue was purified by silica gel chromatography (0-40% ethyl acetate in hexanes) to yield 46-3 (545 mg) as a clear solid film. LCMS-ESI$^+$ (m/z): [M+H]$^+$ calcd for $C_{36}H_{49}F_2N_4O_7$: 687.35; found: 687.57.

Step 4. Preparation of 46-4: A mixture of 46-3 (480 mg, 0.699 mmol) and Zhan 1B catalyst (61 mg, 0.083 mmol, Strem) in 140 mL of DCE was deoxygenated with argon for 18 minutes. The mixture was then heated at 95° C. for 70 minutes. An additional 20 mg of Zhan 1B catalyst was added and mixture stirred at 95° C. for one hour. After cooling to room temperature, reaction mixture was concentrated in vacuo. The resulting residue was purified by silica gel chromatography (0-35% ethyl acetate in hexanes) to yield an inseparable mixture of 46-4 (major), and approximately 15% of 47-1 (minor; 233 mg total) as an off white solid.

Major component 46-4: LCMS-ESI⁺ (m/z): [M+H]⁺ calcd for $C_{34}H_{45}F_2N_4O_7$: 665.38; found: 665.50. Minor component 47-1: LCMS-ESI⁺ (m/z): [M+H]⁺ calcd for $C_{34}H_{44}FN_4O_7$: 639.31; found: 639.49.

Step 5. Preparation of mixture of 46-5 and 47-2: Palladium on carbon (10 wt % Pd, 70 mg, 0.066 mmol) was added to a solution of the mixture of 46-4 and 47-1 (232 mg, 0.353 mmol) from the previous step in 9 mL of ethanol. The atmosphere was replaced with hydrogen and stirred for 7 h. The reaction was filtered over Celite, washing with ethanol. Filtrate was concentrated in vacuo to yield a mixture of 46-5 (major) and 47-2 (minor; 216 mg total) as an off white solid, which was used in the next step without further purification. Major component 46-5: LCMS-ESI⁺ (m/z): [M+H]⁺ calcd for $C_{34}H_{47}F_2N_4O_7$: 661.33; found: 661.52. Minor component 47-2: LCMS-ESI⁺ (m/z): [M+H]⁺ calcd for $C_{34}H_{48}FN_4O_7$: 643.34; found: 643.57.

Step 6. Preparation of mixture of 46-6 and 47-3: TMSOTf (0.35 mL, 1.90 mmol) was added dropwise to a solution of a mixture of 46-5 and 47-2 (215 mg, 0.326 mmol) from the previous step in 6.5 mL of dichloromethane under argon at rt. After 1 h, an additional 0.18 mL of TMSOTf was added. After an additional hour, 0.30 mL of TMSOTf was added. After 2 h, 0.18 mL of TMSOTf was added. After 1 h. an additional 0.18 mL of TMSOTf was added. After 45 minutes, reaction mixture was taken up in 25 mL of dichloromethane and quenched by addition of 30 mL of 1 N aqueous HCl with stirring. The aqueous layer was extracted with dichloromethane (3×40 mL). Combined organics were washed with brine, dried over anhydrous $Na_2SO_4$, filtered, and concentrated in vacuo to yield an inseparable mixture of 46-6 (major) and 47-3 (minor; 187 mg total), which was used in the next step without further purification. Major component 46-6: LCMS-ESI⁺ (m/z): [M+H]⁺ calcd for $C_{30}H_{39}F_2N_4O_7$: 605.27; found: 605.44. Minor component 47-3: LCMS-ESI⁺ (m/z): [M+H]⁺ calcd for $C_{30}H_{39}FN_4O_7$: 587.28; found: 587.38.

Step 7. Preparation of Example 46 and Example 47: HATU (160 mg, 0.421 mmol, Oakwood) and DIPEA (0.25 mL, 1.44 mmol) were added to a mixture of 46-6 and 47-3 (150 mg, 0.248 mmol) from the previous step and Intermediate A10 (150 mg, 0.496 mmol) in 6.5 mL of acetonitrile under argon. After stirring for overnight, reaction mixture was taken up in 30 mL of ethyl acetate and poured into 30 mL of 1 N aqueous HCl. The aqueous layer was extracted three times with ethyl acetate. Combined organics were washed with water and brine, dried over anhydrous $Na_2SO_4$, filtered, and concentrated in vacuo. The resulting residue was purified by silica gel chromatography (0-50% ethyl acetate in hexanes) and reverse phase prep HPLC (50-100% acetonitrile in water, with 0.1% trifluoroacetic acid buffer) to yield the trifluoroacetic acid salt of Example 46 (107 mg) as a light yellow solid and the trifluoroacetic acid salt of the 1:1 mixture of diastereomers of Example 47 (12 mg) as a light yellow solid. Example 46: Analytic HPLC RetTime: 8.60 min LCMS-ESI⁺ (m/z): [M+H]⁺ calcd for $C_{39}H_{51}F_4N_6O_9S$: 855.33; found: 855.63. ¹H NMR (400 MHz, $CD_3OD$): δ 9.23 (s, 1H), 7.94 (d, J=9.2 Hz, 1H), 7.31 (dd, J=9.2, 2.8 Hz, 1H), 7.28 (d, J=2.8 Hz, 1H), 5.78 (td, $J_{H-F}$=66 Hz, J=6.8 Hz, 1H), 5.68-5.66 (m, 1H), 4.57 (d, J=6.4 Hz, 1H), 4.41 (d, J=12 Hz, 1H), 4.35 (s, 1H), 4.22-4.16 (dd, J=12.4 Hz, 1H), 3.97 (s, 3H), 3.72-3.66 (m, 1H), 2.86-2.76 (m, 1H), 2.64-2.48 (m, 1H), 2.11-1.94 (m, 3H), 1.86-1.74 (m, 3H), 1.73-1.62 (m, 1H), 1.58-1.54 (m, 2H), 1.50 (s, 3H), 1.49-1.44 (m, 1H) 1.42-1.38 (m, 1H), 1.11-1.04 (m, 4H), 1.09 (s, 9H), 1.02-0.94 (m, 2H), 0.93-0.86 (m, 2H), 0.78-0.66 (m, 1H), 0.54-0.46 (m, 1H). Example 47 (1:1 mixture of diastereomers): Analytic HPLC RetTime: 8.45 min. LCMS-ESI⁺ (m/z): [M+H]⁺ calcd for $C_{39}H_{52}F_3N_6O_9S$: 837.34; found: 837.63. ¹H NMR (400 MHz, $CD_3OD$): δ 9.13 (s, 1H), 7.89 (d, J=8.8 Hz, 1H), 7.27 (dd, J=9.2, 2.8 Hz, 1H), 7.24 (d, J=2.8 Hz, 1H), 5.99-5.43 (m, 1H), 5.79 (td, $J_{H-F}$=55 Hz, J=6.8 Hz, 1H), 5.53-5.50 (m, 1H), 4.57-4.44 (m, 2H), 4.11 (s, 1H), 4.35 (s, 1H), 4.22-413 (dd, J=12.4, 4 Hz, 1H), 3.95 (s, 3H), 3.83-3.79 (m, 1H), 2.94-2.80 (m, 2H), 2.28-2.14 (m, 1H), 2.06-1.96 (m, 2H), 1.88-1.69 (m, 4H), 1.58-1.54 (m, 2H), 1.51 (s, 3H), 1.44-1.36 (m, 1H), 1.32-1.26 (m, 1H), 1.14-1.04 (m, 4H), 1.10 (s, 9H), 1.02-0.86 (m, 4H), 0.74-0.64 (m, 1H), 0.58-0.48 (m, 1H).

Example 48

Preparation of (1aR,5S,8S,9S,10R,22aR)-5-tert-butyl-N-{(1R,2S)-1-[(cyclopropylsulfonyl)carbamoyl]-2-ethenylcyclopropyl}-14-methoxy-9-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

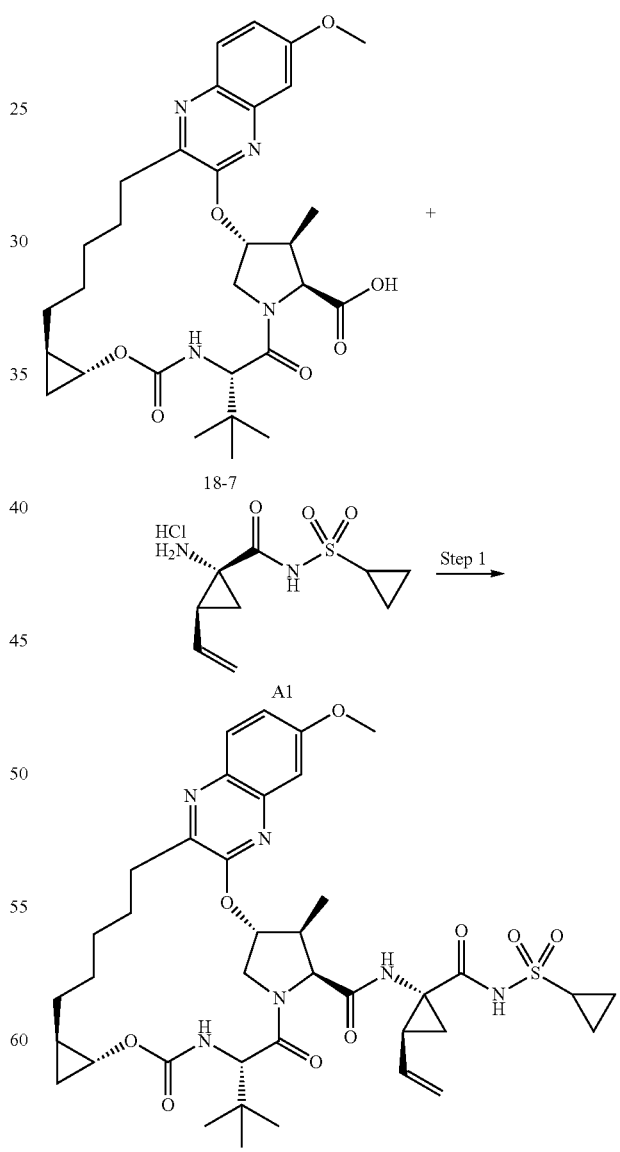

Example 48

Step 1: Preparation of Example 48: To a suspension of acid 18-7 (9.7 mg, 0.017 mmol) and Intermediate A1 (13 mg, 0.049 mmol) in MeCN (0.4 mL) was added DIPEA (40 µL, 0.23 mmol). To the resulting solution was added HATU (12.5 mg, 0.033 mmol). The reaction was stirred at rt for 1 h and was diluted with EtOAc (2 mL), 0.2 M aqueous HCl (1 mL), and brine (1 mL). The phases were separated and the aqueous phase was extracted with EtOAc (3×2 mL). The combined organic phase was dried over anhydrous $Na_2SO_4$, filtered, and concentrated to afford a crude residue that was dissolved in $CH_2Cl_2$ and adsorbed onto 1 g silica gel. Purification by silica gel chromatography (10% to 50% acetone in hexanes) provided a residue that was lyophilized from water and MeCN to provide Example 48 as a white amorphous solid (8.4 mg). Analytic HPLC RetTime: 8.52 min. LCMS-ESI⁺ (m/z): [M+H]⁺ calcd for $C_{39}H_{53}N_6O_9S$: 781.4; found: 781.2. ¹H NMR (400 MHz, CDCl₃) δ 9.91 (s, 1H), 7.83 (d, J=9.1 Hz, 1H), 7.19 (dd, J=9.1, 2.7 Hz, 1H), 7.10 (d, J=2.7 Hz, 1H), 6.73 (s, 1H), 5.86-5.72 (m, 1H), 5.57 (d, J=3.8 Hz, 1H), 5.48 (d, J=9.9 Hz, 1H), 5.27-5.15 (m, 1H), 5.15-5.07 (m, 1H), 4.48-4.35 (m, 3H), 4.12 (dd, J=11.8, 4.1 Hz, 1H), 3.94 (s, 3H), 3.81-3.71 (m, 1H), 2.98-2.75 (m, 4H), 2.16-2.09 (m, 1H), 1.94 (dd, J=8.2, 5.8 Hz, 1H), 1.87-1.24 (m, 9H), 1.17 (d, J=7.4 Hz, 3H), 1.09 (s, 9H), 1.04-0.91 (m, 5H), 0.75-0.65 (m, 1H), 0.52-0.42 (m, J=6.0 Hz, 1H).

Example 49

Preparation of (1aS,2aR,6S,9S,10S,11R,23aR, 23bS)-6-tert-butyl-N-[(1R,2R)-2-(difluoromethyl)-1-{[(1-methylcyclopropyl)sulfonyl] carbamoyl}cyclopropyl]-15-methoxy-10-methyl-4,7-dioxo-1a,2,2a,4,5,6,7,10,11,19,20,21,22,23,23a,23b-hexadecahydro-1H,9H-8,11-methanocyclopropa[4', 5']cyclopenta[1',2':18,19][1,10,3,6] dioxadiazacyclononadecino[11,12-b]quinoxaline-9-carboxamide

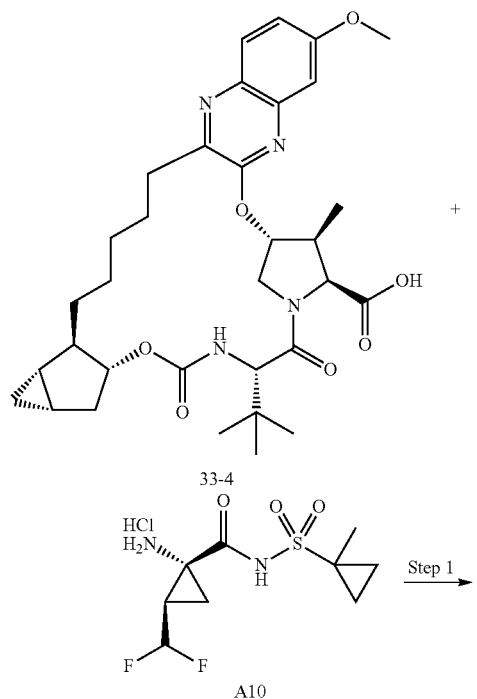

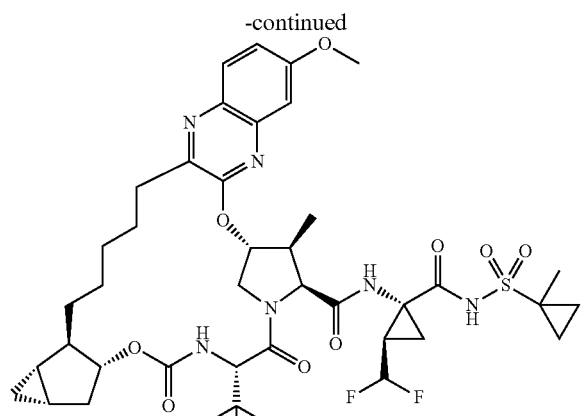

Example 49

Step 1: Preparation of Example 49: To a suspension of acid 33-4 (30 mg, 0.049 mmol) and intermediate A10 (31 mg, 0.10 mmol) in MeCN (700 µL) was added DIPEA (70 µL, 0.40 mmol) HATU (32 mg, 0.084 mmol) was added to the resulting solution, and the reaction was stirred at rt for 1.5 h. An additional portion of intermediate A10 (6 mg, 0.02 mmol) was then added. The reaction was stirred an additional 30 min and was then diluted with EtOAc (30 mL), 0.2 M aqueous HCl (15 mL) and brine (15 mL). The phases were separated and the aqueous phase was extracted with EtOAc (30 mL). The combined organic phase was dried over anhydrous $Na_2SO_4$, filtered, and concentrated to afford a crude residue. This residue was dissolved in $CH_2Cl_2$ and adsorbed onto 2 g silica gel. Purification by silica gel chromatography (10% to 50% acetone in hexanes) provided an amorphous residue that was lyophilized from water and MeCN to provide Example 49 as a white amorphous solid (30.5 mg). Analytic HPLC RetTime: 9.15 min. LCMS-ESI⁺ (m/z): [M+H]⁺ calcd for $C_{42}H_{57}F_2N_6O_9S$: 859.4; found: 859.2. ¹H NMR (400 MHz, CDCl₃) δ 9.86 (s, 1H), 7.82 (d, J=9.1 Hz, 1H), 7.45 (s, 1H), 7.18 (dd, J=9.1, 2.7 Hz, 1H), 7.08 (d, J=2.7 Hz, 1H) 6.14-5.71 (m, 1H), 5.61 (d, J=3.7 Hz, 1H), 5.28 (d, J=9.8 Hz, 1H), 5.00 (d, J=7.4 Hz, 1H), 4.49 (d, J=7.0 Hz, 1H), 4.42-4.31 (m, 2H), 4.12 (dd, J=11.6, 4.0 Hz, 1H), 3.93 (s, 3H), 3.00-2.63 (m, 4H), 2.25-2.16 (m, 1H), 2.09-1.90 (m, 4H), 1.81-0.95 (m, 26H), 0.92-0.75 (m, 3H), 0.57-0.45 (m, 1H), 0.44-0.36 (m, 1H).

Example 50

Preparation of (1aR,5S,8S,9S,10R,22aR)-5-tert-butyl-9-(cyanomethyl)-N-[(1R,2R)-2-(difluoromethyl)-1-{[(1-methylcyclopropyl)sulfonyl]carbamoyl}cyclopropyl]-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 50

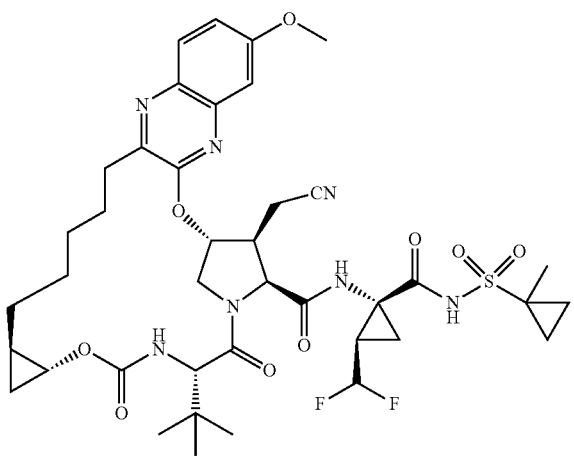

Example 50 was prepared in a similar fashion to Example 1, substituting Intermediate B8 for Intermediate B4 in step 1. Example 50 was purified by reverse phase HPLC (Gemini column, 58-98% ACN/H$_2$O+0.1% TFA) and lyophilized to afford solid (5 mg) as a TFA salt. Analytic HPLC RetTime: 8.29 min. LCMS-ESI$^+$ (m/z): [M+H]$^+$ calcd for C$_{40}$H$_{51}$F$_2$N$_7$O$_9$S: 844.94; found: 844.58. $^1$H NMR (400 MHz, CD$_3$OD) δ 9.71 (s, 1H), 7.79 (d, J=8.8 Hz, 1H), 7.22 (m, 2H), 6.25 (m, 1H), 6.08-5.80 (m, 1H), 4.39 (m, 1H), 4.29 (m, 2H), 4.13 (m, 1H), 3.92 (s, 3H), 3.65 (m, 1H), 3.06-2.83 (m, 4H), 2.55 (m, 1H), 2.14-1.47 (m, 17H), 1.03 (s, 9H), 0.92 (m, 4H), 0.65 (m, 1H), 0.45-0.43 (m, 1H).

Example 51

Preparation of (3aR,7S,10S,11S,12R,24aR)-7-tert-butyl-N-{(1R,2R)-1-[(cyclopropylsulfonyl)carbamoyl]-2-ethylcyclopropyl}-11-ethyl-6-methoxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide Example 51

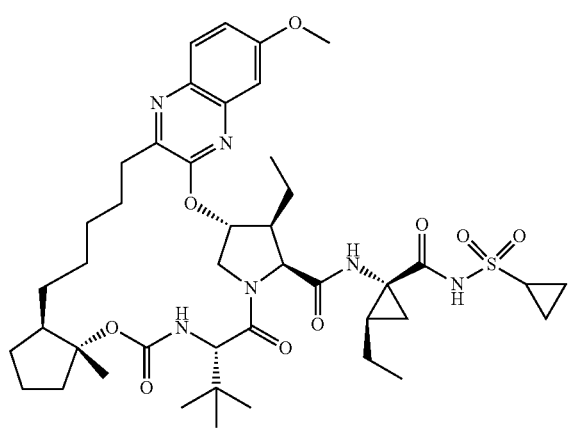

Example 51 was prepared in a similar fashion to Example 39, substituting Intermediate A3 for Intermediate A10 in step 8. Example 51 was isolated (12.3 mg) in approximately 96.5% purity. Analytic HPLC RetTime: 9.38 min. LCMS-ESI$^+$ (m/z): [M+H]$^+$ calcd for C$_{43}$H$_{63}$N$_6$O$_9$S: 839.48 found 839.5. $^1$H NMR (300 MHz, CD$_3$OD) δ 7.60 (d, J=8.4 Hz, 1H), 6.98-7.08 (m, 2H), 6.53 (d, J=9.6 Hz, 1H), 5.57-5.83 (m, 2H), 4.52 (d, J=8.4 Hz, 2H), 4.24 (dd, J=10.8, 6.0 Hz, 1H), 4.02 (d, J=9.6 Hz, 1H), 3.82 (dd, J=10.8, 2.4 Hz, 1H), 3.73 (s, 3H), 2.93-3.10 (m, 1H), 2.80-2.90 (m, 2H), 2.30-2.58 (m, 2H), 0.60-2.10 (m, 32H), 0.84 (s, 9H).

Example 52

Preparation of (3aR,7S,10S,11S,12R,24aR)-7-tert-butyl-11-ethyl-N-[(1R,2S)-2-(2-fluoroethyl)-1-{[(1-methylcyclopropyl)sulfonyl]carbamoyl}cyclopropyl]-16-methoxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide Example 52

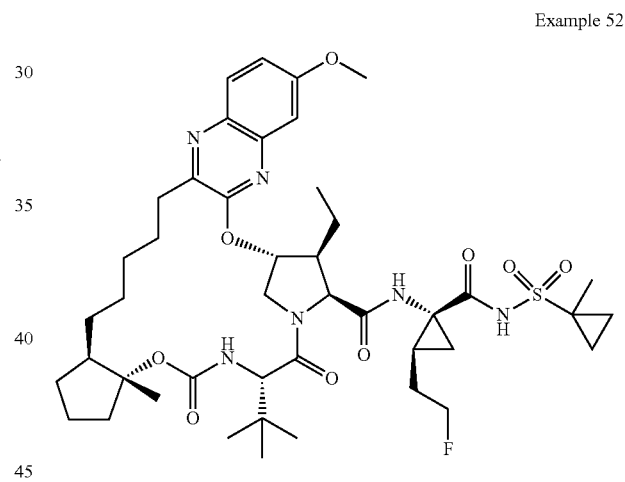

Example 52 was prepared in a similar fashion to Example 39, substituting Intermediate A6 for Intermediate A10 in step 8. Example 52 was isolated (12.3 mg) in approximately 96.5% purity. Analytic HPLC RetTime: 8.60 min. Analytic HPLC RetTime: 9.31 min. LCMS-ESI$^+$ (m/z): [M+H]$^+$ calcd for C$_{44}$H$_{64}$FN$_6$O$_9$S: 871.4; found: 871.5. $^1$H NMR (300 MHz, CD$_3$OD) δ 7.81 (d, J=8.4 Hz, 1H), 7.20-7.30 (m, 2H), 6.73 (d, J=9.6 Hz, 1H), 5.75-6.02 (m, 2H), 4.74 (d, J=8.4 Hz, 2H), 4.54 (t, J=6.0 Hz, 2H), 4.36-4.49 (m, 1H), 4.23 (d, J=9.6 Hz, 1H), 4.04 (dd, J=12.0, 2.4 Hz, 1H), 3.75 (s, 3H), 3.28-3.16 (m, 1H), 2.50-2.70 (m, 2H), 2.30-0.80 (m, 35H), 1.04 (s, 9H).

Example 53

Preparation of (1aR,5S,8S,9S,10R,22aR)-5-tert-butyl-N-[(1R,2R)-1-[(cyclopropylsulfonyl)carbamoyl]-2-(difluoromethyl)cyclopropyl]-9-ethyl-18,18-difluoro-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 53

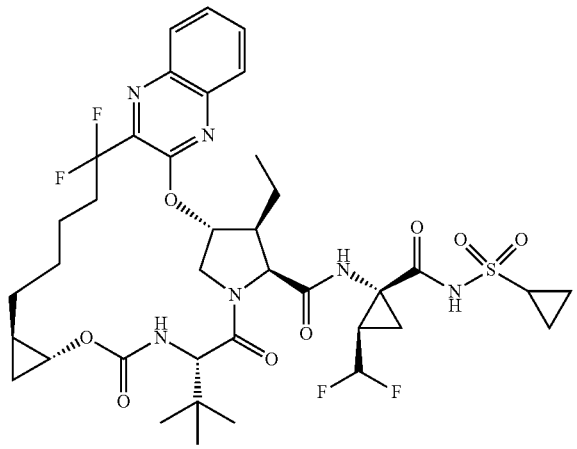

Example 53 was prepared similarly to Example 17 substituting Intermediate E4 for Intermediate E3 in Step 1 and Intermediate A9 for Intermediate A10 in Step 7. Example 53 was isolated (8.8 mg) as a white solid. LCMS-ESI$^+$ (m/z): [M+H]$^+$ calcd for $C_{38}H_{48}F_4N_6O_8S$: 825.32; found: 825.75. $^1$H NMR (400 MHz, CDCl$_3$) δ 10.13 (s, 1H), 8.15 (d, J=82 Hz, 1H), 7.91-7.74 (m, 2H), 7.69 (t, J=7.6 Hz, 1H), 6.92 (s, 1H), 5.47 (d, J=9.6 Hz, 1H), 4.48 (t, J=10.3 Hz, 2H), 4.36 (d, J=9.4 Hz, 1H), 4.12 (dd, J=12.1, 3.6 Hz, 1H), 370-3.59 (m, 1H), 3.08-275 (m, 1H), 2.58-2.38 (m, 1H), 2.14 (t, J=6.8 Hz, 1H), 1.95-1.67 (m, 4H), 1.47 (tt, J=13.9, 7.1 Hz, 4H), 1.35 (s, 2H), 1.20 (t, J=7.3 Hz, 3H), 1.15-0.64 (m, 19H), 0.51 (q, J=6.4 Hz, 1H).

Example 54

Preparation of (1aR,5S,8S,9S,10R,22aR)-5-tert-butyl-N-{(1R,2R)-1-[(cyclopropylsulfonyl)carbamoyl]-2-ethylcyclopropyl}-9-ethyl-18,18-difluoro-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 54

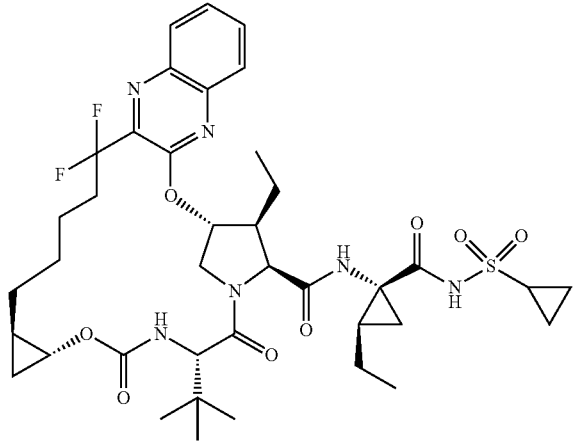

Example 54 was prepared similarly to Example 53 replacing Intermediate A9 with Intermediate A3. Example 54 was isolated (10.0 mg) as a white solid. LCMS-ESI$^+$ (m/z): [M+H]$^+$ calcd for $C_{39}H_{52}F_2N_6O_8S$: 803.35; found: 803.79. $^1$H NMR (400 MHz, CDCl$_3$) δ 9.88 (s, 1H), 8.12 (d, J=8.2 Hz, 1H), 7.88-7.69 (m, 2H), 7.66 (t, J=7.6 Hz, 1H), 6.68 (s, 1H), 5.95 (d, J=3.4 Hz, 1H), 5.46 (d, J=9.4 Hz, 1H), 4.45 (dd, J=13.8, 9.7 Hz, 2H), 4.09 (dd, J=12.0, 3.6 Hz, 2H), 3.71-3.57 (m, 1H), 2.53 (dd, J=21.4, 14.6 Hz, 1H), 1.85-1.39 (m, 10H), 1.38-0.96 (m, 20H), 1.01 (dd; J=17.2, 9.5 Hz, 3H), 1.04-0.78 (m, 6H), 0.70 (s, 1H), 0.49 (dd, J=12.7, 6.3 Hz, 1H).

Example 55

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-3,6-dioxo-14-(2,2,2-trifluoroethoxy)-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

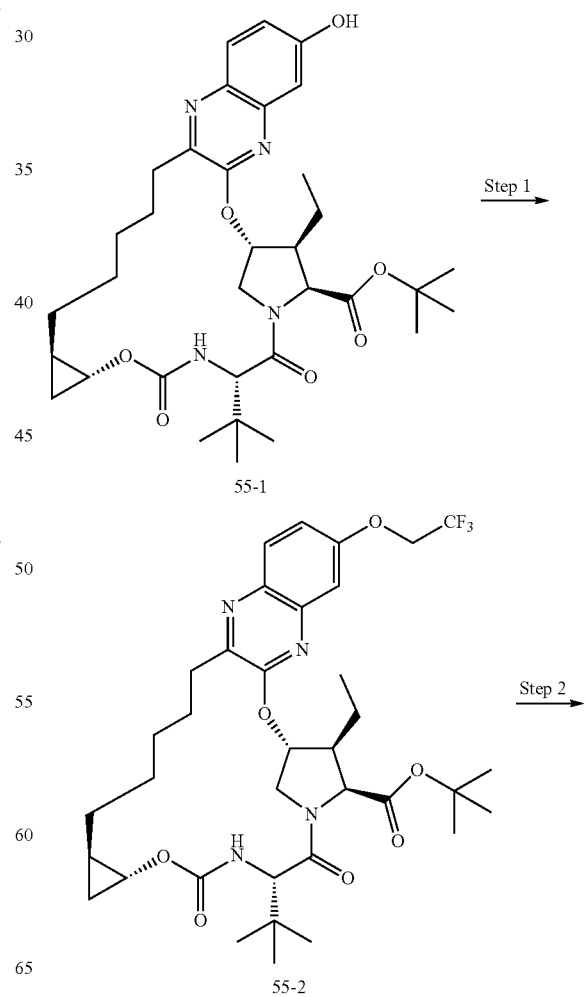

-continued

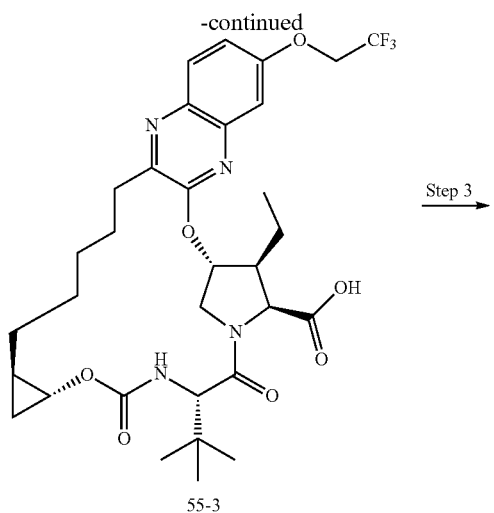

55-3

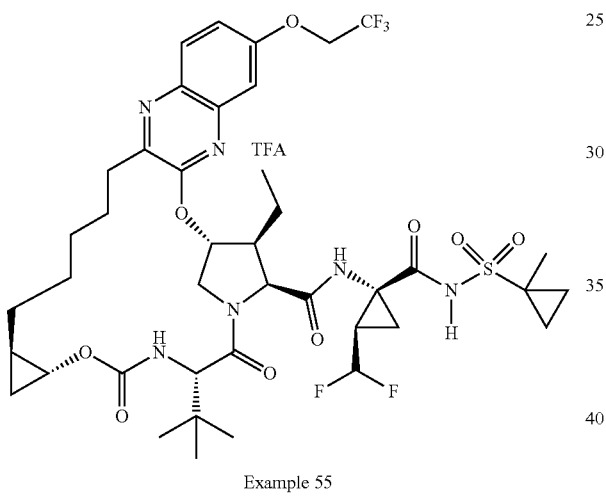

Example 55

Intermediate 55-1 was prepared by following Steps 1 through 6 of Example 1, substituting for Intermediate E2 for Intermediate E1 in Step 1. LCMS-ESI⁺ (m/z): [M+H]⁺ calcd for $C_{34}H_{49}N_4O_7$: 625.36; found: 625.25.

Step 1. Preparation of 55-2. Quinoxalinol 55-1 (24 mg, 0.038 mmol) was suspended in DMF (2 mL) and treated with Cs₂CO₃ (63 mg, 0.19 mmol) and 2,2,2-trifluoroethyl trifluoromethanesulfonate (0.055 mL, 0.38 mmol). The reaction mixture was stirred at RT for 5 h, then diluted with EtOAc. The organic layer was washed with H₂O and brine, dried over MgSO₄, filtered and concentrated under reduced pressure to afford 55-2, which was carried on without further purification. LCMS-ESI⁺ (m/z): [M+H]⁺ calcd for $C_{36}H_{50}F_3N_4O_7$: 707.36; found: 707.38.

Step 2. Preparation of 55-3. Trifluoroethyl ether 55-2 (0.038 mmol theoretical) was treated with DCM (4 mL) and TMSOTf (0.14 mL, 0.77 mmol) at RT. After 1 h, the reaction was quenched by addition of 1M NaOH (2 mL). After stirring vigorously for 5 min, the mixture was poured into a separatory funnel followed by 10% HCl (20 mL). The aqueous layer was extracted 3× with DCM (20 mL). The combined organics were dried over MgSO₄, filtered and concentrated under reduced pressure to afford 55-3, which was carried on without further purification. LCMS-ESI⁺ (m/z): [M+H]⁺ calcd for $C_{32}H_{42}F_3N_4O_7$: 651.30; found: 651.18.

Step 3. Preparation of Example 55. Carboxcylic acid 55-3 (0.038 mmol theoretical) was treated with intermediate A10 (23 mg, 0.077 mmol), TBTU (25 mg, 0.077 mmol), DMAP (9 mg, 0.077 mmol), DCM (1 mL) and DIPEA (0.134 mL, 0.768 mmol). The reaction mixture was stirred at RT for 20 h, then concentrated under reduced pressure and purified by reverse phase HPLC to afford Example 55 as a TFA salt (7 mg, 18% over 3 steps). LCMS-ESI⁺ (m/z): [M+H]⁺ calcd for $C_{41}H_{54}F_5N_6O_9S$: 901.36; found: 902.08. ¹H NMR (400 MHz, CD₃OD) δ 9.18 (s, 1H), 7.86 (d, J=9.1 Hz, 1H), 7.32 (dd, J=9.1, 2.8 Hz, 1H), 7.25 (d, J=2.7 Hz, 1H), 6.02-5.63 (m, 2H), 4.76-4.62 (m, 2H), 4.56 (d, J=7.1 Hz, 1H), 4.39 (t, J=6.0 Hz, 2H), 4.15 (dt, J=17.2, 8.6 Hz, 1H), 3.74 (dd, J=6.7, 2.8 Hz, 1H), 3.05-2.89 (m, 1H), 2.82 (td, J=13.2, 4.2 Hz, 1H), 2.65-2.50 (m, 1H), 2.02 (d, J=10.4 Hz, 2H), 1.78 (dt, J=23.5, 10.7 Hz, 3H), 1.68-1.26 (m, 14H), 1.22 (t, J=7.3 Hz, 3H), 1.10 (s, 9H), 0.97 (d, J=2.5 Hz, 2H), 0.95-0.84 (m, 2H), 0.71 (s, 1H), 0.51 (t, J=9.8 Hz, 1H).

Example 56

Preparation of (3aR,7S,10S,11S,12R,24aR)-7-tert-butyl-11-ethyl-N-[(1R,2R)-2-ethyl-1-{[(1-methylcyclopropyl)sulfonyl]carbamoyl}cyclopropyl]-16-methoxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide

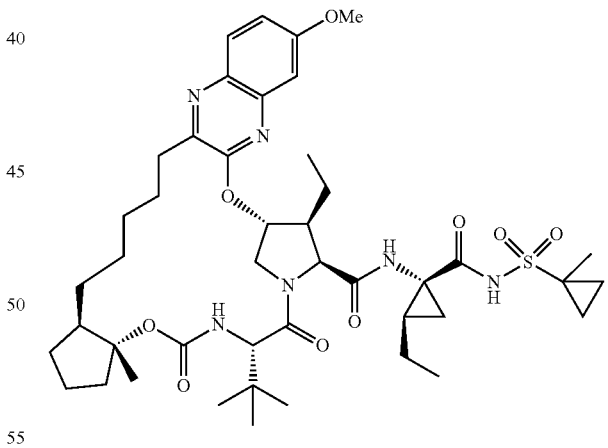

Example 56 was prepared in a similar fashion to Example 39, substituting Intermediate A9 for Intermediate A3 in Step 8. Example 56 was isolated (8.8 mg, 0.0103 mmol, 53.7%). Analytic HPLC RetTime: 9.56 min. LCMS-ESI⁺ (m/z): [M+H]⁺ calcd for $C_{44}H_{65}N_6O_9S$: 853.45; found: 853.5. ¹H NMR (300 MHz, CD₃OD) δ 7.81 (d, J=9.6 Hz, 1H), 7.20-7.30 (m, 2H), 6.73 (d, J=9.6 Hz, 1H), 5.76-6.01 (m, 2H), 4.75 (d, J=8.4 Hz, 1H), 4.46 (dd, J=12.0, 6.0 Hz, 1H), 4.23 (d, J=9.6 Hz, 1H), 4.00-4.08 (m, 1H), 3.95 (s, 3H), 2.50-2.78 (m, 3H), 0.80-2.30 (m, 30H), 1.54 (s, 3H), 1.35 (s, 3H), 1.05 (s, 9H).

Example 57

Preparation of (1aS,2aR,6S,9S,10S,11R,23aR, 23bS)-6-tert-butyl-N-[(1R,2S)-1-[(cyclopropylsulfonyl)carbamoyl]-2-(2,2-difluoroethyl)cyclopropyl]-15-methoxy-10-methyl-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

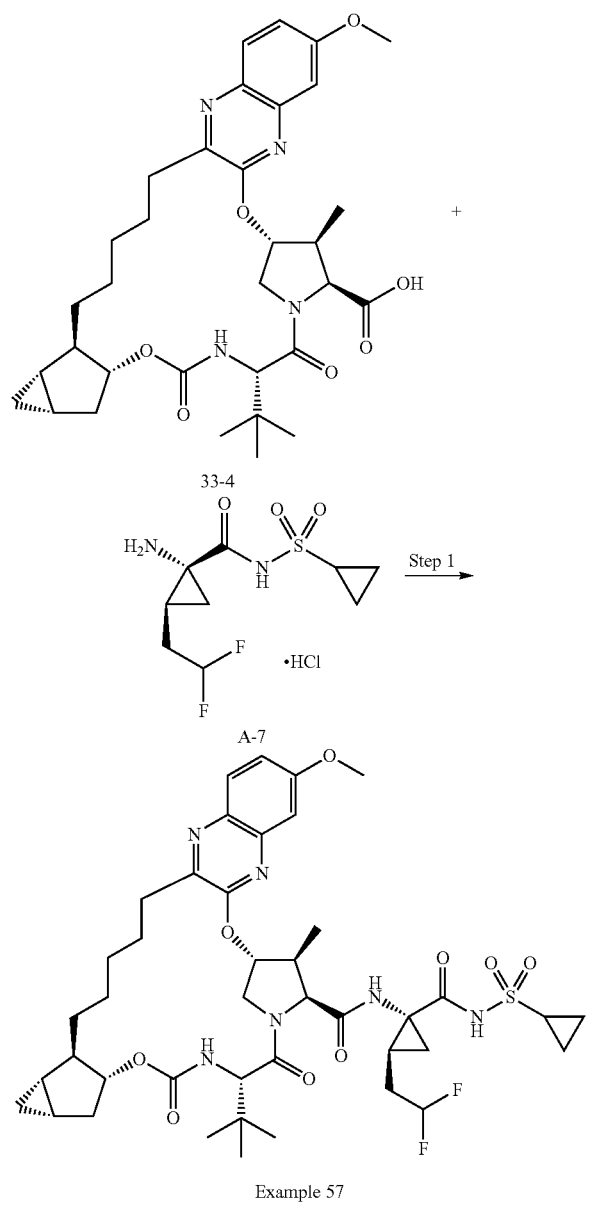

Step 1. Preparation of Example 57. To a suspension of acid 33-4 (14.9 mg, 0.0245 mmol) and amine hydrochloride A-7 (16.3 mg, 0.0535 mmol) in MeCN (500 μL) was added DIPEA (40 μL, 0.23 mmol). HATU (15.5 mg, 0.0408 mmol) was added to the resulting solution, and the reaction was stirred at rt for 17 h. The reaction was then diluted with EtOAc (2 mL), 0.2 M aqueous HCl (1.5 mL) and brine (1.5 mL). The phases were separated and the aqueous phase was extracted with EtOAc (4×1.5 mL). The combined organic phase was dried over $Na_2SO_4$, filtered, and concentrated to afford a crude residue. This residue was dissolved in $CH_2Cl_2$ and was concentrated onto 1.5 g silica gel. Purification by silica gel chromatography (10% to 40% acetone in hexanes) provided an amorphous residue that was lyophilized from water and MeCN to provide Example 57. LCMS-ESI$^+$ (m/z): [M+H]$^+$ calcd for $C_{42}H_{57}F_2N_6O_9S$: 859.4; found: 859.0. $^1$H NMR (300 MHz, CDCl$_3$) δ 10.00 (s, 1H), 7.82 (d, J=9.1 Hz, 1H), 7.19 (dd, J=9.1, 2.7 Hz, 1H), 7.09 (d, J=2.6 Hz, 1H), 6.75 (s, 1H), 6.07-5.57 (m, 2H), 5.26 (d, J=9.8 Hz, 1H), 5.01 (d, J=7.4 Hz, 1H), 4.50-4.29 (m, 3H), 4.12 (dd, J=11.7, 3.9 Hz, 1H), 3.93 (s, 3H), 3.00-2.62 (m, 4H), 2.34-0.96 (m, 33H), 0.95-0.78 (m, 1H), 0.51 (dd, J=13.0, 7.9 Hz, 1H), 0.39 (d, J=4.2 Hz, 1H).

Example 58

Preparation of (1aS,2aR,6S,9S,10S,11R,23aR,23bS)-6-tert-butyl-N-[(1R,2S)-2-(2,2-difluoroethyl)-1-{[(1-methylcyclopropyl)sulfonyl]carbamoyl}cyclopropyl]-15-methoxy-10-methyl-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

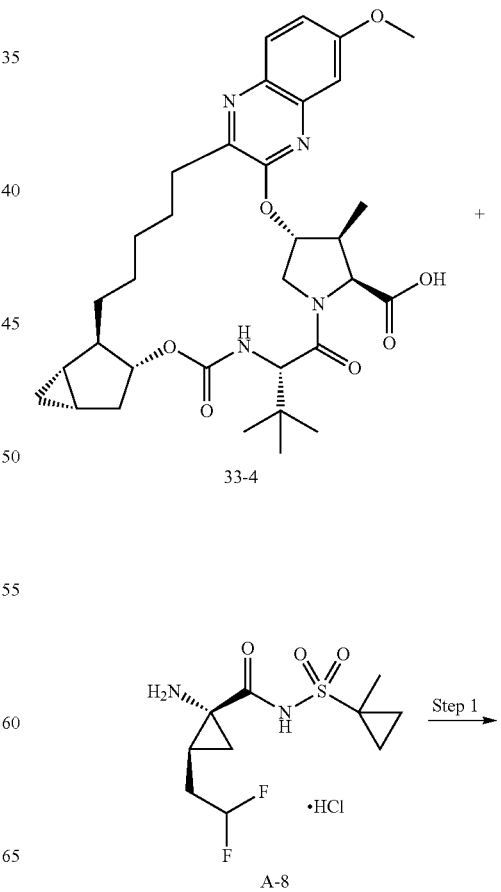

309

-continued

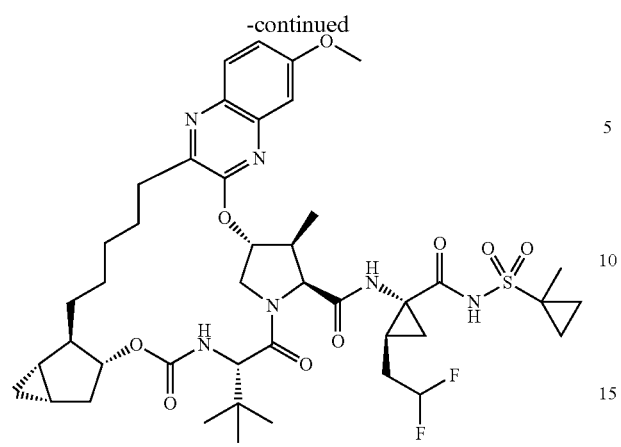

Example 58

Step 1. Preparation of Example 58. To a suspension of acid 33-4 (14.5 mg, 0.0238 mmol) and amine hydrochloride A-8 (16.0 mg, 0.0502 mmol) in MeCN (500 μL) was added DIPEA (40 μL, 0.23 mmol). HATU (15.5 mg, 0.0408 mmol) was added to the resulting solution, and the reaction was stirred at rt for 17 h. The reaction was then diluted with EtOAc (2 mL), 0.2 M aqueous HCl (1.5 mL) and brine (1.5 mL). The phases were separated and the aqueous phase was extracted with EtOAc (4×1.5 mL). The combined organic phase was dried over $Na_2SO_4$, filtered, and concentrated to afford a crude residue. This residue was dissolved in $CH_2Cl_2$ and was concentrated onto 1.5 g silica gel. Purification by silica gel chromatography (10% to 40% acetone in hexanes) provided an amorphous residue that was lyophilized from water and MeCN to provide Example 58. LCMS-ESI$^+$ (m/z): [M+H]$^+$ calcd for $C_{43}H_{59}F_2N_6O_9S$: 873.4; found: 873.3. $^1$H NMR (300 MHz, CDCl$_3$) δ 9.72 (s, 1H), 7.82 (d, J=9.1 Hz, 1H), 7.19 (dd, J=9.1, 2.7 Hz, 1H), 7.09 (d, J=2.7 Hz, 1H), 6.82 (s, 1H), 6.12-5.54 (m, 2H), 5.25 (d, J=9.8 Hz, 1H), 5.01 (d, J=7.2 Hz, 1H), 4.50-430 (m, 3H), 4.13 (dd, J=11.7, 4.2 Hz, 1H), 3.93 (s, 3H), 3.03-2.65 (m, 4H), 2.34-0.97 (m, 33H), 0.94-0.76 (m, 3H), 0.60-0.45 (m, 1H), 0.45-0.34 (m, 1H).

Example 59

Preparation of (1aS,2aR,6S,9S,10 S,11R,23aR, 23bS)-6-tert-butyl-N-[(1R,2R)-1-[(cyclopropylsulfonyl)carbamoyl]-2-(difluoromethyl)cyclopropyl]-10-ethyl-19,19-difluoro-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

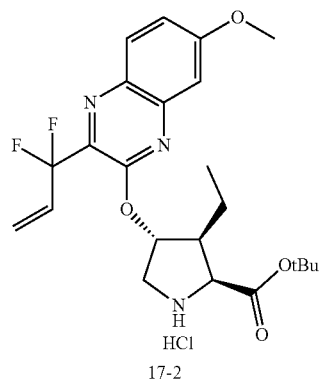
17-2

310

-continued

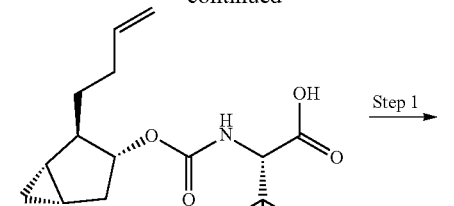
D16

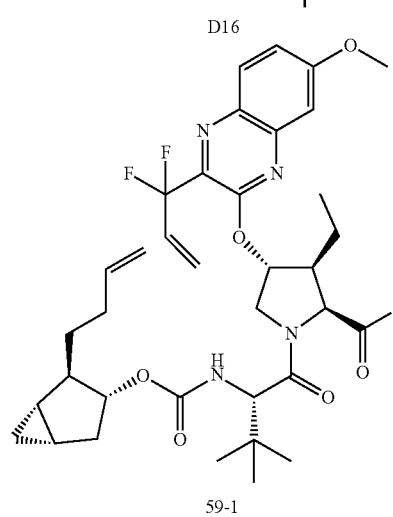
59-1

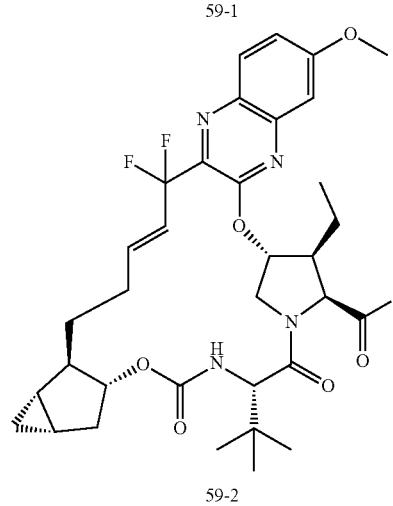
59-2

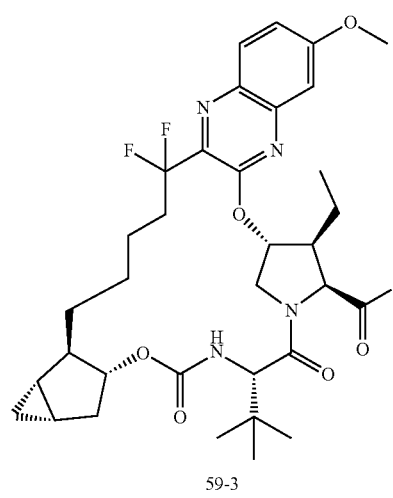
59-3

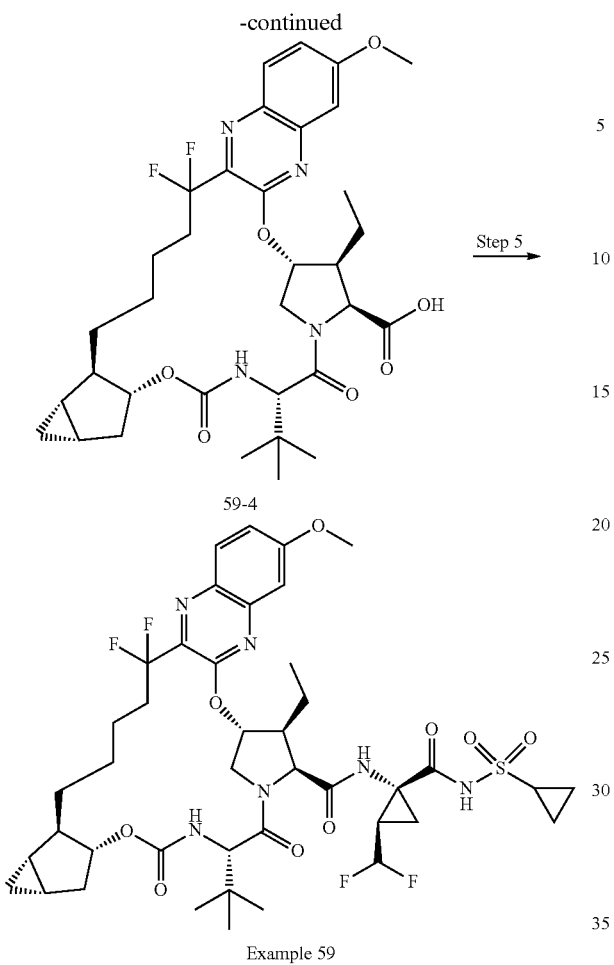

59-4

Example 59

Step 1. Preparation of 59-1. A solution of Intermediate D16 (0.50 g, 1.6 mmol) in DMF (7 mL) was treated subsequently with COMU (0.80 g, 1.9 mmol). DIPEA (1.2 mL, 6.7 mmol) and Intermediate 17-2 (0.65 g, 1.3 mmol) and stirred overnight at rt. The reaction was quenched with 1 M citric acid solution (5 mL) and extracted with EA. The combined organics were washed with brine, dried over anhydrous MgSO$_4$ and concentrated in vacuo. The resulting residue was purified by silica gel chromatography (15-100% EA/hex) to afford 59-1. LCMS-ESI$^+$ (m/z): [M+H]$^+$ calcd for C$_{40}$H$_{55}$F$_2$N$_4$O$_7$: 741.88; found: 741.51.

Step 2. Preparation of 59-2. A solution of 59-1 (0.51 g, 0.69 mmol) in DCE (140 mL) is sparged with argon for 30 min prior to addition of Zhan 1B catalyst (0.051 g, 0.07 mmol). The reaction was heated to 85° C. for 45 min, and another portion of Zhan 1B catalyst was added. After an additional 30 min, the reaction was cooled to rt, concentrated in vacuo and purified by silica gel chromatography (5-100% EA/hex) to produce 59-2. LCMS-ESI$^+$ (m/z): [M+H]$^+$ calcd for C$_{38}$H$_{51}$F$_2$N$_4$O$_7$: 713.83. found: 713.54.

Step 3. Preparation of 59-3. A solution of 59-2 was taken up in EtOH (8 mL). Pd/C (0.072 g, 10% w/w) was added and the atmosphere replaced with H$_2$. After 1 h, additional catalyst was added. After 4 h, EA and additional catalyst was added. After an additional 3 h, the reaction was filtered, concentrated in vacuo and the residue taken up in EtOH (8 mL) and treated with 0.5 g Pd/C (10% w/w) and the atmosphere replaced with H. The reaction was stirred overnight, and then worked up again as previously described to produce of 59-3 that was used subsequently without further purification. LCMS-ESI$^+$ (m/z): [M+H]$^+$ calcd for C$_{38}$H$_{53}$F$_2$N$_4$O$_7$: 715.85; found: 715.52.

Step 4. Preparation of 59-4. A solution of 59-3 (0.40 g, 0.56 mmol) in DCM (1.5 mL) was treated with 2.5 mL TFA at rt. After 1.5 h, the reaction was concentrated in vacuo. The residue was taken up in EA, washed with saturated aqueous NaHCO$_3$, brine and then dried over anhydrous MgSO$_4$. Concentration in vacuo produced 59-4 that was used subsequently without further purification. LCMS-ESI$^+$ (m/z): [M+H]$^+$ calcd for C$_{34}$H$_{45}$F$_2$N$_4$O$_7$: 659.74; found: 659.56.

Step 5. Preparation of Example 59: A solution of 59-4 (0.20 g, 0.30 mmol) in DMF (2 mL) was treated subsequently with HATU (0.21 g, 0.55 mmol), DIPEA (0.27 mL, 1.5 mmol), DMAP (0.056 g, 0.46 mmol), and Intermediate A9 (0.13 g, 0.46 mmol) and stirred for 5 h at rt. The reaction mixture is purified by preparatory HPLC to produce the TFA salt of Example 59. Analytic HPLC RetTime: 9.20 min. LCMS-ESI$^+$ (m/z): [M+H]$^+$ calcd for C$_{42}$H$_{55}$F$_4$N$_6$O$_9$S: 895.98; found: 895.60. $^1$H NMR (400 MHz, CD$_3$OD) δ 9.31 (s, 1H); 7.94 (d, J=9.2 Hz, 1H); 7.32 (dd, J=9.2, 2.4 Hz, 1H); 7.21 (d, J=2.4 Hz, 1H); 5.98 (br s, 1H); 5.85 (td, J$_{H-F}$=55.2 Hz, J=6 Hz, 1H); 4.94 (d, J=7.6 Hz, 1H); 4.58 (d, J=7.2 Hz, 1H); 4.35 (d, J=7.2 Hz, 1H); 4.33 (brs, 1H); 4.18 (dd, J=12, 3.6 Hz, 1H); 3.97 (br s, 3H); 2.98 (m, 1H); 2.64-2.41 (m, 2H); 2.22 (m, 1H); 2.15-1.92 (m, 4H); 1.84-1.22 (m, 14H); 1.18 (t, J=7.2 Hz, 3H); 1.14-0.98 (m, 2H); 1.08 (s, 9H); 0.60-0.48 (m, 2H).

Example 60

Preparation of (1aR,5S,8S,9S,10R,22aR)-5-tert-butyl-N-[(1R,2R)-1-[(cyclopropylsulfonyl)carbamoyl]-2-(difluoromethyl)cyclopropyl]-18,18-difluoro-14-methoxy-3,6-dioxo-9-propyl-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

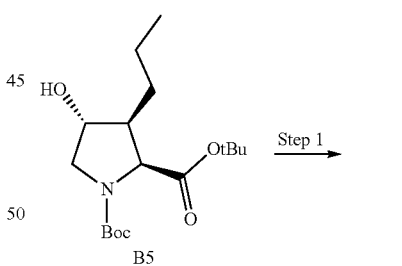

60-1

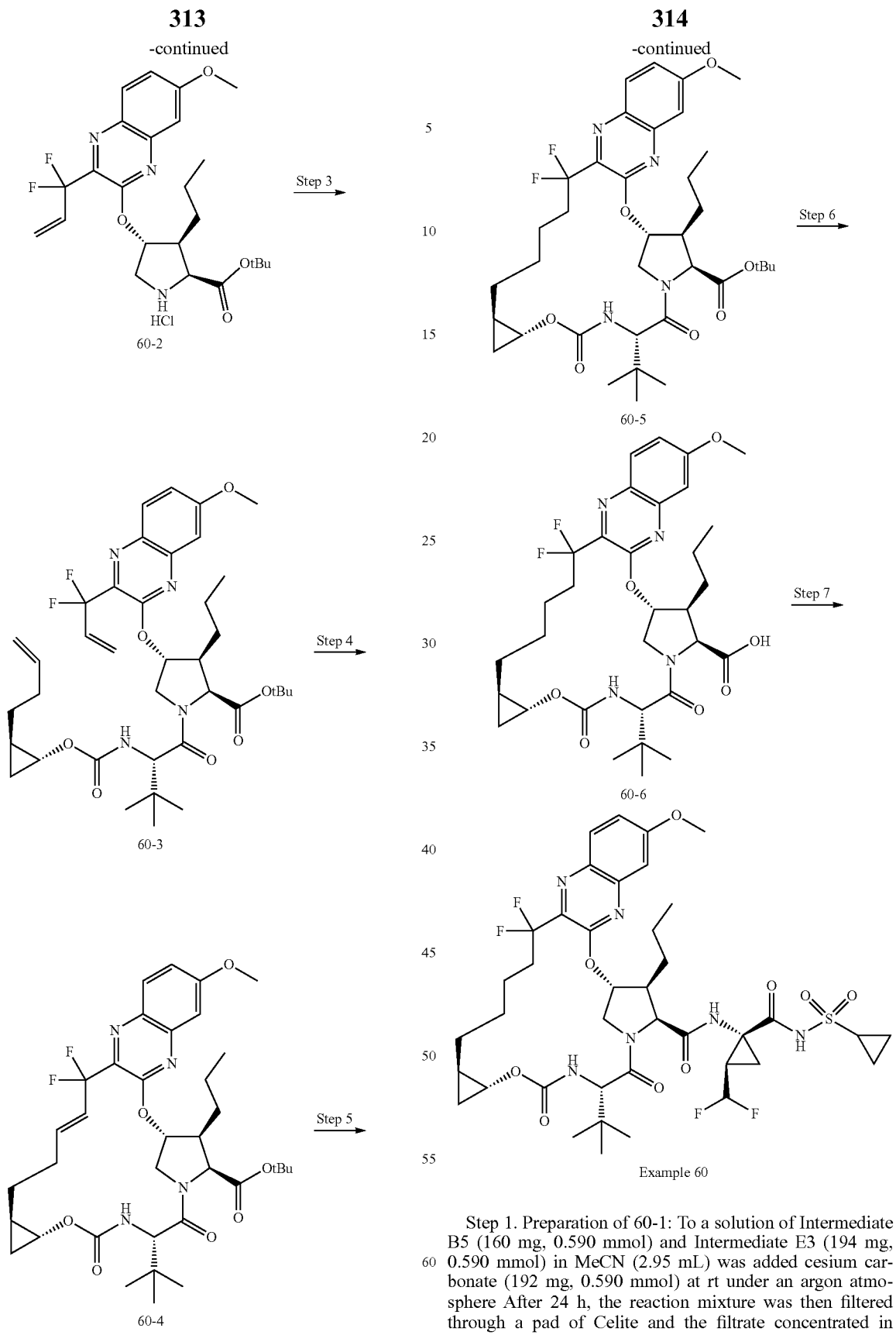

Step 1. Preparation of 60-1: To a solution of Intermediate B5 (160 mg, 0.590 mmol) and Intermediate E3 (194 mg, 0.590 mmol) in MeCN (2.95 mL) was added cesium carbonate (192 mg, 0.590 mmol) at rt under an argon atmosphere After 24 h, the reaction mixture was then filtered through a pad of Celite and the filtrate concentrated in vacuo. The crude residue was purified by silica gel chromatography (0-100% ethyl acetate/hexanes gradient) to afford substituted quinoxaline 60-1. LCMS-ESI⁺ (m/z): [M+H]⁺ calcd for $C_{29}H_{40}F_2N_3O_6$: 564.28; found 564.44.

Step 2. Preparation of 60-2: To a solution 60-1 (193 mg, 0.343 mmol) in tert-butyl acetate (1.36 mL) was added a solution of methanesulfonic acid (111 μL, 1.72 mmol) in dichloromethane (0.34 mL) and the reaction was stirred at rt. After 2 h. the reaction mixture was diluted with saturated sodium bicarbonate solution (20 mL) and the resulting mixture was extracted with ethyl acetate (2×20 mL). The combine organics were dried over anhydrous sodium sulfate and were concentrated in vacuo to afford amine hydrochloride 60-2, which was used directly in the next step without further purification. LCMS-ESI$^+$ (m/z): [M+H]$^+$ calcd for $C_{24}H_{32}F_2N_3O_4$: 464.23; found: 464.35.

Step 3. Preparation of 60-3: To a solution of 60-2 (133 mg, 0.289 mmol) and Intermediate D11 (133 mg, 0.412 mmol) in MeCN (1.7 mL) was added HATU (157 mg, 0.412 mmol) followed by DIPEA (298 μL, 1.72 mmol) at rt under and argon atmosphere. After 1 h, the reaction mixture was concentrated in vacuo, and the crude residue was purified by silica gel chromatography (0-100% ethyl acetate/hexanes gradient) to afford amide 60-3. LCMS-ESI$^+$ (m/z): [M+H]$^+$ calcd for $C_{38}H_{53}F_2N_4O_7$: 715.38; found: 715.55.

Step 4. Preparation of 60-4: To a solution of 60-3 (188 mg, 264 μmol) in DCE (52.8 mL) was added Zhan 1B catalyst (19.4 mg, 26.4 μmol) and the reaction mixture was degassed for 10 minutes with argon. The reaction mixture was then heated to 100° C. After 1 h, the reaction mixture was allowed to cool to rt and was concentrated in vacuo. The crude residue was purified by silica gel chromatography (0-100% ethyl acetate/hexanes gradient) to afford macrocycle 60-4. LCMS-ESI$^+$ (m/z): [M+H]$^+$ calcd for $C_{38}H_{49}F_2N_4O_7$: 687.35; found: 687.54.

Step 5. Preparation of 60-5: To a solution of macrocycle 60-4 (119 mg, 173 μmol) in ethanol (1.0 mL) was added Pd/C (10 wt %, 18.4 mg, 17.3 μmol) at rt under an argon atmosphere. The reaction vessel was evacuated and refilled with 1 atm hydrogen gas (3×) and the reaction mixture was stirred vigorously at rt. After 1 h, the reaction mixture was filtered through a pad of Celite with ethyl acetate washings (3×2 mL). The filtrate was concentrated in vacuo to afford macrocycle 60-5, which was used directly in the next step without further purification. LCMS-ESI$^+$ (m/z): [M+H]$^+$ calcd for $C_{36}H_{51}F_2N_4O_7$: 689.36; found: 689.56.

Step 6. Preparation of 60-6: To a solution of 60-5 (150 mg, 218 μmol) in DCM (1.1 mL) was added TMSOTf (197 μL, 1.09 mmol) at rt under an argon atmosphere. After 2 h, the reaction mixture was transferred to a solution of 0.5 N NaOH solution (5 mL) precooled to 0° C. The resulting mixture was acidified with 1N HCl solution to pH=2 and was extracted with dichloromethane (3×5 mL). The combined organic extracts were dried over anhydrous sodium sulfate and were concentrated in vacuo to afford carboxylic acid 60-6, which was used directly in the next step without further purification. LCMS-ESI$^+$ (m/z): [M+H]$^+$ calcd for $C_{32}H_{43}F_2N_4O_7$: 633.30; found: 633.49.

Step 7. Preparation of Example 60: To a solution of 60-6 (100 mg, 158 μmol) and Intermediate A9 (69.0 mg, 237 μmol) in MeCN (790 μL) was added HATU (91.5 mg, 237 μmol) followed by DIPEA (137 μL, 790 μmol) at rt under an argon atmosphere. After 3 h, the reaction mixture was concentrated in vacuo, was purified by preparatory HPLC (Gemini 5u C18 110 Å column, 5-100% MeCN/H$_2$O, 0.1% trifluoroacetic acid modifier) and was lyophilized to afford Example 60 as a TFA salt. Analytic HPLC RetTime: 8.89 min. LCMS-ESI$^+$ (m/z): [M+H]$^+$ calcd for $C_{40}H_{53}F_4N_6O_9S$: 869.35; found: 859.66. $^1$H NMR (400 MHz, CD$_3$OD) δ 9.29 (br s, 1H), 7.94 (d, J=9.2 Hz, 1H), 7.31 (d, J=9.2 Hz, 1H), 7.19 (br s, 1H), 587 (br s, 1H), 5.84 (td, J$_{HF}$=55.8 Hz, J=5.4 Hz, 1H), 4.56 (d, J=6.9 Hz, 1H), 4.40 (d, J=12.6 Hz, 1H), 4.36 (s, 1H), 4.17 (dd, J=11.9, 3.4 Hz, 1H), 3.96 (br s, 4H), 3.68 (br s, 1H), 3.01-2.91 (m, 1H), 2.71-2.61 (m, 1H), 2.61-2.43 (m, 1H), 2.02 (br s, 4H), 1.88-1.59 (m, 4H), 1.59-1.35 (m, 4H), 1.33-1.20 (m, 3H), 1.09 (s, 9H), 1.04-0.95 (app t, J=7.0 Hz, 5H), 0.79-0.65 (m, 1H), 0.49 (d, J=6.5 Hz, 1H).

Example 61

Preparation of (1aS,2aR,6S,9S,10S,11R,23aR,23bS)-6-tert-butyl-N-[(1R,2R)-2-(difluoromethyl)-1-{[(1-methylcyclopropyl)sulfonyl]carbamoyl}cyclopropyl]-10-ethyl-19,19-difluoro-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

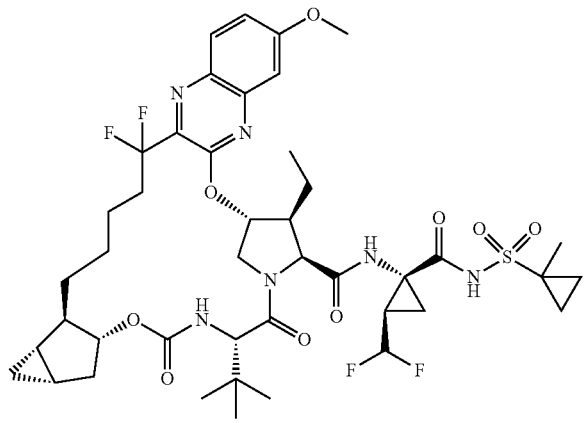

Example 61

Example 61 was prepared similarly to Example 59 substituting Intermediate A10 for Intermediate A9 in Step 5. The TFA salt of Example 61 was isolated. Analytic HPLC RetTime: 9.28 min. LCMS-ESI$^+$ (m/z): [M+H]$^+$ calcd for $C_{43}H_{57}F_4N_6O_9S$: 909.38; found: 909.59. $^1$H NMR (400 MHz, CD$_3$OD) δ 9.28 (s, 1H); 7.95 (d, J=9.2 Hz, 1H); 7.33 (dd, J=9.2, 2.4 Hz, 1H); 7.23 (d, J=2.4 Hz, 1H); 6.0 (br s, 1H); 5.83 (br s, 1H); 5.83 (td, J$_{H-F}$=55 Hz, J=6 Hz, 1H); 4.94 (d. J=7.6 Hz, 1H); 4.61 (d, J=7.6 Hz, 1H); 4.34 (d, J=7.6 Hz, 1H); 4.32 (br s, 1H); 4.18 (m, 1H); 3.97 (s, 3H); 2.63-2.47 (m, 2H); 2.28-2.17 (m, 1H), 2.12-1.96 (m, 4H); 1.83-1.26 (m, 14H); 1.53 (s, 3H); 1.19 (t, J=7.2 Hz, 3H); 1.08 (s, 9H); 0.94-0.88 (m, 2H); 0.62-0.48 (m, 2H).

Example 62

Preparation of (1aS,2aR,6S,9S,10S,11R,23aR, 23bS)-6-tert-butyl-N-[(1R,2R)-1-[(cyclopropylsulfonyl)carbamoyl]-2-(difluoromethyl)cyclopropyl]-19, 19-difluoro-15-methoxy-10-methyl-4,7-dioxo-1a,2, 2a,4,5,6,7,10,11,19,20,21,22,23,23a,23b-hexadecahydro-1H,9H-8,11-methanocyclopropa[4', 5']cyclopenta[1',2':18,19][1,10,3,6] dioxadiazacyclononadecino[11,12-b]quinoxaline-9-carboxamide

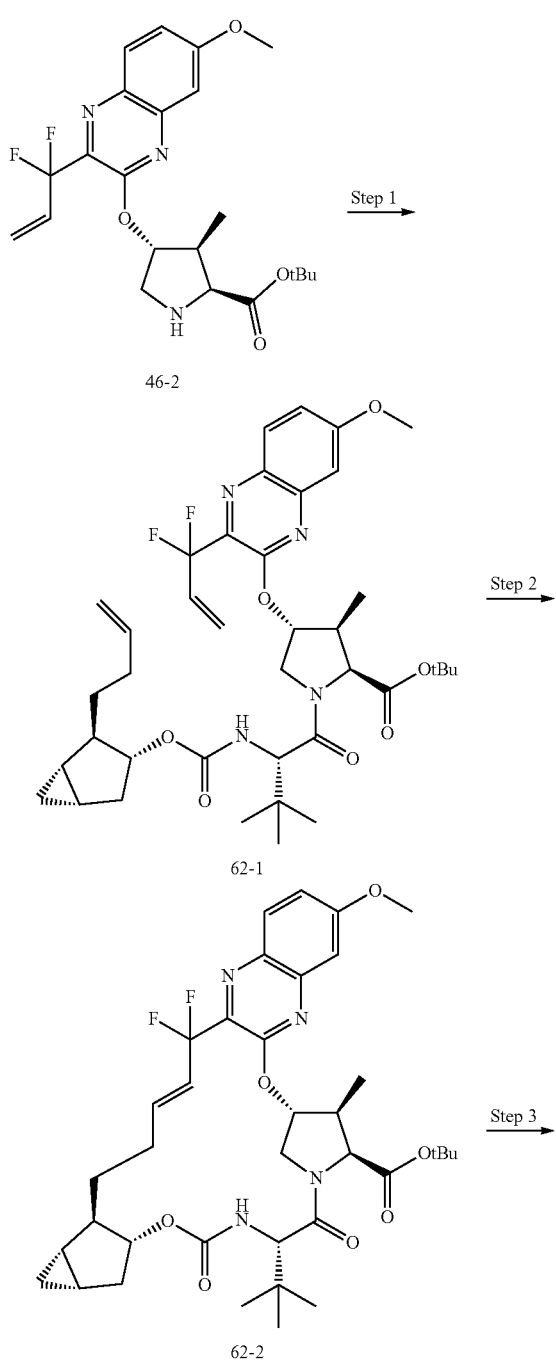

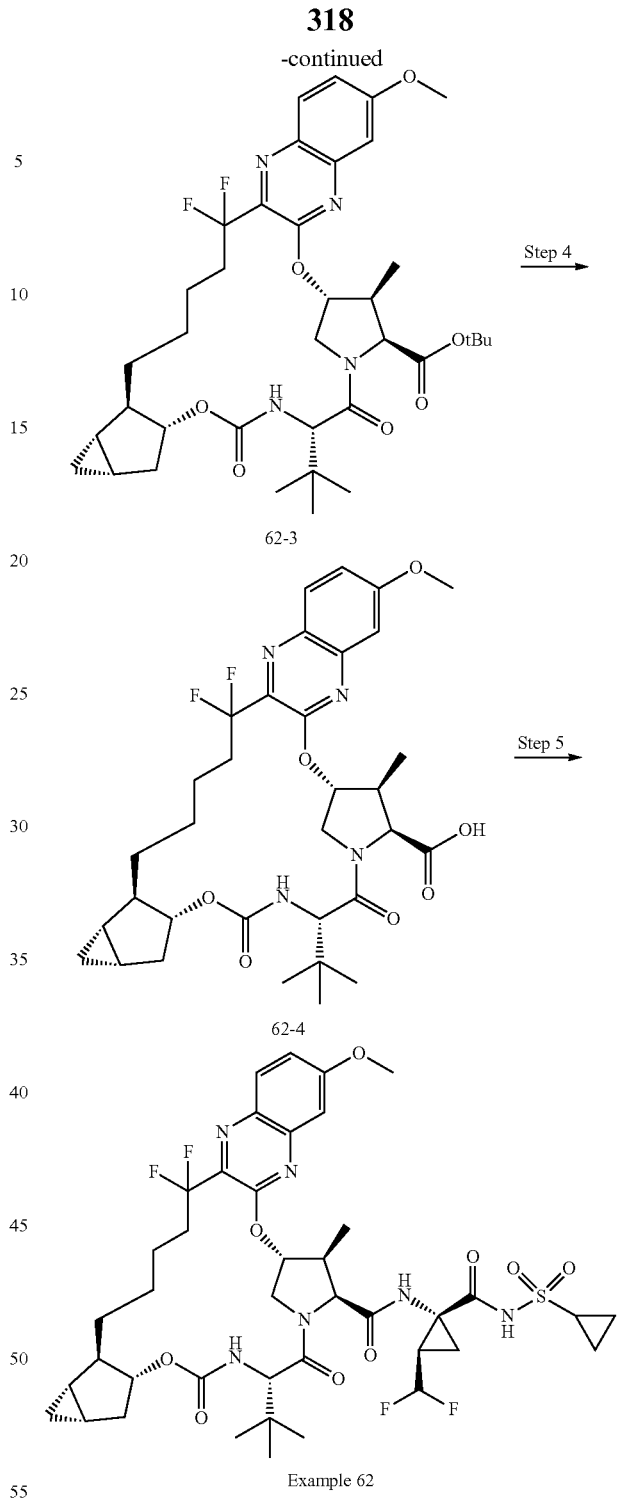

Step 1. Preparation of Example 62-1: HATU (214 mg, 0.563 mmol, Oakwood) and DIPEA (0.30 mL, 1.72 mmol) were added to a mixture of 46-2 (186 mg, 0.428 mmol) and Intermediate D16 (157 mg, 0.508 mmol) in 10 mL of acetonitrile under argon. After stirring overnight, the reaction mixture was concentrated under reduced pressure and the resulting residue was purified by silica gel chromatography (0-30% ethyl acetate in hexanes) to yield Intermediate 62-1. LCMS-ESI$^+$ (m/z): [M+H]$^+$ calcd for $C_{39}H_{53}F_2N_4O_7$: 727.38; found: 727.51.

Step 2. Preparation of 62-2: A mixture of 62-1 (275 mg, 0.378 mmol) and Zhan 1B catalyst (34 mg, 0.046 mmol, Strem) in 75 mL of DCE was deoxygenated with argon for 17 minutes. The mixture was then heated at reflux for 80 minutes. An additional 8 mg of Zhan 1B catalyst was added and mixture stirred at reflux for twenty minutes. After cooling to room temperature, reaction mixture was concentrated in vacuo. The resulting residue was purified by silica gel chromatography (0-25% ethyl acetate in hexanes) to yield intermediate 62-2. LCMS-ESI$^+$ (m/z): [M+H]$^+$ calcd for $C_{37}H_{49}F_2N_4O_7$: 699.35; found: 669.50.

Step 3. Preparation of mixture of 62-3: Palladium on carbon (10 wt % Pd, 60 mg, 0.057 mmol) was added to a solution of 62-2 (207 mg, 0.297 mmol) in 7 mL of ethanol. The atmosphere was replaced with hydrogen and mixture was stirred overnight. The reaction was filtered over Celite, washing with ethanol. Filtrate was concentrated in vacuo to yield intermediate 62-3, which was used in the next step without further purification. LCMS-ESI$^+$ (m/z): [M+H]$^+$ calcd for $C_{37}H_{51}F_2N_4O_7$: 701.36; found: 701.65.

Step 4. Preparation of 62-4: TFA (1.6 mL, 20.9 mmol) was added slowly to a solution of 62-3 (202 mg, 0.289 mmol) in 4.5 mL of dichloromethane. After 3.5 hours, mixture was concentrated under reduced pressure to near dryness. Resulting residue was taken up in 30 mL of ethyl acetate, washed with 20 mL of water, 20 mL of sat. NaHCO$_3$ (aq), and separated. Aqueous layers were extracted with ethyl acetate (3×20 mL). Combined organics were washed with 30 mL of brine, dried over anhydrous MgSO$_4$, filtered, and concentrated in vacuo to yield intermediate 62-4, which was used in the next step without further purification. LCMS-ESI$^+$ (m/z): [M+H]$^+$ calcd for $C_{33}H_{43}F_2N_4O_7$: 645.30; found: 645.53.

Step 5. Preparation of Example 62: HATU (113 mg, 0.297 mmol, Oakwood) and DIPEA (0.17 mL, 0.978 mmol) were added to a mixture of 62-4 (120 mg, 0.186 mmol) and Intermediate A9 (110 mg, 0.379 mmol) in 6 mL of acetonitrile under argon. After stirring for overnight, reaction mixture was taken up in 30 mL of ethyl acetate and washed with 20 mL of 1 N aqueous HCl. The aqueous layer was extracted three times with ethyl acetate. Combined organics were washed with 50% brine, dried over anhydrous Na$_2$SO$_4$, filtered, and concentrated in vacuo. The resulting residue was purified by silica gel chromatography (0-50% ethyl acetate in hexanes) and reverse phase prep HPLC (50-100% acetonitrile in water, with 0.1% trifluoroacetic acid buffer) to yield the trifluoroacetic acid salt of Example 62. Analytic HPLC RetTime: 9.03 min. LCMS-ESI$^+$ (m/z): [M+H]$^+$ calcd for $C_{41}H_{53}F_4N_6O_9S$: 881.35; found: 881.57. $^1$H NMR (400 MHz, CD$_3$OD): δ 9.27 (s, 1H), 7.94 (d, J=8.8 Hz, 1H), 7.33 (dd, J=9.2, 2.8 Hz, 1H), 7.27 (d, J=2.8 Hz, 1H), 5.84 (td, J$_{H-F}$=56 Hz, J=6.8 Hz, 1H), 5.75 (d, J=3.6 Hz, 1H), 4.94 (d, J=7.2 Hz, 1H), 4.55 (d, J=7.2 Hz, H), 4.35 (d, J=12 Hz, 1H), 4.32 (s, 1H), 4.22-4.16 (dd, J=12.4 Hz, 1H) 3.97 (s, 3H), 3.01-2.94 (m, 1H), 2.81-2.72 (m, 1H), 2.66-2.40 (m, 1H), 2.36-2.28 (m, 1H), 2.10-1.94 (m, 4H), 1.82-1.72 (m, 2H), 1.70-1.22 (m, 10H), 1.14-1.02 (m, 7H), 1.10 (s, 9H), 0.61-0.49 (m, 2H).

Example 63

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-1a-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

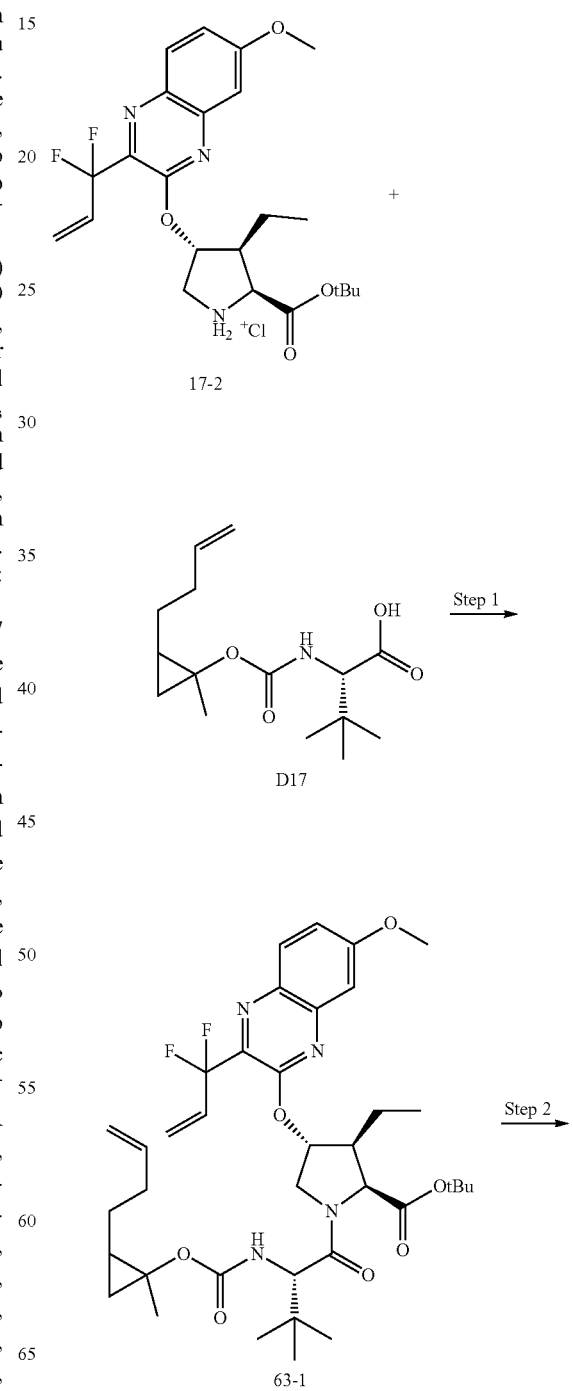

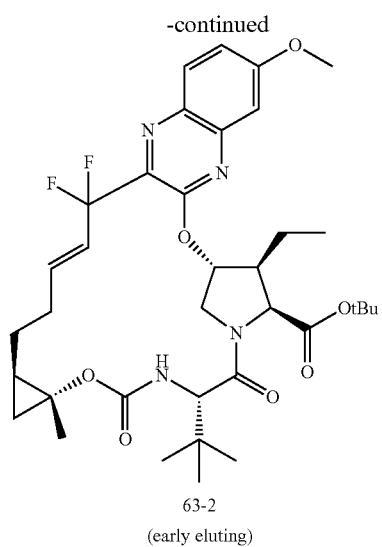

63-2
(early eluting)

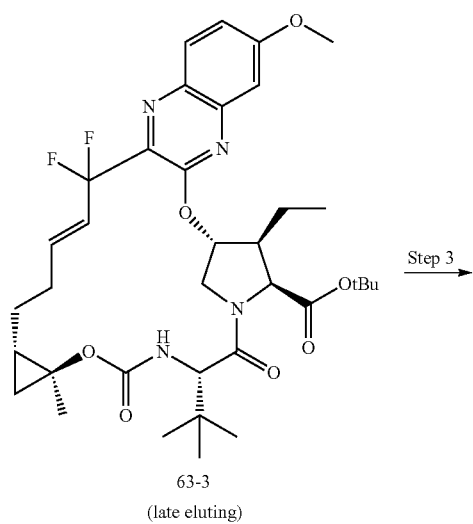

63-3
(late eluting)

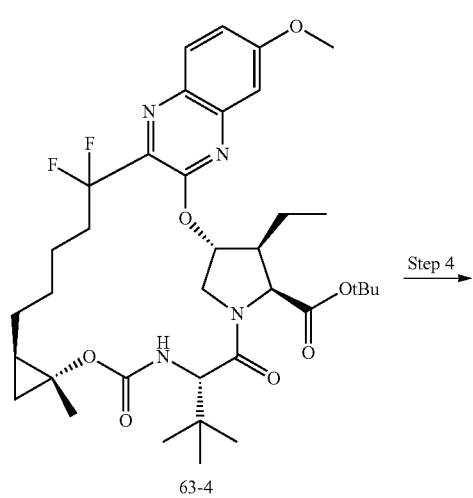

63-4

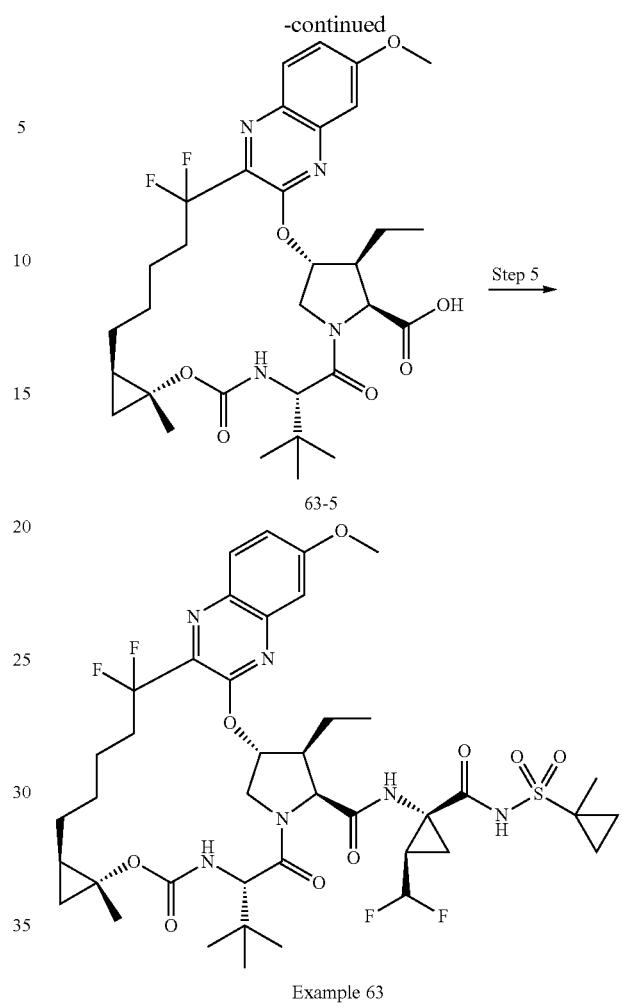

Example 63

Step 1. Preparation of 63-1: Amine hydrochloride 17-2 (500 mg, 1.03 mmol) was combined with intermediate mixture D17 (378.5 mg, 1.34 mmol), DIPEA (1.8 mL, 10.3 mmol) and DMF (3 mL). HATU (587.1 mg, 1.55 mmol) was then added to the reaction mixture, which was stirred at room temperature for 18 hrs. Reaction mixture was then diluted with water (20 mL) and 1N HCl (10.5 mL) and taken up into methylene chloride (20 mL). Organics were separated and aqueous layer was extracted three times with methylene chloride (10 mL). Combined organics were then washed with brine, dried over MgSO$_4$, filtered, and concentrated in vacuo. Crude residue was then purified via silica gel chromatography to give 63-1 as a 1:1 diastereomeric mixture. LCMS-ESI$^+$ (m/z): [M+H]$^+$ calcd for C$_{38}$H$_{53}$F$_2$N$_4$O$_7$: 715.4, found: 715.4.

Step 2. Preparation of 63-2 and 63-3: Diastereomeric mixture 63-1 (496 mg, 0.695 mmol) and Zhan 1B catalyst (53.8 mg, 0.0695 mmol, Strem) were dissolved in 140 mL of anhydrous DCE and sparged with N$_2$ for 30 minutes. The mixture was then heated to 100° C. for 90 minutes, and an additional portion of Zhan 1B catalyst was added (54 mg, 0.695 mmol, Strem). Reaction was then cooled to room temperature and concentrated in vacuo. The resulting residue was purified via silica gel chromatography (0% to 40% ethyl acetate in hexanes) to yield single diastereomers 63-2 (early eluting fraction) and 63-3 (late eluting fraction). Early eluting fraction: LCMS-ESI$^+$ (m/z): [M+H]$^+$ calcd for C$_{36}$H$_{49}$F$_2$N$_4$O$_7$: 687.4; found: 687.2. Late eluting fraction. LCMS-ESI$^+$ (m/z): [M+H]$^+$ calcd for C$_{36}$H$_{49}$F$_2$N$_4$O$_7$: 687.4; found: 687.3.

Step 3. Preparation of 63-4: Palladium on carbon (10% w/w, 155 mg) was added to a solution of 63-2 (155 mg, 0.226 mmol) in a ethanol (3 mL), Mixture was stirred under an atmosphere of hydrogen for 1 hr and was then filtered through a plug of Celite, and washed with ethyl acetate. Filtrate was concentrated under reduced pressure to yield 63-4, which was used in the next step without further purification, LCMS-ESI$^+$ (m/z): [M+H]$^+$ calcd for $C_{36}H_{51}F_2N_4O_7$: 689.4; found: 689.3.

Step 6. Preparation of 63-5: Intermediate 63-4 (153.5 mg, 0.222 mmol) was dissolved in a mixture of 1:1 TFA:DCM (6 mL) and stirred at room temperature for 3 hrs. Reaction mixture was then concentrated in vacuo to give 63-5, which was used in the subsequent step without further purification. LCMS-ESI$^+$ (m/z): [M+H]$^+$ calcd for $C_{32}H_{44}N_4O_7$: 633.3; found: 633.2.

Step 7. Preparation of Example 63: HATU (99.2 mg, 0.261 mmol) and DIPEA (271 μL, 2.1 mmol) were added to a mixture of 63-5 (140.5 mg, 0.222 mmol) and A10 (100 mg, 0.316 mmol) in 1 mL of DMF. After stirring overnight at room temperature, reaction mixture was poured into water, acidified to pH 1 with 1 N aqueous HCl, and extracted three times with methylene chloride (15 mL). Combined organics were washed with water, brine, dried over MgSO$_4$, filtered, and concentrated under reduced pressure. The resulting residue was purified by reverse phase prep HPLC (5-100% acetonitrile in water, with 0.1% trifluoroacetic acid buffer) to afford Example 63. Analytic HPLC RetTime: 8.951 min. LCMS-ESI$^+$ (m/z): [M+H]$^+$ calcd for $C_{41}H_{55}F_4N_6O_9S$: 883.4; found: 883.2. $^1$H NMR (400 MHz, CD$_3$OD) δ 7.96 (d, J=9.2 Hz, 1H), 7.33 (dd, J=9.2, 2.8 Hz, 1H), 7.23 (d, J=2.7 Hz, 1H), 6.03 (d, J=3.9 Hz, 1H), 5.80 (td, J=55.8, 6.7 Hz, 1H), 4.61 (d, J=6.9 Hz, 1H), 4.46 (d, J=12.2 Hz, 1H), 4.26-4.14 (m, 2H), 4.01-3.91 (m, 3H), 2.65-2.47 (m, 2H), 2.11-1.85 (m, 5H), 1.84-1.61 (m, 3H), 1.61-1.46 (m, 10H), 1.46-1.32 (m, 3H), 1.33-1.17 (m, 4H), 1.09 (d, J=15.9 Hz, 10H), 1.04-0.95 (m, 1H), 0.94-0.84 (m, 2H), 0.21-0.12 (m, 1H).

Example 64

Preparation of (1aS,5S,8S,9S,10R,22aS)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-1a-methyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

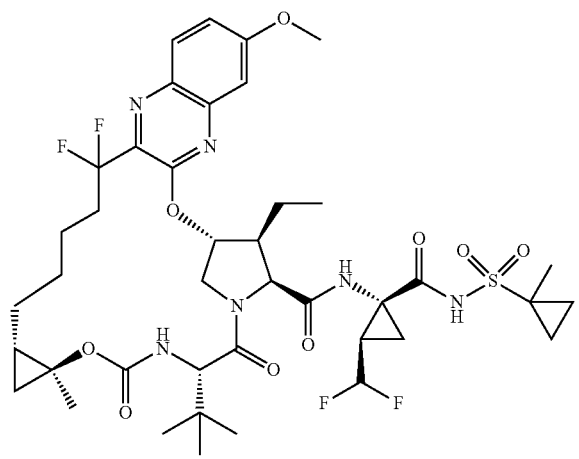

Example 64

Example 64 was prepared in a similar fashion to Example 63, substituting late eluting 63-3 for early eluting 63-2 in Step 3. Example 64 was then isolated. Analytic HPLC RetTime: 8.535 min. LCMS-ESI$^+$ (m/z): [M+H]$^+$ calcd for $C_{41}H_{57}F_2N_6O_9S$: 883.4; found: 883.3. $^1$H NMR (400 MHz, CD$_3$OD) δ 7.97 (d, J=8.9 Hz, 1H), 7.45-7.16 (m, 2H), 5.97-5.52 (m, 2H), 4.74 (d, J=7.6 Hz, 1H), 4.50-4.16 (m, 1H), 4.06-3.86 (m, 5H), 2.77-2.57 (m, 1H), 2.51-2.18 (m, 2H), 2.16-1.86 (m, 5H), 1.75-1.32 (m, 16H), 1.33-1.03 (m, 14H), 1.02-0.76 (m, 2H), 0.42-0.09 (m, 1H).

Example 65

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-18,18-difluoro-14-methoxy-3,6-dioxo-9-propyl-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

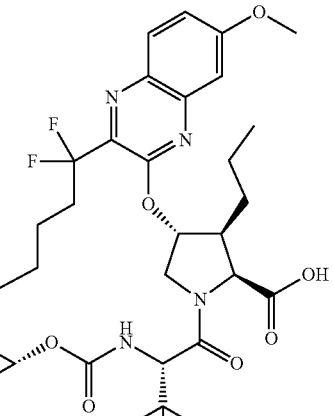

60-6

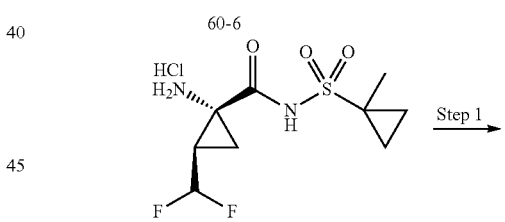

Step 1

A10

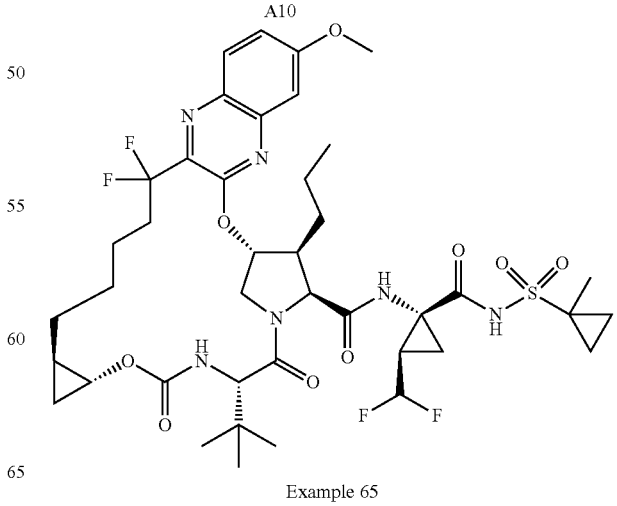

Example 65

Step 1. Preparation of Example 65: To a solution of 60-6 (52 mg, 82 μmol) and Intermediate A10 (37.5 mg, 123 μmol) in MeCN (411 μL) was added HATU (47.5 mg, 123 μmol) followed by DIPEA (73 μL, 411 μmol) at rt under an argon atmosphere. After 20 h, the reaction mixture was concentrated in vacuo, was purified by preparatory HPLC (Gemini 5u C18 110 Å column, 5-100% MeCN/H$_2$O, 0.1% trifluoroacetic acid modifier) and was lyophilized to afford Example 65 as a TFA salt. Analytic HPLC RetTime 8.99 min. LCMS-ESI$^+$ (m/z): [M+H]$^+$ calcd for C$_{41}$H$_{55}$F$_4$N$_6$O$_9$S: 883.36, found: 883.60. $^1$H NMR (400 MHz, CD$_3$OD) δ 9.26 (s, 1H), 7.95 (d, J=9.1 Hz, 1H), 7.33 (dd, J=9.2, 2.8 Hz, 1H), 7.22 (d, J=2.8 Hz, 1H), 5.89 (d, J=3.2 Hz, 1H), 5.81 (td, J$_{H-F}$=55.5 Hz, J=6.5 Hz, 1H), 4.59 (d, J=7.0 Hz, 1H), 4.40 (d, J=12.5 Hz, 1H), 4.36 (s, 1H), 4.17 (dd, J=12.2, 3.8 Hz, 1H), 3.97 (s, 3H), 3.73-3.66 (m, 1H), 2.73-2.64 (m, 1H), 2.63-2.45 (m, 1H), 2.01 (br s, 3H), 1.85-1.62 (m, 4H), 1.62-1.53 (m, 3H), 1.51 (s, 3H), 1.48-1.22 (m, 5H), 1.08 (s, 9H), 1.01 (app t, J=7.3 Hz, 4H), 0.94-0.87 (m, 2H), 0.80-0.69 (m, 1H), 0.50 (d, J=7.1 Hz, 1H).

Example 66

Preparation of (4aR,8S,11S,12S,13R,25aR)-8-tert-butyl-N-[(1R,2R)-1-[(cyclopropylsulfonyl)carbamoyl]-2-(difluoromethyl)cyclopropyl]-12-ethyl-17-methoxy-6,9-dioxo-2,3,4,4a,6,7,8,9,12,13,21,22,23,24,25,25a-hexadecahydro-1H,11H-10,13-methanoquinoxalino[2,3-k][1,10,3,6]benzodioxadiazacyclononadecine-11-carboxamide

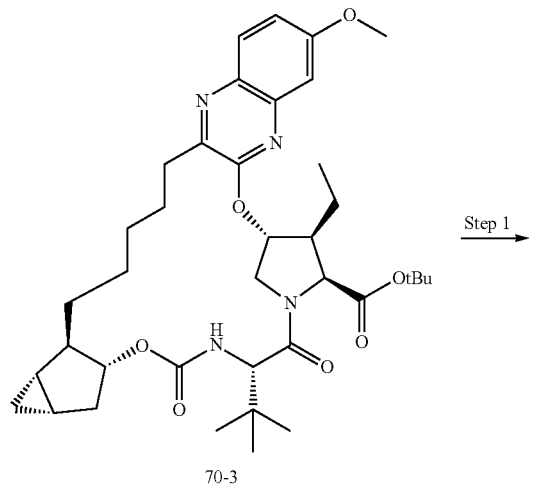

70-3

Step 1

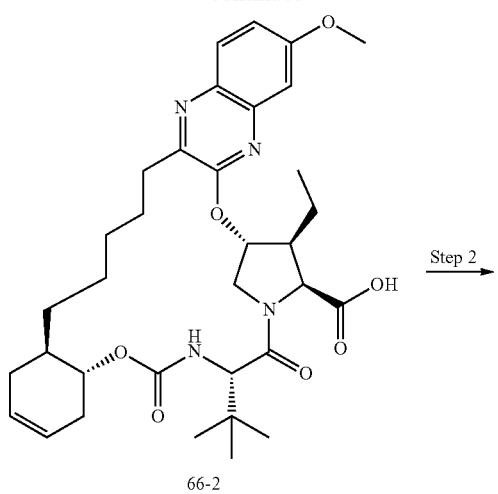

66-2

Step 2

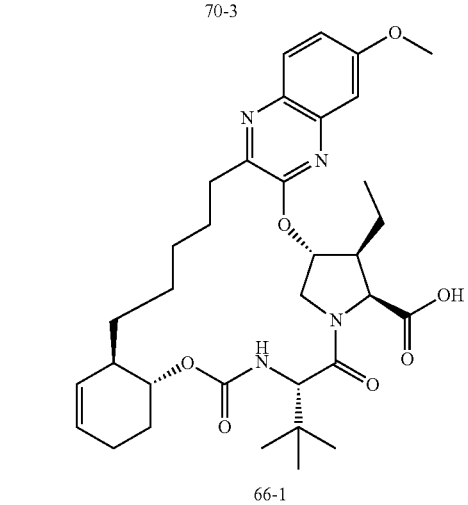

and 66-1

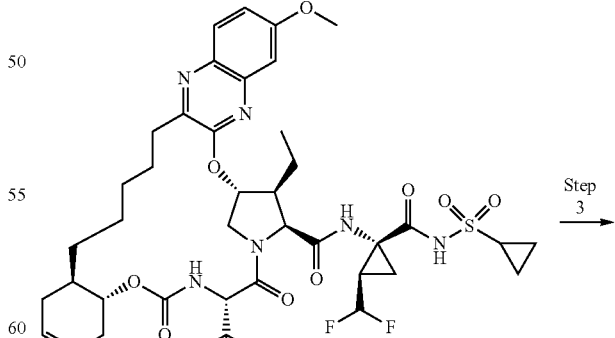

and 66-3

66-4

Step 3

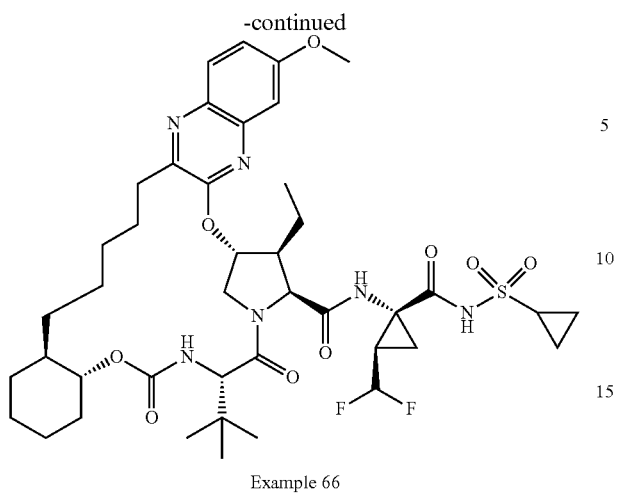

Example 66

Step 1. Preparation of 66-1 and 66-2. To a solution of Intermediate 70-3 (283 mg, 0.42 mmol) in CH$_2$Cl$_2$ (5 mL) was added TMSOTf (380 μL 2.1 mmol). After stirring for 2 h, the reaction mixture was poured into stirring 1 N NaOH (12 mL). The mixture was transferred to a separatory funnel, acidified to pH 3 with 1N HCl, extracted with CH$_2$Cl$_2$, dried over magnesium sulfate, and concentrated. The crude residue was purified by silica gel chromatography (0-10% MeOH/EtOAc) to yield a mixture of 66-1 and 66-2. LCMS-ESI$^+$ (m/z): [M+H]$^+$ calcd for C$_{34}$H$_{47}$N$_4$O$_7$: 623.34; found: 623.66.

Step 2. Preparation of 66-3 and 66-4. To a solution of 66-1 and 66-2 (58 mg 0.09 mmol), intermediate A9 (32 mg, 0.11 mmol), TBTU (42 mg, 0.13 mmol) and DMAP (16 mg, 0.14 mmol) in DMF (3 mL) was added DIPEA (47 μL, 0.27 mmol) and the reaction was stirred at rt for 23 h. The reaction was quenched with water, diluted with EtOAc, washed with sat. NaHCO$_3$, brine, dried over magnesium sulfate, and concentrated. The crude material was purified by reverse phase HPLC (Gemini, 30-85% ACN/H$_2$O+0.1% TFA) and lyophilized to give the TFA salt of Intermediate 66-3 and 66-4 mixture. LCMS-ESI$^+$ (m/z): [M+H]$^+$ calcd for C$_{42}$H$_{57}$F$_2$N$_6$O$_9$S: 859.39; found: 859.65.

Step 3. Preparation of Example 66: To 66-3 and 66-4 (5 mg, 0.005 mmol) that was taken up in EtOH (2 mL) and treated with Pd/C (10%, 5 mg). The atmosphere was replaced with hydrogen and stirred at rt for 2.5 h. The reaction was filtered over Celite, washed with EtOAc and concentrated. The residue was purified by silica gel chromatography (0-10% MeOH/EtOAc) and lyophilized to give the parent compound. Analytical HPLC RetTime: 9.15 min. LCMS-ESI$^+$ (m/z): [M+H]$^+$ calcd for C$_{42}$H$_{59}$F$_2$N$_6$O$_9$S: 862.01; found: 862.37. $^1$H NMR (400 MHz, CD$_3$OD) δ 7.94-7.73 (m, 1H), 7.25 (m, 1H), 6.87 (d, J=9.8 Hz, 1H), 6.05 (m, 2H), 4.83-4.74 (m, 1H), 4.70 (d, J=7.6 Hz, 1H), 4.52-4.28 (m, 2H), 4.16 (m, 2H), 4.05-3.86 (m, 4H), 3.86-3.45 (m, 4H), 3.22-3.00 (m, 1H), 2.89 (s, 1H), 2.77-2.55 (m, 1H), 2.25 (t, J=7.3 Hz, 1H), 2.09-0.81 (m, 35H).

Example 67

Preparation of (1aR,5S,8S,9S,10R,22aR)-5-tert-butyl-N-[(1R,2S)-2-(2,2-difluoroethyl)-1-{[(1-methylcyclopropyl)sulfonyl]carbamoyl}cyclopropyl]-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

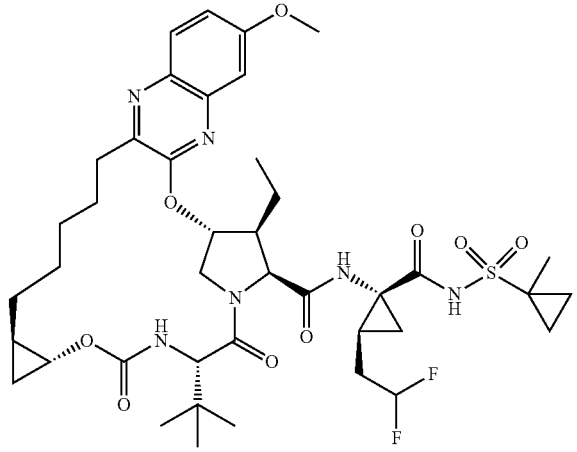

Example 67

Example 67 was prepared similarly to Example 1 substituting Intermediate A8 for Intermediate A10 in Step 8. The TFA salt of Example 67 was isolated. Analytic HPLC RetTime: 8.85 min. LCMS-ESI$^+$ (m/z): [M+H]$^+$ calcd for C$_{41}$H$_{57}$F$_2$N$_6$O$_9$S: 847.99; found: 847.64. $^1$H NMR (400 MHz, CD$_3$OD) δ 9.00 (s, 1H); 7.79 (d, J=9.2 Hz, 1H); 7.23 (dd, J=9.2, 2.4 Hz, 1H); 7.15 (d, J=2.4 Hz, 1H); 5.89 (tt, J$_{H-F}$=54 Hz, J=4.4 Hz, 1H); 5.89 (br s, 1H); 4.61 (d, J=7.2 Hz, 1H); 4.39 (br s, 1H); 4.37 (d, J=9.2 Hz, 1H); 4.16 (dd, J=9.2 Hz, 7.2 Hz, 1H); 3.92 (s, 3H); 3.78-3.72 (m, 1H); 3.10-2.88 (m, 1H); 2.86-2.74 (td, J=12, 4.4 Hz, 1H); 2.62-2.53 (m, 1H); 2.18-2.04 (m, 1H); 1.88-1.46 (m, 14H); 1.53 (s, 3H); 1.28-1.20 (m, 4H); 1.10 (s, 9H); 1.02-0.96 (m, 2H); 0.96-0.86 (m, 2H); 0.78-0.67 (m, 1H); 0.54-0.47 (m, 1H).

Example 68

Preparation of (4aR,8S,11 S,12S,13R,25aS)-8-tert-butyl-N-[(1R,2R)-1-[(cyclopropylsulfonyl)carbamoyl]-2-(difluoromethyl)cyclopropyl]-21,21-difluoro-17-methoxy-12-methyl-6,9-dioxo-2,3,4,4a,6,7,8,9,12,13,21,22,23,24,25,25a-hexadecahydro-1H,11H-10,13-methanoquinoxalino[2,3-k][1,10,3,6]benzodioxadiazacyclononadecine-11-carboxamide

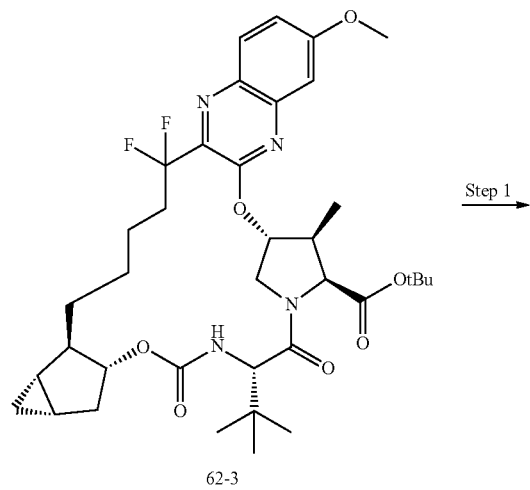

62-3

Step 1 →

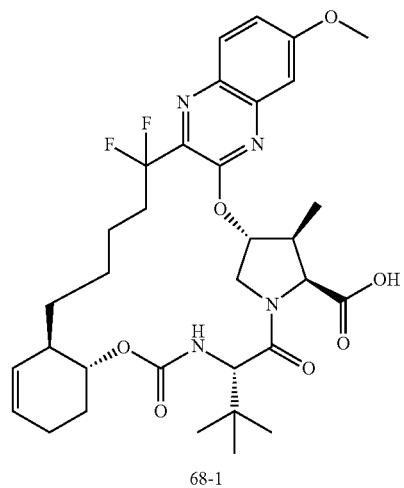

68-1 and

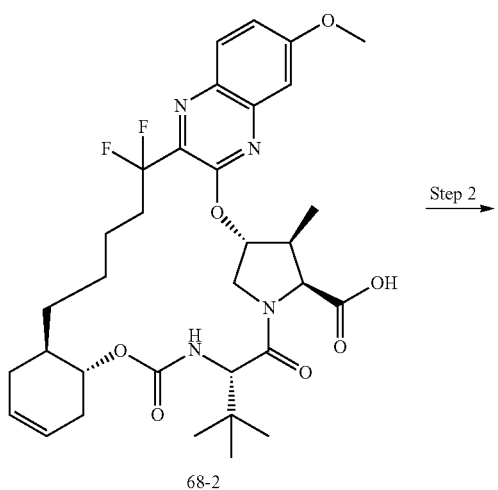

68-2

Step 2 →

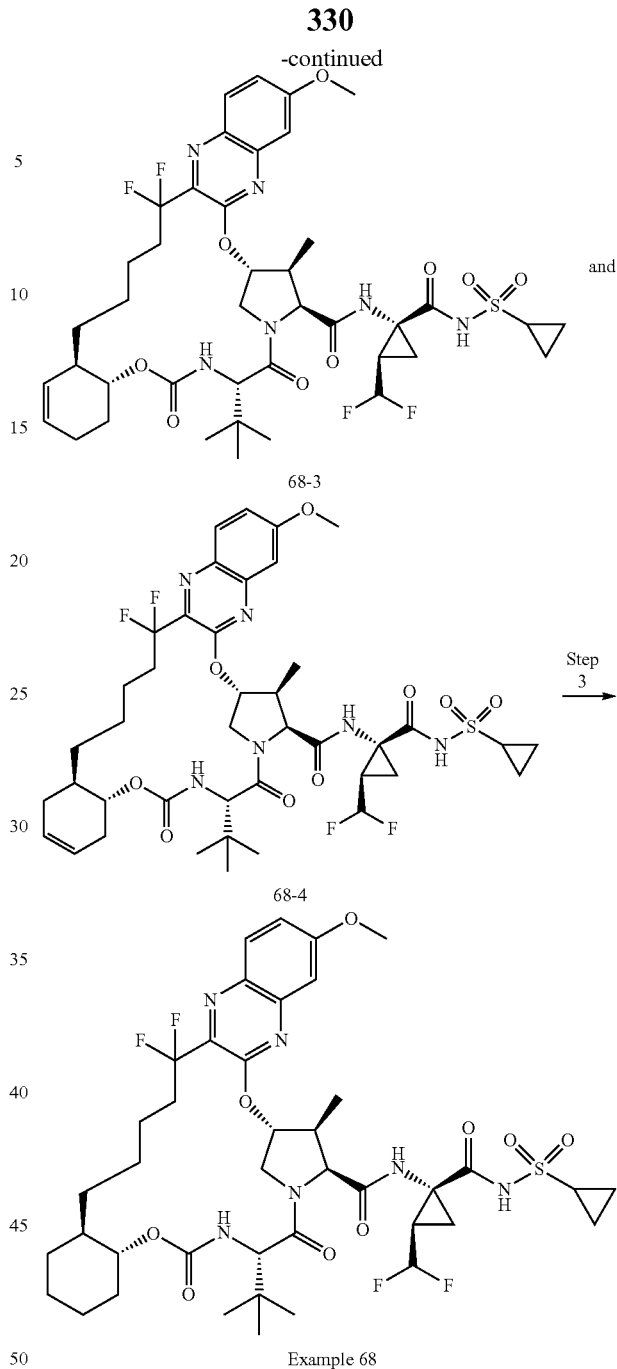

68-3 and 68-4

Step 3 →

Example 68

Step 1. Preparation of 68-1 and 68-2 (mixture): TMSOTf (0.6 mL, 3.3 mmol) was added to a solution of intermediate 62-3 (424 mg, 0.606 mmol) in 7 mL of dichloromethane at room temperature. After 1 hour, an additional 0.2 mL of TMSOTf was added. After a total of three hours, reaction mixture was concentrated to yield a mixture of 68-1 and 68-2 isomers, which was used in the next step without further purification. LCMS-ESI+ (m/z): [M+H]+ calcd for $C_{33}H_{43}F_2N_4O_7$: 645.30; found: 645.49.

Step 2. Preparation of 68-3 and 68-4 (mixture): HATU (209 mg, 0.550 mmol, Oakwood) and DIPEA (0.25 mL, 1.43 mmol) were added to the mixture of 68-1 and 68-2 from the previous step (176 mg, 0.273 mmol) and intermediate A9 (161 mg, 0.555 mmol) in 4 mL of acetonitrile and 2 mL of DMF under argon. After one hour, an additional 100 mg of Intermediate A9 was added. After two hours, reaction mixture was taken up in 30 mL of ethyl acetate and washed with 20 mL of 1 N aqueous HCl. The aqueous layer was extracted three times with ethyl acetate. Combined organics were washed with 50% brine, dried over anhydrous $Na_2SO_4$, filtered, and concentrated in vacuo. The resulting residue was purified by silica gel chromatography (0-50% ethyl acetate in hexanes) and reverse phase prep HPLC (50-100% acetonitrile in water, with 0.1% trifluoroacetic acid buffer) to yield the trifluoroacetic acid salts of a mixture of 68-3 and 68-4. LCMS-ESI$^+$ (m/z): [M+H]$^+$ calcd for $C_{41}H_{53}F_4N_6O_9S$: 881.35; found: 881.50.

Step 3. Preparation of Example 68: Palladium on carbon (10 wt % Pd, 2 mg, 0.0019 mmol) was added to a solution of the mixture of 68-3 and 68-4 from the previous step (4.5 mg, 0.0045 mmol) in 1 mL of ethanol. The atmosphere was replaced with hydrogen and mixture was stirred for two hours. The reaction was filtered over Celite, washing with ethanol. Filtrate was concentrated in vacuo to yield Example 68 Analytic HPLC RetTime: 8.81 min. LCMS-ESI$^+$ (m/z): [M+H]$^+$ calcd for $C_{41}H_{55}F_4N_6O_9S$: 883.36; found 883.64. $^1$H NMR (400 MHz, $CD_3OD$): δ 7.94 (d, J=10.4 Hz, 1H), 7.34-7.30 (m, 2H), 6.13 (td, $J_{H-F}$=57 Hz, J=6.8 Hz, 1H), 5.88-5.84 (m, 1H), 4.62 (d, J=7.6 Hz, 1H), 4.38-4.30 (m, 2H), 4.20-4.05 (m, 2H), 3.98 (s, 3H), 2.87-2.76 (m, 2H), 2.34-2.16 (m, 2H), 1.92-1.54 (m, 6H), 1.46-1.36 (m, 3H), 1.34-1.12 (m, 8H), 1.20 (d, J=7.6 Hz, 3H), 1.08-0.96 (m, 4H), 1.04 (s, 9H), 0.93-0.78 (m, 4H).

Example 69

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-14-ethoxy-9-ethyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

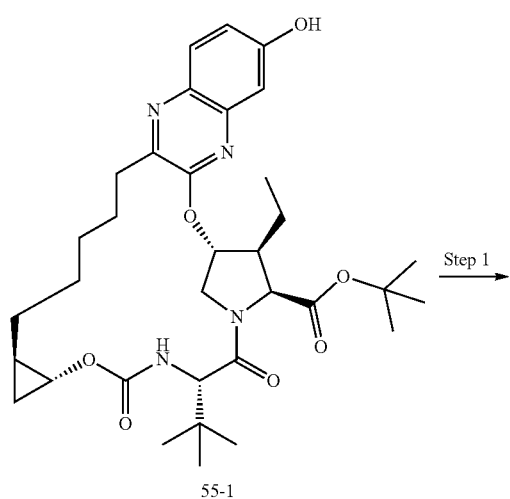

55-1

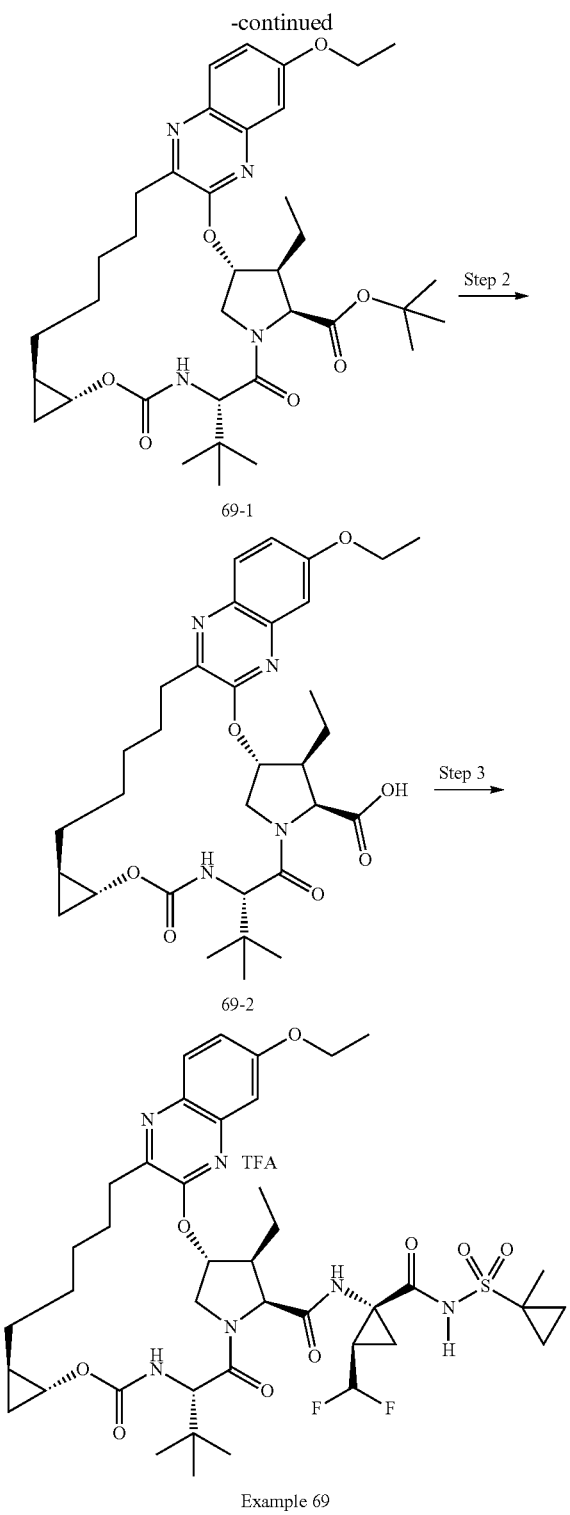

69-1

69-2

Example 69

Step 1. Preparation of 69-2. Quinoxalinol 55-1 (54 mg, 0.086 mmol) was suspended in ACN (2 mL) and treated with $Cs_2CO_3$ (84 mg, 0.259 mmol) and bromoethane (0.032 mL, 0.432 mmol). The reaction mixture was stirred at RT for 16 h. The reaction was filtered and the crude material was purified by flash column chromatography to afford 69-2. LCMS-ESI$^+$ (m/z): [M+H]$^+$ calcd for $C_{36}H_{52}N_4O_7$: 652.38; found: 653.41.

Step 2. Preparation of 69-3. Intermediate 69-2 (0.086 mmol theoretical) was treated with DCM (10 mL) and TMSOTf (1.0 mL) at RT. After 1 h, the reaction was complete determined by LCMS. The reaction was concentrated under reduced pressure to afford 69-3, which was carried on without further purification. LCMS-ESI$^+$ (m/z): [M+H]$^+$ calcd for $C_{32}H_{44}N_4O_7$: 596.32; found: 597.38.

Step 3. Preparation of Example 69. Carboxcylic acid 69-3 (0.0.086 mmol theoretical) was treated with intermediate A10 (40 mg, 0.130 mmol), TBTU (47 mg, 0.147 mmol), DMAP (18 mg, 0.147 mmol), DCM (3 mL) and DIPEA (0.075 mL, 0.432 mmol). The reaction mixture was stirred at RT for 20 h, then concentrated under reduced pressure and purified by reverse phase HPLC to afford Example 69 as a TFA salt. LCMS-ESI$^+$ (m/z): [M+H]$^+$ calcd for $C_{41}H_{56}F_2N_6O_9S$: 846.38; found: 847.75.

Example 70

Preparation of (1aS,2aR,6S,9S,10S,11R,23aR, 23bS)-6-tert-butyl-N-[(1R,2R)-1-[(cyclopropylsulfonyl)carbamoyl]-2-(difluoromethyl)cyclopropyl]-10-ethyl-15-methoxy-4,7-dioxo-1a,2,2a,4,5,6,7,10,11, 19,20,21,22,23,23a,23b-hexadecahydro-1H,9H-8,11-methanocyclopropa[4',5']cyclopenta[1',2':18,19][1, 10,3,6]dioxadiazacyclononadecino[11,12-b] quinoxaline-9-carboxamide

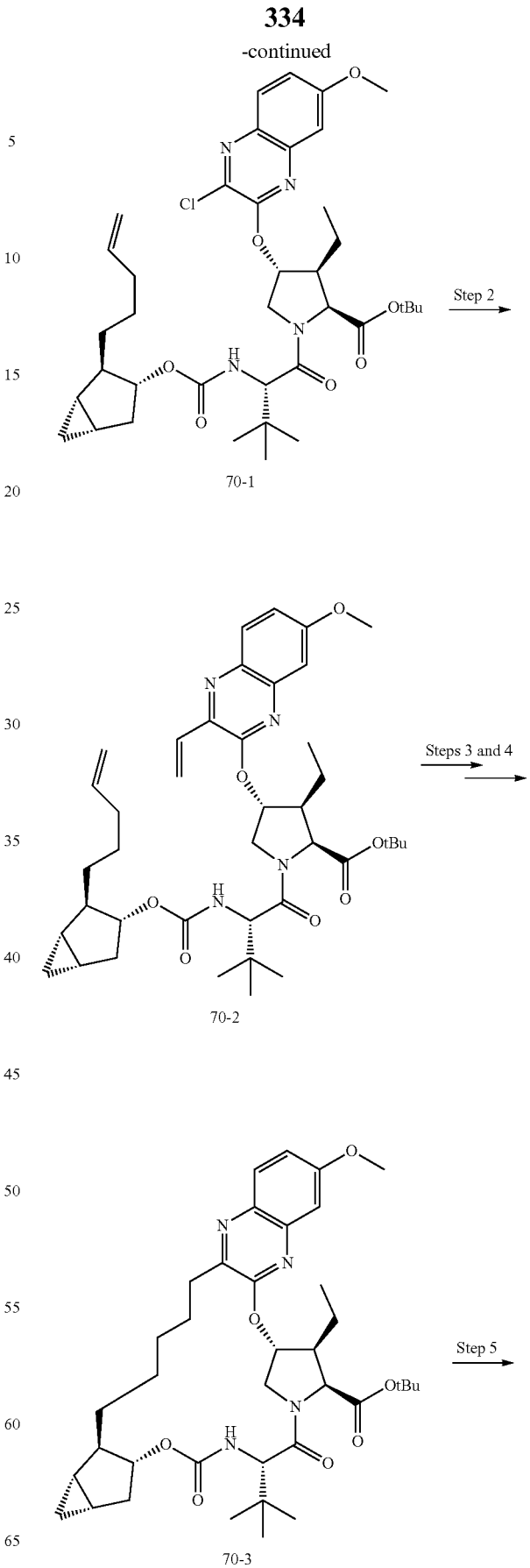

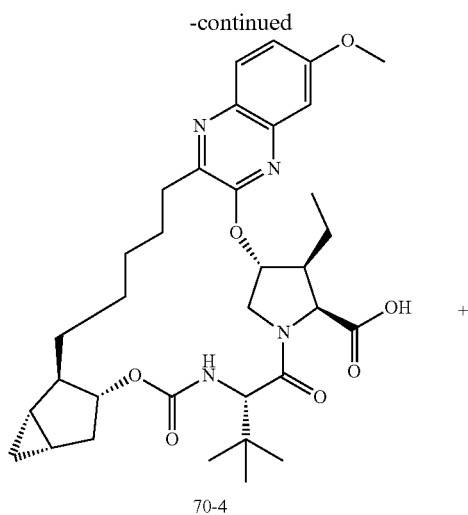

70-4

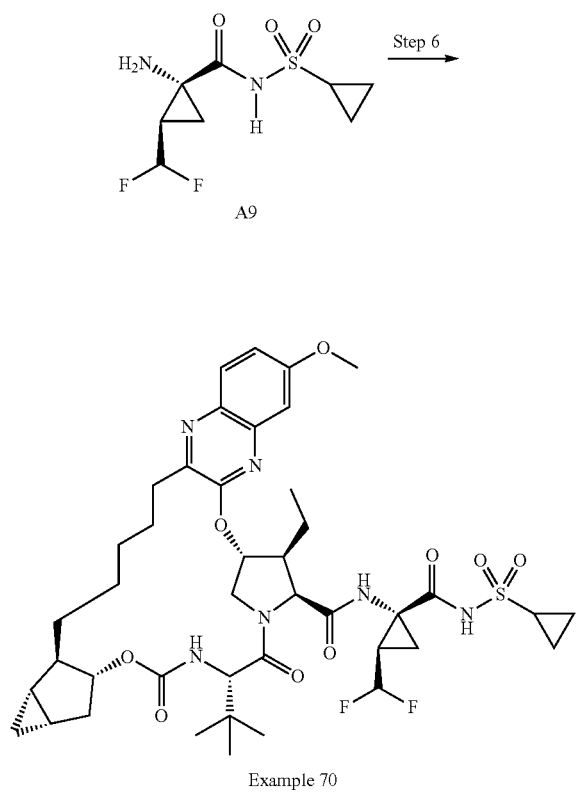

A9

Example 70

Step 1. Preparation of 70-1: To a solution of 1-2 (575 mg, 1.41 mmol), D12 (410 mg, 1.26 mmol) and HATU (696 mg, 1.80 mmol) in DMF (12 mL) was added DIPEA (1.0 mL, 5.64 mmol) and the reaction was stirred at rt. After stirring for 2 h, additional HATU (350 mg, 0.92 mmol) and DIPEA (0.5 mL, 2.8 mmol) was added to the reaction, and the mixture was stirred for 14 h. The reaction was quenched with sat. NaHCO$_3$ solution and extracted with EtOAc, washed subsequently with brine, dried over magnesium sulfate and concentrated. The crude product was purified by silica gel chromatography (10-30% EtOAc/hexanes) to yield intermediate 70-1. LCMS-ESI$^+$ (m/z): [M+H]$^+$ calcd for C$_{38}$H$_{54}$ClN$_4$O$_7$: 713.37; found: 713.95.

Step 2. Preparation of 70-2: To a solution of 70-1 (542 mg, 0.76 mmol), TEA (0.16 mL, 1.14 mmol) and potassium vinyltrifluoroborate (153 mg, 1.14 mmol) in EtOH (10 mL) was added PdCl$_2$(dppf) (62 mg, 0.08 mmol). The reaction was degassed with N$_2$ for 10 min and heated to 80° C. for 1 h. The reaction was quenched with sat. NaHCO$_3$ solution and extracted with EtOAc, washed subsequently with brine, dried over magnesium sulfate and concentrated. The residue was purified using silica gel chromatography (0-20% EtOAc/hexanes) to give intermediate 70-2. LCMS-ESI$^+$ (m/z): [M+H]$^+$ calcd for C$_{40}$H$_{57}$N$_4$O$_7$: 705.42; found: 705.05.

Step 3 and 4. Preparation of 70-3: To a solution of 70-2 (470 mg, 0.66 mmol) in DCE (100 mL) was added Zhan 1B catalyst (49 mg, 0.07 mmol) and the reaction was degassed for 30 minutes with N$_2$. The reaction was heated to 100° C. for 1 h, allowed to cool to rt and concentrated. The crude product was purified by silica gel chromatography to give product (358 mg; LCMS-ESI$^+$ (m/z): [M+H]$^+$ calcd for C$_{38}$H$_{53}$N$_4$O$_7$: 677.39; found: 677.52) that was taken up in EtOH (6 mL) and EtOAc (2 mL) and treated with Pd/C (10%, 350 mg). The atmosphere was replaced with hydrogen and stirred at rt for 1.5 h. The reaction was filtered over Celite, washed with EtOAc and concentrated (358 mg intermediate 70-3) that was used subsequently without further purification. LCMS-ESI$^+$ (m/z): [M+H]$^+$ calcd for C$_{38}$H$_{55}$N$_4$O$_7$: 679.41; found: 679.44.

Step 5. Preparation of 70-4: To a solution of 70-3 (100 mg, 0.15 mmol) in DCM (1 mL) was added TFA (1 mL) and stirred at rt for 2 h. The reaction was diluted with EtOAc, washed with H$_2$O, basicified to pH 7 with sat. NaHCO$_3$ solution, dried over magnesium sulfate, and concentrated to give a residue of intermediate 70-4 that was used subsequently without further purification LCMS-ESI$^+$ (m/z): [M+H]$^+$ calcd for C$_{34}$H$_{47}$N$_4$O$_7$: 623.34; found: 623.44.

Step 6. Preparation of Example 70: To a solution of 70-4 (94 mg, 0.15 mmol), intermediate A9 (65 mg, 0.22 mmol). TBTU (87 mg, 0.27 mmol) and DMAP (27 mg, 0.22 mmol) in DCM (3 mL) was added DIPEA (0.13 mL, 0.75 mmol) and the reaction was stirred at rt for 2 h. The reaction was quenched with water, diluted with EtOAc, washed with sat. NaHCO$_3$, brine, dried over magnesium sulfate, and concentrated. The crude material was purified by reverse phase HPLC (Gemini, 30-85% ACN/H$_2$O+0.1% TFA) and lyophilized to give Example 70 (23 mg) as a TFA salt.

Analytical HPLC RetTime: 9.32 min. LCMS-ESI$^+$ (m/z): [M+H]$^+$ calcd for C$_{42}$H$_{57}$F$_2$N$_6$O$_9$S: 859.39; found: 859.54. $^1$H NMR (400 MHz, CD$_3$OD) δ 9.31 (s, 1H), 7.83 (d, J=9.1 Hz, 1H), 7.26 (dd, J=9.1, 2.8 Hz, 1H), 7.20 (d, J=2.7 Hz, 1H), 6.09-5.68 (m, 2H), 5.51 (s, 1H), 5.07-4.97 (m, 1H), 4.70-4.55 (m, 1H), 4.42-4.29 (m, 2H), 4.22 (dd, J=12.0, 4.1 Hz, 1H), 3.96 (s, 1H), 3.75 (t, J=6.7 Hz, 2H), 3.02 (m, 2H), 2.93-2.67 (m, 1H), 2.56 (m, 1H), 2.13-1.04 (m, 30H), 1.00 (d, J=6.6 Hz, 1H), 0.90 (m, 3H), 0.65-0.46 (m, 2H).

Example 71

Preparation of (4aR,8S,11S,12S,13R,25aR)-8-tert-butyl-N-[(1R,2R)-1-[(cyclopropylsulfonyl)carbamoyl]-2-(difluoromethyl)cyclopropyl]-17-methoxy-12-methyl-6,9-dioxo-2,3,4,4a,6,7,8,9,12,13,21,22,23,24,25,25a-hexadecahydro-1H,11H-1,3,10,13-dimethanoquinoxalino[2,3-k][1,10,3,6]benzodioxadiazacyclononadecine-11-carboxamide and

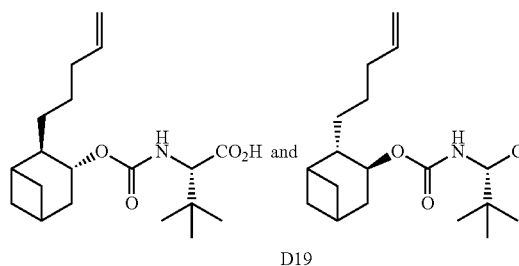

D19

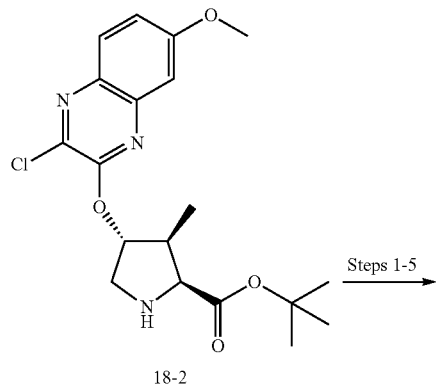

18-2

↓ Steps 1-5

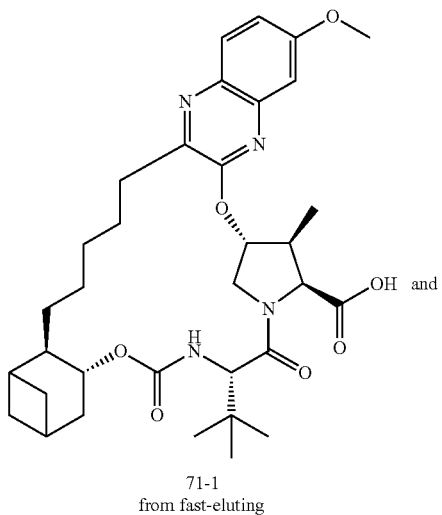

71-1
from fast-eluting

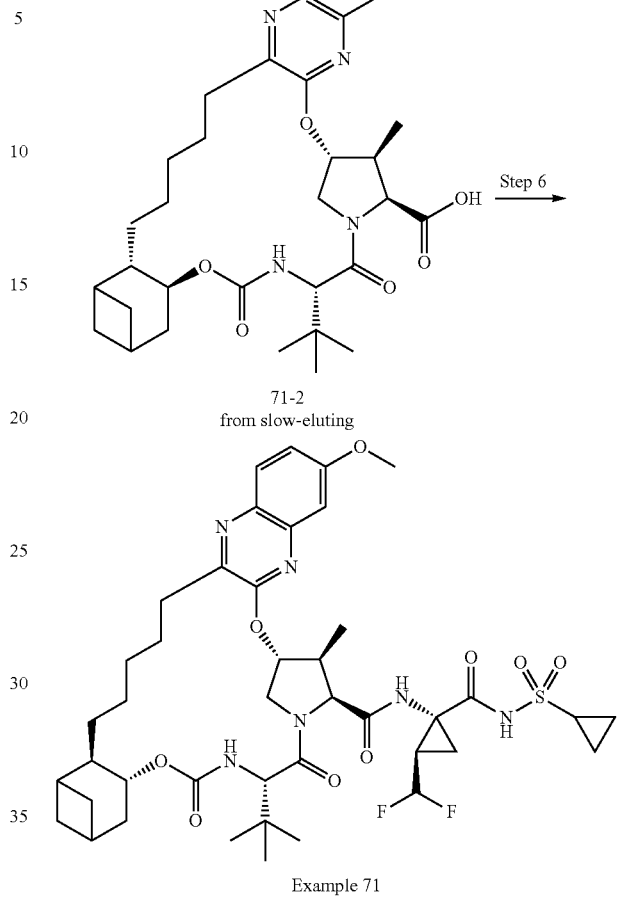

71-2
from slow-eluting

Example 71

Step 1: To a solution of amine 18-2 (315 mg, 0.80 mmol), DIPEA (350 µL, 2.0 mmol) and a 1:1 mixture of acids D19 (270 mg, 0.80 mmol) in MeCN (8 mL) was added HATU (400 mg, 1.05 mmol). The resulting solution was stirred for 2.5 h at r.t., at which time it was diluted with EtOAc (50 mL) and 0.2 N aqueous HCl (30 mL). The phases were separated, and the organic phase was dried over MgSO$_4$, filtered, and concentrated to afford a crude residue. Purification by silica gel chromatography (10% to 30% EtOAc in hexanes) provided 474 mg of a colorless oil that was used directly in the next step.

Step 2: A suspension of the product from step 1 (474 mg, ca. 0.65 mmol). PdCl$_2$(dppf).CH$_2$Cl$_2$ (40 mg, 0.049 mmol) and potassium vinyltrifluoroborate (189 mg, 1.41 mmol) in EtOH (8 mL) was sparged with Ar for several minutes and Et$_3$N (200 µL, 1.4 mmol) was added. The resulting mixture was heated under Ar to 75° C. via oil bath. After stirring 2.25 h, the reaction mixture was cooled to r.t. and was diluted with EtOAc (35 mL) and half-saturated brine (20 mL). The phases were separated, and the organic phase was dried over Na$_2$SO$_4$, filtered, and concentrated to afford a crude residue. Purification by silica gel chromatography provided a yellow oil that was used directly in the next step.

Step 3: A solution of the product from Step 3 (395 mg, 0.56 mmol) in 1,2-DCE (180 mL) was sparged with Ar for 10 min. Zhan 1B metathesis catalyst (61 mg, 0.083 mmol) was then added as a solution in DCE (4 mL), and the resulting solution was heated to 85° C. After stirring 1.75 h, the reaction mixture was cooled to ambient temperature, concentrated onto silica gel (5 g), and purified by silica gel chromatography (10 to 15 to 25% EtOAc in hexanes) to afford 116 mg of a fast-eluting product and 84 mg of a slow-eluting product.

Step 4-5 (fast-eluting diastereomer): The fast-eluting product from Step 3 was dissolved in 1:1 EtOAc:EtOH (4 mL). Pd/C (10 wt. % Pd, 45 mg) was added, and the reaction vessel was purged twice with 1 atm $H_2$. The reaction mixture was stirred for 2.5 h under 1 atm $H_2$ and was then filtered through celite with EtOAc to afford a crude residue. This residue was dissolved in $CH_2Cl_2$ (1 mL) and was treated with TFA (2 mL). After stirring 2 h, the reaction mixture was concentrated in vacuo and was partitioned between EtOAc (15 mL) and 15% saturated aqueous $NaHCO_3$ (10 mL). The phases were separated, and the organic phase was washed with brine (10 mL), dried over $Na_2SO_4$, and filtered to provide 71-1. LCMS-ESI$^+$ (m/z): [M+H]$^+$ calcd for $C_{34}H_{47}N_4O_7$: 623.3; found: 623.2.

Step 4-5 (slow-eluting diastereomer): The slow-eluting product from Step 3 was dissolved in EtOAc (1 mL) and EtOH (7 mL). Pd/C (10 wt. % Pd, 85 mg) was added, and the reaction vessel was purged twice with 1 atm $H_2$. The reaction mixture was stirred for 3 h under 1 atm $H_2$ and was then filtered through celite with EtOAc to afford a crude residue. This residue was dissolved in $CH_2Cl_2$ (1 mL) and was treated with TFA (2 mL). After stirring 2 h, the reaction mixture was concentrated in vacuo and was partitioned between EtOAc (15 mL) and 15% saturated aqueous $NaHCO_3$ (10 mL). The phases were separated, and the organic phase was washed with brine (10 mL), dried over $Na_2SO_4$, and filtered to provide 71-2, LCMS-ESI$^+$ (m/z): [M+H]$^+$ calcd for $C_{34}H_{47}N_4O_7$: 623.3; found: 623.2.

Step 6: Preparation of Example 71: To a suspension of acid 71-1 (49 mg, 0.079 mmol) and amine hydrochloride A9 (41 mg, 0.14 mmol) in MeCN (1 mL) was added DIPEA (100 μL, 0.57 mmol). HATU (45 mg, 0.12 mmol) was added to the resulting solution, and the reaction was stirred at rt for 14.5 h. The reaction was then diluted with EtOAc (20 mL), 0.2 M aqueous HCl (10 mL) and brine (10 mL). The phases were separated and the aqueous phase was extracted with EtOAc (20 mL). The combined organic phase was dried over $Na_2SO_4$, filtered, and concentrated to afford a crude residue. This residue was dissolved in $CH_2Cl_2$ and was concentrated onto 2 g silica gel. Purification by silica gel chromatography (4% to 45% acetone in hexanes) provided an amorphous residue that was lyophilized from water and MeCN to provide Example 71. LCMS-ESI$^+$ (m/z): [M+H]$^+$ calcd for $C_{42}H_{57}F_2N_6O_9S$: 859.4; found: 859.1. $^1$H NMR (400 MHz, CDCl$_3$) δ 10.13 (s, 1H), 7.81 (d, J=9.1 Hz, 1H), 7.63 (s, 1H), 7.19 (dd J=9.1, 2.8 Hz, 1H), 7.09 (d, J=27 Hz, 1H), 5.97 (td, J=55.5, 6.9 Hz, 1H), 5.59-5.45 (m, 2H), 4.96 (dd, J=14.4, 6.2 Hz, 1H), 4.51 (d, J=7.2 Hz, 1H), 4.42 (d, J=9.8 Hz, 1H), 4.13 (d, J=12.0, 7.7 Hz, 2H), 3.93 (s, 3H), 2.99-2.63 (m, 4H), 2.40-2.23 (m, 2H), 2.15-0.83 (m, 34H).

Example 72

Preparation of (4aS,8S,11S,12S,13R,25aS)-8-tert-butyl-N-[(1R,2R)-1-[(cyclopropylsulfonyl)carbamoyl]-2-(difluoromethyl)cyclopropyl]-17-methoxy-12-methyl-6,9-dioxo-2,3,4,4a,6,7,8,9,12,13,21,22,23,24,25,25a-hexadecahydro-1H,11H-1,3:10,13-dimethanoquinoxalino[2,3-k][1,10,3,6]benzodioxadiazacyclononadecine-11-carboxamide Example 72

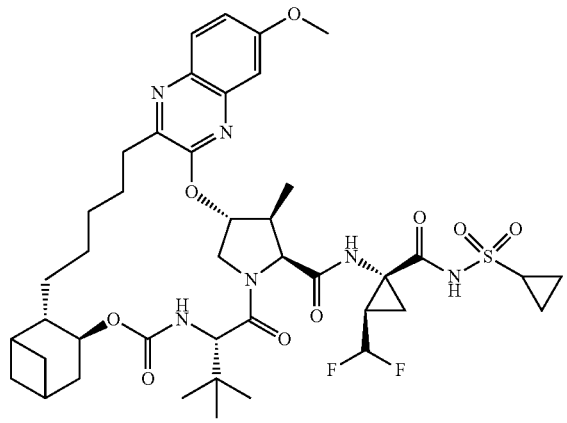

Step 1: Preparation of Example 72: To a suspension of acid 71-2 (49 mg, 0.079 mmol) and amine hydrochloride A9 (38 mg, 0.13 mmol) in MeCN (1 mL) was added DIPEA (100 μL, 0.57 mmol). HATU (41 mg, 0.11 mmol) was added to the resulting solution, and the reaction was stirred at rt for 14.5 h. The reaction was then diluted with EtOAc (20 mL), 0.2 M aqueous HCl (10 mL) and brine (10 mL). The phases were separated and the aqueous phase was extracted with EtOAc (20 mL). The combined organic phase was dried over $Na_2SO_4$, filtered, and concentrated to afford a crude residue. This residue was dissolved in $CH_2Cl_2$ and was concentrated onto 2 g silica gel. Purification by silica gel chromatography (4% to 45% acetone in hexanes) provided an amorphous residue that was lyophilized from water and MeCN to provide Example 72. LCMS-ESI$^+$ (m/z): [M+H]$^+$ calcd for $C_{42}H_{57}F_2N_6O_9S$: 859.4; found: 859.0. $^1$H NMR (400 MHz, CDCl$_3$)δ 9.72 (s, 1H), 9.36 (s, 1H), 7.86 (d, J=9.1 Hz, 1H), 7.28 (d, J=2.7 Hz, 1H), 7.25-7.17 (m, 2H), 5.98-5.88 (m, 1H), 5.69 (td. J=55.4, 6.9 Hz, 1H), 4.81-4.69 (m, 1H), 4.68-4.56 (m, 2H), 4.33 (d, J=10.1 Hz, 1H), 3.99 (s, 3H), 3.35 (dd, J=9.7, 7.0 Hz, 1H), 324-3.13 (m, 1H), 2.97-2.87 (m, 1H), 2.87-2.72 (m, 2H) 2.57-2.45 (m, 1H), 2.38-2.28 (m, 1H), 2.17-0.71 (m, 34H).

Example 73

Preparation of (1aR,5S,8S,9S,10R,22aR)-5-tert-butyl-9-ethyl-14-methoxy-N-[(1R,2R)-2-methyl-1-{[(1-methylcyclopropyl)sulfonyl]carbamoyl}cyclopropyl]-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

Example 74

Preparation of (1aR,5S,8S,9S,10R,22aR)-5-tert-butyl-N-[(1R,2R)-2-(difluoromethyl)-1-{[(1-fluorocyclopropyl)sulfonyl]carbamoyl}cyclopropyl]-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

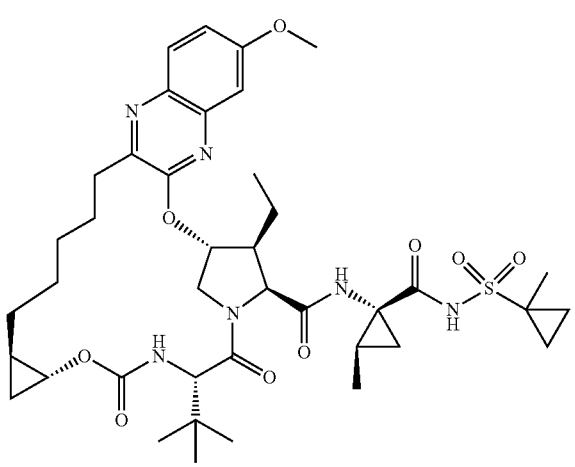

Example 73

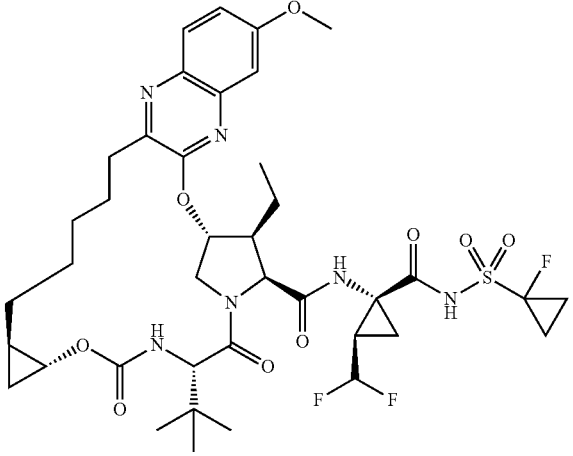

Example 74

Example 73 was prepared similarly to Example 1 substituting Intermediate A11 for Intermediate A10 in Step 8. The TFA salt of Example 73 was isolated. Analytic HPLC RetTime: 8.72 min. LCMS-ESI$^+$ (m/z): [M+H]$^+$ calcd for $C_{40}H_{57}N_6O_9S$: 797.98; found: 797.54. $^1$H NMR (400 MHz, CD$_3$OD) δ 8.84 (s, 1H); 7.79 (d, J=9.2 Hz, 1H); 7.22 (dd, J=92, 2.4 Hz, 1H); 7.13 (d, J=2.4 Hz, 1H); 5.87 (d, J=3.2 Hz, 1H); 4.57 (d, J=7.2 Hz, 1H); 4.39 (br s, 1H); 4.37 (br d J=10 Hz, 1H); 4.15 (dd, J=12, 4 Hz, 1H); 3.92 (s, 3H); 3.74 (m, 1H); 3.10-2.88 (m, 1H); 2.80 (td, J=12.4, 4 Hz, 1H); 2.58 (m, 1H); 1.89-1.66 (m, 3H); 1.66-1.38 (m, 11H); 1.52 (s, 3H); 1.23 (t, J=7.2 Hz, 3H); 1.16 (d, J=6 Hz, 3H); 1.10 (s, 9H); 1.02-0.84 (m, 4H); 0.78-0.66 (m, 1H); 0.55-0.20 (m, 1H).

Example 74 was prepared similarly to Example 1 substituting Intermediate A12 for Intermediate A10 in Step 8. The TFA salt of Example 74 was isolated. Analytic HPLC RetTime: 8.81 min. LCMS-ESI$^+$ (m/z): [M+H]$^+$ calcd for $C_{39}H_{52}F_3N_6O_9S$: 837.35; found: 837.54. $^1$H NMR (400 MHz, CD$_3$OD) δ 9.26 (s, 1H); 7.79 (d, J=9.2 Hz, 1H); 7.22 (dd, J=9.2, 2.4 Hz, 1H); 7.14 (d, J=2.4 Hz, 1H); 5.89 (d, J=3.6 Hz, 1H); 5.82 (td. $J_{H-F}$=56 Hz, J=6.4 Hz, 1H); 4.56, (d, J=7.2 Hz, 1H); 4.39 (s, 1H); 4.38 (d, J=12 Hz, 1H); 4.16 (dd, J=12, 7.2 Hz, 1H); 3.92 (s, 3H); 3.78-3.72 (m, 1H), 3.10-2.89 (m, 1H); 2.80 (td, J=12, 4 Hz, 1H); 2.63-2.54 (m, 1H); 2.02 (m, 2H); 1.95-1.66 (m, 3H); 1.66-1.36 (m, 9H); 1.22 (t, J=7.2 Hz, 3H); 1.14-1.04 (m, 2H); 1.09 (s, 9H); 1.04-0.92 (m, 2H); 0.78-0.68 (m, 1H); 0.57-0.46 (m, 1H).

Example 75

Preparation of (1aR,5S,8S,9S,10R,22aR)-5-tert-butyl-N-[(1R,2R)-1-{[(1-chlorocyclopropyl)sulfonyl]carbamoyl}-2-(difluoromethyl)cyclopropyl]-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

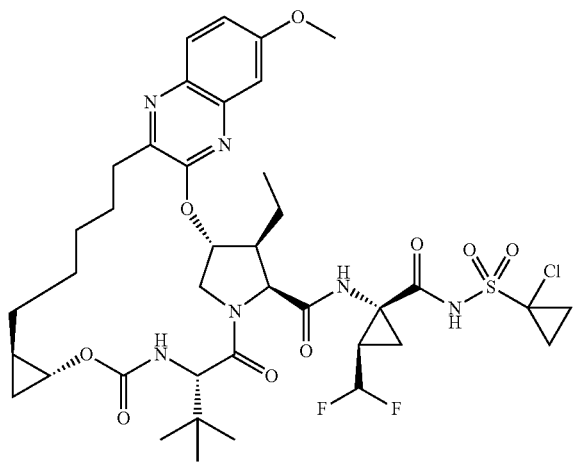

Example 75

Example 75 was prepared similarly to Example 1 substituting Intermediate A13 for Intermediate A10 in Step 8. The TFA salt of Example 75 was isolated. Analytic HPLC RetTime: 8.89 min. LCMS-ESI+ (m/z): [M+H]+ calcd for $C_{39}H_{52}ClF_2N_6O_9S$: 853.32; found: 853.94. $^1$H NMR (400 MHz, $CD_3OD$) δ 9.24 (s, 1H); 7.79 (d, J=9.2 Hz, 1H); 7.22 (dd, J=9.2, 2.4 Hz, 1H); 7.13 (d, J=2.4 Hz, 1H); 5.88 (d, J=3.2 Hz, 1H); 5.84 (td, $J_{H-F}$=55.6 Hz, J=6.8 Hz, 1H); 4.57 (d, J=7.2 Hz, 1H); 4.39 (br s, 1H); 4.38 (d, J=12 Hz, 1H); 4.16 (dd, J=12, 7.2 Hz, 1H); 3.92 (s, 3H); 3.77-3.73 (m, 1H); 3.00-2.88 (m, 1H); 2.86-2.75 (m, 1H); 2.64-2.54 (m, 1H), 2.10-1.90 (m, 4H); 1.90-1.37 (m, 12H); 1.23 (t, J=7.2 Hz, 3H), 1.10 (s, 9H); 1.02-0.96 (m, 2H), 0.78-0.64 (m, 1H); 0.56-0.45 (m, 1H).

Example 76

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-18,18-difluoro-14-methoxy-1a,9-dimethyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

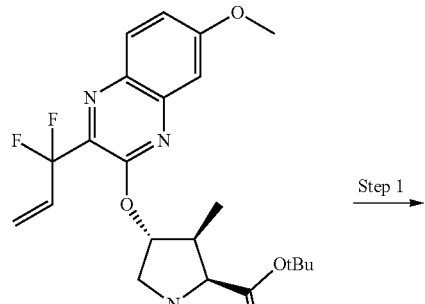

46-2

Step 1 →

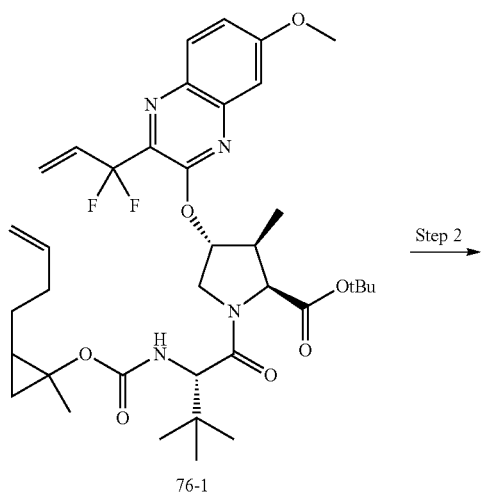

76-1

Step 2 →

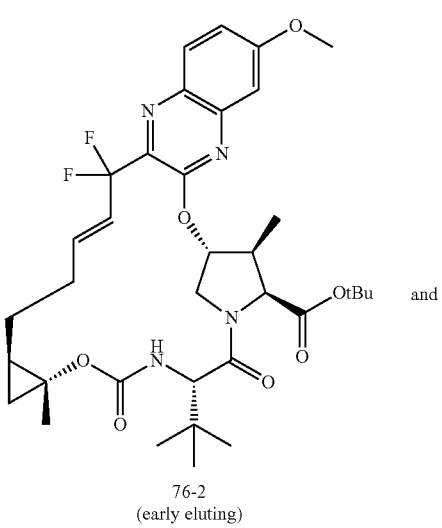

76-2
(early eluting)

and

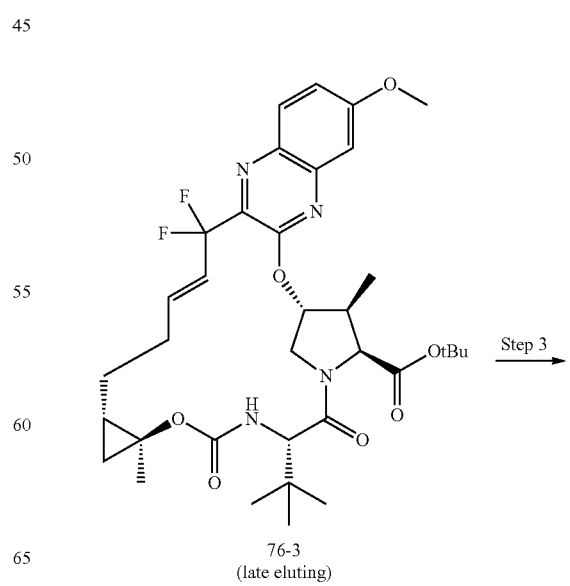

76-3
(late eluting)

Step 3 →

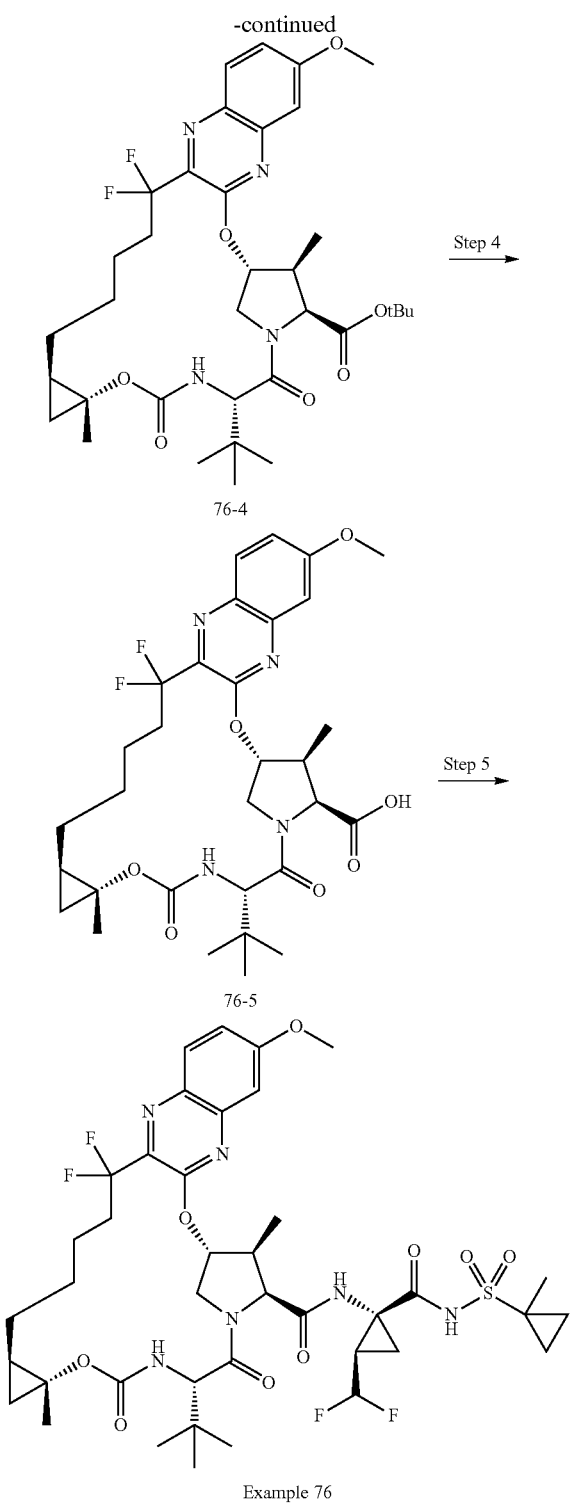

Step 1. Preparation of 76-1: HATU (502 mg, 1.32 mmol, Oakwood) and DIPEA (0.70 mL, 4.02 mmol) were added to a mixture of 46-2 (434 mg, 0.998 mmol) and intermediate D17 (350 mg, 1.24 mmol) in 16 mL of acetonitrile under argon. After stirring overnight, the reaction mixture was concentrated under reduced pressure and the resulting residue was purified by silica gel chromatography (0-25% ethyl acetate in hexanes) to yield 76-1. LCMS-ESI$^+$ (m/z): [M+H]$^+$ calcd for $C_{37}H_{51}F_2N_4O_7$: 701.36; found: 701.57.

Step 2. Preparation of 76-2 and 76-3: A diastereomeric mixture 76-1 (550 mg, 0.786 mmol) and Zhan 1B catalyst (69 mg, 0.094 mmol. Strem) in 157 mL of DCE was deoxygenated under argon for 25 minutes. The mixture was then heated at reflux for 90 minutes. An additional 35 mg of Zhan 1B catalyst was added and reaction mixture was heated at reflux for 45 minutes. After cooling to room temperature, reaction mixture was concentrated in vacuo. The resulting residue was purified by silica gel chromatography (0-35% ethyl acetate in hexanes) to yield single diastereomers 76-2 (early eluting component) as a white solid film and 76-3 (late eluting component) as a brown solid film. Early eluting 76-2: LCMS-ESI$^+$ (m/z): [M+H]$^+$ calcd for $C_{35}H_{47}F_2N_4O_7$: 673.33; found: 673.45. Late eluting 76-3: LCMS-ESI$^+$ (m/z): [M+H]$^+$ calcd for $C_{35}H_{47}F_2N_4O_7$: 673.33; found: 673.47.

Step 3. Preparation of 76-4: Palladium on carbon (10 wt % Pd, 51 mg, 0.048 mmol) was added to a solution of 76-2 (175 mg, 0.260 mmol) in 9 mL of ethanol. The atmosphere was replaced with hydrogen and the reaction stirred overnight. The reaction mixture was filtered over Celite and washed with ethanol. Filtrate was concentrated in vacuo to yield 76-4, which was used in the next step without further purification. LCMS-ESI$^+$ (m/z): [M+H]$^+$ calcd for $C_{35}H_{49}F_2N_4O_7$: 675.35; found: 675.53.

Step 4. Preparation of 76-5: TFA (1.2 mL, 15.6 mmol) was added slowly to a solution of 76-4 (155 mg, 0.230 mmol) in 3.4 mL of dichloromethane. After 4 hours, mixture was concentrated under reduced pressure to near dryness. Resulting residue was taken up in 25 mL of ethyl acetate, washed with 15 mL of water, 15 mL of sat. NaHCO$_{3\ (aq)}$, and separated. Aqueous layers were extracted with ethyl acetate (3×20 mL). Combined organics were washed with 30 mL of brine, dried over anhydrous MgSO$_4$, filtered, and concentrated in vacuo to yield 76-5, which was used in the next step without further purification. LCMS-ESI$^+$ (m/z). [M+H]$^+$ calcd for $C_{31}H_{41}F_2N_4O_7$: 619.29; found: 619.44.

Step 5. Preparation of Example 76: HATU (160 mg, 0.421 mmol) and DIPEA (0.20 mL, 1.15 mmol) were added to a mixture of 76-5 (140 mg, 0.226 mmol) and Intermediate A10 (139 mg, 0.457 mmol) in 7.5 mL of MeCN under argon. After stirring for overnight, reaction mixture was taken up in 30 mL of ethyl acetate and washed with 20 mL of 1 N aqueous HCl. Layers were separated and aqueous was extracted three times with ethyl acetate. Combined organics were washed with brine, dried over anhydrous MgSO$_4$, filtered, and concentrated in vacuo. The resulting residue was purified by silica gel chromatography (0-45% ethyl acetate in hexanes) and reverse phase prep HPLC (50-100% acetonitrile in water, with 0.1% trifluoroacetic acid buffer) to yield the trifluoroacetic acid salt of Example 76 (Analytic HPLC RetTime: 8.80 min. LCMS-ESI$^+$ (m/z): [M+H]$^+$ calcd for $C_{40}H_{53}F_4N_6O_9S$: 869.35; found: 869.59. $^1$H NMR (400 MHz, CD$_3$OD): 9.19 (s, 1H), 7.94 (d, J=9.2 Hz, 1H), 7.32 (dd, J=9.2, 2.8 Hz, 1H), 7.27 (d, J=2.8 Hz, 1H), 5.78 (td, J$_{H-F}$=56 Hz, J=7.2 Hz, 1H), 5.76-5.74 (m, 1H), 4.56 (d, J=6.4 Hz, 1H), 4.48 (d, J=12 Hz, 1H), 4.27-4.19 (m, 1H), 4.22 (s, 1H), 3.97 (s, 3H), 2.76-2.70 (m, 1H), 2.62-2.43 (m, 1H), 2.14-1.94 (m, 3H), 1.90-1.80 (m, 1H), 1.80-1.62 (m, 3H), 1.56-1.52 (m, 2H), 1.51 (s, 3H), 1.49 (s, 3H), 1.41-1.36 (m, 1H), 1.27-1.18 (m, 1H), 1.11 (s, 9H), 1.09-1.04 (m, 5H), 1.03-0.94 (m, 2H), 0.87-0.81 (m, 3H), 0.17-0.12 (m, 1H).

Example 77

Preparation of (1 aS,5S,8S,9S,10R,22aS)-5-tert-butyl-N-[(1R,2R)-2-(difluoromethyl)-1-{[(1-methylcyclopropyl)sulfonyl]carbamoyl}cyclopropyl]-18,18-difluoro-14-methoxy-1a,9-dimethyl-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

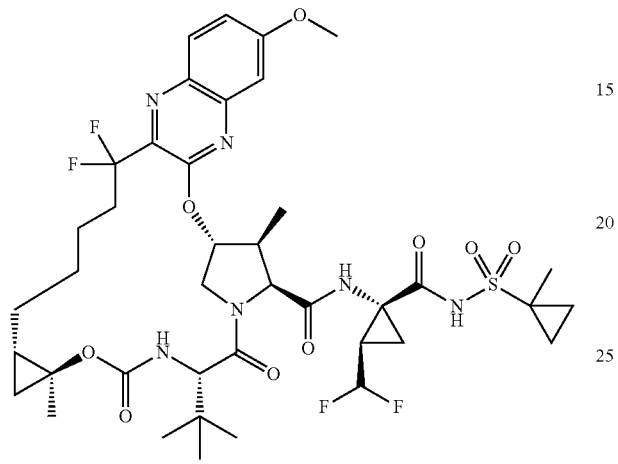

Example 77

Example 77 was prepared in a similar fashion to Example 76, substituting late eluting 76-3 for early eluting 76-2 in step 3. Example 76 was then isolated. Analytic HPLC RetTime: 8.46 min. LCMS-ESI$^+$ (m/z): [M+H]$^+$ calcd for $C_{40}H_{53}F_4N_6O_9S$: 869.35; found: 869.53. $^1$H NMR (400 MHz, CD$_3$OD): 7.95 (d, J=8.8 Hz, 1H), 7.32 (d, J=8.8 Hz, 1H), 7.28 (s, 1H), 6.58-6.54 (m, 1H), 5.75 (td, J$_{H-F}$=55 Hz, J=6.8 Hz, 1H), 5.54-5.50 (m, 1H), 4.65 (d, J=6.8 Hz, 1H), 4.46 (d, J=12.8 Hz, 1H), 4.26-4.18 (m, 1H), 3.97 (s, 3H), 2.92-2.71 (m, 1H), 2.50-1.94 (m, 6H), 1.68-1.57 (m, 2H), 1.56-1.52 (m, 2H), 1.51 (s, 3H), 1.50-1.47 (m, 1H), 1.46-1.38 (m, 3H), 1.44 (s, 3H), 1.27-1.18 (m, 2H), 1.17-1.01 (m, 3H), 1.09 (s, 9H), 0.94-0.82 (m, 4H), 0.17-0.12 (m, 1H).

Example 78

Preparation of (1aR,5S,8S,9S,10R,19E,22aR)-5-tert-butyl-14-cyano-N-[(1R,2R)-2-(difluoromethyl)-1-{[(1-methylcyclopropyl)sulfonyl]carbamoyl}cyclopropyl]-9-ethyl-8,18-difluoro-3,6-dioxo-1,1a,3,4,5,6,9,10,17,17a,18,21,22,22a-tetradecahydro-8H-7,10-methanocyclopropa[18,19][1,10,3,6]dioxadiazacyclononadecino[11,12-b]quinoxaline-8-carboxamide

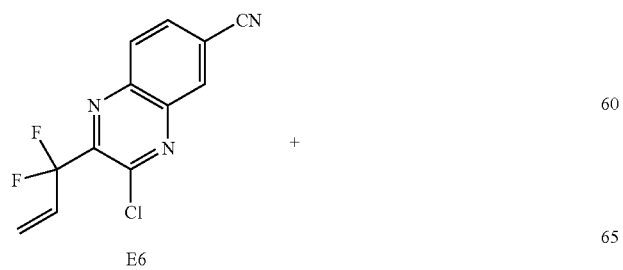

E6

+

-continued

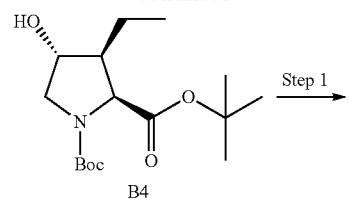

B4

Step 1

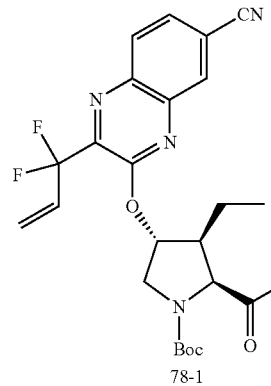

78-1

Step 2

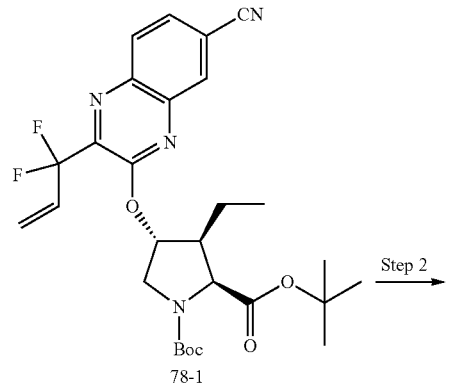

78-2

Step 3

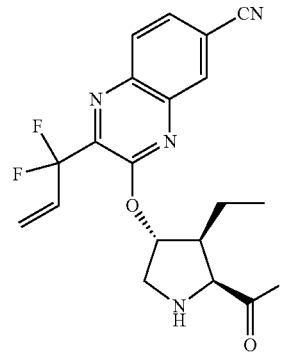

78-3

Step 4

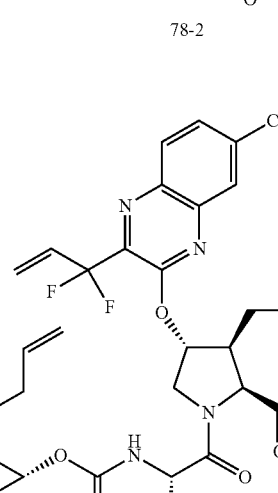

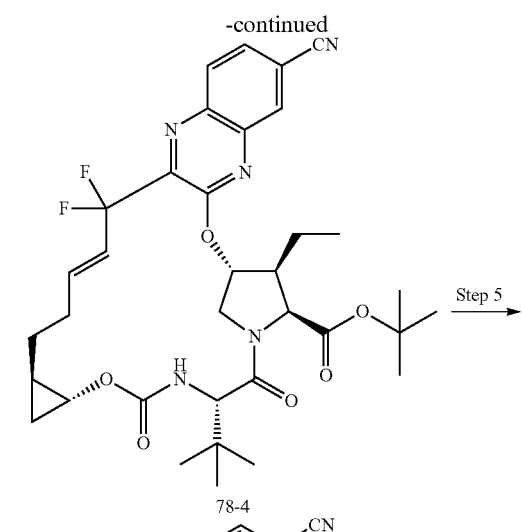

78-4

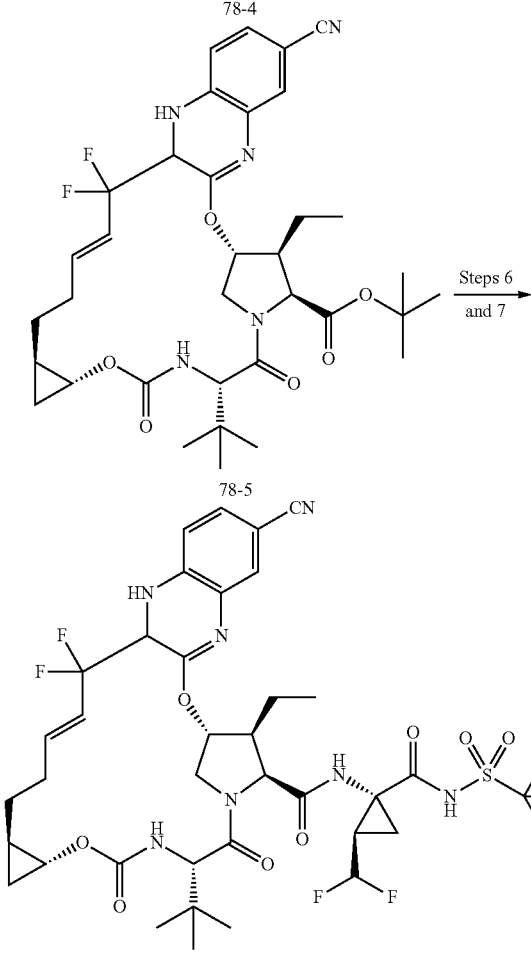

78-5

Example 78

Steps 1-4. Intermediate 78-4 was prepared similarly to Intermediate 17-4, using E6 in place of E3.

Step 5: To a solution of 78-4 (90 mg, 0.135 mmol) in EtOH (0.7 mL) was added NaBH$_4$ (21 mg, 0.54 mmol). The reaction mixture was stirred at rt for 1 h. After which time the reaction mixture was filtered through a pad of celite and concentrated to give intermediate 78-5, which was used subsequently without further purification. LCMS-ESI$^+$ (m/z): [M+H]$^+$ calcd for C35H45F2N5O6: 669.76; found: 669.73.

Steps 6 and 7: Preparation of Example 78: To a solution of 78-5 (35 mg, 0.31 mmol) in DCM (0.4 mL), TFA (0.2 mL) was added and the mixture was stirred at 20° C. for 3 h. Solvents were removed in vacuo to afford a residue was used subsequently without further purification. To a suspension of this residue (33 mg, 0.05 mmol) and Intermediate A10 (27 mg, 0.1 mmol) in DCM (0.3 mL) was added TBTU (26 mg, 0.08 mmol) and DIPEA (35 μL, 0.2 mmol) at rt. After 1 h, the solution was directly purified by reverse phase HPLC (Gemini 5u C18 110 Å column, 50-100% ACN/H$_2$O+0.1% TFA) and lyophilized to afford the TFA salt of Example 78. Analytical HPLC RetTime: 7.994 min. LCMS-ESI$^+$ (m/z): [M+H]$^+$ calcd for C, 40; H, 49; F, 4; N, 7; O, 8; S: 863.92; found: 864.20. $^1$H NMR (400 MHz. CD3OD) δ 9.35 (s, 1H), 7.29 (d, 1H), 7.18 (dd, 1H), 6.64 (d, 1H), 6.01-5.82 (m, 2H), 5.41 (m, 2H), 4.57-4.07 (m, 5H), 3.52 (m, 1H), 2.55-2.28 (m, 2H), 2.06-1.98 (m, 2H), 1.85 (m, 1H), 1.69-1.37 (m, 9H), 1.33 (m, 2H), 1.06-0.87 (m, 16H), 0.70 (m, 2H), 0.49 (m, 1H).

Example 79

Preparation of (1aS,2aR,6S,9S,10S,11R,23aR, 23bS)-6-tert-butyl-15-chloro-N-[(1R,2R)-1-[(cyclopropylsulfonyl)carbamoyl]-2-(difluoromethyl)cyclopropyl]-10-methyl-4,7-dioxo-1a,2,2a,4,5,6,7,10,11, 19,20,21,22,23,23a,23b-hexadecahydro-1H,9H-8,11-methanocyclopropa[4',5']cyclopenta[1',2':18,19][1, 10,3,6]dioxadiazacyclononadecino[11,12-b] quinoxaline-9-carboxamide

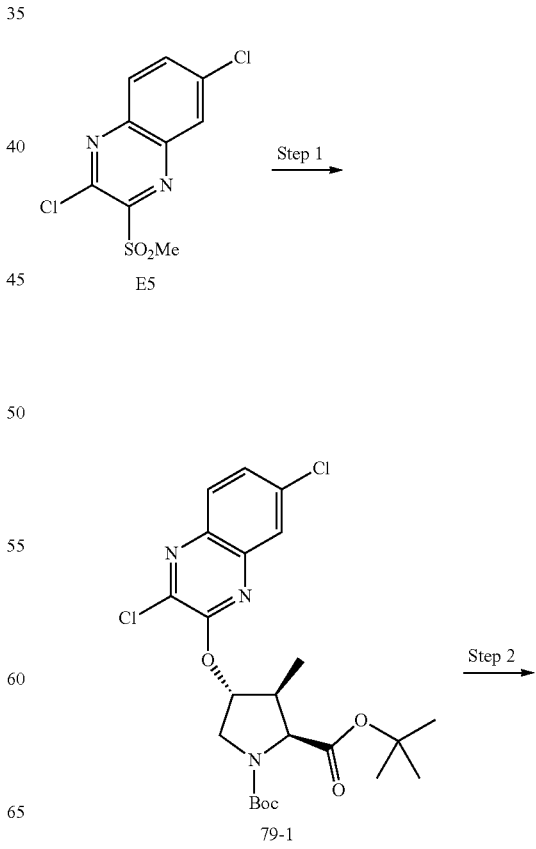

351
-continued
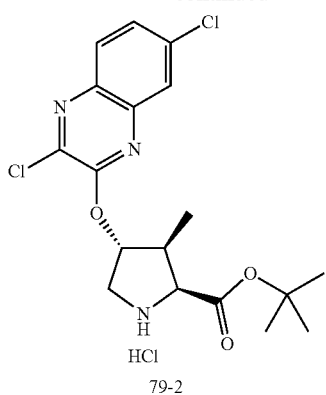
79-2
Step 3 →
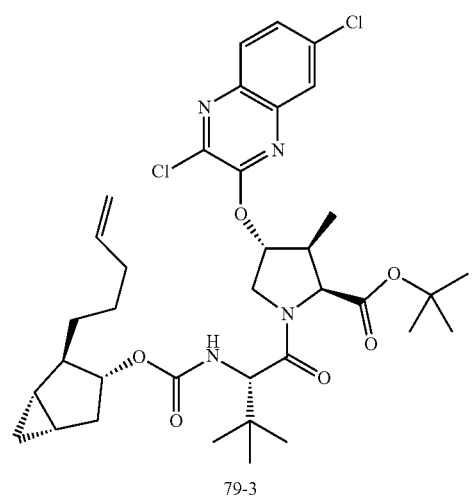
79-3
Step 4 →
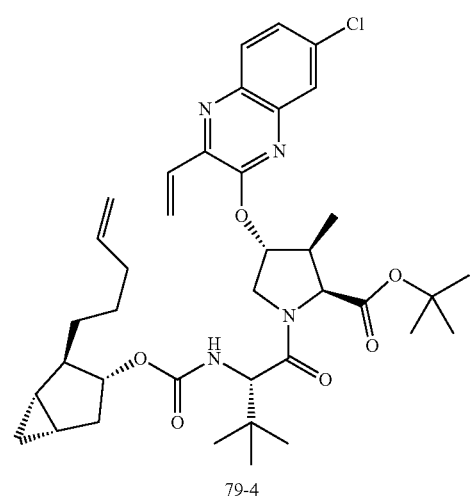
79-4
Step 5 →
352
-continued
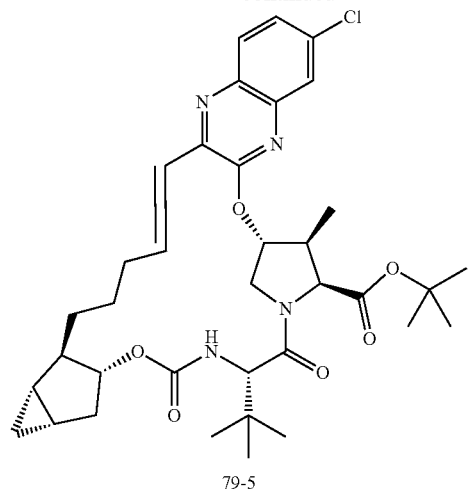
79-5
Step 6 →
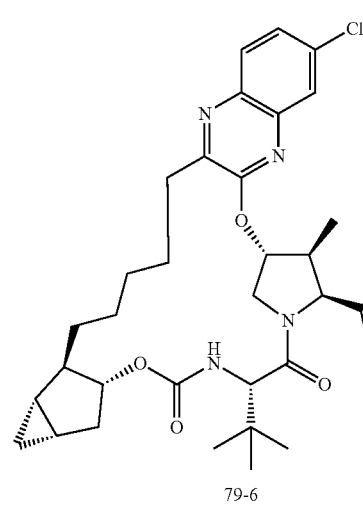
79-6
Step 7 →
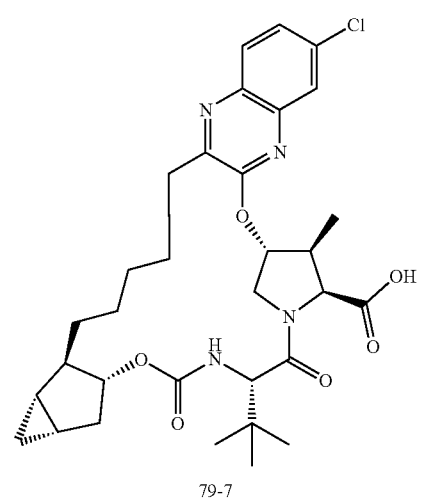
79-7
Step 8 →

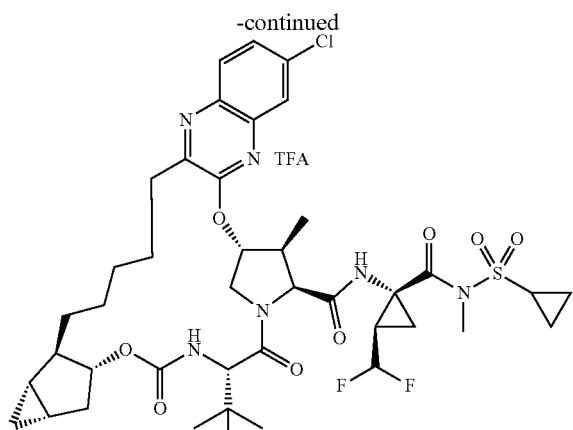

Example 79

Step 1. Preparation of 79-1. Sulfonyl quinoxaline E5 (920 mg, 3.32 mmol) was suspended in MeCN (17 mL), then treated with intermediate B1 (1.00 g, 3.32 mmol) and Cs$_2$CO$_3$. After 17 h, the reaction mixture was filtered over celite and concentrated under reduced pressure. The crude residue was purified by silica column chromatography (10% to 30% EtOAc/Hex) to afford ether 79-1. LCMS-ESI$^+$ (m/z): [M-Boc+2H]$^+$ calcd for C$_{18}$H$_{22}$Cl$_2$N$_3$O$_3$: 398.10; found: 398.12.

Step 2. Preparation of 79-2. tert-Butyl carbamate 79-1 (513 mg, 1.03 mmol) was dissolved in DCM (10 mL) and treated with HCl (4.0 mL in dioxane, 5 mL, 20 mmol). The reaction mixture was stirred at RT for 1.5 h, then concentrated under reduced pressure to afford amine hydrochloride 79-2, which was carried on without purification. LCMS-ESI$^+$ (m/z): [M+H]$^+$ calcd for C$_{18}$H$_{22}$Cl$_2$N$_3$O$_3$: 398.10; found: 398.16.

Step 3. Preparation of 79-3. Amine hydrochloride 79-2 (1.03 mmol theoretical) and intermediate D12 (336 mg, 1.04 mmol) were combined and treated with BEP (285 mg, 1.04 mmol), EtOAc (9 mL), NMP (1 mL) and DIPEA (0.90 mL, 5.2 mmol). The reaction mixture was stirred at 50° C. for 3 h, then cooled to RT. After an additional 15 h. the reaction mixture was diluted with EtOAc. The organic solution was washed with saturated aqueous NaHCO$_3$ and brine, then dried over MgSO$_4$, filtered and concentrated under reduced pressure. The crude residue was purified by silica column chromatography (10% to 25% EtOAc/Hex) to afford amide 79-3. LCMS-ESI$^+$ (m/z): [M+H]$^+$ calcd for C$_{36}$H$_{49}$Cl$_2$N$_4$O$_6$: 703.30; found: 703.91.

Step 4. Preparation of 79-4. Chloro quinoxaline 79-3 (541 mg, 0.769 mmol) was treated with potassium vinyltrifluoroborate (154 mg, 1.15 mmol). Pd(dppf)Cl$_2$ dichloromethane adduct (63 mg, 0.077 mmol). EtOH (8 mL) and triethylamine (0.16 mL, 1.15 mmol). The stirred mixture was heated to reflux for 1 h. then cooled to RT and diluted with EtOAc. The organic solution was washed with saturated aqueous NaHCO$_3$ and brine, then dried over MgSO$_4$, filtered and concentrated under reduced pressure. The crude residue was purified by silica column chromatography (10% to 30% EtOAc/Hex) to afford vinyl quinoxaline 79-4. LCMS-ESI$^+$ (m/z): [M+H]$^+$ calcd for C$_{38}$H$_{52}$ClN$_4$O$_6$: 695.36; found: 695.10.

Step 5. Preparation of 79-5. Vinyl quinoxaline 79-4 (390 mg, 0.561 mmol) was treated with DCE (112 mL) and Zhan-B catalyst (38 mg, 0.0561 mmol). The stirred mixture was degassed with bubbling N$_2$ for 25 min, then heated to reflux under an Ar atmosphere. After 1.5 h, the mixture was cooled to RT and concentrated under reduced pressure. The crude residue was purified by silica column chromatography (10% to 30% EtOAc/Hex) to afford macrocycle 79-5. LCMS-ESI$^+$ (m/z): [M+H]$^+$ calcd for C$_{36}$H$_{48}$ClN$_4$O$_6$: 667.33; found: 667.86.

Step 6. Preparation of 79-6. Macrocycle 79-5 (198 mg, 0.297 mmol) was treated with EtOAc (100 mL) and 5% Rh/alumina (100 mg). H$_2$ gas was bubbled through the solution for 1 min and the reaction mixture was stirred at RT under an atmosphere of H$_2$. After 45 min, more 5% Rh/alumina (200 mg) was added. Again, H$_2$ gas was bubbled through the solution for 1 min and the reaction mixture was stirred at RT under an atmosphere of H$_2$. After another 1 h, the reaction mixture was filtered over celite and concentrated under reduced pressure. The material (79-6) was carried on without purification. LCMS-ESI$^+$ (m/z): [M+H]$^+$ calcd for C$_{36}$H$_{50}$ClN$_4$O$_6$: 669.34; found: 669.63.

Step 7. Preparation of 79-7. Macrocycle 79-6 (0.297 mmol theoretical) was treated with DCM (10 mL) and TFA (10 mL). The reaction mixture was stirred at RT for 14 h, then concentrated under reduced pressure. The crude residue was dissolved in EtOAc and the organic solution was washed with saturated aqueous NaHCO$_3$ and 1 M citric acid. Brine was added after the citric acid wash to break up the emulsion that formed. The organic layer was dried over MgSO$_4$, filtered and concentrated under reduced pressure. The crude residue was purified by silica column chromatography (100% EtOAc) to afford impure 79-7 that was carried on without further purification LCMS-ESI$^+$ (m/z): [M+H]$^+$ calcd for C$_{32}$H$_{42}$ClN$_4$O$_6$: 613.28; found: 613.22.

Step 8. Preparation of Example 79. Carboxcylic acid 79-7 (0.264 mmol theoretical) was treated with intermediate A9 (156 mg, 0.537 mmol), TBTU (170 mg, 0.528 mmol), DMAP (65 mg, 0.528 mmol), DCM (2 mL) and DIPEA (0.23 mL, 1.3 mmol). The reaction mixture was stirred at RT for 19 h then concentrated under reduced pressure. The crude residue was purified by reverse phase HPLC to afford Example 79 as a TFA salt. LCMS-ESI$^+$ (m/z): [M+H]$^+$ calcd for C$_{40}$H$_{52}$ClF$_2$N$_6$O$_8$S: 849.32; found: 849.16. $^1$H NMR (400 MHz, CD$_3$OD) δ 9.17 (s, 1H), 7.86 (t, J=8.1 Hz, 1H), 7.77 (t, J=3.5 Hz, 1H), 7.55 (dd, J=8.8, 2.3 Hz, 1H), 5.84 (td, J=55.7, 6.7 Hz, 1H), 5.62 (d, J=3.5 Hz, 1H), 4.98 (t, J=10.6 Hz, 1H), 4.53 (t, J=9.3 Hz, 1H), 4.42-4.26 (m, 2H), 4.19 (dd, J=12.0, 3.9 Hz, 1H), 3.34 (d, J=7.6 Hz, 1H), 2.99 (t, J=8.2, 4.8 Hz, 2H), 2.78 (ddt, J=21.6, 14.2, 5.7 Hz, 2H), 2.28-2.12 (m, 1H), 2.08-1.16 (m, 19H), 1.16-0.96 (m, 17H), 0.58 (dd, J=8.3, 4.1 Hz, 1H), 0.55-0.44 (m, 1H).

Example 80
Preparation of (3aR,7S,10S,11S,12R)-1-acetyl-7-tert-butyl-N-[(1R,2R)-2-(difluoromethyl)-1-{[(1-methylcyclopropyl)sulfonyl]carbamoyl}cyclopropyl]-16-methoxy-11-methyl-5,8-dioxo-1,2,3,3a,5,6,7,8,11,12,20,21,22,23,24,24a-hexadecahydro-10H-9,12-methanopyrrolo[2',3':18,19][1,10,3,6]dioxadiazacyclononadecino[11,12-b]quinoxaline-10-carboxamide
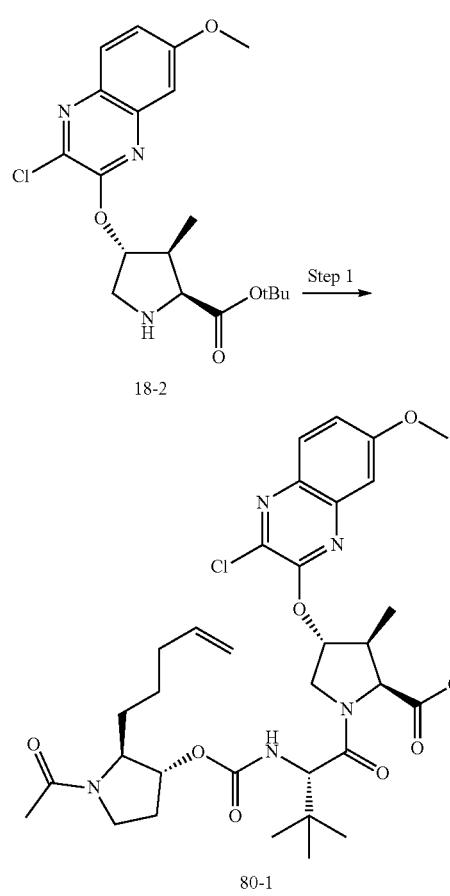
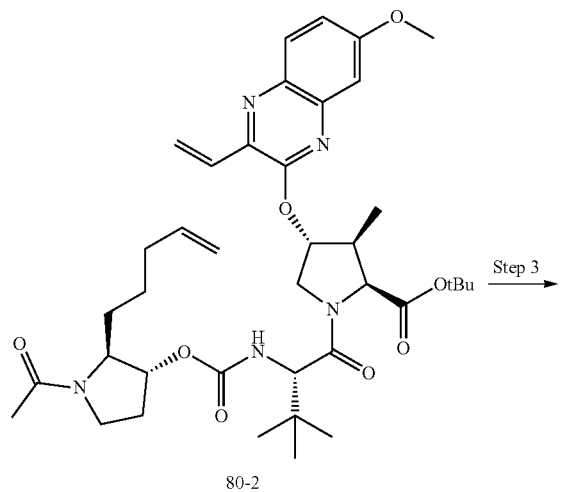
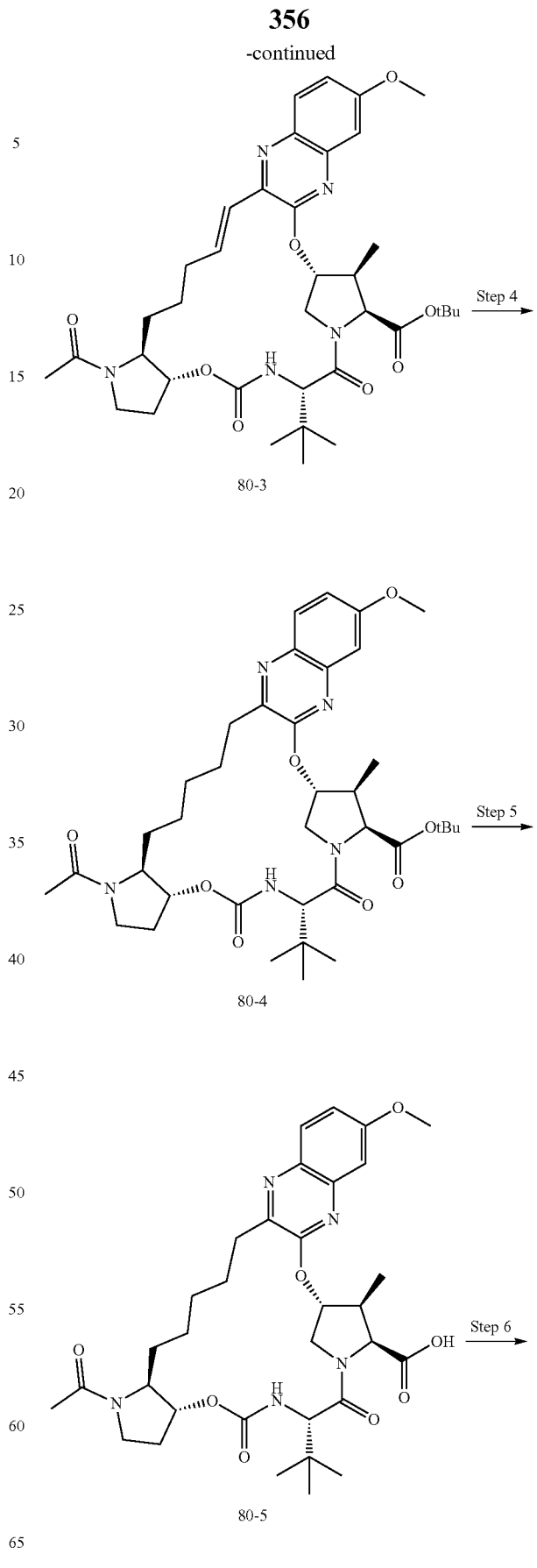

357

-continued

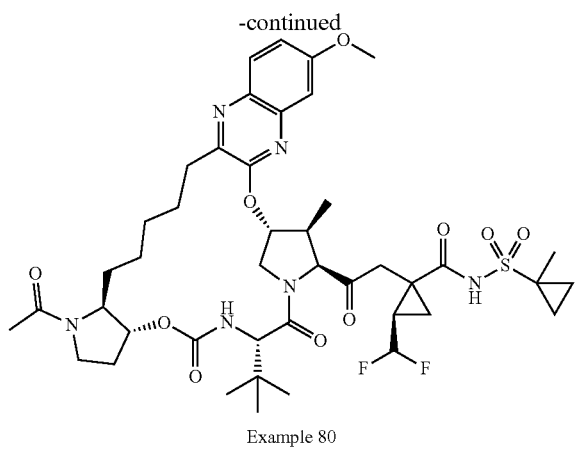

Example 80

Step 1. Preparation of 80-1: Amine 18-2 (195 mg, 0.495 mmol) and Intermediate D18 (192.8 mg, 0.544 mmol) were dissolved in DMF (10 mL). DIPEA (430 µL, 2.48 mmol) was added followed by HATU (207 mg, 0.544 mmol) at room temperature. After 1.5 h, the reaction mixture was concentrated in vacuo and the crude residue was directly purified by silica gel chromatography (0-100% ethyl acetate/hexanes gradient) to afford 80-1 (2:1 diastereomeric ratio favoring desired). LCMS-ESI$^+$ (m/z): [M+H]$^+$ calcd for $C_{37}H_{53}ClN_5O_8$: 730.3; found: 730.48.

Step 2. Preparation of 80-2: A stirred heterogeneous mixture of 80-1 (314 mg, 0.431 mmol), PdCl$_2$(dppf).CH$_2$Cl$_2$ (35.2 mg, 0.043 mmol) and potassium vinyltrifluoroborate (86.6 mg, 0.646 mmol) in EtOH (2.2 mL) was sparged with argon for 15 min, Triethylamine (320 µL, 2.3 mmol) was added and the mixture was heated to 80° C. After 40 min, the reaction mixture was cooled to ambient temperature and was diluted with toluene (5 mL). The resulting mixture was concentrated and the crude residue was directly purified by silica gel chromatography (0-100% ethyl acetate/hexanes gradient) to afford 80-2 (2:1 diastereomeric ratio favoring desired). LCMS-ESI$^+$ (m/z): [M+H]$^+$ calcd for $C_{39}H_{56}N_5O_8$: 722.4; found: 722.54.

Step 3. Preparation of 80-3: 80-2 (228 mg, 0.320 mmol) was dissolved in DCE (64 mL) and the solution was sparged with Ar for 15 min. Zhan 1B catalyst (23 mg, 0.032 mmol) was added and the resulting solution was stirred at 100° C. under Ar, After 45 min, the reaction mixture was cooled to rt, was concentrated in vacuo and was directly purified by silica gel chromatography (0-100% ethyl acetate/hexanes gradient) to afford 80-3 (5:2 diastereomeric ratio favoring desired). LCMS-ESI$^+$ (m/z): [M+H]$^+$ calcd for $C_{37}H_{52}N_5O_8$: 694.37; found: 694.53.

Step 4: Preparation of 80-4: Olefin 80-3 (164 mg, 0.237 mmol) was dissolved in ethanol (1.19 mL) and the reaction vessel was purged with Ar. Pd/C (10 wt % Pd, 25 mg) was added in a single portion and the reaction vessel was purged thrice with H$_2$. The reaction was stirred at rt under 1 atm H$_2$ for 2 h and was diluted with ethyl acetate (10 mL). The resulting mixture was filtered through a pad of Celite and concentrated to afford a crude residue of 80-4 (5:2 diastereomeric ratio favoring desired) that was used without further purification (LCMS-ESI$^+$ (m/z): [M+H]$^+$ calcd for $C_{37}H_{54}N_5O_8$: 696.39; found: 696.56.

Step 5. Preparation of 80-5: To a solution of 80-4 (164 mg, 240 µmol) in DCM (1.2 mL) was added TFA (0.45 mL) at rt. After 7 h, the reaction was diluted with ethyl acetate (50 mL) and the resulting mixture was extracted with 1 N aqueous sodium hydroxide solution (40 mL). The aqueous layer was then slowly acidified to pH=3 with concentrated hydrochloric acid, and was extracted with ethyl acetate (2×50 mL). The combined organic extracts were dried over anhydrous sodium sulfate and were concentrated in vacuo. The residue was azeotropically dried with toluene (3×5 mL) to afford 80-5 (5:2 diastereomeric ratio favoring desired) that was used without further purification. LCMS-ESI$^+$ (m/z): [M+H]$^+$ calcd for $C_{33}H_{46}N_5O_8$: 640.33; found: 640.48.

Step 6. Preparation of Example 80: To a solution of 80-5 (140 mg, 219 µmol) and Intermediate A10 (133 mg, 438 µmol) in MeCN (1.1 mL) was added HATU (169 mg, 438 µmol) followed by DIPEA (190 µL, 1.09 mmol) at rt under an argon atmosphere. After 15 h, the reaction mixture was concentrated in vacuo, was purified by preparatory HPLC (Gemini 5u C18 110 Å column, 5-100% MeCN/H$_2$O, 0.1% trifluoroacetic acid modifier) and was lyophilized to afford Example 80 (5:2 diastereomeric ratio favoring desired) as a light yellow solid TFA salt. Analytic HPLC RetTime: 7.91 min. LCMS-ESI$^+$ (m/z): [M+H]$^+$ calcd for $C_{42}H_{58}F_2N_7O_{10}S$: 890.39; found: 890.64. $^1$H NMR (400 MHz, CD$_3$OD, Minor diastereomer denoted by *) δ 9.18 (s, 1H), 9.14 (s, 1H*), 7.78 (br d, J=9.0 Hz, 1H, 1H*), 7.21 (br d, J=9.0 Hz, 1H, 1H*), 7.18 (br s, 1H, 1H*), 5.80 (br td, $J_{H-F}$=55.8 Hz, J=6.8 Hz, 1H, 1H*), 5.64 (br s, 1H, 1H*), 5.23 (d, J=4.7 Hz, 1H*), 5.15 (d, J=47 Hz, 1H), 4.56 (d, J=6.7 Hz, 1H, 1H*), 4.46 (d, J=12.1 Hz, 1H*), 4.41 (d, J=12.0 Hz, 1H), 4.30-4.22 (m, 1H, 1H*), 4.22-4.07 (m, 1H, 1H*), 4.02-3.79 (m, 1H, 1H*) 3.92 (br s, 3H, 3H*), 3.73-3.52 (m, 2H, 2H*), 3.05-2.68 (m, 3H, 3H*), 2.40-2.21 (m, 1H, 1H*), 2.13-1.94 (m, 4H, 4H*), 1.83 (s, 2H, 2H*), 1.75-1.20 (m, 12H, 12H*), 1.12 (s, 9H*), 1.10 (s, 9H), 1.06 (br d, J=7.3 Hz, 3H, 3H*), 0.92-0.85 (m, 4H, 4H*).

Example 81

Preparation of (1aS,2aR,6S,9S,10S,11R,23aR,23bS)-6-tert-butyl-N-[(1R,2R)-2-(difluoromethyl)-1-{[(1-methylcyclopropyl)sulfonyl]carbamoyl}cyclopropyl]-19,19-difluoro-15-methoxy-10-methyl-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide Example 81

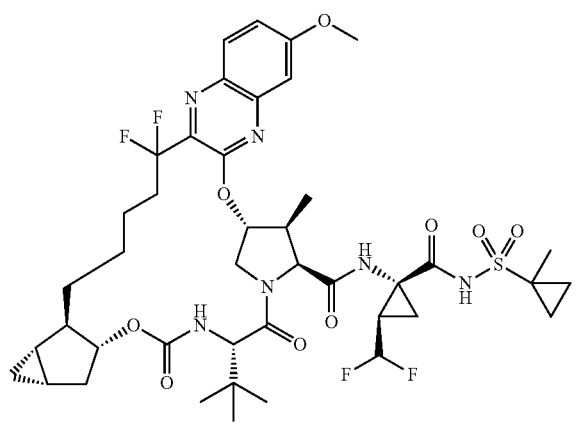

Example 81 was prepared in a similar fashion to Example 62, substituting Intermediate A10 for Intermediate A9 in Step 5. Example 81 was isolated. Analytic HPLC RetTime: 9.36 min. LCMS-ESI$^+$ (m/z): [M+H]$^+$ calcd for $C_{42}H_{55}F_4N_6O_9S$: 895.36; found: 895.59. $^1$H NMR (400 MHz, CD$_3$OD): δ 9.23 (s, 1H), 7.93 (d, J=8.8 Hz, 1H), 7.31 (dd, J=8.8, 2.4 Hz, 1H), 7.26 (d, J=2.4 Hz, 1H), 5.80 (td, $J_{H-F}$=56 Hz, J=6.8 Hz, 1H), 5.73 (d, J=3.2 Hz, 1H), 4.94 (d, J=7.2 Hz, 1H), 4.56 (d, J=6.8 Hz, 1H), 4.36 (d, J=6.8 Hz, 1H), 4.32 (s, 1H), 4.22-4.16 (dd, J=12, 4 Hz, 1H), 3.97 (s, 3H), 2.79-2.71 (m, 1H), 2.61-2.52 (m, 1H), 2.26-2.16 (m, 1H), 2.08-1.92 (m, 4H), 1.82-1.64 (m, 3H), 1.60-1.54 (m, 3H), 1.53-1.46 (m, 1H), 1.52 (s, 3H), 1.44-1.26 (m, 5H), 1.08 (s, 9H), 1.07-0.98 (m, 4H), 0.94-0.84 (m, 3H), 0.60-0.48 (m, 2H).

Example 82

Preparation of (1aS,2aR,6S,9S,10S,11R,23aR, 23bS)-6-tert-butyl-N-[(1R,2R)-2-(difluoromethyl)-1-{[(1-methylcyclopropyl)sulfonyl]carbamoyl}cyclopropyl]-19,19-difluoro-10-methy-4, 7-dioxo-1a,2,2a,4,5,6,7,10,11,19,20,21,22,23,23a, 23b-hexadecahydro-1H,9H-8,11-methanocyclopropa [4',5']cyclopenta[1',2':18,19][1,10,3,6] dioxadiazacyclononadecino[11,12-b]quinoxaline-9-carboxamide

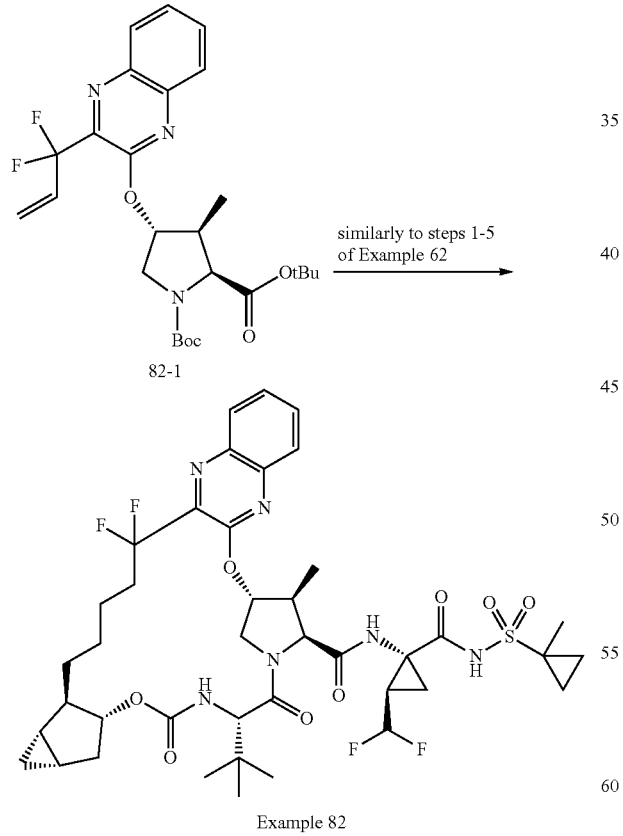

82-1

Example 82

Intermediate 82-1 was prepared in a similar fashion to intermediate 46-2, substituting intermediate E3 with E4 in Step 1. LCMS-ESI$^+$ (m/z): [M+H]$^+$ calcd for $C_{26}H_{34}F_2N_3O_5$: 506.25; found: 506.59.

Example 82 was prepared in a similar fashion to Example 62, substituting Intermediate 82-1 for Intermediate 46-2 in Step 1. Example 82 was isolated. LCMS-ESI$^+$ (m/z): [M+H]$^+$ calcd for $C_{41}H_{52}F_4N_6O_8S$: 864.35; found: 865.43. $^1$H NMR (400 MHz, cdcl$_3$) δ 9.82 (s, 1H), 7.89-7.72 (m, 2H), 7.67 (t, J=7.6 Hz, 1H), 6.93 (s, 1H), 6.12-5.65 (m, 2H), 5.34 (d, J=8.6 Hz, 1H), 4.90 (d, J=7.4 Hz, 1H), 4.45 (t, J=9.3 Hz, 2H), 4.27 (d, J=7.9 Hz, 1H), 4.13 (dd, J=11.9, 3.9 Hz, 1H), 2.77-2.64 (m, 2H), 2.27-2.12 (m, 1H), 2.13-1.86 (m, 4H), 1.82-1.19 (m, 15H), 1.18-0.98 (m, 13H), 0.89-0.77 (m, 2H), 0.53 (dd, J=13.3, 8.1 Hz, 1H), 0.43 (d, J=4.2 Hz, 1H).

Example 83

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-3,6-dioxo-14-(trifluoromethoxy)-1,1a,3,4,5,6,9,10,18,19,20,21,22, 22a-tetradecahydro-8H-7,10-methanocyclopropa[18, 19][1,10,3,6]dioxadiazacyclononadecino[11,12-b]quinoxaline-8-carboxamide

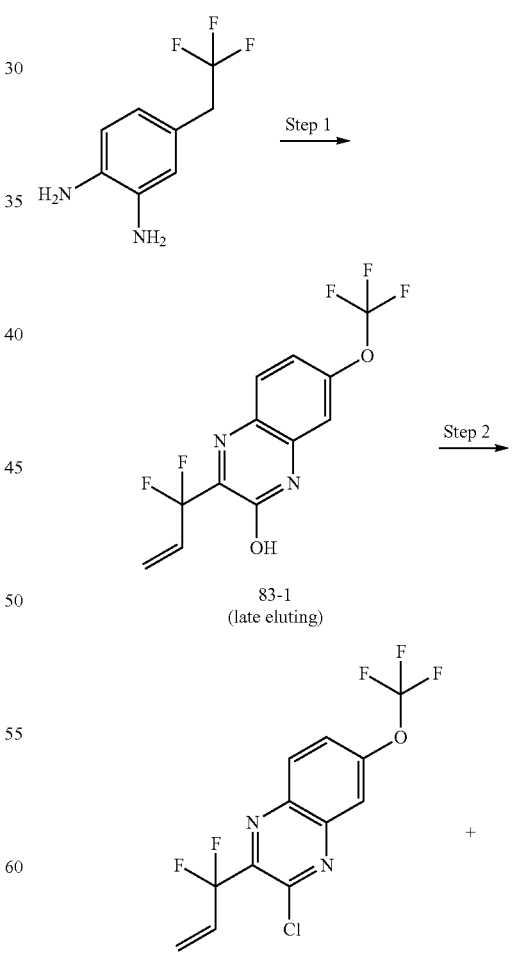

83-1
(late eluting)

83-2

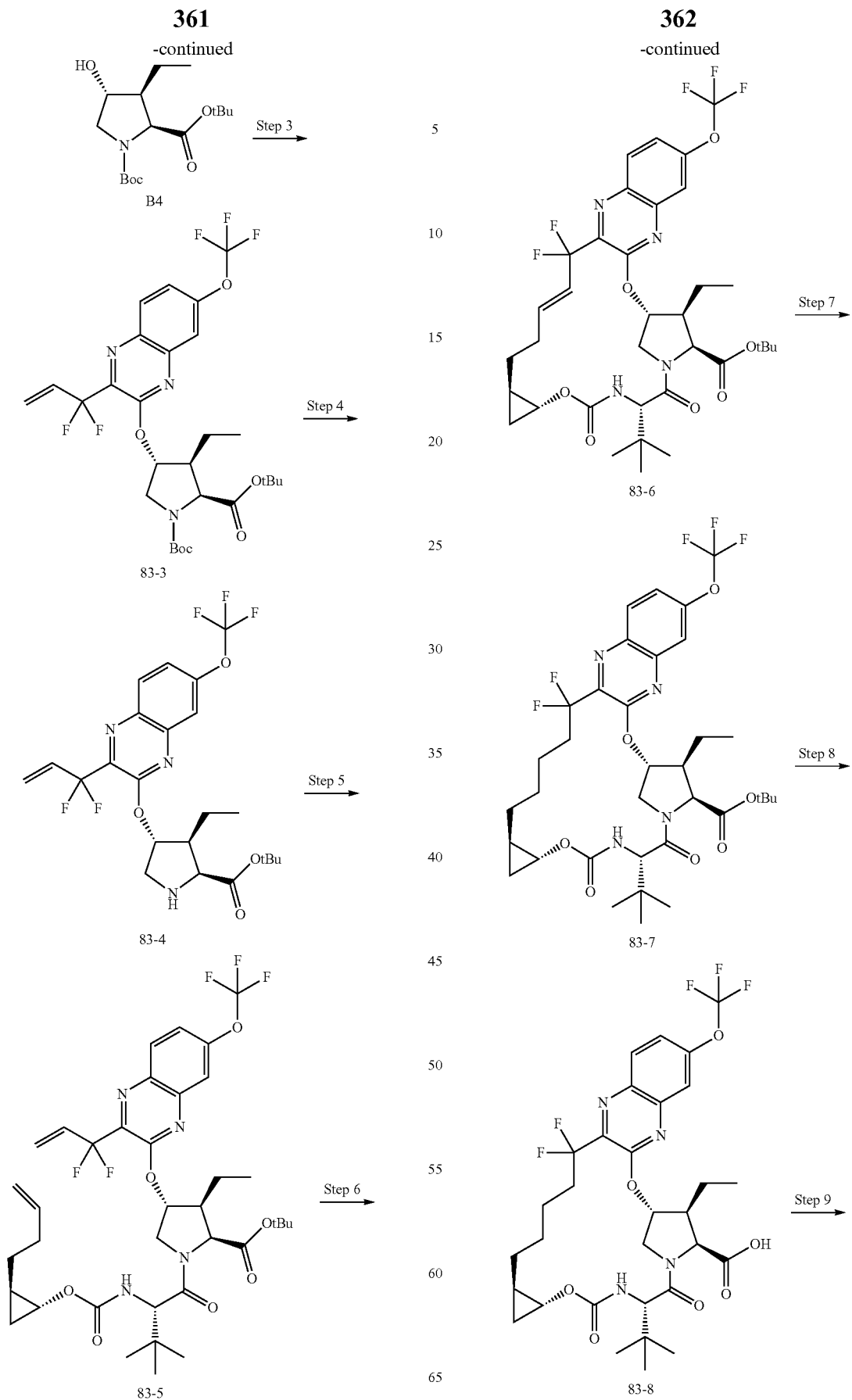

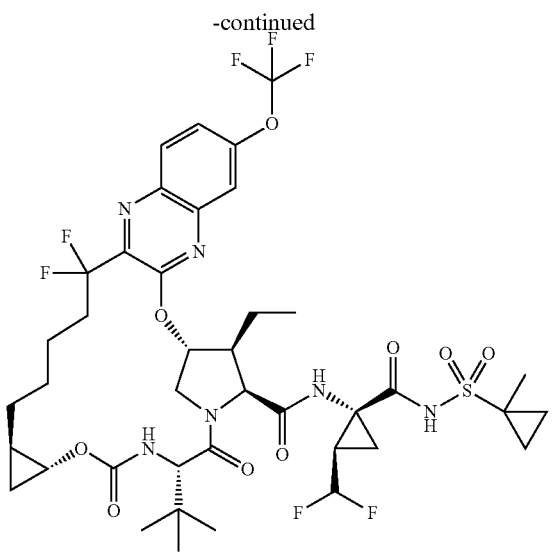

Example 83

Step 1. Preparation of 83-1: HATU (3.06 g, 8.05 mmol) was added slowly to a solution of 3,3-difluoro-2-oxopent-4-enoic acid (1.03 g, 6.86 mmol) in 10 mL of DMF. A mixture of 4-(trifluoromethoxy)benzene-1,2-diamine (1.29 g, 6.71 mmol) and DIPEA (1.4 mL, 8.05 mmol) in 12 mL of DMF was then added. After stirring overnight, reaction mixture was poured into 175 mL of water and extracted with ethyl acetate (4×100 mL). Combined organics were washed with 50% brine, dried over anhydrous $Na_2SO_4$, filtered, and concentrated under reduced pressure. Resulting solid was purified via silica gel column chromatography (0-25% ethyl acetate in hexanes) to yield intermediate 83-1, the late eluting product. LCMS-ESI$^+$ (m/z): [M+H]$^+$ calcd for $C_{12}H_8F_5N_2O_2$: 307.04: found: 307.29.

Step 2. Preparation of 83-2: A solution of 83-1 (924 mg, 3.01 mmol) in 2 mL DMF was treated with POCl$_3$ (0.56 mL, 6.04 mmol) and heated at 80° C. for 2.5 hours. After cooling to room temperature, reaction mixture was diluted with 25 mL of EtOAc and added slowly to 20 mL of water with vigorous stirring. Layers were separated and aqueous was extracted with ethyl acetate. Combined organics were washed subsequently with saturated aqueous sodium bicarbonate and brine, dried over anhydrous sodium sulfate and concentrated under reduced pressure to give intermediate 83-2. LCMS-ESI$^+$ (m/z): [M+H]$^+$ calcd for $C_{12}H_7ClF_5N_2O$: 324.01; found: 324.13.

Step 3. Preparation of 83-3: $Cs_2CO_3$ (606 mg, 1.86 mmol) was added to a mixture of intermediate 83-2 (460 mg, 1.54 mmol) and intermediate B4 (564 mg, 1.79 mmol) in 12 mL of DMF at room temperature. Reaction mixture was heated at 85° C. overnight. After cooling to room temperature, mixture was poured into 50 mL of water and extracted with ethyl acetate (4×40 mL). Combined organics were washed with 90 mL of 50% brine, dried over anhydrous sodium sulfate and concentrated under reduced pressure. Resulting solid was purified via silica gel column chromatography (0-30% ethyl acetate in hexanes) to give 83-3. LCMS-ESI$^+$ (m/z): [M+H]$^+$ calcd for $C_{28}H_{35}F_5N_3O_6$: 604.24; found: 604.20.

Step 4. Preparation of 83-4: Quinoxaline ether 83-3 (290 mg, 0.647 mmol) was dissolved in 4.1 mL of tert-butyl acetate and 1.1 mL of dichloromethane at room temperature. MeSO$_3$H (0.25 mL, 3.88 mmol) was added dropwise and reaction mixture stirred at rt for 2 h. The reaction mixture was transferred to a stirred mixture of EtOAc (20 mL) and saturated aqueous NaHCO$_3$ (30 mL). The phases were separated, and the aqueous phase was extracted with EtOAc (2×20 mL). The combined organic phase was dried over anhydrous Na$_2$SO$_4$, filtered, and concentrated in vacuo to afford amine 83-4. LCMS-ESI$^+$ (m/z): [M+H]$^+$ calcd for $C_{23}H_{27}F_5N_3O_4$: 504.18; found: 504.31.

Step 5. Preparation of 83-5: HATU (260 mg, 0.684 mmol, Oakwood) and DIPEA (0.40 mL, 2.30 mmol) were added to a mixture of 83-4 (258 mg, 0.512 mmol) and Intermediate D11 (177 mg, 0.657 mmol) in 7 mL of acetonitrile under argon. After stirring overnight, the reaction mixture was concentrated under reduced pressure and the resulting residue was purified by silica gel chromatography (0-20% ethyl acetate in hexanes) to yield 83-5. LCMS-ESI$^+$ (m/z): [M+H]$^+$ calcd for $C_{37}H_{48}F_5N_4O_7$: 755.34; found: 755.49.

Step 6. Preparation of 83-6: A mixture of 83-5 (215 mg, 0.285 mmol) and Zhan 1B catalyst (29 mg, 0.040 mmol, Strem) in 60 mL of DCE was deoxygenated with argon for 15 minutes. The mixture was then heated at reflux for 90 minutes. After cooling to room temperature, reaction mixture was concentrated in vacuo. The resulting residue was purified by silica gel chromatography (0-40% ethyl acetate in hexanes) to yield 83-6. LCMS-ESI$^+$ (m/z): [M+H]$^+$ calcd for $C_{35}H_{44}F_5N_4O_7$: 727.31; found: 727.43.

Step 7. Preparation of 83-7: Palladium on carbon (10 wt % Pd, 40 mg, 0.038 mmol) was added to a solution of 83-6 (129 mg, 0.178 mmol) in 9 mL of ethanol. The atmosphere was replaced with hydrogen and the reaction stirred overnight. The reaction mixture was filtered over Celite and washed with ethanol. Filtrate was concentrated in vacuo to yield a residue, which was purified via silica gel column chromatography (0-30% ethyl acetate in hexanes) to yield 83-7. LCMS-ESI$^+$ (m/z): [M+H]$^+$ calcd for $C_{35}H_{46}F_5N_4O_7$: 729.32; found: 729.45.

Step 8. Preparation of 83-8: TFA (0.62 mL, 8.09 mmol) was added slowly to a solution of 83-7 (79 mg, 0.109 mmol) in 1.8 mL of dichloromethane. After 4 hours, mixture was concentrated under reduced pressure to near dryness. Resulting residue was taken up in 10 mL of ethyl acetate, washed with 8 mL of water, 8 mL of sat. NaHCO$_{3\,(aq)}$, and separated. Aqueous layers were extracted with ethyl acetate (3×10 mL). Combined organics were washed with 10 mL of brine, dried over anhydrous Na$_2$SO$_4$, filtered, and concentrated in vacuo to yield 83-8, which was used in the next step without further purification. LCMS-ESI$^+$ (m/z): [M+H]$^+$ calcd for $C_{31}H_{38}F_5N_4O_7$: 673.26; found: 673.10.

Step 9. Preparation of Example 83: HATU (84 mg, 0.221 mmol, Oakwood) and DIPEA (0.095 mL, 0.547 mmol) were added to a mixture of 83-8 (72 mg, 0.107 mmol) and Intermediate A10 (66 mg, 0.217 mmol) in 4 mL of acetonitrile under argon. After stirring for overnight, reaction mixture was taken up in 20 mL of ethyl acetate and washed with 10 mL of 1 N aqueous HCl. The aqueous layer was extracted three times with ethyl acetate. Combined organics were washed with 50% brine, dried over anhydrous Na$_2$SO$_4$, filtered, and concentrated in vacuo. The resulting residue was purified by silica gel chromatography (0-50% ethyl acetate in hexanes) and reverse phase prep HPLC (50-100% acetonitrile in water, with 0.1% trifluoroacetic acid buffer) to yield the trifluoroacetic acid salt of Example 83. Analytic HPLC RetTime: 9.12 min. LCMS-ESI$^+$ (m/z): [M+H]$^+$ calcd for $C_{40}H_{50}F_7N_6O_9S$: 923.32; found: 923.10. $^1$H NMR (400 MHz, CD$_3$OD): δ 9.26 (s, 1H), 8.01-7.91 (m, 2H), 7.78-7.63 (m, 1H), 5.95 (d, J=3.6 Hz, 1H), 5.83 (td, J$_{H\text{-}F}$=61 Hz, J=6.0 Hz, 1H), 4.59 (d, J=7.2 Hz, 1H), 4.42 (d, J=12.4

Hz, 1H), 4.35 (s, 1H), 4.22-4.11 (m, 1H), 3.72-3.66 (m, 1H), 2.71-2.49 (m, 2H), 2.18-1.94 (m, 3H), 1.90-1.75 (m, 3H), 1.74-1.62 (m, 2H), 1.60-1.48 (m, 3H), 1.51 (s, 3H), 1.50-1.24 (m, 4H), 1.22-1.18 (m, 2H), 1.08 (s, 9H), 1.07-0.84 (m, 5H), 0.81-0.64 (m, 1H), 0.54-0.44 (m, 1H).

Example 84

Preparation of (1aR,5S,8S,9S,10R,19E,22aR)-5-tert-butyl-14-cyano-N-[(1R,2R)-2-(difluoromethyl)-1-{[(1-methylcyclopropyl)sulfonyl]carbamoyl}cyclopropyl]-9-ethyl-18,18-difluoro-3,6-dioxo-1,1a,3,4,5,6,9,10,18,21,22,22a-dodecahydro-8H-7,10-methanocyclopropa[18,19][1,10,3,6]dioxadiazacyclononadecino[11,12-b]quinoxaline-8-carboxamide

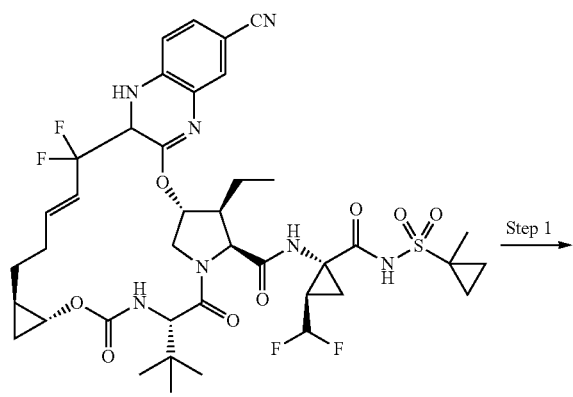

Example 78

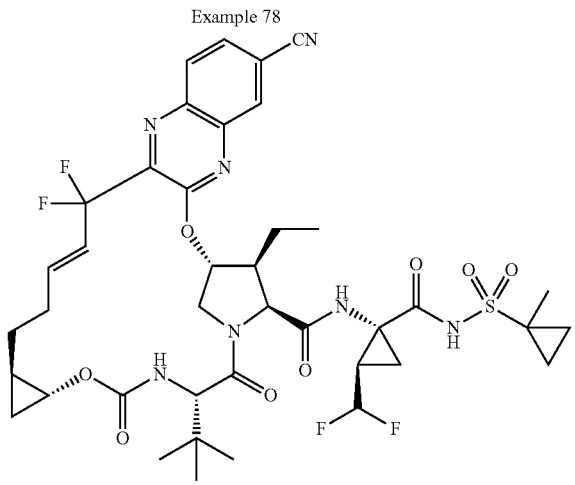

Example 84

Step 1: Preparation of Example 84. Crude Example 78 (8.7 mg, 0.01 mmol) was redissolved in ACN (0.3 mL) and treated with DDQ (3.4 mg, 0.015 mmol). After 10 min, the solution was directly purified by reverse phase HPLC (Gemini 5u C18 110 Å column, 50-100% ACN/H$_2$O+0.1% TFA) and lyophilized to afford the TFA salt of Example 84. Analytical HPLC RetTime: 8.385 min. LCMS-ESI$^+$ (m/z): [M+H]$^+$ calcd for C40H47F4N7O8S: 861.90, found: 862.89. $^1$H NMR (400 MHz, CD3OD) $^1$H NMR (400 MHz, CD3OD) δ 9.21 (s, 1H), 8.25 (d, 1H), 8.20 (d, 1H), 7.91 (dd, 1H), 6.32 (m, 2H), 5.97-5.61 (m, 2H), 4.82 (m, 1H), 4.58-4.13 (m, 4H), 3.71-3.49 (m, 3H), 2.61 (m, 2H), 2.23 (m, 1H), 2.00-1.80 (m, 3H), 1.56-1.20 (m, 10H), 1.20 (m, 3H), 1.07 (m, 8H), 0.98-0.82 (m, 3H), 0.55 (m, 1H).

Example 85

Preparation of (1aR,5S,8S,9S,10R,22aR)-5-tert-butyl-14-(difluoromethoxy)-N-[(1R,2R)-2-(difluoromethyl)-1-{[(1-methylcyclopropyl)sulfonyl]carbamoyl}cyclopropyl]-9-ethyl-18,18-difluoro-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide Example 85

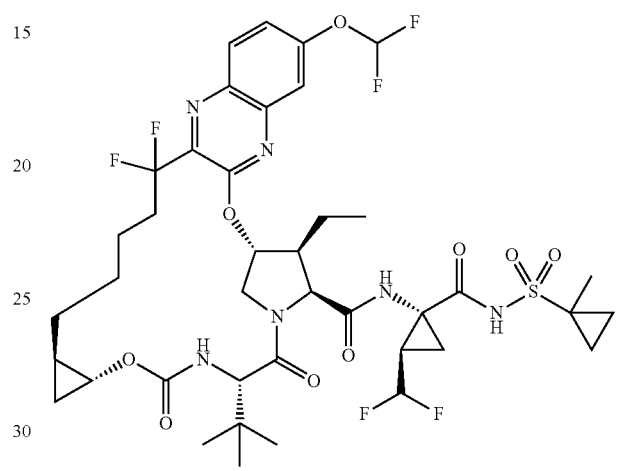

Example 85 was prepared similarly to Example 83, by using intermediate E7 in place of 83-2 in step 3. Analytical HPLC RetTime: 8.725 min. LCMS-ESI$^+$ (m/z): [M+H]$^+$ calcd for C, 40; H, 50; F, 6; N, 6; O, 9; S: 904.92; found: 905.16. $^1$H NMR (400 MHz, CD3OD) δ 9.23 (s, 1H), 7.88 (d, 1H), 7.76 (d; H), 0.7.62 (dd, 1H), 7.03 (dd, 1H), 5.94-5.65 (m, 3H), 4.57-4.14 (m, 4H), 3.66 (m, 1H), 2.57 (m, 2H), 2.01-1.97 (m, 3H), 1.82-1.77 (m, 3H), 1.64 (m, 1H), 1.57-1.33 (m, 10H), 1.20 (m, 3H), 1.06-0.87 (m, 12H), 0.87 (m, 2H), 0.48 (m, 1H).

Example 86

Preparation of (1aS,2aR,6S,9S,10S,11R,23aR,23bS)-6-tert-butyl-N-[(1R,2R)-2-(difluoromethyl)-1-{[(1-methylcyclopropyl)sulfonyl]carbamoyl}cyclopropyl]-15-fluoro-10-methyl-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

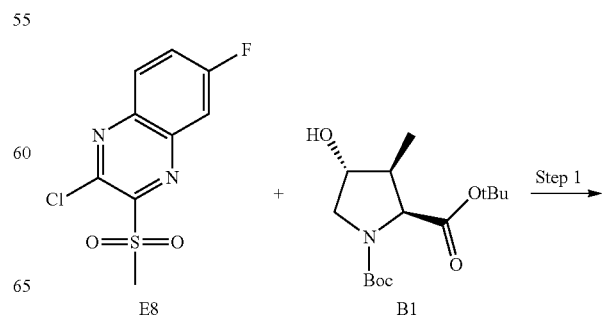

E8     B1

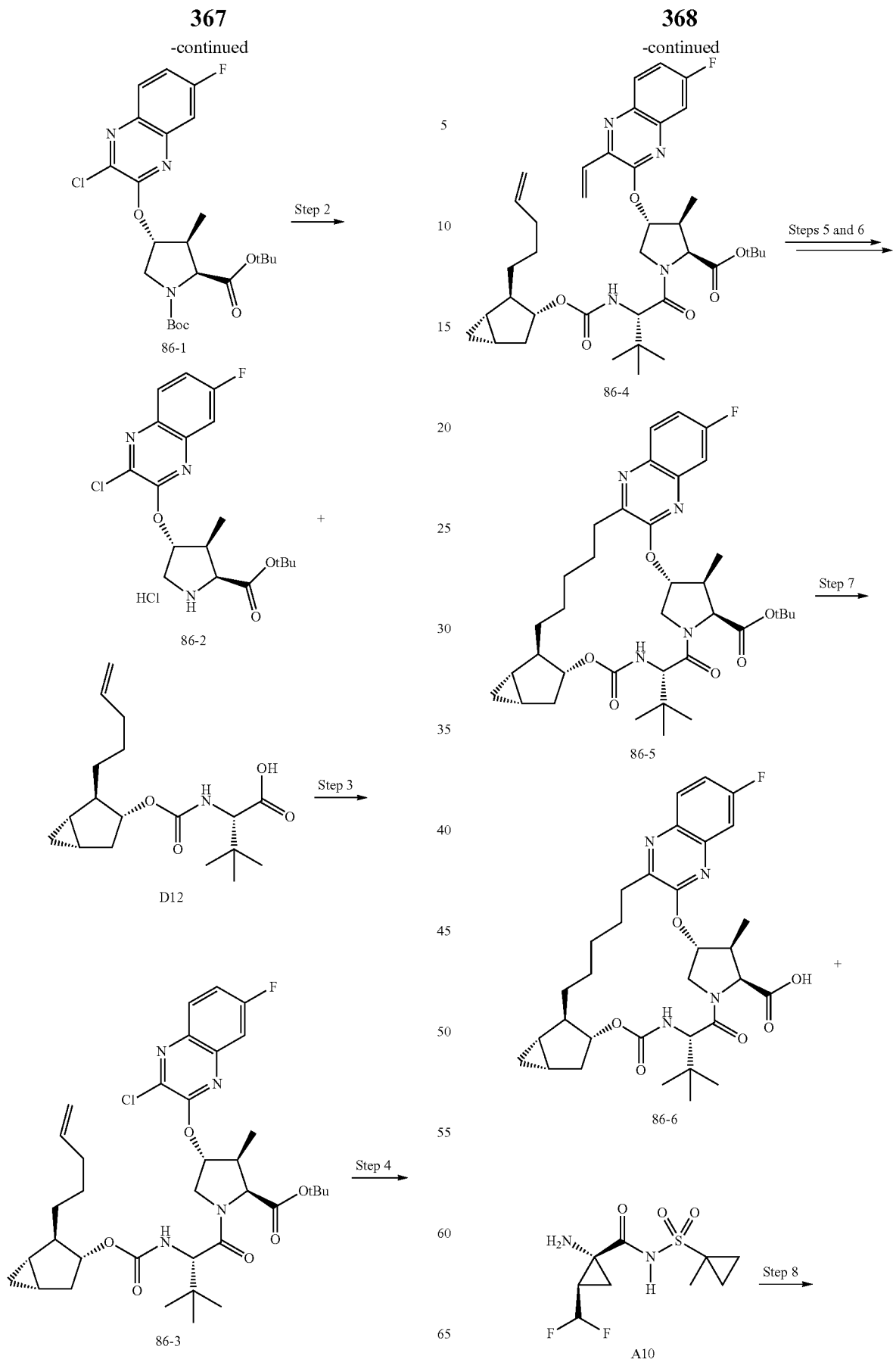

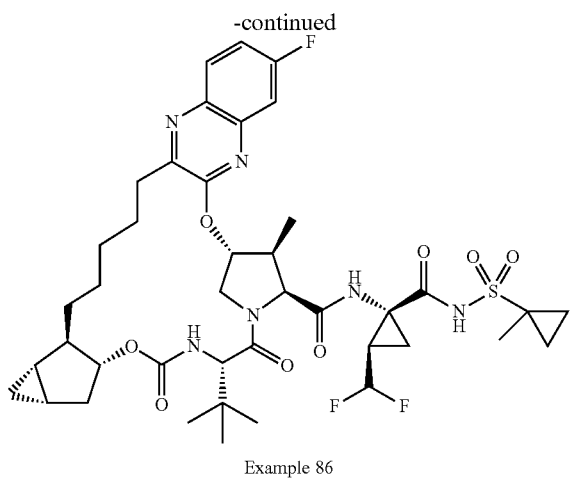

Example 86

Step 1. Preparation of 86-1: To a solution of E8 (1.5 g, 5.75 mmol) and B1 (1.9 g, 6.34 mmol) in MeCN (50 mL) is added Cs$_2$CO$_3$ (3.09 g, 9.49 mmol). After stirring at rt for 60 h, the reaction mixture was filtered over celite and concentrated. The crude residue was purified by silica gel chromatography (5-35% EtOAc/hexanes) to yield product 86-1. LCMS-ESI$^+$ (m/z): [M+H]$^+$ calcd for C$_{23}$H$_{30}$ClFN$_3$O$_5$-Boc: 482.13; found: 382.04.

Step 2. Preparation of 86-2: To a solution of 86-1 (747 mg, 1.55 mmol) in CH$_2$Cl$_2$ (5 mL) is added HCl (5 mL, 4 M in dioxane) and allowed to stir for 3 h. The reaction mixture was concentrated to give a residue that was used subsequently without further purification. LCMS-ESI$^+$ (m/z): [M+H]$^+$ calcd for C$_{18}$H$_{23}$C$_{12}$FN$_3$O$_3$—HCl: 382.13; found: 382.08.

Step 3. Preparation of 86-3: To a solution of 86-2 (397 mg, 0.95 mmol), D12 (308 mg, 0.95 mmol) and BEP (312 mg, 1.14 mmol) in EtOAc (9 mL) and NMP (1 mL) was added DIPEA (0.7 mL, 3.8 mmol) and the reaction was stirred at 50° C. overnight. The reaction was quenched with sat. NaHCO$_3$ solution and extracted with EtOAc, washed subsequently with brine, dried over magnesium sulfate and concentrated. The crude product was purified by silica gel to yield 86-3. LCMS-ESI$^+$ (m/z): [M+H]$^+$ calcd for C$_{36}$H$_{49}$ClFN$_4$O$_6$: 687.33; found: 687.44.

Step 4. Preparation of 86-4: To a solution of 86-3 (266 mg, 0.39 mmol), TEA (0.08 mL, 0.58 mmol) and potassium vinyltrifluoroborate (78 mg, 0.58 mmol) in EtOH (8 mL was added PdCl$_2$(dppf) (32 mg, 004 mmol). The reaction was degassed with N$_2$ for 10 min and heated to 75° C. for h. The reaction was quenched with sat. NaHCO$_3$ solution and extracted with EtOAc, washed subsequently with brine, dried over magnesium sulfate and concentrated. The residue was purified using silica gel chromatography (0-25% EtOAc/hexanes) to give 86-4. LCMS-ESI$^+$ (m/z): [M+H]$^+$ calcd for C$_{38}$H$_{52}$FN$_4$O$_6$: 679.39; found: 679.52.

Step 5 and 6. Preparation of 86-5: To a solution of 86-4 (262 mg, 0.38 mmol) in DCE (50 mL) was added Zhan 1B catalyst (28 mg, 0.04 mmol) and the reaction was degassed for 25 minutes with N$_2$. The reaction was heated to 100° C. for 1 h, allowed to cool to rt and concentrated. The crude product was purified by silica gel chromatography (0-30% EtOAc/hexanes) to give olefin product (182 mg; LCMS-ESI$^+$ (m/z): [M+H]$^+$ calcd for C$_{36}$H$_{48}$FN$_4$O$_6$: 651.36; found: 651.38) that was taken up in EtOH (5 mL) and EtOAc (1 mL) and treated with Pd/C (10%, 55 mg). The atmosphere was replaced with hydrogen and stirred at rt for 1.25 h. The reaction was filtered over Celite, washed with EtOAc and concentrated to give 86-5 that was used subsequently without further purification. LCMS-ESI$^+$ (m/z): [M+H]$^+$ calcd for C$_{36}$H$_{50}$FN$_4$O$_6$: 653.37; found: 653.46.

Step 7. Preparation of 86-6: To a solution of 86-5 (182 mg, 0.28 mmol) in DCM (3 mL) was added TFA (3 mL) and stirred at rt for 18 h. The reaction was diluted with EtOAc, washed with H$_2$O, basicified to pH 7 with sat. NaHCO$_3$ solution, washed with 1M citric acid solution, dried over magnesium sulfate, and concentrated to give a residue of 86-6 that was used subsequently without further purification. LCMS-ESI$^+$ (m/z): [M+H]$^+$ calcd for C$_{32}$H$_{42}$FN$_4$O$_6$: 597.31; found: 597.15.

Step 8. Preparation of Example 86: To a solution of 86-6 (24 mg, 0.04 mmol), intermediate A10 (18 mg, 0.06 mmol), TBTU (23 mg, 0.07 mmol) and DMAP (7 mg, 0.06 mmol) in DMF (3 mL) was added DIPEA (35 µL, 0.20 mmol) and the reaction was stirred at rt for 3 h. Additional intermediate A10 (18 mg, 0.06 mmol), TBTU (23 mg, 0.07 mmol), DMAP (7 mg, 0.06 mmol), and DIPEA (35 µL, 0.20 mmol) was added and the reaction was stirred at rt for 16 h. The crude material was purified by reverse phase HPLC (Gemini, 30-85% ACN/H$_2$O+0.1% TFA) and lyophilized to give Example 86 as a TFA salt. Analytical HPLC RetTime: 9.25 min. LCMS-ESI$^+$ (m/z): [M+H]$^+$ calcd for C$_{41}$H$_{54}$F$_3$N$_6$O$_9$S: 847.37: found: 847.18. $^1$H NMR (400 MHz, CD$_3$OD) δ 9.18 (s, 1H), 8.13-7.84 (m, 2H), 7.59-7.21 (m, 2H), 6.07-5.58 (m, 2H), 5.00 (d, J=7.4 Hz, 1H), 4.57 (d, J=7.0 Hz, 1H), 4.45-4.27 (m, 2H), 4.20 (dd, J=12.0, 4.0 Hz, 1H), 3.11-2.94 (m, 3H), 2.92-2.70 (m, 4H), 2.32-2.14 (m, 1H), 2.10-1.94 (m, 2H), 1.86 (m, 1H), 1.77 (d, J=14.5 Hz, 1H), 1.74-1.21 (m, 15H), 1.21-1.01 (m, 10H), 1.00-0.84 (m, 2H), 0.60 (m, 1H), 0.53 (m, 1H).

Example 87

Preparation of (1aR,5S,8S,9S,10R,22aR)-5-tert-butyl-14-cyano-N-[(1R,2R)-2-(difluoromethyl)-1-{[(1-methylcyclopropyl)sulfonyl]carbamoyl}cyclopropyl]-9-ethyl-18,18-difluoro-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

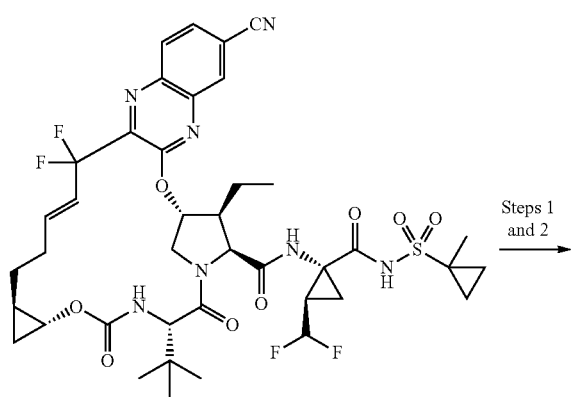

Example 84

Steps 1 and 2

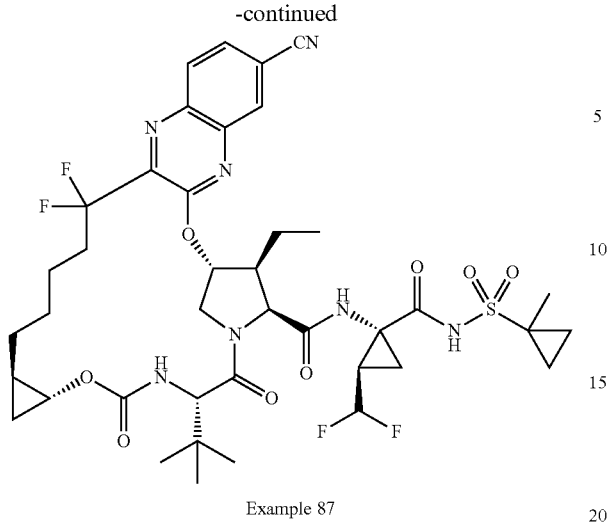

Example 87

Steps 1 and 2. Preparation of Example 87. To a solution of Example 84 (100 mg, 0.11 mmol) in EtOAc (3 mL) was added Pd/C (10 wt % Pd, 30 mg). The reaction vessel was purged twice with $H_2$ and was stirred at rt under 1 atm $H_2$ for 6 h. After which time the reaction mixture was filtered through a pad of celite and concentrated. The reaction reduced the quinoxaline ring. The crude material was redissolved in ACN (5 mL) and treated with DDQ (34 mg, 0.15 mmol). After 1 h, the solution was directly purified by reverse phase HPLC (Gemini 5u C18 110 Å column, 50-100% ACN/$H_2O$+0.1% TFA) and lyophilized to afford the TFA salt of Example 87. Analytical HPLC RetTime: 8.463 min. LCMS-ESI$^+$ (m/z): [M+H]$^+$ calcd for C, 40; H, 49; F, 4; N, 7; O, 8; S: 863.92; found: 864.18. $^1$H NMR (400 MHz, CD3OD) δ 9.24 (s, 1H), 8.27 (d, 1H), 8.20 (d, 1H), 7.91 (dd, 1H), 5.93-5.82 (m, 3H), 4.88 (m, 1H), 4.58-4.13 (m, 5H) 3.71-3.49 (m, 3H), 2.59 (m, 2H), 2.03-1.96 (m, 3H), 1.82-1.77 (m, 3H), 1.65-1.35 (m, 11H) 120 (m, 3H), 1.06-0.87 (m, 8H), 0.71 (m, 2H), 0.48 (m, 1H).

Example 88

Preparation of (1aR,5S,8S,9S,10R,22aR)-5-tert-butyl-14-chloro-N-[(1R,2R)-2-(difluoromethyl)-1-{[(1-methylcyclopropyl)sulfonyl]carbamoyl}cyclopropyl]-18,18-difluoro-9-methyl-3,6-dioxo-1,1a,3,4,5,6,9,10,18,19,20,21,22,22a-tetradecahydro-8H-7,10-methanocyclopropa[18,19][3,6]dioxadiazacyclononadecino[11,12-b]quinoxaline-8-carboxamide

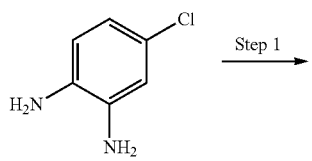

Step 1 →

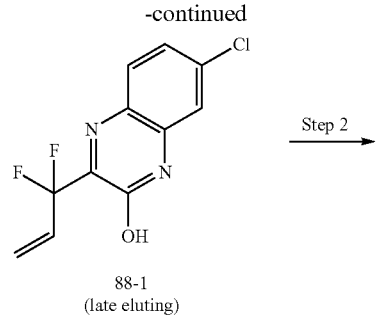

88-1
(late eluting)

Step 2 →

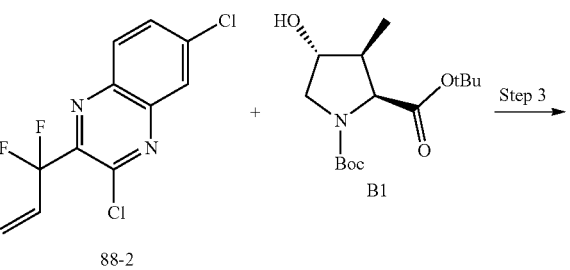

88-2

Step 3 →

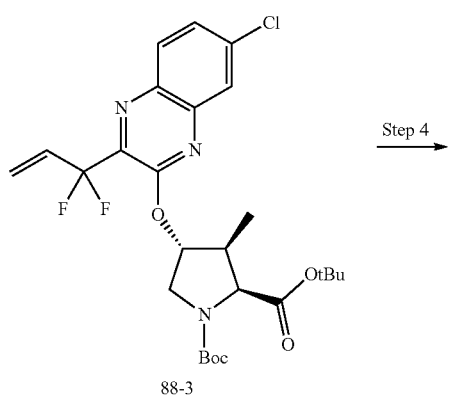

88-3

Step 4 →

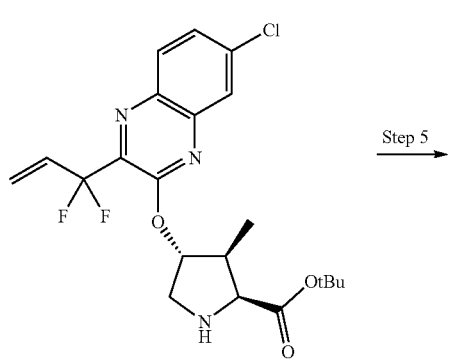

88-4

Step 5 →

373
-continued

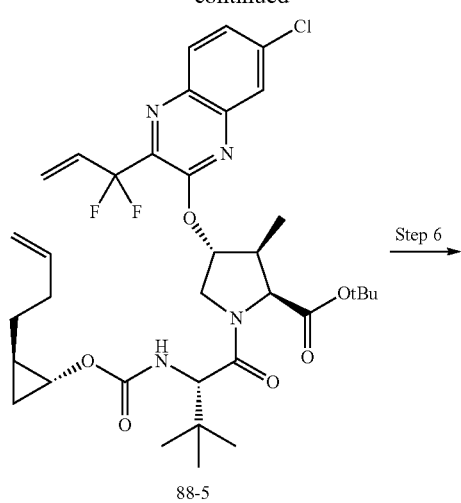

88-5

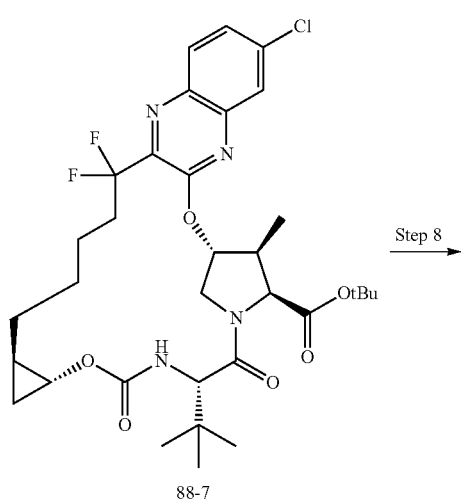

88-6

88-7

374
-continued

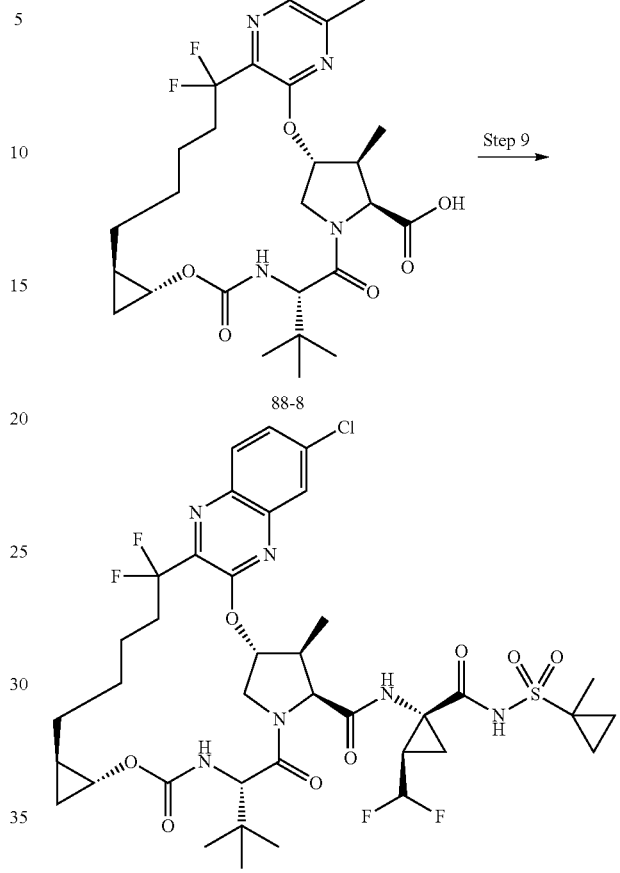

88-8

Example 88

Step 1. Preparation of 88-1: HATU (4.56 g, 12 mmol) was added slowly to a solution of 3,3-difluoro-2-oxopent-4-enoic acid (1.52 g, 10.1 mmol) in 14 mL of DMF. A mixture of 4-chlorobenzene-1,2-diamine (1.43 g, 10 mmol) and DIPEA (2.1 mL, 12 mmol) in 20 mL of DMF was then added. After stirring overnight, reaction mixture was poured into 30 mL of 1 N aqueous HCl and extracted with ethyl acetate (5×40 mL) Combined organics were dried over anhydrous $Na_2SO_4$, filtered, and concentrated under reduced pressure. Resulting solid was purified via silica gel column chromatography (0-45% ethyl acetate in hexanes) to yield intermediate 88-1 as the late eluting product. $^1$H NMR (400 MHz, $CDCl_3$): δ 12.1 (s, 1H), 7.99 (m, 1H), 7.61-7.58 (m, 1H), 7.33-7.31 (m, 1H), 6.61-6.48 (m, 1H), 5.96-590 (m, 1H), 5.67-5.63 (m, 1H).

Step 2. Preparation of 88-2: A solution of intermediate 88-1 (648 mg, 2.53 mmol) in 2 mL DMF was treated with $POCl_3$ (0.49 mL, 5.26 mmol) and heated at 80° C. for 3 hours, After cooling to room temperature, reaction mixture was diluted with 20 mL of EtOAc and added slowly to 15 mL of water with vigorous stirring. Layers were separated and aqueous was extracted with ethyl acetate. Combined organics were washed subsequently with saturated aqueous sodium bicarbonate and brine, dried over anhydrous sodium sulfate and concentrated under reduced pressure to give intermediate 88-2. $^1$H NMR (400 MHz, $CDCl_3$) δ 8.184 (d, J=1.6 Hz, 1H), 8.01 (d, J=8.8 Hz, 1H), 7.82 (dd, J=9.4, 2 Hz, 1H), 6.56-6.43 (m, 1H), 5.88 (m, 1H), 5.70 (d, J=10.8 Hz, 1H).

Step 3. Preparation of 88-3: $Cs_2CO_3$ (660 mg, 2.03 mmol) was added to a mixture of intermediate 88-2 (425 mg, 1.54 mmol) and intermediate B1 (570 mg, 1.89 mmol) in 9 mL of DMF at room temperature. Reaction mixture was heated at 85° C. overnight. After cooling to room temperature, mixture was poured into 40 mL of water and extracted with ethyl acetate (4×30 mL). Combined organics were washed with 75 mL of 50% brine, dried over anhydrous sodium sulfate and concentrated under reduced pressure. Resulting solid was purified via silica gel column chromatography (0-20% ethyl acetate in hexanes) to give 88-3. LCMS-ESI$^+$ (m/z): [M+H]$^+$ calcd for $C_{26}H_{33}ClF_2N_3O_5$: 540.20; found: 540.12.

Step 4. Preparation of 88-4: Quinoxaline ether 88-3 (458 mg, 0.848 mmol) was dissolved in 4.2 mL of tert-butyl acetate and 1.2 mL of dichloromethane at room temperature. $MeSO_3H$ (0.30 mL, 4.67 mmol) was added dropwise and reaction mixture stirred at rt for 2 h. The reaction mixture was transferred to a stirred mixture of EtOAc (20 mL) and saturated aqueous $NaHCO_3$ (30 mL). The phases were separated, and the aqueous phase was extracted with EtOAc (2×20 mL). The combined organic phase was dried over anhydrous $Na_2SO_4$, filtered, and concentrated in vacuo to afford amine 88-4 as a yellow solid film LCMS-ESI$^+$ (m/z): [M+H]$^+$ calcd for $C_{21}H_{25}ClF_2N_3O_3$: 440.15; found: 440.29.

Step 5. Preparation of 88-5: HATU (360 mg, 0.947 mmol, Oakwood) and DIPEA (0.51 mL, 2.91 mmol) were added to a mixture of 88-4 (320 mg, 0.727 mmol) and Intermediate D11 (237 mg, 0.880 mmol) in 10 mL of acetonitrile under argon. After stirring overnight, the reaction mixture was concentrated under reduced pressure and the resulting residue was purified by silica gel chromatography (0-20% ethyl acetate in hexanes) to yield 88-5. LCMS-ESI$^+$ (m/z): [M+H]$^+$ calcd for $C_{35}H_{46}ClF_2N_4O_6$: 691.30; found: 691.50.

Step 6. Preparation of 88-6: A mixture of 88-5 (390 mg, 0.564 mmol) and Zhan 1B catalyst (55 mg, 0.075 mmol, Strem) in 100 mL of DCE was deoxygenated with argon for 15 minutes. The mixture was then heated at reflux for 110 minutes. After cooling to room temperature, reaction mixture was concentrated in vacuo. The resulting residue was purified by silica gel chromatography (0-25% ethyl acetate in hexanes) to yield 88-6. LCMS-ESI$^+$ (m/z): [M+H]$^+$ calcd for $C_{33}H_{42}ClF_2N_4O_6$: 663.27; found: 663.33.

Step 7. Preparation of mixture of 88-7: Rhodium on alumina (5 wt % Rh, 31 mg, 0.015 mmol) was added to a solution of 88-6 (90 mg, 0.136 mmol) in 9 mL of ethanol. The atmosphere was replaced with hydrogen and mixture was stirred overnight. The reaction was filtered over Celite, washing with ethanol. LC/MS analysis indicated about 60% starting material remained. A solution of the residue in 8 mL of ethanol was resubjected to hydrogenation conditions utilizing 25 mg of Rhodium on alumina (5 wt % Rh) overnight. The reaction was filtered over Celite, washing with ethanol. Filtrate was concentrated in vacuo to yield as residue, which was purified via silica gel column chromatography (0-30% ethyl acetate in hexanes) to yield 88-7. LCMS-ESI$^+$ (m/z): [M+H]$^+$ calcd for $C_{33}H_{44}ClF_2N_4O_6$: 665.28; found: 665.48.

Step 8. Preparation of 88-8: TFA (0.45 mL, 5.86 mmol) was added slowly to a solution of 88-7 (52 mg, 0.078 mmol) in 2 mL of dichloromethane. After 3 hours, mixture was concentrated under reduced pressure to near dryness. Resulting residue was taken up in 10 mL of ethyl acetate, washed with 8 mL of water, 8 mL of sat. $NaHCO_{3\ (aq)}$, and separated. Aqueous layers were extracted with ethyl acetate (3×10 mL). Combined organics were washed with 10 mL of brine, dried over anhydrous $MgSO_4$, filtered, and concentrated in vacuo to yield 88-8, which was used in the next step without further purification. LCMS-ESI$^+$ (m/z): [M+H]$^+$ calcd for $C_{29}H_{36}ClF_2N_4O_6$: 609.22; found: 609.42.

Step 9. Preparation of Example 88: HATU (58 mg, 0.153 mmol, Oakwood) and DIPEA (0.065 mL, 0.374 mmol) were added to a mixture of 88-8 (45 mg, 0.074 mmol) and Intermediate A10 (49 mg, 0.161 mmol) in 2.5 mL of acetonitrile under argon. After stirring for overnight, reaction mixture was taken up in 15 mL of ethyl acetate and washed with 10 mL of 1 N aqueous HCl. The aqueous layer was extracted three times with ethyl acetate. Combined organics were washed with 50% brine, dried over anhydrous $Na_2SO_4$, filtered, and concentrated in vacuo. The resulting residue was purified by silica gel chromatography (0-50% ethyl acetate in hexanes) and reverse phase prep HPLC (50-100% acetonitrile in water, with 0.1% trifluoroacetic acid buffer) to yield the trifluoroacetic acid salt of Example 88. Analytic HPLC RetTime: 8.92 min. LCMS-ESI$^+$ (m/z): [M+H]$^+$ calcd for $C_{38}H_{48}ClF_4N_6O_8S$: 859.28; found: 859.42. $^1$H NMR (400 MHz, CD$_3$OD): δ 9.23 (s, 1H), 8.10 (s, 1H), 7.90 (d, J=8.8 Hz, 1H), 7.81 (d, J=8.8 Hz, 1H), 5.81 (td, J$_{H-F}$=56 Hz, J=6.0 Hz, 1H); 5.69-5.66 (m, 1H), 4.56 (d, J=7.2 Hz, 1H), 4.43 (d, J=12 Hz, 1H), 4.34 (s, 1H), 4.22-4.16 (dd, J=12, 4 Hz, 1H), 3.71-3.66 (m, 1H), 2.83-2.76 (m, 1H), 2.61-2.48 (m, 1H), 2.11-1.94 (m, 4H), 1.88-1.72 (m, 4H), 1.71-1.62 (m, 1H), 1.58-1.54 (m, 2H), 1.51 (s, 3H), 1.50-1.36 (m, 2H), 1.09 (s, 9H), 1.08-1.01 (m, 3H), 1.01-0.94 (m, 2H), 0.93-0.86 (m, 2H), 0.80-0.68 (m, 1H), 0.52-0.46 (m, 1H).

Example 89

Preparation of (1aR,5S,8S,9S,10R,19E,22aR)-5-tert-butyl-N-[(1R,2R)-2-(difluoromethyl-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,21,22,22a-dodecahydro-8H-7,10-methanocyclopropa[18,19][1,10,3,6]dioxadiazacyclononadecino[11,12-b]quinoxaline-8-carboxamide

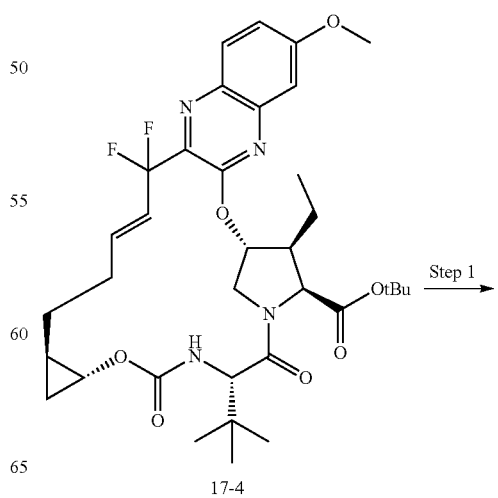

17-4

-continued

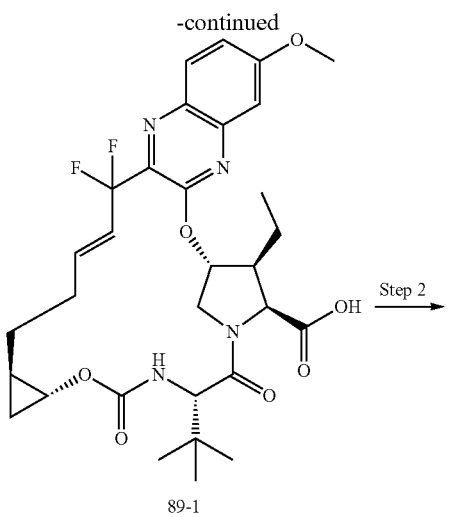

89-1

J=8.8, 2.4 Hz, 1H), 7.06 (d, J=2.8 Hz, 1H), 6.75 (br s, 1H), 6.30-5.93 (m, 2H), 5.92 (td, $J_{H-F}$=52 Hz, J=6.8 Hz, 1H), 5.47 (d, J=10 Hz, 1H), 4.53 (d, J=12 Hz, 1H), 4.48 (d, J=10.4 Hz, 1H), 4.42 (d, J=6.8 Hz, 1H), 4.07 (dd, J=11.6, 3.2 Hz, 1H), 3.98-3.94 (m, 1H), 3.95 (s, 3H), 3.57 (m, 1H), 2.60-2.48 (m, 2H), 2.20 (m, 1H), 2.06 (m, 1H), 1.90 (m, 1H), 1.80 (m, 1H), 1.63 (m, 2H), 1.50 (s, 3H), 1.56-1.36 (m, 2H), 1.26 (m, 1H), 1.19 (t, J=7.2 Hz, 3H), 1.09 (s, 9H), 1.03-0.93 (m, 2H), 0.85 (m, 2H), 0.76 (m, 1H); 0.53 (m, 1H).

Example 90

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18-fluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

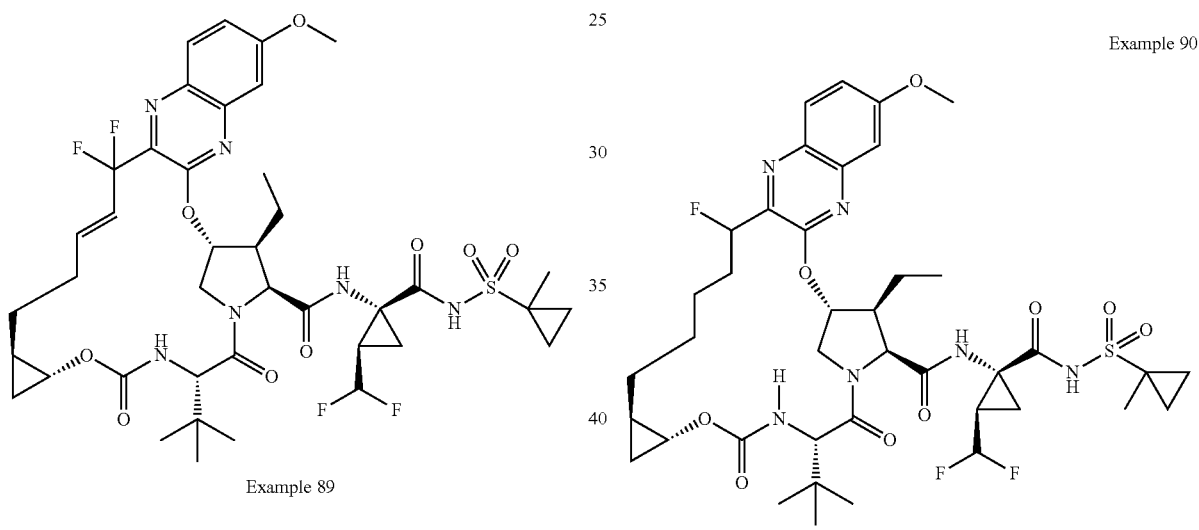

Example 89                    Example 90

Step 1. Preparation of 89-1: 17-4 (95 mg, 0.14 mmol) in 0.4 mL DCM was treated with 0.4 mL TFA and stirred at rt for 2 h. The reaction mixture was diluted with 5 mL DCM and then treated with water and saturated sodium bicarbonate to pH 6.5. The layers were separated and the organic phase was washed once more with water, then dried over anhydrous sodium sulfate, filtered and concentrated to give 89-1. LCMS-ESI⁺ (m/z): [M+H]⁺ calcd for $C_{31}H_{39}F_2N_4O_7$: 617.3; found: 616.7.

Step 2. Preparation of Example 89: A mixture of 89-1 from step 1 (41 mg, 0.066 mmol), Intermediate A10 (24 mg, 0.079 mmol), HATU (30 mg, 0.079 mmol), and DIPEA (0.057 mL, 0.33 mmol) in DMF (0.4 mL) was stirred at rt overnight. The mixture was diluted with 2 N HCl (1 mL) and extracted with dichloromethane. The organic phase was dried over sodium sulfate, filtered and concentrated. The crude product mixture was purified by reverse phase prep HPLC (10-99% acetonitrile in water, with 0.1% trifluoroacetic acid buffer) to give Example 89. Analytic HPLC RetTime: 8.65 min. LCMS-ESI⁺ (m/z): [M+H]⁺ calcd for $C_{40}H_{51}F_4N_6O_9S$: 867.3; found: 866.9. ¹H NMR (400 MHz, CDCl₃) δ 9.890 (s, 1H), 7.98 (d, J=9.2 Hz, 1H), 728 (dd, Further purification of a synthesis of compound 17 by reverse phase prep HPLC (60-88% acetonitrile in water, with 0.1% trifluoroacetic acid buffer) allowed isolation of example 93 as a minor side product. Analytic HPLC RetTime: 8.64 min. LCMS-ESI⁺ (m/z): [M+H]⁺ calcd for $C_{40}H_{54}F_3N_6O_9S$: 851.4; found: 851.4. ¹H NMR (400 MHz, CDCl₃) δ 9.93 (br s, 1H), 7.88 (d, J=9.1 Hz, 1H), 7.22 (d, J=2.4 Hz, 1H), 7.06 (d, J=2.4 Hz, 1H), 6.55 (s, 1H), 5.91 (td, $J_{H-F}$=136 Hz, J=8 Hz, 1H), 5.81 (td, $J_{H-F}$=52 Hz, J=8 Hz, 1H), 5.30 (d, J=9.7 Hz, 1H), 4.44 (d, J=12.0 Hz, 1H), 4.38 (d, J=6.7 Hz, 1H), 4.32 (d, J=9.8 Hz, 1H), 4.07 (m, 1H), 3.93 (s, 3H), 3.72 (m, 1H), 2.59 (m, 1H), 2.35 (m, 1H), 2.06 (m, 4H), 1.88 (m, 1H), 1.78 (m, 1H), 1.71-1.52 (m, 4H), 1.48 (s, 3H), 1.48-1.41 (m, 2H), 1.23 (m, 2H) 1.21 (t, J=8.0 Hz, 3H), 1.08 (s, 9H), 1.05-0.90 (m, 2H), 0.84 (m, 2H), 0.66 (m, 1H), 0.48 (m, 1H).

Example 91

Preparation of (1aR,5S,8S,9S,10R,22aR)-5-tert-butyl-N-{(1R,2S)-1-[(cyclopropylsulfonyl)carbamoyl]-2-ethenylcyclopropyl}-9-ethyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

Example 92

Preparation of (1aR,5S,8S,9S,10R,22aR)-5-tert-butyl-N-{(1R,2S)-1-[(cyclopropylsulfonoyl)carbamoyl]-2-ethenylcyclopropyl}-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

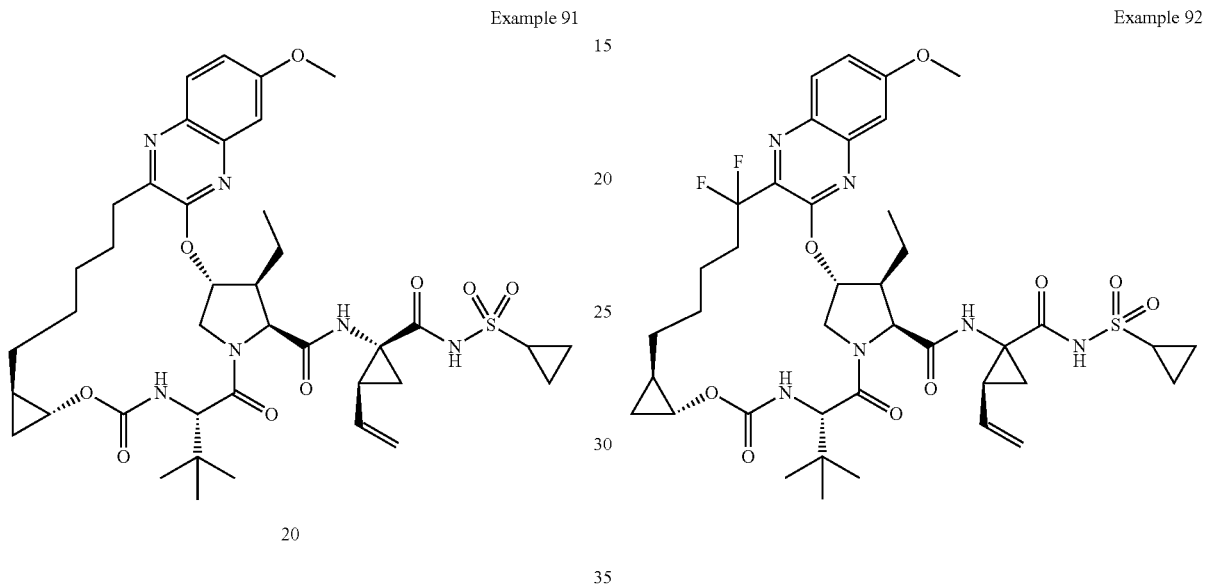

Example 91

Example 92

Example 91 was prepared similarly to Example 1 substituting Intermediate A1 for Intermediate A10 in Step 8. The TFA salt of Example 91 was isolated. Analytic HPLC RetTime: 8.72 min. LCMS-ESI+ (m/z): [M+H]+ calcd for $C_{40}H_{55}N_6O_9S$: 795.96; found: 795.94. $^1$H NMR (400 MHz, CD$_3$OD) δ 9.03 (s, 1H); 7.80 (d, J=9.2 Hz, 1H); 7.24 (dd, J=9.2, 2.4 Hz, 1H); 7.16 (d, J=2.4 Hz, 1H); 5.90 (d, J=3.6 Hz, 1H); 5-68 (m, 1H); 5.25 (d, J=17.2 Hz, 1.6 Hz, 1H); 5.10 (d, J=11.2, 1.6 Hz, 1H); 4.57 (d, J=6.8 Hz, 1H); 4.39 (br s, 1H) 4.37 (d, J=9.2 Hz, 1H); 4.16 (dd, J=12.8, 4.4 Hz, 1H); 3.93 (s, 3H); 3.77-3.72 (m, 1H); 3.02-2.88 (m, 1H); 2.86-2.75 (m, 1H); 2.64-2.54 (m, 1H); 2.18 (q, J=8.8 Hz, 1H) 1.90-1.66 (m, 4H); 1.66-1.40 (m, 6H); 1.38-1.32 (m, 1H); 1.30-1.20 (m, 5H); 1.10 (s, 9H); 1.14-1.02 (m, 2H), 0.77-0.68 (m, 1H); 0.54-0.45 (m, 1H).

Example 92 was prepared in a similar fashion to Example 17, substituting Intermediate A1 for Intermediate A10 in Step 7. Example 92 was isolated. Analytic HPLC RetTime: 8.75 min. LCMS-ESI+ (m/z): [M+H]+ calcd for $C_{40}H_{53}F_2N_6O_9S$: 831.36; found: 831.25 $^1$H NMR (400 MHz. Chloroform-d) δ 9.98 (s, 1H), 7.96 (d, J=9.2 Hz, 1H), 7.40-7.19 (m, 1H), 7.08 (s, 1H), 6.56 (s, 1H), 5.91 (d, J=3.8 Hz, 1H), 5.86-5.64 (m, 1H), 5.34 (d, J=9.7 Hz, 1H), 5.21 (d, J=17.2 Hz, 1H), 5.10 (d, J=10.3 Hz, 1H), 4.53-4.26 (m, 2H), 4.15-4.02 (m, 1H), 3.95 (s, 3H), 3.73-3.57 (m, 1H), 2.97-2.81 (m, 1H), 2.64-2.37 (m, 2H), 2.21-2.06 (m, 1H), 2.06-1.88 (m, 2H), 1.88-1.55 (m, 4H), 1.55-1.12 (m, 10H), 1.07 (s, 9H), 1.02-0.78 (m, 5H), 0.78-0.61 (m, 1H), 0.47 (q, J=7.3, 6.2 Hz, 1H).

Example 93

Preparation of (1aR,5S,8S,9S,10R,22aR)-5-tert-butyl-9-ethyl-N-[(2R)-2-ethyl-1-{[(1-methylcyclopropyl)sulfonyl]carbamoyl}cyclopropyl]-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide

Example 94

Preparation of (1aR,5S,8S,9S,10R,22aR)-5-tert-butyl-N-[(2R)-1-[(cyclopropylsulfonyl)carbamoyl]-2-(difluoromethyl)cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[1,12-b]quinoxaline-8-carboxamide

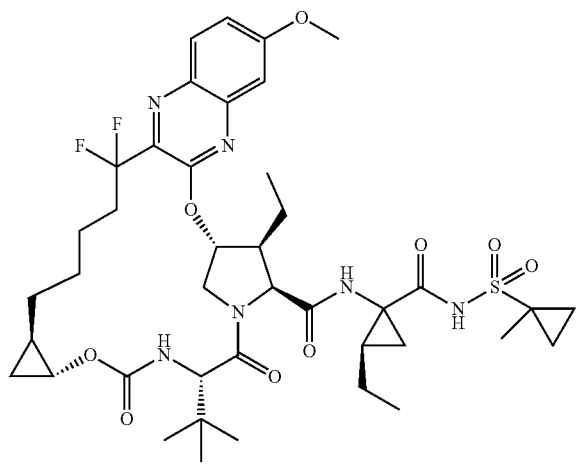

Example 93

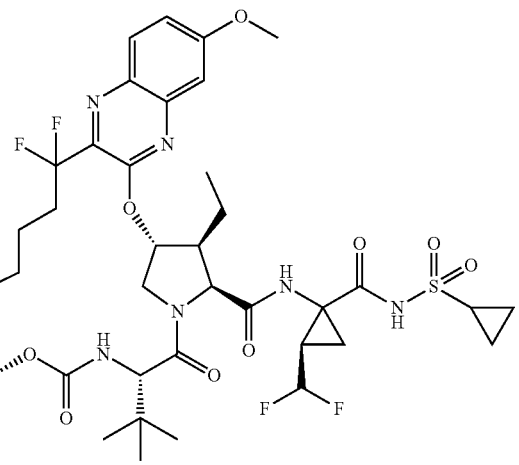

Example 94

Example 93 was prepared in a similar fashion to Example 17, substituting Intermediate A4 for Intermediate A10 in Step 7. Example 93 was isolated. Analytic HPLC RetTime: 8.03 min. LCMS-ESI$^+$ (m/z): [M+H]$^+$ calcd for $C_{41}H_{57}F_2N_6O_9S$: 847.39; found: 846.99. $^1$H NMR (400 MHz, CDCl$_3$) δ 7.95 (d, J=8.9 Hz, 1H), 7.27 (m, 1H), 7.08 (s, 1H), 6.65 (s, 1H), 5.91 (s, 1H), 5.41 (d, J=9.0 Hz, 1H), 4.82 (m, 2H), 4.47 (d, J=6.2 Hz, 1H), 4.35 (dd, J=35.7, 10.7 Hz, 2H), 4.07 (m, 1H), 3.94 (s, 3H), 3.63 (m, 1H), 2.50 (m, 2H), 1.95 (m, 2H), 1.94 (m, 2H), 1.78 (m 3H), 1.64 (m, 4H), 1.48 (m, 6H), 1.19 (m, 4H), 1.07 (s, 9H), 1.05-0.88 (m, 4H), 0.88-0.75 (m, 1H), 0.67 (m, 1H), 0.47 (m, 1H).

Example 94 was prepared in a similar fashion to Example 17, substituting Intermediate A9 for Intermediate A10 in Step 7. Example 94 was isolated. Analytic HPLC RetTime: 8.71 min. LCMS-ESI$^+$ (m/z): [M+H]$^+$ calcd for $C_{39}H_{51}F_4N_6O_9S$: 855.34; found: 855.26. $^1$H NMR (400 MHz, CDCl$_3$) δ 10.22 (s, 1H), 8.02 (d, J=9.2 Hz 1H), 7.33 (d, J=12 Hz, 1H), 7.12 (s, 1H), 5.95 (td, J$_{HF}$=52 Hz, J=8 Hz, 1H), 5.50 (d, J=9.7 Hz, 1H), 4.53 (d, J=6.4 Hz, 1H), 4.46 (dd, J=26.4, 10.7 Hz, 2H), 4.13 (d, J=11.5 Hz, 1H), 4.00 (s, 3H), 3.68 (m, 1H), 2.91 (m, 1H), 2.57 (m, 3H), 2.13 (m, 2H), 1.94 (m, 2H), 1.73 (m, 3H), 1.50 (m, 3H), 1.33 (m, 3H), 1.22 (t, J=72 Hz 3H), 1.13 (s, 9H), 1.00-0.95 (m, 4H), 0.95-0.85 (m, 1H), 0.69 (m, 1H), 0.51 (m, 1H).

Example 95

Preparation of (1aS,2aR,6S,9S,10S,11R,23aR,23bS)-6-tert-butyl-15-cyano-N-[(1R,2R)-2-(difluoromethyl)-1-{[(1-methylcyclopropyl)sulfonyl]carbamoyl}cyclopropyl]-19,19-difluoro-10-methyl-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

Example 96

Preparation of (1aS,2aR,6S,9S,10S,11R,21E,24aR,24bS)-6-tert-butyl-15-chloro-N-[(1R,2R)-2-(difluoromethyl)-1-{[(1-methylcyclopropyl)sulfonyl]carbamoyl}cyclopropyl]-10-methyl-4,7,18-trioxo-1a,2,2a,4,5,6,7,10,11,20,23,24,24a,24b-tetradecahydro-1H,9H,18H-8,11-methanocyclopropa[4',5']cyclopenta[1',2':18,19][1,10,3,6,12]dioxatriazacyclononadecino[11,12-b]quinazoline-9-carboxamide

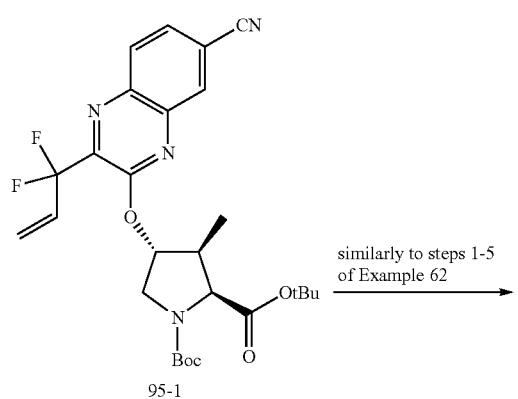

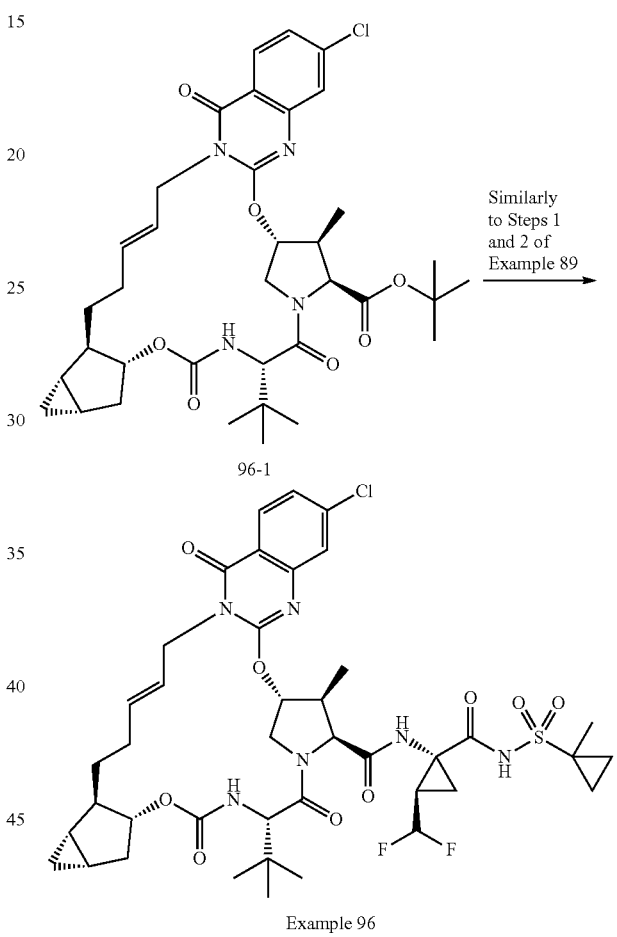

Example 95

Example 96

Intermediate 95-1 was prepared in a similar fashion to Intermediate 46-2, substituting E6 for Intermediate E3 in Step 1. LCMS-ESI+ (m/z). [M+H]+ calcd for $C_{27}H_{33}F_2N_4O_5$: 531.24; found: 531.2.

Example 95 was prepared in a similar fashion to Example 62, substituting Intermediate 95-1 for Intermediate 46-2 in Step 1 and substituting Intermediate A10 for Intermediate A9 in Step 5. Example 95 was isolated. Analytic HPLC RetTime: 8.86 min. LCMS-ESI+ (m/z): [M+H]+ calcd for $C_{42}H_{52}F_4N_7O_8S$: 890.35; found: 889.94. $^1$H NMR (400 MHz, CDCl$_3$) δ 9.34 (s, 1H), 7.80 (m, 2H), 7.42 (d, J=8.6 Hz, 1H), 6.85 (s, 1H), 6.69 (s, 1H), 5.38 (m, 1H), 5.29 (m, 3H), 5.02 (d, J=8.8 Hz, 1H) 4.46 (d J=7.4 Hz, 1H), 4.10-3.97 (m, 2H), 3.84 (d, J=7.9 Hz, 1H), 3.74 (d, J=8.6 Hz, 1H), 2.42-2.29 (m, 1H), 2.10 (s, 1H), 1.87-1.72 (m, 1H), 1.69-1.48 (m, 4H), 1.38 (d, J=14.8 Hz, 2H), 1.30-1.08 (m, 4H), 0.99 (s, 5H), 0.89 (m, 3H), 0.69 (s, 10H), 0.64 (m, 1H), 0.43 (s, 1H), 0.11 (m, 1H), 0.01 (m, 1H).

Example 96 was prepared in a similar fashion to Example 89, substituting intermediate 96-1 for intermediate 17-4 in Step 1. Intermediate 96-1 was prepared in a similar fashion to intermediate 17-4 of Example 17, substituting E9 for E3 and B1 for B4 in Step 1, and substituting intermediate D16 for intermediate D11 in Step 3. Example 96 was isolated, Analytic HPLC RetTime: 9.18 min. LCMS-ESI+ (m/z): [M+H]$^{30}$ calcd for $C_{41}H_{52}ClF_2N_6O_9S$: 877.32; found: 877.61. $^1$H NMR (400 MHz, Chloroform-d) δ 9.76 (s, 1H), 8.03 (d, J=8.6 Hz, 1H) 7.39 (m, 1H), 7.27 (m, 1H), 6.80 (s, 1H), 5.92 (m, 1H), 5.87-5.73 (m, 1H), 5.68 (m, 1H), 5.64-5.51 (m, 1H), 5.21 (m, 1H), 4.93 (m, 2H), 4.52-4.32 (m, 3H), 4.15-3.94 (m, 2H), 2:86-2.71 (m, 1H), 2.26 (m, 1H), 2.15 (m, 2H), 2.10-2.02 (m, 1H), 202-1.84 (m, 2H), 1.77 (m, 2H), 1.61 (s, 3H), 1.50 (m, 4H), 1.42-1.17 (m, 6H), 1.17-0.92 (m, 10H), 0.92-0.78 (m, 2H), 0.51-0.37 (m, 1H).

Example 97
Preparation of (1aS,2aR,6S,9S,10S,11R,23aR,23bS)-6-tert-butyl-15-cyano-N-[(2R)-2-(difluoromethyl)-1-{[(1-methylcyclopropyl)sulfonyl]carbamoyl}cyclopropyl]-10-methyl-4,7-dioxo-1a,2,2a,4,5,6,7,10,11,19,20,21,22,23,23a,23b-hexadecahydro-1H, 9H-8,11-methanocyclopropa[4',5']cyclopenta[1',2':18,19][1,10,3,6]dioxadiazacyclononadecino[11,12-b]quinoxaline-9-carboxamide
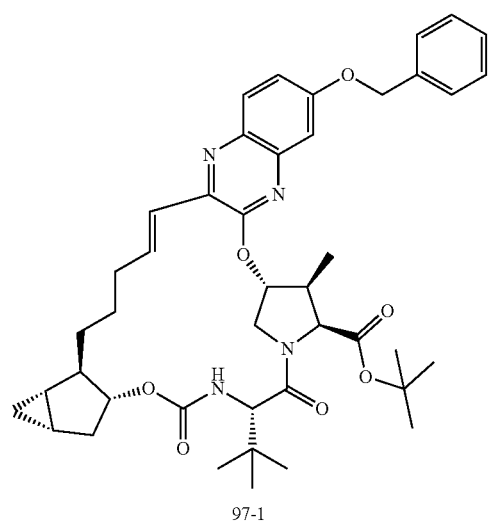
97-1
Step 1 →
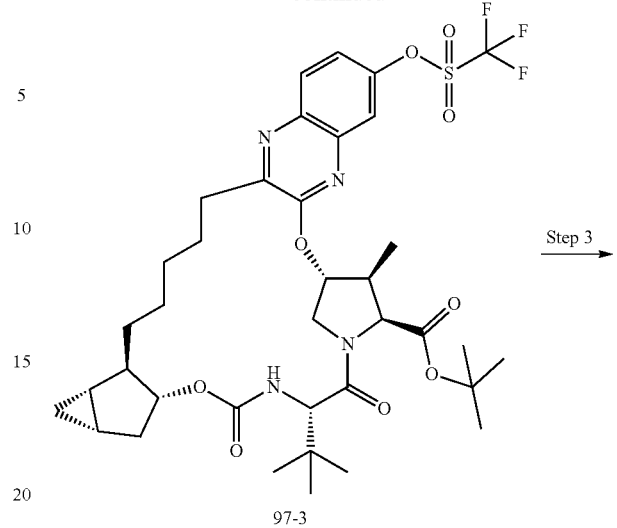
97-3
Step 3 →
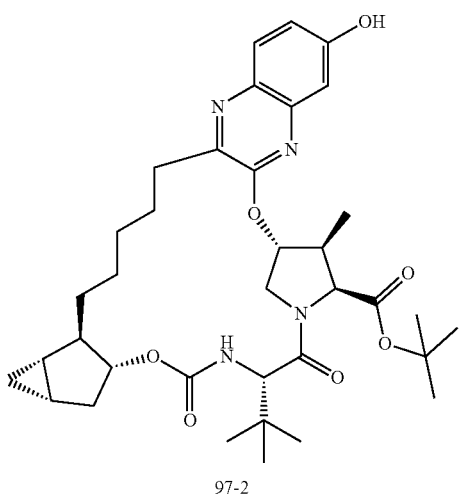
97-2
Step 2 →
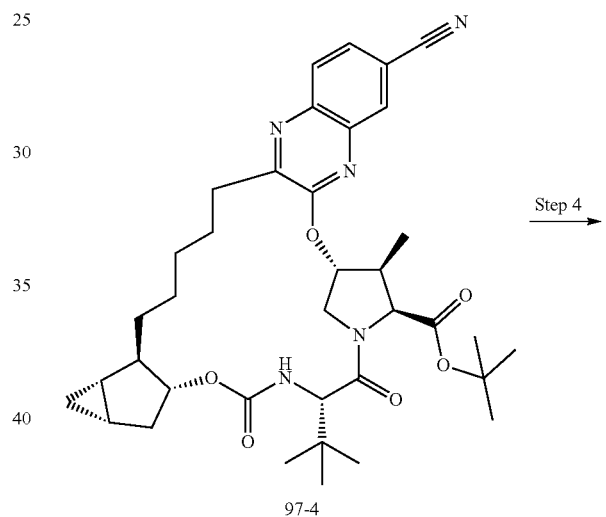
97-4
Step 4 →
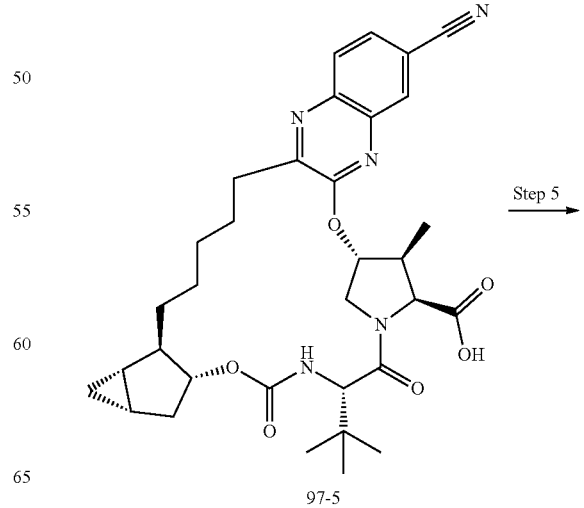
97-5
Step 5 →

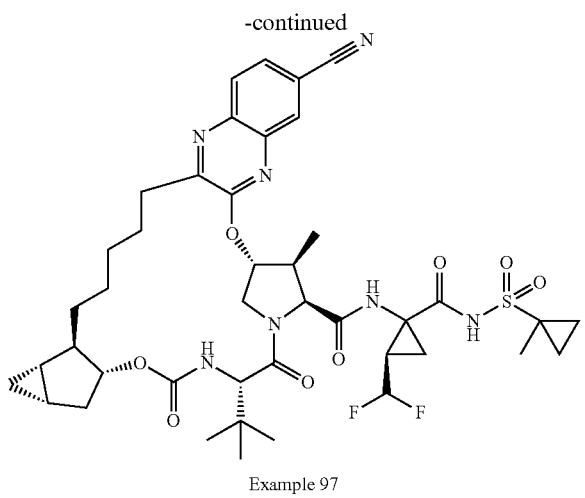

Example 97

Intermediate 97-1 was prepared in a similar fashion to intermediate 79-5, substituting E2 for E5 in Step 1. LCMS-ESI+ (m/z): [M+H]+ calcd for $C_{43}H_{55}N_4O_7$: 739.41 found: 739.31.

Step 1. Preparation of 97-2. Macrocyclic olefin 97-1 (0.84 g, 1.14 mmol) was dissolved in 114 mL ethanol and 114 mL ethyl acetate After degassing with Argon, 0.84 g of 5% Pd/C Degussa-type was added and the mixture was hydrogenated for 4 hours at 1 atm. Filtration through celite, concentration, and silica gel chromatography (40%-60% ethyl acetate in hexanes gradient) provided intermediate 97-2. LCMS-ESI+ (m/z): [M+H]+ calcd for $C_{36}H_{51}N_4O_7$: 651.38; found: 651.32.

Step 2. Preparation of 97-3. An ice cold solution of macrocycle phenol 97-2 (0.47 g, 0.73 mmol) and triethylamine (0.81 ml, 5.81 mmol) in 3 mL DCM was treated with trifluoromethanesulfonic anhydride solution, 1 M in methylene chloride (0.18 ml, 1.09 mmol) dropwise. After stirring for 2 hours, the reaction was quenched with water and extracted with ethyl acetate. The organic layer was washed with water and brine, dried over $Na_2SO_4$, filtered and concentrated. Silica gel chromatography using a 5%-50% ethyl acetate in hexanes gradient gave 97-3 as the first eluting peak (55 mg). LCMS-ESI+ (m/z): [M+H]+ calcd for $C_{37}H_{50}F_3N_4O_9S$: 783.33; found: 782.96.

Step 3. Preparation of 97-4. Degassed a mixture of macrocycle triflate 97-3 (408 mg, 0.52 mmol), tetrakis(triphenylphosphine)palladium (30.11 mg, 0.03 mmol), Zinc cyanide, 98% (61.21 mg, 0.52 mmol) in 2.6 mL DMF for 10 minutes. The reaction was heated at 80° C. for 1 hour. An additional 60 mg tetrakis(triphenylphosphine)palladium and 120 mg Zinc cyanide were added and heating was continued for 30 minutes. The reaction was quenched with saturated ammonium chloride solution and extracted with ethyl acetate. The organic phase was separated, dried over anhydrous sodium sulphate, filtered and concentrated. The crude product was purified by silica gel chromatography using a gradient of 5%-70% ethyl acetate in hexanes to give intermediate 97-4. LCMS-ESI+ (m/z): [M+H]+ calcd for $C_{37}H_{50}N_5O_5$: 660.38; found: 660.10.

Step 4. Preparation of 97-5. A solution of 97-4 (290 mg, 0.44 mmol) in 1 mL DCM was treated with 0.5 mL of TFA and stirred overnight. Water was added and the mixture was extracted with ethyl acetate. The organic phase was separated, dried over anhydrous sodium sulphate, filtered and concentrated. The crude product was purified by silica gel chromatography using a gradient of 10%-70% ethyl acetate in hexanes to give intermediate 97-5 (216 mg) as a white solid. LCMS-ESI+ (m/z): [M+H]+ calcd for $C_{33}H_{42}N_5O_6$: 604.31; found: 604.00.

Step 5. Preparation of Example 97. A mixture of 97-5 (50 mg, 0.08 mmol), HATU (37.79 mg, 0.1 mmol), in 0.3 mL DMF was stirred 5 min, then A10 (50 mg, 0.08 mmol) and DIPEA (0.06 ml, 0.33 mmol) were added. After 45 min at rt, the reaction was incomplete (LCMS). Added another 20 mg of A10 and stirred for 2 hours, 2 mL of 1 N HCl was added, and the mixture was extracted with DCM. The crude product was purified by silica gel chromatography using a gradient of 30%-65% ethyl acetate in hexanes. Combined product fractions contained some residual DMF. Water was added, which generated a precipitate (14 mg). The filtrate was extracted with ethyl acetate, and the extracts were combined with the precipitate. The resulting solution was dried over anhydrous sodium sulphate, filtered, concentrated and dried under reduced pressure to give Example 97. Analytic HPLC RetTime: 9.06 min. LCMS-ESI+ (m/z): [M+H]+ calcd for $C_{42}H_{54}F_2N_7O_8S$: 854.98; found: 853.88. 1H NMR (400 MHz, $CDCl_3$) δ 9.77 (br s, 1H), 8.05 (m, 1H), 7.93 (m, 1H), 7.62 (m, 1H), 7.20 (m, 1H), 7.08 (m, 1H), 6-5.65 (m, 1H), 5.56 (m, 1H), 5.17 (m, 1H), 4.90 (m, 1H), 4.38 (m, 2H), 4.22 (m, 1H), 4.06 (m, 1H), 3.57 (m, 1H), 2.88 (m, 1H), 2.70 (m, 5H), 2.28-2.08 (m, 1H), 2.04-1.30 (m, 12H), 1.29-1.09 (m, 9H), 1.08-0.96 (m, 4H), 0.85-0.67 (m, 3H), 0.43 (m, 1H), 0.34 (m, 1H), 0.19-0.03 (m, 1H).

The following compounds can be made with the synthetic methods of this disclosure, or by means generally well known in the art:

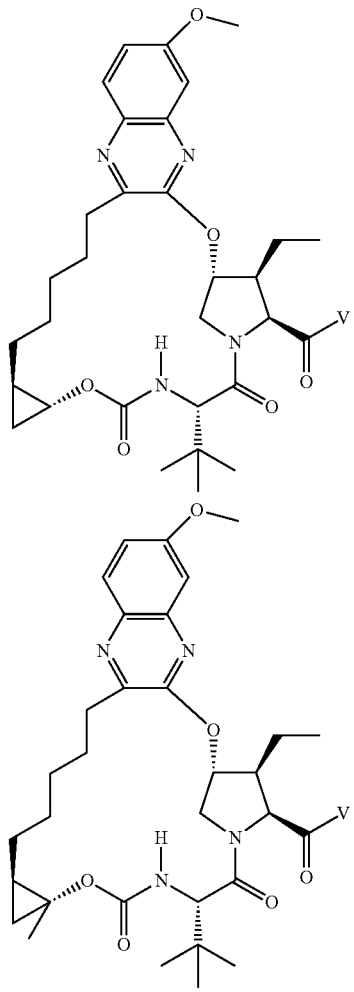

389
-continued
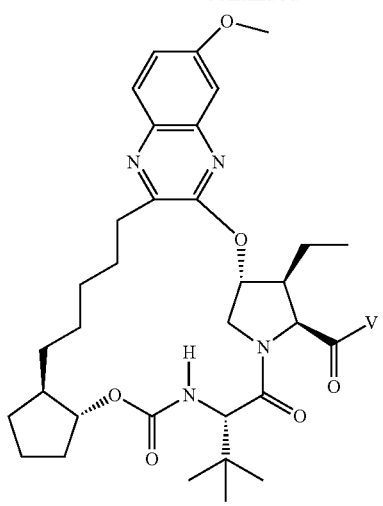
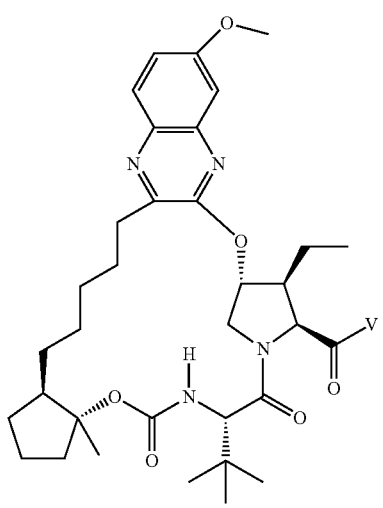
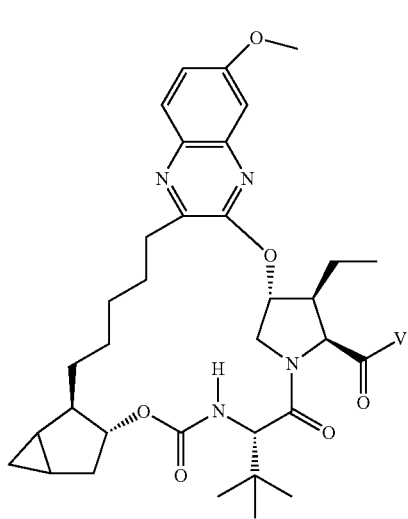
390
-continued
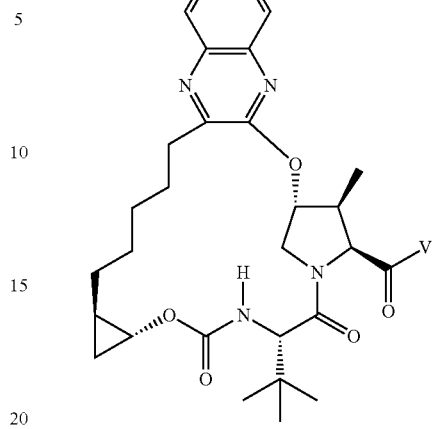
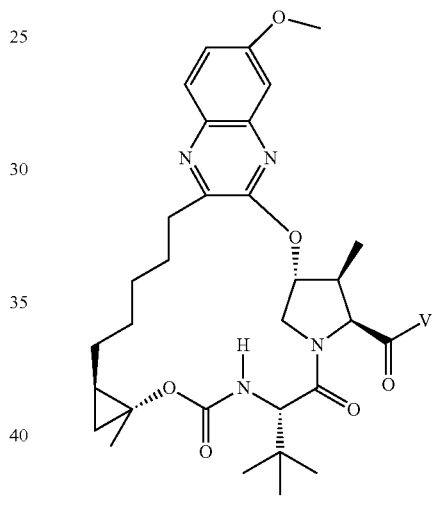
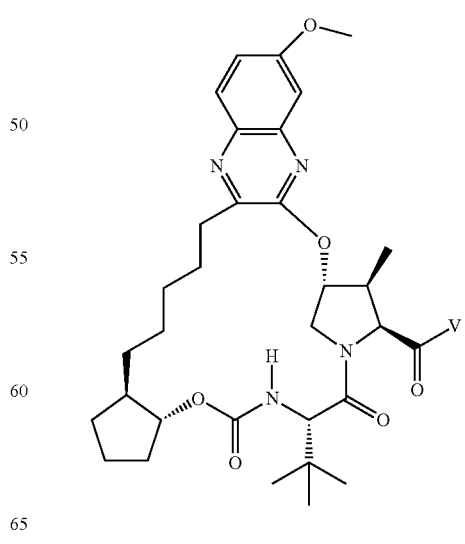

391
-continued
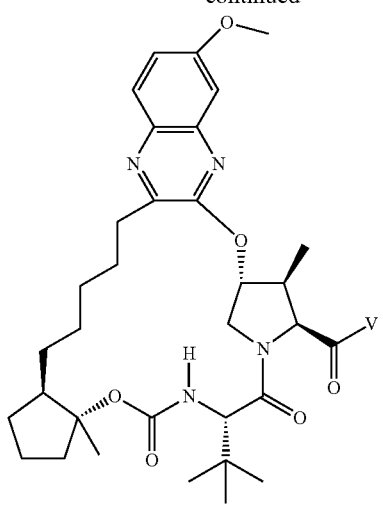
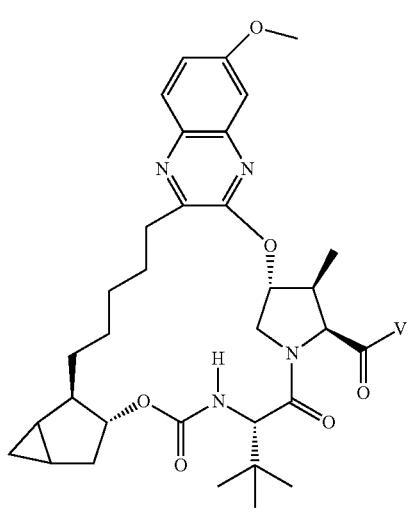
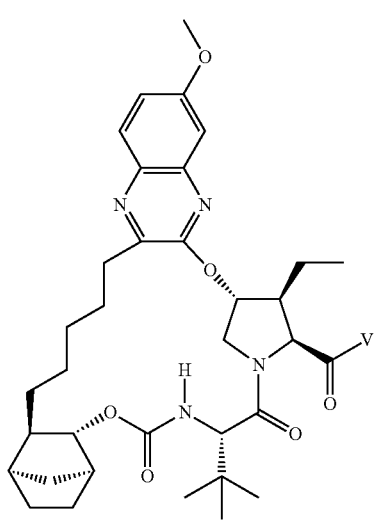
392
-continued
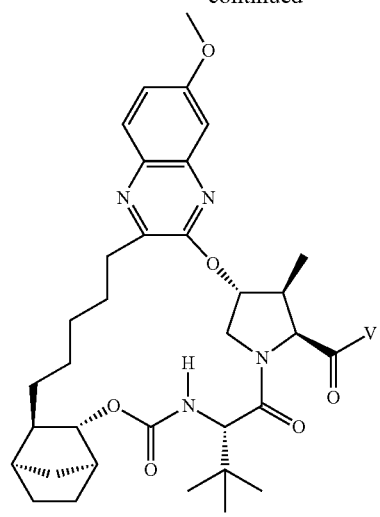
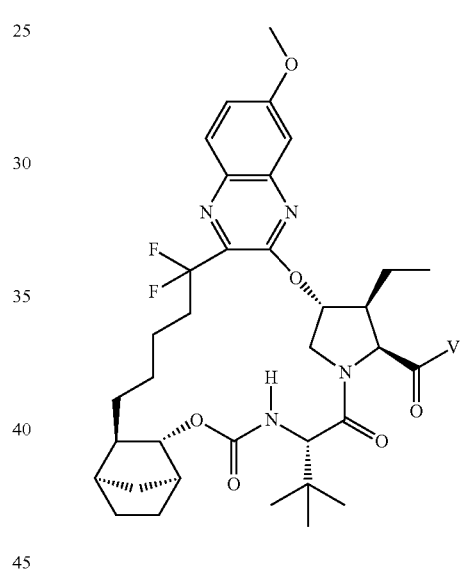
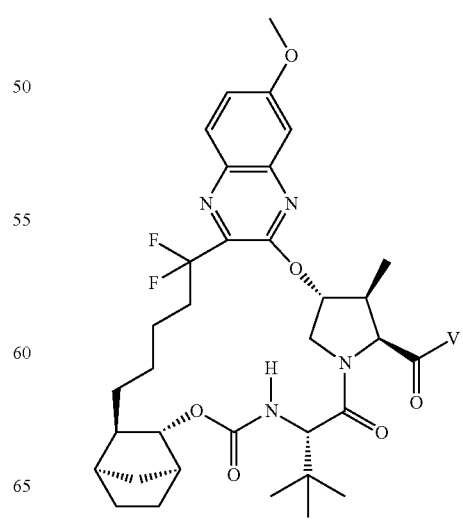

393
-continued
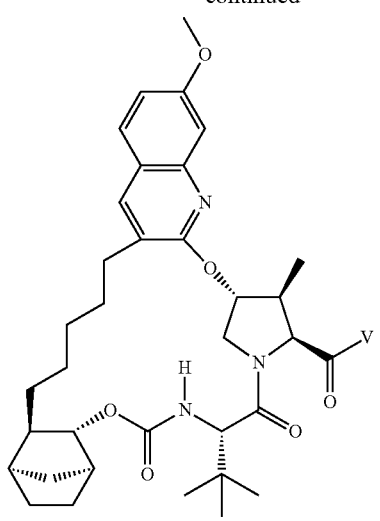
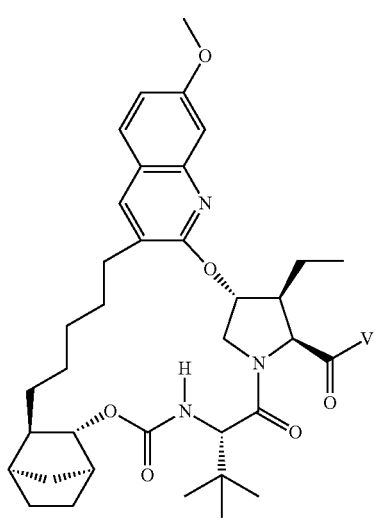
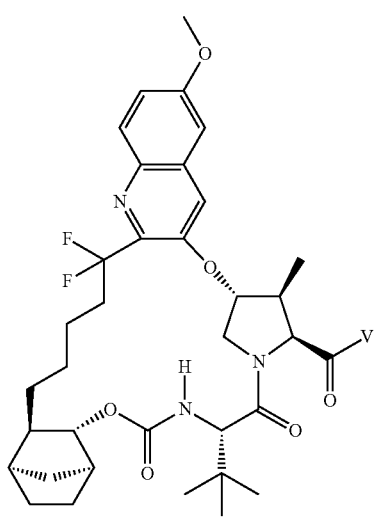
394
-continued
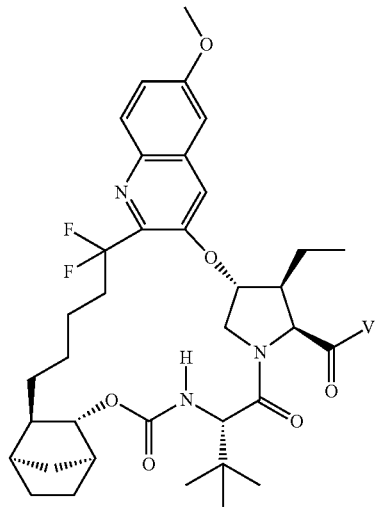
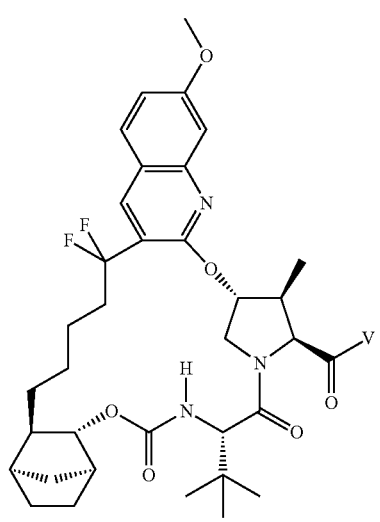
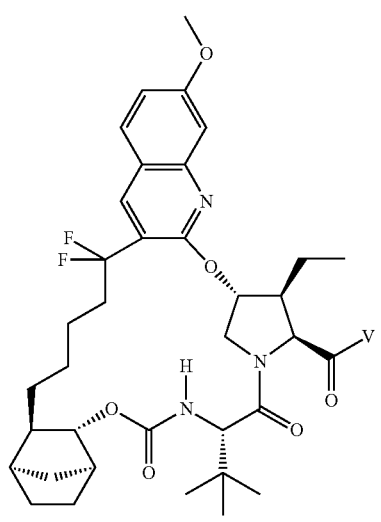

395
-continued
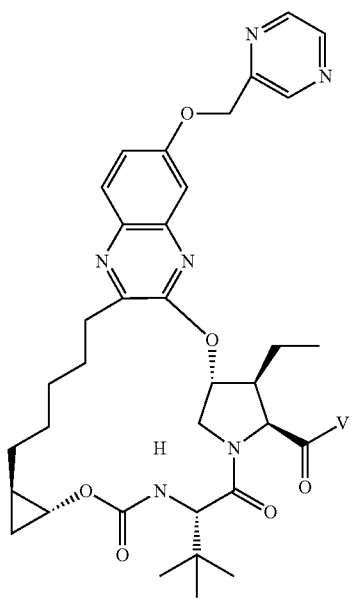
396
-continued
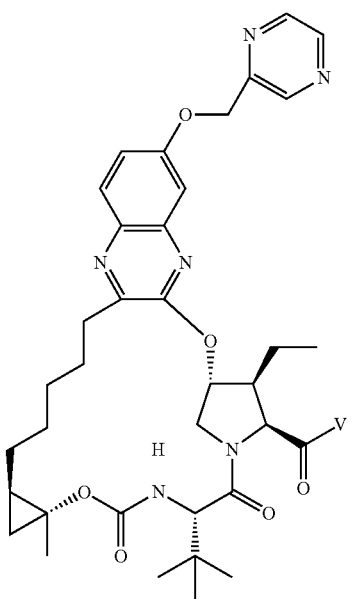
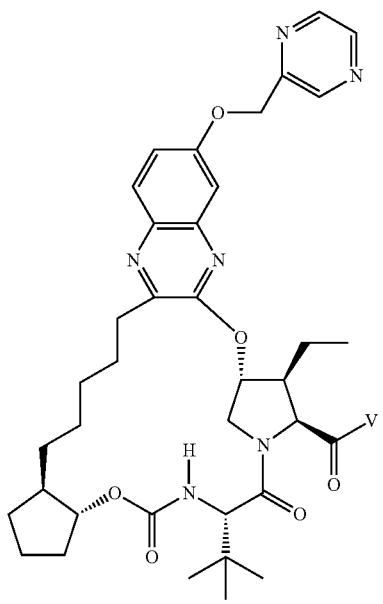
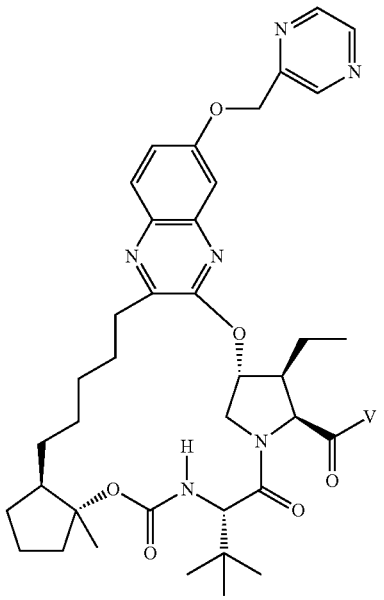

397
-continued
398
-continued
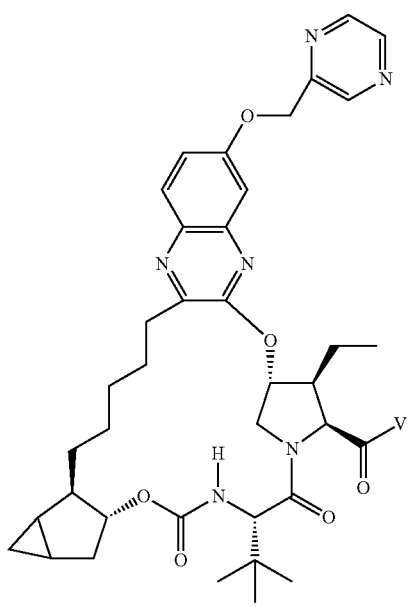
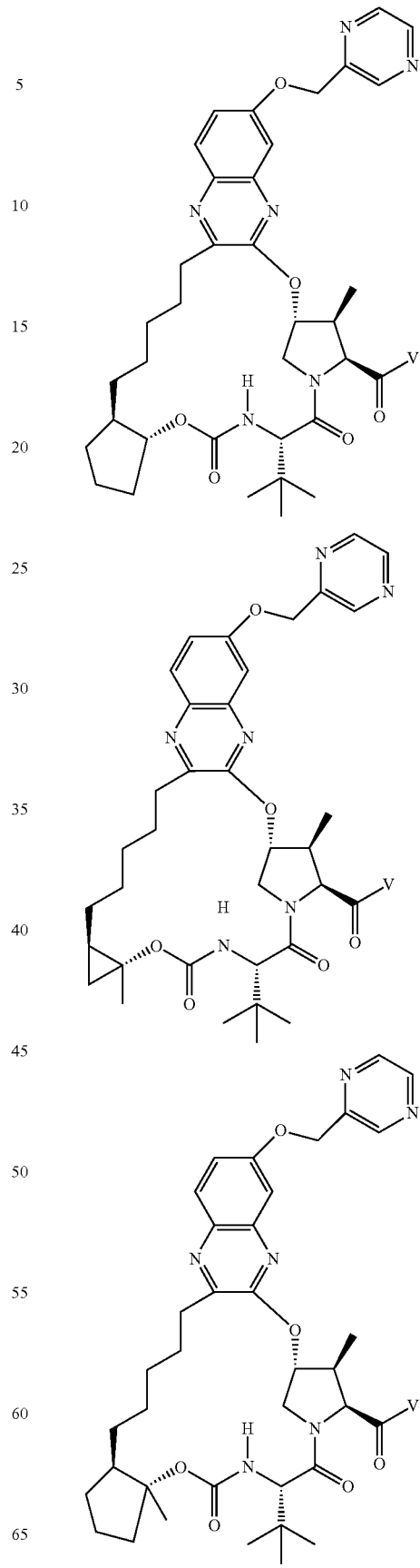

399
-continued
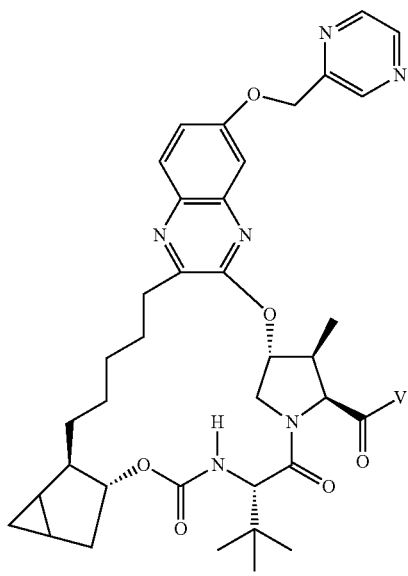
400
-continued
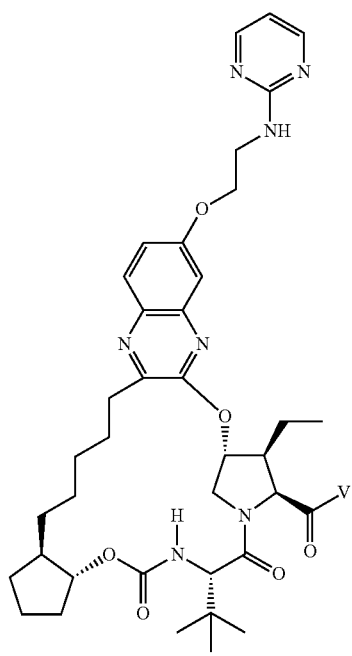
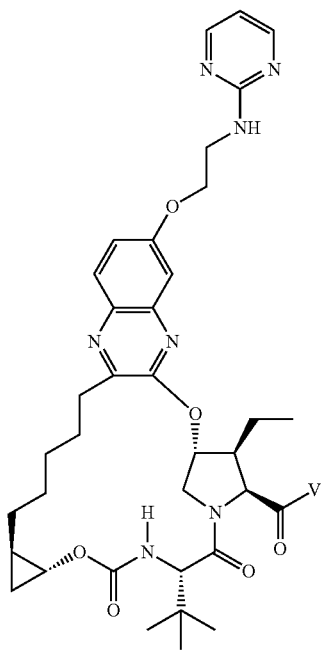
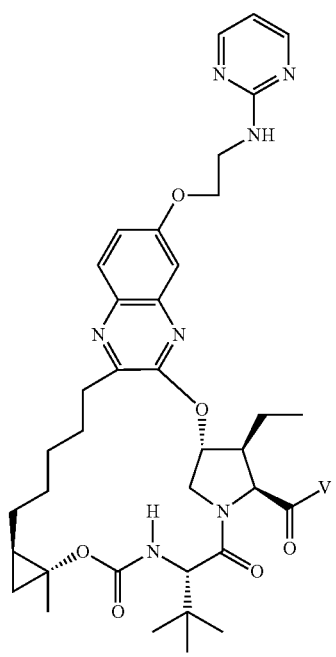

401
-continued
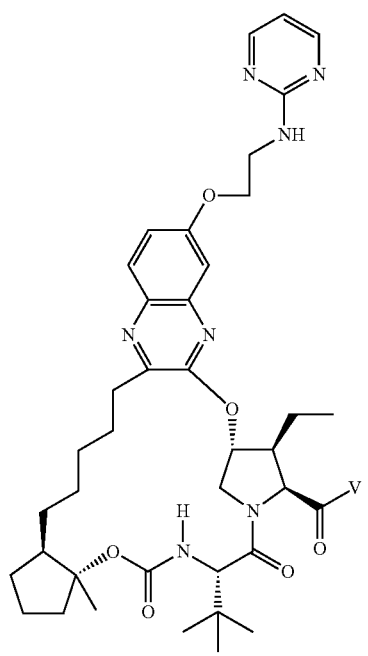
402
-continued
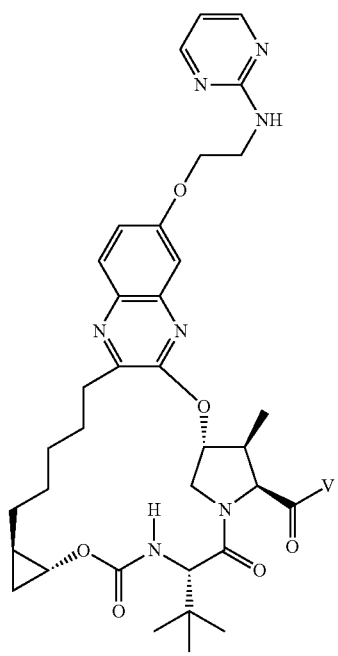
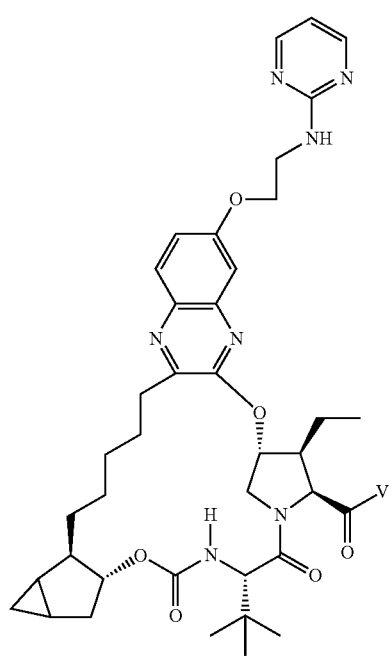
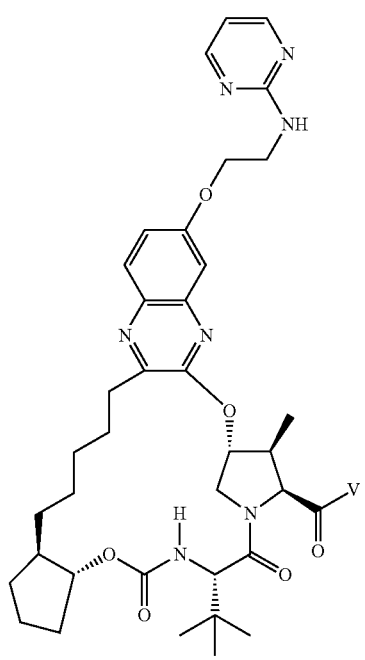

403
-continued
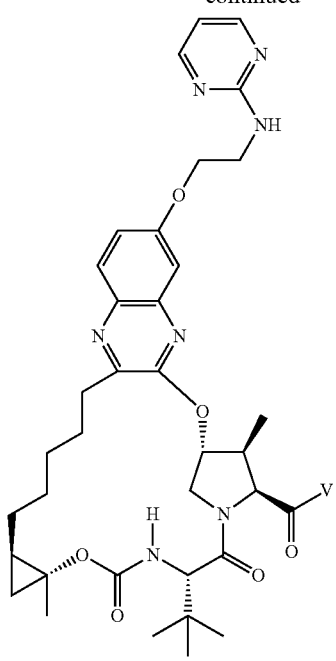
404
-continued
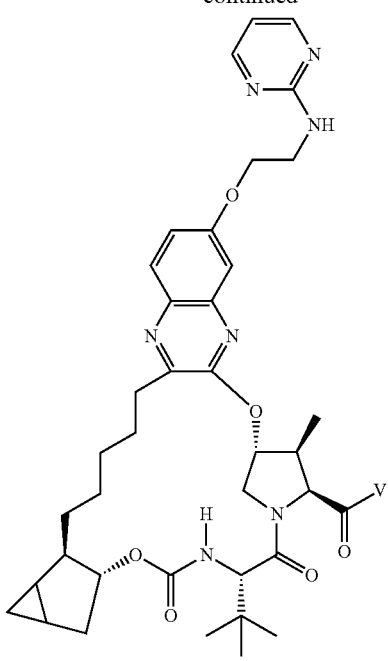
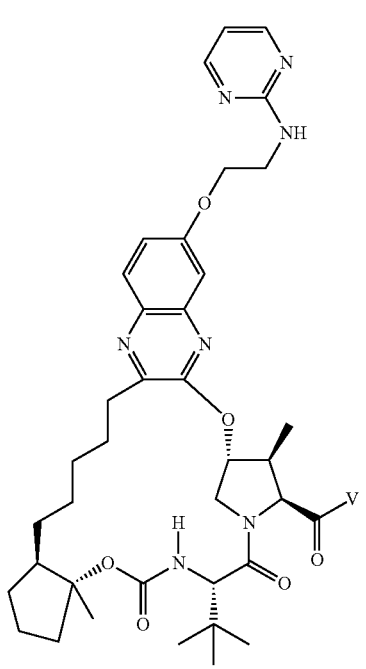
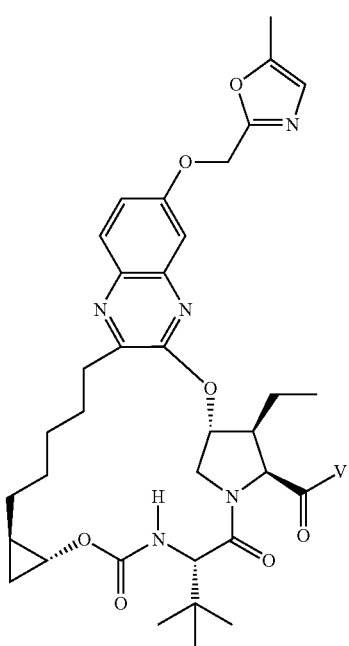

405
-continued
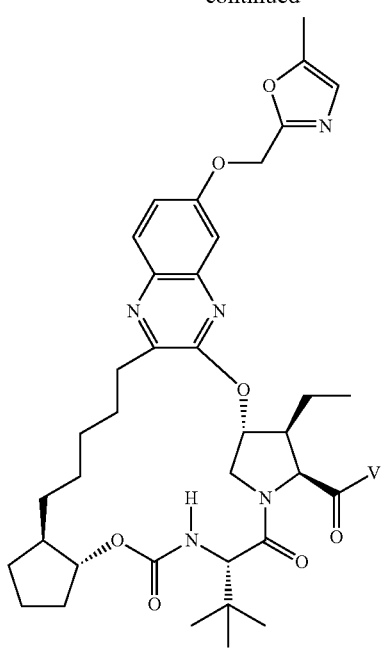
406
-continued
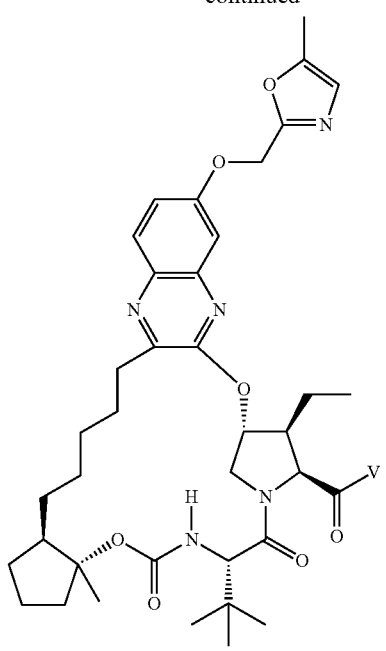
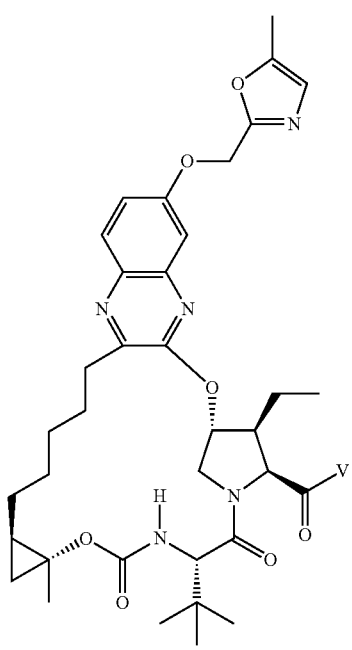
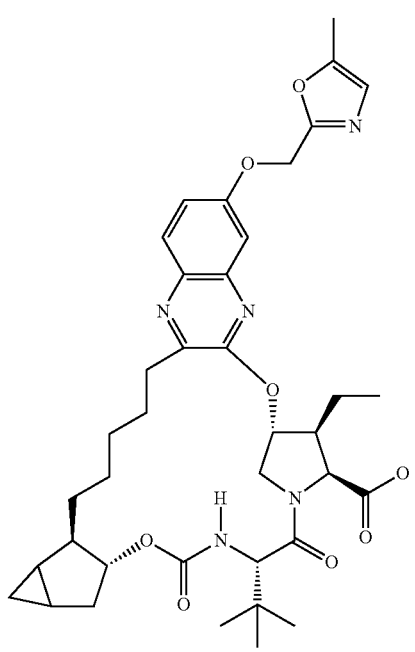

407
-continued
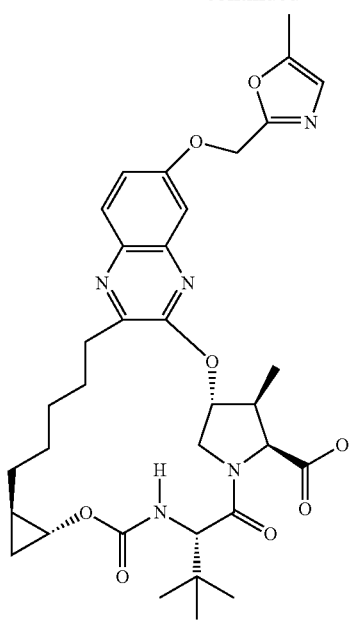
408
-continued
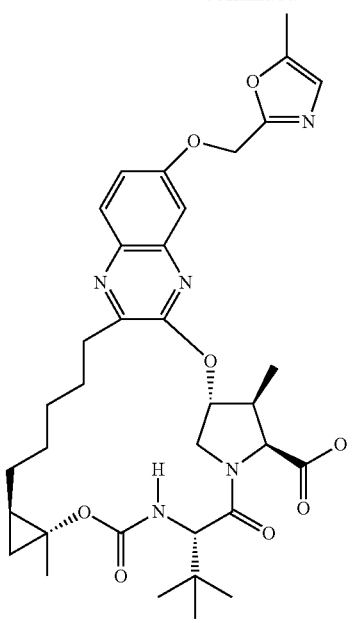
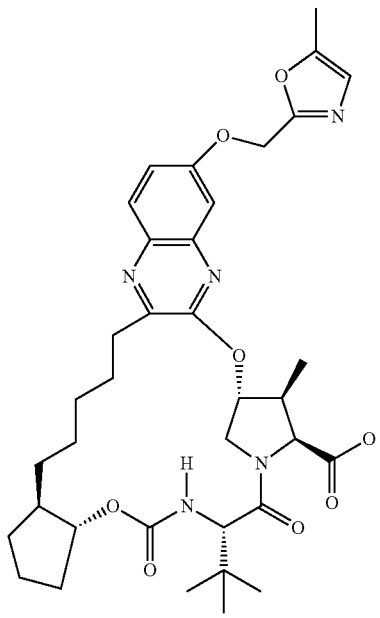
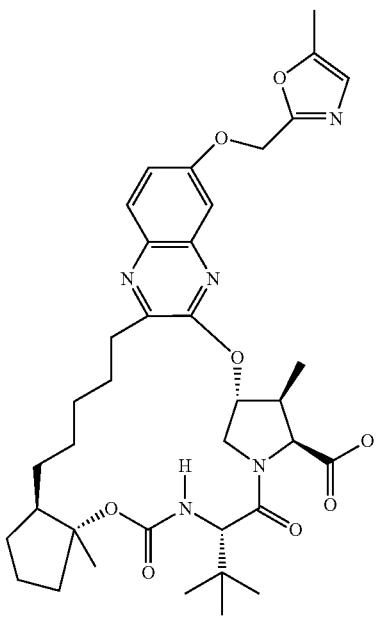

409
-continued
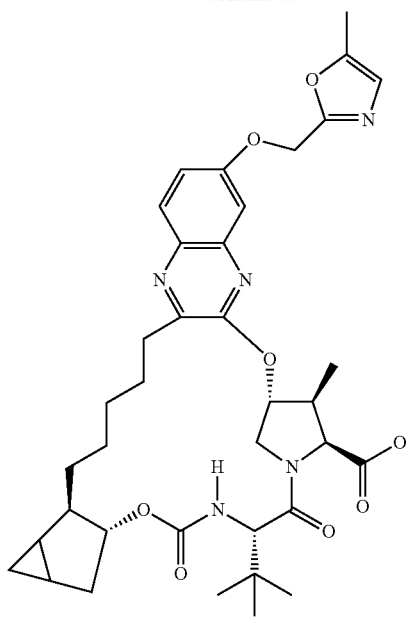
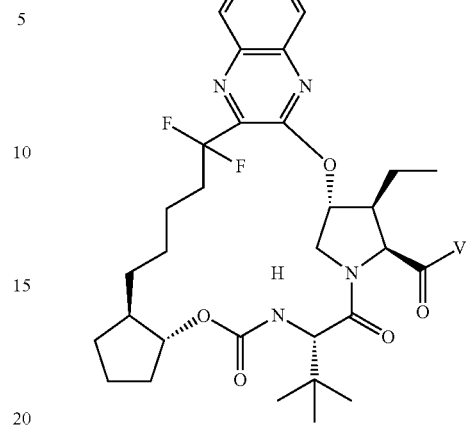
410
-continued
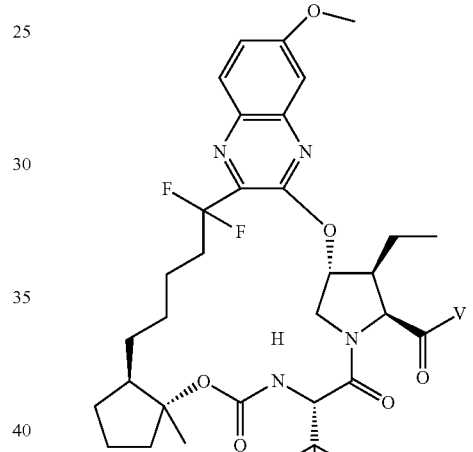
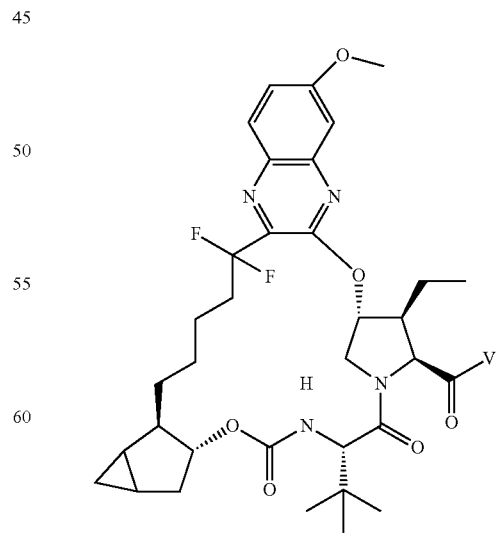

411
-continued
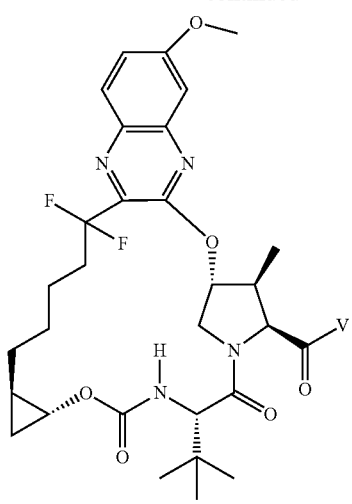
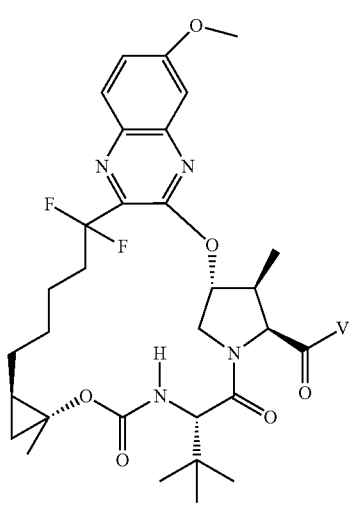
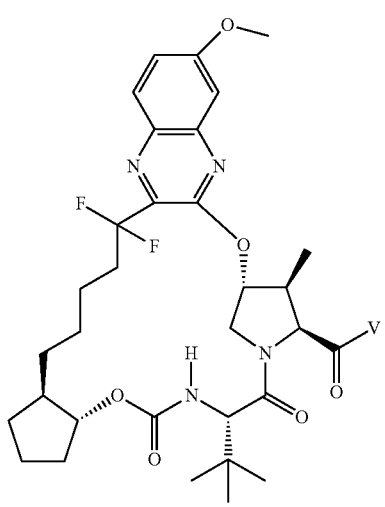
412
-continued
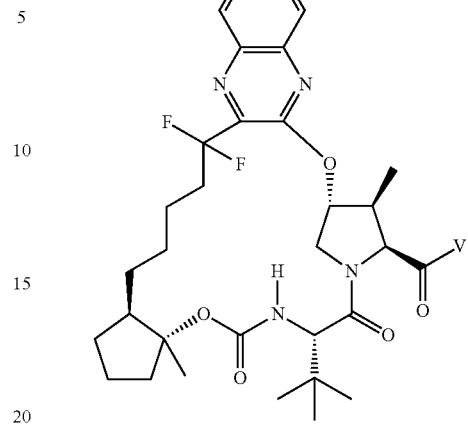
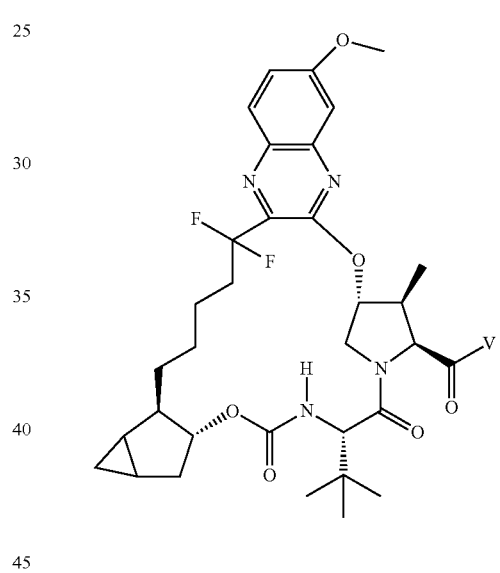
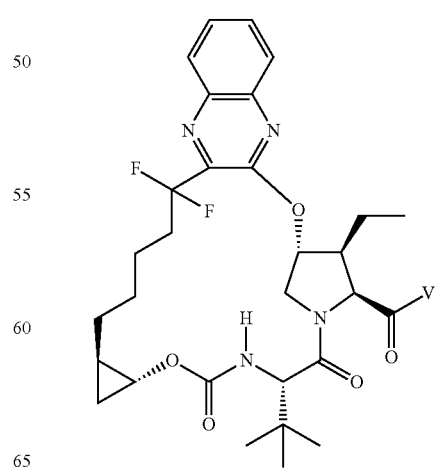

413
-continued
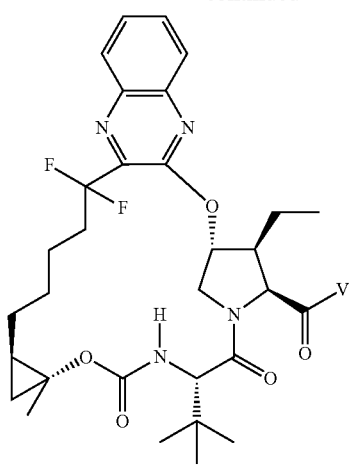
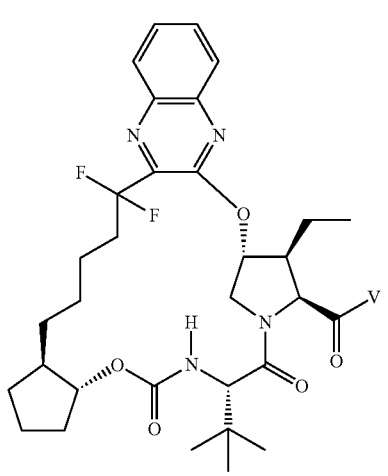
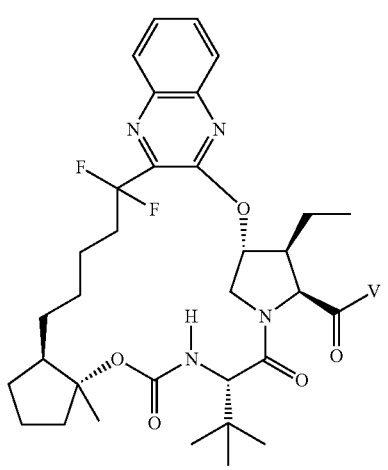
414
-continued
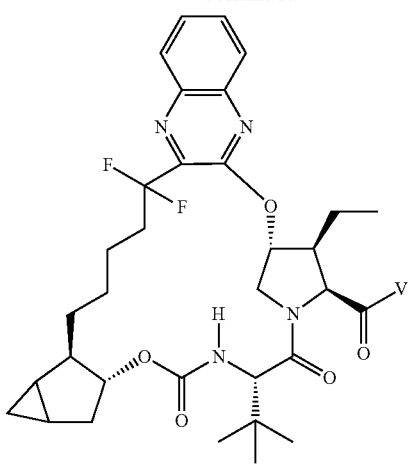
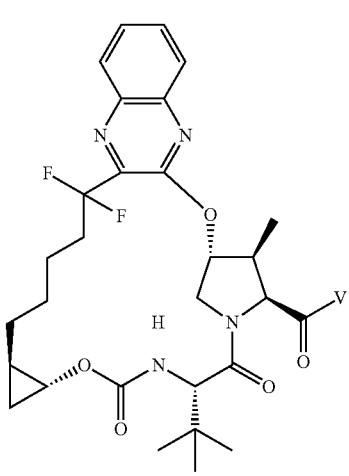
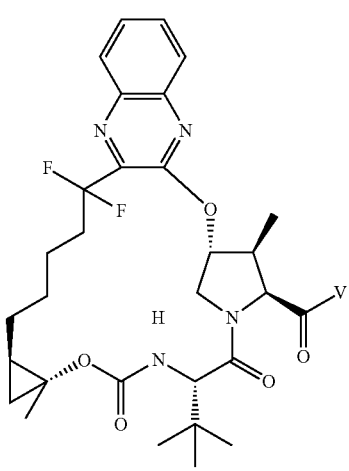

415
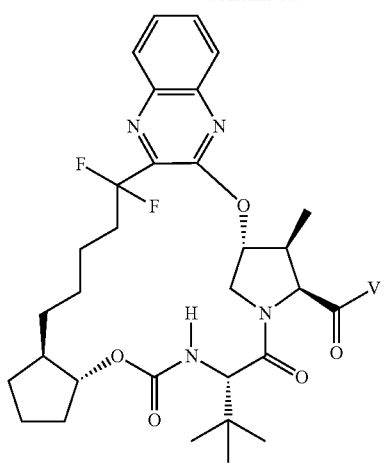
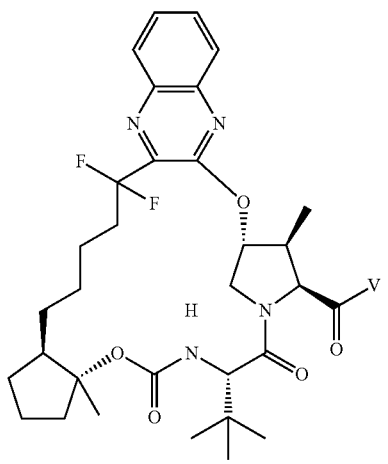
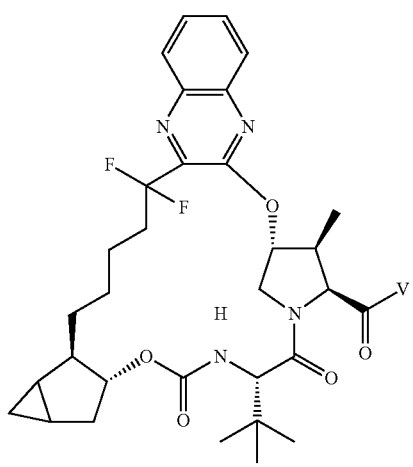
416
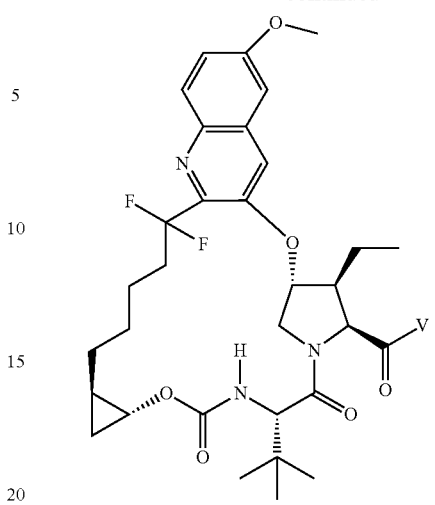
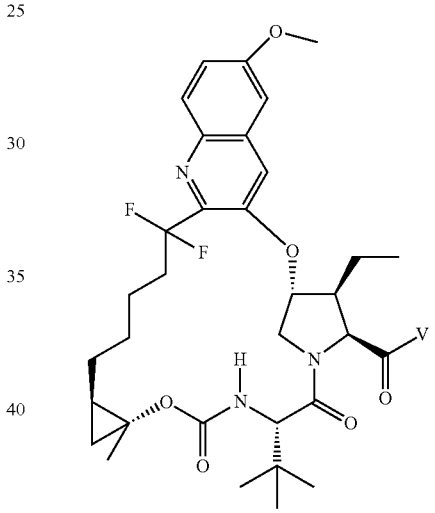
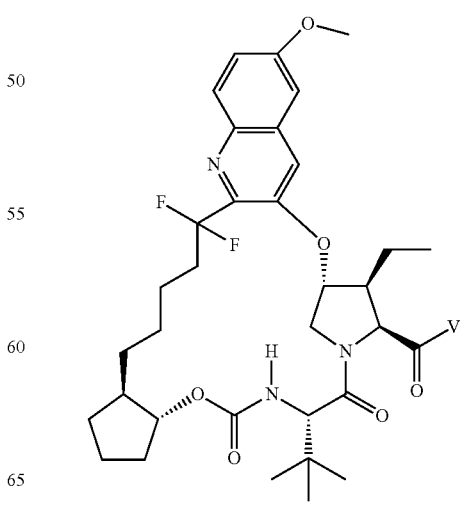

417
-continued
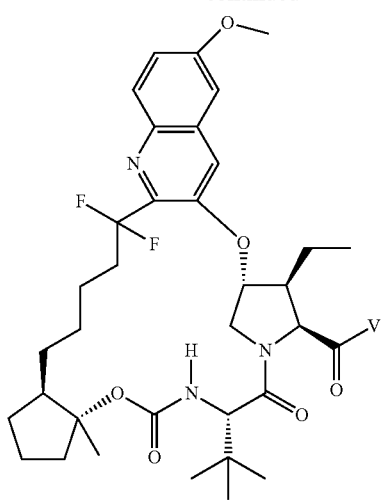
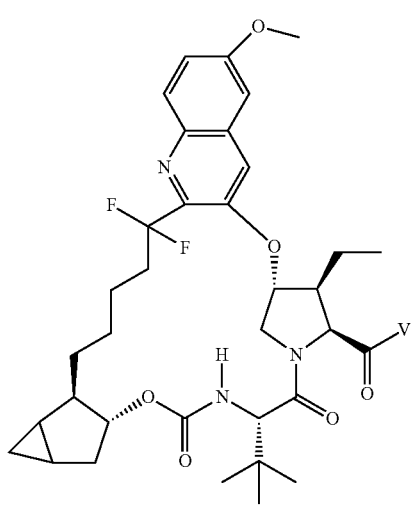
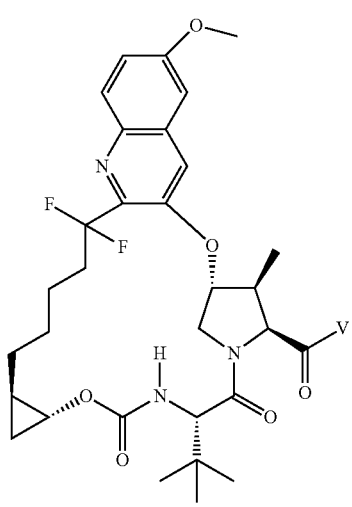
418
-continued
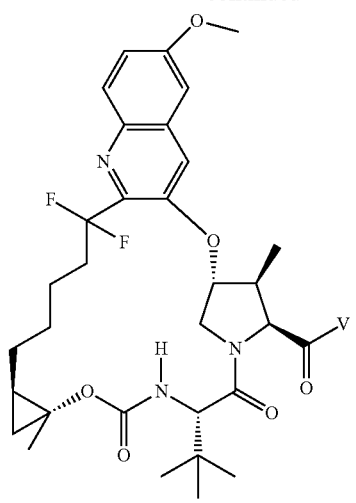
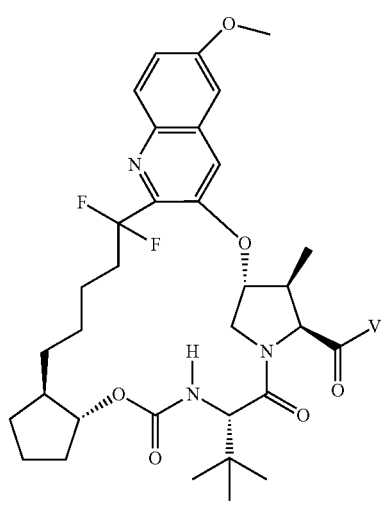
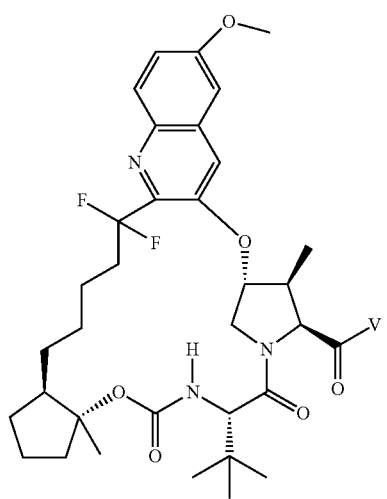

419
-continued
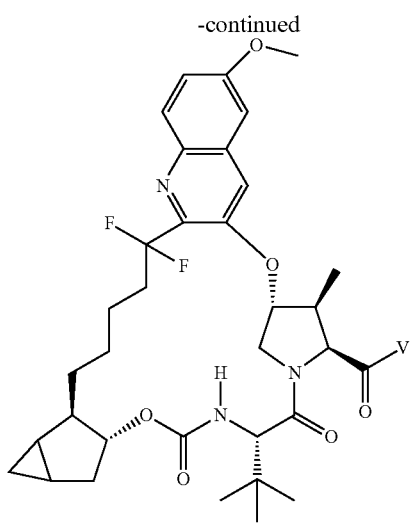
420
-continued
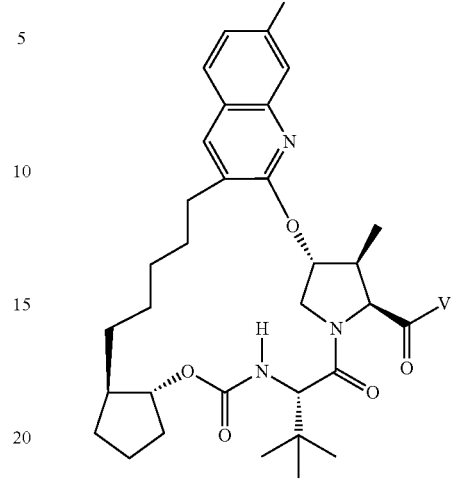
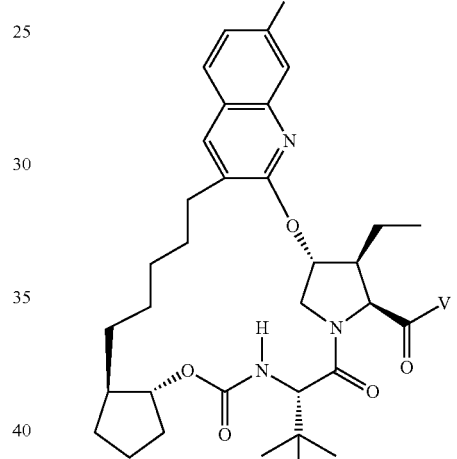
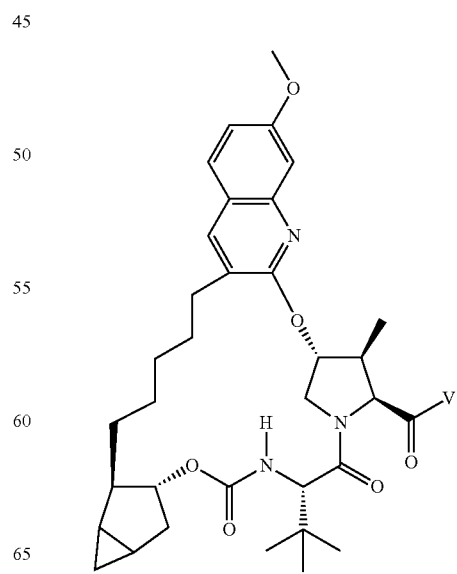

421
-continued
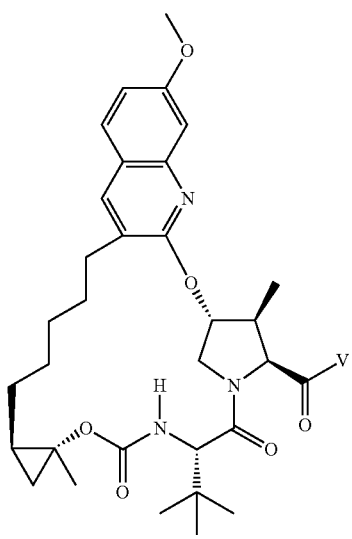
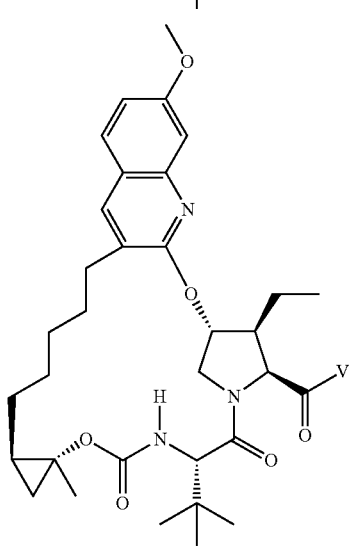
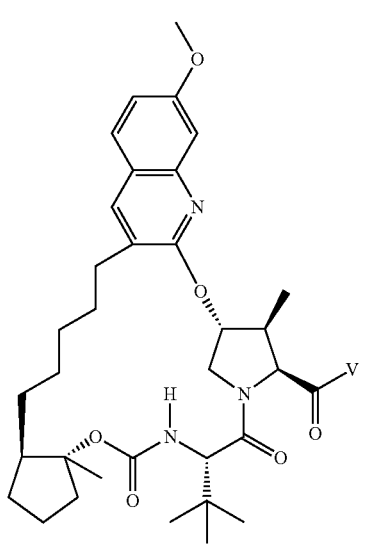
422
-continued
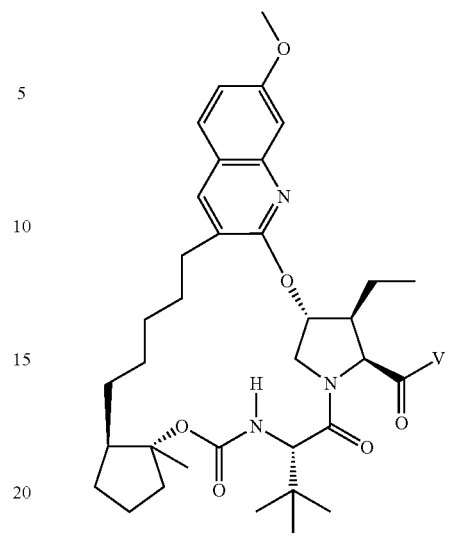
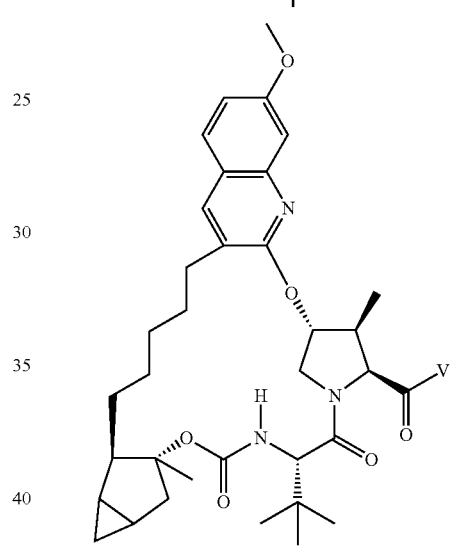
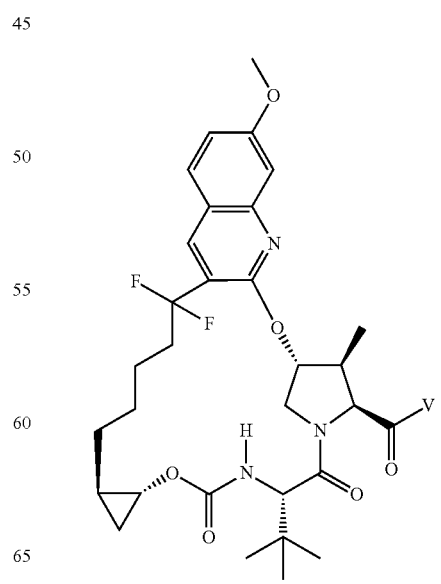

423
-continued
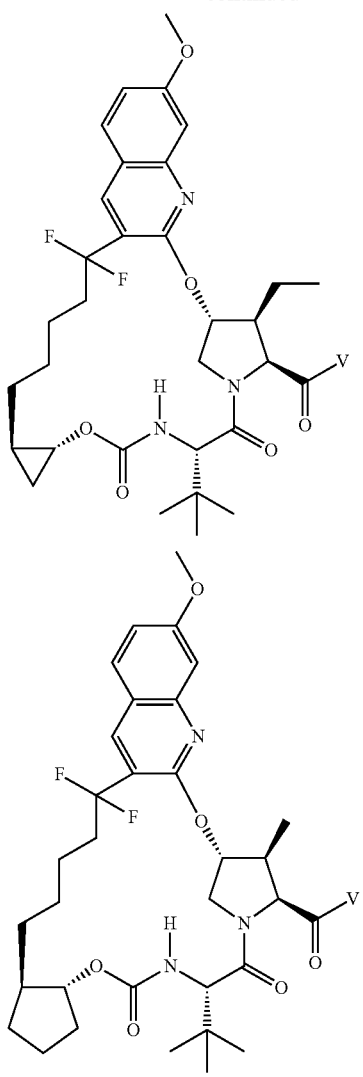
424
-continued
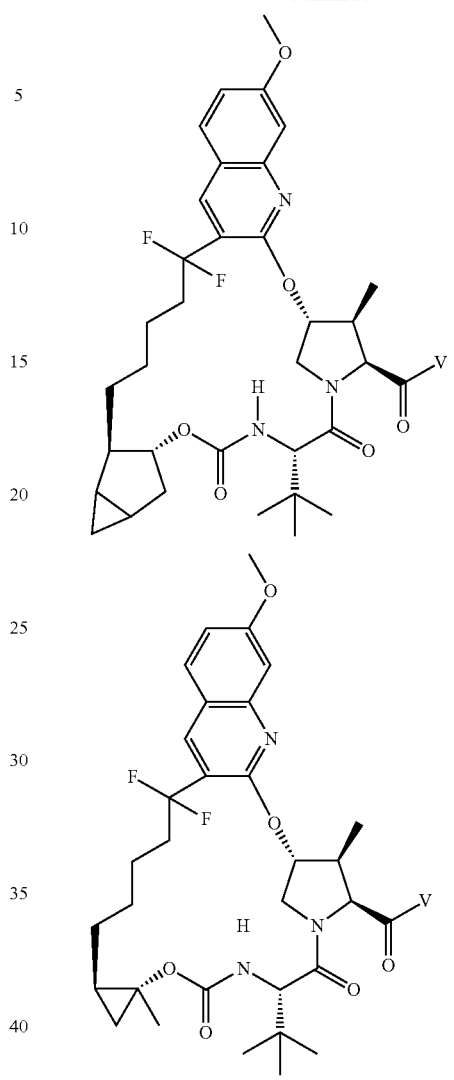
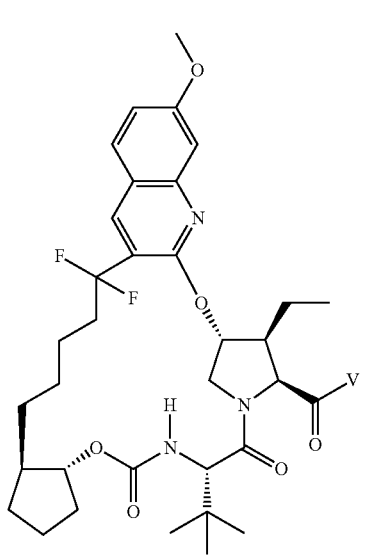

425
-continued
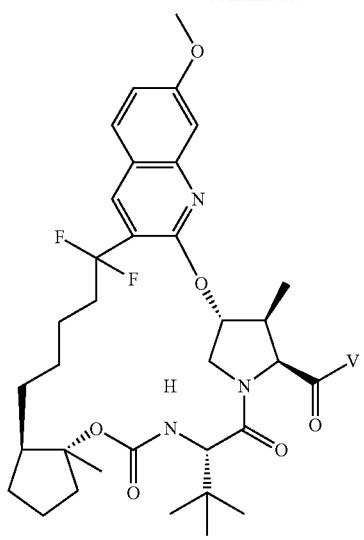
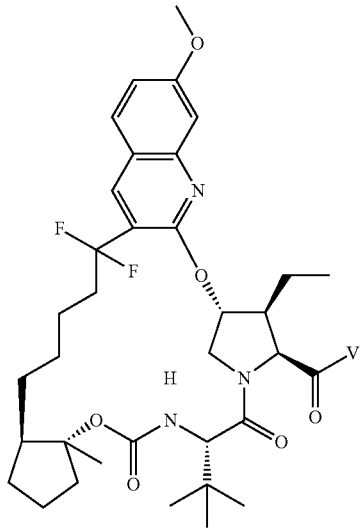
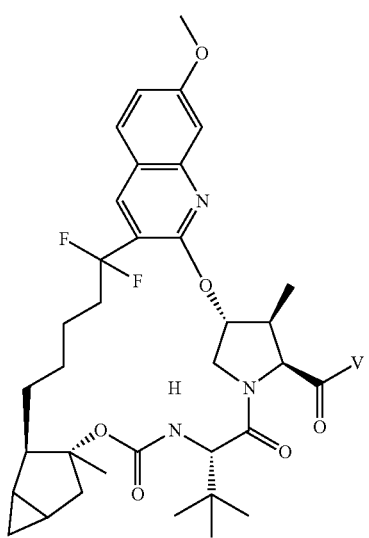
426
-continued
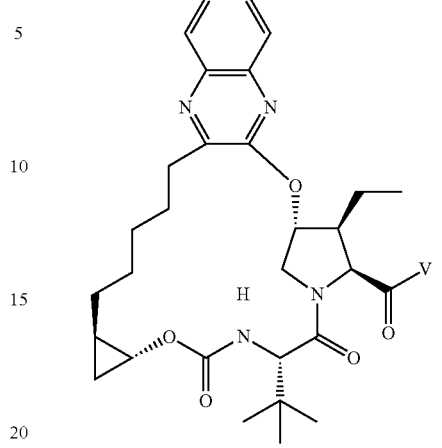
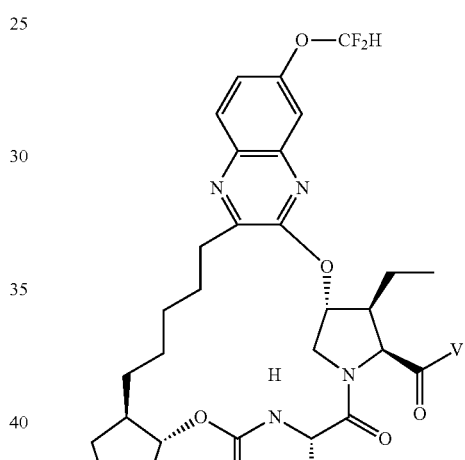
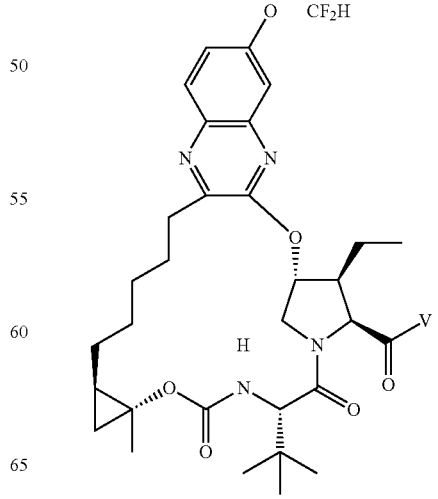

427
-continued
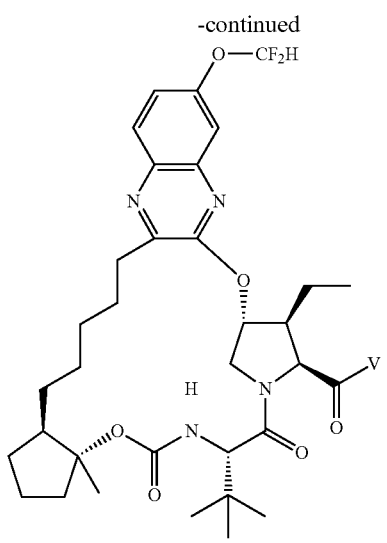
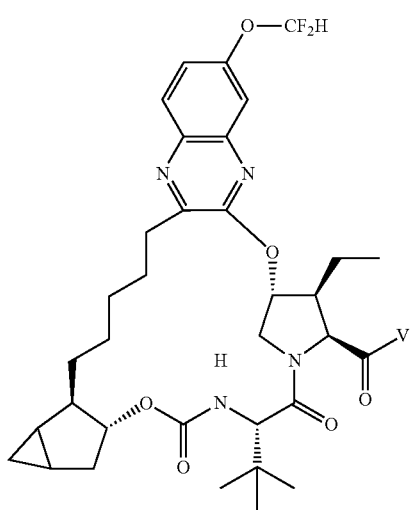
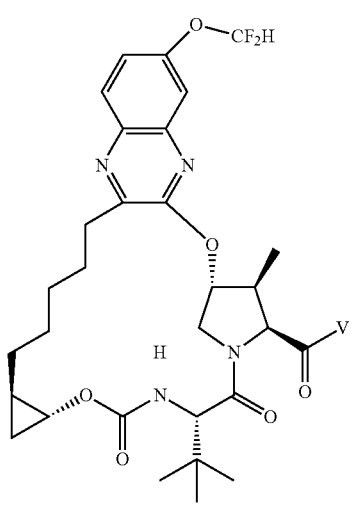
428
-continued
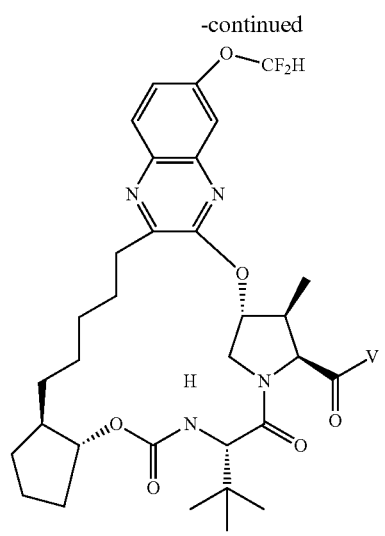
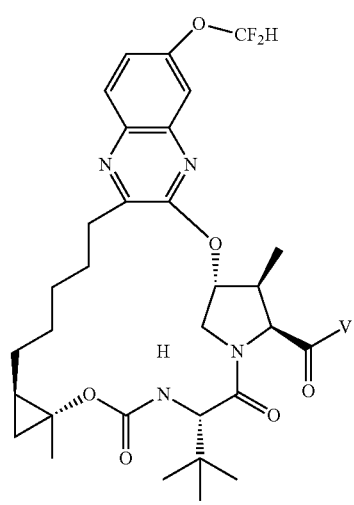
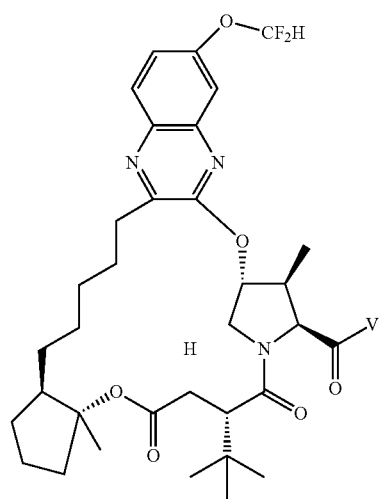

429
-continued
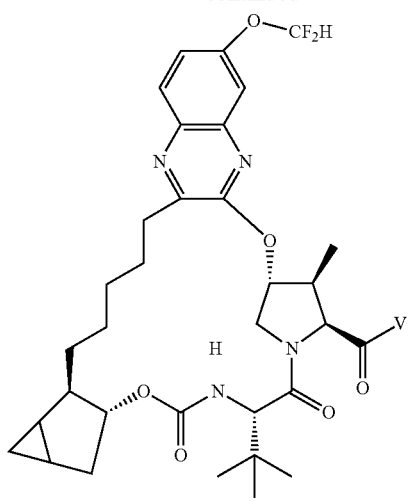
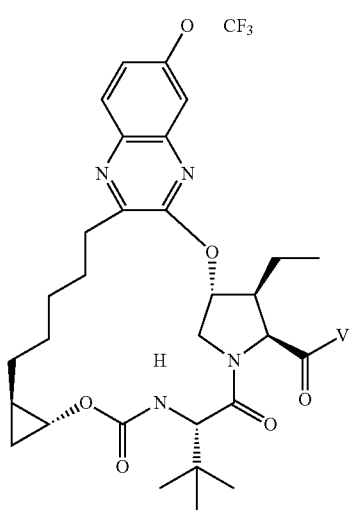
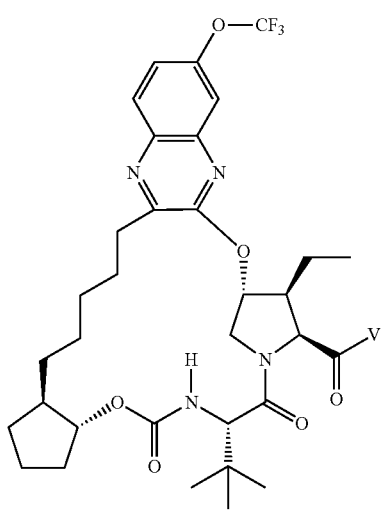
430
-continued
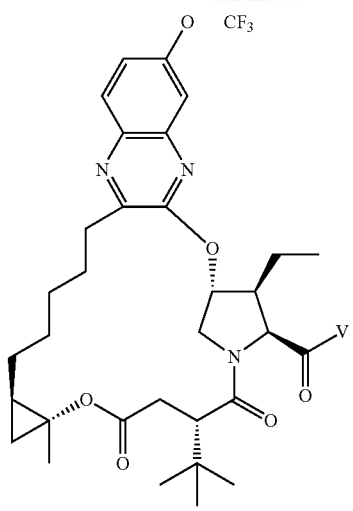
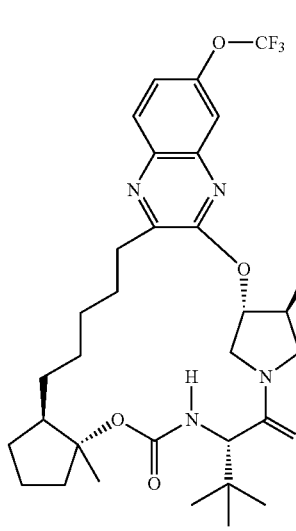
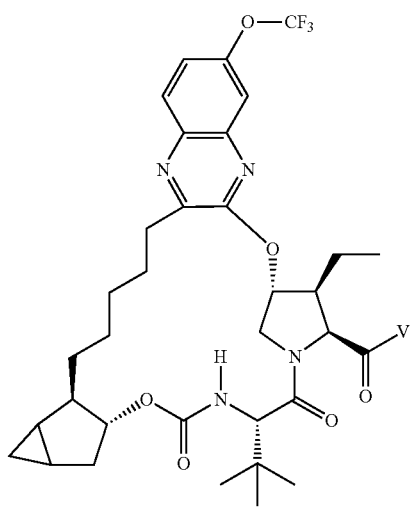

431
-continued
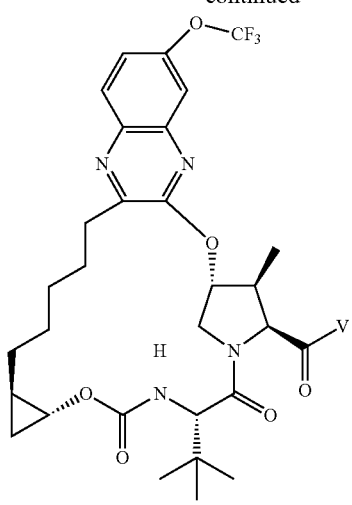
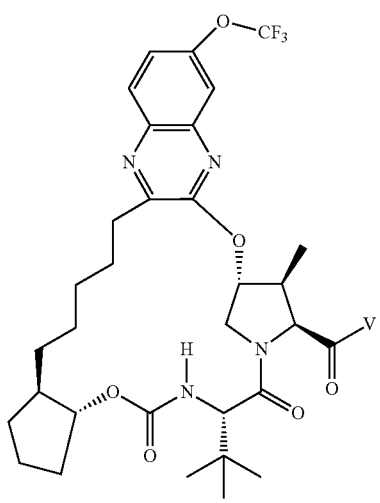
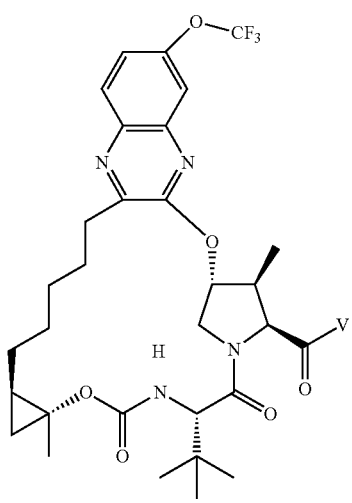
432
-continued
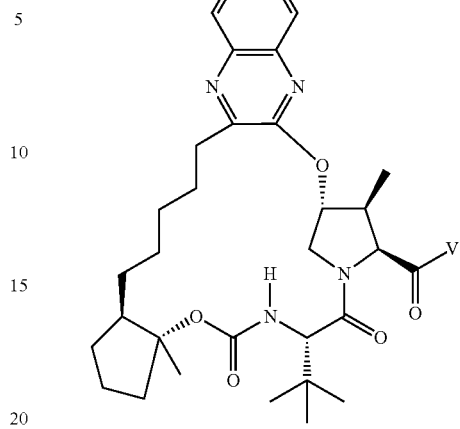
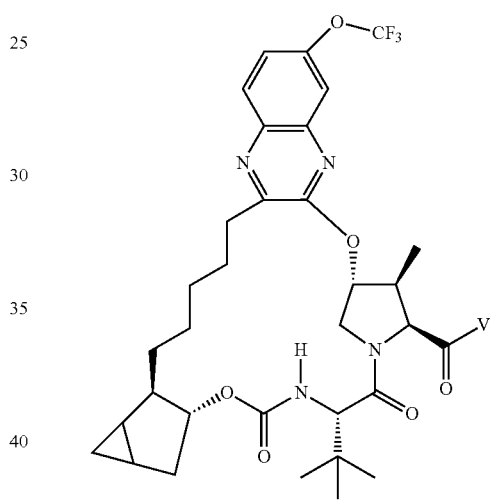
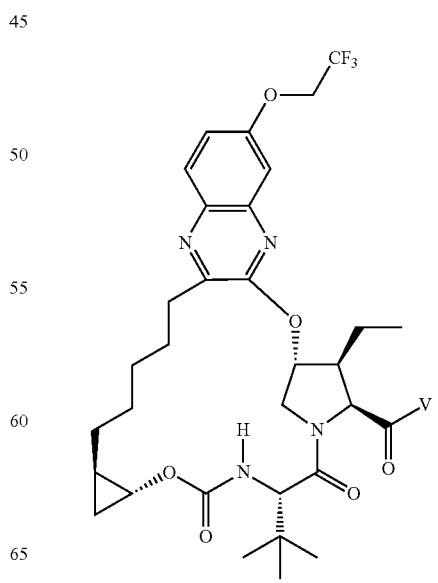

433
-continued
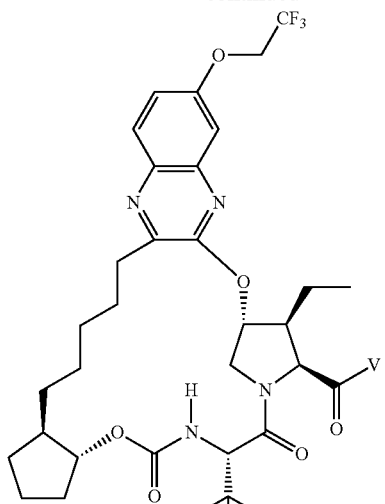
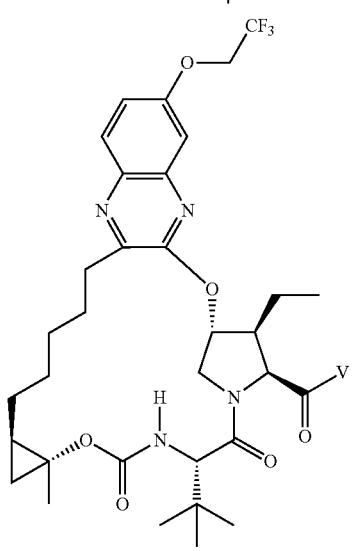
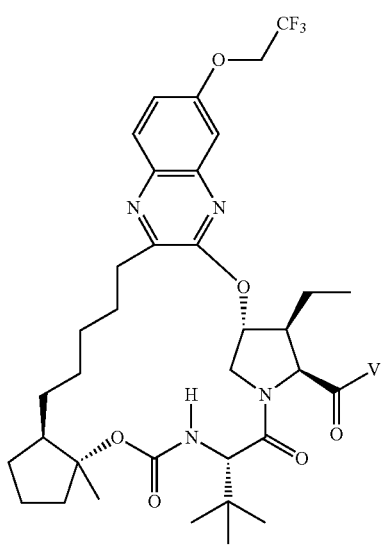
434
-continued
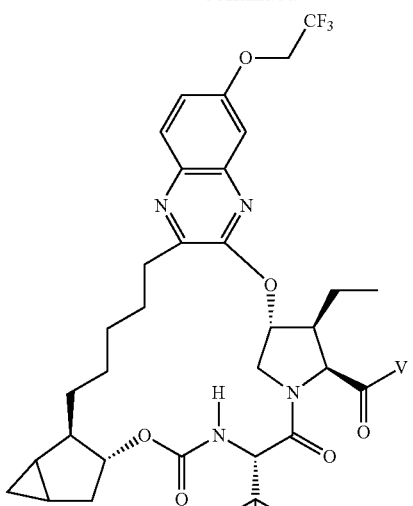
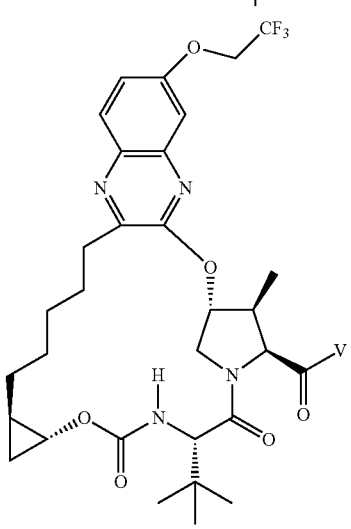
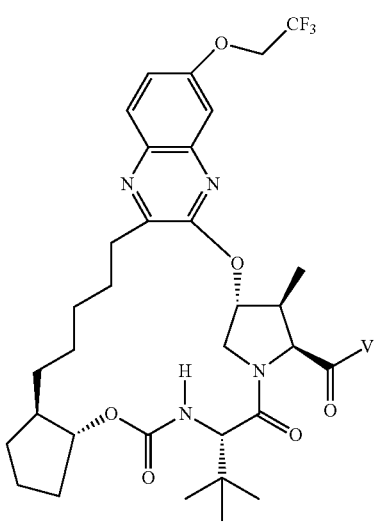

435
-continued
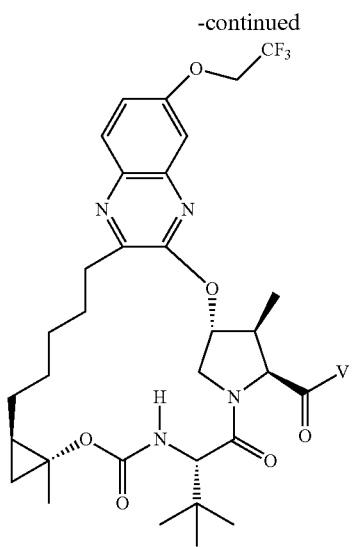
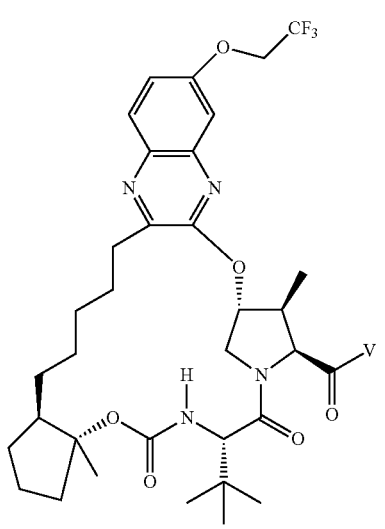
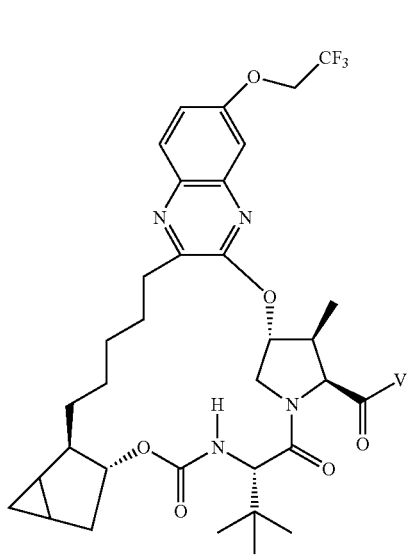
436
-continued
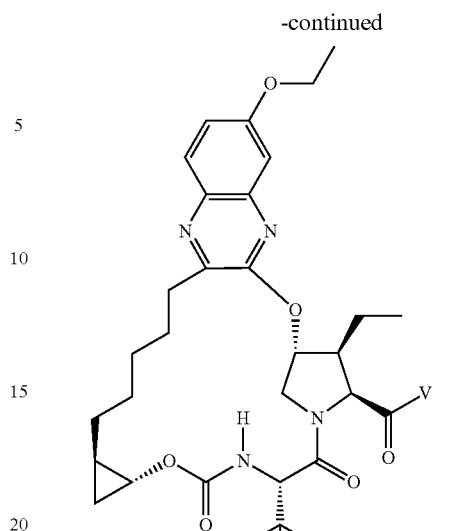
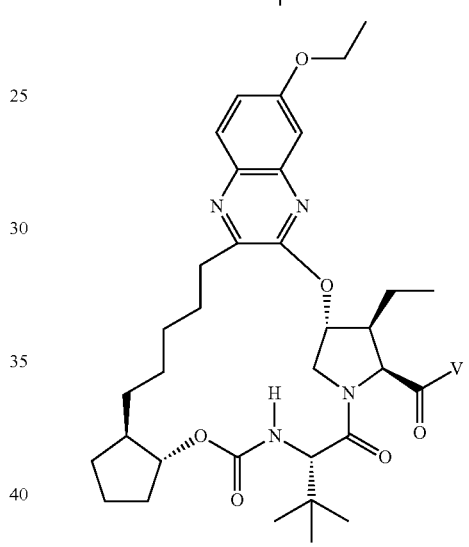
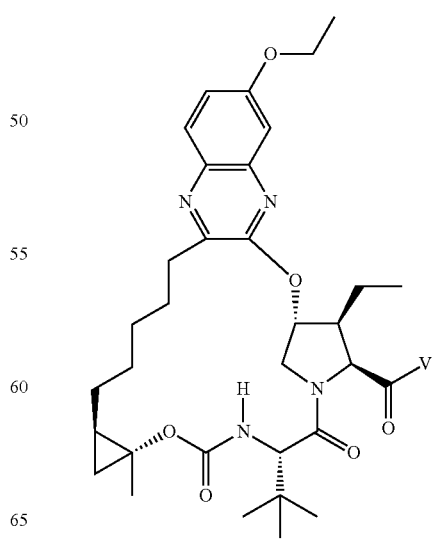

437
-continued
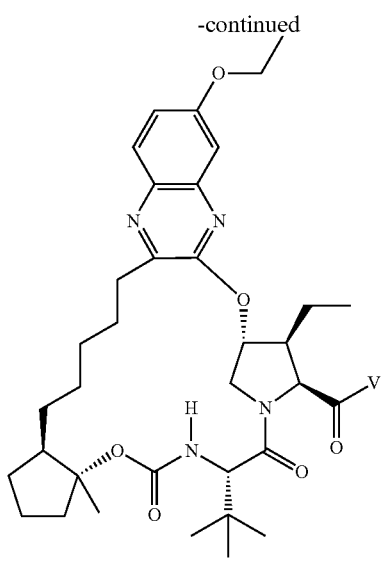
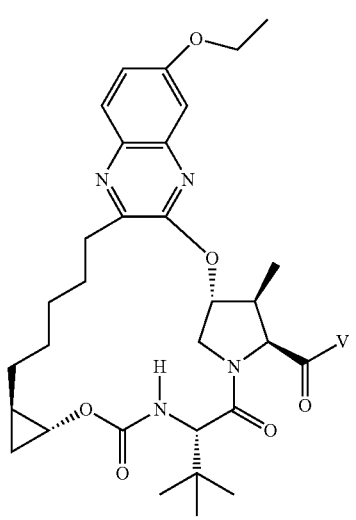
438
-continued
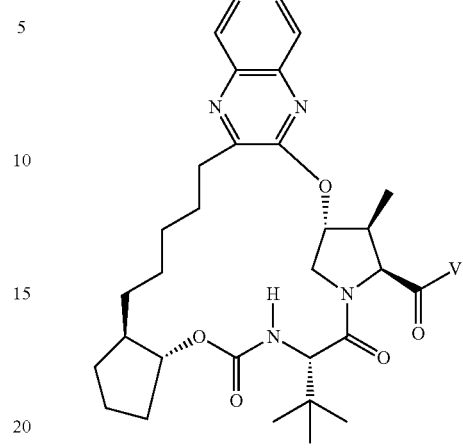
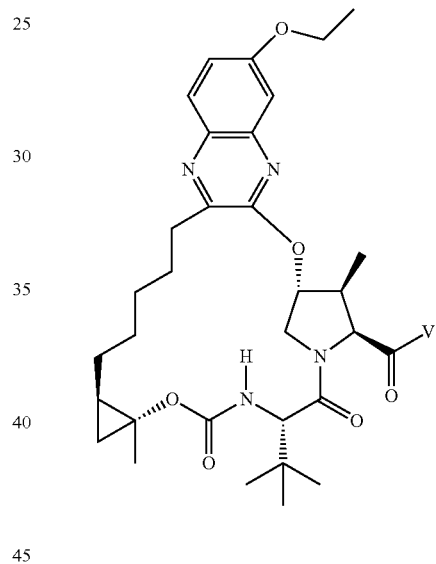
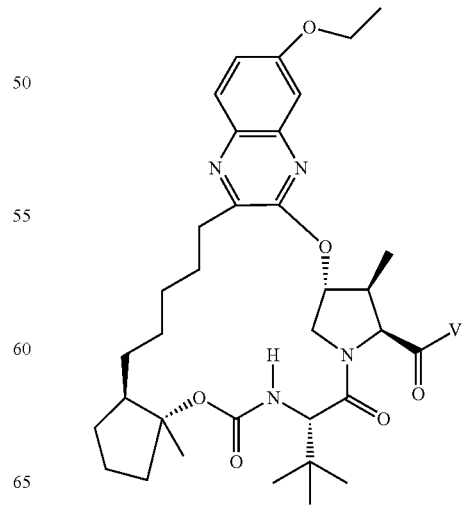

439
-continued
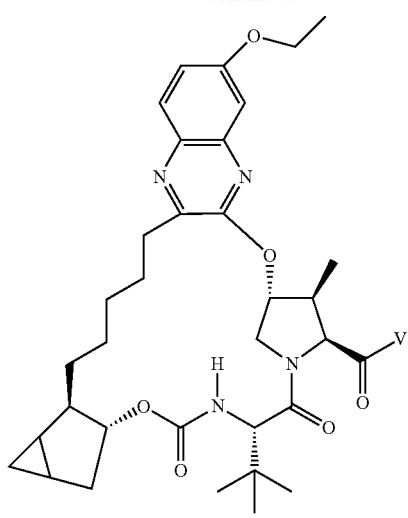
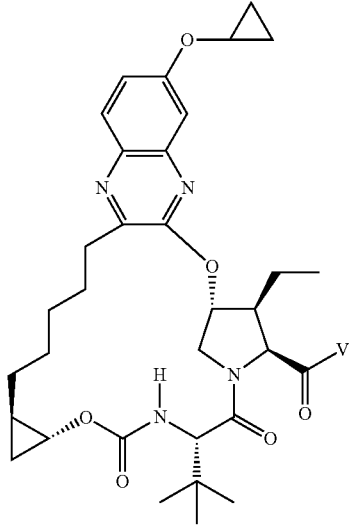
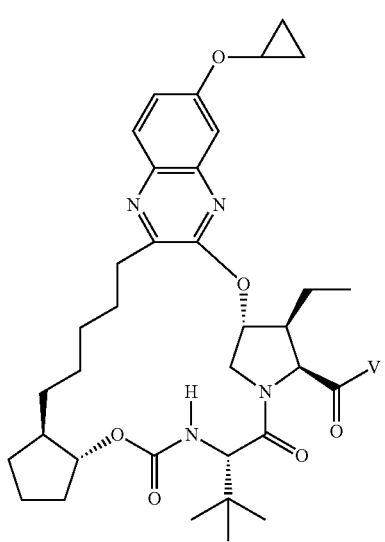
440
-continued
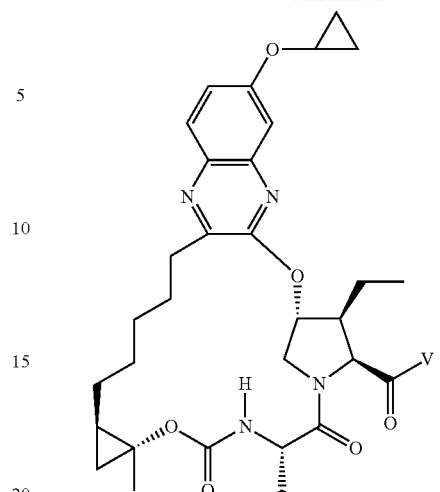
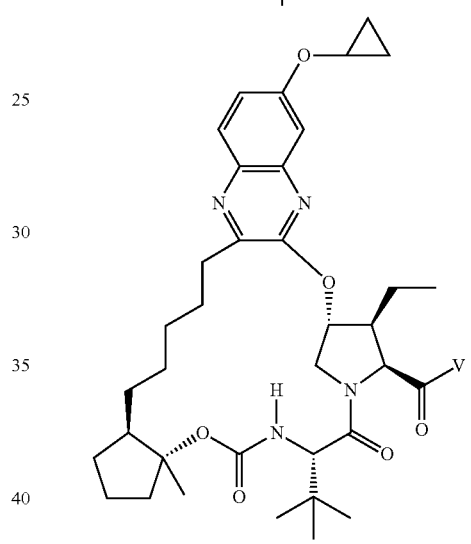
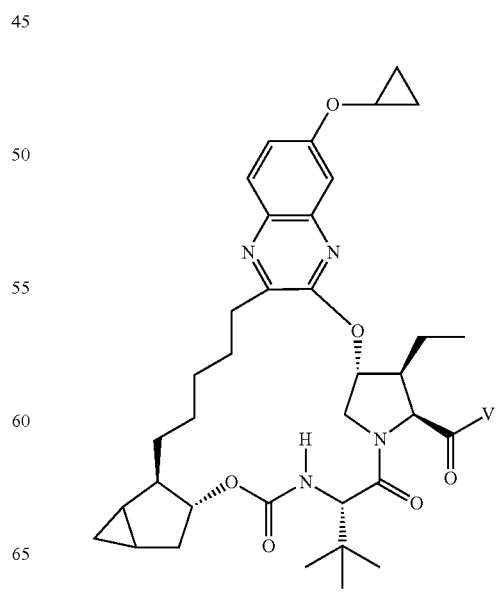

441
-continued
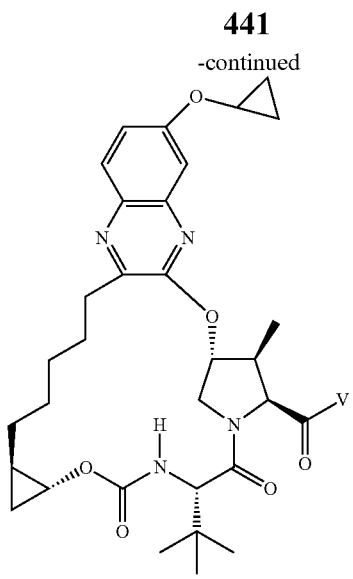
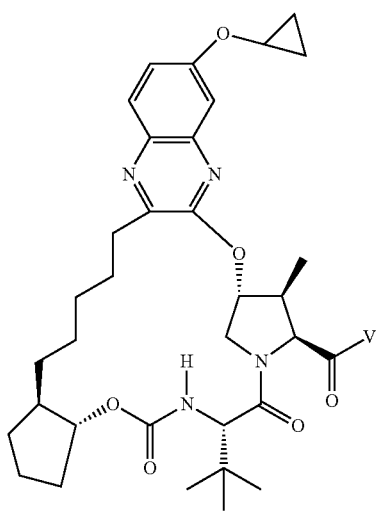
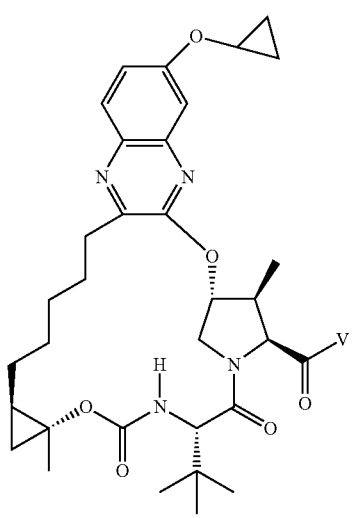
442
-continued
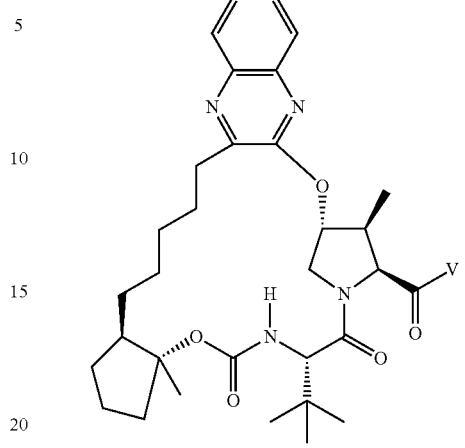
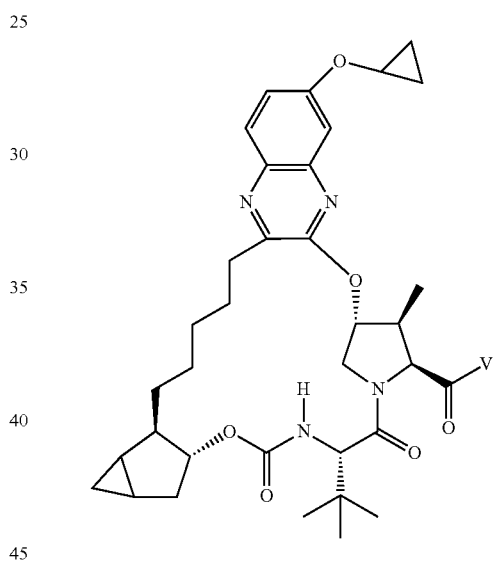
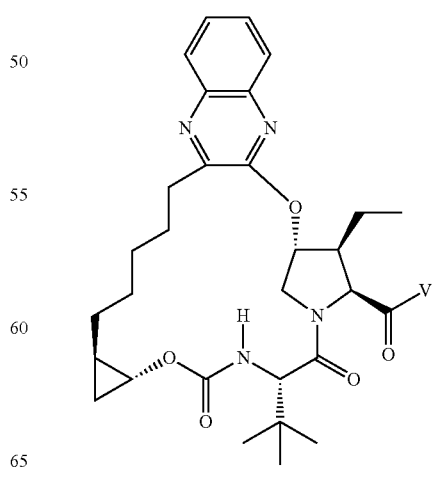

443
-continued
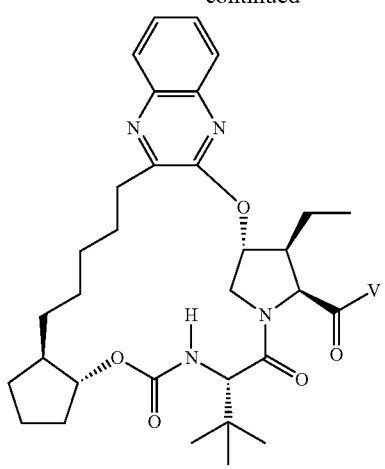
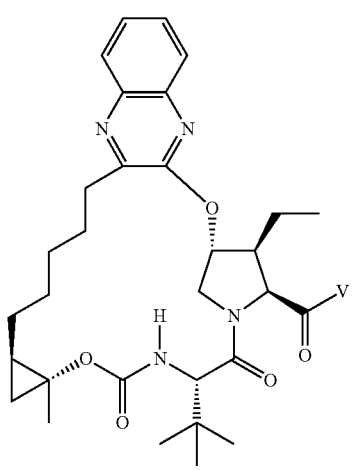
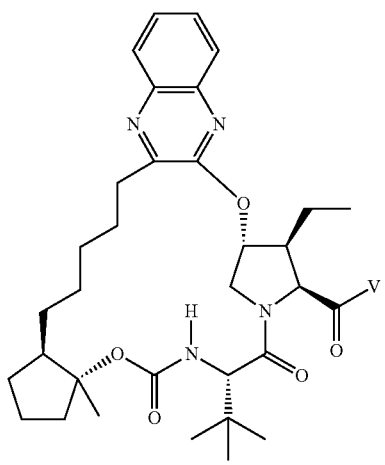
444
-continued
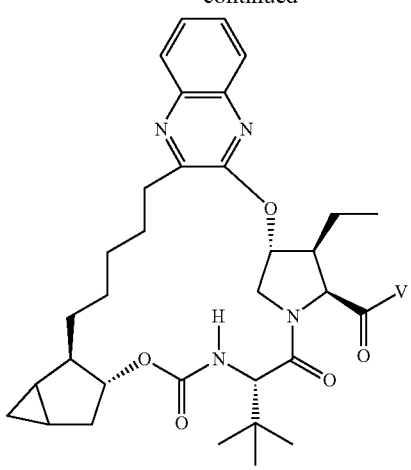
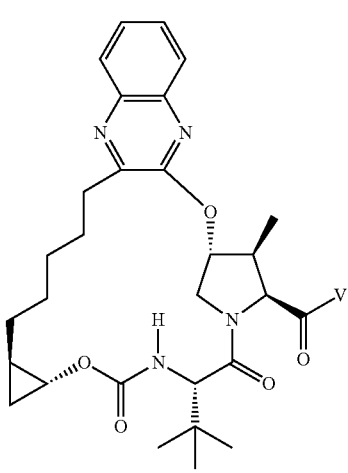
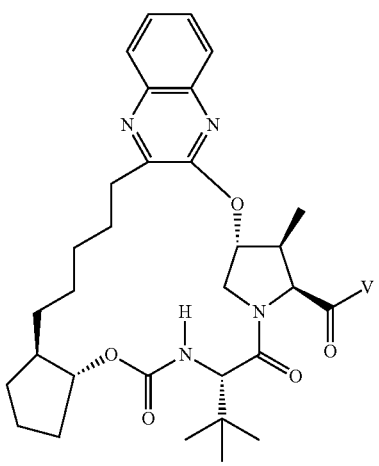

445
-continued
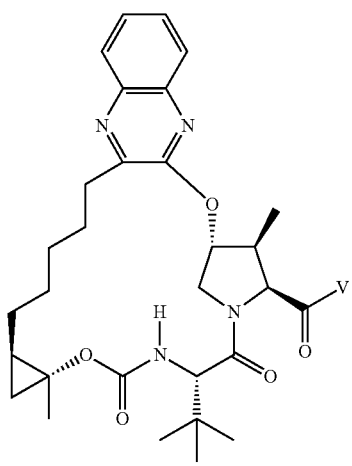
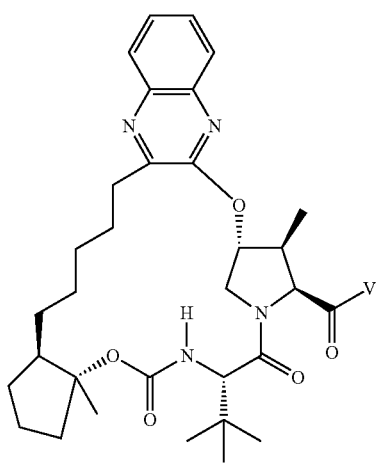
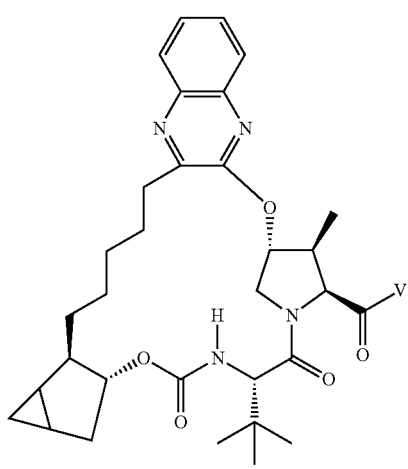
446
-continued
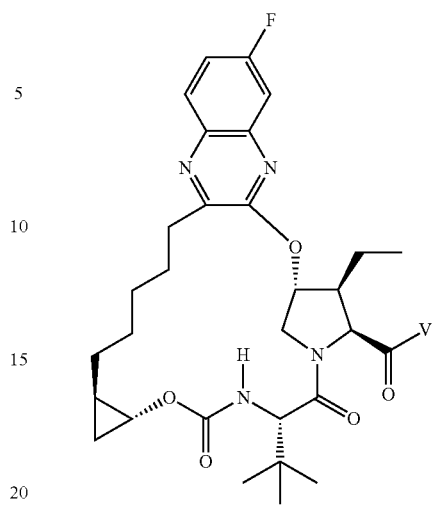
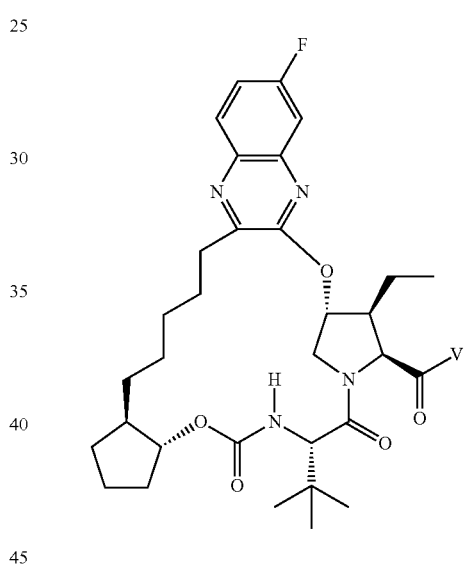
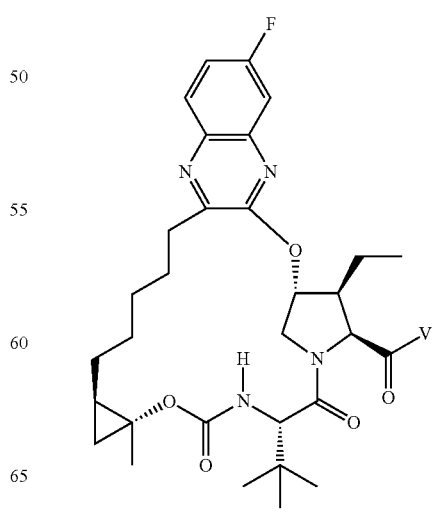

447
-continued
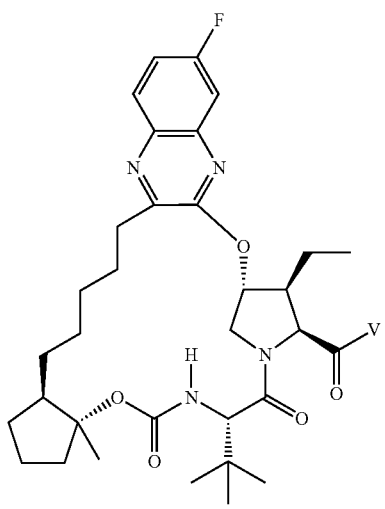
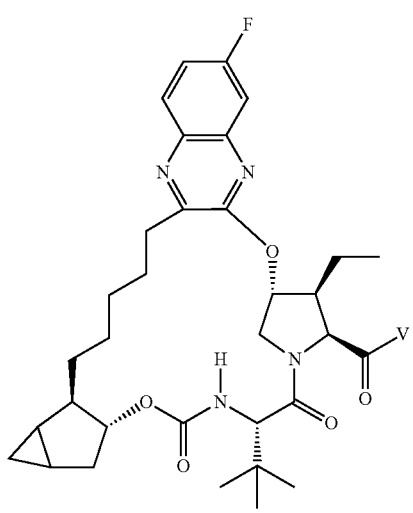
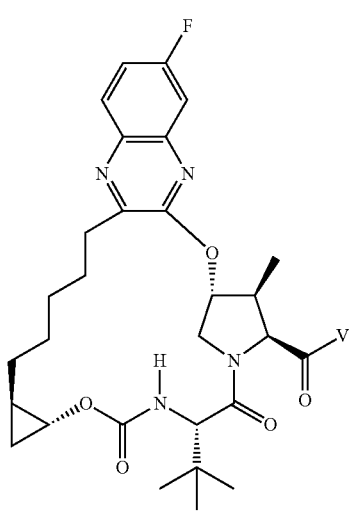
448
-continued
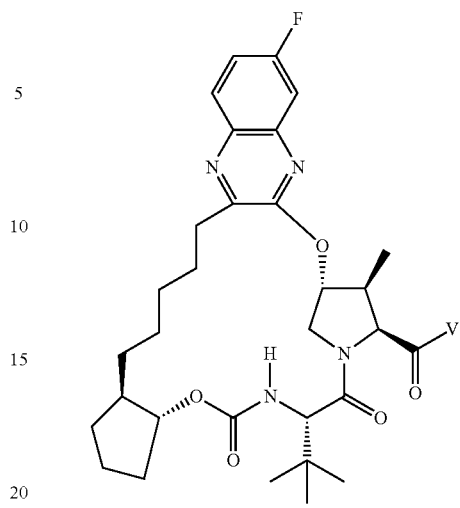
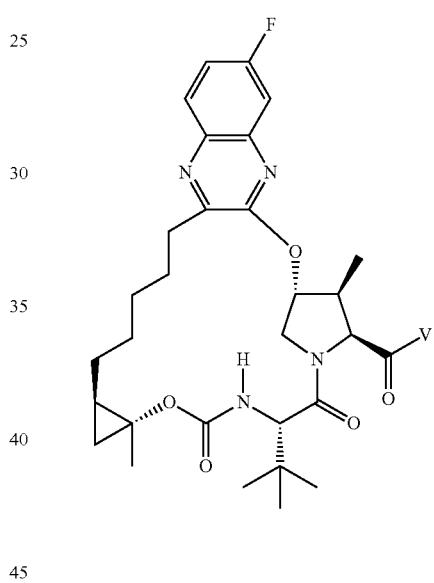
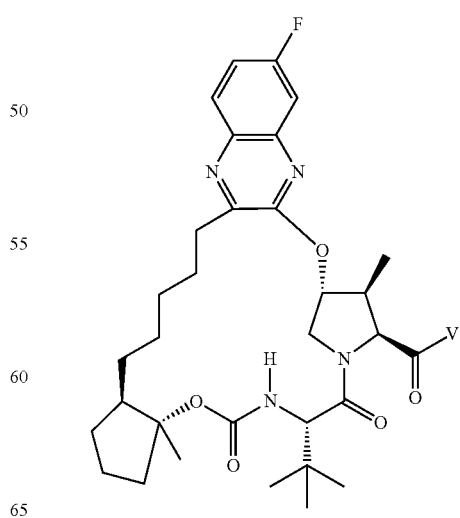

449
-continued
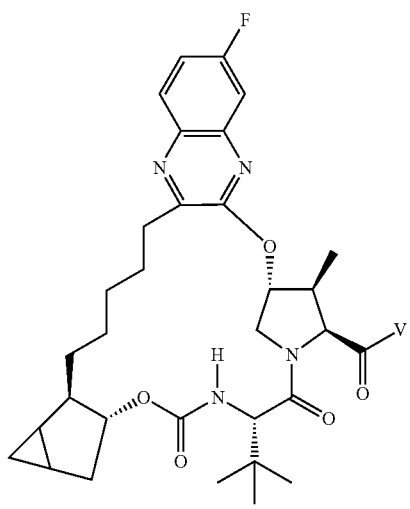
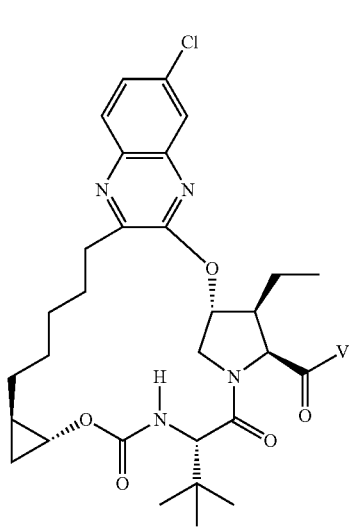
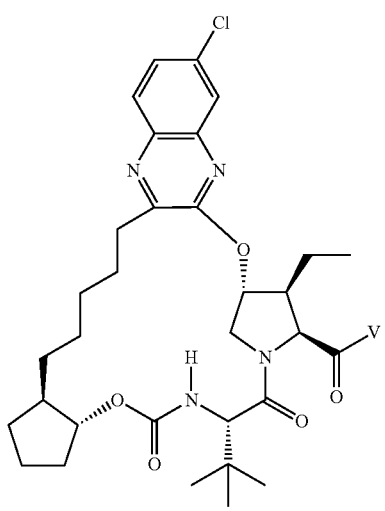
450
-continued
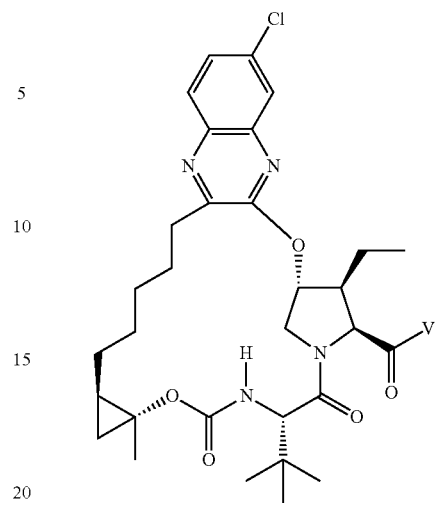
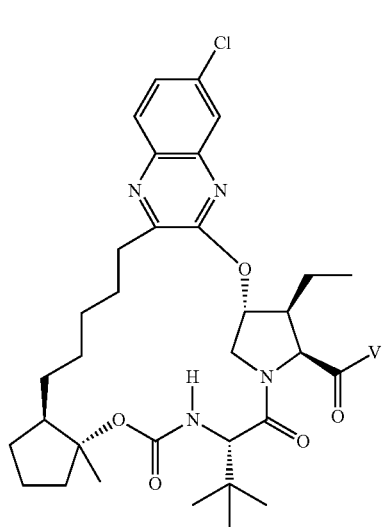
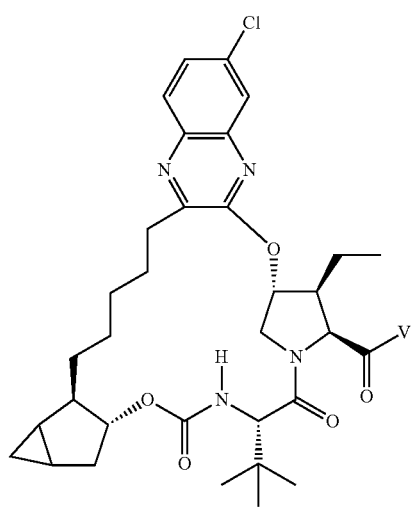

451
-continued
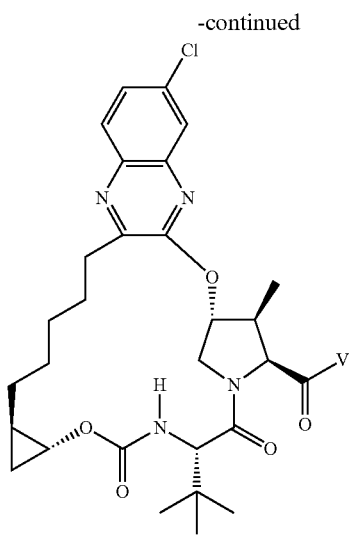
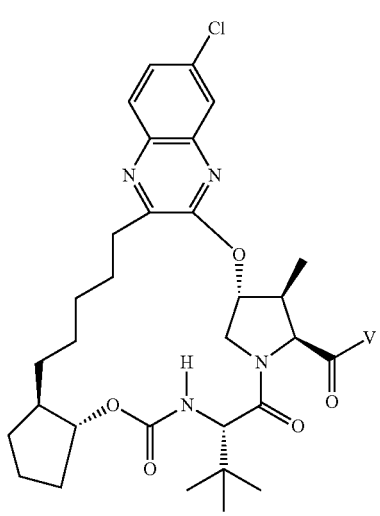
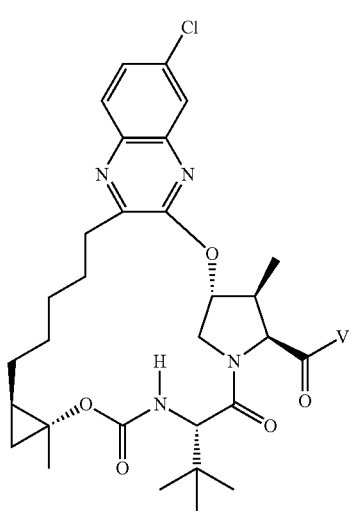
452
-continued
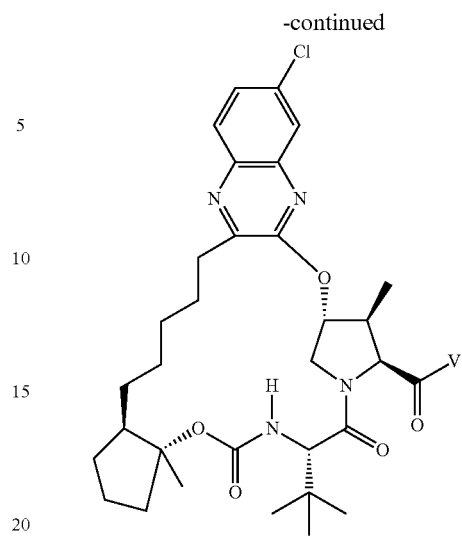
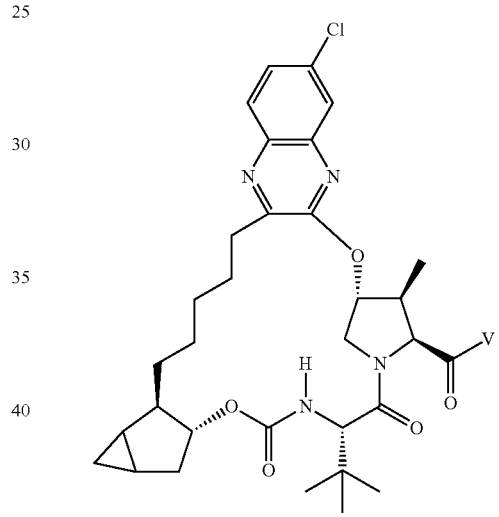
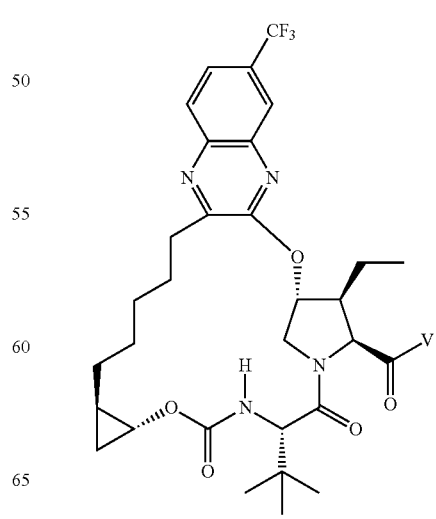

453
-continued
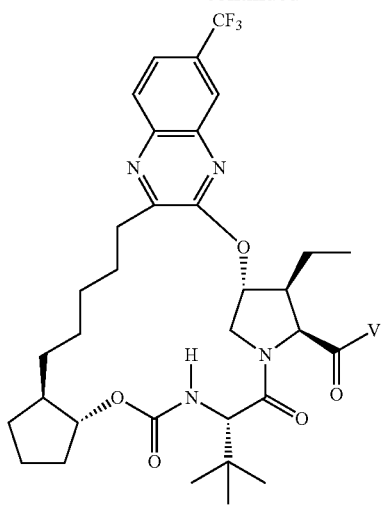
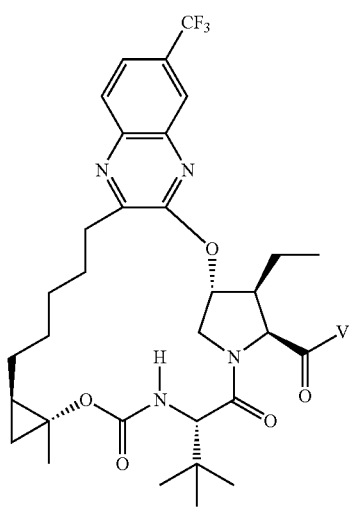
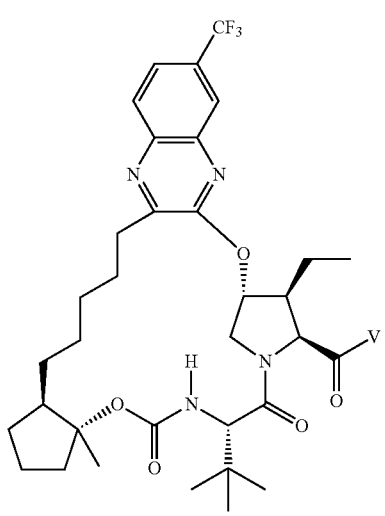
454
-continued
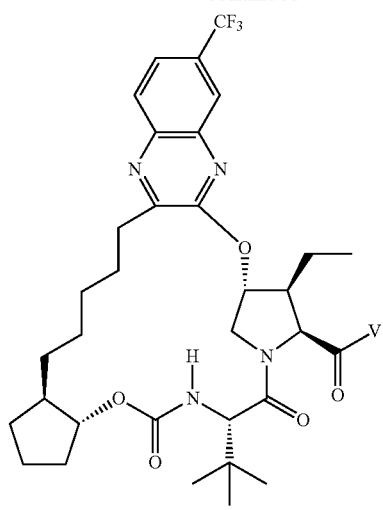
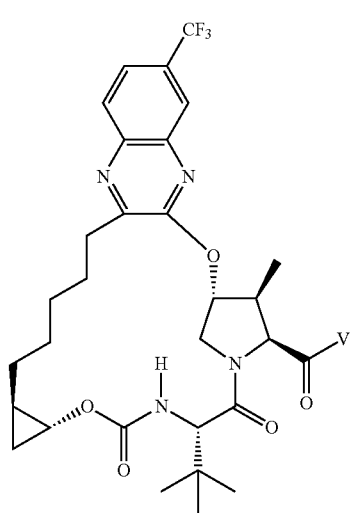
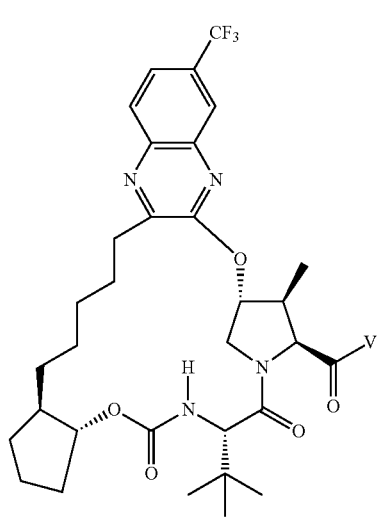

455
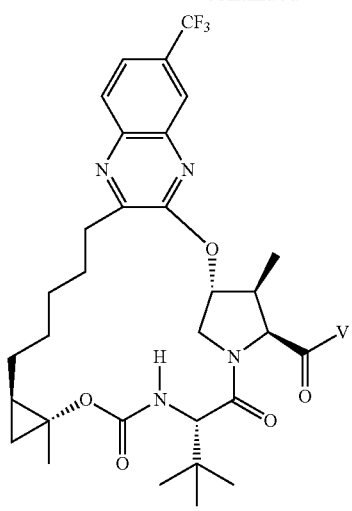
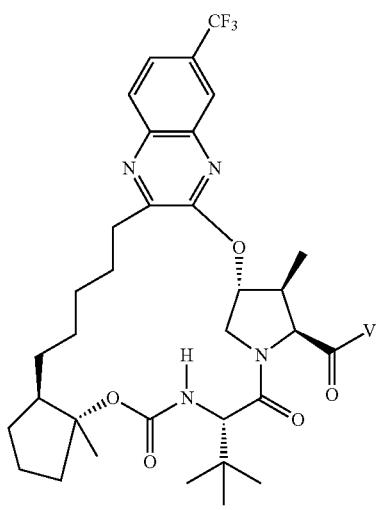
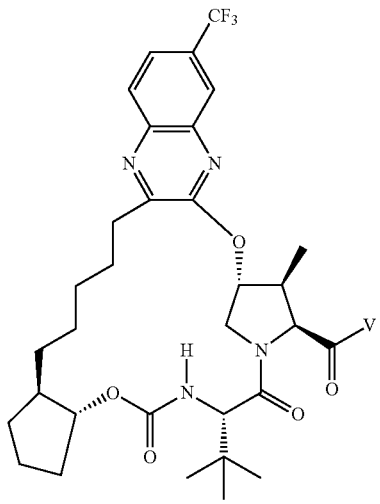
456
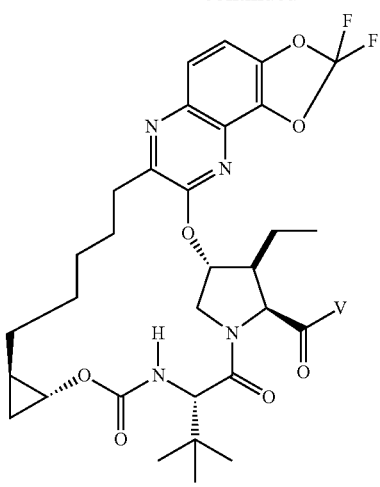
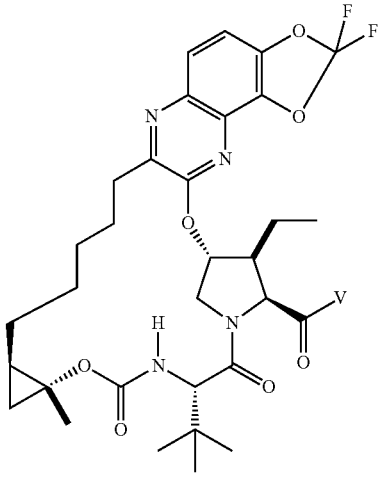
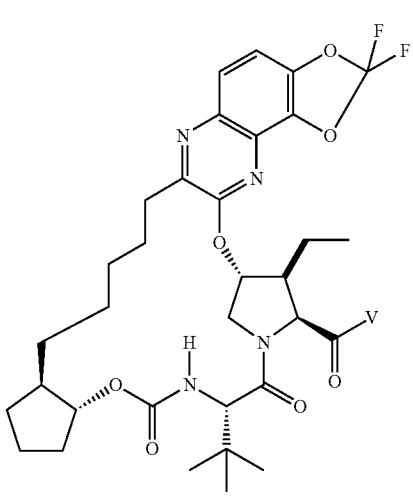

457
-continued
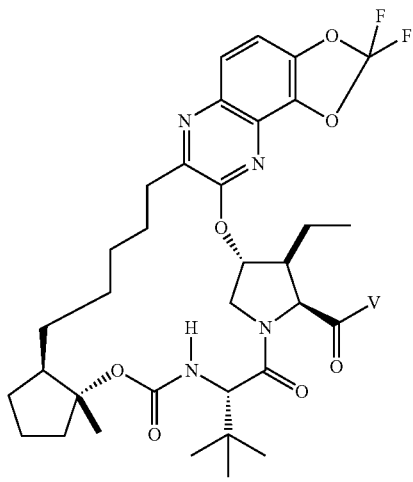
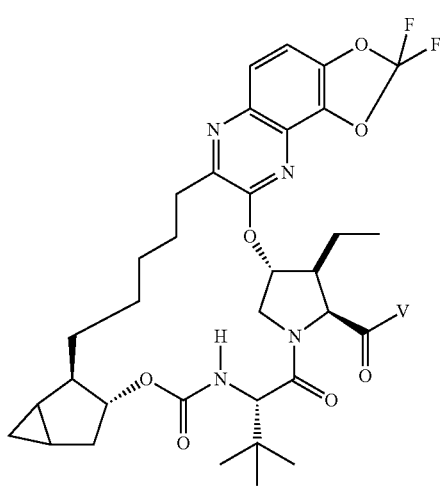
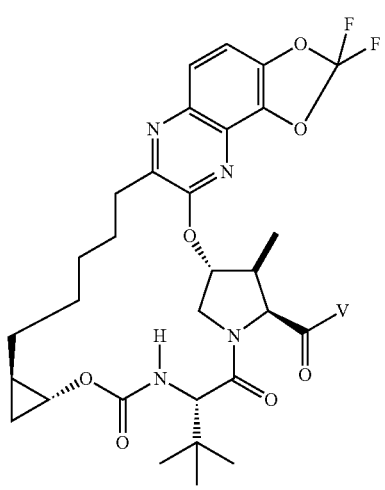
458
-continued
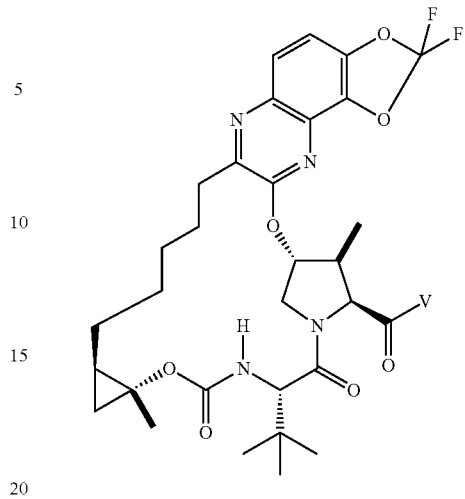
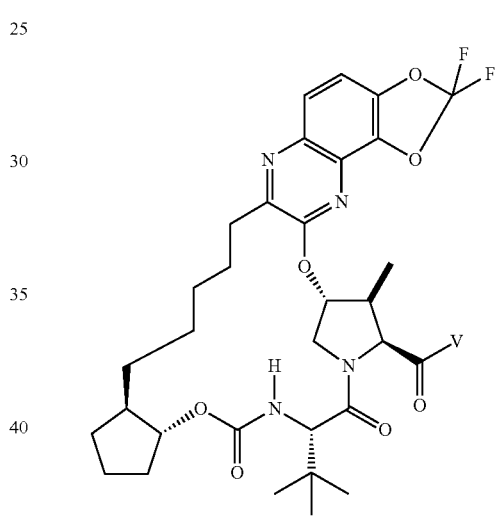
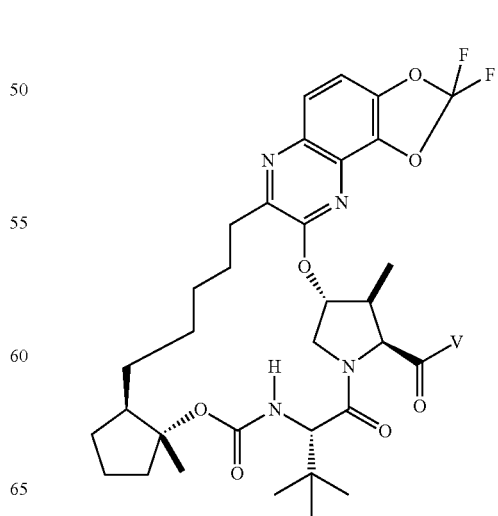

459
-continued
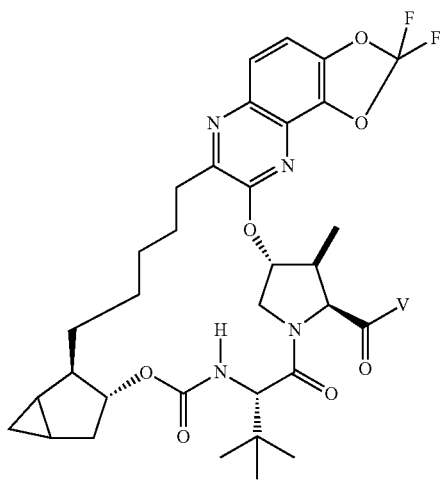
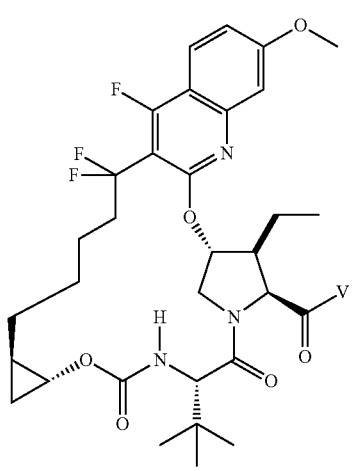
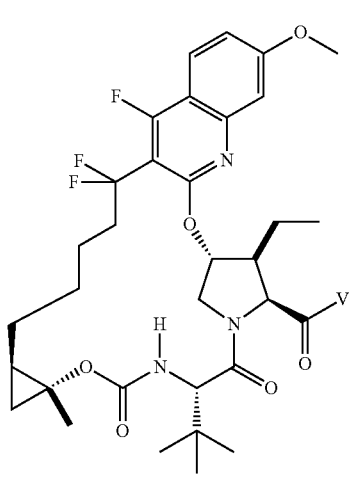
460
-continued
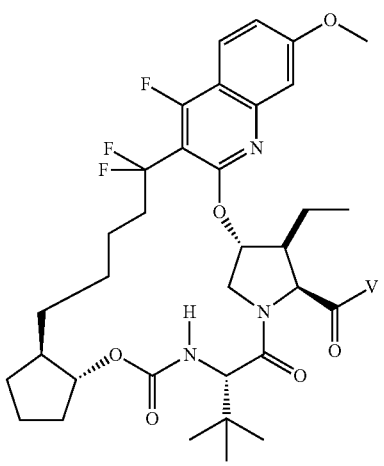
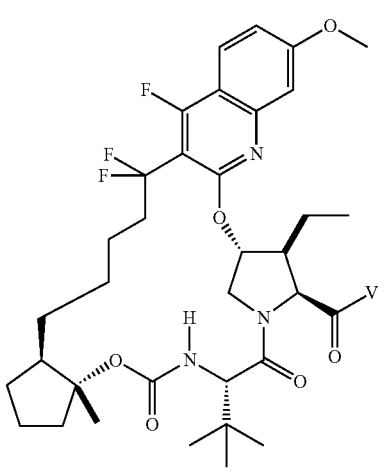
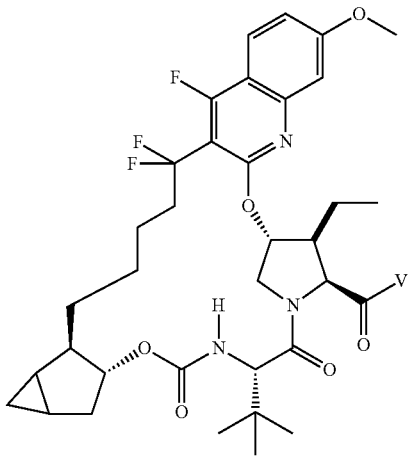

461
-continued
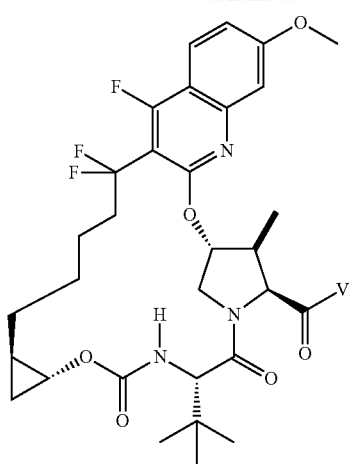
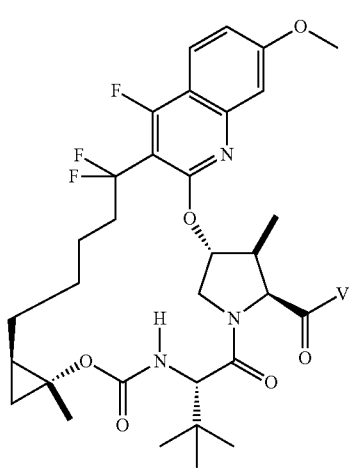
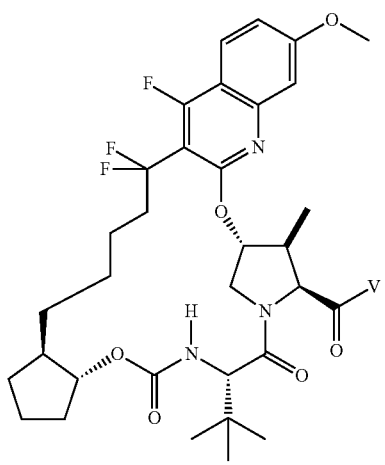
462
-continued
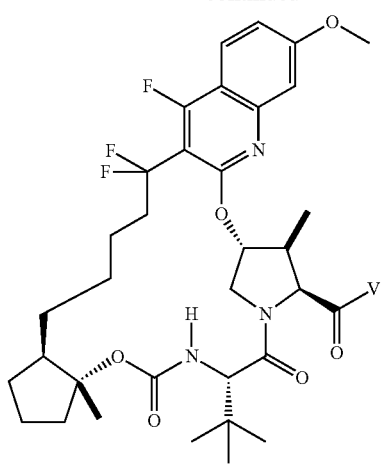
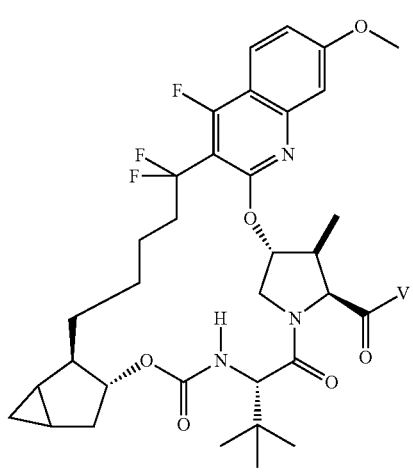
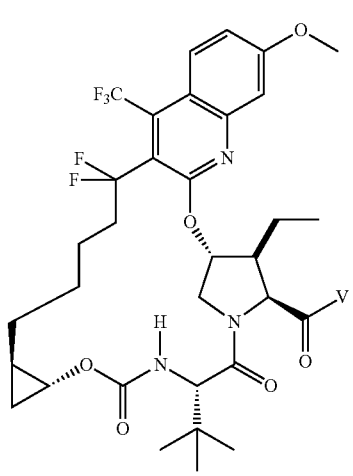

463
-continued
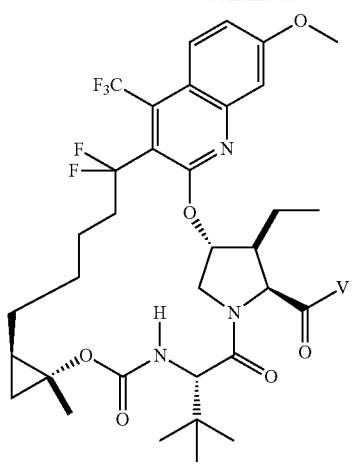
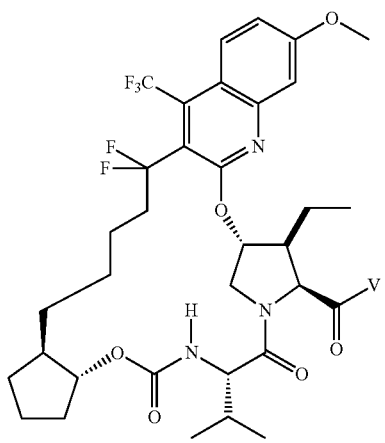
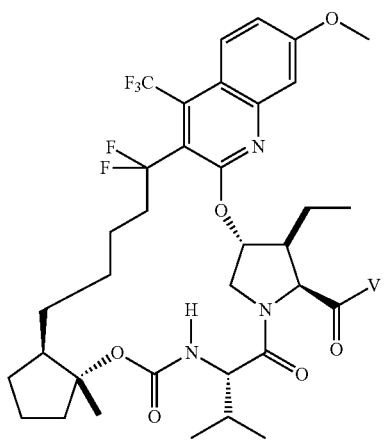
464
-continued
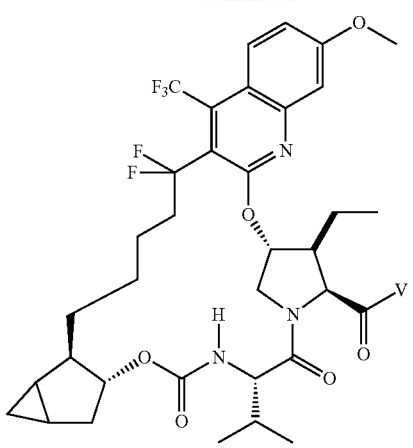
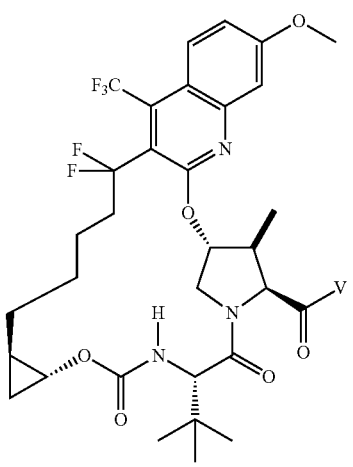
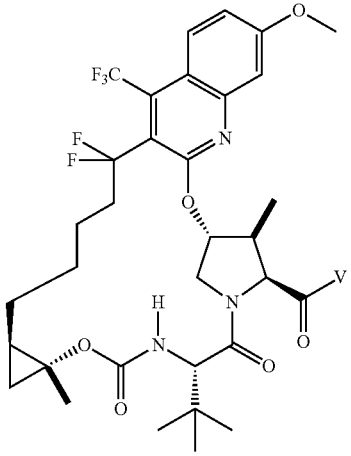

465
-continued
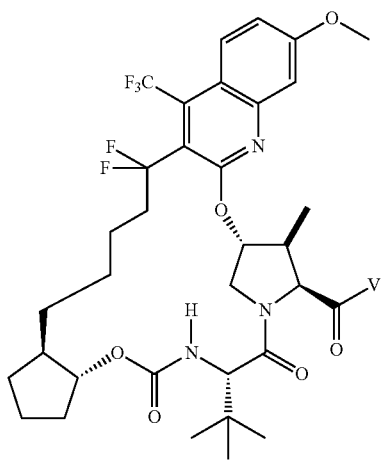
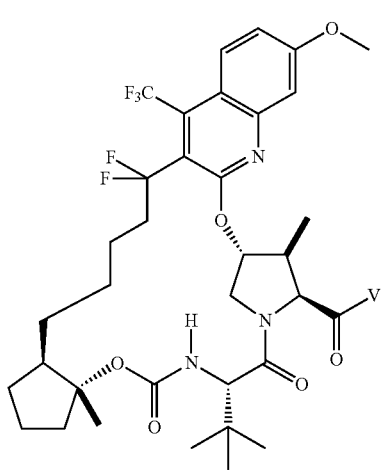
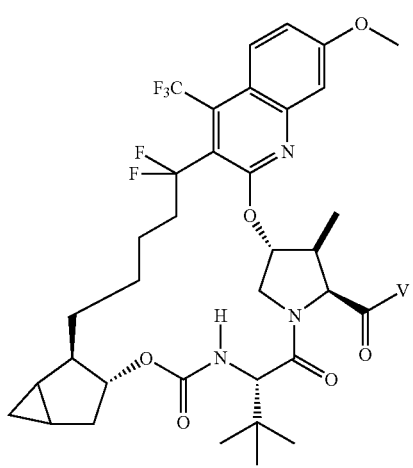
466
-continued
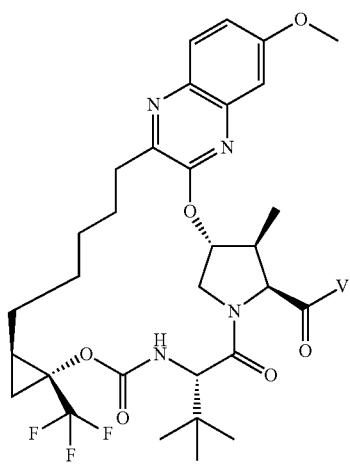
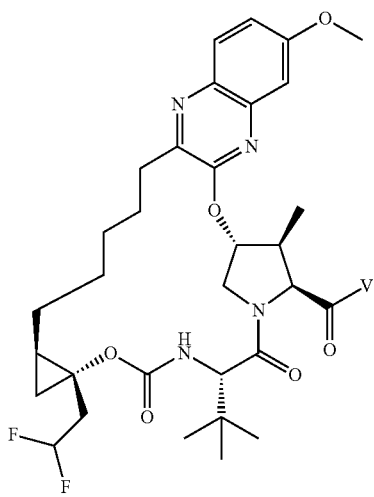
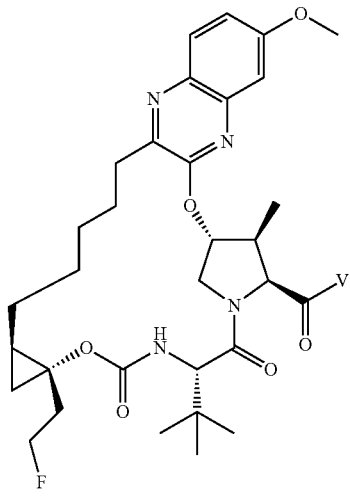

467
-continued
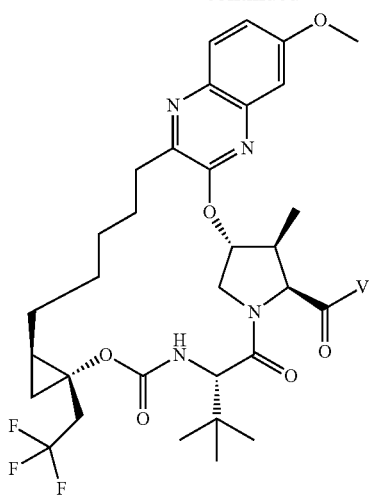
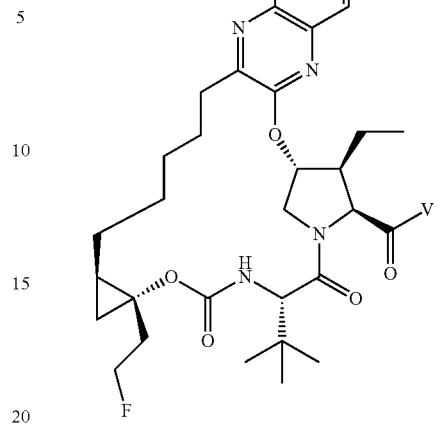
468
-continued
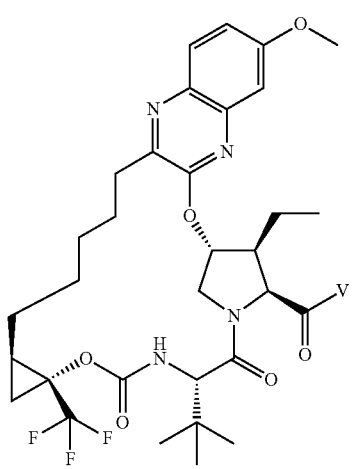
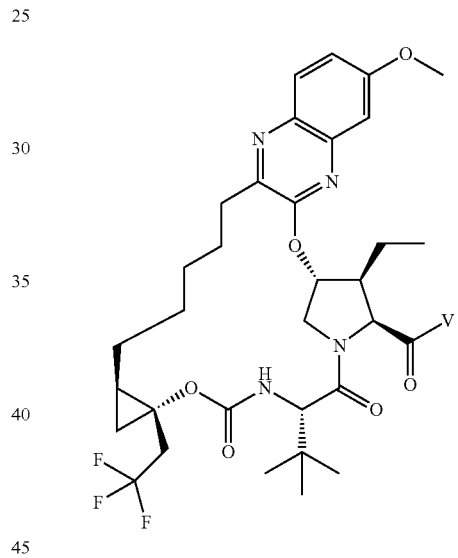
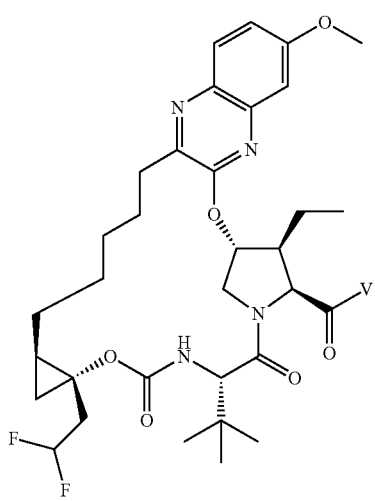
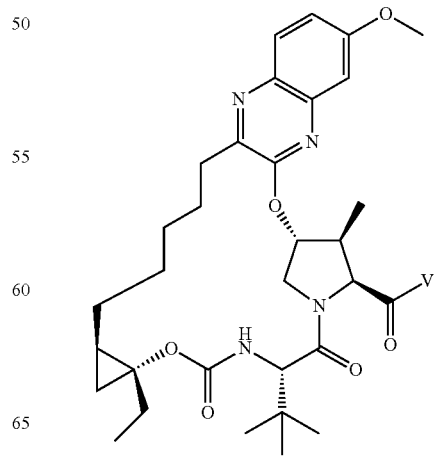

469
-continued
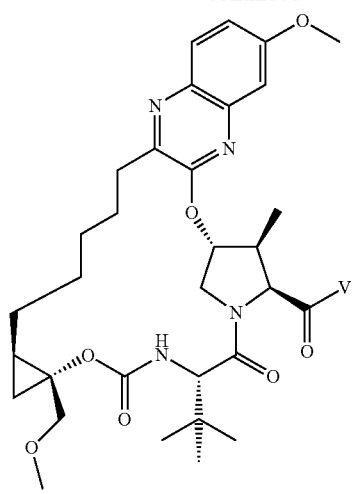
470
-continued
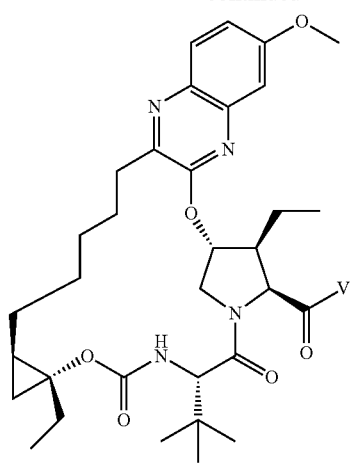
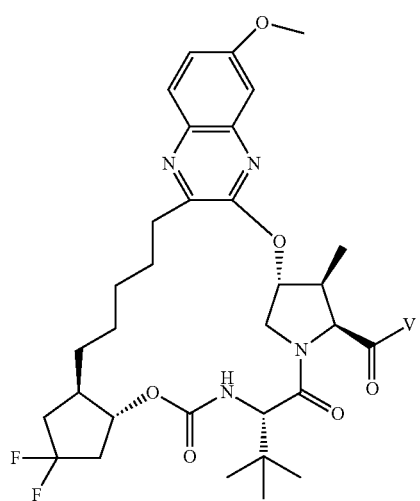
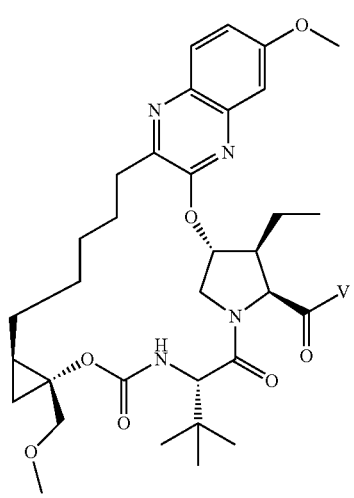
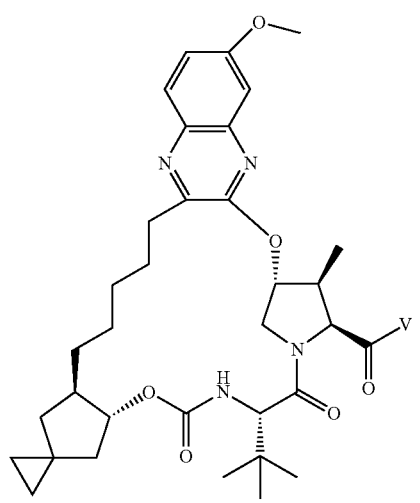
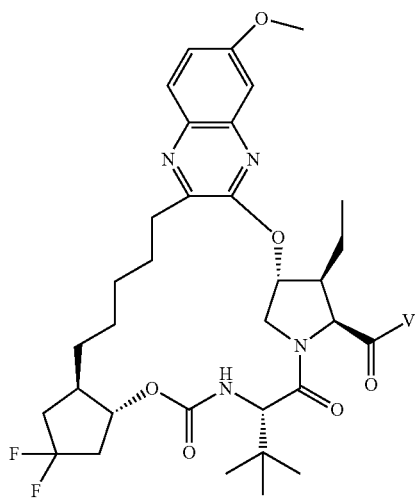

471
-continued
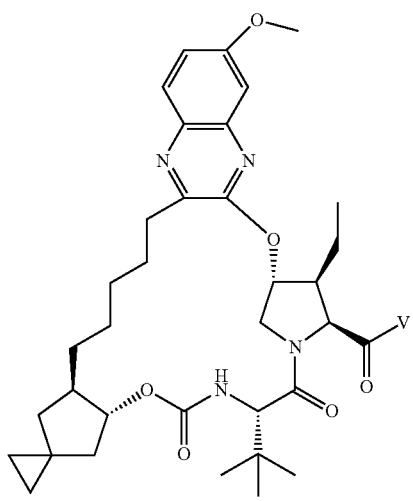
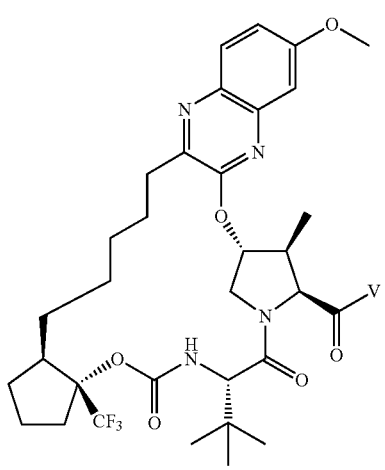
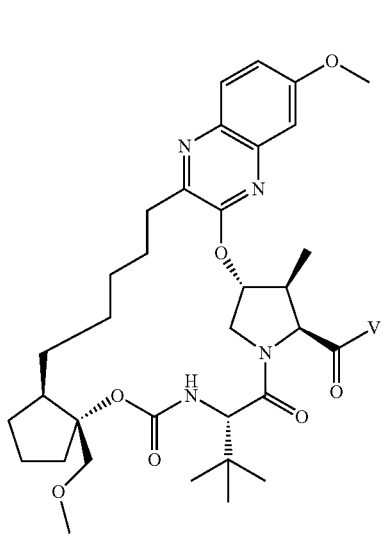
472
-continued
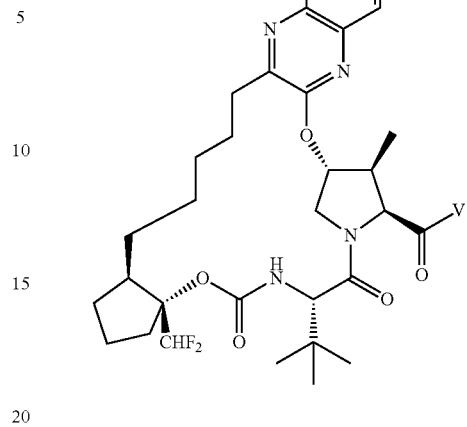
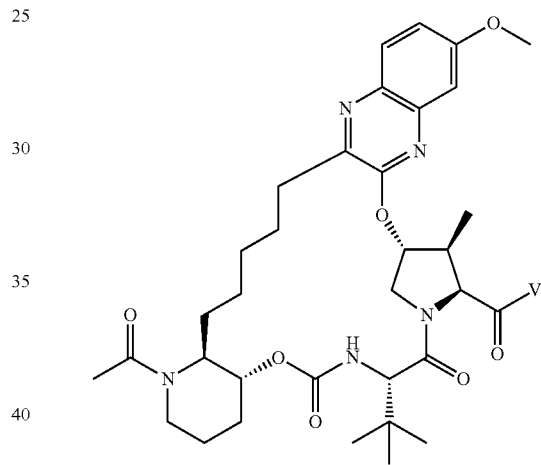
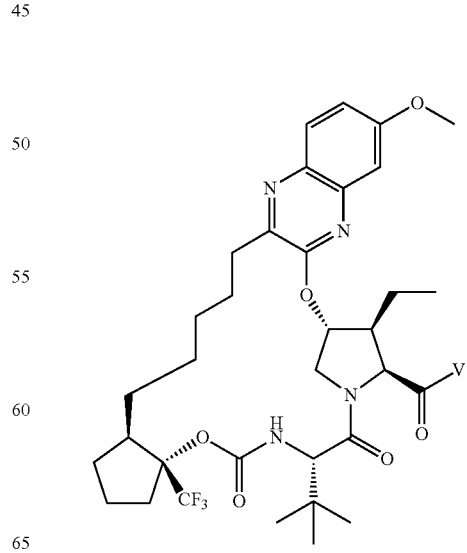

473
-continued
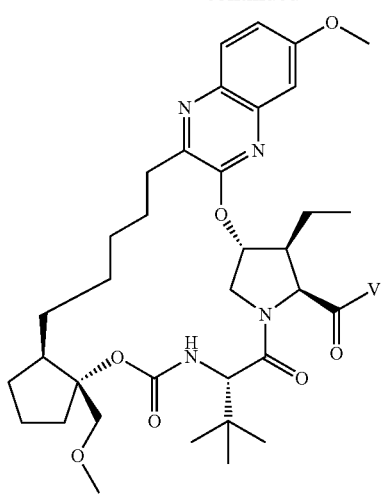
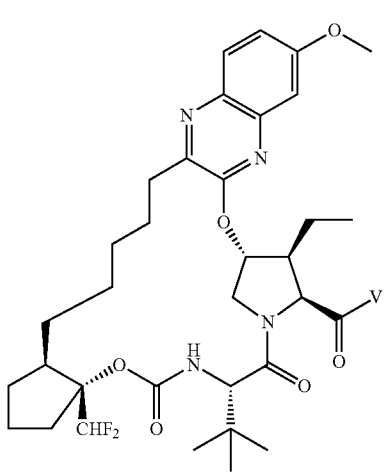
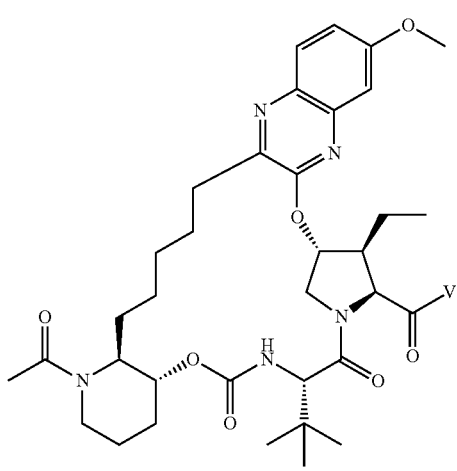
474
-continued
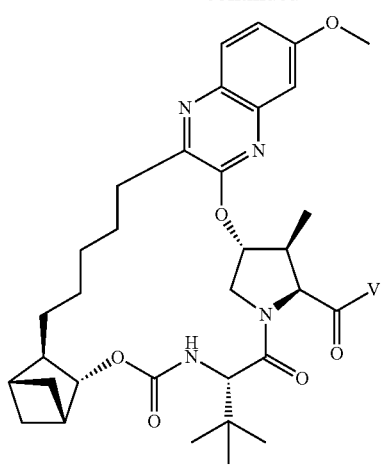
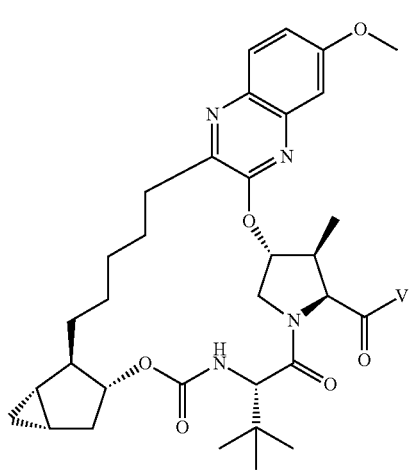
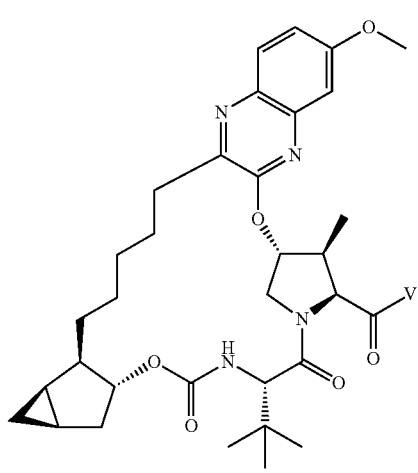

475
-continued
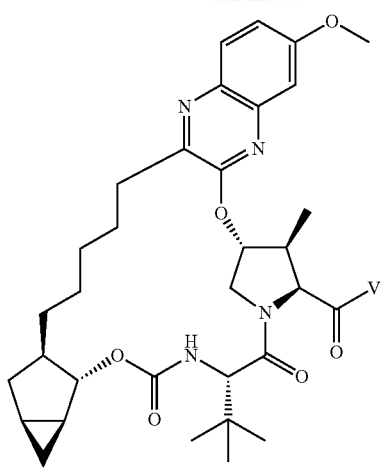
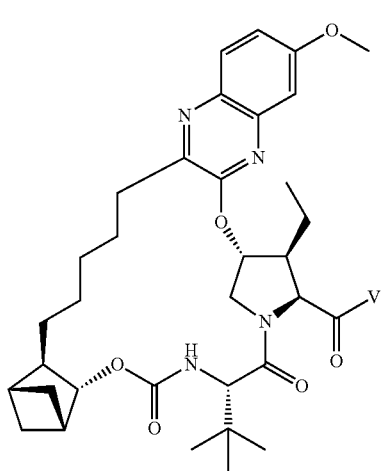
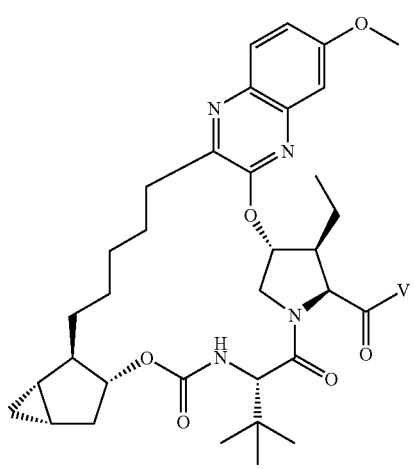
476
-continued
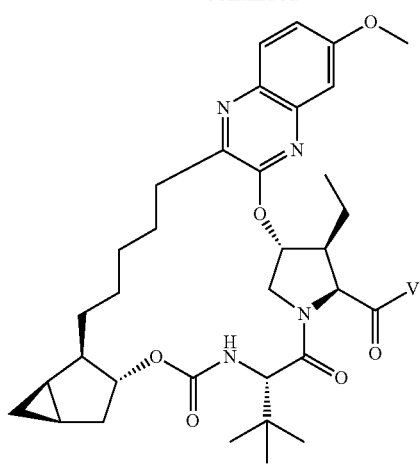
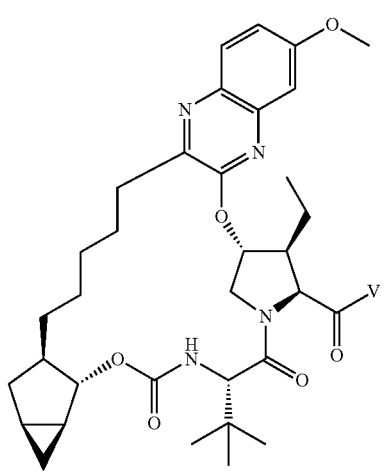
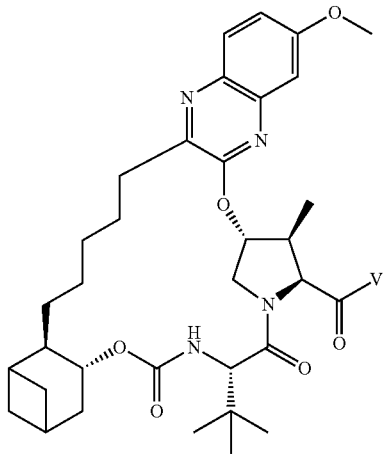

477
-continued
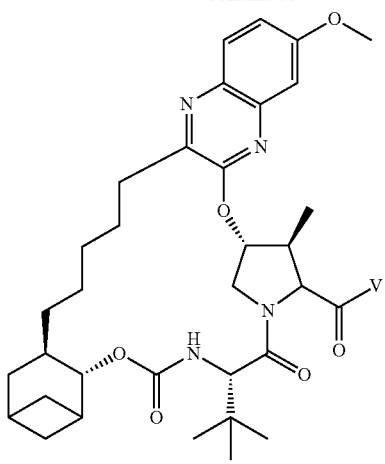
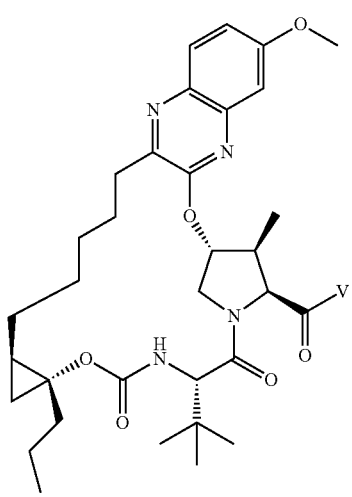
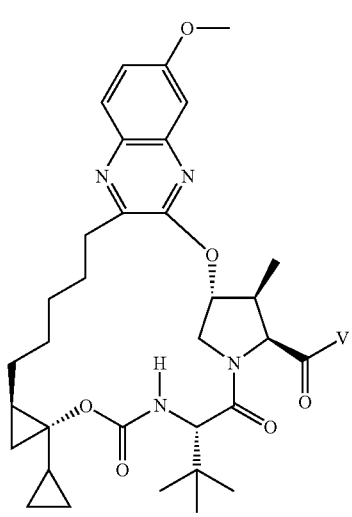
478
-continued
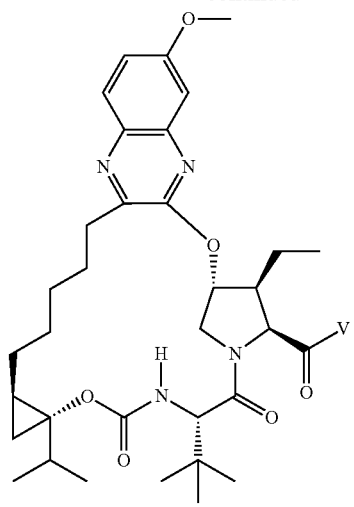
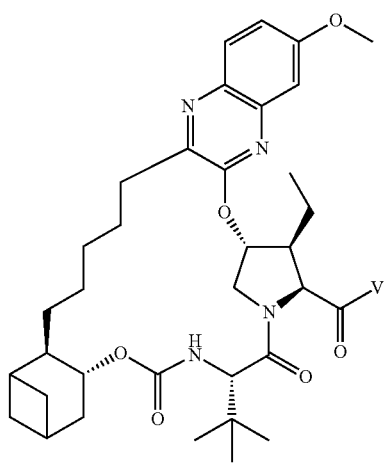
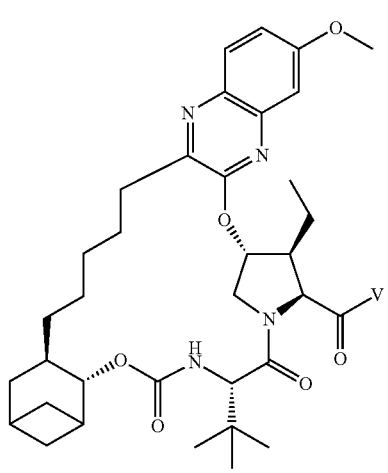

479
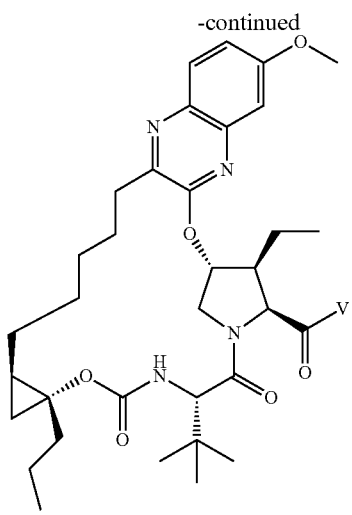
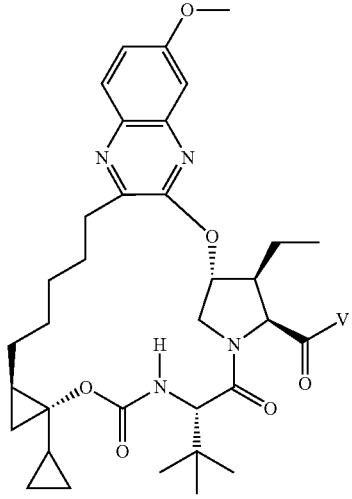
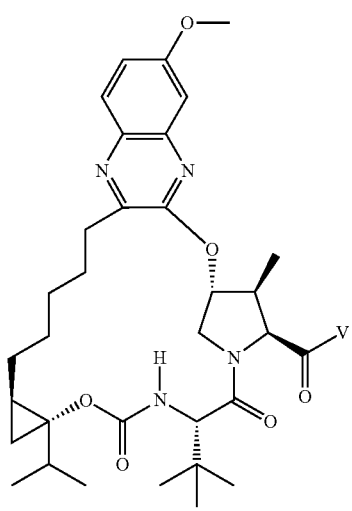
480
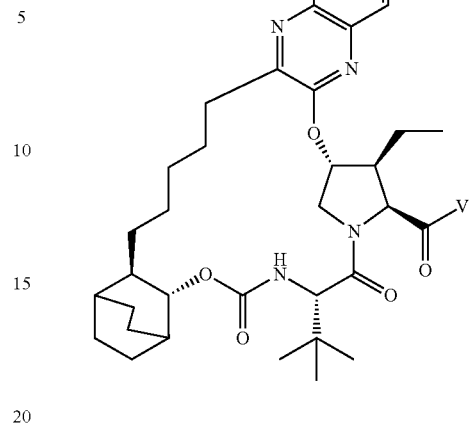
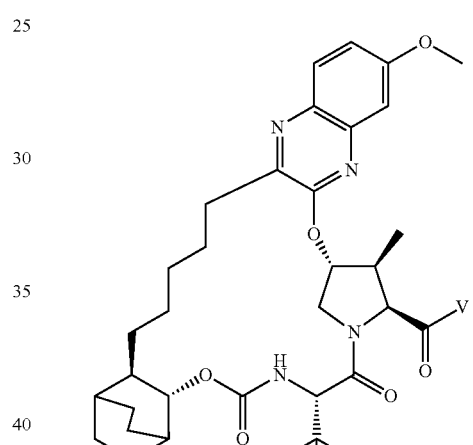
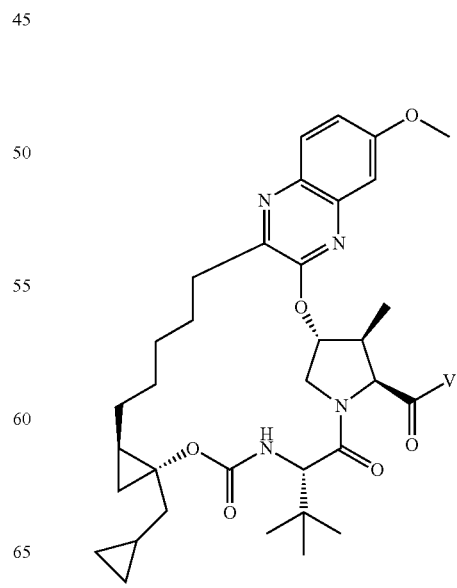

481
-continued
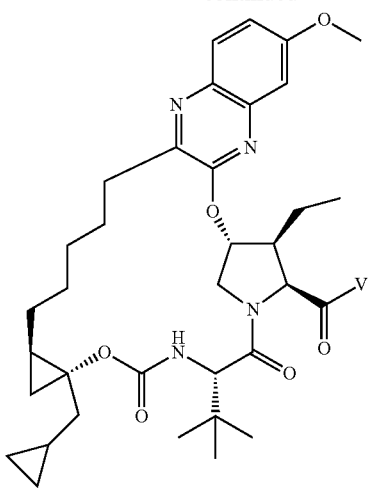
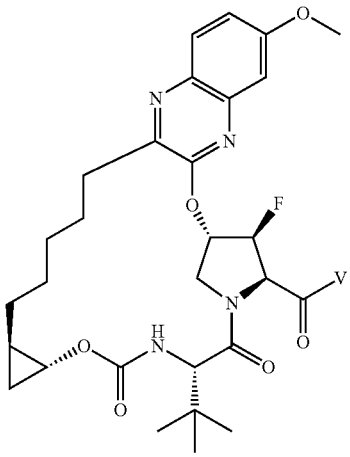
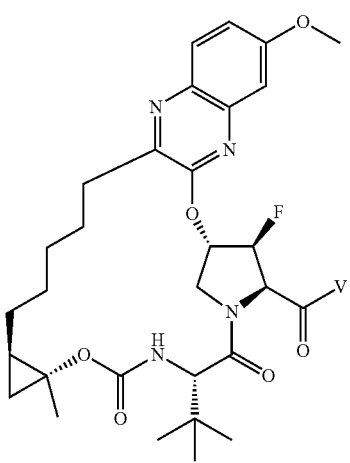
482
-continued
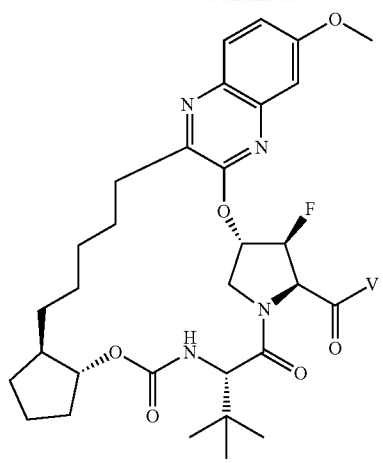
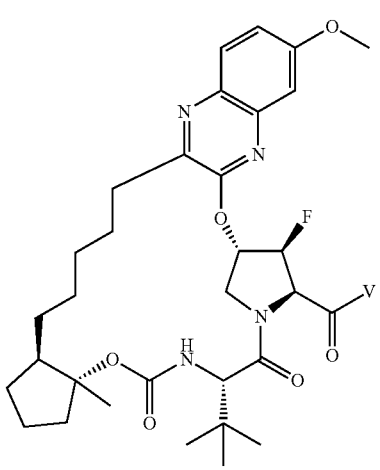
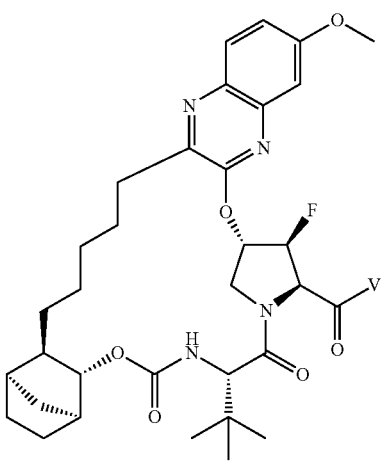

483
-continued
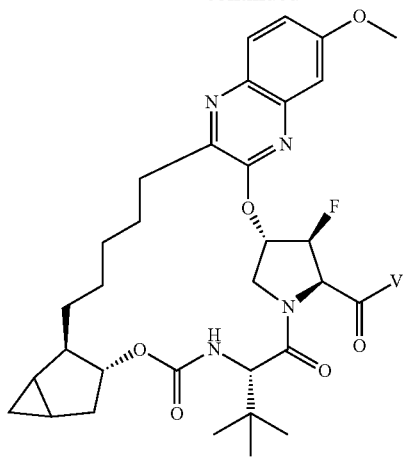
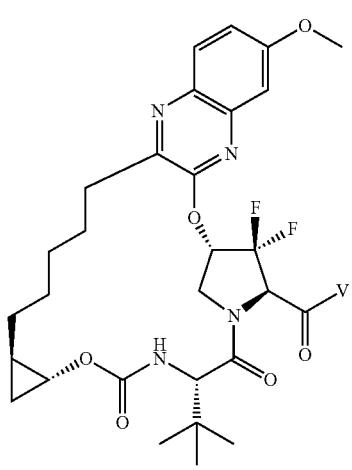
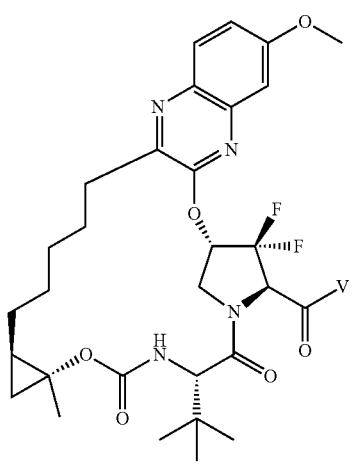
484
-continued
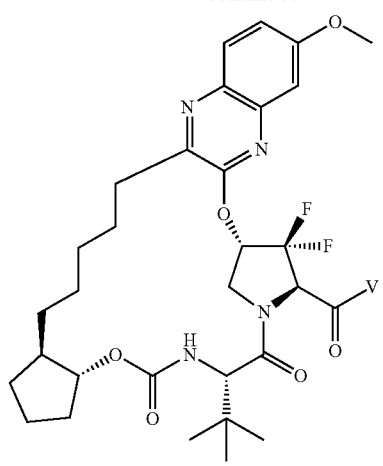
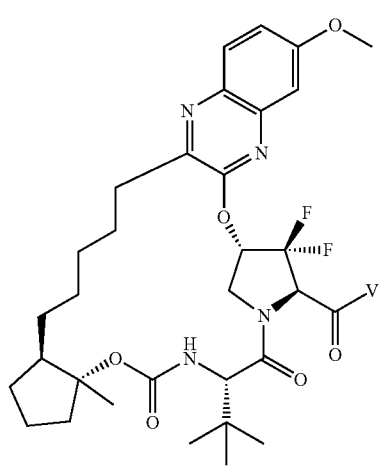
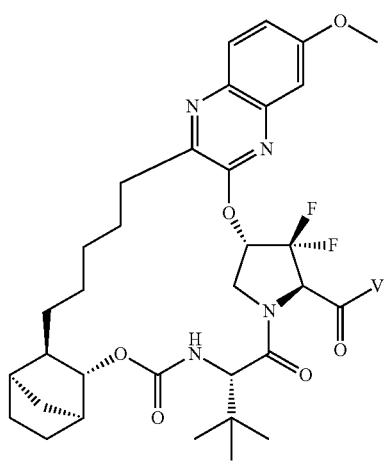

485
-continued
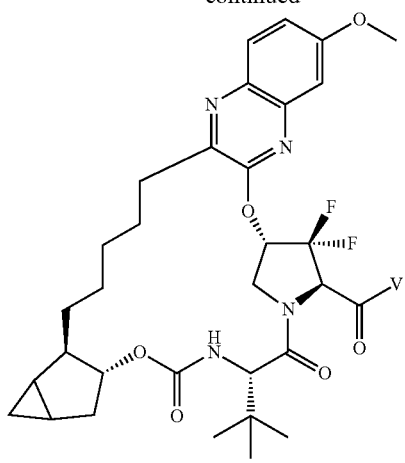
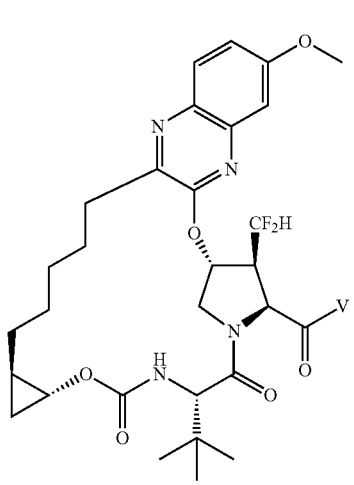
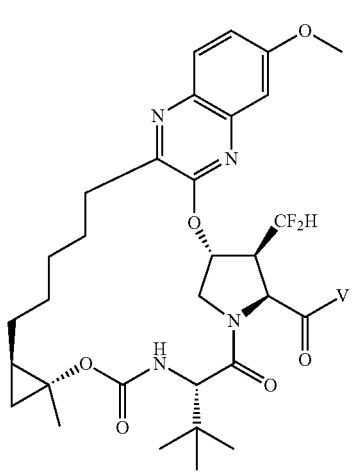
486
-continued
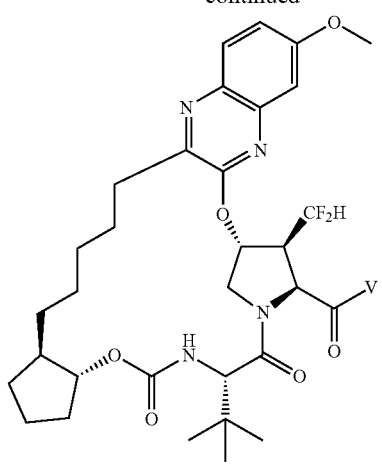
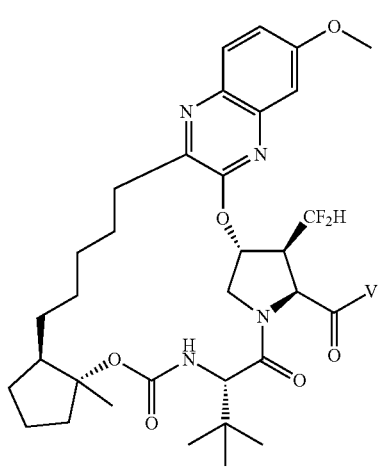
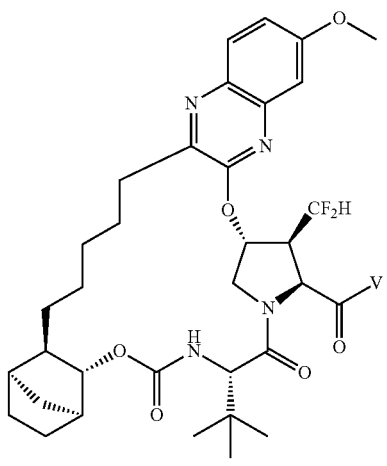

487
-continued
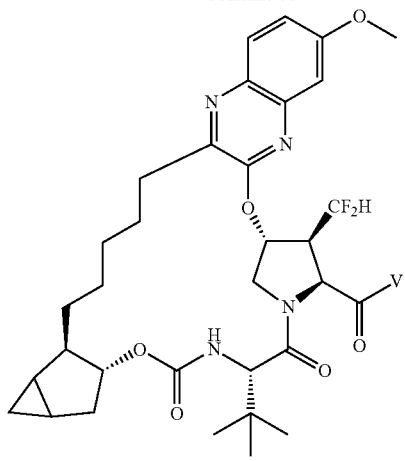
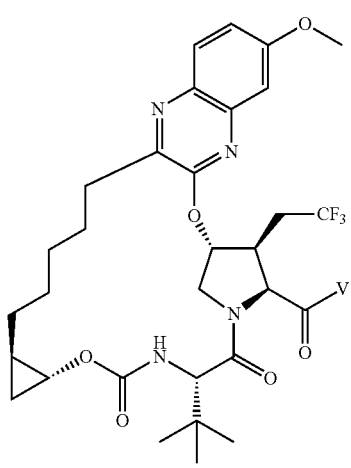
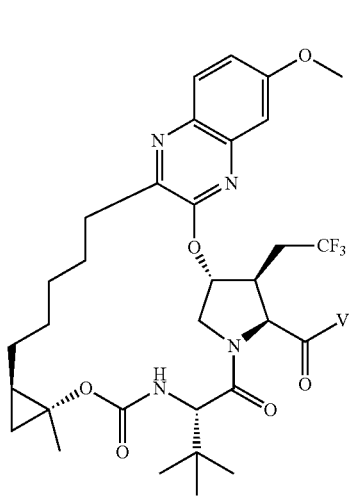
488
-continued
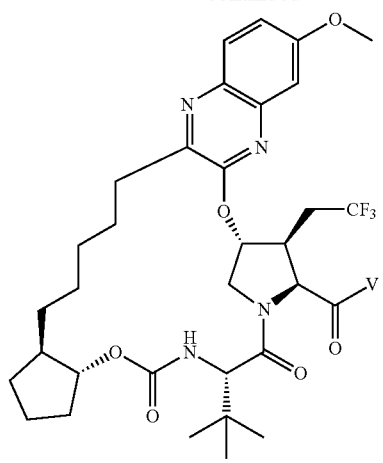
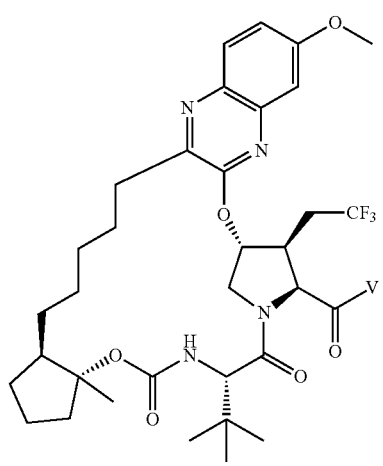
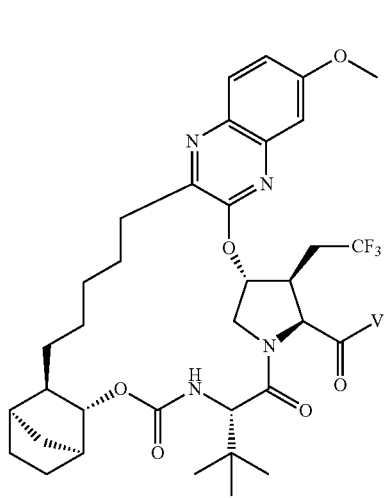

489
-continued
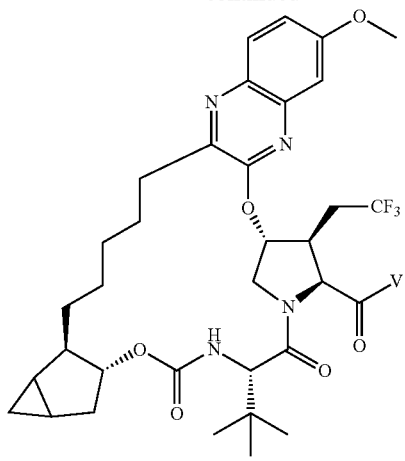
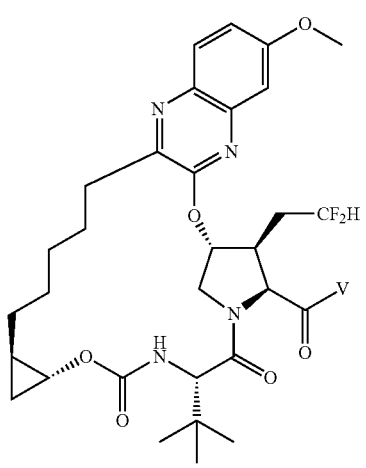
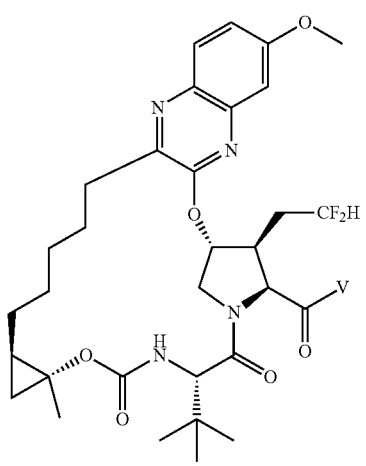
490
-continued
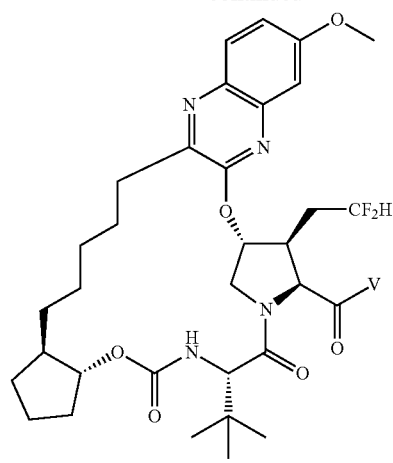
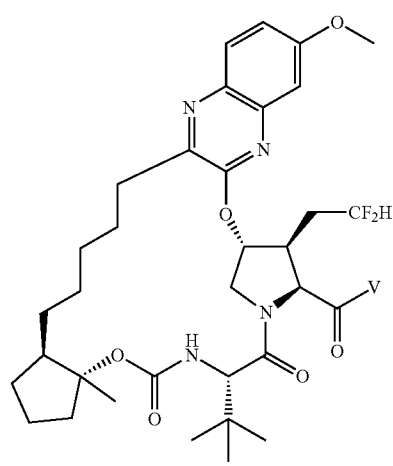
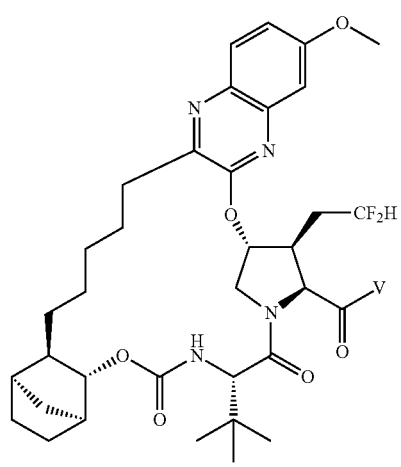

491
-continued
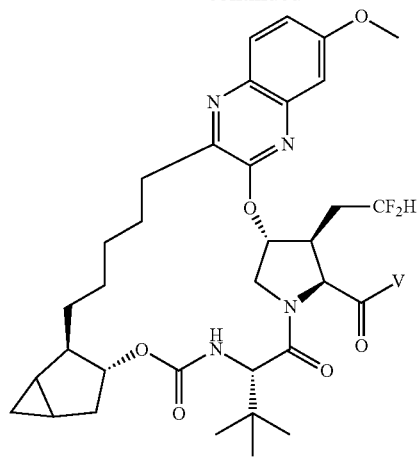
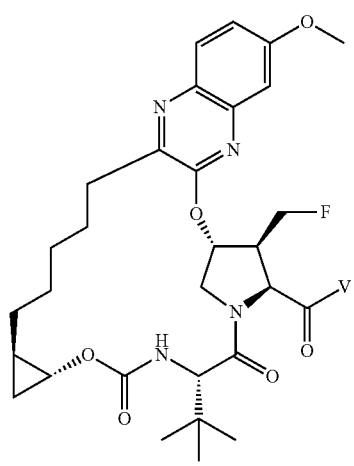
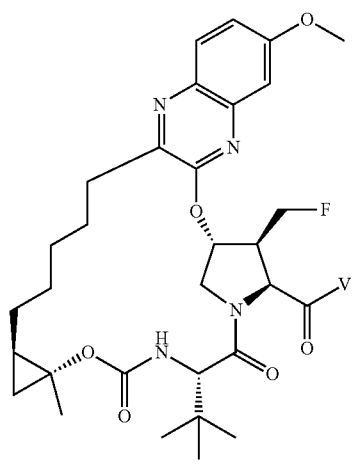
492
-continued
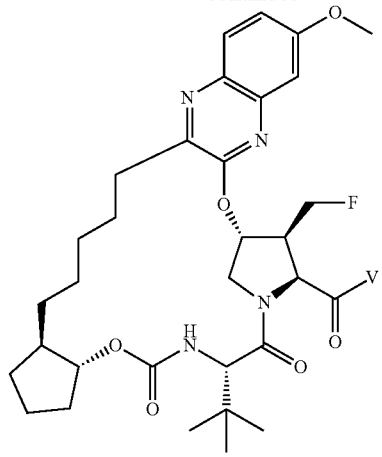
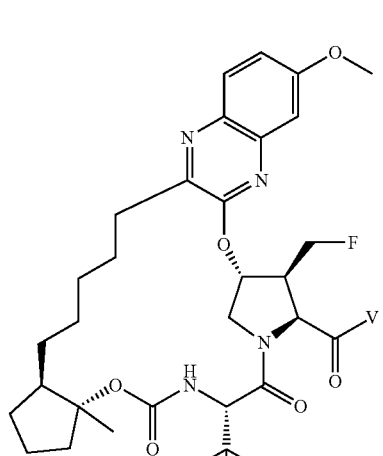
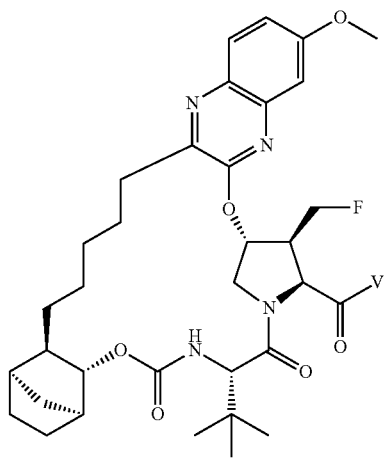

493
-continued
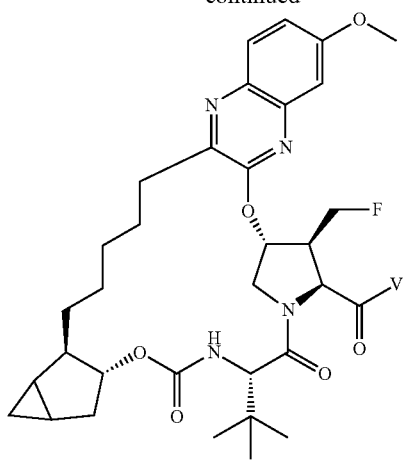
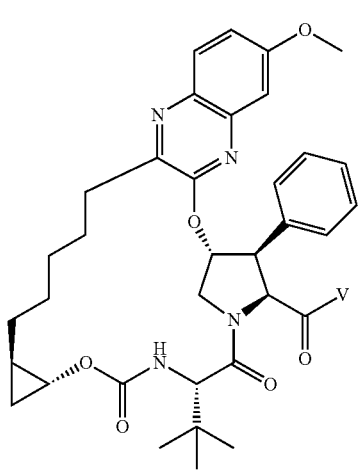
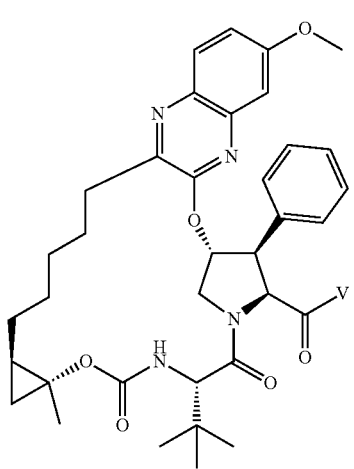
494
-continued
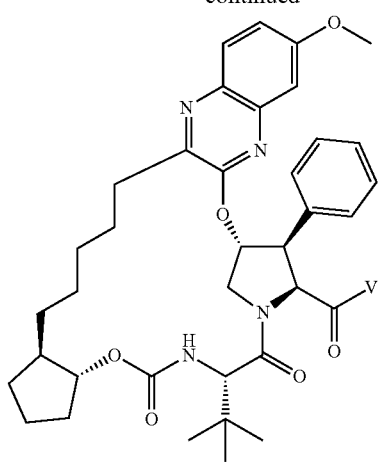
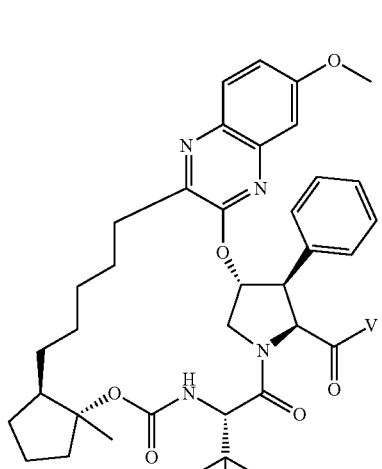
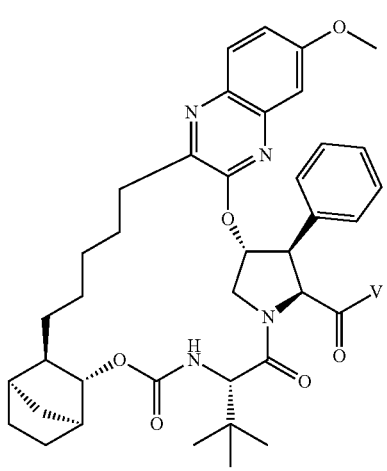

495
-continued
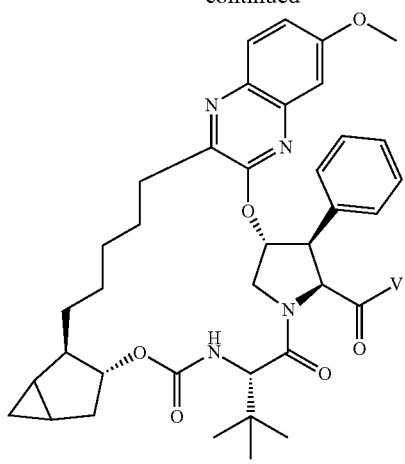
496
-continued
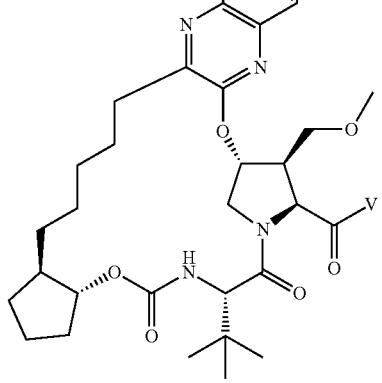
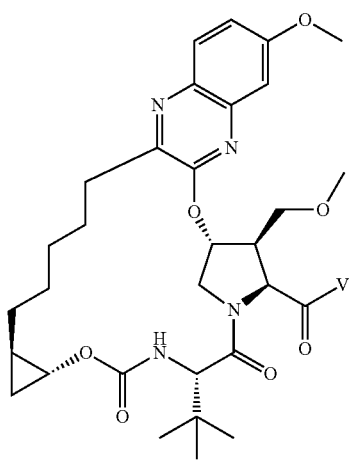
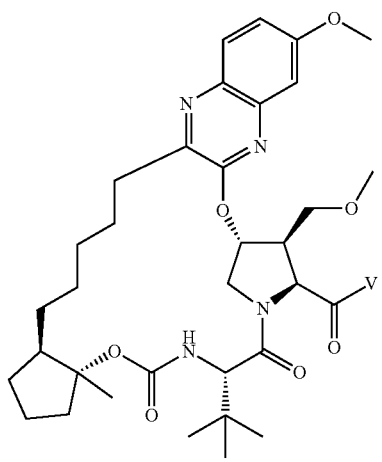
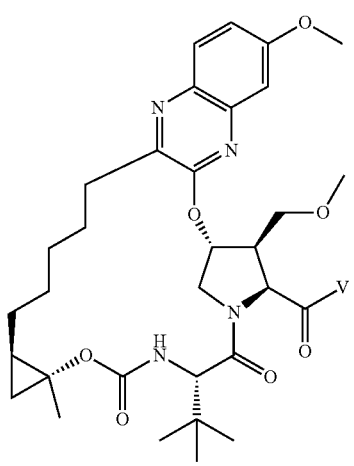
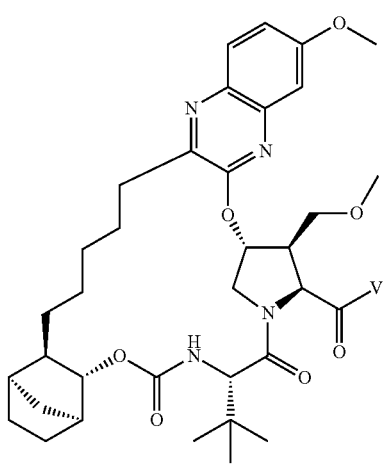

497
-continued
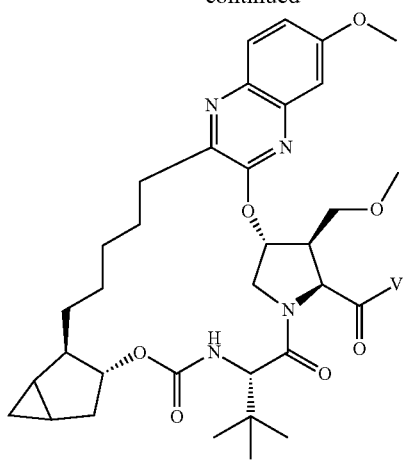
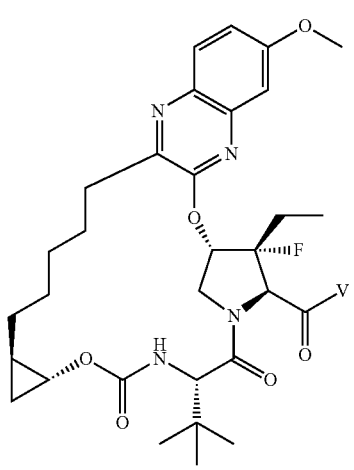
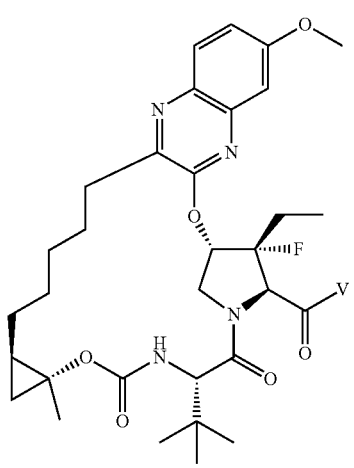
498
-continued
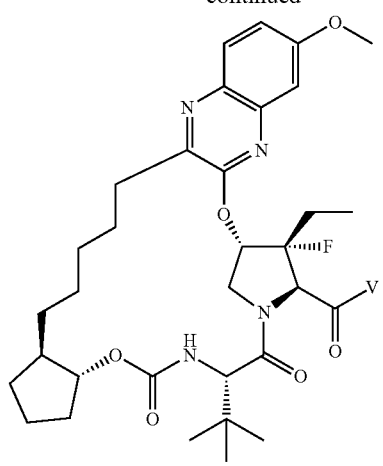
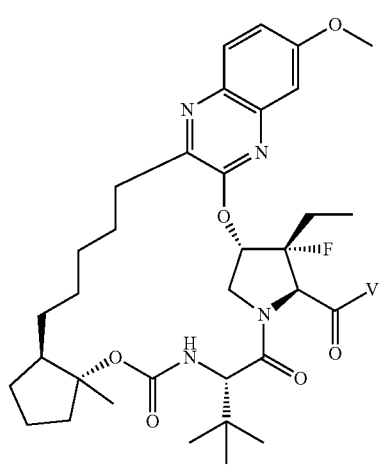
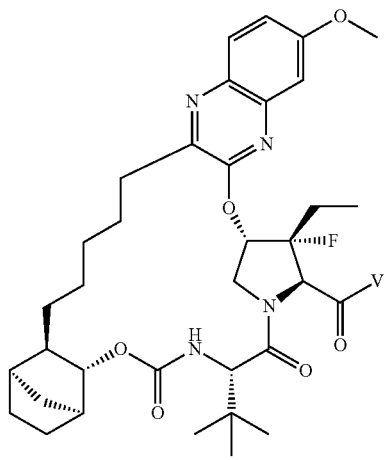

499 -continued
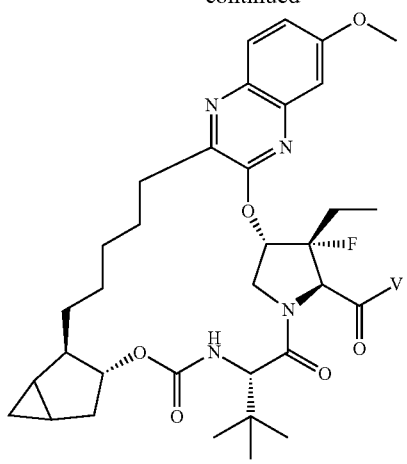
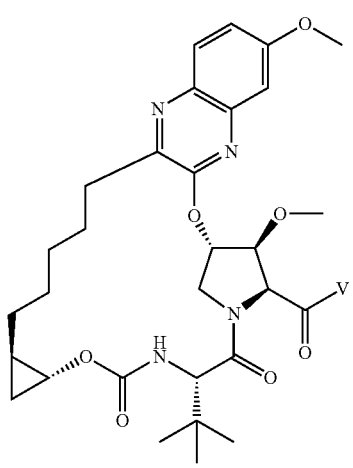
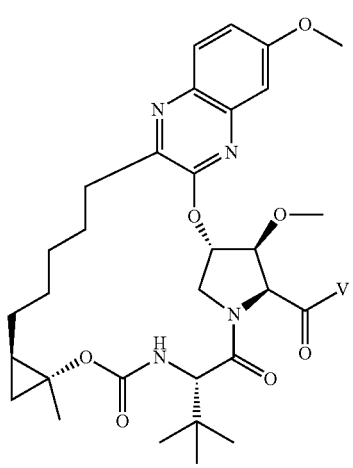
500 -continued
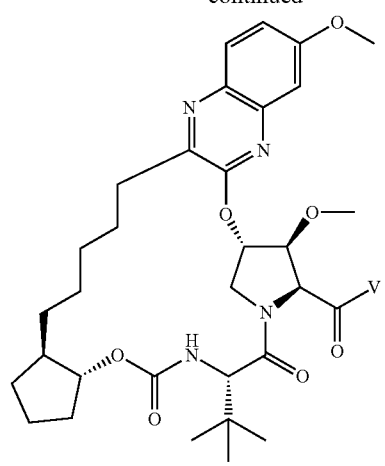
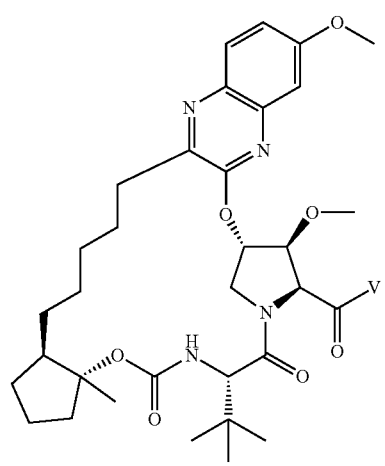
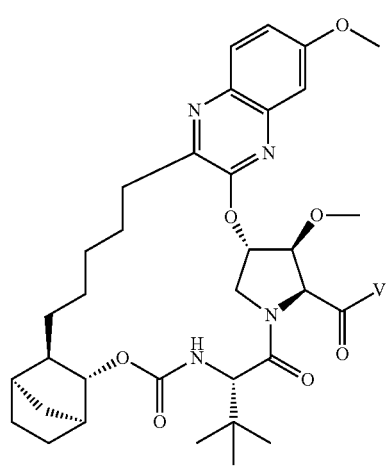

501
-continued
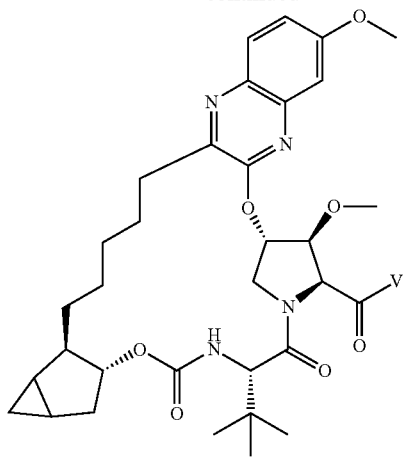
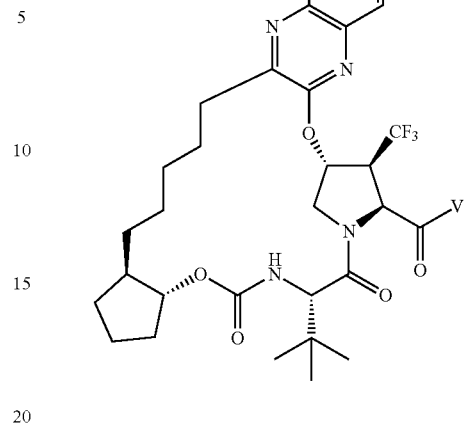
502
-continued
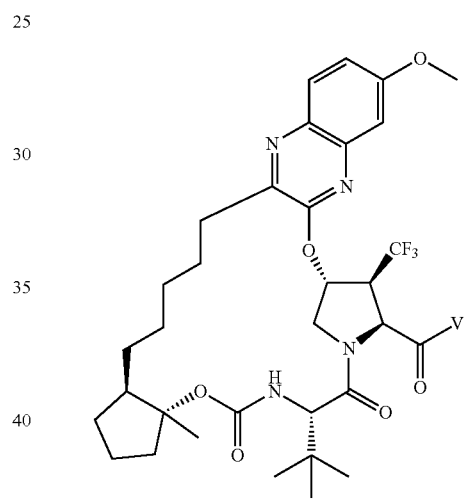
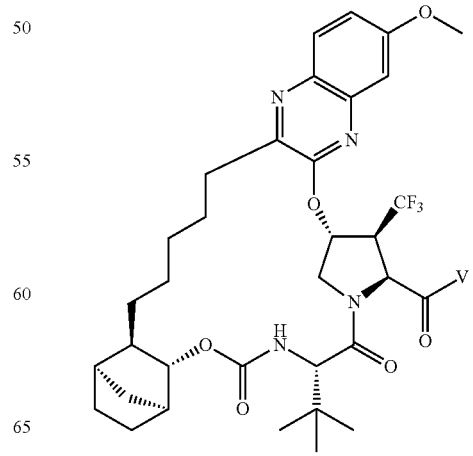

503
-continued
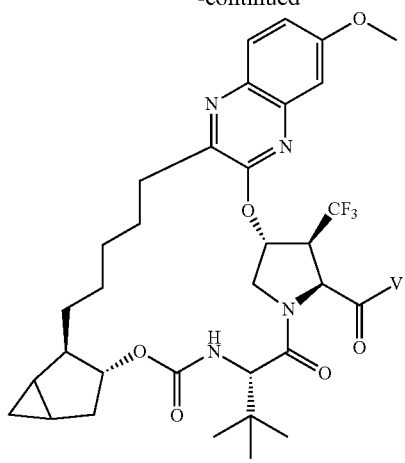
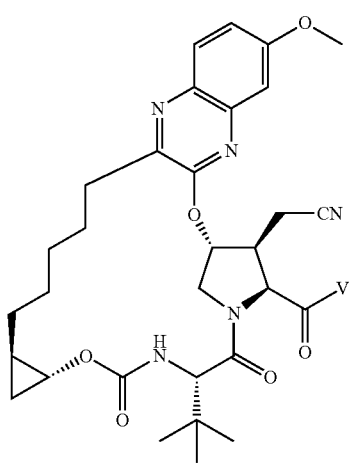
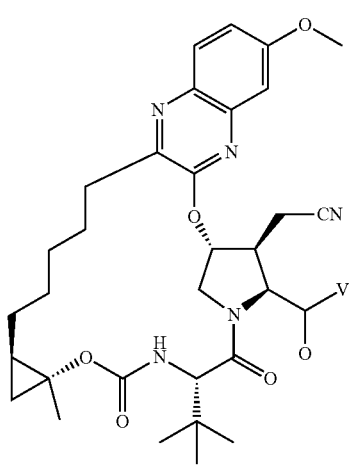
504
-continued
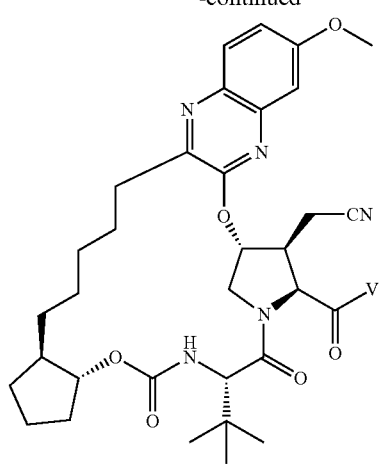
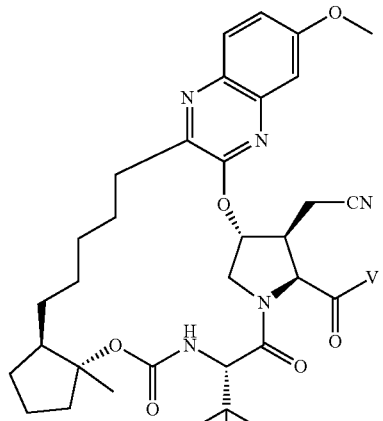
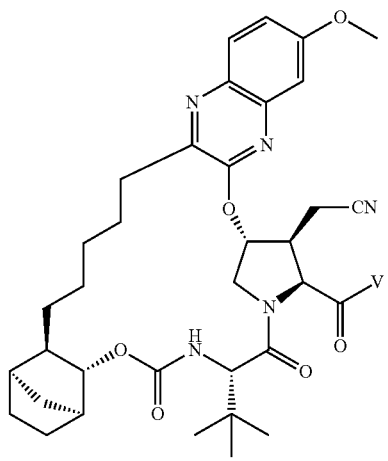

505
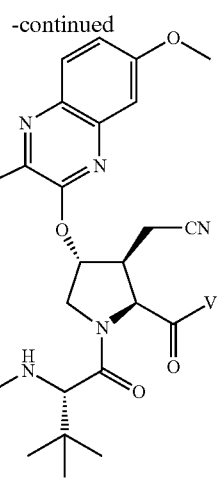
506
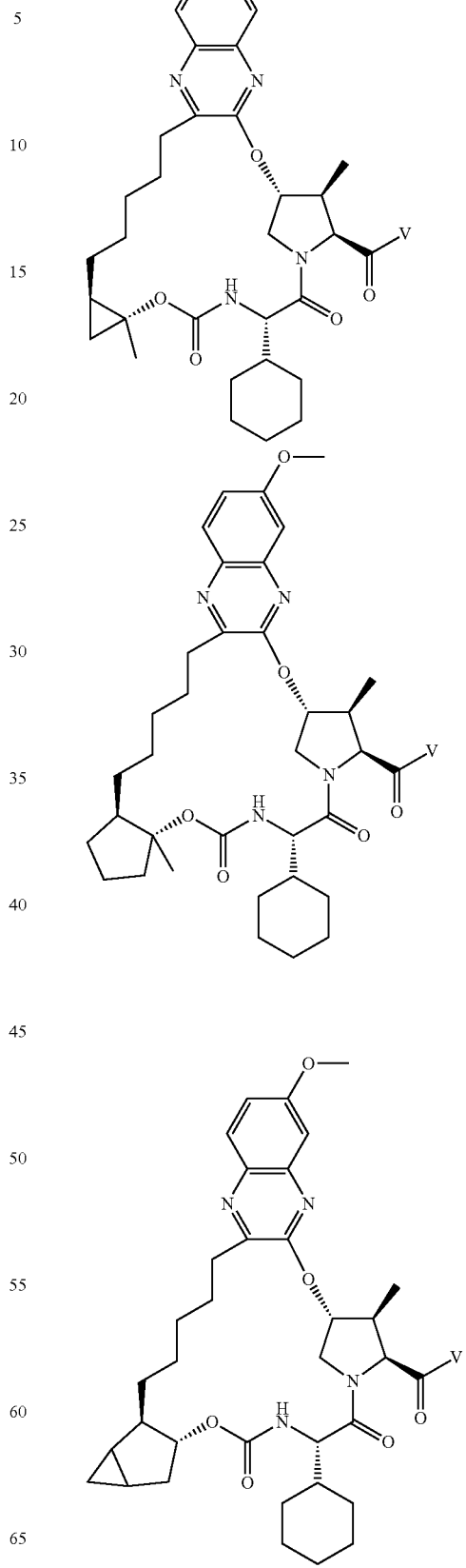
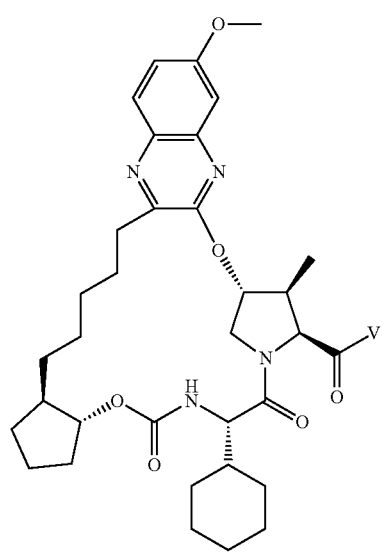

507
-continued
508
-continued
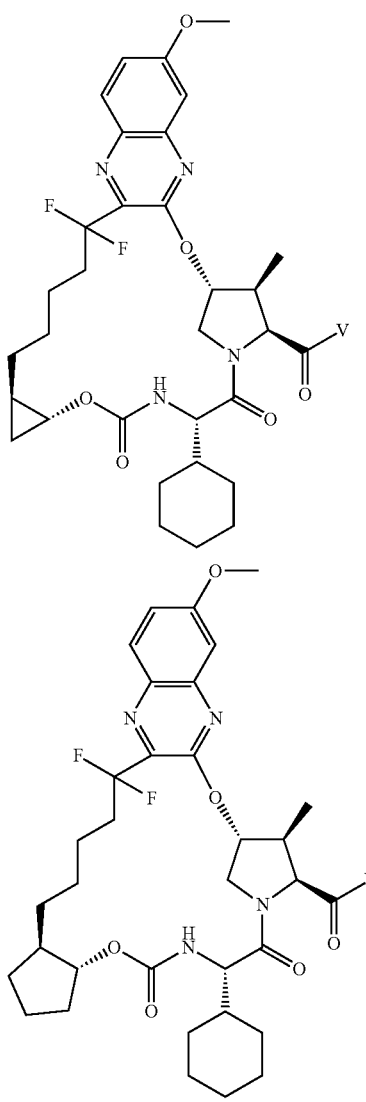
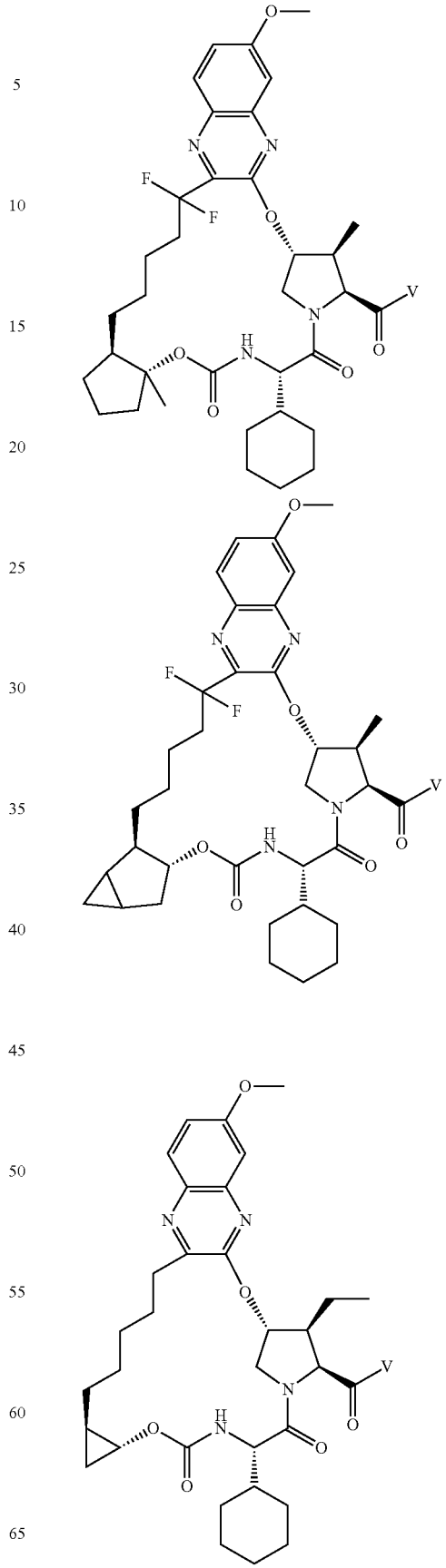

509
-continued
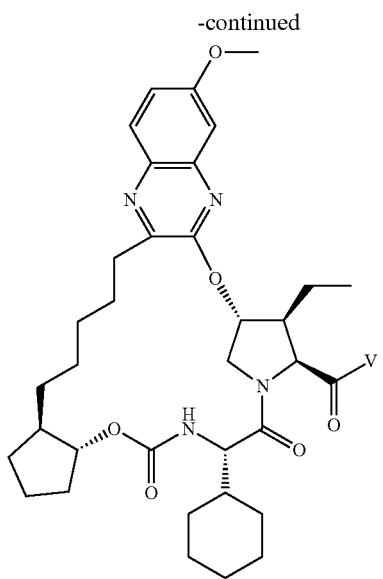
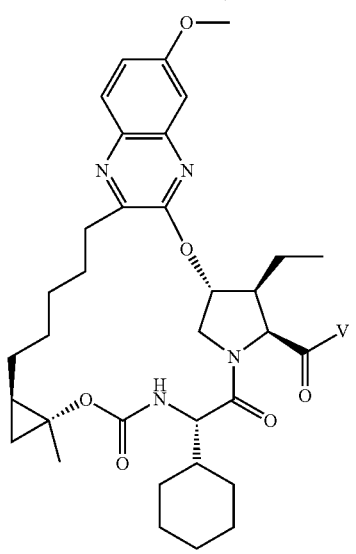
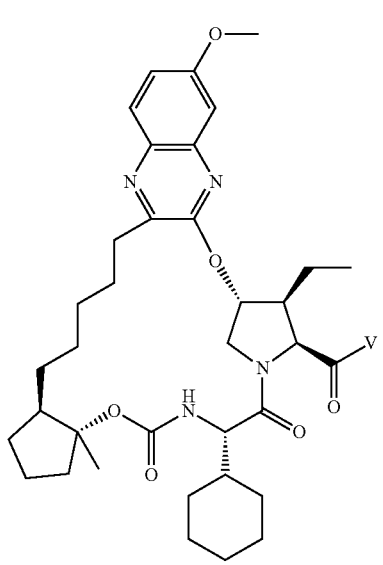
510
-continued
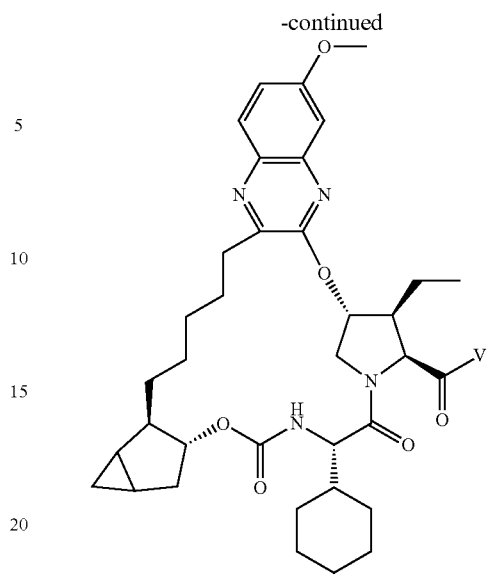
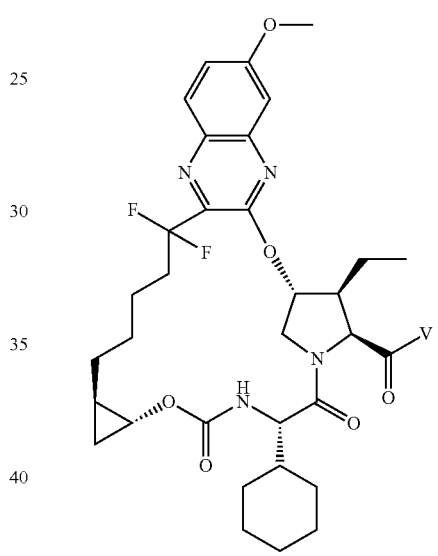
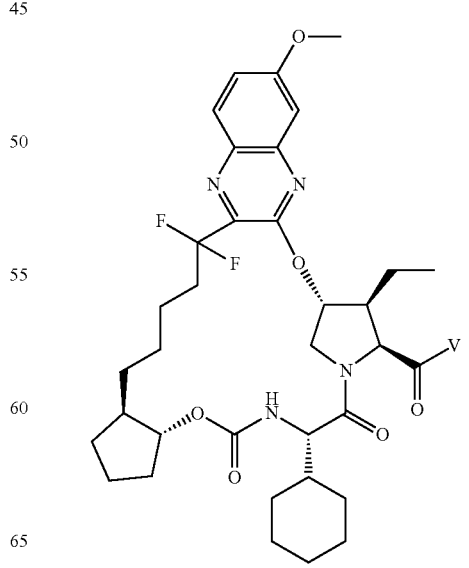

511
-continued
512
-continued
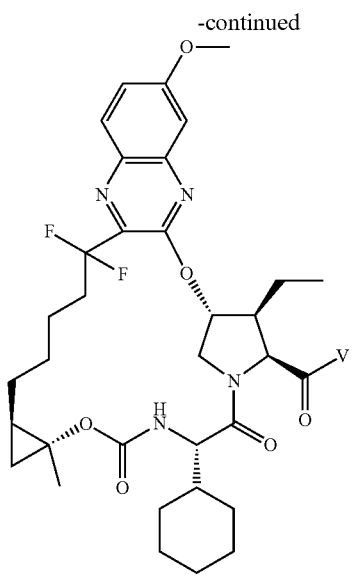
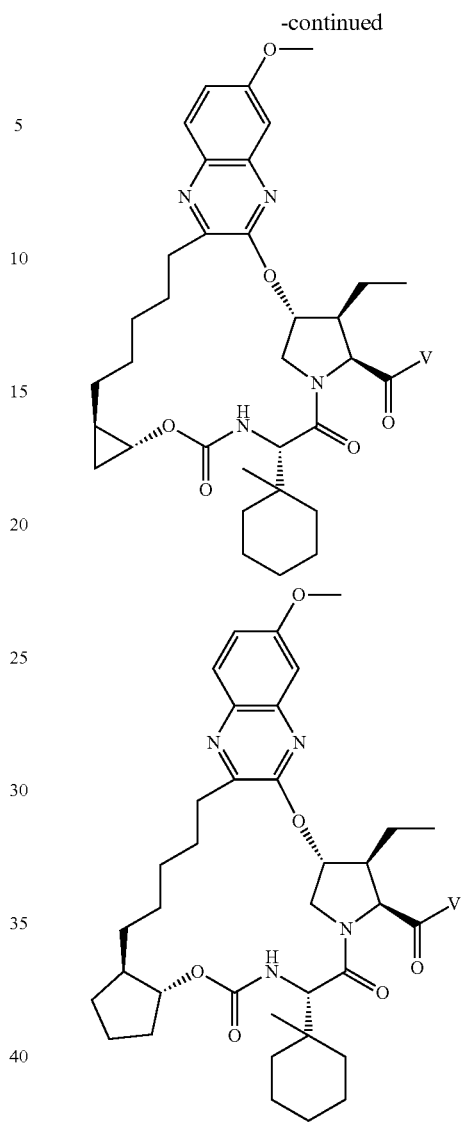
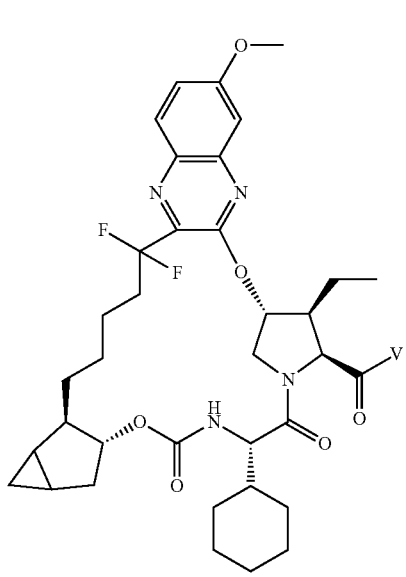

513
-continued
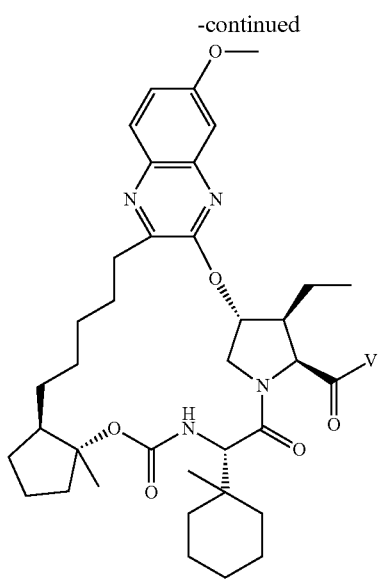
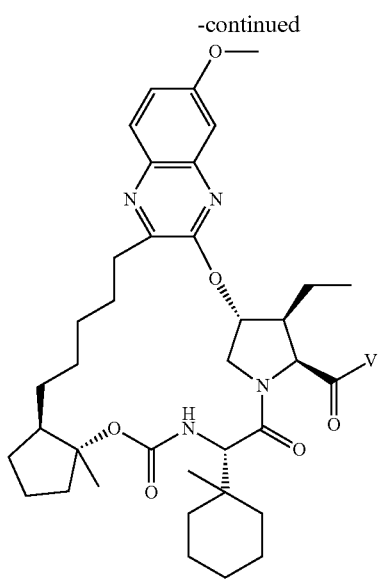
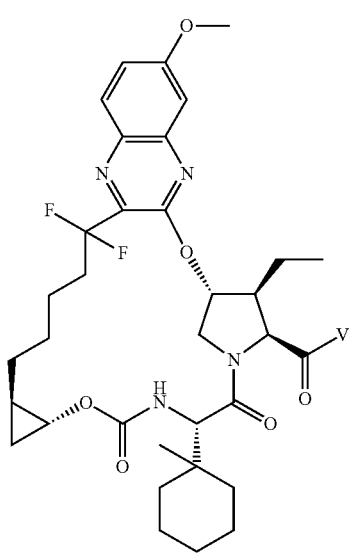
514
-continued
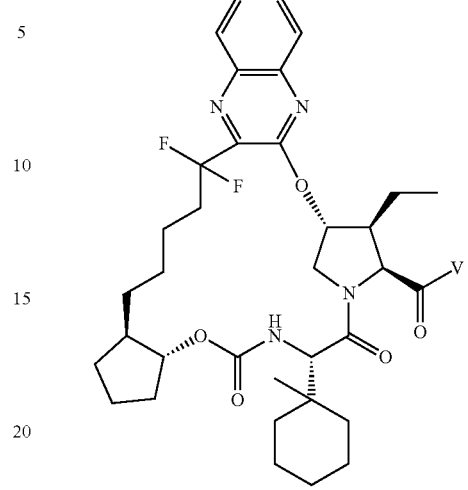
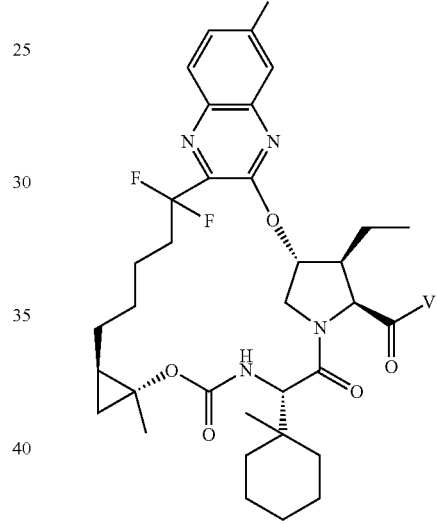
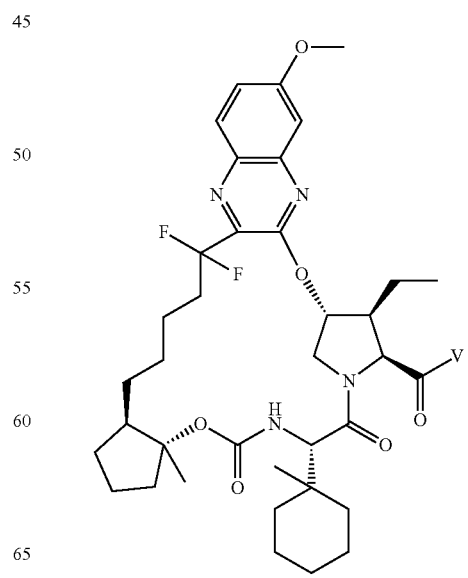

515
-continued
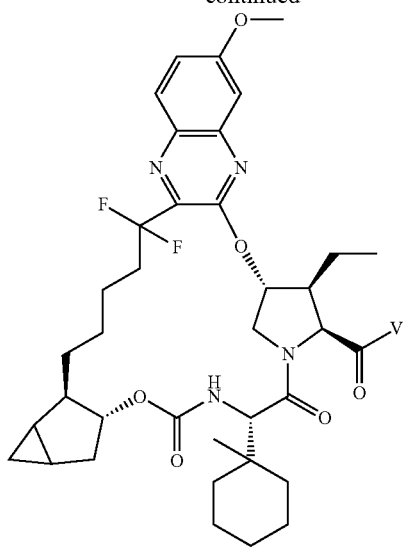
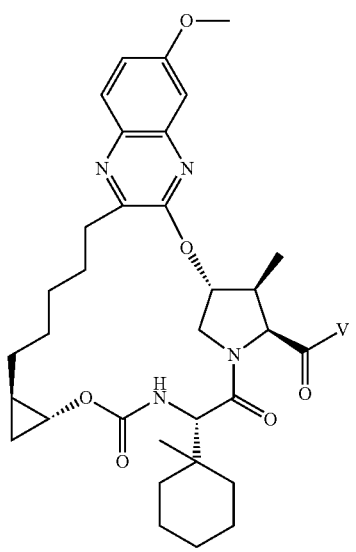
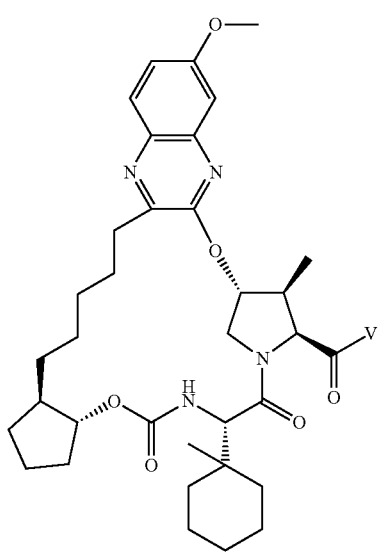
516
-continued
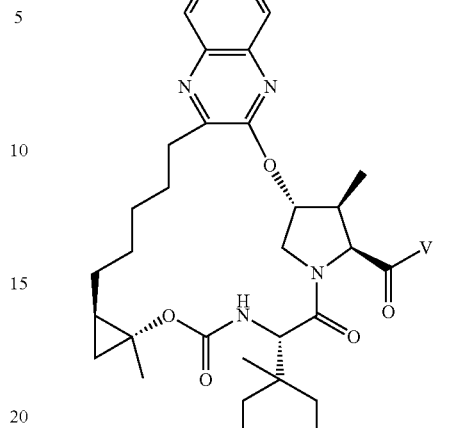
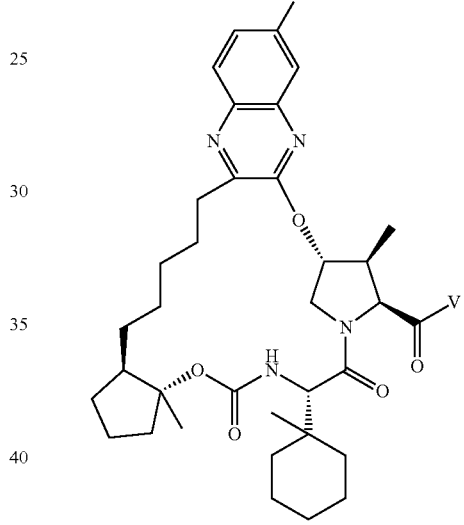
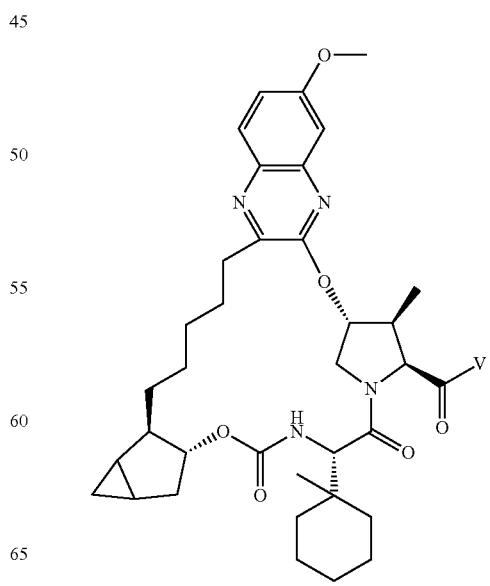

517
-continued
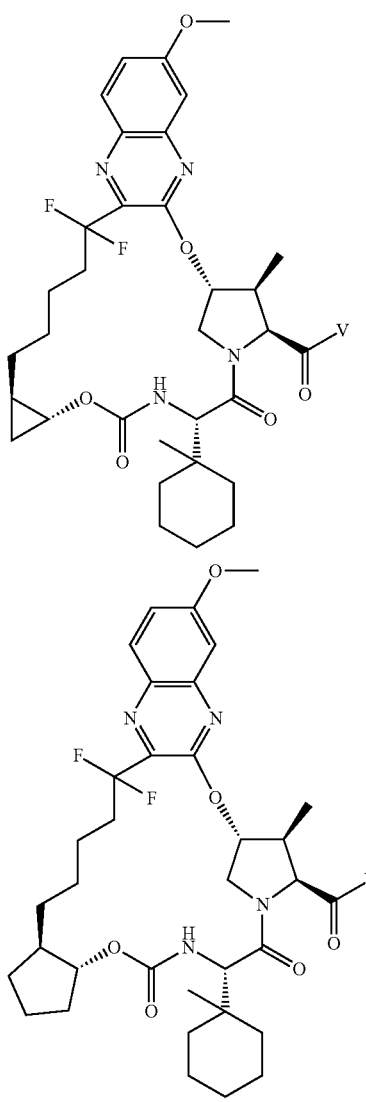
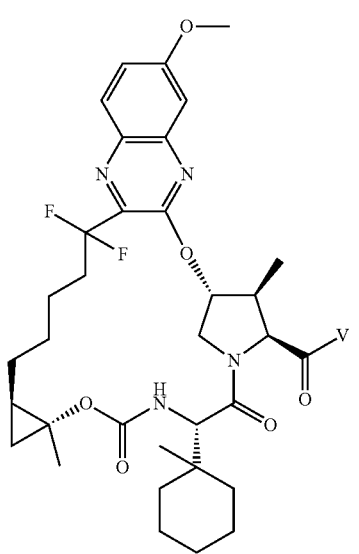
518
-continued
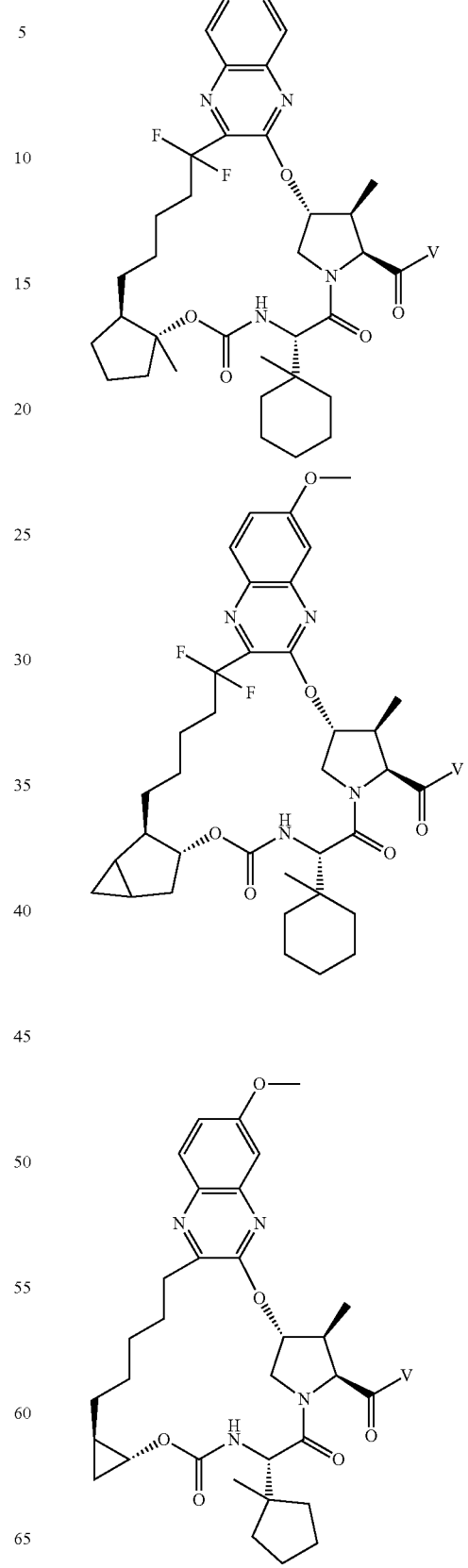
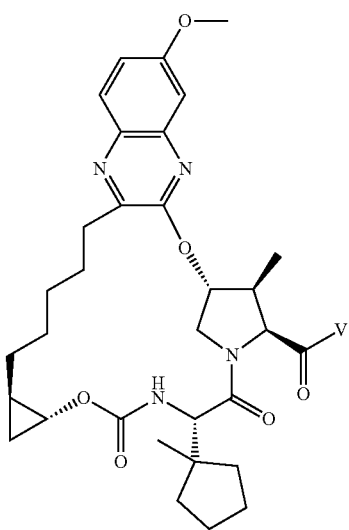

519
-continued
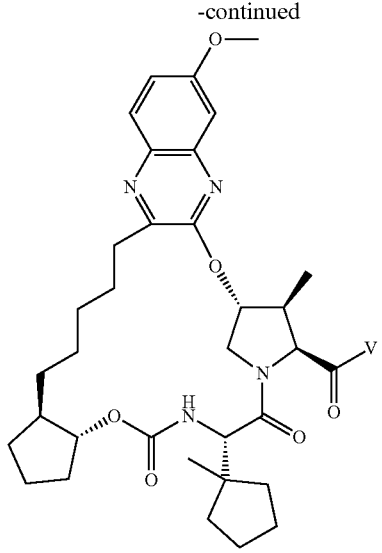
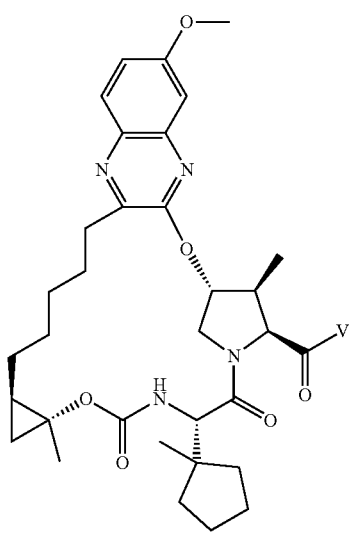
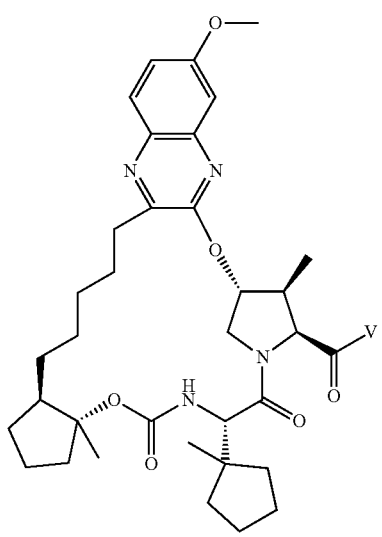
520
-continued
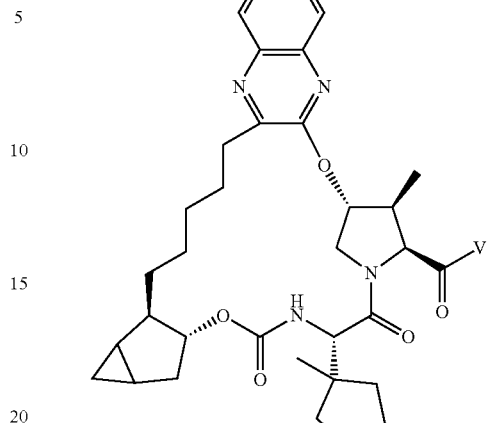
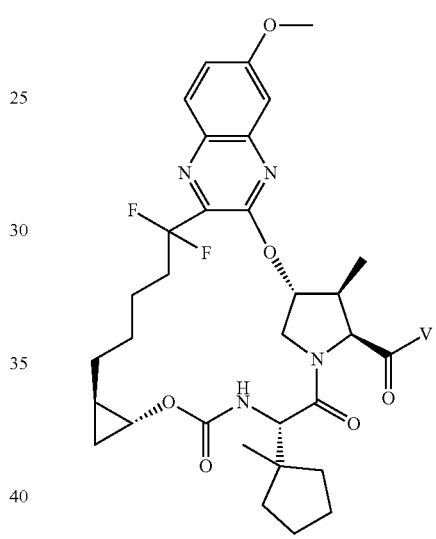
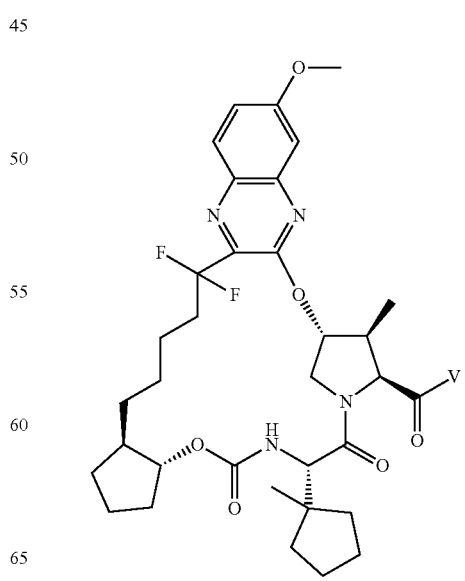

521
-continued
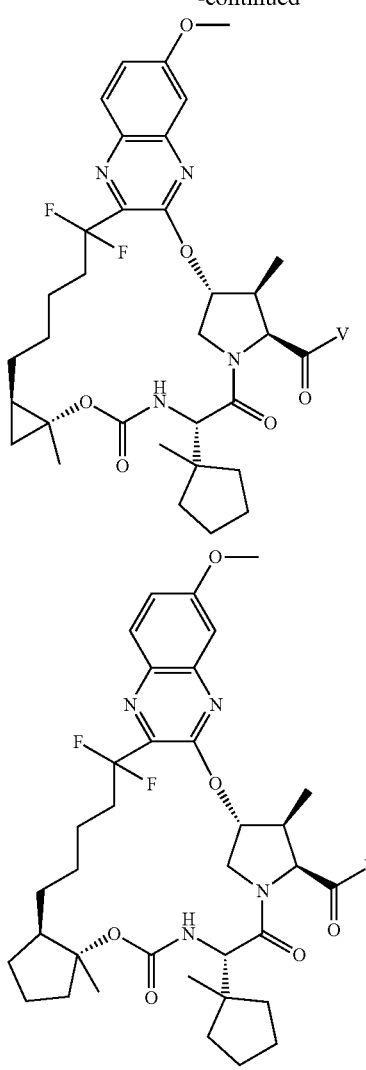
522
-continued
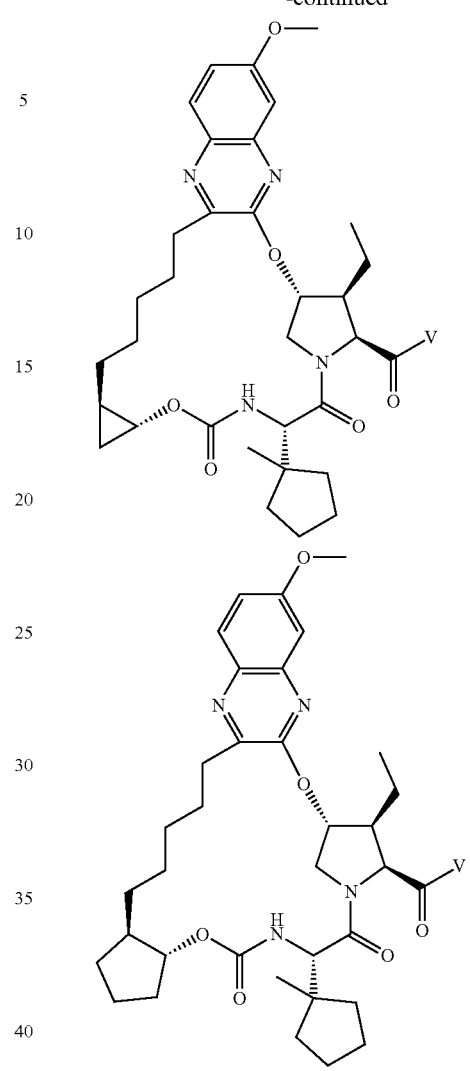
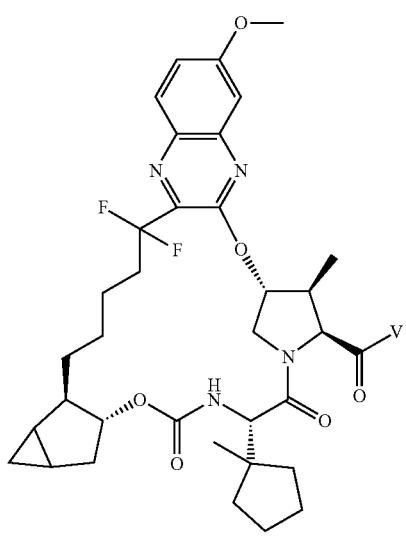
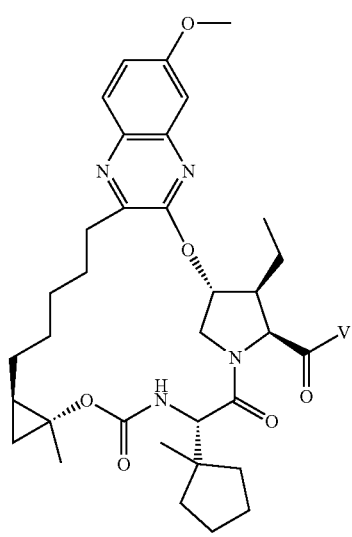

523
-continued
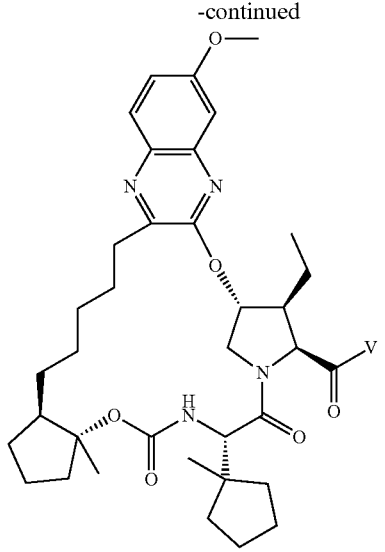
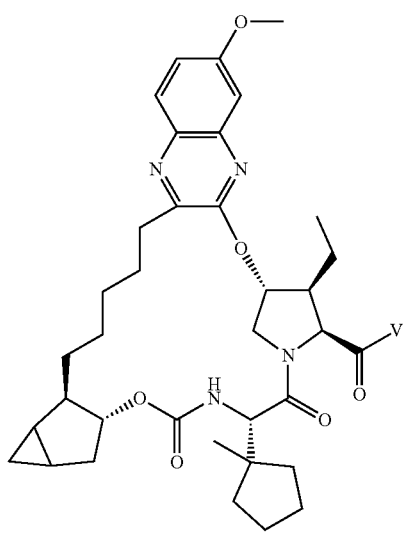
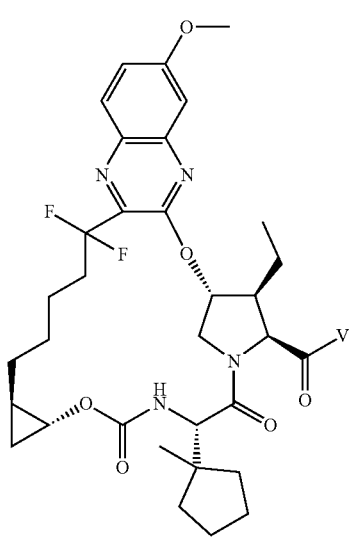
524
-continued
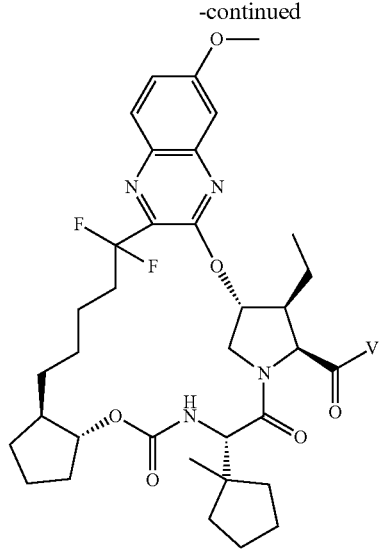
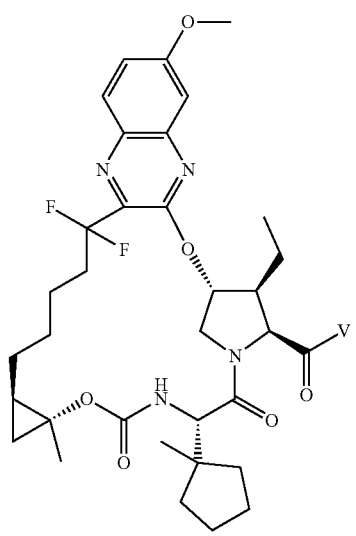
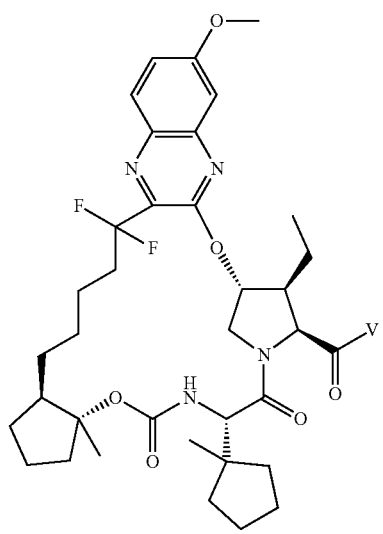

525
-continued
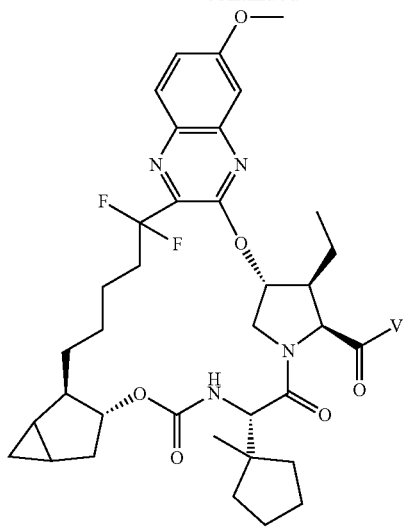
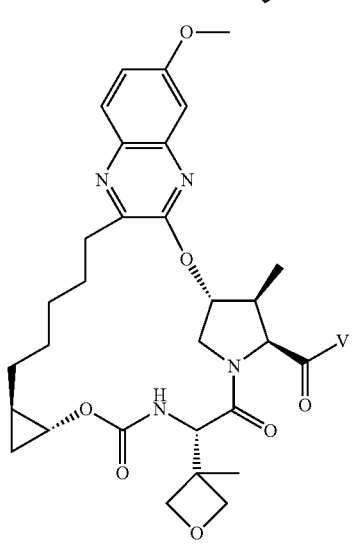
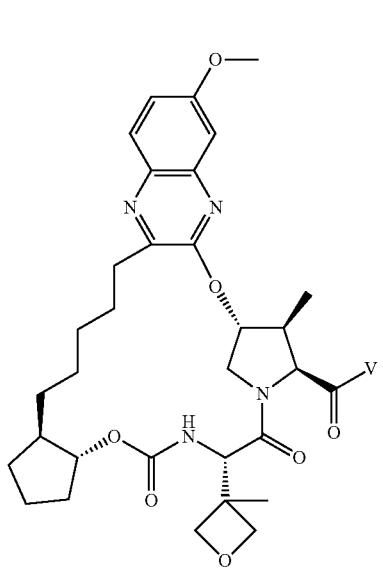
526
-continued
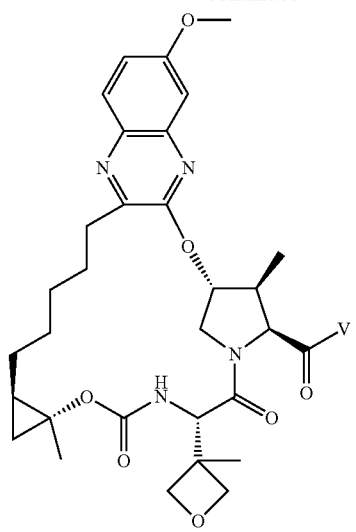
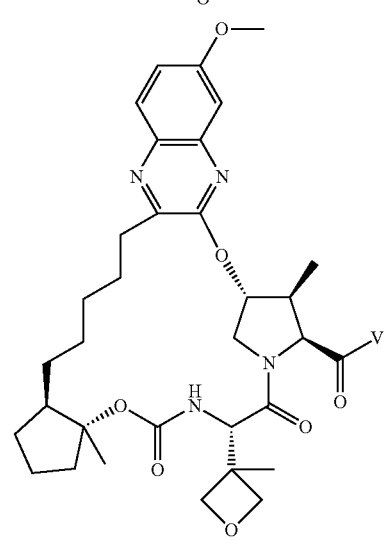
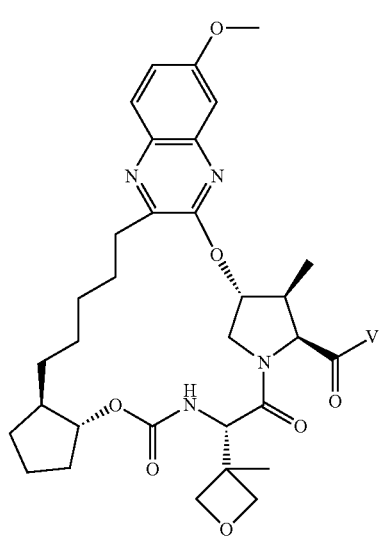

527
-continued
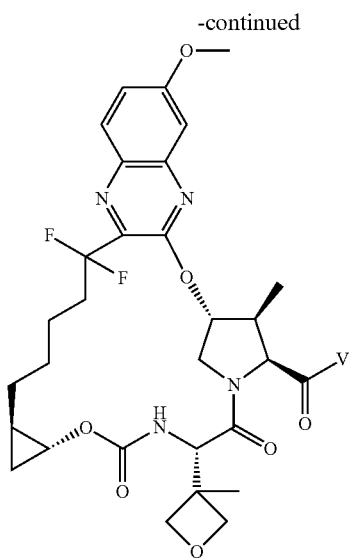
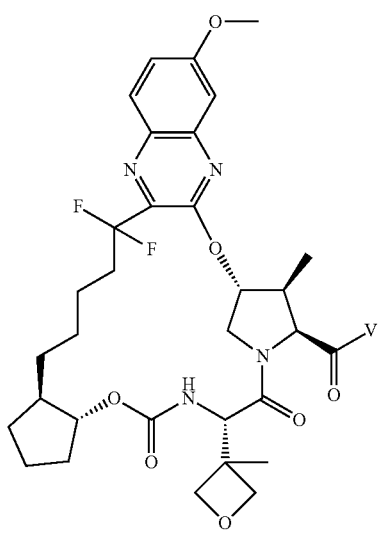
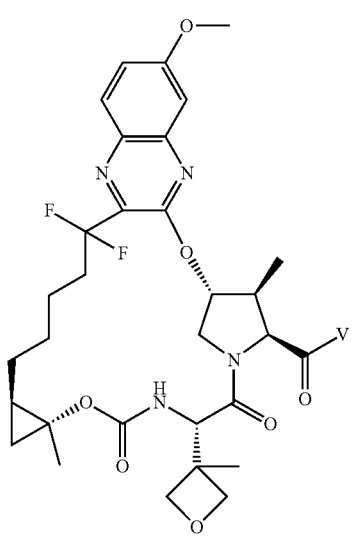
528
-continued
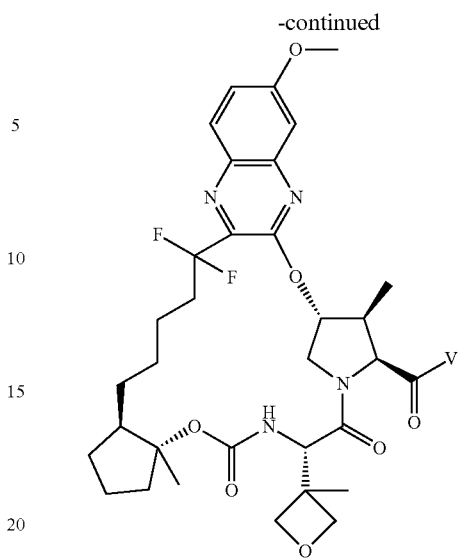
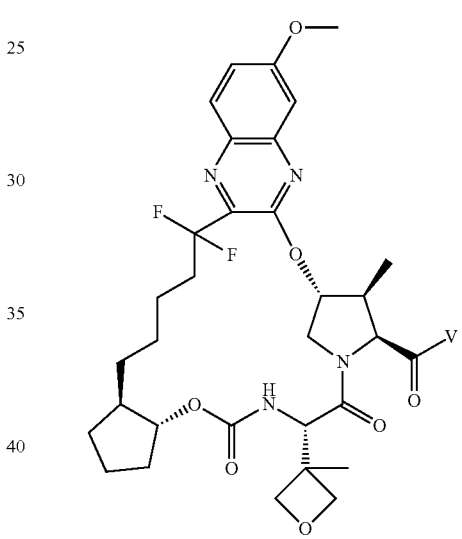
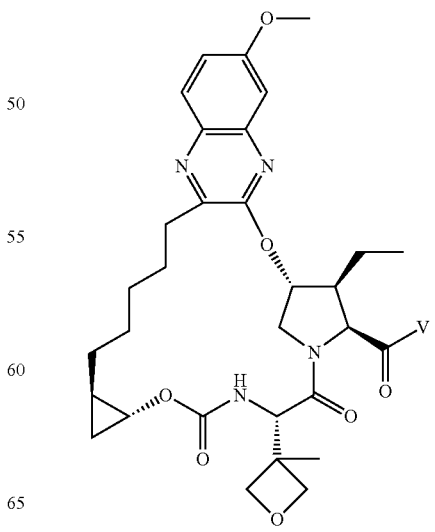

529
-continued
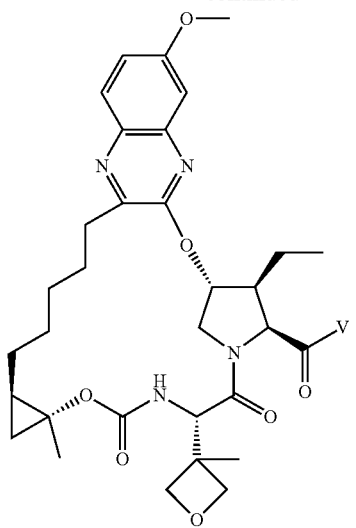
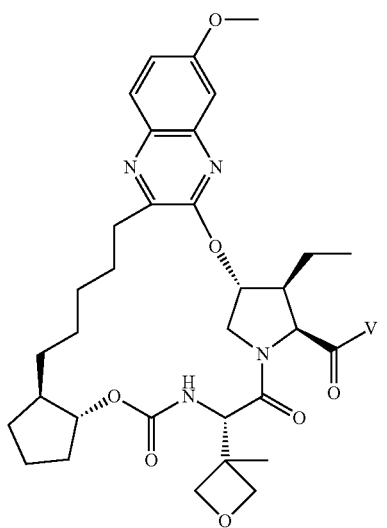
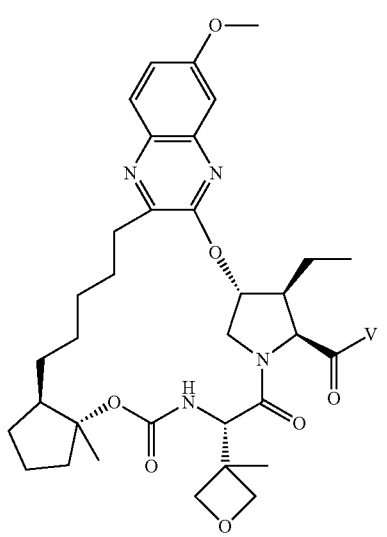
530
-continued
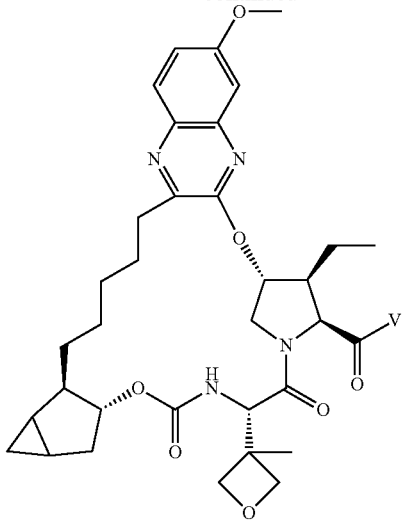
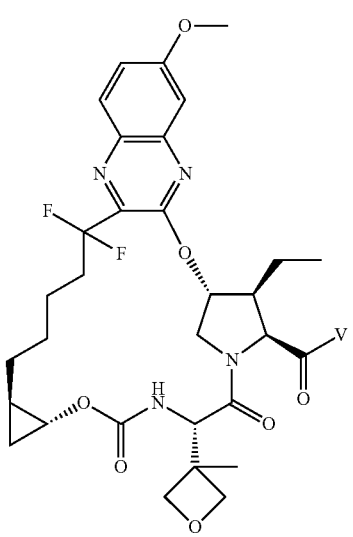
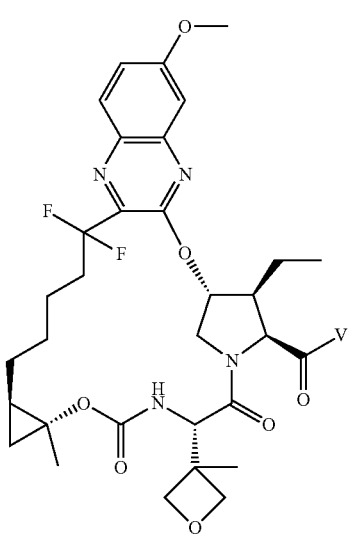

531
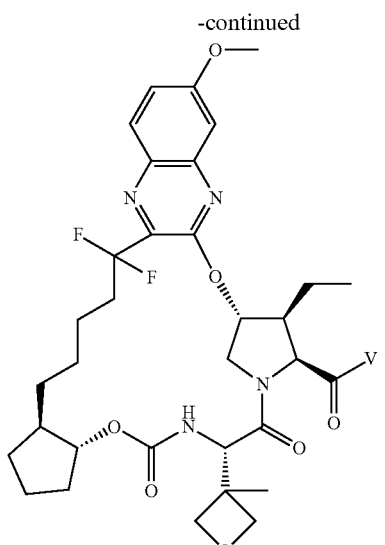
532
-continued
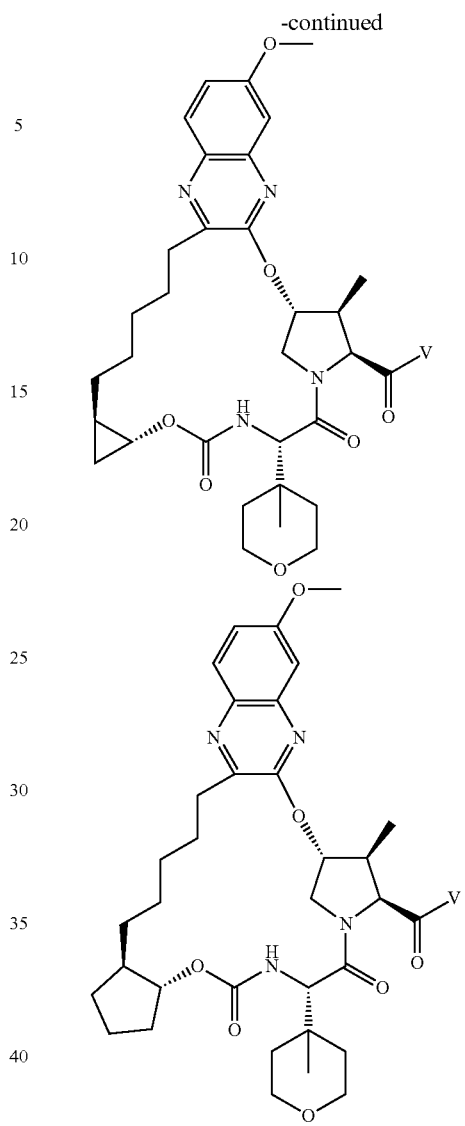
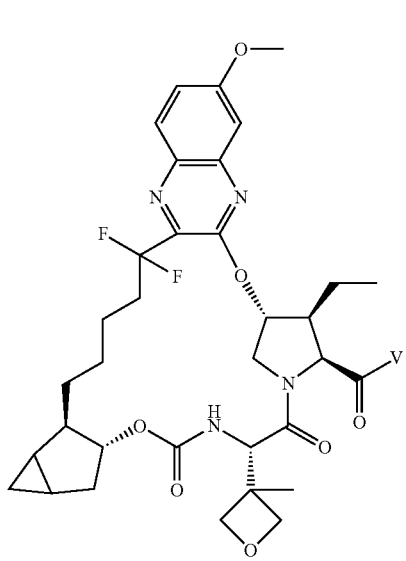

533
-continued
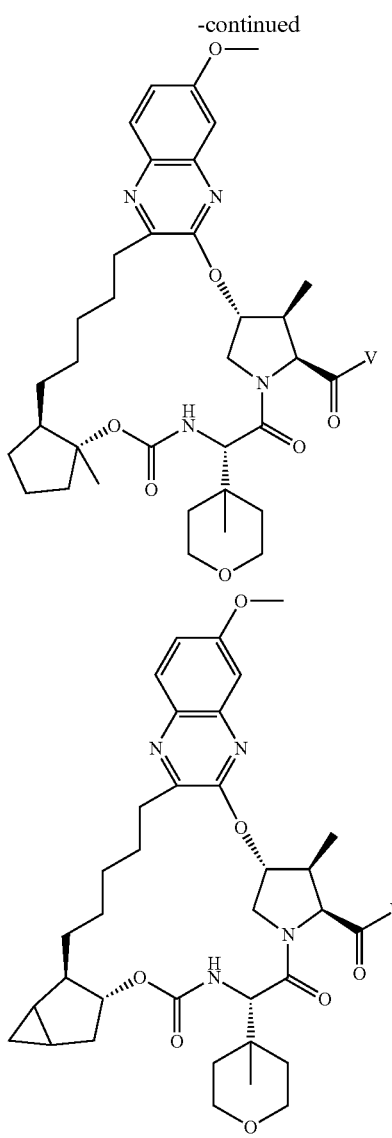
534
-continued
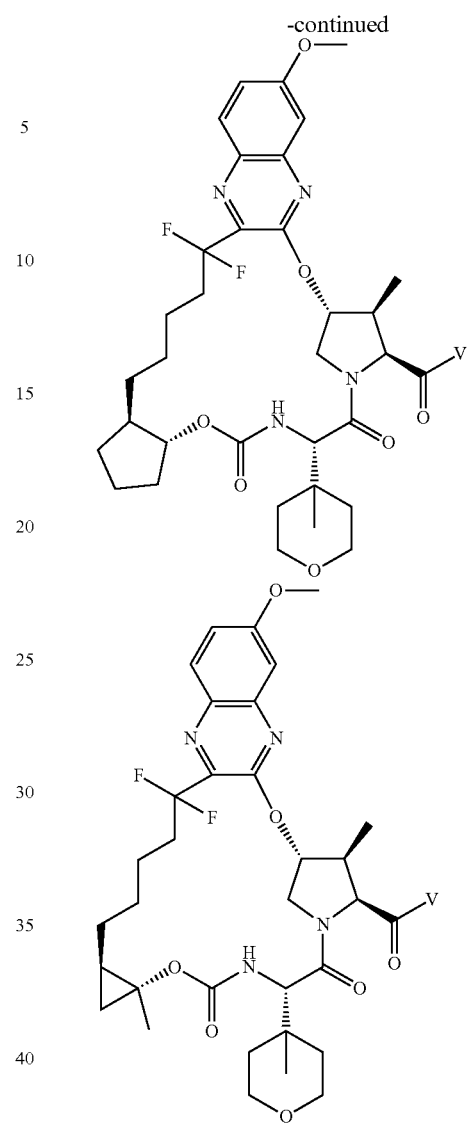
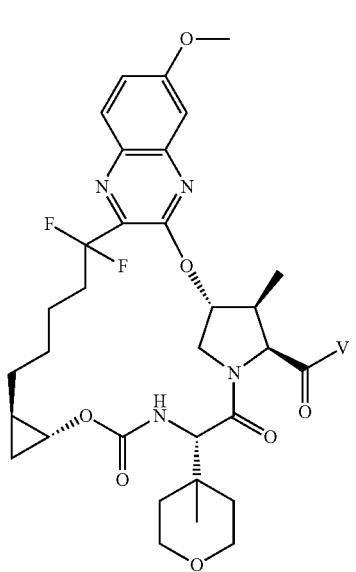
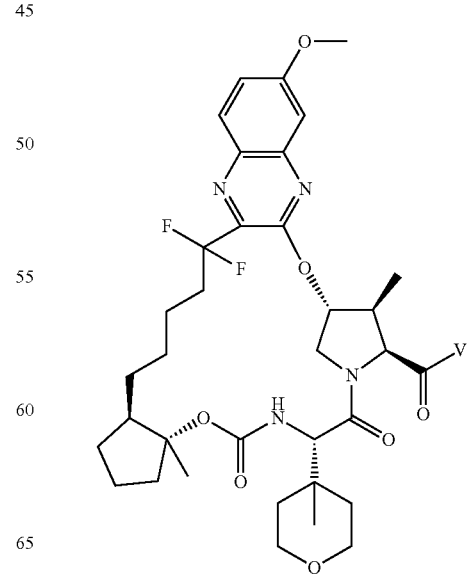

535
-continued
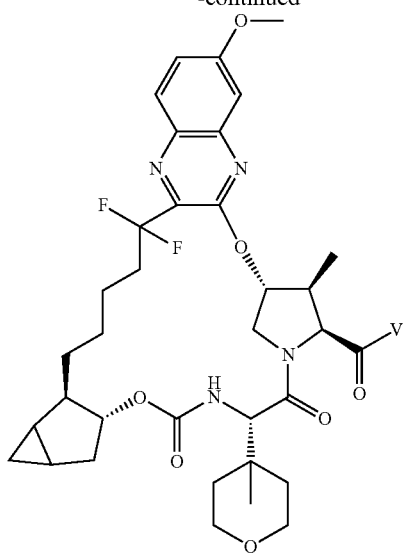
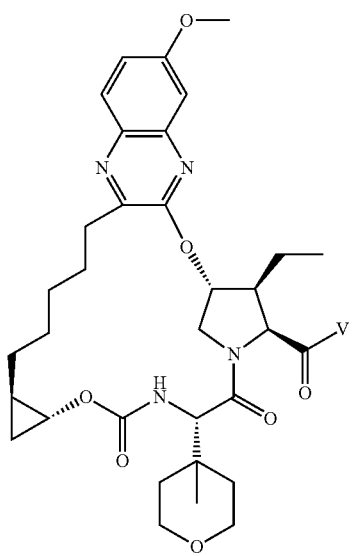
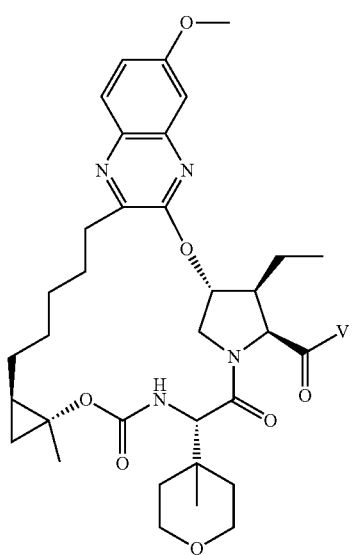
536
-continued
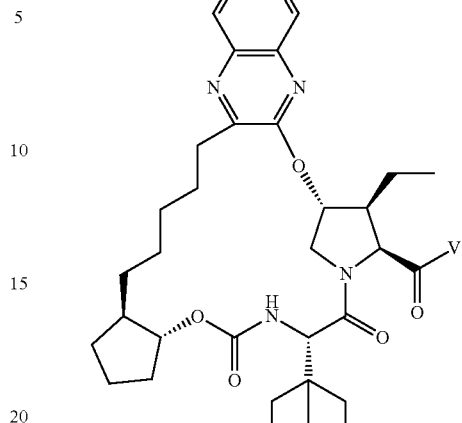
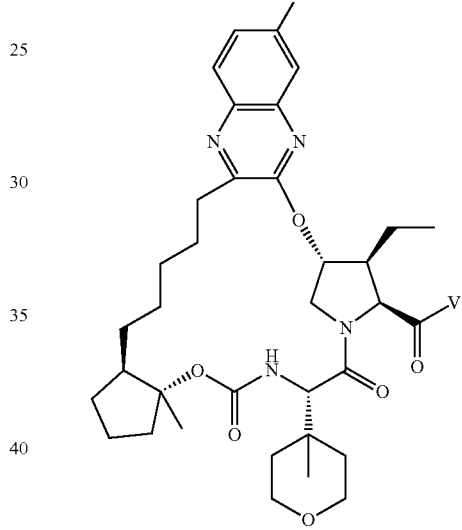
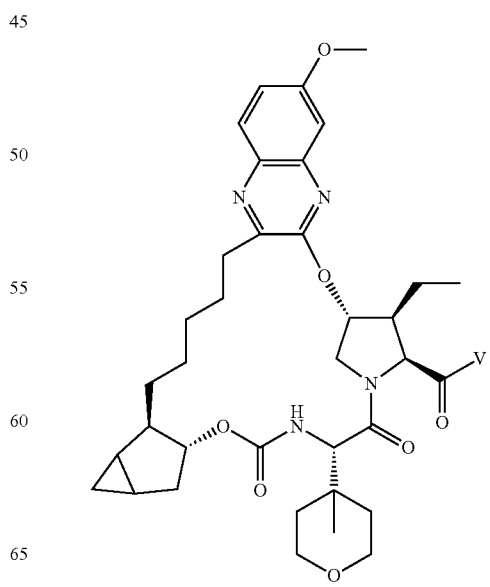

537
-continued
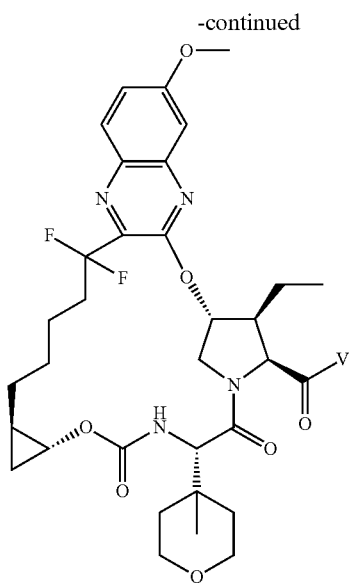
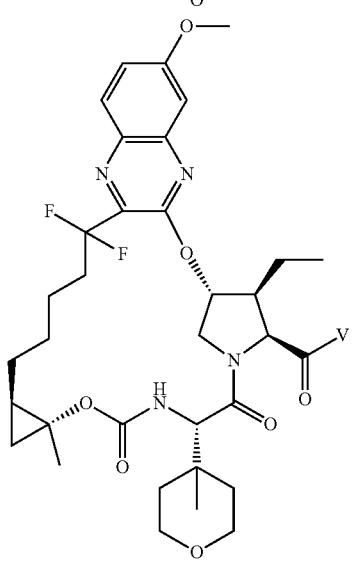
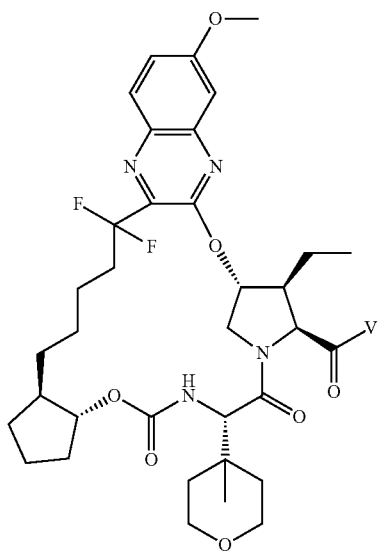
538
-continued
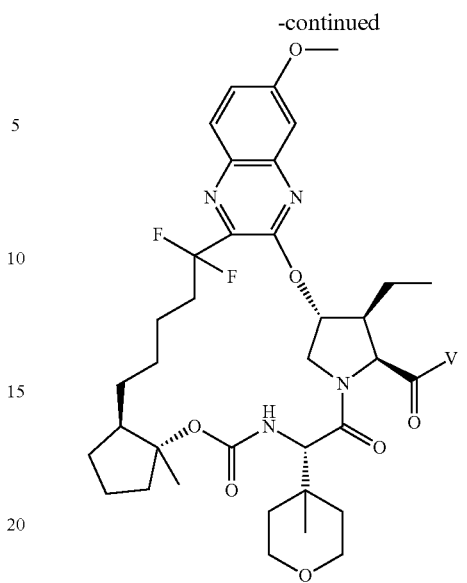
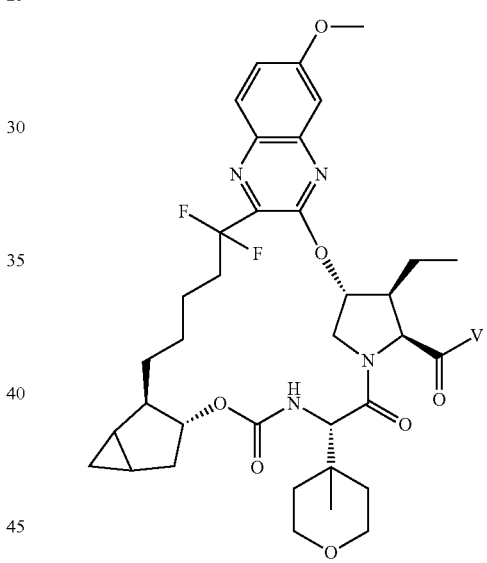
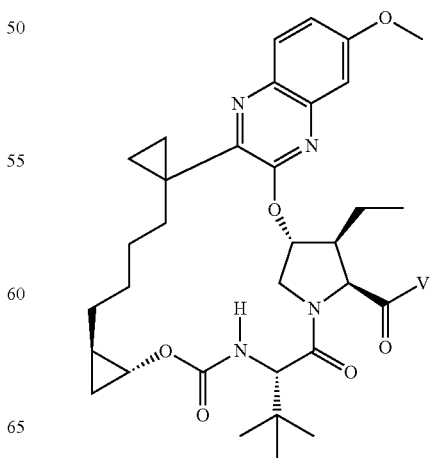

539
-continued
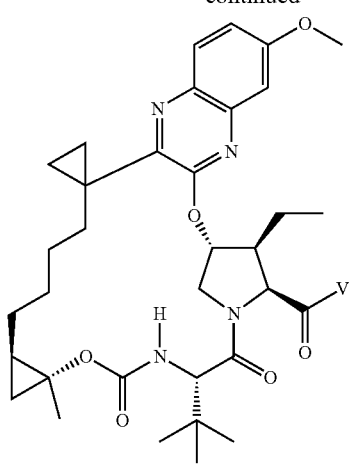
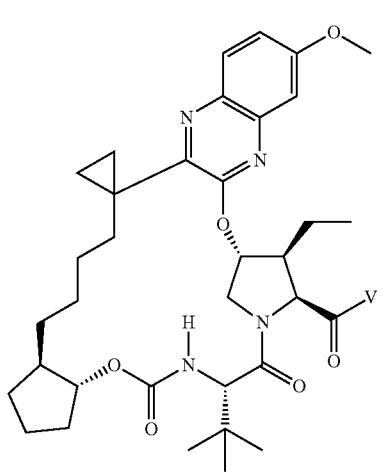
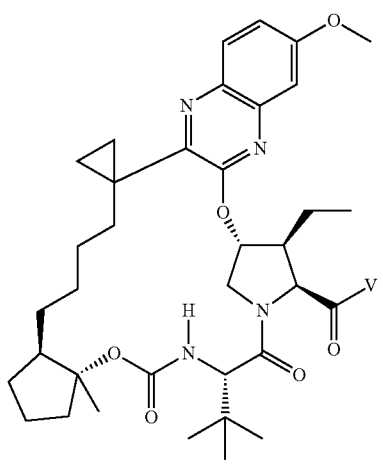
540
-continued
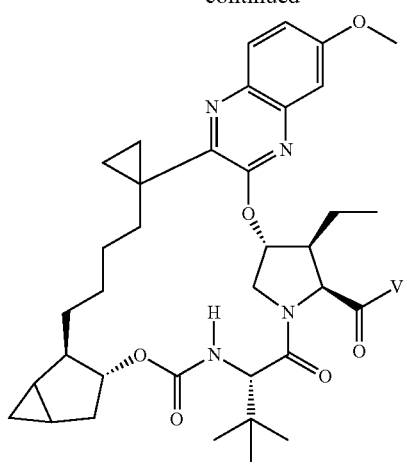
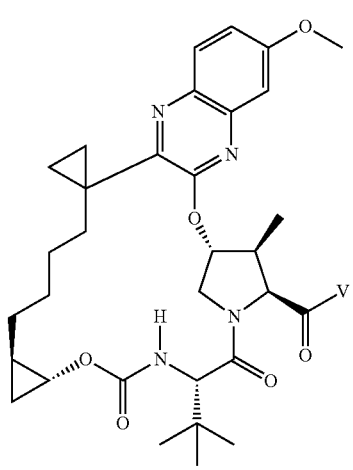
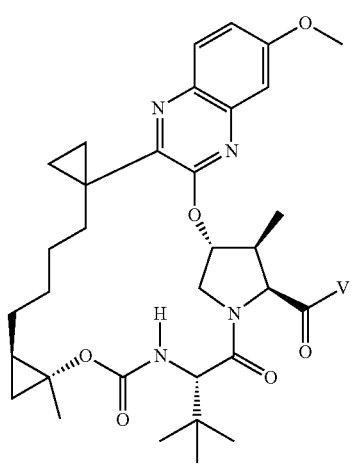

541
-continued
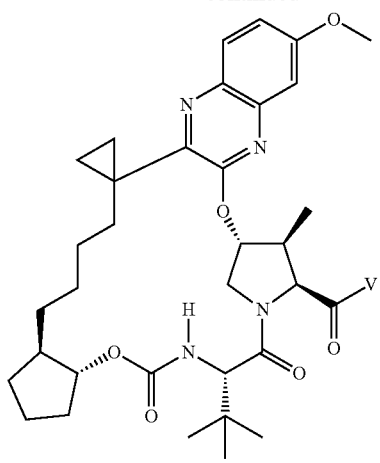
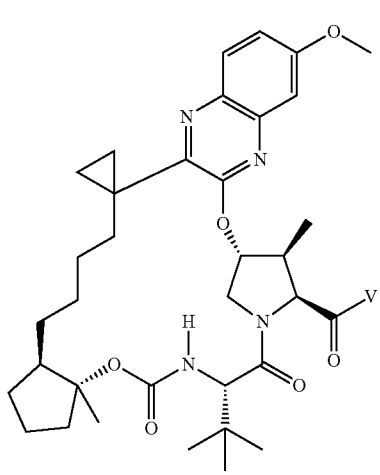
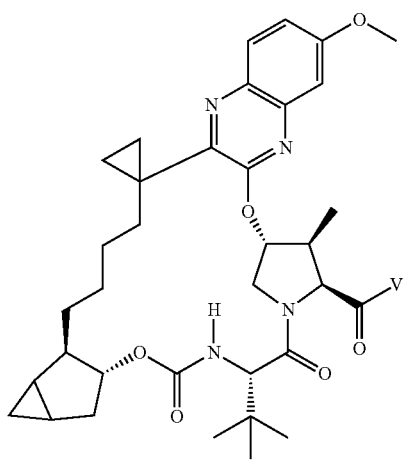
542
-continued
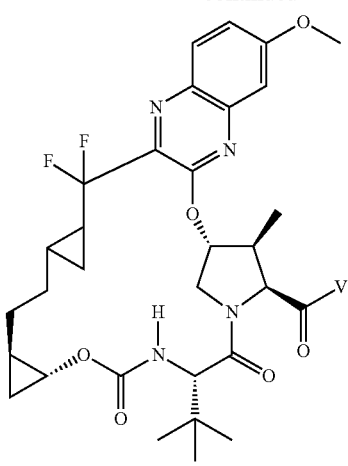
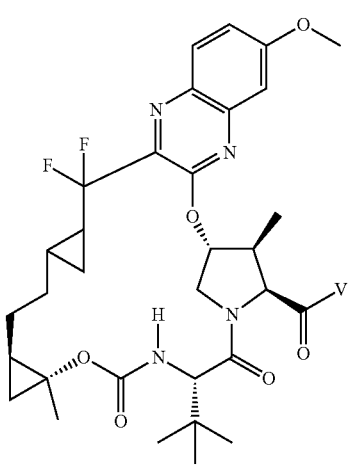
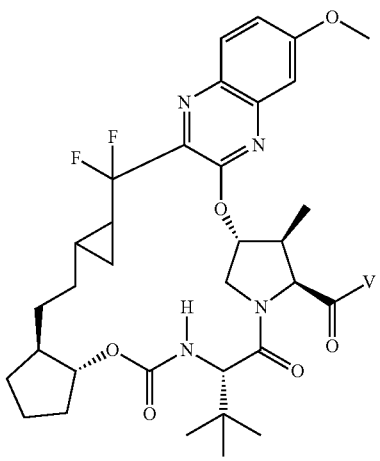

543
-continued
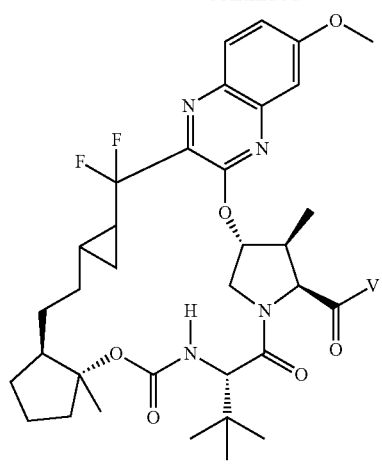
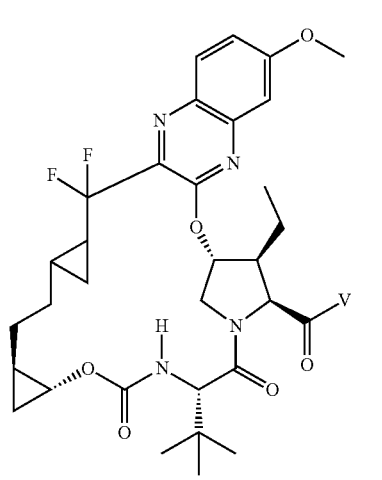
544
-continued
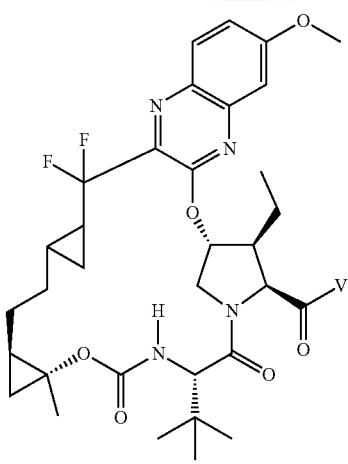

545
-continued
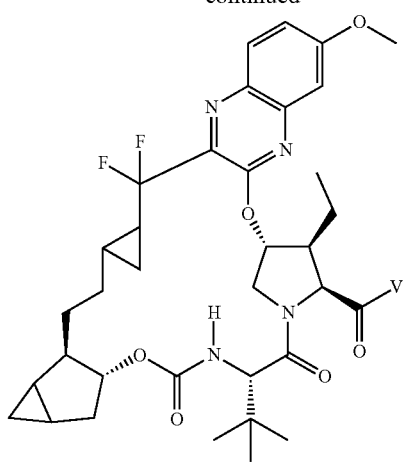
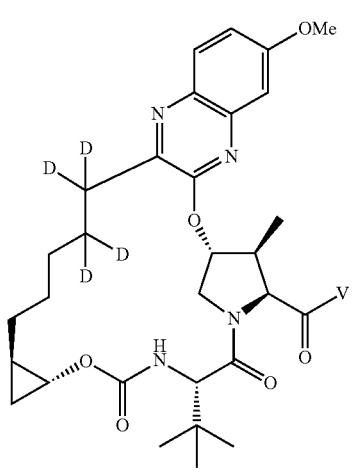
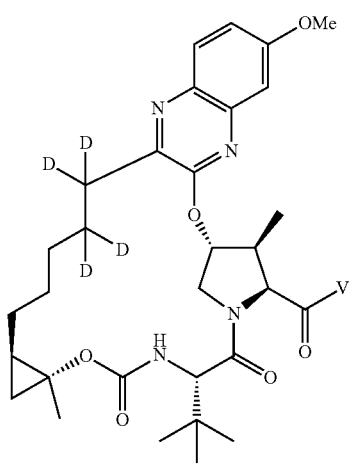
546
-continued
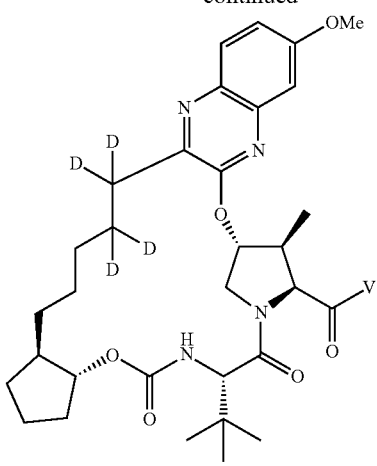
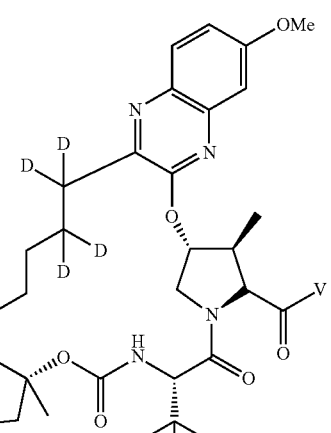
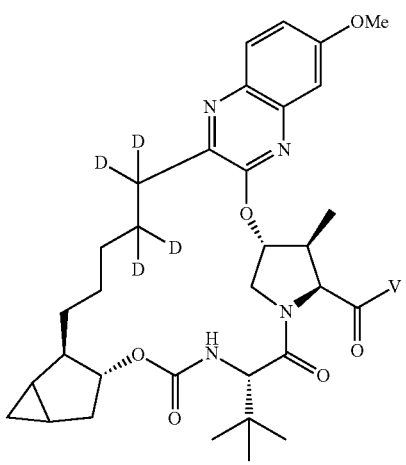

547
-continued
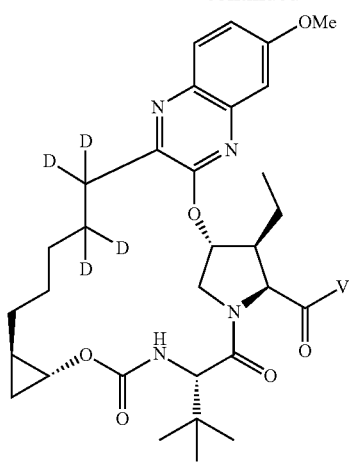
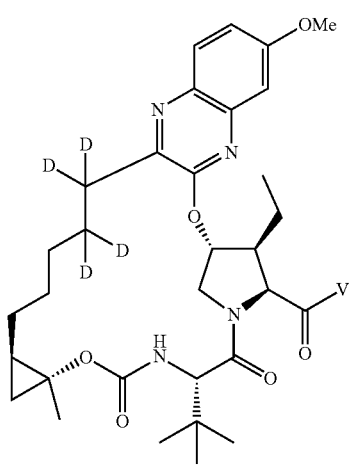
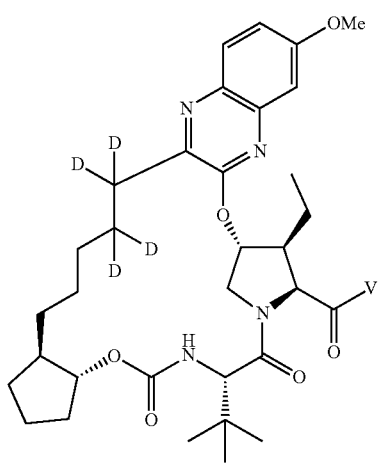
548
-continued
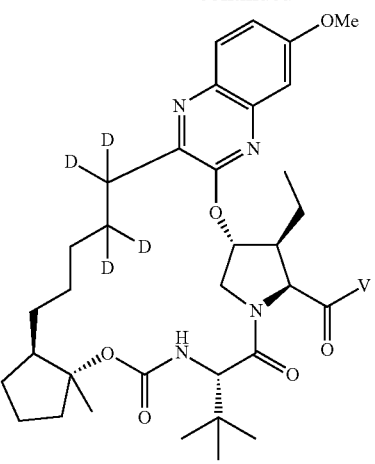
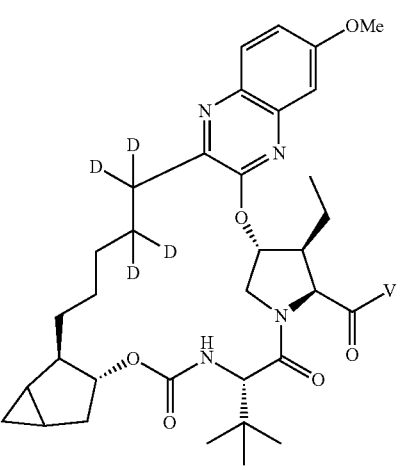
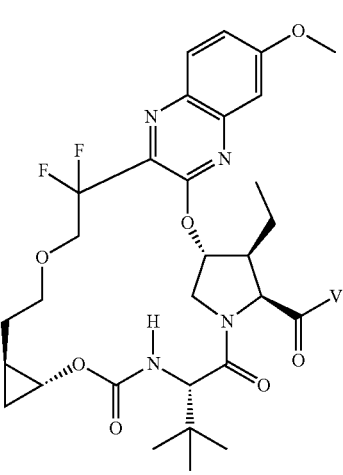

549
-continued
550
-continued
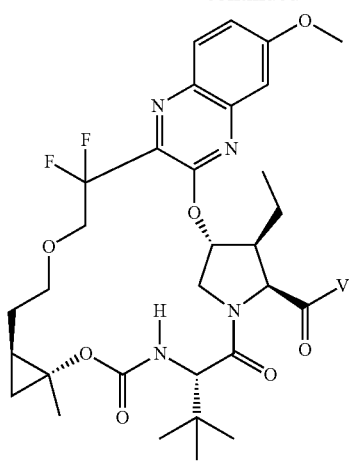
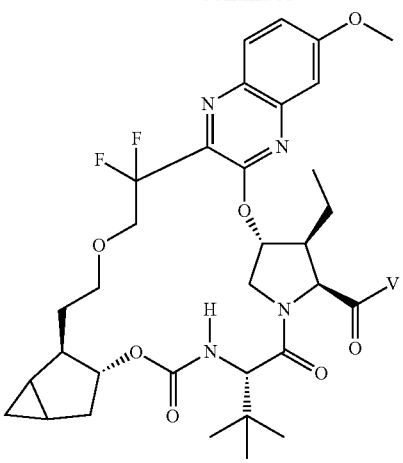

551
-continued
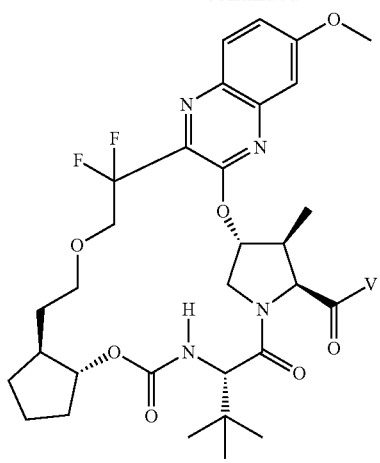
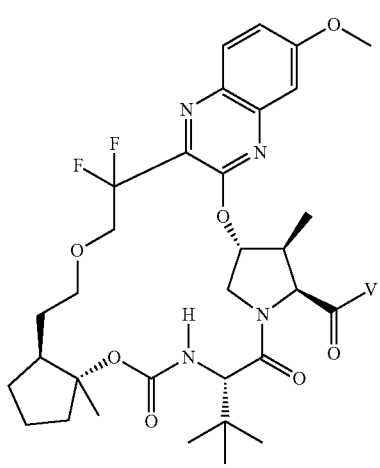
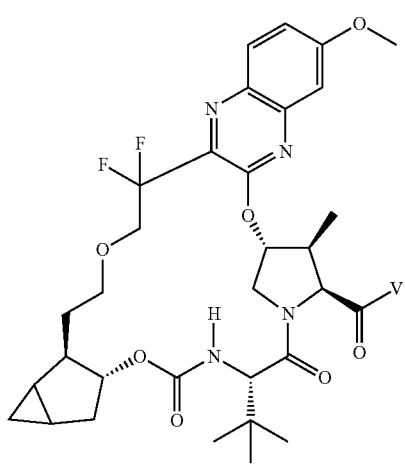
552
-continued
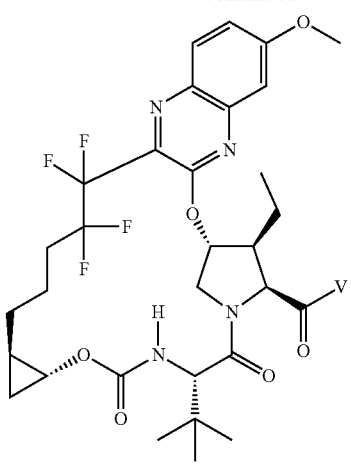
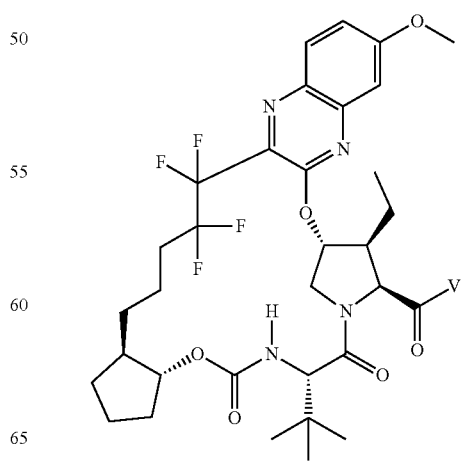

553
-continued
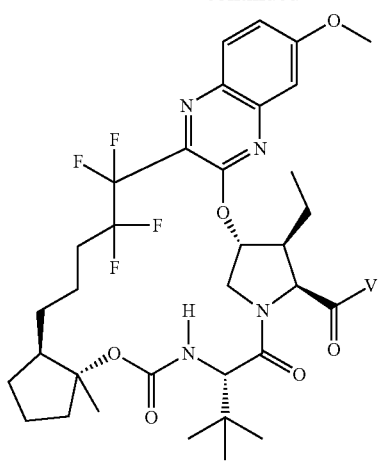
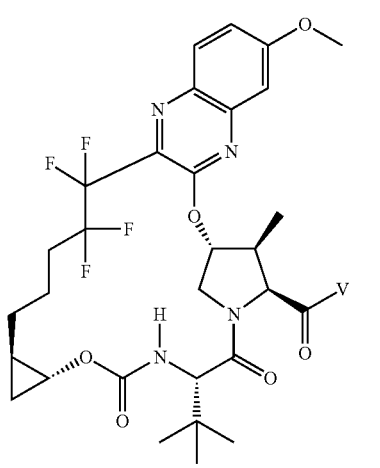
554
-continued
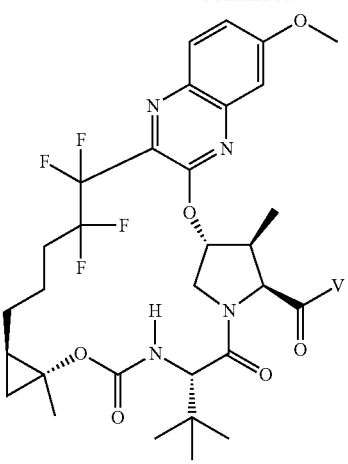

555
-continued
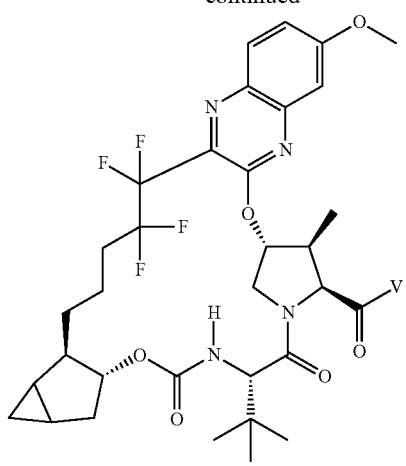
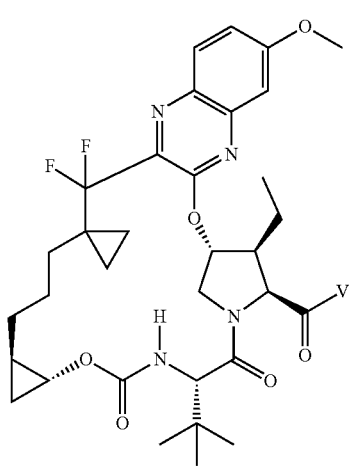
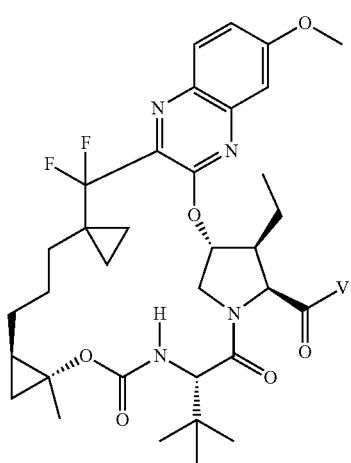
556
-continued
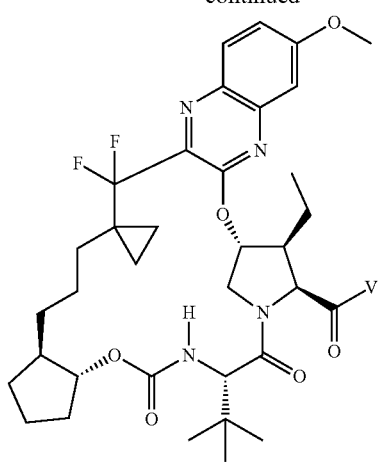
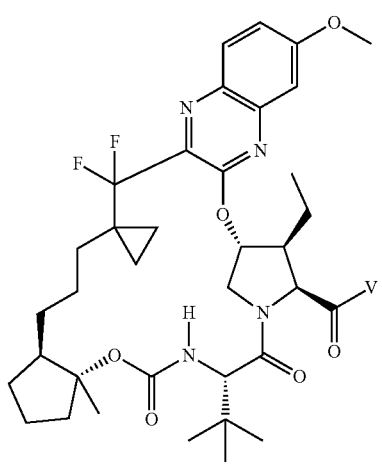
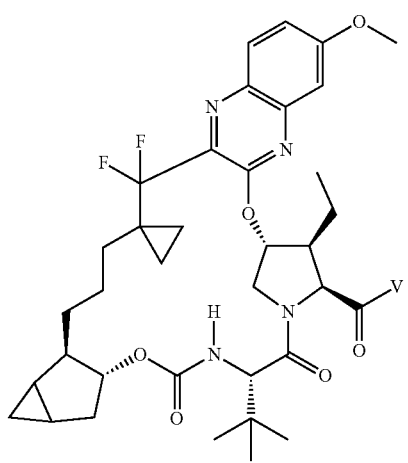

557
-continued
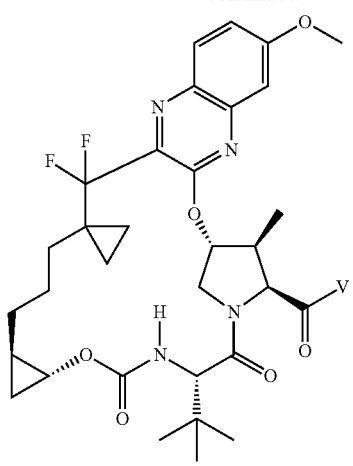
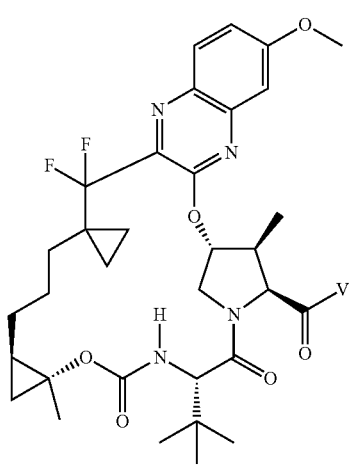
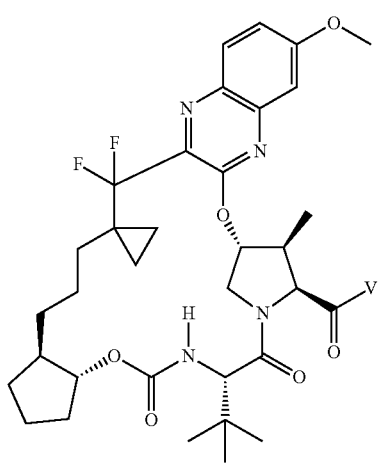
558
-continued
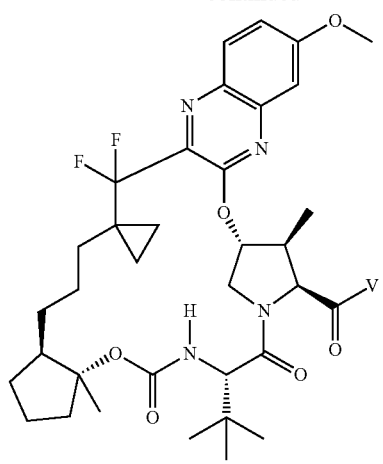
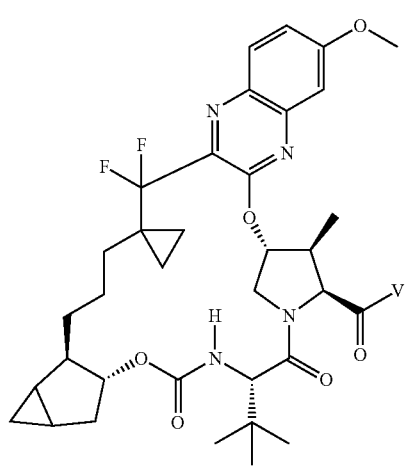
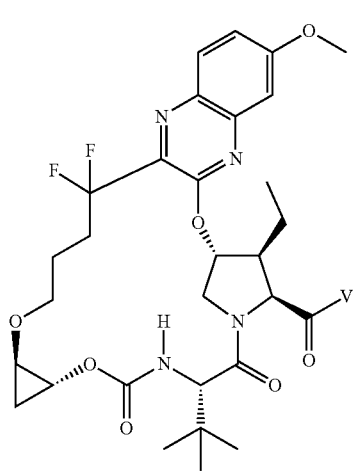

559
-continued
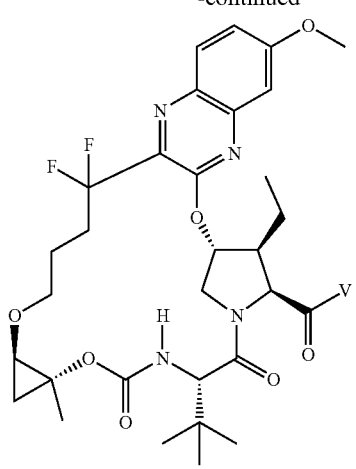
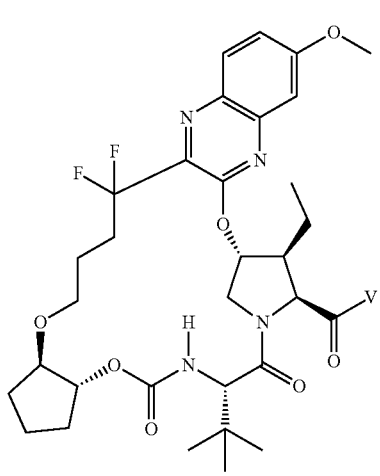
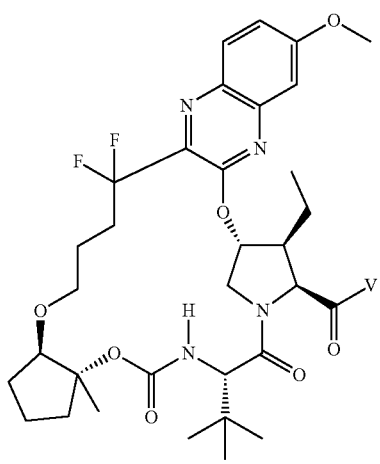
560
-continued
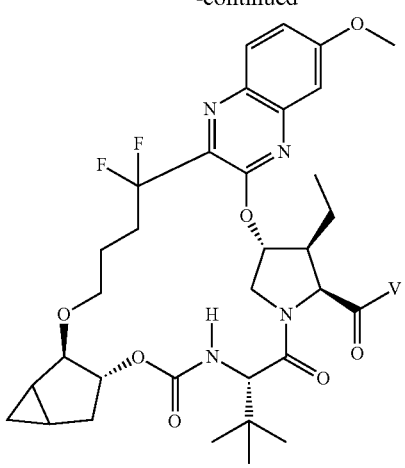
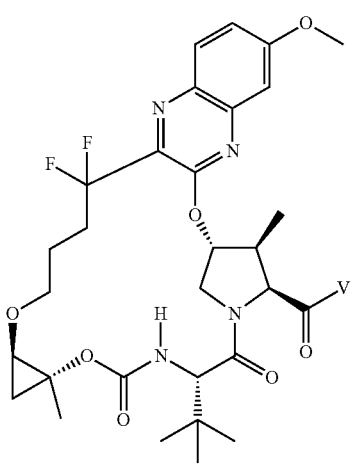

561
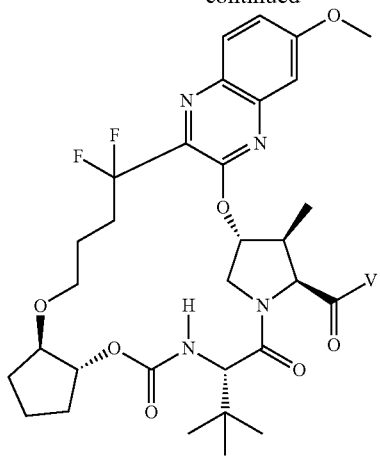
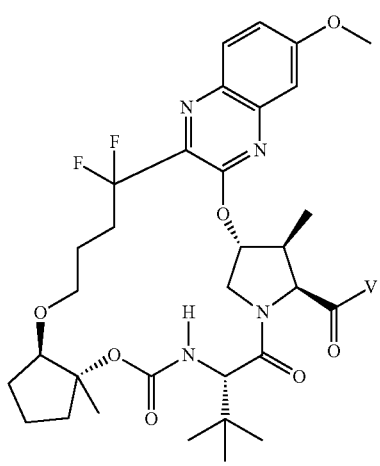
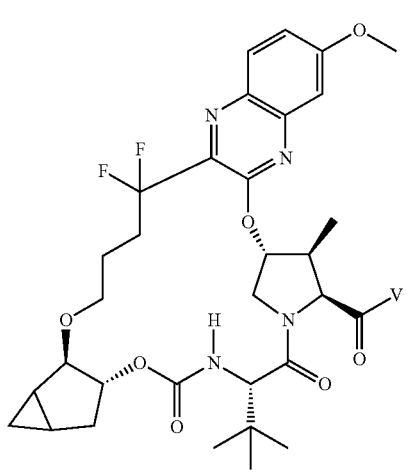
562
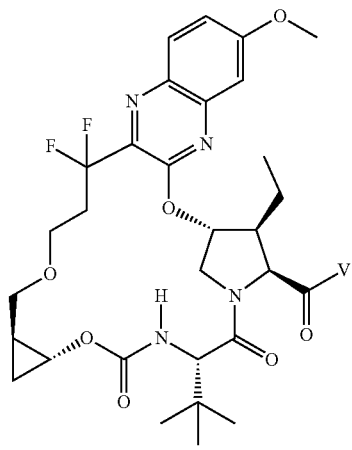
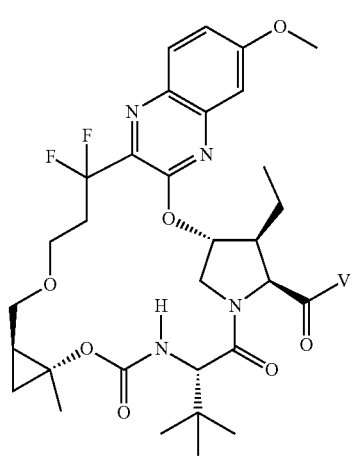
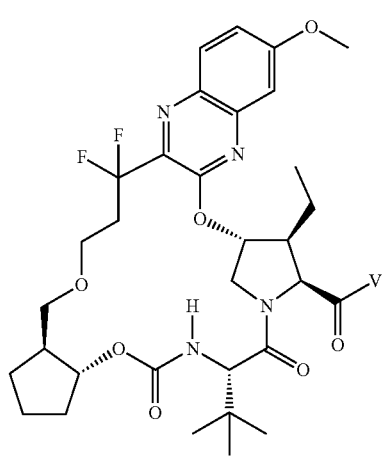

563
-continued
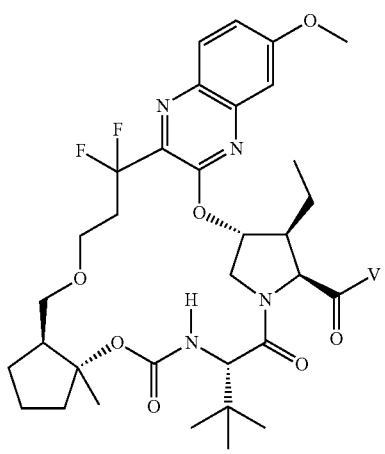
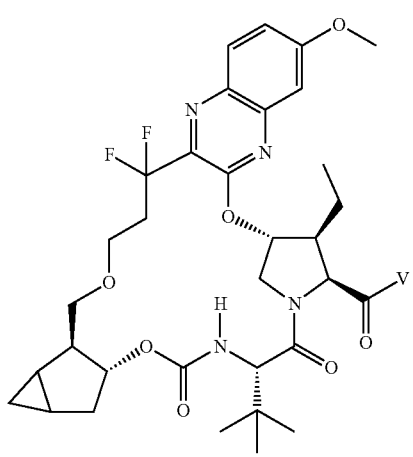
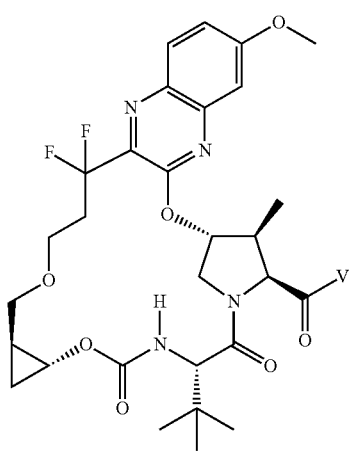
564
-continued
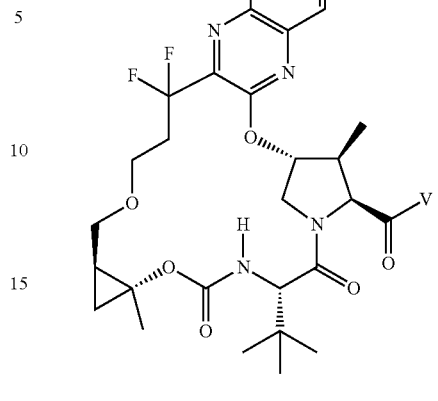
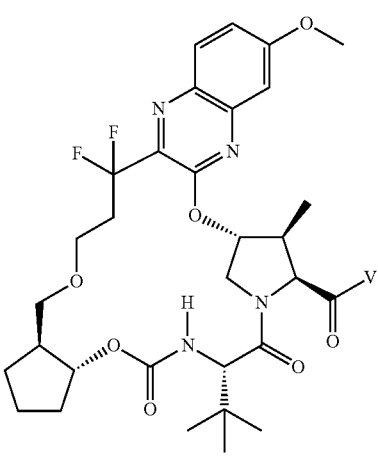
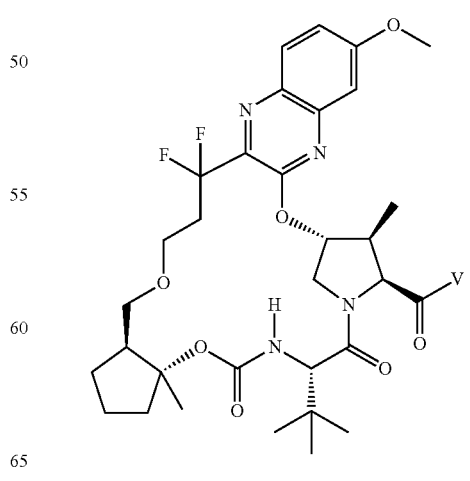

565
-continued
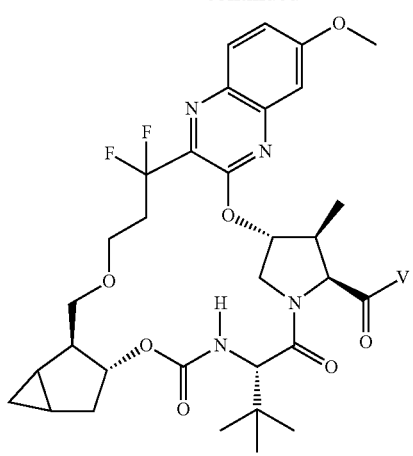
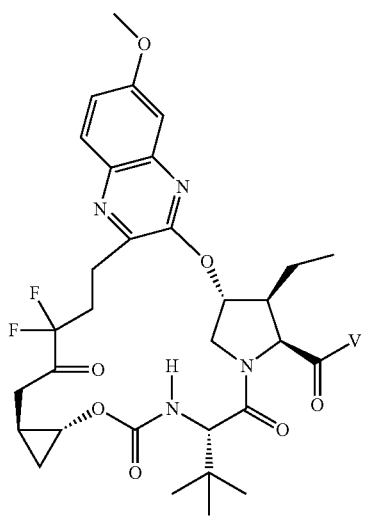
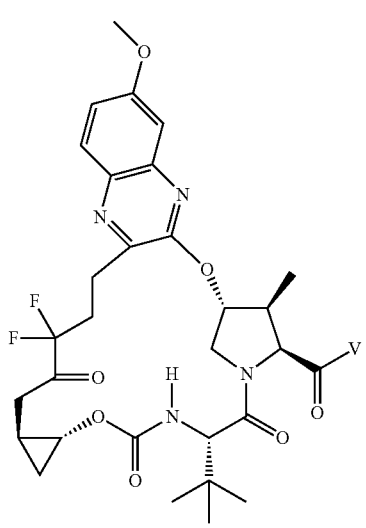
566
-continued
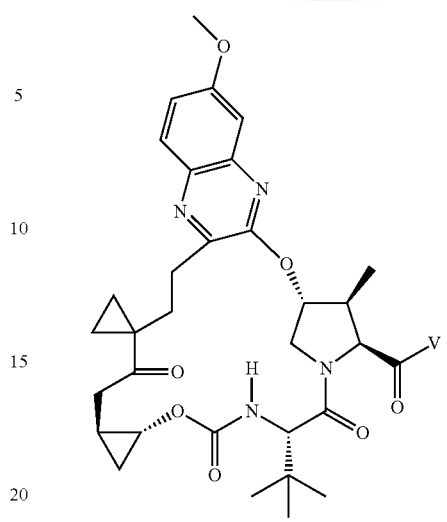
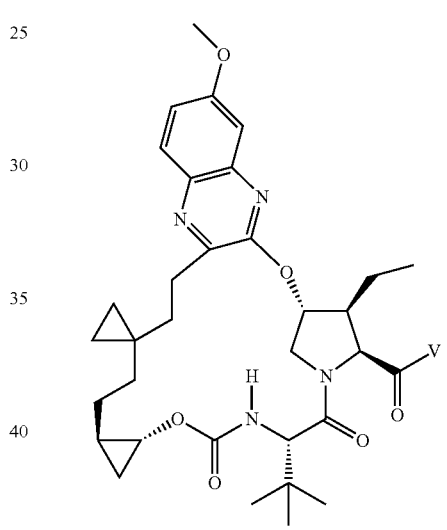
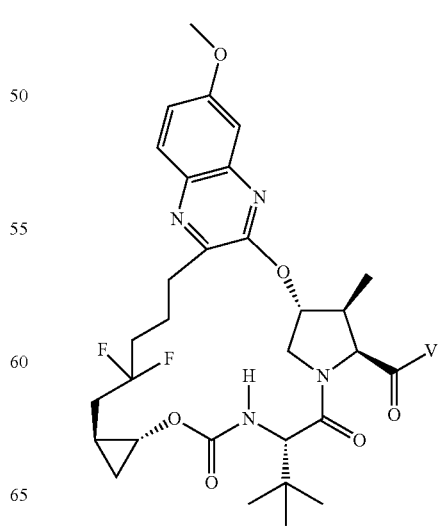

567
-continued
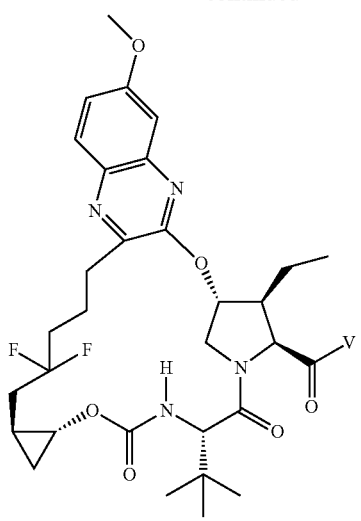
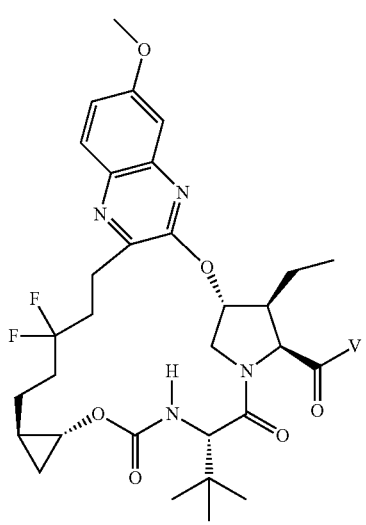
568
-continued
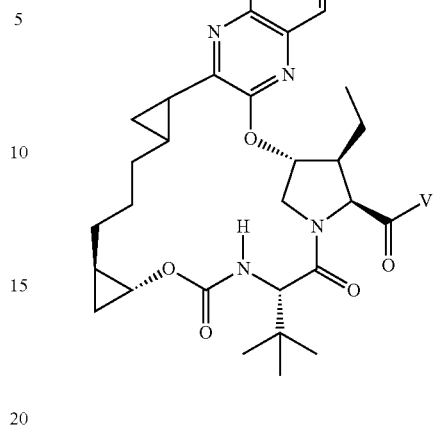
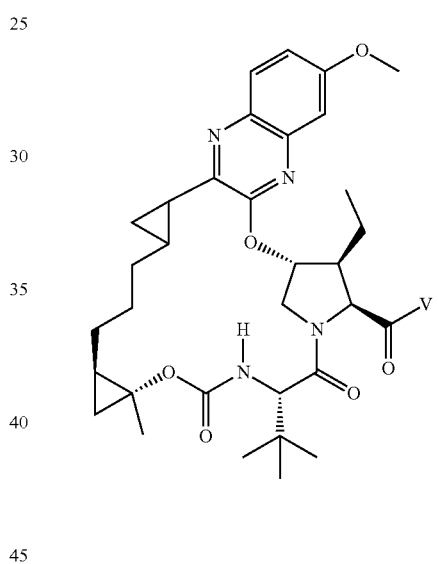
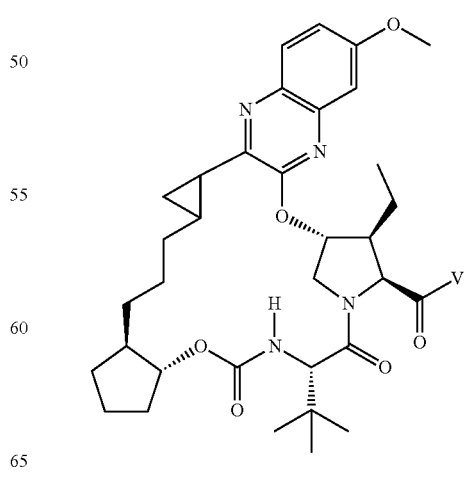

569
-continued
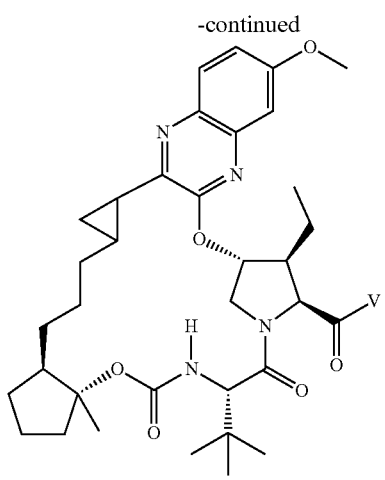
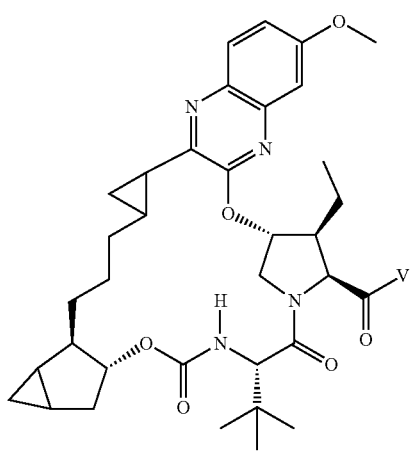
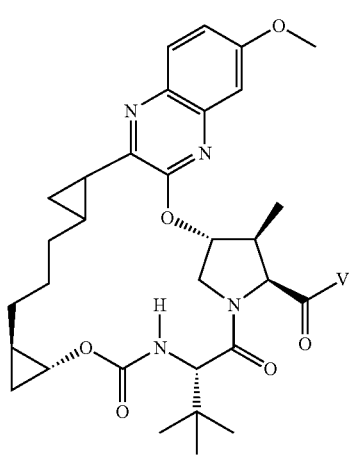
570
-continued
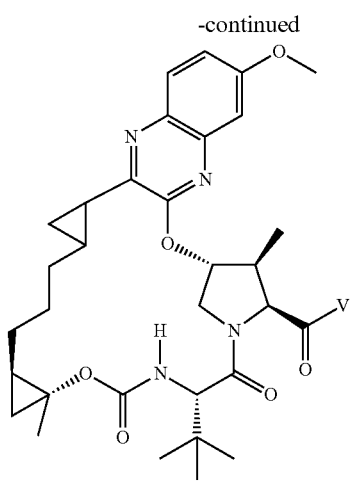
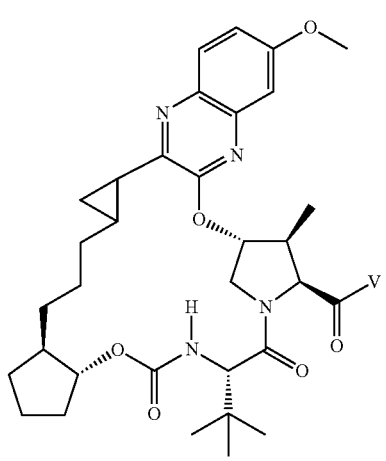
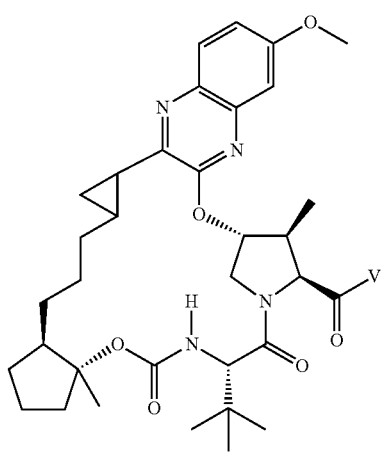

571
-continued
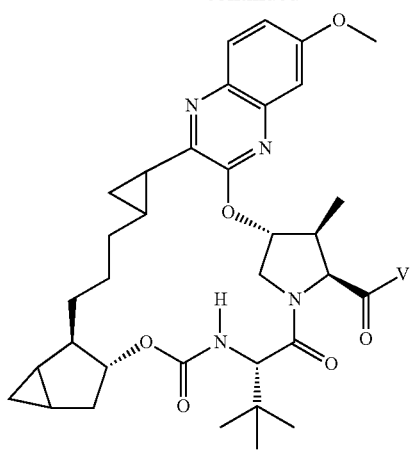
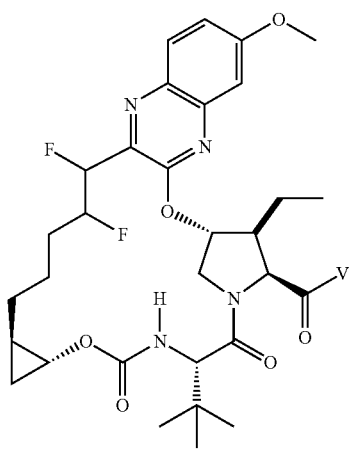
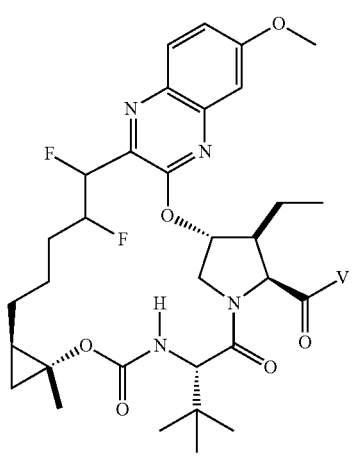
572
-continued
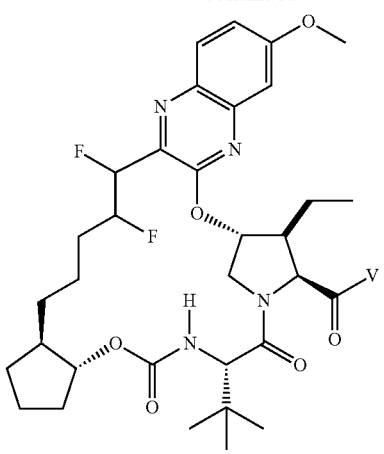
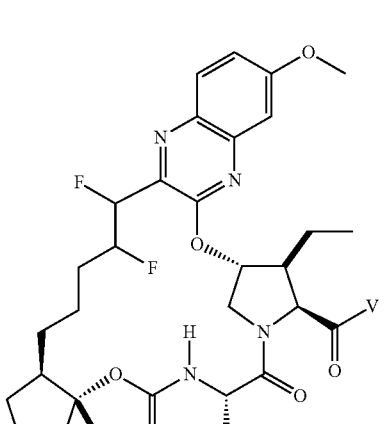
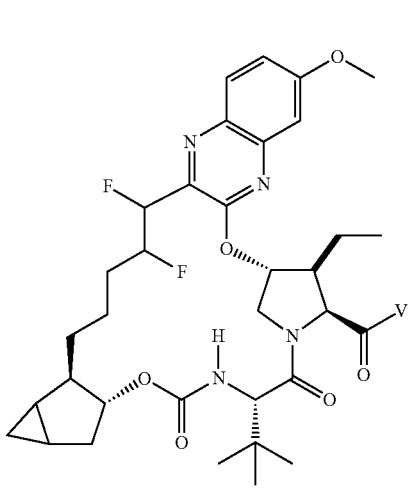

573
-continued
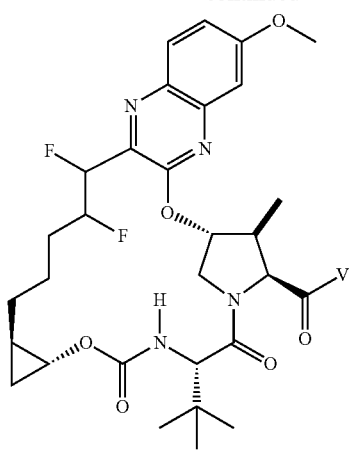
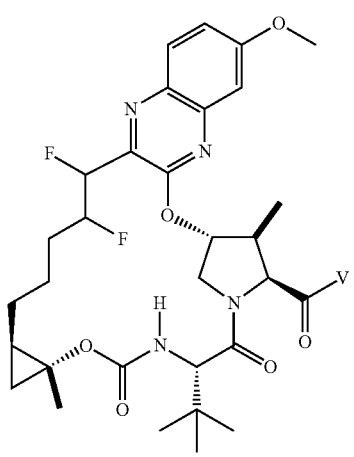
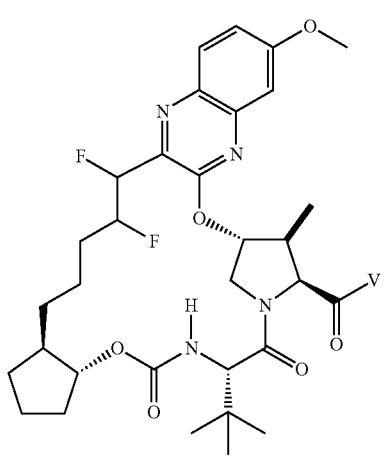
574
-continued
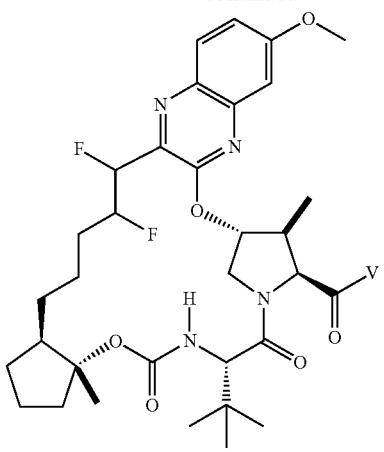
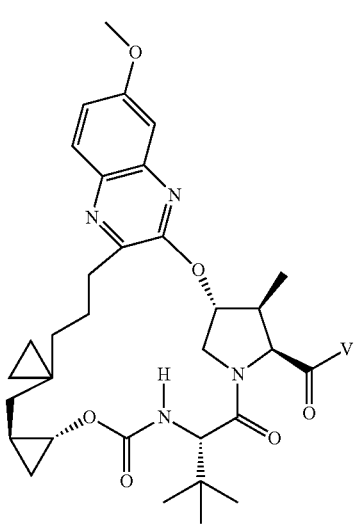

575
-continued
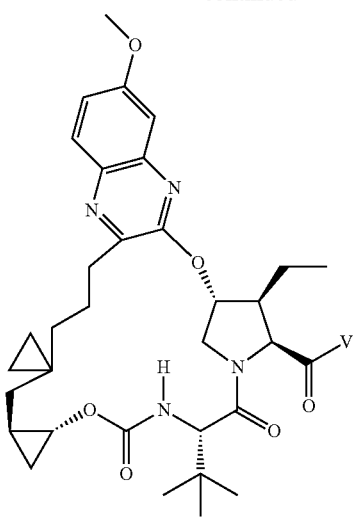
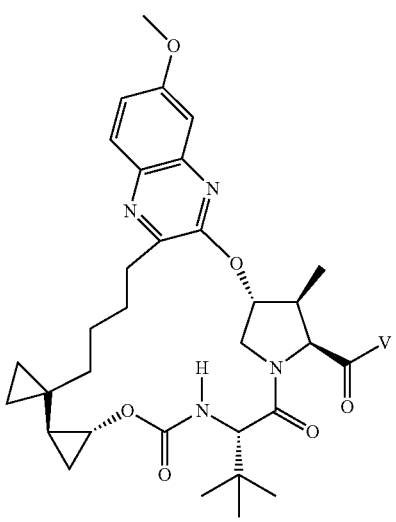
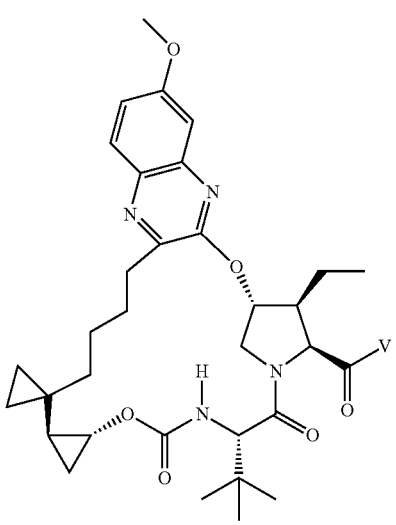
576
-continued
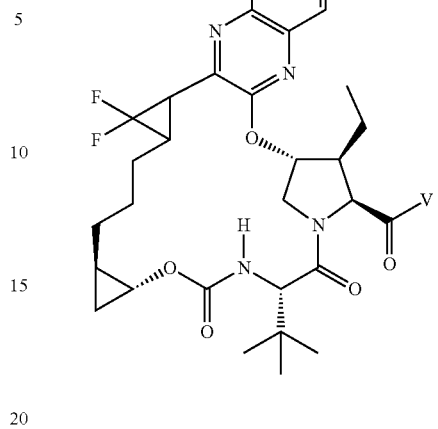
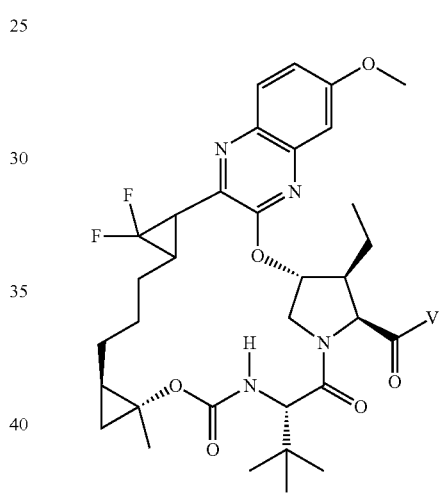
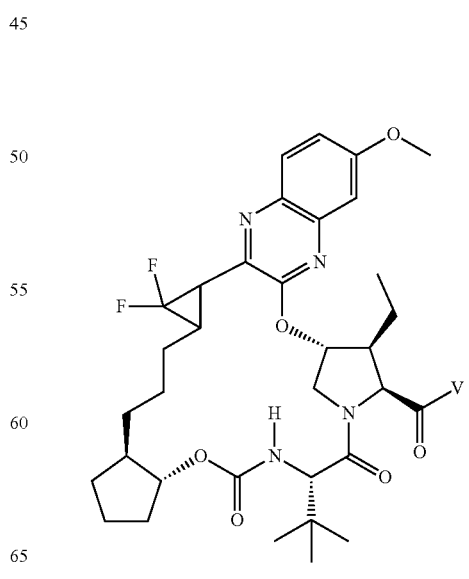

577
-continued
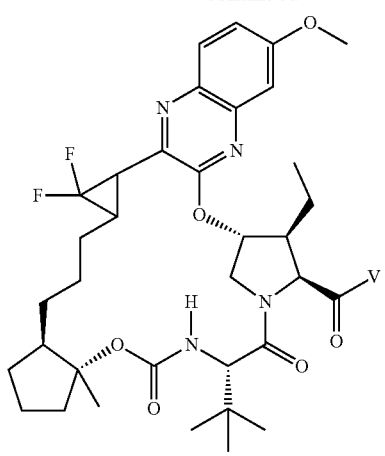
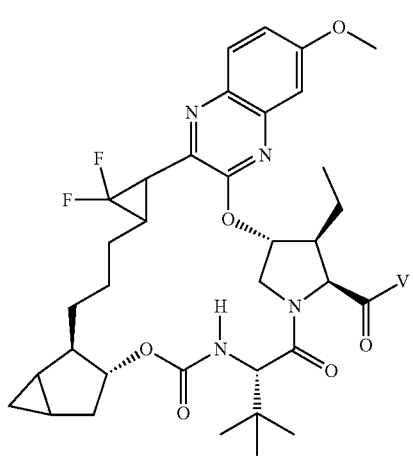
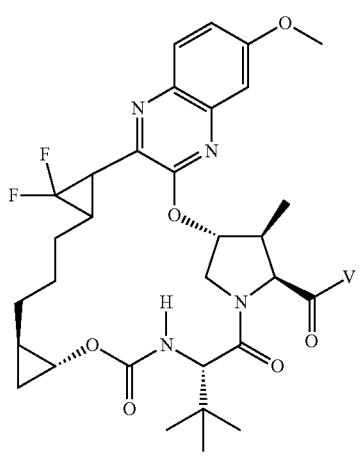
578
-continued
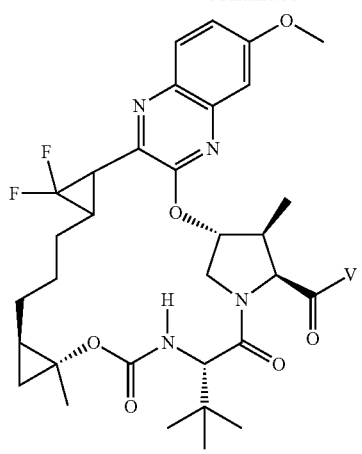
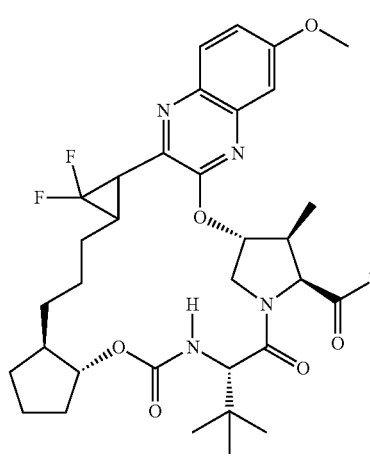
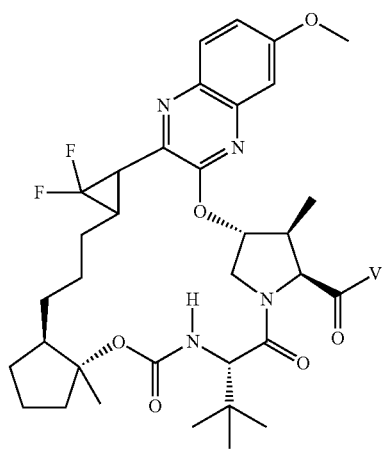

579
-continued
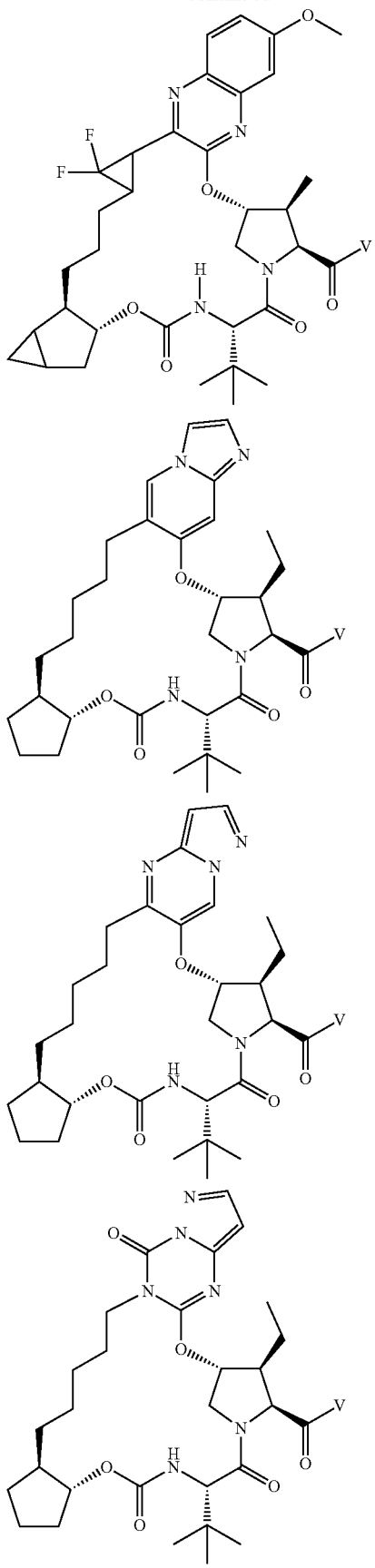
580
-continued
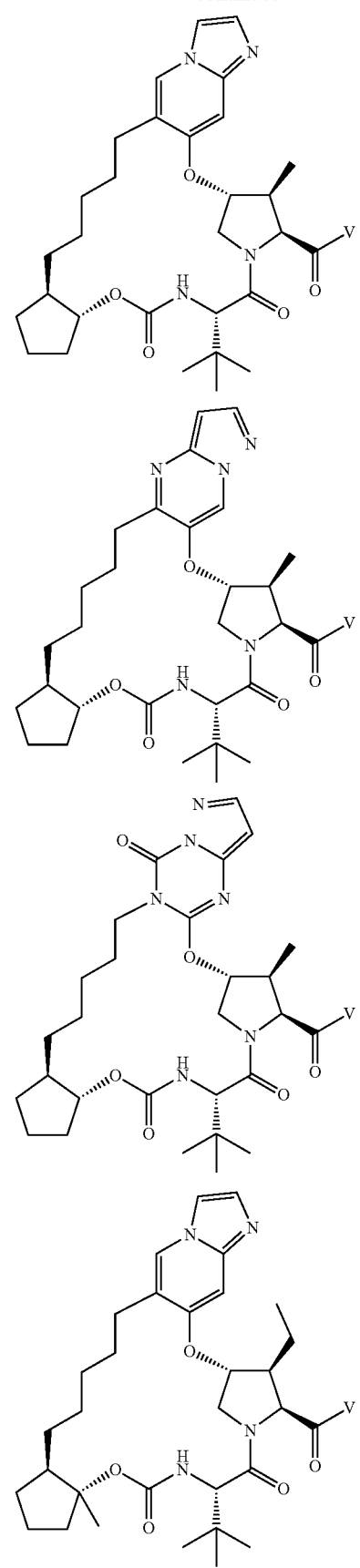

581
-continued
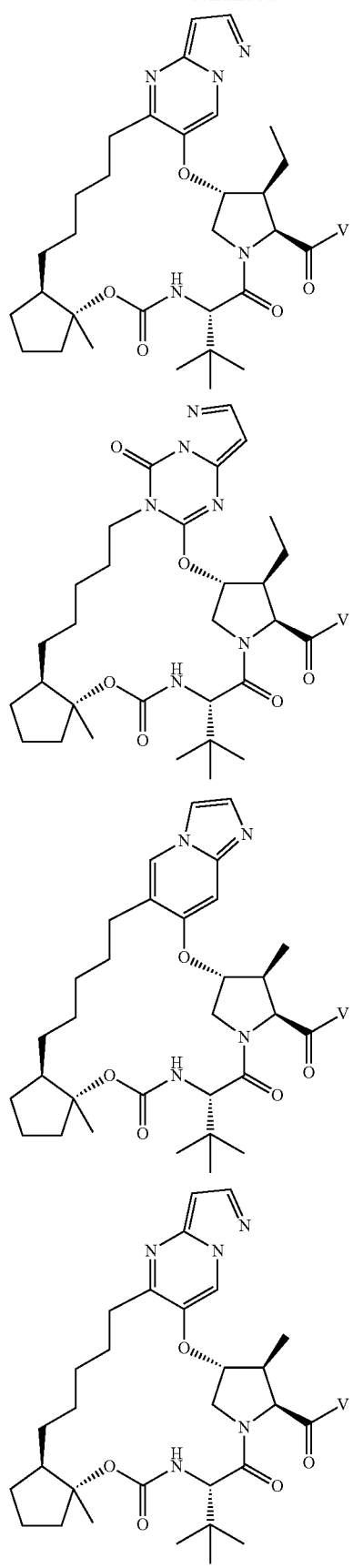
582
-continued
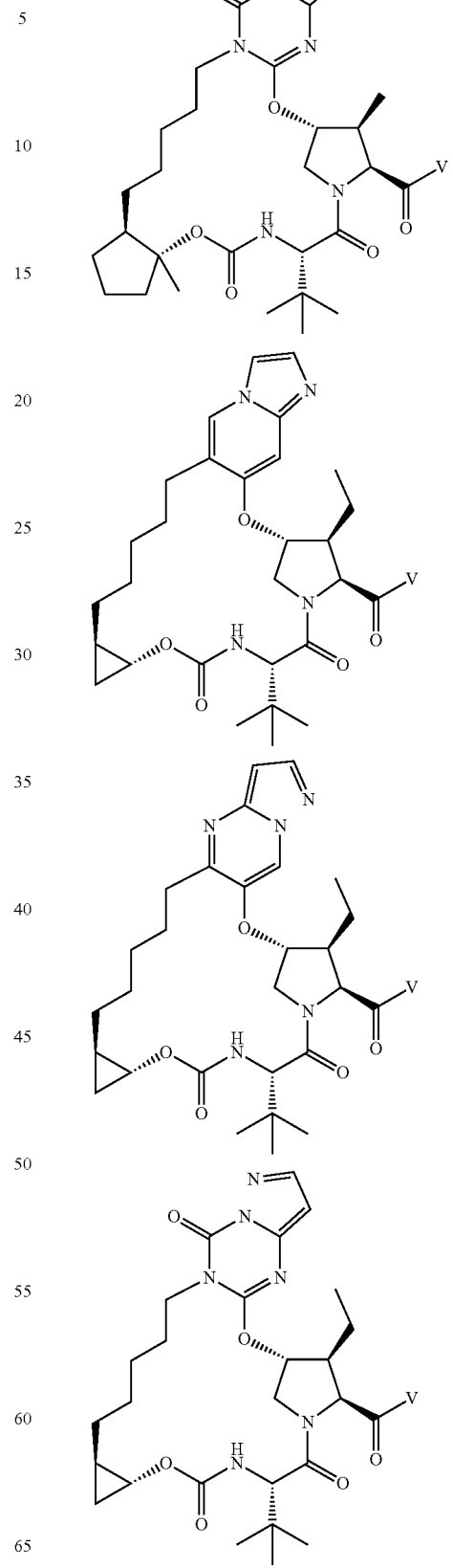

583
-continued
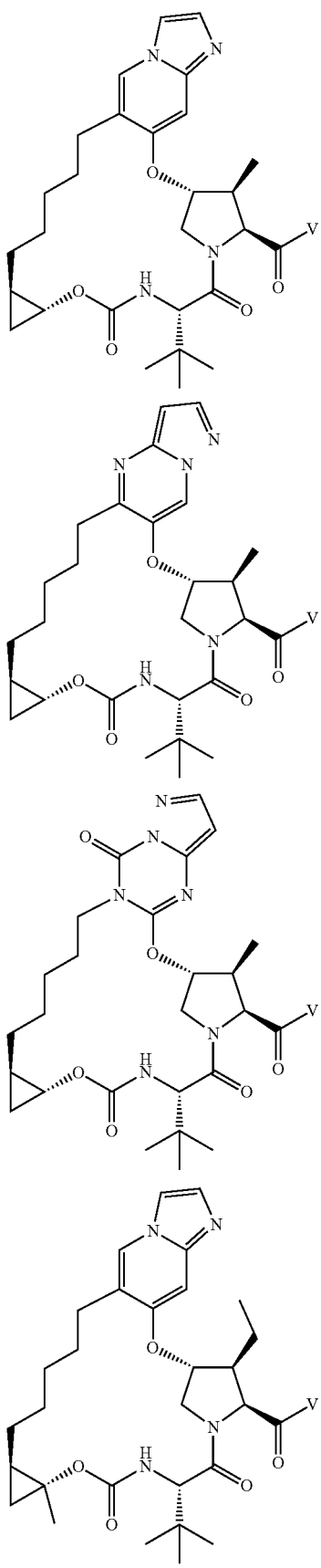
584
-continued
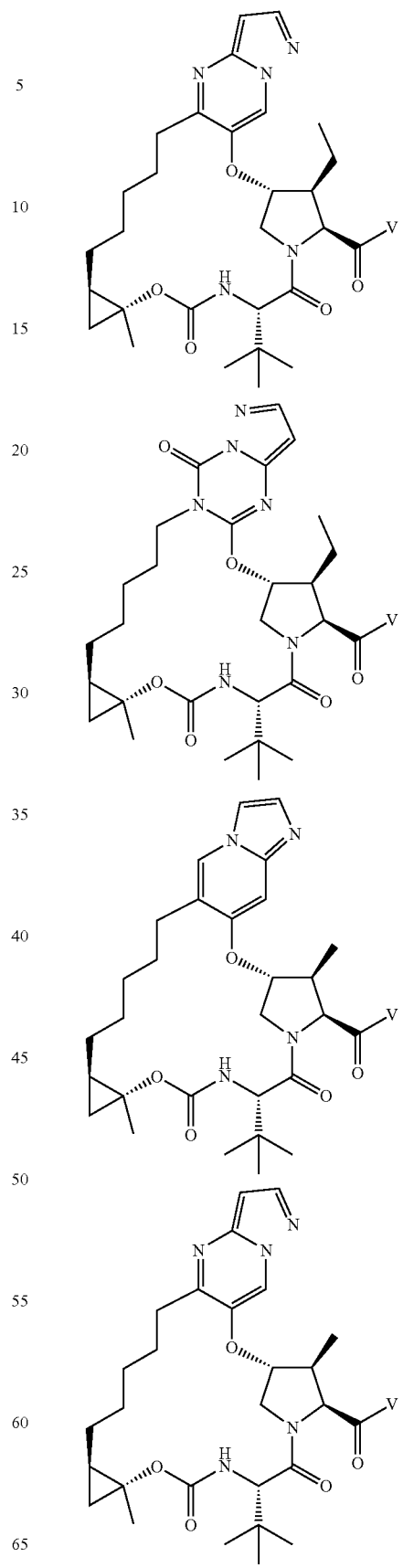

585
-continued
586
-continued
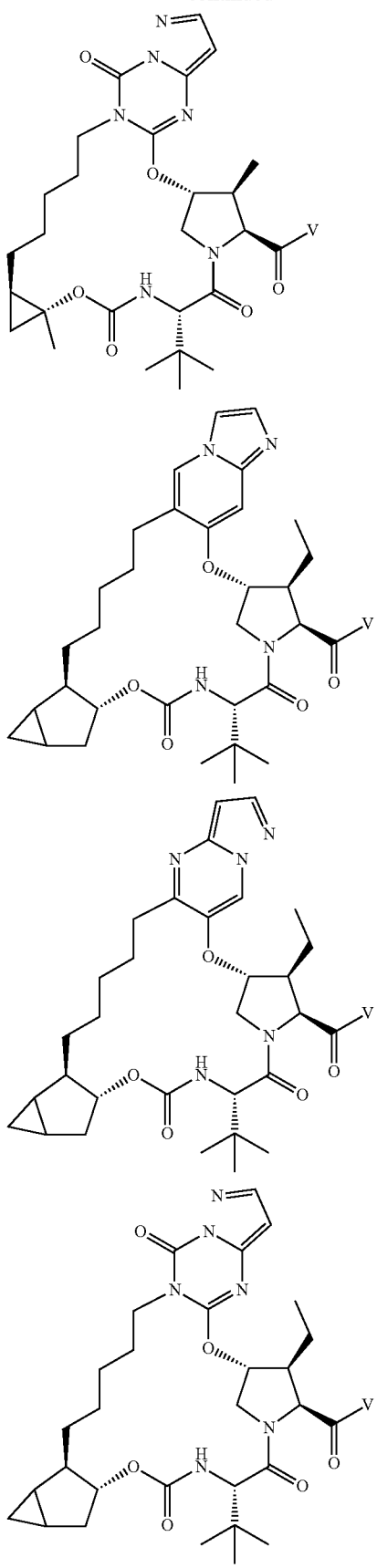
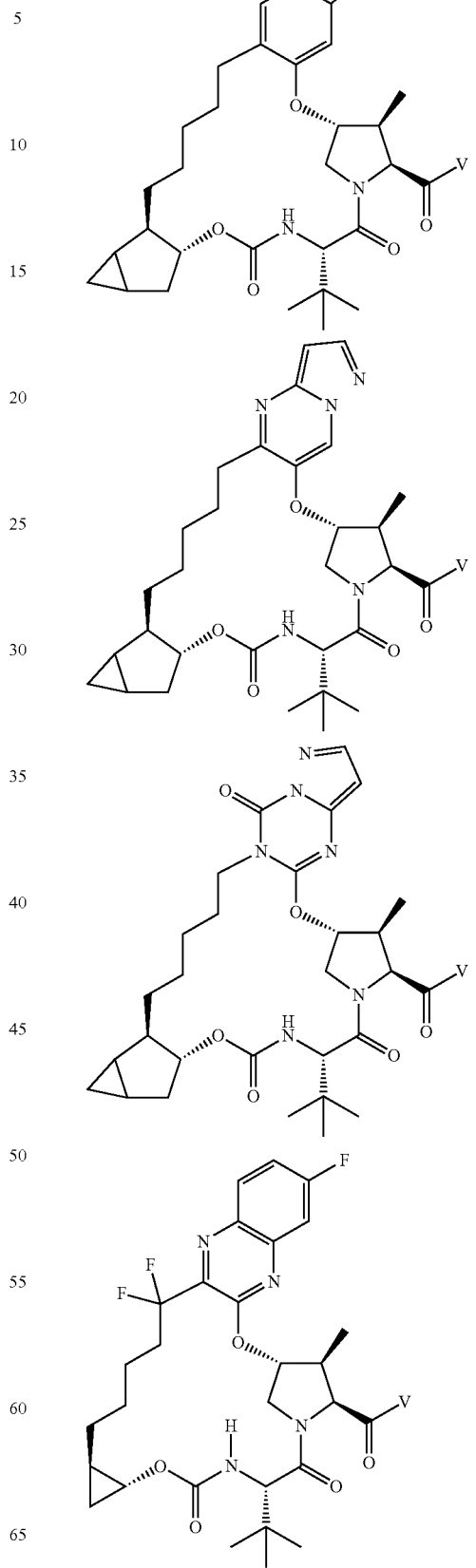

587
-continued
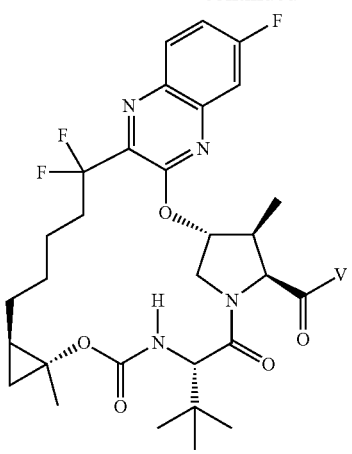
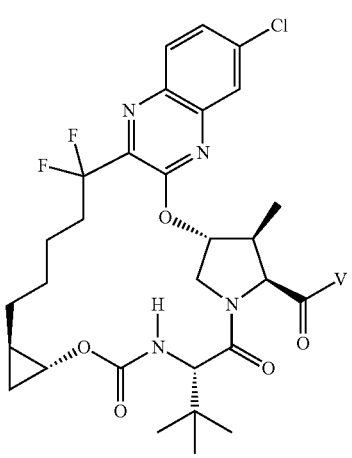
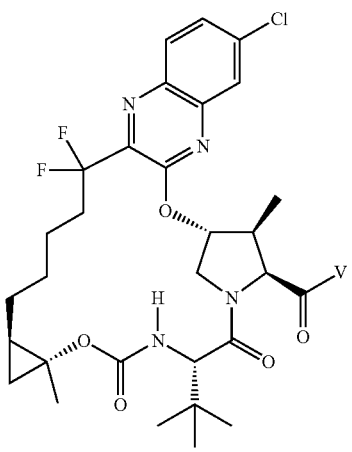
588
-continued
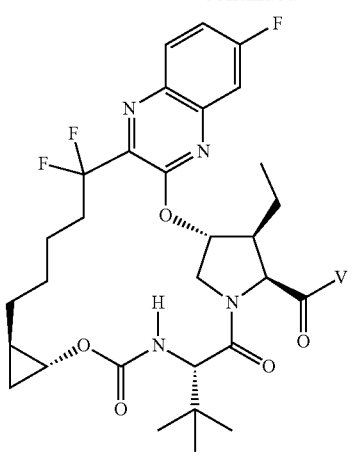
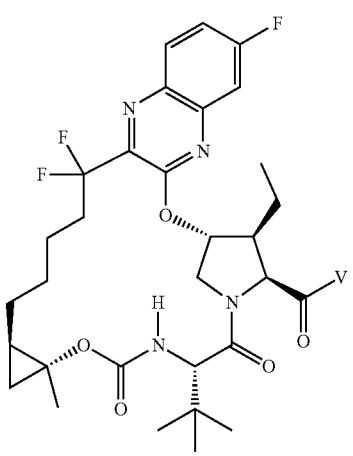
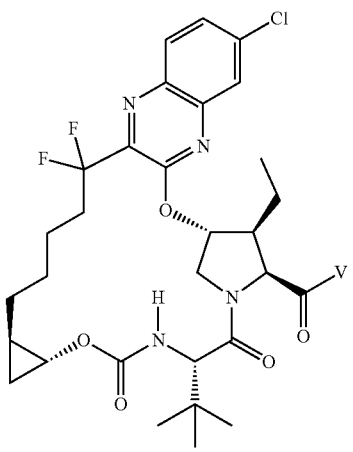

589
-continued
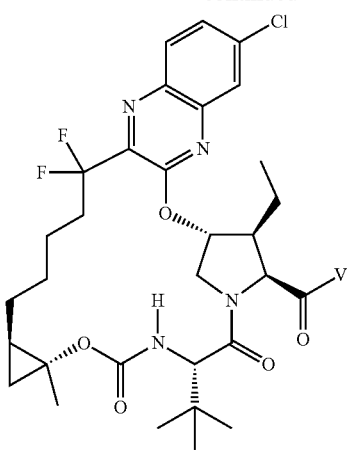
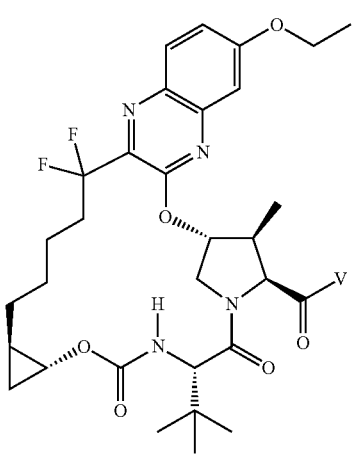
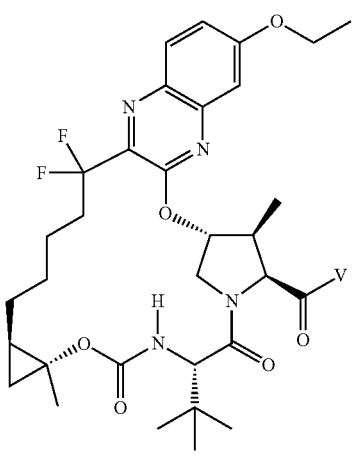
590
-continued
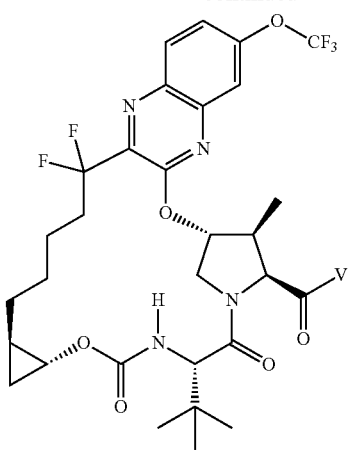
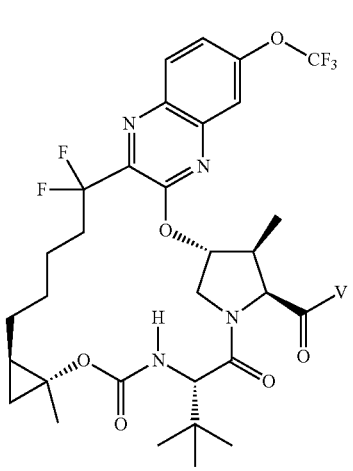
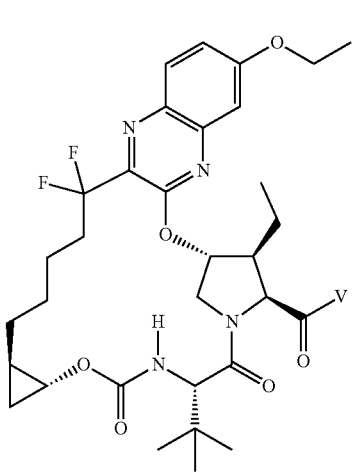

591
-continued
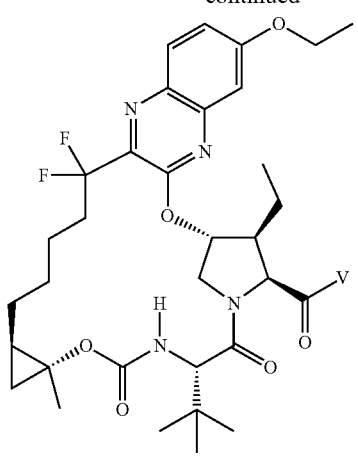
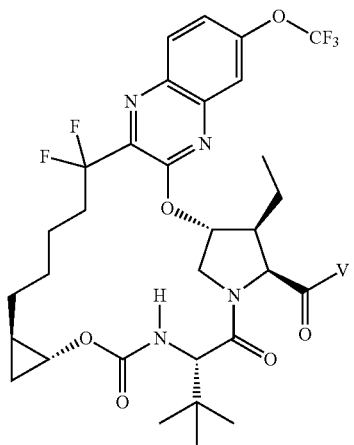
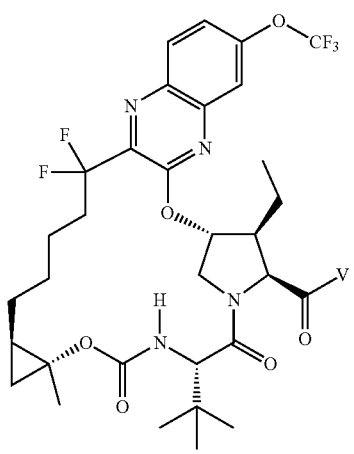
592
-continued
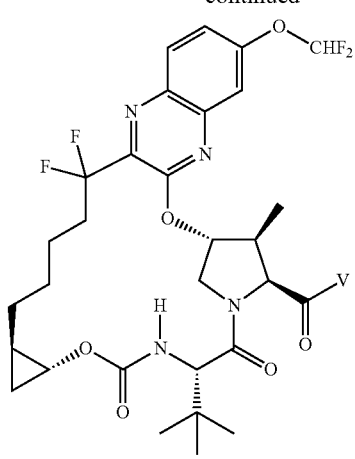
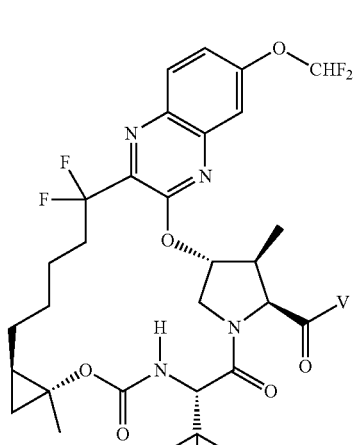
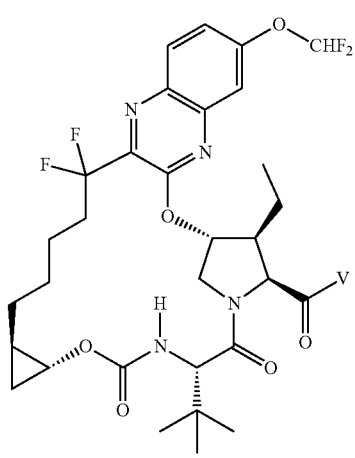

593
-continued
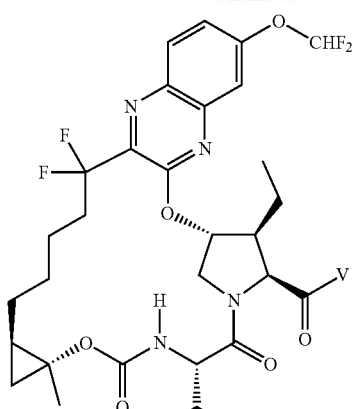
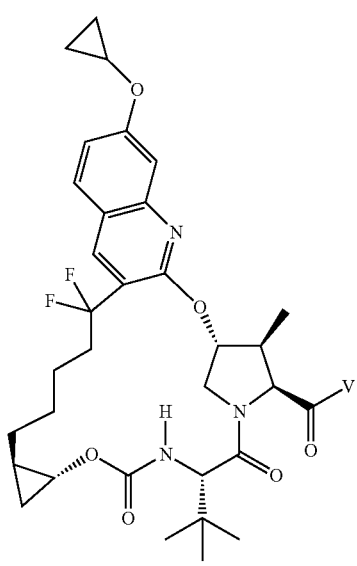
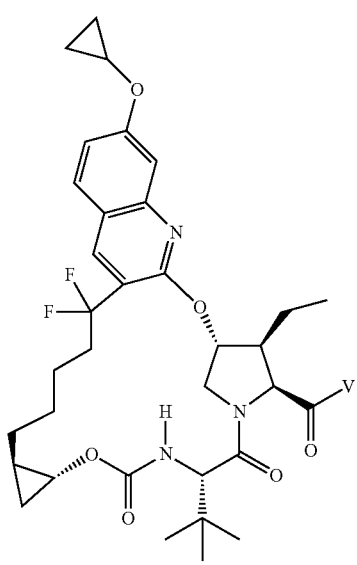
594
-continued
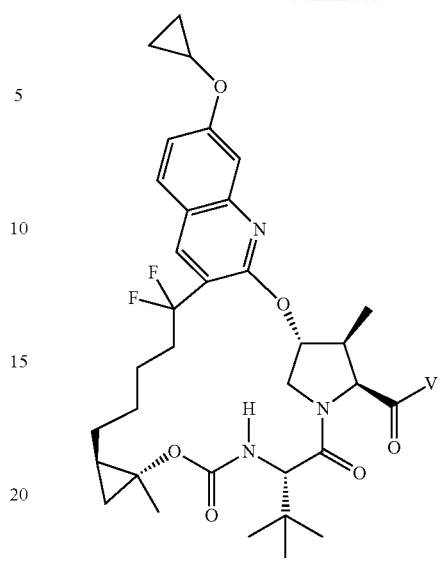
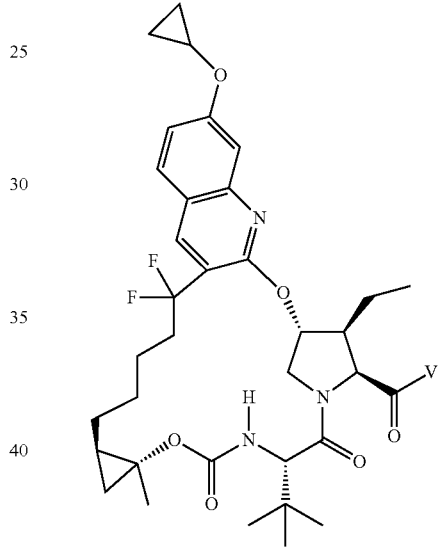
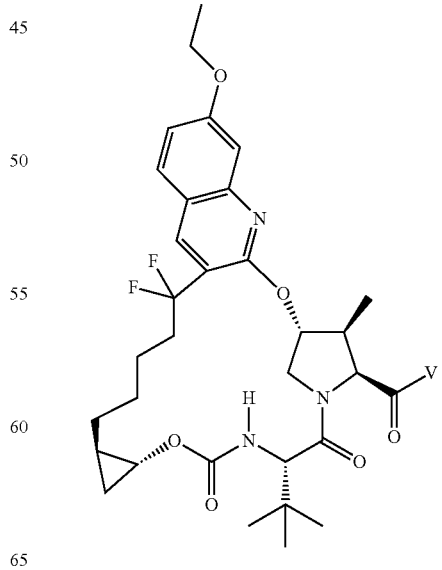

595
-continued
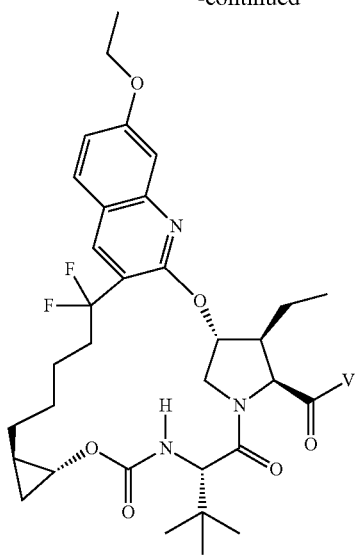
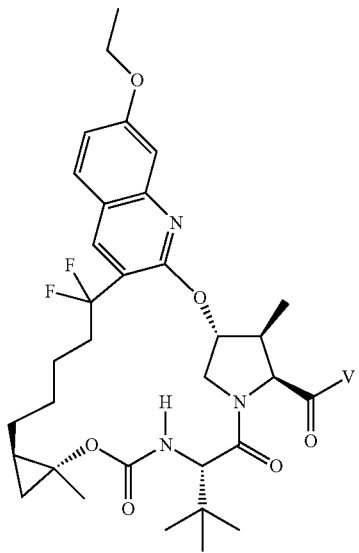
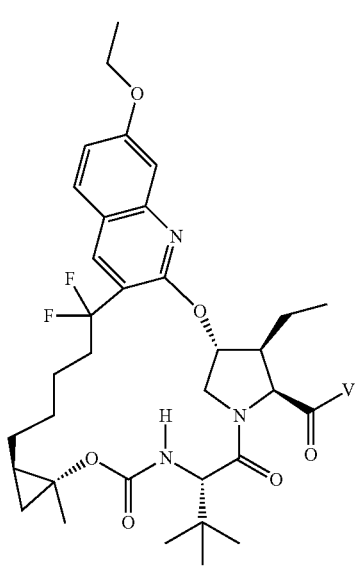
596
-continued
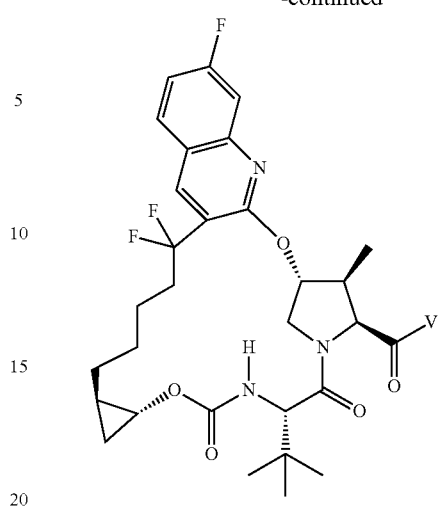
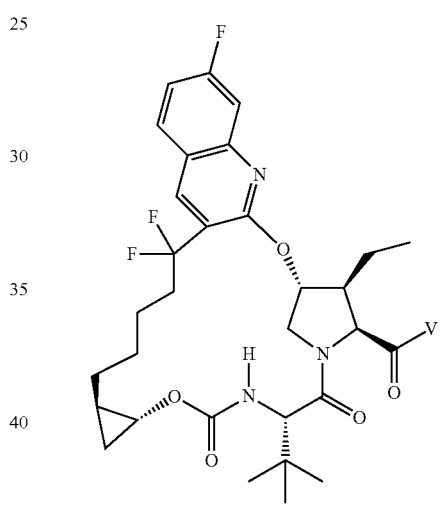
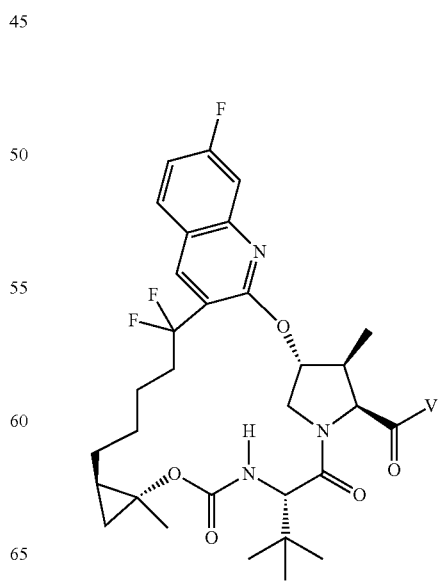

597
-continued
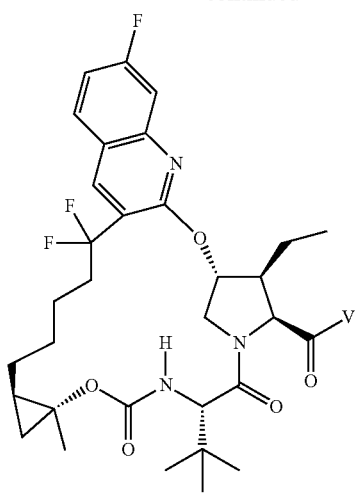
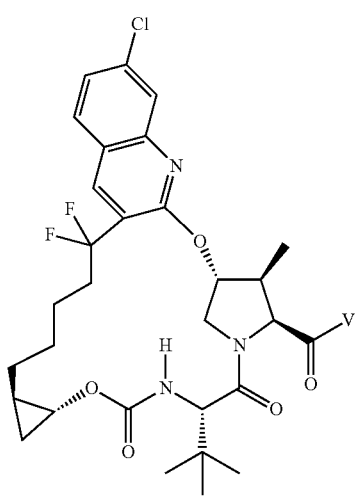
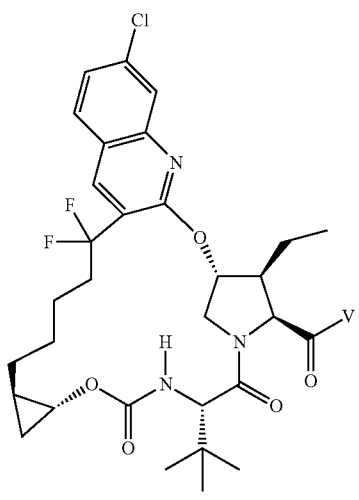
598
-continued
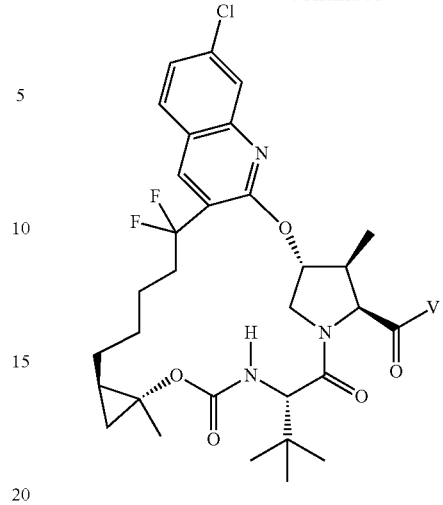
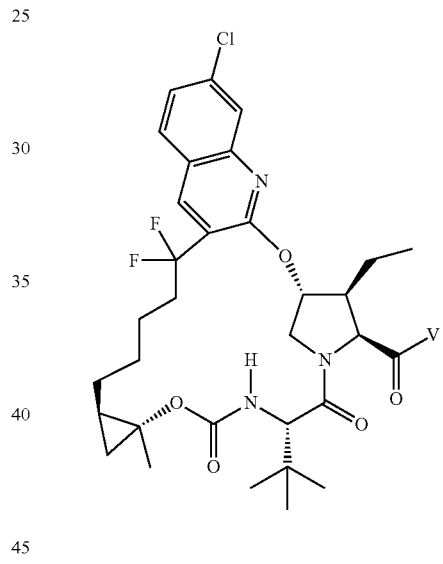
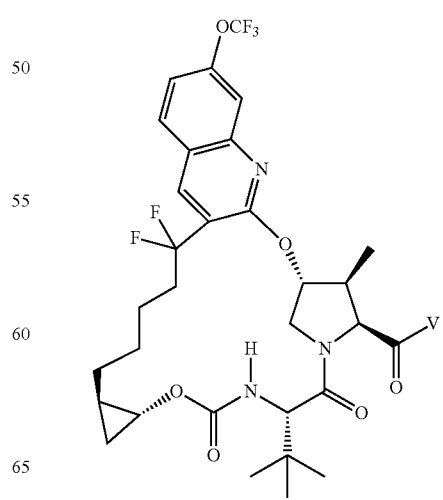

599
-continued
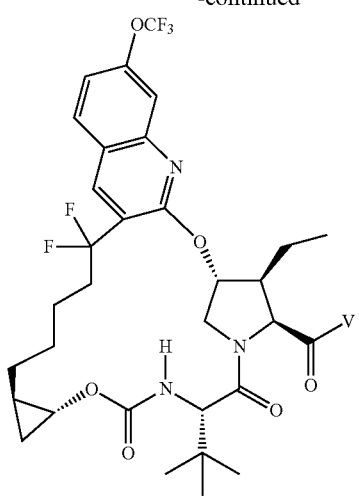
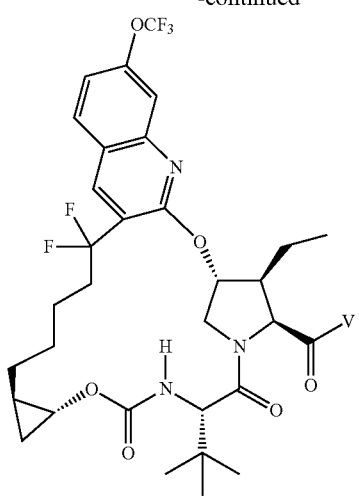
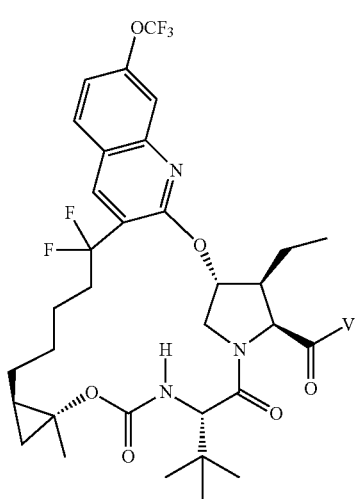
600
-continued
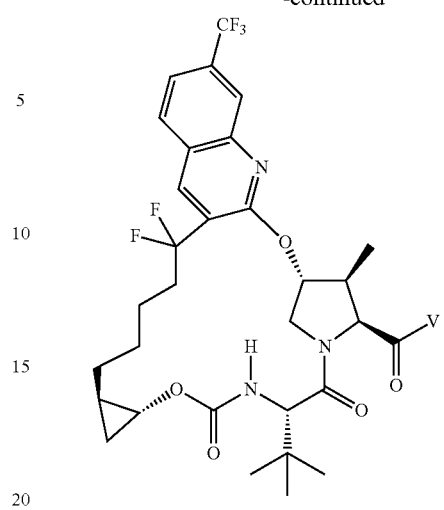
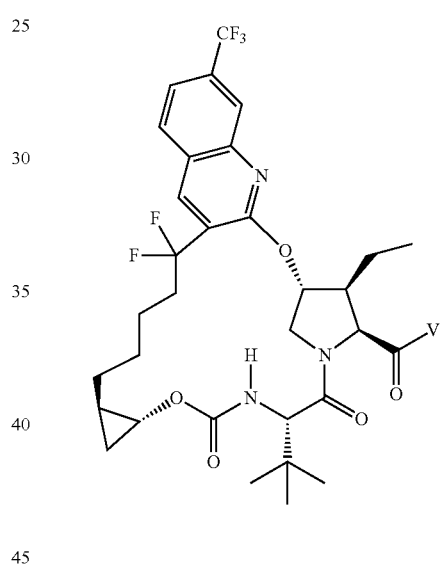
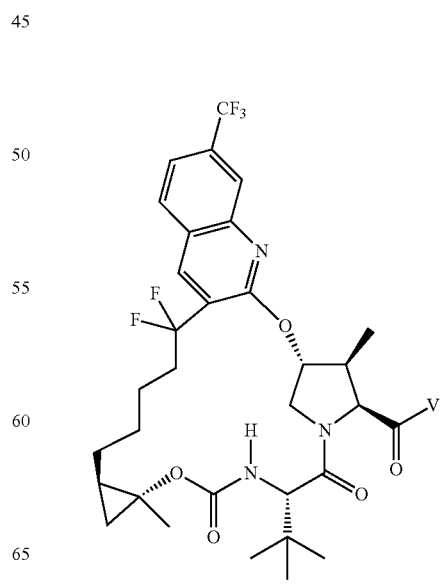

601
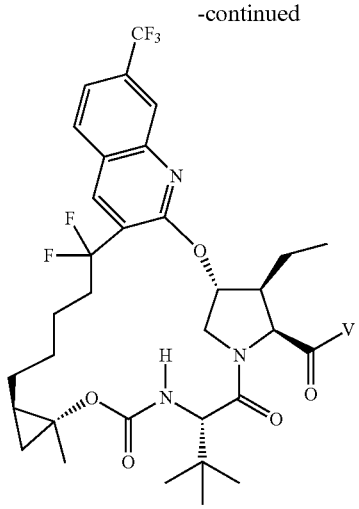
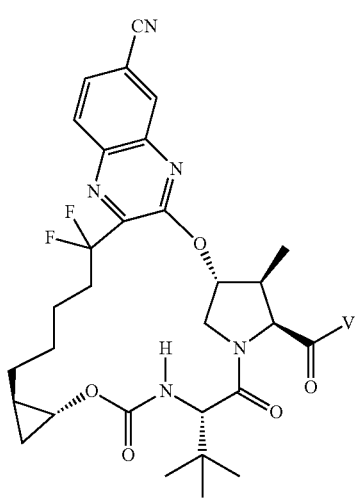
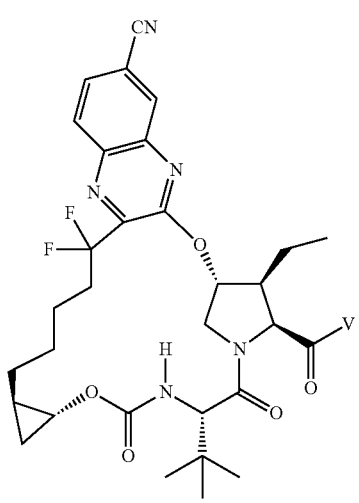
602
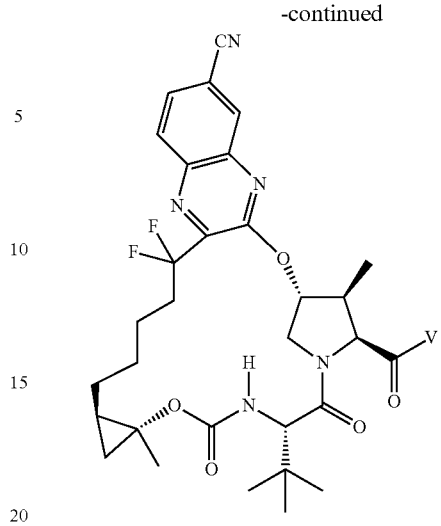
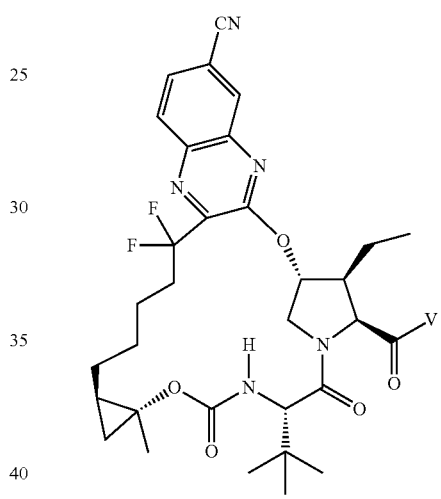
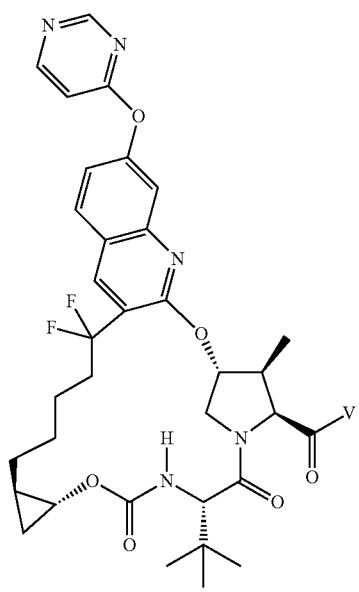

603
-continued
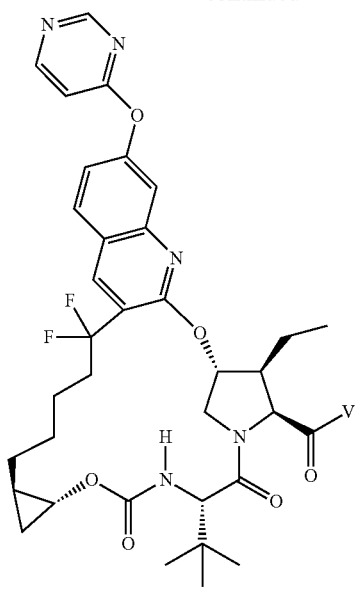
604
-continued
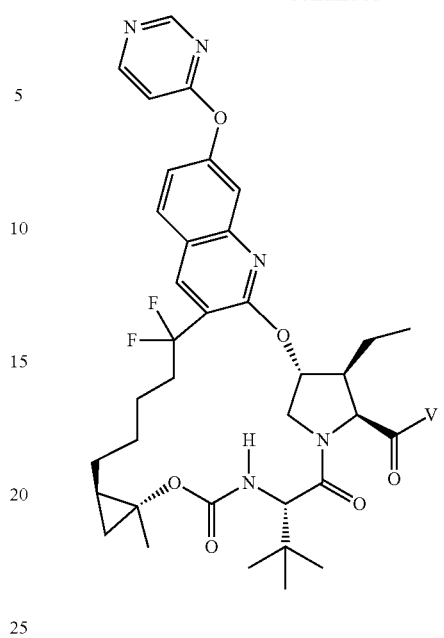
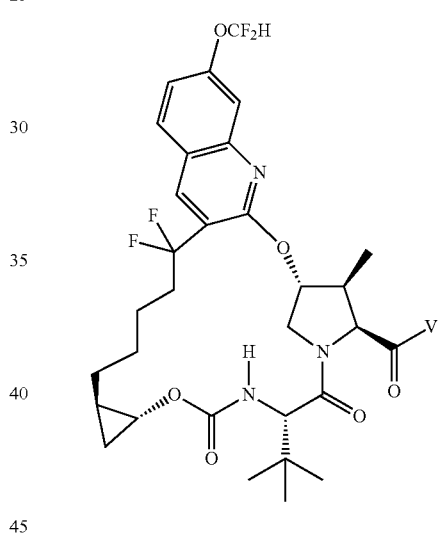
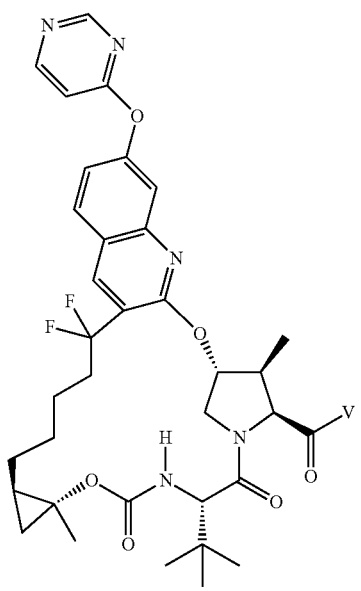
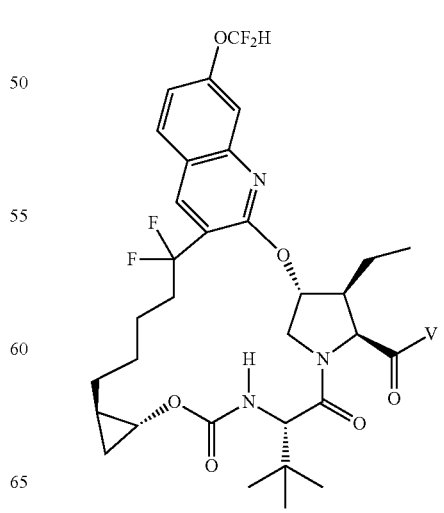

605
-continued
606
-continued
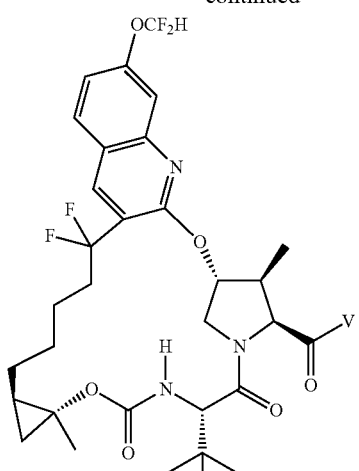
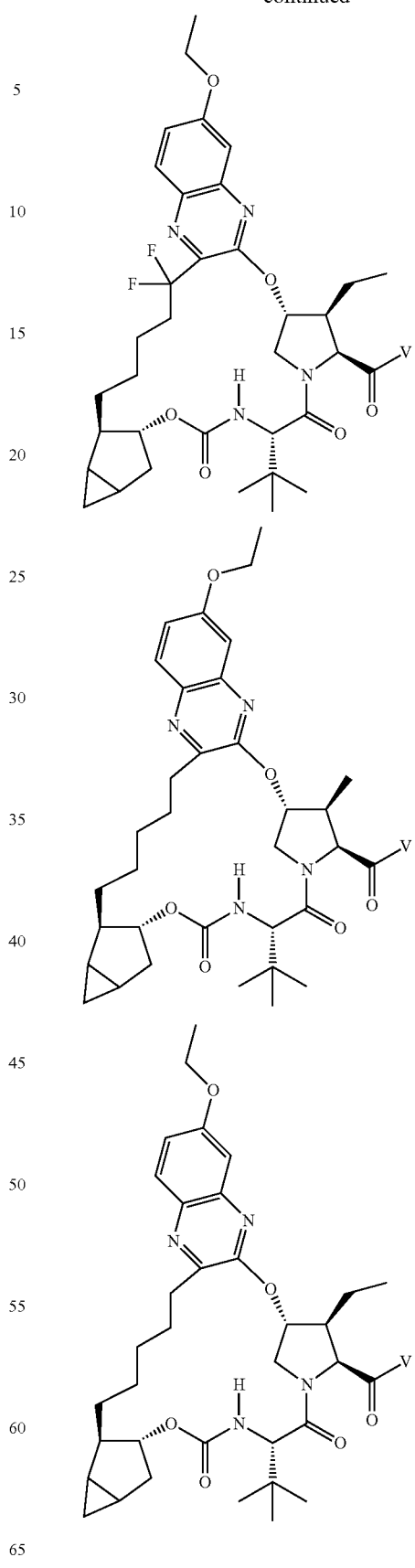

607
-continued
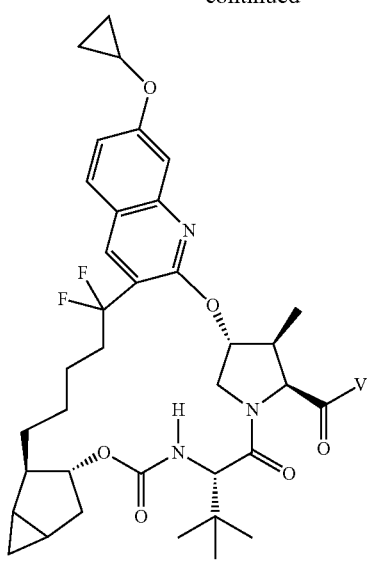
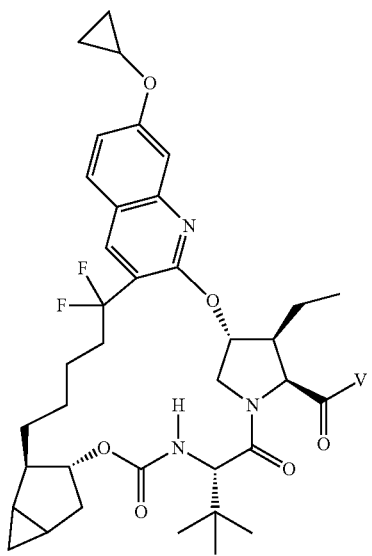
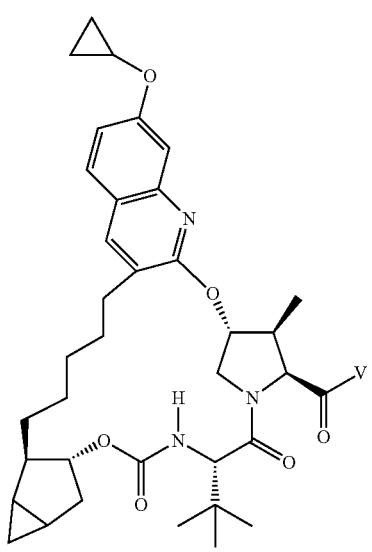
608
-continued
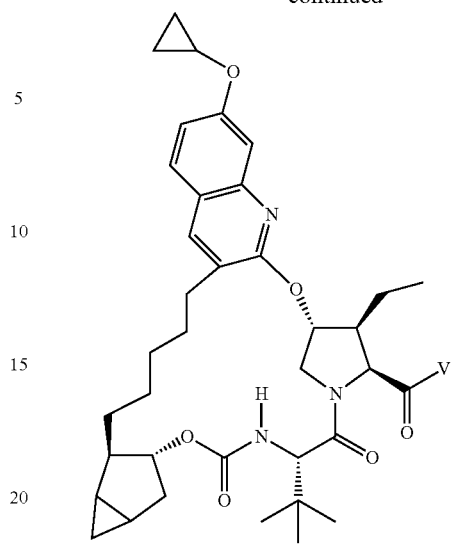
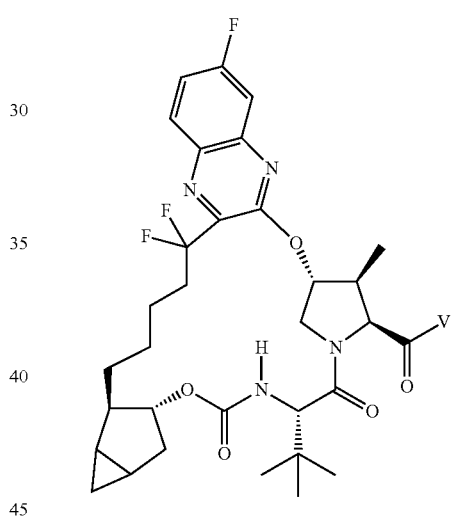
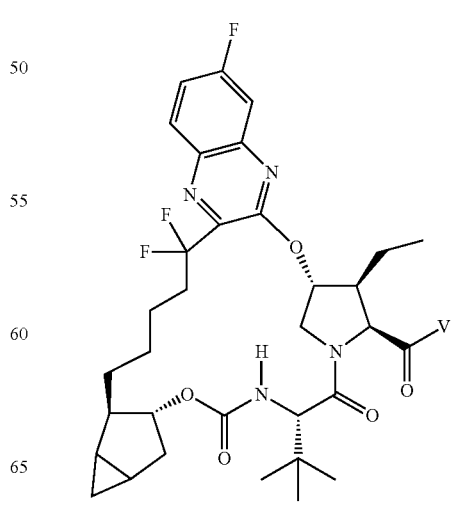

609
-continued
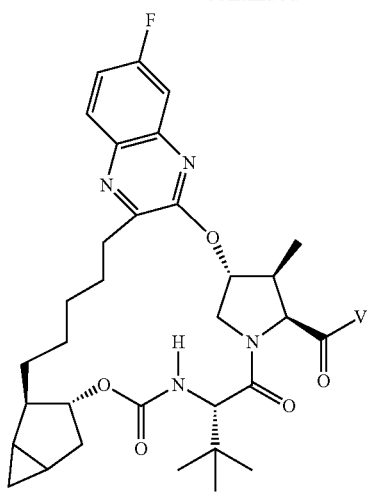
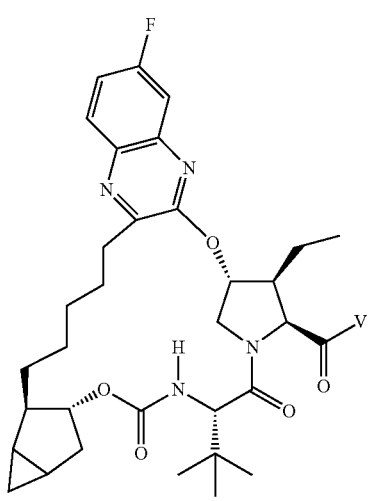
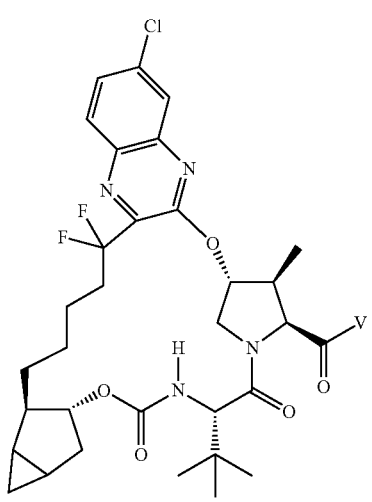
610
-continued
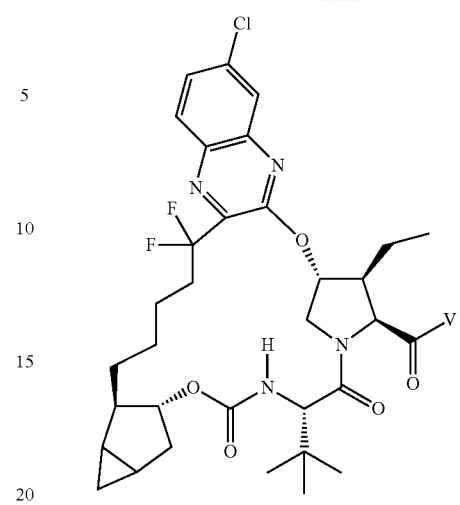
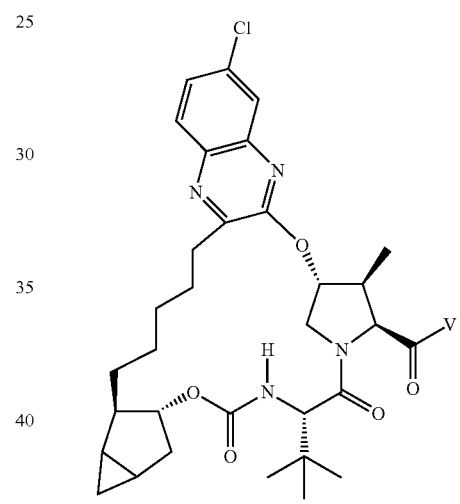
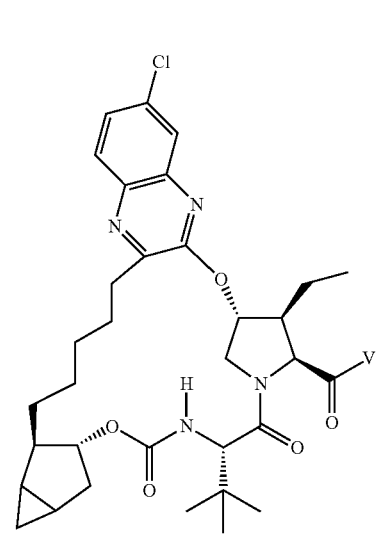

611
-continued
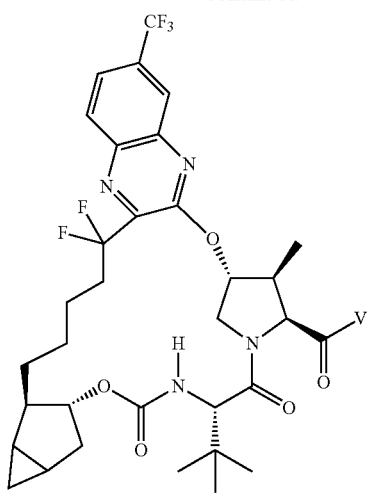
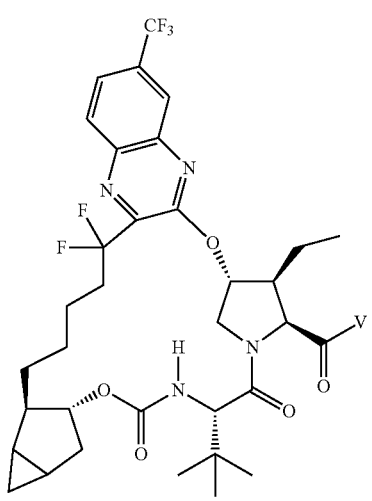
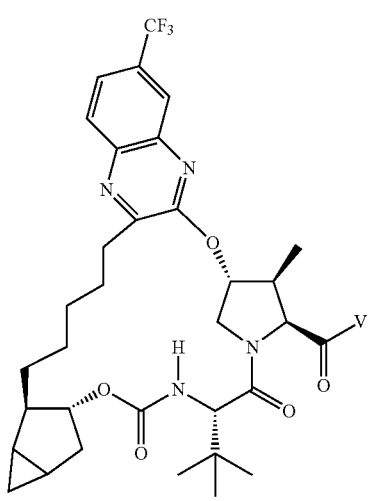
612
-continued
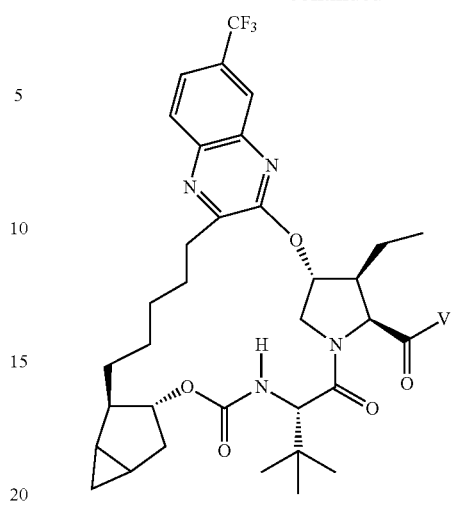
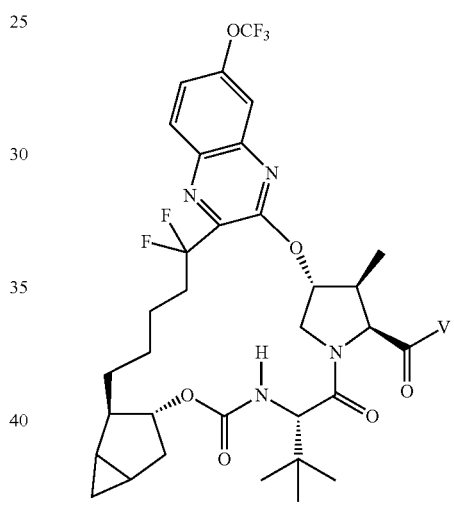
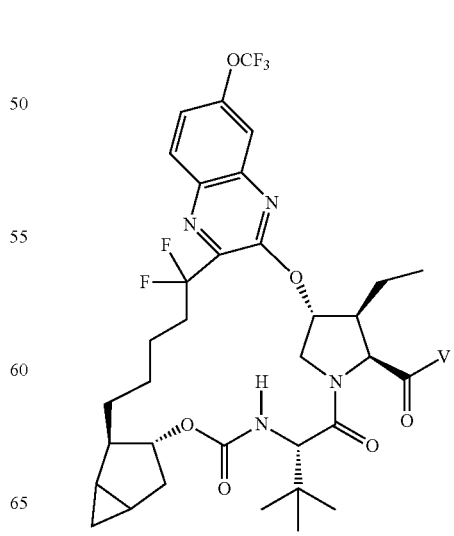

613
-continued
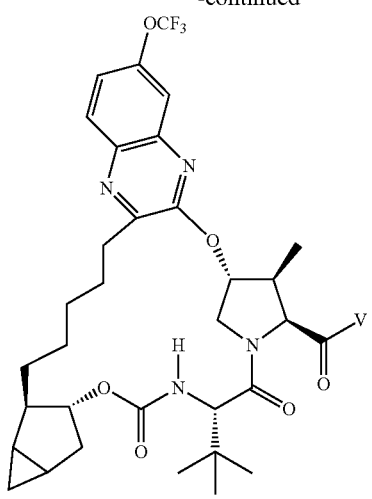
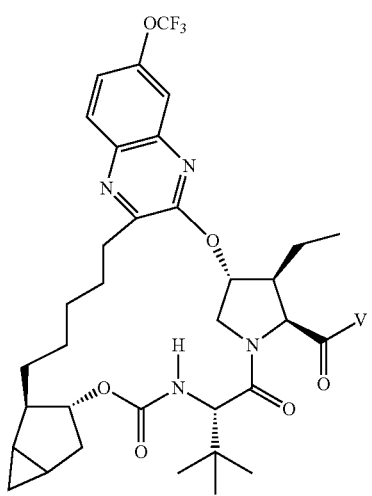
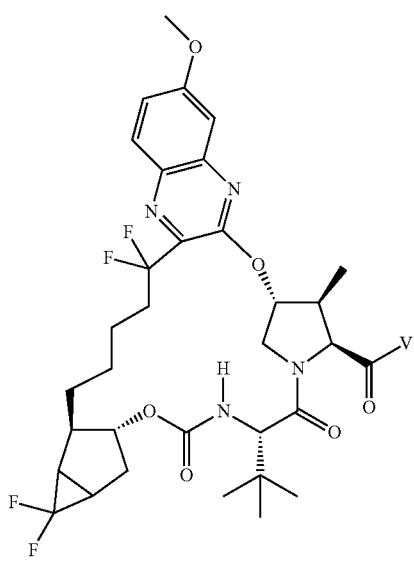
614
-continued
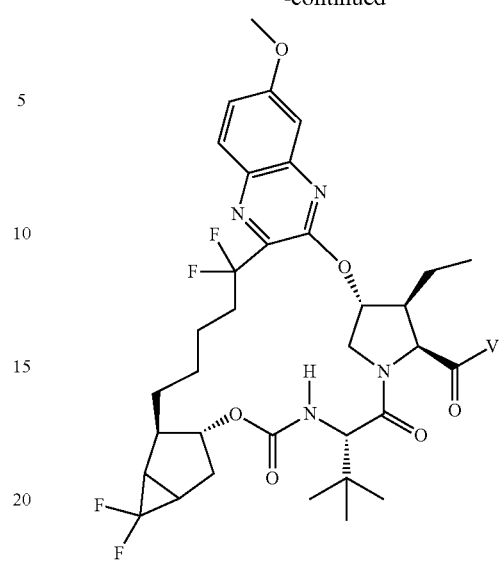
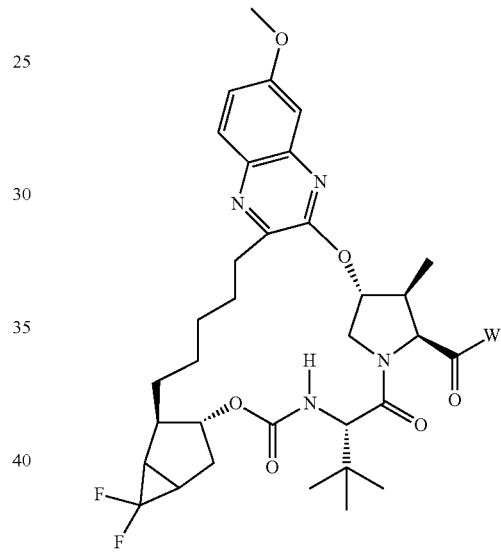
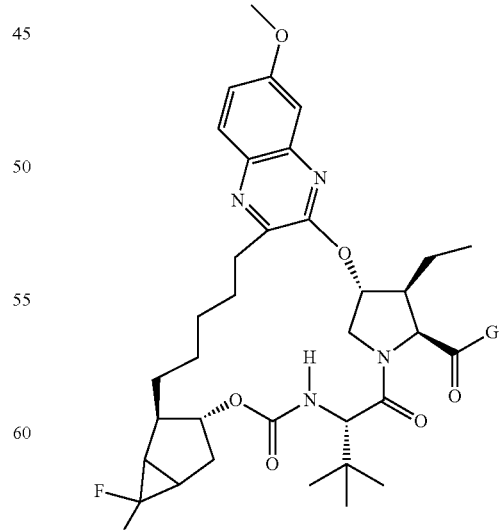

615
-continued
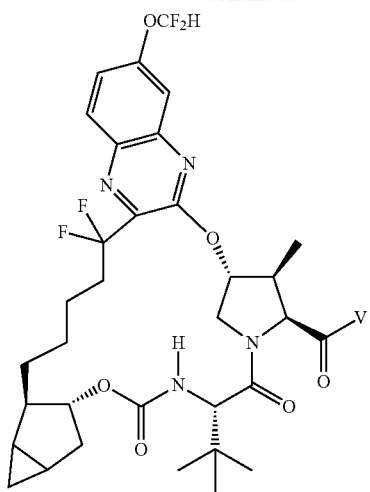
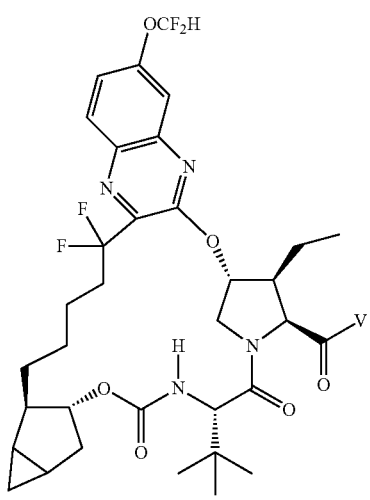
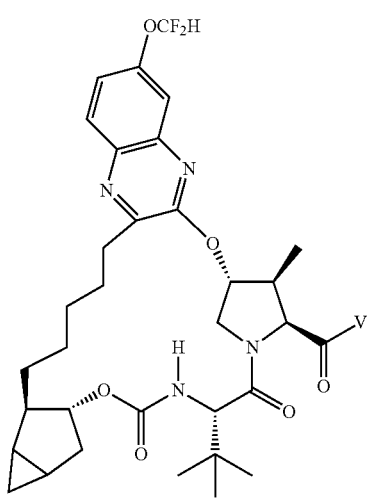
616
-continued
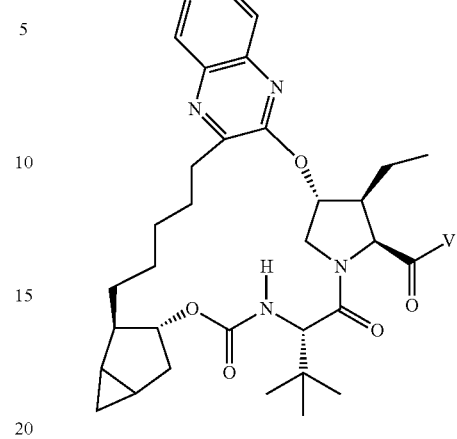
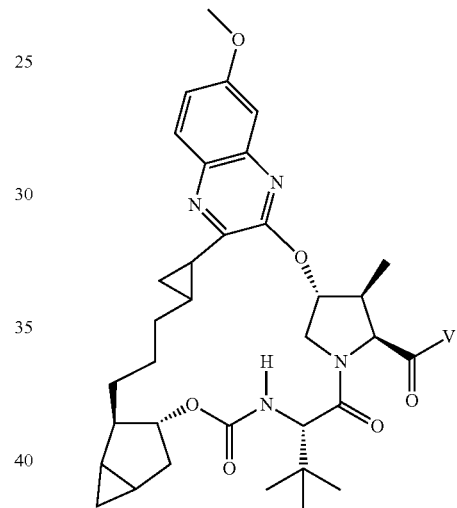
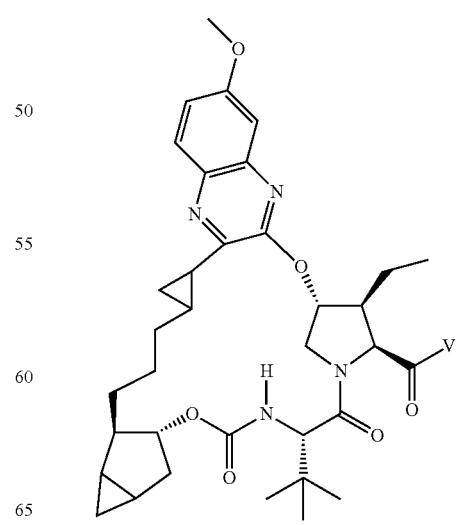

wherein V is a structure of Formula:

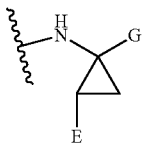

and wherein E and G are defined as above.
Biological Activity
Expression and Purification of Genotype 1a, 2a, and 3 NS3 Proteases Generation of NS3 Protease Expression Plasmids The coding sequence of the genotype 1b (con-1 strain) HCV NS3 protease domain was PCR amplified from a plasmid encoding the I389luc-ubi-neo/NS3-3'/ET replicon (Reblikon, Mainz. Germany). The 5'-PCR primer was designed to encode an N-terminal $K_3$ hexahistidine tag and to insert an in-frame recombinant Tobacco Etch virus (rTEV) protease cleavage site into the NS3 coding sequence. The resulting DNA fragment was cloned into the pET28 protein expression vector (Invitrogen, Carlsbad, Calif.) yielding the p28-N6H-Tev-NS3(181)1b.

The coding sequences for the genotype 3 HCV protease domain was amplified by RT-PCR using a Titan One Tube RT-PCR Kit (Roche, Indianapolis, Ind.) and RNA extracted from HCV-positive human serum (BBI Diagnostics, MA) using a QIAmp UltraSens Virus Kit (Qiagen, Valencia, Calif.). 5' PCR primers were designed to encode N-terminal hexahistidine tags and to insert in-frame rTEV protease cleavage sites into the NS3 protease coding sequences. The resulting DNA fragments were cloned into pET28 yielding the expression vectors p28-N6H-Tev-NS3(181)1a and p28-N6H-Tev-NS3(181)3, respectively.

NS3 Protease Protein Expression

BL21AI bacteria (Invitrogen, Carlsbad, Calif.) were transformed with genotype 1b or 3 NS3 expression vectors and used to inoculate a 20 L fermentation vessel (Sartorius BBI System Inc., Bethlehem, Pa.), containing 18 L of fresh 2YT medium supplemented with 50 µg/mL kanamycin. When cell densities reached an $D_{600}$ of 1, the temperature of the cultures was reduced from 37° C. to 28° C. and induction was immediately initiated by the addition of 30 µM $ZnSO_4$. 14 mM L-arabinose and 1 mM Isopropyl β-D-thiogalactoside (IPTG) final concentrations. Cells were harvested by centrifugation four hours post-induction and were stored as frozen pellets at −80° C. prior to NS3 protein purification.

Purification of NS3 Proteases

Purification of Genotype 1b NS3 Protease
Cell pellets were thawed and resuspended at 10 mL/g cells in lysis buffer containing 50 mM tris pH 7.6, 300 mM NaCl, 0.1% 3-[(3-cholamidopropyl)dimethylammonio]-1-propanesulfonate (CHAPS), 5% glycerol, and 2 mM β-mercaptoethanol. Cell suspensions were then sonicated, filtered through cheesecloth, and passed three times through a microfluidizer at 18,000 pounds/in². The resulting lysates were centrifuged at 15500 rpm for 45 minutes and supernatants were loaded onto a HisTrap HP column (GE Lifesciences) pre-equilibrated with five volumes of Ni buffer A (50 mM tris pH 7.6, 300 mM NaCl, 0.1% CHAPS, 5% glycerol, 2 mM β-mercaptoethanol, 50 mM imidazole-HCl). Proteins were eluted with a 0-100% gradient of Ni buffer A plus 500 mM imidazole-HCl and fractions were collected and pooled. The HisTrap pool was diluted 1:10 with SP-A buffer (50 mM tris pH 7.0, 10% glycerol, 2 mM dithiothreitol (DTT)) and loaded onto a HiTrap SP-HP column (GE Lifesciences) equilibrated with SP-A buffer. NS3 protease was eluted with a 0-100% SP-B buffer (SP-A buffer plus 1 M NaCl) gradient. Concentrated pools of NS3-containing SP fractions were aliquoted, snap frozen in liquid nitrogen and stored at −80° C.

Purification of Genotype 3 NS3 Protease
Bacterial pellets collected from the expression of genotype 3 HCV NS3 protease were homogenized in Lysis Buffer (25 mM tris, pH 7.5 buffer containing 150 mM NaCl and 1 mM phenylmethanesulfonyl fluoride (PMSF)) and passed through a microfluidizer at 18,000 pounds/in². Homogenized cell lysates were centrifuged at 30,000×g for 30 minutes at 4° C. The resulting P1 pellets were washed with Wash Buffer I (25 mM tris, pH 7.5 containing 1% CHAPS) followed by centrifugation at 10,000×g for 30 minutes at 4° C. The resulting P2 pellets were washed with Wash Buffer II (50 mM CAPS buffer, pH 10.8, containing 2 M NaCl and 2 M urea) followed by centrifugation at 30,000×g for 2 minutes at 4° C. The resulting P3 pellets were resuspended in Solubilization Buffer (20 ml of 25 mM tris, pH 7.5 containing 150 mM NaCl and 8 M urea) and incubated at 4° C. for one hour. Solubilized proteins were passed through a 0.45 micron filter. Protein concentrations were measured and the solutions were adjusted to 40 mM DTT, incubated for 30 minutes at 4° C. and then quickly diluted into Refolding Buffer (25 mM tris, pH 8.5, 0.8 M Guanidine-HCl, 0.4 M L-Arginine, 10 mM $ZnSO_4$) while stirring. Protein solutions were incubated at 4° C. overnight to allow refolding. Refolded proteases were centrifuged at 30,000×g for 10 minutes to remove residual precipitates. Final protein concentrations were then measured and the NS3 proteases were aliquoted, snap frozen in liquid nitrogen and stored at −80° C.

Ki Determination for Genotypes 1b and 3a NS3 Protease.
Purified NS3 protease domain (amino acids 1-181) of the genotype 1b and 3a virus were generated as above. The internally quenched fluorogenic depsipeptide substrate Ac-DED(Edans)-EEAbuΨ[COO]ASK(Dabcyl)-$NH_2$ and a synthetic peptide containing the hydrophobic core residues of the NS4A protein cofactor (KKGSVVIVGRIILSGRKK; NS4A peptide) were obtained from Anaspec, Inc. (San Jose, Calif.). Other chemicals and biochemicals were of reagent grade or better and were purchased from standard suppliers.

Reactions were run at room temperature in buffer consisting of 50 mM HEPES, 40% glycerol, 0.05% Triton X-100, 10 mM DTT, and 10% DMSO. The final assay solutions contained 50 pM NS3 genotype 1 b protease or 200 pM genotype 3a protease, 20 µM NS4A peptide, and 4 µM substrate (genotype 1b) or 2 µM substrate (genotype 3a). Inhibitor concentrations varied from 100 nM to 5 pM in 3-fold dilutions, and no-inhibitor controls were included.

Compound dilutions were made in DMSO at 20× final concentration. Reaction mixtures were prepared in 96-well assay plates. A solution of enzyme and NS4A peptide in assay buffer (25 µL volume with both reagents at 4× final concentration) was mixed with 45 µL assay buffer and 5 µL of either inhibitor or DMSO, and pre-incubated at room temperature for 1 hour. The reaction was started by addition of 25 µL substrate solution at 4× final concentration. Plates were mixed vigorously for 5-10 seconds and reactions were allowed to proceed for 90 minutes, fluorescence was measured every 30 s between 90 and 120 minutes reaction time using a Tecan InfiniTe M1000 or PerkinElmer Envision multimode plate reader with an excitation wavelength of 340 nm and an emission wavelength of 490 nm.

Rates were calculated from the progress curves at steady state, in the time frame of 90-120 minutes after addition of substrate. To determine the $K_i$, rates were plotted as a function of inhibitor concentration, and the data were fit with equation 1 (Morrison, J. F., *Biochimica et Biophysica Acta* 1969, 185, 269-286) to calculate $K_i^{app}$ using GraphPad Prism 5. Active fraction of enzyme was determined by active site titration with known potent inhibitors. $K_i$ was calculated from $K_i^{app}/(1+[[S]/K_m])$. $K_i$ results for representative compounds for genotype 1b and 3a (Ki 1B and Ki 3A, respectively) are reported in Table 1.

$$\frac{v}{v_0} = \frac{[E]_t - [I]_t - K_i^{app} + \sqrt{([E]_t - [I]_t - K_i^{app})^2 + 4[E]_t K_i^{app}}}{2[E]_t} \quad (1)$$

Evaluation of Cell-based Anti-HCV Activity:

Antiviral potency ($EC_{50}$) was determined in both stable subgenomic HCV replicon cell lines and transient-transfected HCV replicon cells. The term half maximal effective concentration ($EC_{50}$) refers to the concentration of a drug which induces a response halfway between the baseline and maximum after the exposure time specified below.

Stable subgenomic HCV replicons for genotype 1a, 1b, 2a, 3a, and 4a were established in Huh-7-derived cells as described by Lohmann et al (Lohmann V, Korner F, Koch J, et al Replication of subgenomic hepatitis C virus RNAs in a hepatoma cell line. Science 1999; 285:119-3) Each stable cell line contains a bicistronic HCV replicon that encodes a humanized *Renilla* luciferase (hRLuc) reporter gene fused to a selectable neomycin-resistance gene, followed by an EMCV IRES and the NS3-NS5B coding region of HCV. Selection for cells constitutively expressing the HCV replicon was achieved in the presence of the selection antibiotic, neomycin (G418). Luciferase activity was measured as a marker for intracellular HCV replication levels.

The genotype 1a stable replicon was derived from the H77 HCV strain and contained adaptive mutations P1496L and S2204I. The genotype 1b stable replicon was derived from the Con1 HCV strain and contained adaptive mutations E1202G, T1280I and K1846T. The genotype 2a stable replicon was derived from the JFH-1 HCV strain and did not require adaptive mutations. The genotype 3a stable replicon was derived from the S52 HCV strain and contained adaptive mutations P1121L, A1198T and S2210I (equivalent to S2204I in genotype 1). The genotype 4a stable replicon was derived from the ED43 HCV strain and contained adaptive mutations Q1691R and S2204I. All replicon cell lines were propagated in Huh-7-derived cells and maintained in Dulbecco's modified Eagle's Medium (DMEM) supplemented with 10% fetal bovine serum (FBS) and 0.5 mg/mL G418.

Transient-transfected HCV replicons were established for genotype 1a, 1b, 3a and NS3/4a protease inhibitor resistant variants D168A in genotype 1b or R155K in genotype 1a. Transient-transfected replicons are also bicistronic subgenomic replicons but do not contain the neomycin selectable marker present in stable replicons. These replicons encode the poliovirus IRES followed by the hRLuc reporter gene, the EMCV IRES and finally the NS3-NS5B coding region of HCV. The genotype 1a (H77) and 1b (Con1) wild-type replicons were derived from the same strain and contained the same adaptive mutations as listed above. The genotype 3a transient replicon was derived from the S52 HCV strain as above, but contained slightly different adaptive mutations P1112L, K1615E and S2210I. Specifically, the secondary adaptive mutation A1198T (A166T) in the protease domain of the stable genotype 3a replicon was replaced with K1615E (K583E) in the NS3 helicase, with no effect on replication efficiency. Removal of A166T located in the protease domain minimizes the impact of this variant on inhibitors targeting the protease domain and represents a protease domain closer to wild type for genotype 3a. Resistant replicons encoding NS3/4 protease inhibitor mutations were introduced into the 1b or 1a wild-type NS3 gene by site directed mutagenesis. In vitro transcribed RNAs from all transient replicons were transfected into naive Huh-7-derived cell lines by electroporation. Luciferase activity was measured as a marker for intracellular HCV replication levels To perform $EC_{50}$ assays, cells from each HCV replicon were dispensed into 384-well plates. Compounds were dissolved in DMSO at a concentration of 10 mM and diluted in DMSO using an automated pipetting instrument. Three-fold serially diluted compounds were directly added to the cells using an automated instrument. DMSO was used as a negative (solvent; no inhibition) control, and a combination of three HCV inhibitors including a protease inhibitor; an NS5A inhibitor and a nucleoside inhibitor was used at concentrations >100×$EC_{50}$ as a positive control (100% inhibition). Seventy-two hours later, cells were lysed and *Renilla* luciferase activity were quantified as recommended by the manufacturer (Promega-Madison, Wis.). Non-linear regression was performed to calculate $EC_{50}$ values.

Results are shown in Tables 1 and 2:

TABLE 1

Biological Activity Values
For Stable Subgenonic HCV Replicon Cell Lines

| Example | Ki 1B (nM) | Ki 3A (nM) | $EC_{50}$ 1A RLUC* (nM) | $EC_{50}$ 1B RLUC* (nM) | $EC_{50}$ 2A RLUC* (nM) | $EC_{50}$ 3A RLUC* (nM) | $EC_{50}$ 4A RLUC* (nM) |
|---|---|---|---|---|---|---|---|
| 1 | 0.03 | 0.07 | 4.4 | 3.9 | 4.1 | 46 | 3.1 |
| 2 | 0.01 | 0.04 | 4.0 | 3.1 | 3.9 | 77 | 2.7 |
| 3 | 0.18 | 0.56 | 11.7 | 9.8 | 28 | 546 | 10 |
| 4 | 0.17 | 0.56 | 10.7 | 9.6 | 16 | 271 | 7.9 |
| 5 | 0.04 | 0.17 | 8.7 | 7.4 | 11 | 405 | 6.9 |
| 6 | 0.20 | 0.62 | 35 | 36 | 34 | 1361 | 34 |
| 7 | 0.05 | 0.06 | 4.9 | 3.8 | 4.2 | 67 | 3.2 |
| 8 | 0.07 | 0.42 | 16 | 8.6 | 20 | 465 | 13 |
| 9 | 0.15 | 0.59 | 17 | 7.9 | 23 | 1268 | 11 |

TABLE 1-continued

Biological Activity Values
For Stable Subgenonic HCV Replicon Cell Lines

| Example | Ki 1B (nM) | Ki 3A (nM) | $EC_{50}$ 1A RLUC* (nM) | $EC_{50}$ 1B RLUC* (nM) | $EC_{50}$ 2A RLUC* (nM) | $EC_{50}$ 3A RLUC* (nM) | $EC_{50}$ 4A RLUC* (nM) |
|---|---|---|---|---|---|---|---|
| 10 | 0.16 | 0.52 | 30 | 22 | 49 | 978 | 26 |
| 11 | 0.23 | 0.88 | 28 | 17 | 34 | 1162 | 19 |
| 12 | 0.27 | 1.2 | 34 | 18 | 25 | 2013 | 21 |
| 13 | 0.04 | 0.18 | 13 | 9.5 | 26 | 685 | 11 |
| 14 | 0.07 | 0.24 | 9.7 | 6.8 | 7.0 | 308 | 7.3 |
| 15 | 0.05 | 0.30 | 11 | 6.8 | 9.8 | 550 | 7.8 |
| 16 | 0.09 | 0.21 | 12 | 7.4 | 6.2 | 201 | 8.1 |
| 17 | 0.04 | 0.06 | 3.9 | 3.3 | 3.7 | 15 | 2.9 |
| 18 | 0.03 | 0.10 | 3.9 | 2.6 | 5.0 | 70 | 2.8 |
| 19 | 0.02 | 0.13 | 4.0 | 2.6 | 4.6 | 89 | 3.1 |
| 20 | 0.12 | 0.53 | 8.1 | 5.2 | 19 | 392 | 5.9 |
| 21 | 0.10 | 0.45 | 6.8 | 4.7 | 12 | 263 | 6.2 |
| 22 | 0.07 | 1.3 | 15 | 7.5 | 27 | 727 | 11 |
| 23 | 0.08 | 1.1 | 13 | 7.5 | 23 | 587 | 9.9 |
| 24 | 0.05 | 0.92 | 12 | 7.5 | 20 | 663 | 9.2 |
| 25 | 0.05 | 0.39 | 8.8 | 6.3 | 13 | 409 | 7.1 |
| 26 | 0.05 | 0.17 | 6.3 | 4.3 | 12 | 297 | 6.0 |
| 27 | 0.03 | 0.08 | 6.6 | 5.2 | 6.7 | 266 | 6.1 |
| 28 | 0.03 | 0.08 | 6.7 | 4.6 | 6.2 | 266 | 4.1 |
| 29 | 0.06 | 0.12 | 10 | 8.9 | 11 | 137 | 7.2 |
| 30 | 0.14 | 0.63 | 55 | 35 | 47 | 2437 | 31 |
| 31 | 0.13 | 4.9 | 40 | 18 | 63 | 2071 | 20 |
| 32 | 0.18 | 0.87 | 59 | 30 | 35 | 2311 | 30 |
| 33 | 0.03 | 0.06 | 7.6 | 2.8 | 4.9 | 16 | 2.3 |
| 34 | 0.10 | 0.28 | 12 | 13 | 18 | 322 | 9.7 |
| 35 | 0.07 | 0.23 | 9.1 | 11 | 7.4 | 162 | 7.6 |
| 36 | 0.10 | 1.7 | 23 | 14 | 53 | 585 | 9.1 |
| 37 | 0.10 | 0.19 | 24 | 22 | 16 | 575 | 15 |
| 38 | 0.03 | 0.70 | 7.8 | 4.2 | 5.4 | 151 | 5.5 |
| 39 | 0.08 | 0.20 | 34 | 39 | 41 | 321 | 26 |
| 40 | 0.08 | 0.18 | 25 | 22 | 48 | 360 | 18 |
| 41 | 0.18 | 0.79 | 135 | 142 | 106 | 2606 | 135 |
| 42 | 0.10 | 0.75 | 20 | 16 | 17 | 343 | 14 |
| 43 | 0.06 | 0.16 | 4.9 | 3.8 | 5.2 | 92 | 3.6 |
| 44 | 0.03 | 0.08 | 3.1 | 2.1 | 2.9 | 53 | 2.2 |
| 45 | 0.04 | 0.48 | 21 | 8.3 | 24 | 549 | 13 |
| 46 | 0.03 | 0.05 | 3.1 | 2.7 | 3.8 | 17 | 2.5 |
| 47 | 0.07 | 0.19 | 3.8 | 3.6 | 12 | 58 | 4.2 |
| 48 | 0.07 | 0.09 | 2.0 | 1.8 | 9.7 | 73 | 2.2 |
| 49 | 0.04 | 0.07 | 3.7 | 4.1 | 5.2 | 20 | 3.5 |
| 50 | 63 | 100 | 4444 | 4444 | 379 | 19708 | 4444 |
| 51 | 0.31 | 0.84 | 40 | 39 | 103 | 1221 | 30 |
| 52 | 0.25 | 1.3 | 195 | 245 | 380 | 2307 | 161 |
| 53 | 0.03 | 0.09 | 51 | 7.7 | 13 | 18 | 2.8 |
| 54 | 0.11 | 0.50 | 33 | 18 | 76 | 260 | 13 |
| 55 | 0.09 | 0.20 | 13 | 3.8 | 12 | 140 | 3.5 |
| 56 | 0.38 | 1.0 | 41 | 37 | 57 | 1026 | 57 |
| 57 | 0.07 | 0.28 | 12 | 11 | 21 | 166 | 4.9 |
| 58 | 0.07 | 0.17 | 12 | 9.7 | 12 | 134 | 12 |
| 59 | 0.04 | 0.06 | 5.4 | 11 | 13 | 20 | 5.6 |
| 60 | 0.04 | 0.08 | 11 | 4.8 | 7.7 | 45 | 5.4 |
| 61 | 0.06 | 0.09 | 13 | 10 | 8.7 | 28 | 11 |
| 62 | 0.04 | 0.03 | 3.4 | 3.0 | 5.0 | 8.5 | 2.4 |
| 63 | 0.03 | 0.01 | 4.2 | 2.9 | 3.2 | 11 | 3.2 |
| 64 | 0.07 | 1.2 | 100 | 38 | 48 | 671 | 34 |
| 65 | 0.08 | 0.07 | 12 | 8.4 | 7.7 | 30 | 8.1 |
| 66 | 0.04 | 0.06 | 37 | 20 | 105 | 1786 | 25 |
| 67 | 0.04 | 0.32 | 11 | 12 | 24 | 383 | 12 |
| 68 | 0.05 | 0.63 | 13 | 7.7 | 18 | 364 | 9.4 |
| 69 | 0.07 | 0.17 | 5.2 | 4.9 | 11 | 64 | 5.8 |
| 70 | 0.05 | 0.05 | 8.4 | 8.5 | 15 | 41 | 6.4 |
| 71 | 0.03 | 0.14 | 6.5 | 5.3 | 23 | 160 | 5.3 |
| 72 | 0.05 | 4.1 | 365 | 300 | 740 | 1819 | 383 |
| 73 | 0.11 | 0.82 | 7.9 | 7.5 | 22 | 178 | 7.2 |
| 74 | 0.03 | 0.12 | 8.0 | 5.0 | 18 | 374 | 8.3 |
| 75 | 0.03 | 0.12 | 9.9 | 6.4 | 18 | 240 | 10 |
| 76 | 0.03 | 0.06 | 2.4 | 2.2 | 2.4 | 9.0 | 1.9 |
| 77 | nt | nt | 23 | 12 | 29 | 741 | 16 |
| 78 | 0.21 | 0.82 | 267 | 394 | 195 | 1115 | 225 |
| 79 | 0.06 | 0.06 | 7.0 | 5.8 | 4.1 | 71 | 5.6 |
| 80 | 0.49 | 13 | 1127 | 344 | 748 | 44444 | 1182 |
| 81 | 0.04 | 0.05 | 4.0 | 3.6 | 3.6 | 12 | 4.3 |
| 82 | 0.03 | 0.04 | 8.5 | 9.3 | 4.7 | 25 | 10 |

TABLE 1-continued

Biological Activity Values
For Stable Subgenonic HCV Replicon Cell Lines

| Example | Ki 1B (nM) | Ki 3A (nM) | $EC_{50}$ 1A RLUC* (nM) | $EC_{50}$ 1B RLUC* (nM) | $EC_{50}$ 2A RLUC* (nM) | $EC_{50}$ 3A RLUC* (nM) | $EC_{50}$ 4A RLUC* (nM) |
|---|---|---|---|---|---|---|---|
| 83 | 0.09 | 0.48 | 62 | 58 | 19 | 1219 | 42 |
| 84 | 0.04 | 0.08 | 5.9 | 5.7 | 7.2 | 27 | 6.4 |
| 85 | 0.05 | 0.03 | 16 | 17 | 7.7 | 304 | 9.2 |
| 86 | 0.04 | 0.07 | 5.6 | 5.5 | 5.9 | 42 | 5.7 |
| 87 | 0.02 | 0.05 | 4.8 | 3.9 | 3.3 | 14 | 3.8 |
| 88 | 0.02 | 0.29 | 9.3 | 4.6 | 2.7 | 105 | 4.1 |
| 89 | 0.03 | 0.05 | 6.0 | 6.1 | 4.3 | 19 | 4.6 |
| 90 | 0.06 | 0.13 | 12 | 9.6 | 8.8 | 114 | 10.4 |
| 91 | nt | nt | 2.4 | 1.9 | 4.0 | 149 | 2.4 |
| 92 | nt | nt | 3.3 | 3.2 | 4.6 | 58 | 3.2 |
| 93 | nt | nt | 12 | 14 | 15 | 116 | 11 |
| 94 | nt | nt | 3.8 | 5.2 | 3.3 | 32 | 3.0 |
| 96 | nt | nt | 12 | 11 | 5.4 | 77 | 8.9 |
| 97 | nt | nt | 6.3 | 4.6 | 5.8 | 67 | 5.3 | nt—not tested
*RULC: *Renilla* luciferase

TABLE 2

Biological Activity Values For Transient-Transfected HCV Replicon Cell Lines

| Example | $EC_{50}$ 3A WT* (nM) | $EC_{50}$ 1A WT* (nM) | $EC_{50}$ 1A R155K† (nM) | $EC_{50}$ 1B WT* (nM) | $EC_{50}$ 1B D168A‡ (nM) |
|---|---|---|---|---|---|
| 1 | 17 | 3.2 | 4.9 | 2.2 | 17 |
| 2 | nt | 2.4 | 7.0 | 1.0 | 33 |
| 3 | nt | 6.6 | 32 | 3.5 | 128 |
| 4 | 68 | 7.1 | 20 | 6.5 | 66 |
| 5 | nt | 3.7 | 17 | 3.2 | 91 |
| 6 | nt | 26 | 58 | 11 | 216 |
| 7 | 14 | 3.8 | 6.7 | 2.3 | 20 |
| 8 | nt | 8.8 | 28 | 4.8 | 89 |
| 9 | nt | 12 | 208 | 2.5 | 360 |
| 10 | nt | 37 | 131 | 10 | 493 |
| 11 | nt | 20 | 159 | 9.4 | 605 |
| 12 | nt | 14 | 283 | 5.7 | 640 |
| 13 | nt | 8.6 | 59 | 3.1 | 209 |
| 14 | nt | 7.4 | 21 | 4.0 | 99 |
| 15 | nt | 6.5 | 20 | 3.0 | 182 |
| 18 | nt | 9.4 | 22 | 5.8 | 61 |
| 17 | 6.1 | 2.9 | 2.8 | 1.7 | 4.3 |
| 18 | nt | 2.3 | 5.0 | 1.2 | 24 |
| 19 | nt | 2.1 | 3.4 | 1.1 | 28 |
| 20 | Nt | 3.4 | 17 | 2.7 | 90 |
| 21 | nt | 4.1 | 15 | 3.8 | 70 |
| 22 | nt | 8.6 | 48 | 2.6 | 242 |
| 23 | nt | 9.5 | 36 | 3.6 | 173 |
| 24 | nt | 9.3 | 49 | 3.2 | 284 |
| 25 | nt | 4.4 | 17 | 3.6 | 116 |
| 26 | nt | 3.6 | 12 | 1.9 | 109 |
| 27 | nt | 6.0 | 20 | 4.3 | 70 |
| 28 | nt | 3.0 | 9 | 3.4 | 54 |
| 29 | nt | 4.8 | 11 | 3.1 | 48 |
| 30 | nt | 41 | 296 | 31 | 503 |
| 31 | nt | 27 | 154 | 6.6 | 805 |
| 32 | nt | 44 | 547 | 14 | 653 |
| 33 | 5.3 | 2.6 | 2.5 | 1.6 | 4.2 |
| 34 | 46 | 15 | 18 | 9 | 64 |
| 35 | 35 | 12 | 17 | 10 | 38 |
| 36 | 128 | 16 | 271 | 9.4 | 333 |
| 37 | 69 | 29 | 51 | 22 | 159 |
| 38 | nt | 4.5 | 8.4 | 2.8 | 25 |
| 39 | 89 | 23 | 63 | 16 | 105 |
| 40 | 156 | 17 | 74 | 8.6 | 129 |
| 41 | 539 | 164 | 505 | 154 | 715 |
| 42 | nt | 17 | 35 | 10 | 109 |
| 43 | nt | 3.8 | 8.7 | 2.4 | 41 |
| 44 | 7.0 | 2.4 | 4.0 | 1.4 | 15 |
| 45 | nt | 13 | 35 | 5.3 | 88 |
| 46 | 6.788 | 2.4 | 3.2 | 1.2 | 4.5 |
| 47 | 17 | 5.4 | 6.1 | 2.0 | 12 |
| 48 | 13 | 1.7 | 4.0 | 1.1 | 6.5 |
| 49 | 6.3 | 3.5 | 3.8 | 2.8 | 4.2 |
| 50 | 26825 | 4444 | 3830 | 4444 | 4444 |
| 51 | 265 | 28 | 92 | 24 | 318 |
| 52 | 538 | 150 | 516 | 161 | 887 |
| 53 | 15 | 5.3 | 5.6 | 2.0 | 11 |
| 54 | 147 | 19 | 27 | 10 | 123 |
| 55 | 71 | 8.0 | 32 | 2.3 | 53 |
| 56 | 226 | 63 | 168 | 59 | 252 |
| 57 | 54 | 12 | 17 | 7.5 | 48 |
| 58 | 38 | 12 | 18 | 14 | 23 |
| 59 | 15 | 10 | 6.8 | 6.8 | 6.4 |
| 60 | 9.8 | 5.8 | 8.6 | 2.3 | 15 |
| 61 | 13 | 12 | 10 | 9.3 | 6.7 |
| 62 | 4.0 | 3.5 | 2.7 | 1.5 | 2.0 |
| 63 | 6.9 | 4.1 | 4.0 | 2.1 | 3.4 |
| 64 | 256 | 37 | 50 | 17 | 104 |
| 65 | 17 | 9.4 | 8.1 | 6.4 | 11 |
| 66 | 735 | 35 | 240 | 14 | 396 |
| 67 | 107 | 14 | 42 | 10 | 86 |
| 68 | 139 | 14 | 37 | 4.4 | 78 |
| 69 | 42 | 8.2 | 15 | 3.9 | 28 |
| 70 | 17 | 7.7 | 5.4 | 6.1 | 7.3 |
| 71 | 49 | 9.1 | 30 | 3.8 | 66 |
| 72 | 642 | 600 | 227 | 165 | 687 |
| 73 | 45 | 8.8 | 25 | 6.2 | 75 |
| 74 | 138 | 8.8 | 44 | 2.1 | 56 |
| 75 | 56 | 14 | 45 | 3.5 | 51 |
| 76 | 3.4 | 2.0 | 2.1 | 1.0 | 2.8 |
| 77 | 472 | 21 | 34 | 5.0 | 80 |
| 78 | 194 | 189 | 225 | 156 | 248 |
| 79 | 9.2 | 6.1 | 7.1 | 3.0 | 11 |
| 80 | nt | 403 | 2862 | 53 | 443 |
| 81 | 4.3 | 3.7 | 2.5 | 2.4 | 2.7 |
| 82 | 16 | 7.8 | 6.2 | 4.1 | 5.7 |

TABLE 2-continued

Biological Activity Values For Transient-Transfected HCV Replicon Cell Lines

|  | $EC_{50}$ 3A WT* (nM) | $EC_{50}$ 1A WT* (nM) | $EC_{50}$ 1A R155K† (nM) | $EC_{50}$ 1B WT* (nM) | $EC_{50}$ 1B D168A‡ (nM) |
|---|---|---|---|---|---|
| 83 | 300 | 62 | 133 | 27 | 202 |
| 84 | 11 | 5.4 | 4.0 | 2.5 | 5.2 |
| 85 | 101 | 12 | 22 | 7.0 | 57 |
| 86 | 16 | 4.0 | 3.7 | 3.4 | 10 |
| 87 | 7.7 | 2.9 | 2.8 | 1.3 | 4.0 |
| 88 | 35 | 5.0 | 14 | 5.5 | 24 |
| 89 | 5.5 | 6.0 | 3.7 | 3.2 | 5.1 |
| 90 | 43 | nt | nt | nt | nt |
| 91 | 25 | 2.3 | 3.5 | 1.3 | 9.2 |
| 92 | 8.0 | 3.0 | 3.0 | 1.7 | 5.3 |
| 93 | 26 | 13 | 13 | 14 | 39 |
| 94 | 10 | 3.2 | 3.1 | 1.9 | 9.2 |
| 96 | 12 | 5.2 | 3.8 | 4.1 | 3.6 |
| 97 | 5.8 | 3.6 | 3.7 | 2.5 | 8.8 | nt: not tested

*WT = wild type

†NS3/4a protease inhibitor resistant variants R155K in genotype 1a

‡NS3/4a protease inhibitor resistant variants D168A in genotype 1b

The data in Tables 1 and 2 represent an average over time of each assays for each compound. For certain compounds, multiple assays have been conducted over the life of the project Thus, the data reported in Tables 1 and 2 include the data reported in the priority document, as well as data generated in the intervening period.

Pharmaceutical Compositions

The following illustrate representative pharmaceutical dosage forms, containing a compound of Formulas I, II, III, or IV (such as any one of IVa-IVh) ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
|  | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
|  | 600.0 |

| (iv) Injection (1 mg/ml) | mg/ml |
|---|---|
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims, No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A compound of formula:

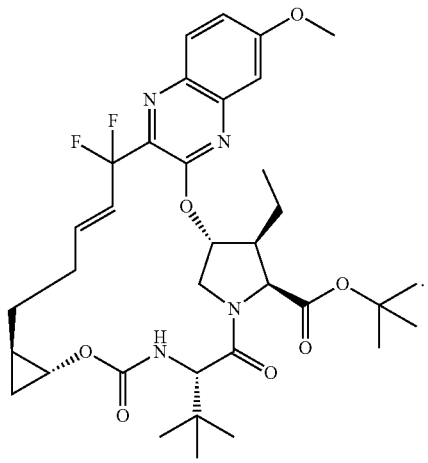 [SMILES: CC[C@@H]1[C@@H]2CN(C(=O)[C@H](C(C)(C)C)NC(=O)O[C@@H]3C[C@H]3CC/C=C/C(F)(F)c3nc4ccc(OC)cc4nc3O2)[C@@H]1C(=O)OC(C)(C)C]

2. A compound of formula:

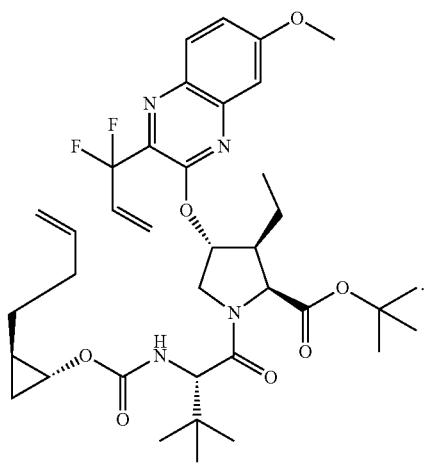 [SMILES: C=CCC[C@@H]1C[C@H]1OC(=O)N[C@H](C(=O)N1C[C@H](Oc2nc3cc(OC)ccc3nc2C(F)(F)C=C)[C@@H](CC)[C@H]1C(=O)OC(C)(C)C)C(C)(C)C]

* * * * *